US007728030B2

(12) United States Patent
Berger et al.

(10) Patent No.: US 7,728,030 B2
(45) Date of Patent: Jun. 1, 2010

(54) CHEMICAL COMPOUNDS 572

(75) Inventors: Markus Berger, Berlin (DE); Jan Dahmén, Lund (SE); Karl Edman, Mölndal (SE); Anders Eriksson, Lund (SE); Balint Gabos, Lund (SE); Thomas Hansson, Lund (SE); Martin Hemmerling, Lund (SE); Krister Henriksson, Lund (SE); Svetlana Ivanova, Lund (SE); Matti Lepistö, Lund (SE); Darren McKerrecher, Macclesfield (GB); Magnus Munck af Rosenschöld, Lund (SE); Stinabritt Nilsson, Lund (SE); Hartmut Rehwinkel, Berlin (DE); Camilla Taflin, Lund (SE)

(73) Assignees: AstraZeneca AB (SE); Bayer Schering Pharma Aktiengesellschaft (DE)

( * ) Notice: Subject to any disclaimer, the term of this patent is extended or adjusted under 35 U.S.C. 154(b) by 0 days.

(21) Appl. No.: 12/005,066

(22) Filed: Dec. 20, 2007

(65) Prior Publication Data

US 2008/0214641 A1     Sep. 4, 2008

Related U.S. Application Data

(60) Provisional application No. 60/978,526, filed on Oct. 9, 2007, provisional application No. 60/941,745, filed on Jun. 4, 2007, provisional application No. 60/871,184, filed on Dec. 21, 2006.

(51) Int. Cl.
*A61K 31/415* (2006.01)
*C07D 231/56* (2006.01)
*C07D 487/00* (2006.01)
*C07D 231/00* (2006.01)

(52) U.S. Cl. ............... 514/406; 514/403; 514/405; 548/356.1; 548/358.1; 548/360.1; 548/361.1

(58) Field of Classification Search ............ 548/356.1, 548/358.1, 360.1, 361.1; 514/403, 405, 406
See application file for complete search history.

(56) References Cited

U.S. PATENT DOCUMENTS

| | | | |
|---|---|---|---|
| 3,992,441 | A | 11/1976 | Helland |
| 4,443,477 | A | 4/1984 | Witte et al. |
| 4,948,809 | A | 8/1990 | Witte et al. |
| 5,861,401 | A | 1/1999 | Bradbury |
| 6,323,199 | B1 | 11/2001 | Lehmann et al. |
| 7,297,709 | B2 | 11/2007 | Dai et al. |
| 2004/0235892 | A1 | 11/2004 | Dai et al. |
| 2007/0265326 | A1 | 11/2007 | Biggadike et al. |
| 2008/0207721 | A1 | 8/2008 | Berger et al. |
| 2008/0214641 | A1 | 9/2008 | Berger et al. |
| 2009/0093485 | A1 | 4/2009 | Bladh et al. |
| 2009/0124607 | A1 | 5/2009 | Bladh et al. |

| 2009/0170898 A1 | 7/2009 | Bengtsson et al. |

FOREIGN PATENT DOCUMENTS

| | | | |
|---|---|---|---|
| EP | 0031954 | | 3/1984 |
| EP | 0201735 | | 11/1986 |
| EP | 0261539 | | 3/1988 |
| EP | 0558258 | | 9/1993 |
| EP | 0569193 | | 11/1993 |
| EP | 0610896 | | 8/1994 |
| EP | 0679641 | | 11/1995 |
| EP | 0947500 | | 10/1999 |
| EP | 0976722 | | 2/2000 |
| EP | 1190710 | A1 | 3/2002 |
| EP | 1447401 | | 8/2004 |
| GB | 0607840.6 | * | 4/2006 ............ 548/356.1 |
| WO | WO95/02580 | | 1/1995 |
| WO | WO95/03279 | | 2/1995 |
| WO | WO95/33461 | | 12/1995 |
| WO | WO96/06822 | | 3/1996 |
| WO | WO96/36595 | | 11/1996 |
| WO | WO99/33786 | | 7/1999 |
| WO | WO99/38845 | | 8/1999 |
| WO | WO2001/24786 | | 4/2001 |
| WO | WO01/46172 | | 6/2001 |
| WO | WO02/20474 | | 3/2002 |
| WO | WO02/28820 | | 4/2002 |
| WO | WO03/028641 | | 4/2003 |
| WO | WO03/076401 | | 9/2003 |
| WO | WO03/086294 | A2 | 11/2003 |

(Continued)

OTHER PUBLICATIONS

Bradbury, Robert H. et al., "New Non-Peptide Endothelin-A Receptor Antagonists: Synthesis, Biological Properties, and Structure—Activity Relationships of 5-(Dimethylamino)-*N*-pyridyl-, -*N*-pyrimidinyl-, -*N*-puridazinyl-, and -*N*-pyrazinyl-l-naphthalenesulfonamides", *Journal of Medicinal Chemistry*, vol. 40, No. 6, pp. 996-1004, (1997).

(Continued)

*Primary Examiner*—Kamal A Saeed
*Assistant Examiner*—Samantha L Shterengarts
(74) *Attorney, Agent, or Firm*—Fish & Richardson P.C.

(57) ABSTRACT

Compounds of formula (I):

(I)

[Chemical structure showing: A—C(Z)—N with $R^X$ substituent, connected to C with $R^1$, $R^2$, $R^{1a}$ substituents, then to C with $R^3$, connected via X to an indazole ring system with $R^4$ substituent, Y, W, and N positions]

The present invention relates to novel indazolyl ester or amide derivatives, to pharmaceutical compositions comprising such derivatives, to processes for preparing such novel derivatives and to the use of such derivatives as medicaments.

4 Claims, No Drawings

FOREIGN PATENT DOCUMENTS

| | | |
|---|---|---|
| WO | WO03/099773 | 12/2003 |
| WO | WO2004/018414 | 3/2004 |
| WO | WO2004/019935 A1 | 4/2004 |
| WO | WO2004/050631 | 6/2004 |
| WO | WO2004/073634 | 9/2004 |
| WO | WO2004/089913 | 10/2004 |
| WO | WO2004/110418 | 12/2004 |
| WO | WO2005/004810 | 1/2005 |
| WO | WO2005/060963 | 7/2005 |
| WO | WO2005/077895 | 8/2005 |
| WO | WO2005/086904 | 9/2005 |
| WO | WO2005/123688 A2 | 12/2005 |
| WO | WO2006/046914 | 5/2006 |
| WO | WO2006/046916 A1 | 5/2006 |
| WO | WO2006/135826 A1 | 12/2006 |
| WO | WO2006/138373 A2 | 12/2006 |
| WO | WO2007/046747 | 4/2007 |
| WO | WO2007/054294 A1 | 5/2007 |
| WO | WO2007/114763 | 10/2007 |
| WO | WO2007/122165 A1 | 11/2007 |
| WO | WO2008/008882 | 1/2008 |
| WO | WO2008/043788 | 4/2008 |
| WO | WO2008/043789 | 4/2008 |
| WO | WO2008/051532 | 5/2008 |
| WO | WO2008/057856 | 5/2008 |
| WO | WO2008/057857 | 5/2008 |
| WO | WO2008/063116 | 5/2008 |
| WO | WO2008/070507 | 6/2008 |
| WO | WO2008/076048 | 6/2008 |
| WO | WO2008/079073 | 7/2008 |
| WO | WO2008/124665 | 10/2008 |
| WO | WO2008/124745 | 10/2008 |
| WO | WO2008/135578 | 11/2008 |
| WO | WO2009/050218 | 4/2009 |
| WO | WO2009/050220 | 4/2009 |
| WO | WO2009/050221 | 4/2009 |
| WO | WO2009/050243 | 4/2009 |
| WO | WO2009/050244 | 4/2009 |
| WO | WO2009/062950 | 5/2009 |
| WO | WO2009/074590 | 6/2009 |
| WO | WO2009/108525 | 9/2009 |
| WO | WO2009/111214 | 9/2009 |

OTHER PUBLICATIONS

Gaedcke, Frauke et al. "Structure Dependance of Antiplasmodic Activity of 3-[N-(4'-Amidosulfonyl)-phenyl]-aminomethyl-chinolin", *Arch. Pharm (Weinheim)*, vol. 313, pp. 166-173, (1980).

Jansen, Michaela, et al., Hydantoin-Substituted 4,6-Dichloroindole-2-carboxylic Acids as Ligands with High Affinity for the Glycine Binding Site of the NMDA Receptor, *Journal of Medicinal Chemistry*, vol. 46, pp. 64-73, (2003).

Fabiana et al., "Mode of Action of Sulfanilyl Fluoroquinolones", *Antimicrobial Agents and Chemotherapy* 42:1495-1498 (1998).

STN International file Registry: RN 321722-44-5, RN 321704-10-3, RN 321704-02-3, RN 321703-82-6, RN 321703-77-9, RN 321703-75-7.

STN International file Registry: RN 674768-65-1, RN 343372-84-9, RN 343372-70-3, RN 339016-98- 7, RN 519018-69-0, RN 261623-54-5.

Clark et al., "1*H*-Pyrazolo[3,4-*g*]hexahydro-isoquinolines as selective glucocorticoid receptor antagonists with high functional activity", *Bioorg. Med. Chem. Lett.* 18:1312-1317 (2008).

Mohler et al., "Dissociated non-steroidal glucocorticoids: tuning out untoward effects", *Expert Opin. Ther. Patents* 17:37-58 (2007).

Mohler et al., "Non-steroidal glucocorticoid receptor antagonists: the race to replace RU-486 for anti- glucocorticoid therapy", *Expert Opin. Ther. Patents* 17:59-81 (2007).

Schäcke et al., "Dissociated non-steroidal glucocorticoid receptor modulators: an update on new compounds", *Expert Opin. Ther. Patents* 18:339-352 (2008).

* cited by examiner

CHEMICAL COMPOUNDS 572

This application claims the benefit under 35 U.S.C. § 119(e) of U.S. Provisional Application No. 60/978,526, filed on Oct. 9, 2007, U.S. Provisional Application No. 60/941,745, filed on Jun. 4, 2007, and U.S. Provisional Application No. 60/871,184, filed on Dec. 21, 2006. Each of these three prior applications is incorporated herein by reference in its entirety.

The present invention relates to novel indazolyl ester or amide derivatives, to pharmaceutical compositions comprising such derivatives, to processes for preparing such novel derivatives and to the use of such derivatives as medicaments (for example in the treatment of an inflammatory disease state).

Sulphonamide derivatives are disclosed as anti-inflammatories in WO 2004/019935 and WO 2004/050631. Pharmaceutically active sulphonamides are also disclosed in Arch. Pharm. (1980) 313 166-173, J. Med. Chem. (2003) 46 64-73, J. Med. Chem. (1997) 40 996-1004, EP 0031954, EP 1190710 (WO 200124786), U.S. Pat. No. 5,861,401, U.S. Pat. No. 4,948,809, U.S. Pat. No. 3,992,441 and WO 99/33786.

It is known that certain non-steroidal compounds interact with the glucocorticoid receptor (GR) and, as a result of this interaction, produce a suppression of inflammation (see, for example, U.S. Pat. No. 6,323,199). Such compounds can show a clear dissociation between anti-inflammatory and metabolic actions making them superior to earlier reported steroidal and non-steroidal glucocorticoids. The present invention provides further non-steroidal compounds as modulators (for example agonists, antagonists, partial agonists or partial antagonists) of the glucocorticoid receptor.

These new compounds are contemplated to have improved properties such as selectivity, efficacy, etc. over the known compounds.

The present invention provides a compound of formula (I):

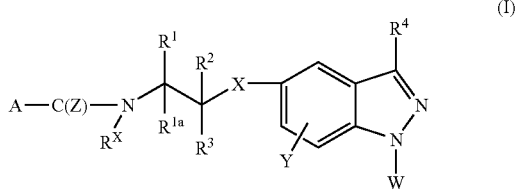

wherein:

A is $C_{1-6}$alkyl, $C_{1-6}$hydroxyalkyl, $C_{1-6}$cyanoalkyl, cyano, $C_{1-6}$nitroalkyl, nitro, $C_{1-4}$alkylS(O)$_n$, $C_{1-6}$alkoxy, $C_{3-7}$cycloalkyl$C_{1-6}$alkyl, $C_{3-7}$cycloalkyl, $C_{3-7}$heterocycloalkyl, $C_{3-7}$heterocycloalkyl$C_{1-6}$alkyl, $C_{1-6}$haloalkyl, $C_{1-6}$alkyl, $C_{1-6}$thioalkyl, $C_{1-6}$thioalkyl, $C_{1-6}$alkylOC$_{1-6}$alkyl, $C_{1-4}$alkylOC$_{1-6}$alkylOC$_{1-6}$alkyl, $C_{1-6}$alkylOC$_{1-6}$alkylO, $C_{1-4}$alkylC(O)$C_{1-6}$alkyl, $C_{1-6}$alkylC(O), $C_{1-6}$alkylC(O)OC$_{1-6}$-alkyl, $C_{1-6}$alkylC(O)O, $C_{1-6}$alkylOC(O)$C_{1-6}$alkyl, $C_{1-6}$alkylOC(O), HOC(O), NR$^5$R$^6$C$_{1-6}$alkyl, NR$^5$R$^6$, NR$^5$R$^6$C(O)$C_{1-6}$alkyl, NR$^5$R$^6$C(O), NR$^5$R$^6$OC(O)$C_{1-6}$alkyl, NR$^5$R$^6$OC(O), R$^7$NH, $C_{5-10}$aryl$C_{1-3}$alkyl, $C_{5-10}$aryl, $C_{5-10}$heteroaryl$C_{1-3}$alkyl or $C_{5-10}$heteroaryl, whereby the cycloalkyl, heterocycloalkyl, aryl or heteroaryl may be optionally substituted by one or more substituents independently selected from halo, cyano, hydroxy, $C_{1-4}$alkyl, $C_{1-4}$alkoxy, $C_{1-4}$haloalkyl, $C_{1-4}$alkylOC(O), $C_{1-4}$alkylOC$_{1-4}$alkyl, $C_{1-4}$alkylS(O)$_2$ and $C_{1-4}$haloalkylO, and R$^x$ is hydrogen, or A forms together with R$^x$ a 5 to 6 membered azacyclic ring optionally having one or more further heteroatoms independently selected from O, N and S;

R$^1$ and R$^{1a}$ are independently selected from hydrogen, $C_{1-4}$alkyl, $C_{1-4}$hydroxyalkyl, $C_{1-4}$alkylOC$_{1-4}$alkyl, $C_{1-4}$alkyl$C_{1-4}$thioalkyl and $C_{1-4}$haloalkyl, or R$^1$ and R$^{1a}$ together are oxo;

R$^2$ is hydrogen or $C_{1-4}$alkyl;

R$^3$ is $C_{5-10}$aryl, $C_{5-10}$aryl$C_{1-4}$alkyl, $C_{5-10}$arylO, $C_{5-10}$arylOC$_{1-4}$alkyl or $C_{5-10}$heteroaryl, which may be optionally substituted by one or more substituents independently selected from B;

B is $C_{1-3}$hydroxyalkyl, hydroxy, $C_{1-4}$alkyl, $C_{1-4}$alkoxy, $C_{1-4}$alkyl$C_{1-4}$thioalkyl, $C_{1-4}$thioalkyl, $C_{3-6}$cycloalkyl$C_{1-4}$thioalkyl, $C_{3-6}$cycloalkylS, $C_{1-3}$alkylS(O)$_n$$C_{1-4}$alkyl, $C_{1-3}$alkylS(O)$_n$, $C_{1-4}$haloalkyl, $C_{1-4}$haloalkylO, halo, nitro, cyano, $C_{1-4}$alkylOC$_{1-4}$alkylOC$_{1-4}$alkyl, $C_{1-4}$alkylC(O)$C_{1-4}$alkyl, $C_{1-4}$alkylC(O), $C_{1-4}$alkylC(O)OC$_{1-4}$alkyl, $C_{1-4}$alkylC(O)O, $C_{1-4}$alkylOC(O)$C_{1-4}$alkyl, $C_{1-4}$alkylOC(O), NR$^8$R$^9$$C_{1-4}$alkyl, NR$^8$R$^9$, NR$^8$R$^9$C(O)$C_{1-4}$alkyl, NR$^8$R$^9$C(O), NR$^8$R$^9$C(O)C$_4$alkyl, NR$^8$R$^9$C(O)O, R$^9$C(O)R$^8$N$C_{1-4}$alkyl, R$^9$C(O)R$^8$NH, $C_{1-4}$alkylNH, $C_{1-4}$alkylOC(O)NH, $C_{1-4}$alkylC(O)OC$_{1-4}$alkylNH, $C_{1-4}$alkylC(O)$C_{1-4}$alkylNH, $C_{1-4}$alkylC(O)NH, NR$^8$R$^9$S(O)$_n$$C_{1-4}$alkyl or NR$^8$R$^9$S(O)$_n$;

n is 1 or 2;

R$^4$ is hydrogen, hydroxy, halo, $C_{1-4}$alkyl or $C_4$haloalkyl;

W is hydrogen, or phenyl, $C_{1-4}$alkyl, $C_{3-7}$cycloalkyl, thienyl, isoxazolyl, pyrazolyl, pyridinyl, pyridazinyl or pyrimidinyl all of which are optionally substituted by one or more substituents independently selected from $C_{1-3}$hydroxyalkyl, hydroxy, $C_{1-4}$alkyl, $C_{1-4}$alkoxy, $C_{1-4}$alkyl$C_{1-4}$thioalkyl, $C_{1-4}$thioalkyl, $C_{3-6}$cycloalkyl$C_{1-4}$thioalkyl, $C_{3-6}$cycloalkylS, $C_{3-6}$cycloalkyl, $C_{3-6}$cycloalkyl$C_{1-4}$alkyl, $C_{3-6}$heterocycloalkyl, $C_{3-6}$heterocycloalkyl$C_{1-4}$alkyl, $C_{1-4}$alkylS(O)$_n$$C_{1-4}$alkyl, $C_{1-4}$alkylS(O)$_n$, $C_{1-4}$haloalkyl, $C_{1-4}$haloalkylO, halo, nitro, cyano, $C_{1-4}$alkylOC$_{1-4}$alkyl, $C_{1-4}$alkylOC$_{1-4}$alkylOC$_{1-4}$alkyl, $C_{1-4}$alkylC(O)$C_{1-4}$alkyl, $C_{1-4}$alkylC(O), $C_{1-4}$alkylC(O)OC$_{1-4}$alkyl, $C_{1-4}$alkylC(O)O, $C_{1-4}$alkylOC(O)$C_{1-4}$alkyl, $C_{1-4}$alkylOC(O), NR$^{10}$R$^{11}$$C_{1-4}$alkyl, NR$^{10}$R$^{11}$, NR$^{10}$R$^{11}$C(O)$C_{1-4}$alkyl, NR$^{10}$R$^{11}$C(O), NR$^{10}$R$^{11}$C(O)OC$_4$alkyl, NR$_{10}$R$^{11}$C(O)O, NR$^{10}$R$^{11}$OC(O)$C_{1-4}$alkyl, NR$^{10}$R$^{11}$OC(O), R$^{11}$C(O)R$^{10}$N$C_{1-4}$alkyl, R$^{11}$C(O)R$^{10}$NH, $C_{1-4}$alkylOC(O)$C_{1-4}$alkylNH, $C_{1-4}$alkylOC(O)NH, $C_{1-4}$alkylC(O)OC$_{1-4}$alkylNH, $C_{1-4}$alkylC(O)$C_{1-4}$alkylNH, $C_{1-4}$alkylC(O)NH, NR$^{10}$R$^{11}$S(O)$_n$$C_{1-4}$alkyl or NR$^{10}$R$^{11}$S(O);

X is $CH_2$, O, S, S(O)$_n$, NH or NC$_{1-4}$alkyl;

Y is hydrogen, halo, $C_{1-4}$alkyl, $C_{1-4}$alkoxy, $C_{1-4}$thioalkyl, $C_{1-4}$haloalkyl, $C_{1-4}$ haloalkylO, nitro, cyano, hydroxy, R$^{12}$C(O), R$^{12}$OC(O), R$^{12}$C(O)O, $C_{1-6}$alkylS(O)$_n$, R$^{12}$R$^{13}$NS(O)$_n$, benzyloxy, imidazolyl, $C_{1-4}$alkylNHC(O), NR$^{12}$R$^{13}$C(O), $C_{1-4}$alkylC(O)NH or NR$^{12}$R$^{13}$;

Z is O or S;

R$^5$, R$^6$, R$^8$, R$^9$, R$^{10}$R$^{11}$, R$^{12}$ and R$^{13}$ are independently selected from hydrogen, $C_{1-6}$alkylC(O), NHR$^7$C(O) and $C_{1-6}$alkyl; and R$^7$ is hydrogen, $C_{1-6}$alkyl, $C_{1-6}$alkylC(O)OC$_{1-3}$alkyl, $C_{1-6}$alkylC(O)O, $C_{1-6}$alkylOC(O)$C_{1-3}$alkyl, $C_{1-6}$alkylOC(O), $C_{1-6}$alkylC(O), $C_{5-10}$heteroaryl$C_{1-3}$alkyl, $C_{5-10}$heteroaryl, $C_{5-10}$aryl$C_{1-3}$alkyl, $C_{5-10}$aryl, $C_{3-6}$cycloalkyl$C_{1-3}$alkyl or $C_{3-6}$cycloalkyl;

or a pharmaceutically acceptable salt thereof.

One embodiment of the invention related to compounds of formula I wherein:

A is $C_{1-6}$alkyl, $C_{1-6}$hydroxyalkyl, $C_{1-6}$cyanoalkyl, cyano, $C_{1-6}$nitroalkyl, nitro, $C_{1-4}$alkylS(O)$_n$, $C_{1-6}$alkoxy, $C_{3-7}$cycloalkyl$C_{1-6}$alkyl, $C_{3-7}$cycloalkyl, $C_{3-7}$heterocycloalkyl, $C_{3-7}$heterocycloalkyl$C_{1-6}$alkyl, $C_{1-6}$haloalkyl, $C_{1-6}$alkyl$C_{1-6}$thioalkyl, $C_{1-6}$thioalkyl, $C_{1-6}$alkylO$C_{1-6}$alkyl, $C_{1-6}$alkylO$C_{1-6}$alkylO$C_{1-6}$alkyl, $C_{1-6}$alkylO$C_{1-6}$alkylO, $C_{1-6}$alkylC(O)$C_{1-6}$alkyl, $C_{1-6}$alkylC(O), $C_{1-6}$alkylC(O)O$C_{1-6}$alkyl, $C_{1-6}$alkylC(O)O, $C_{1-6}$alkylOC(O)$C_{1-6}$alkyl, $C_{1-6}$alkylOC(O), HOC(O), $NR^5R^6C_{1-6}$alkyl, $NR^5R^6$, $NR^5R^6C(O)C_{1-6}$alkyl, $NR^5R^6C(O)$, $NR^5R^6OC(O)C_{1-6}$alkyl, $NR^5R^6OC(O)$, $R^7$NH, $C_{5-10}$aryl$C_{1-3}$alkyl, $C_{5-10}$aryl, $C_{5-10}$heteroaryl$C_{1-3}$alkyl or $C_{5-10}$heteroaryl, whereby the cycloalkyl, heterocycloalkyl, aryl or heteroaryl may be optionally substituted by one or more substituents independently selected from halo, cyano, hydroxy, $C_{1-4}$alkyl, $C_{1-4}$alkoxy, $C_{1-4}$haloalkyl, $C_{1-4}$alkylOC(O), $C_{1-4}$alkylOC 4alkyl, $C_{1-4}$alkylS(O)$_2$ and $C_{1-4}$haloalkylO, and $R^x$ is hydrogen, or A forms together with $R^x$ a 5 to 6 membered azacyclic ring optionally having one or more further heteroatoms independently selected from O, N and S;

$R^1$ and $R^{1a}$ are independently selected from hydrogen, $C_{1-4}$alkyl, $C_{1-4}$hydroxyalkyl, $C_{1-4}$alkylO$C_{1-4}$alkyl, $C_{1-4}$alkyl$C_{1-4}$thioalkyl and $C_{1-4}$haloalkyl, or $R^1$ and $R^{1a}$ together are oxo;

$R^2$ is hydrogen or $C_{1-4}$alkyl;

$R^3$ is $C_{5-10}$aryl, $C_{5-10}$aryl$C_{1-4}$alkyl, $C_{5-10}$arylO, $C_{5-10}$arylO$C_{1-4}$alkyl or $C_{5-10}$heteroaryl, which may be optionally substituted by one or more substituents independently selected from B;

B is $C_{1-3}$hydroxyalkyl, hydroxy, $C_{1-4}$alkyl, $C_{1-4}$alkoxy, $C_{1-4}$alkyl$C_{1-4}$thioalkyl, $C_{1-4}$thioalkyl, $C_{3-6}$cycloalkyl$C_{1-4}$thioalkyl, $C_{3-6}$cycloalkylS, $C_{1-3}$alkylS(O)$_n$$C_{1-4}$alkyl, $C_{1-3}$alkylS(O)$_n$, $C_{1-4}$haloalkyl, $C_{1-4}$haloalkylO, halo, nitro, cyano, $C_{1-4}$alkylO$C_{1-4}$alkylO$C_{1-4}$alkyl, $C_{1-4}$alkylC(O)$C_{1-4}$alkyl, $C_{1-4}$alkylC(O), $C_{1-4}$alkylC(O)O$C_{1-4}$alkyl, $C_{1-4}$alkylC(O)O, $C_{1-4}$alkylOC(O)$C_{1-4}$alkyl, $C_{1-4}$alkylOC(O), $NR^8R^9C_{1-4}$alkyl, $NR^8R^9$, $NR^8R^9C(O)C_{1-4}$alkyl, $NR^8R^9C(O)$, $NR^8R^9OC(O)C_{1-4}$alkyl, $NR^8R^9OC(O)$, $NR^8R^9C(O)OC_{1-4}$alkyl, $NR^8R^9C(O)O$, $R^9C(O)R^8NC_{1-4}$alkyl, $R^9C(O)R^8NH$, $C_{1-4}$alkylNH, $C_{1-4}$alkylOC(O)NH, $C_{1-4}$alkylC(O)O$C_{1-4}$alkylNH, $C_{1-4}$alkylC(O)$C_{1-4}$alkylNH, $C_{1-4}$alkylC(O)NH, $NR^8R^9S(O)_nC_{1-4}$alkyl or $NR^8R^9S(O)_n$;

n is 1 or 2;

$R^4$ is hydrogen, hydroxy, halo, $C_{1-4}$alkyl or $C_{1-4}$haloalkyl;

W is phenyl, $C_{1-4}$alkyl, $C_{3-7}$cycloalkyl, thienyl, isoxazolyl, pyrazolyl, pyridinyl, pyridazinyl or pyrimidinyl all of which are optionally substituted by one or more substituents independently selected from $C_{1-3}$hydroxyalkyl, hydroxy, $C_{1-4}$alkyl, $C_{1-4}$alkoxy, $C_{1-4}$alkyl$C_{1-4}$thioalkyl, $C_{1-4}$thioalkyl, $C_{3-6}$cycloalkyl$C_{1-4}$thioalkyl, $C_{3-6}$cycloalkylS, $C_{3-6}$cycloalkyl, $C_{3-6}$cycloalkyl$C_{1-4}$alkyl, $C_{3-6}$heterocycloalkyl, $C_{3-6}$heterocycloalkyl$C_{1-4}$alkyl, $C_{1-4}$alkylS(O)$_nC_{1-4}$alkyl, $C_{1-4}$alkylS(O)$_n$, $C_{1-4}$haloalkyl, $C_{1-4}$haloalkylO, halo, nitro, cyano, $C_{1-4}$alkylO$C_{1-4}$alkyl, $C_{1-4}$alkylO$C_{1-4}$alkylO$C_{1-4}$alkyl, $C_{1-4}$alkylC(O)$C_{1-4}$alkyl, $C_{1-4}$alkylC(O), $C_{1-4}$alkylC(O)O$C_{1-4}$alkyl, $C_{1-4}$alkylC(O)O, $C_{1-4}$alkylOC(O)$C_{1-4}$alkyl, $C_{1-4}$alkylOC(O), $NR^{10}R^{11}C_{1-4}$alkyl, $NR^{10}R^{11}$, $NR^{10}R^{11}C(O)C_{1-4}$alkyl, $NR^{10}R^{11}C(O)$, $NR^{10}R^{11}C(O)OC_{1-4}$alkyl, $NR^{10}R^{11}C(O)O$, $NR^{10}R^{11}OC(O)C_{1-4}$alkyl, $NR^{10}R^{11}OC(O)$, $R^{11}C(O)R^{10}NC_{1-4}$alkyl, $R^{11}C(O)R^{10}NH$, $C_{1-4}$alkylOC(O)$C_{1-4}$alkylNH, $C_{1-4}$alkylOC(O)NH, $C_{1-4}$alkylC(O)$C_{1-4}$alkyl-NH, $C_{1-4}$alkylC(O)NH, $NR^{10}R^{11}S(O)_nC_{1-4}$alkyl or $NR^{10}R^{11}S(O)_n$;

X is $CH_2$, O, S, S(O)$_n$, NH or $NC_{1-4}$alkyl;

Y is hydrogen, halo, $C_{1-4}$alkyl, $C_{1-4}$alkoxy, $C_{1-4}$thioalkyl, $C_{1-4}$haloalkyl, $C_{1-4}$haloalkylO, nitro, cyano, hydroxy, $R^{12}C(O)$, $R^{12}OC(O)$, $R^{12}C(O)O$, $C_{1-6}$alkylS(O)$_n$, $R^{12}R^{13}NS(O)_n$, benzyloxy, imidazolyl, $C_{1-4}$alkylNHC(O), $NR^{12}R^{13}C(O)$, $C_{1-4}$alkylC(O)NH or $NR^{12}R^{13}$;

Z is O or S;

$R^5$, $R^6$, $R^8$, $R^9$, $R^{10}$ $R^{11}$, $R^{12}$ and $R^{13}$ are independently selected from hydrogen, $C_{1-6}$alkylC(O), $NHR^7C(O)$ and $C_{1-6}$alkyl; and $R^7$ is hydrogen, $C_{1-6}$alkyl, $C_{1-6}$alkylC(O)O$C_{1-3}$alkyl, $C_{1-6}$alkylC(O)O, $C_{1-6}$alkylOC(O)$C_{1-3}$alkyl, $C_{1-6}$alkylOC(O), $C_{1-6}$alkylC(O), $C_{5-10}$heteroaryl$C_{1-3}$alkyl, $C_{5-10}$heteroaryl, $C_{5-10}$aryl$C_{1-3}$alkyl, $C_{5-10}$aryl, $C_{3-6}$cycloalkyl$C_{1-3}$alkyl or $C_{3-6}$cycloalkyl;

or a pharmaceutically acceptable salt thereof.

Another embodiment of the invention related to compounds of formula I wherein:

A is $R^7$NH, and $R^x$ is hydrogen;

$R^1$ and $R^{1a}$ are independently selected from hydrogen, $C_{1-4}$alkyl, $C_{1-4}$hydroxyalkyl, $C_{1-4}$alkylO$C_{1-4}$alkyl, $C_{1-4}$alkyl$C_{1-4}$thioalkyl and $C_{1-4}$haloalkyl, or $R^1$ and $R^{1a}$ together are oxo;

$R^2$ is hydrogen or $C_{1-4}$alkyl;

$R^3$ is $C_{5-10}$aryl, $C_{5-10}$aryl$C_{1-4}$alkyl, $C_{5-10}$arylO, $C_{5-10}$arylO$C_{1-4}$alkyl or $C_{5-10}$heteroaryl, which may be optionally substituted by one or more substituents independently selected from B;

B is $C_{1-3}$hydroxyalkyl, hydroxy, $C_{1-4}$alkyl, $C_{1-4}$alkoxy, $C_{1-4}$alkyl$C_{1-4}$thioalkyl, $C_{1-4}$thioalkyl, $C_{3-6}$cycloalkyl$C_{1-4}$thioalkyl, $C_{3-6}$cycloalkylS, $C_{1-3}$alkylS(O)$_n$$C_{1-4}$alkyl, $C_{1-3}$alkylS(O)$_n$, $C_{1-4}$haloalkyl, $C_{1-4}$haloalkylO, halo, nitro, cyano, $C_{1-4}$alkylO$C_{1-4}$alkylO$C_{1-4}$alkyl, $C_{1-4}$alkylC(O)$C_{1-4}$alkyl, $C_{1-4}$alkylC(O), $C_{1-4}$alkylC(O)O$C_{1-4}$alkyl, $C_{1-4}$alkylC(O)O, $C_{1-4}$alkylOC(O)$C_{1-4}$alkyl, $C_{1-4}$alkylOC(O), $NR^8R^9C_{1-4}$alkyl, $NR^8R^9$, $N^8R^9C(O)C_{1-4}$alkyl, $NR^8R^9C(O)$, $NR^8R^9OC(O)C_{1-4}$alkyl, $NR^8R^9OC(O)$, $NR^8R^9C(O)OC_{1-4}$alkyl, $NR^8R^9C(O)O$, $R^9C(O)R^8NC_{1-4}$alkyl, $R^9C(O)R^8NH$, $C_{1-4}$alkylNH, $C_{1-4}$alkylOC(O)NH, $C_{1-4}$alkylC(O)O$C_{1-4}$alkylNH, $C_{1-4}$alkylC(O)$C_{1-4}$alkylNH, $C_{1-4}$alkylC(O)NH, $NR^8R^9S(O)_nC_{1-4}$alkyl or $NR^8R^9S(O)_n$;

n is 1 or 2;

$R^4$ is hydrogen, hydroxy, halo, $C_{1-4}$alkyl or $C_{1-4}$haloalkyl;

W is phenyl, $C_{1-4}$alkyl, $C_{3-7}$cycloalkyl, thienyl, isoxazolyl, pyrazolyl, pyridinyl, pyridazinyl or pyrimidinyl all of which are optionally substituted by one or more substituents independently selected from $C_{1-3}$hydroxyalkyl, hydroxy, $C_{1-4}$alkyl, $C_{1-4}$alkoxy, $C_{1-4}$alkyl$C_{1-4}$thioalkyl, $C_{1-4}$thioalkyl, $C_{3-6}$cycloalkyl$C_{1-4}$thioalkyl, $C_{3-6}$cycloalkylS, $C_{3-6}$cycloalkyl, $C_{3-6}$cycloalkyl$C_{1-4}$alkyl, $C_{3-6}$heterocycloalkyl, $C_{3-6}$heterocycloalkyl$C_{1-4}$alkyl, $C_{1-4}$alkylS(O)$_nC_{1-4}$alkyl, $C_{1-4}$alkylS(O)$_n$, $C_{1-4}$haloalkyl, $C_{1-4}$haloalkylO, halo, nitro, cyano, $C_{1-4}$alkylO$C_{1-4}$alkyl, $C_{1-4}$alkylO$C_{1-4}$alkylO$C_{1-4}$alkyl, $C_{1-4}$alkylC(O)$C_{1-4}$alkyl, $C_{1-4}$alkylC(O), $C_{1-4}$alkylC(O)O$C_{1-4}$alkyl, $C_{1-4}$alkylC(O)O, $C_{1-4}$alkylOC(O)$C_{1-4}$alkyl, $C_{1-4}$alkylOC(O), $NR^{10}R^{11}C_{1-4}$alkyl, $NR^{10}R^{11}$, $NR^{10}R^{11}C(O)C_{1-4}$alkyl, $NR^{10}R^{11}C(O)$, $NR^{10}R^{11}C(O)OC_{1-4}$alkyl, $NR^{10}R^{11}C(O)O$, $NR^{10}R^{11}OC(O)C_{1-4}$alkyl, $NR^{10}R^{11}OC(O)$, $R^{11}C(O)R^{10}NC_{1-4}$alkyl, $R^{11}C(O)R^{10}NH$, $C_{1-4}$alkylOC(O)$C_{1-4}$alkylNH, $C_{1-4}$alkylOC(O)NH, $C_{1-4}$alkylC(O)$C_{1-4}$alkylNH, $C_{1-4}$alkylC(O)NH, $NR^{10}R^{11}S(O)_nC_{1-4}$alkyl or $NR^{10}R^{11}S(O)_n$;

X is $CH_2$, O, S, $S(O)_n$, NH or $NC_{1-4}$alkyl;
Y is hydrogen, halo, $C_{1-4}$alkyl, $C_{1-4}$alkoxy, $C_{1-4}$thioalkyl, $C_{1-4}$ haloalkyl, $C_{1-4}$ haloalkylO, nitro, cyano, hydroxy, $R^{12}C(O)$, $R^{12}C(O)$, $R^{12}C(O)O$, $C_{1-6}$alkylS$(O)_n$, $R^{12}R^{13}NS(O)_n$, benzyloxy, imidazolyl, $C_{1-4}$alkylNHC(O), $NR^{12}R^{13}C(O)$, $C_{1-4}$alkylC(O)NH or $NR^{12}R^{13}$;
Z is O or S;
$R^5$, $R^6$, $R^8$, $R^9$, $R^{10}$ $R^{11}$, $R^{12}$ and $R^{13}$ are independently selected from hydrogen, $C_{1-6}$alkylC(O), $NHR^7C(O)$ and $C_{1-6}$alkyl; and
$R^7$ is hydrogen, $C_{1-6}$alkyl, $C_{1-6}$alkylC(O)$OC_{1-3}$alkyl, $C_{1-6}$alkylC(O)O, $C_{1-6}$alkylOC(O)$C_{1-3}$alkyl, $C_{1-6}$alkylOC(O), $C_{1-6}$alkylC(O), $C_{5-10}$heteroaryl$C_{1-3}$alkyl, $C_{5-10}$heteroaryl, $C_{5-10}$aryl$C_{1-3}$alkyl, $C_{5-10}$aryl, $C_{3-6}$cycloalkyl$C_{1-3}$alkyl or $C_{3-6}$cycloalkyl;

or a pharmaceutically acceptable salt thereof.

One embodiment of the invention related to compounds of formula I wherein:
A is $C_{1-6}$alkyl, $C_{1-6}$hydroxyalkyl, $C_{1-6}$alkoxy, $C_{3-7}$cycloalkyl, $C_{3-7}$heterocycloalkyl, $C_{1-6}$haloalkyl, $C_{1-6}$alkyl$OC_{1-6}$alkyl, $C_{1-6}$alkylO$C_{1-6}$alkyl$OC_{1-6}$alkyl, $C_{1-6}$alkylC(O)$OC_{1-6}$alkyl, $C_{1-6}$alkylOC(O), HOC(O), $NR^5R^6C_{1-6}$alkyl, $NR^5R^6C(O)$, $NR^5R^6OC(O)$, $R^7NH$, $C_{5-10}$aryl$C_{1-3}$alkyl, $C_{5-10}$aryl or $C_{5-10}$heteroaryl, whereby the cycloalkyl, heterocycloalkyl, aryl or heteroaryl may be optionally substituted by one or more substituents independently selected from halo, cyano, hydroxy, $C_{1-4}$alkyl, $C_{1-4}$alkoxy, $C_{1-4}$haloalkyl, $C_{1-4}$alkylOC(O), $C_{1-4}$alkyl$OC_{1-4}$alkyl and $C_{1-4}$alkylS(O)$_2$ and Rx is hydrogen, or
A forms together with $R^x$ a 5 membered azacyclic ring optionally having one or more further heteroatoms independently selected from O and N;
$R^1$ and $R^{1a}$ are independently selected from hydrogen, $C_{1-4}$alkyl, $C_{1-4}$hydroxyalkyl, $C_{1-4}$alkyl$OC_{1-4}$alkyl and $C_{1-4}$haloalkyl, or $R^1$ and $R^{1a}$ together are oxo;
$R^2$ is hydrogen or $C_{1-4}$alkyl;
$R^2$ is hydrogen;
$R^3$ is $C_{5-10}$aryl, $C_{5-10}$aryl$C_{1-4}$alkyl, $C_{5-10}$arylO, $C_{5-10}$aryl$OC_{1-4}$alkyl or $C_{5-10}$heteroaryl, which may be optionally substituted by one or more substituents independently selected from B;
B is hydroxy, $C_{1-4}$alkyl, $C_{1-4}$alkoxy, $C_{1-4}$alkyl$C_{1-4}$thioalkyl, $C_{1-4}$thioalkyl, $C_{3-6}$cycloalkylS, $C_{1-3}$alkylS$(O)_nC_{1-4}$alkyl, $C_{1-3}$alkylS$(O)_n$, $C_{1-4}$haloalkyl or halo;
n is 1 or 2;
$R^4$ is hydrogen;
W is phenyl, $C_{1-4}$alkyl, $C_{3-7}$cycloalkyl, pyridinyl, pyridazinyl or pyrimidinyl all of which are optionally substituted by one or more substituents independently selected from $C_{1-3}$hydroxyalkyl, $C_{3-6}$heterocycloalkyl$C_{1-4}$alkyl, halo, $C_{1-4}$alkylOC(O) and $NR^{10}R^{11}C_{1-4}$alkyl;
X is O or S;
Y is hydrogen, halo or $C_{1-4}$alkyl;
Z is O or S;
$R^5$, $R^6$, $R^{10}$ and $R^{11}$ are independently selected from hydrogen, $C_{1-6}$alkylC(O), $NHR^7C(O)$ and $C_{1-6}$alkyl; and
$R^7$ is hydrogen, $C_{1-6}$alkyl, $C_{1-6}$alkylC(O)$OC_{1-3}$alkyl, $C_{5-10}$heteroaryl$C_{1-3}$alkyl or $C_{3-6}$cycloalkyl;

or a pharmaceutically acceptable salt thereof.

One embodiment of the invention related to compounds of formula I wherein:
A is $C_{1-3}$hydroxyalkyl, $C_{3-5}$cycloalkyl, $C_{1-3}$haloalkyl or $NR^5R^6C(O)$;
$R^1$ and $R^{1a}$ are independently selected from hydrogen and $C_{1-3}$alkyl;
$R^2$ is hydrogen;
$R^3$ is $C_{5-10}$aryl $C_{5-10}$aryl$OC_{1-2}$alkyl or $C_{5-10}$heteroaryl, which may be optionally substituted by one or more substituents independently selected from B;
B is $C_{1-3}$alkoxy or $C_{1-3}$alkylS$(O)_n$;
n is 2;
$R^4$ is hydrogen;
W is phenyl which is optionally substituted by one or more halo;
X is O;
Y is hydrogen;
Z is O;
$R^5$ and $R^6$ are independently selected from hydrogen and $C_{1-3}$alkyl; and
$R^x$ is hydrogen;

or a pharmaceutically acceptable salt thereof.

One embodiment of the invention relates to compounds of formula I wherein $R^1$, $R^{1a}$, $R^2$, $R^3$, $R^4$, $R^5$, $R^6$, $R^8$, $R^9$, $R^{10}$ $R^{11}$, $R^{12}$, $R^{13}$, $R^x$, Y, W and n are as defined above, and A is $R^7NH$ and $R^7$ is hydrogen, $C_{1-6}$alkyl, $C_{1-6}$alkylOC(O)$C_{1-3}$alkyl, $C_{5-10}$heteroaryl$C_{1-3}$alkyl or $C_{3-6}$cycloalkyl.

In yet a further embodiment relating to compounds of formula I $R^2$ is hydrogen; $R^4$ is hydrogen; X is O; Y is hydrogen; and Z is O.

In one embodiment relating to compounds of formula I $R^1$ is $C_{1-4}$alkyl, $R^{1a}$ is hydrogen, $R^2$ is hydrogen; $R^4$ is hydrogen; X is O; Y is hydrogen; and Z is O.

In yet another embodiment relating to compounds of formula I $R^2$ is hydrogen; $R^4$ is hydrogen; W is phenyl which is optionally substituted by one or more fluoro; X is O; Y is hydrogen; and Z is O.

In one embodiment relating to compounds of formula I A is $C_{1-6}$alkyl, $C_{1-6}$hydroxyalkyl, $C_{1-6}$alkoxy, $C_{3-7}$cycloalkyl, $C_{3-7}$heterocycloalkyl, $C_{1-6}$haloalkyl, $C_{1-6}$alkylO$C_{1-6}$alkyl, $C_{1-6}$alkylO$C_{1-6}$-alkylO$C_{1-6}$alkyl, $C_{1-6}$alkylC(O)$OC_{1-6}$alkyl, $C_{1-6}$alkylOC(O), HOC(O), $NR^5R^6C_{1-6}$alkyl, $NR^5R^6C(O)$, $NR^5R^6OC(O)$, $R^7NH$, $C_{5-10}$aryl$C_{1-3}$alkyl, $C_{5-10}$aryl or $C_{5-10}$heteroaryl, whereby the cycloalkyl, heterocycloalkyl, aryl or heteroaryl may be optionally substituted by one or more substituents independently selected from halo, cyano, hydroxy, $C_{1-4}$alkyl, $C_{1-4}$alkoxy, $C_{1-4}$haloalkyl, $C_{1-4}$alkylOC(O), $C_{1-4}$alkyl$OC_{1-4}$alkyl and $C_{1-4}$alkylS(O)$_2$ and $R^x$ is hydrogen, or
A forms together with Rx a 5 membered azacyclic ring optionally having one or more further heteroatoms independently selected from O and N; and
$R^5$, $R^6$, $R^8$, $R^9$, $R^{10}$ $R^{11}$, $R^{12}$ and $R^{13}$ are independently selected from hydrogen, $C_{1-6}$alkylC(O), $NHR^7C(O)$ and $C_{1-6}$alkyl; and
$R^7$ is hydrogen, $C_{1-6}$alkyl, $C_{1-6}$alkylC(O)$OC_{1-3}$alkyl, $C_{1-6}$alkylC(O)O, $C_{1-6}$alkylOC(O)$C_{1-3}$alkyl, $C_{1-6}$alkylOC(O), $C_{1-6}$alkylC(O), $C_{5-10}$heteroaryl$C_{1-3}$alkyl, $C_{5-10}$heteroaryl, $C_{5-10}$aryl$C_{1-3}$alkyl, $C_{5-10}$aryl, $C_{3-6}$cycloalkyl$C_{1-3}$alkyl or $C_{3-6}$cycloalkyl.

In one embodiment relating to compounds of formula I A is $C_{3-7}$cycloalkyl. In another embodiment A is cyclopropanyl, cyclobutanyl or cyclopentanyl. In a further embodiment A is $C_{3-7}$cycloalkyl substituted with hydroxy or methyl.

In one embodiment relating to compounds of formula I A is $C_{3-7}$heterocycloalkyl. In another embodiment A is pyrrolidinyl optionally substituted with tert-butyl-carboxylate.

In a further embodiment relating to compounds of formula I A is methyl, ethyl, n-propyl, i-propyl, n-butyl, i-butyl, s-butyl, t-butyl, n-pentyl, i-pentyl, neo-pentyl, n-hexyl or i-hexyl. In one embodiment A is methyl, ethyl, n-propyl, i-propyl or i-butyl, In one embodiment relating to compounds of formula I A is $C_{1-2}$haloalkyl. In another embodiment A is fluoromethyl, difluoromethyl, trifluoromethyl, fluoroethyl, difluoroethyl, trifluoroethyl, fluoropropyl, difluoropropyl, trifluoropropyl, chloromethyl, dichloromethyl, trichloromethyl or fluorochloromethyl.

In a further embodiment relating to compounds of formula I A is $C_{1-3}$hydroxyalkyl. In one embodiment A is hydroxymethyl, hydroxyethyl, hydroxy-i-propyl, hydroxy-n-propy, hydroxy-n-butyl, hydroxy-1-butyl, hydroxy-s-butyl or hydroxy-t-butyl.

In yet a further embodiment relating to compounds of formula I A is $C_{1-2}$alkoxy. In one embodiment A is methoxy.

In an alternative embodiment relating to compounds of formula I A is $C_{1-3}$alkylO$C_{1-3}$alkyl. In one embodiment A is methoxymethyl, methylethoxy or ethylmethoxy.

In another embodiment relating to compounds of formula I A is $C_{1-2}$alkylC(O)O$C_{1-2}$alkyl. In a further embodiment A is methylethoxymethyl.

In yet another embodiment relating to compounds of formula I A is t-butyl-OC(O), n-butyl-OC(O), i-propyl-OC(O), n-propyl-OC(O), ethyl-OC(O), methyl-OC(O) or HOC(O).

In one embodiment relating to compounds of formula I A is $C_{5-10}$aryl$C_{1-3}$alkyl or $C_{5-10}$aryl. In another embodiment A is phenyl. In yet a further embodiment A is phenyl substituted with trifluoromethyl. In a further embodiment A is phenyl-$C_{1-3}$alkyl. In another embodiment A is benzyl.

In another embodiment relating to compounds of formula I A is $C_{5-10}$heteroaryl$C_{1-3}$alkyl or $C_{5-10}$heteroaryl. In one embodiment A is oxazolyl, furanyl, thiophene, pyrimidinyl, thiazolyl, pyrazolyl, pyrrolyl, imidazolyl, triazolyl, oxadiazolyl, benzoimidazolyl, benzothiophene, benzothiazolyl, imidazolidine-2,4-dione, pyrazolo[1,5-a]pyridinyl or pyridinyl optionally substituted with one or more substituents independently selected from hydroxy, $C_{1-3}$alkyl, $C_{1-3}$alkoxy, $C_{1-4}$alkylOC(O), $C_{1-3}$haloalkyl, $C_{1-3}$alkylO$C_{1-3}$alkyl, cyano, halo or $C_{1-3}$alkylS(O)$_2$.

In one embodiment A is thiazolyl substituted with methyl.

In yet another embodiment relating to compounds of formula I A forms together with $R^x$ a 5 membered azacyclic ring optionally having one or more further heteroatoms independently selected from O and N. In one embodiment A forms together with $R^x$ an imidazolidine-2,4-dione group.

In a further embodiment relating to compounds of formula I A is NR$^5$R$^6$C$_{1-4}$alkyl or NR$^5$R$^6$.

In one embodiment relating to compounds of formula I A is propanamide or butanamide. In a further embodiment relating to compounds of formula I A is R$^6$NH— wherein R$^6$ is NH$_2$C(O)—.

In an alternative embodiment relating to compounds of formula I A is NR$^5$R$^6$C(O) and R$^5$ and R$^6$ are independently selected from hydrogen, methyl, ethyl, n-propyl, i-propyl, n-butyl, i-butyl, s-butyl, n-pentyl, i-pentyl and neo-pentyl. In one embodiment both R$^5$ and R$^6$ are hydrogen. In another embodiment both R$^5$ and R$^6$ are methyl. In a further embodiment R$^5$ is hydrogen and R$^6$ is methyl, ethyl, n-propyl, i-propyl, n-butyl, i-butyl, s-butyl, t-butyl, n-pentyl, i-pentyl or neo-pentyl.

In another embodiment relating to compounds of formula I A is R$^7$NH. In one embodiment R$^7$ is furan-methyl-. In another embodiment R$^7$ is $C_{1-2}$alkylOC(O)$C_{1-2}$alkyl. In a further embodiment R$^7$ is cyclopentanyl. In one embodiment R$^7$ is dimethylpropyl. In another embodiment R$^7$ is formamide.

In one embodiment relating to compounds of formula I R$^3$ is $C_{5-10}$aryl, $C_{5-10}$aryl$C_{1-4}$alkyl, $C_{5-10}$arylO, $C_{5-10}$arylO-$C_{1-4}$alkyl or $C_{5-10}$heteroaryl, which may be optionally substituted by one or more substituents independently selected from B;

B is hydroxy, $C_{1-4}$alkyl, $C_{1-4}$alkoxy, $C_{1-4}$alkyl$C_{1-4}$thioalkyl, $C_{1-4}$thioalkyl, $C_{3-6}$cycloalkylS, $C_{1-3}$alkylS(O)$_n$$C_{1-4}$alkyl, $C_{1-3}$alkylS(O)$_n$, $C_{1-4}$haloalkyl or halo; and n is 1 or 2.

In one embodiment relating to compounds of formula I R$^3$ is phenyl. In another embodiment R$^3$ is phenyl substituted with one or more B. In a further embodiment R$^3$ is phenyl substituted with one or more substituents independently selected from hydroxy, methoxy, ethoxy, methyl, ethyl, n-propyl, i-propyl, n-butyl, i-butyl, s-butyl, t-butyl, trifluoromethyl, fluoro, chloro, methylsulfanyl, ethylsulfanyl, cyclopropylsulfanyl, methylsulfanylethyl, ethylsulfanylmethyl, ethylsulfinylmethyl, methylsulfinylethyl or methylsulfonyl. In another embodiment R$^3$ is phenyl substituted with methoxy. In yet another embodiment R$^3$ is phenyl substituted with fluoro, In one embodiment R$^3$ is phenyl disubstituted with fluoro. In a further embodiment R$^3$ is phenyl substituted with chloro. In another embodiment R$^3$ is phenyl disubstituted with fluoro and chloro. In yet another embodiment R$^3$ is phenyl substituted with methyl. In one embodiment R$^3$ is phenyl di- or tri-substituted with methyl. In yet a further embodiment R$^3$ is phenyl disubstituted with methyl and fluoro. In another embodiment R$^3$ is phenyl disubstituted with methyl and methoxy. In yet another embodiment R$^3$ is phenyl disubstituted with fluoro and methoxy.

In one embodiment relating to compounds of formula I R$^3$ is $C_6$aryl$C_{1-2}$alkyl. In yet another embodiment R$^3$ is benzyl.

In another embodiment relating to compounds of formula I R$^3$ is phenoxymethyl.

In yet another embodiment relating to compounds of formula I R$^3$ is naphthalenyl.

In another embodiment relating to compounds of formula I R$^3$ is $C_{5-10}$heteroaryl. In one embodiment R$^3$ is 3-pyridinyl or 4-pyridinyl substituted with methoxy. In a further embodiment R$^3$ is dioxabicyclodecatrienyl. In another embodiment R$^3$ is quinolinyl. In one embodiment R$^3$ is dihydrobenzofuranyl.

In one embodiment relating to compounds of formula I W is phenyl substituted with halo. In another embodiment W is phenyl substituted with fluoro. In yet another embodiment W is phenyl para substituted with fluoro. In a further embodiment W is phenyl substituted with chloro. In one embodiment W is phenyl substituted with methylOC(O)—. In a further embodiment W is phenyl substituted with dimethylaminomethyl. In one embodiment W is phenyl substituted with hydroxymethyl.

In another embodiment W is phenyl substituted with morpholinylmethyl.

In yet another embodiment relating to compounds of formula I W is benzoate.

In a further embodiment relating to compounds of formula I W is pyridinyl, pyridazinyl or pyrimidinyl. In another embodiment W is pyridazinyl substituted with halo.

In one embodiment relating to compounds of formula I W is cyclopentanyl. In another embodiment relating to compounds of formula I W is n-propyl.

In one embodiment relating to compounds of formula I X is O. In another embodiment X is S.

In one embodiment relating to compounds of formula I Z is O. In another embodiment Z is S.

In one embodiment relating to compounds of formula I R$^{1a}$ is hydrogen.

In another embodiment relating to compounds of formula I R$^1$ is methyl, ethyl or n-propyl, i-propyl, n-butyl or i-butyl.

In a further embodiment $R'$ is methyl. In another embodiment $R^1$ is ethyl, n-propyl or methylpropyl.

In a further embodiment $R^1$ is methoxymethyl. In yet another embodiment relating to compounds of formula I $R^1$ is hydroxymethyl.

In another embodiment relating to compounds of formula I $R^1$ is trifluoromethyl.

In one embodiment relating to compounds of formula I $R^{1a}$ and $R^1$ are oxo.

In one embodiment relating to compounds of formula I $R^2$ is hydrogen.

In one embodiment relating to compounds of formula I $R^4$ is hydrogen.

In one embodiment relating to compounds of formula I Y is hydrogen. In another embodiment Y is halo. In a further embodiment Y is chloro. In one embodiment Y is methyl.

A further embodiment of the invention related to compounds of formula Ib (Ib)

wherein:

A is $C_{1-6}$alkyl, $C_{1-6}$hydroxyalkyl, $C_{0-6}$cyanoalkyl, $C_{0-6}$nitroalkyl, $C_{1-6}S(O)_n$alkyl, $C_{1-6}$alkoxy, $C_{3-7}$cycloalkyl$C_{0-6}$alkyl, $C_{1-6}$haloalkyl, $C_{0-6}$alkylthio$C_{0-6}$alkyl, $C_{1-6}$alkylOC$_{1-6}$alkyl, $C_{1-6}$alkylOC$_{1-6}$alkylOC$_{1-6}$alkyl, $C_{0-6}$alkylC(O)C$_{0-6}$alkyl, $C_{0-6}$alkylC(O)OC$_{0-6}$alkyl, $C_{0-6}$alkylOC(O)C$_{0-6}$alkyl, NR$^5$R$^6$C$_{0-6}$alkyl, NR$^5$R$^6$C(O)C$_{0-6}$alkyl, NR$^5$R$^6$OC(O)C$_{0-6}$alkyl, $R^7$NH, $C_{5-10}$aryl$C_{0-3}$alkyl or $C_{5-10}$heteroaryl$C_{0-3}$alkyl, whereby the cycloalkyl, aryl or heteroaryl may be optionally substituted by $C_{1-4}$alkyl, $C_{1-4}$alkoxy, $C_{1-4}$haloalkyl, $C_{1-4}$haloalkoxy;

$R^1$ and $R^{1a}$ are independently selected from hydrogen, $C_{1-4}$ alkyl, $C_{1-4}$hydroxyalkyl, $C_{1-4}$alkylOC$_{1-4}$alkyl, $C_{1-4}$alkylSC$_{1-4}$alkyl and $C_{1-4}$ haloalkyl;

$R^2$ is hydrogen or $C_{1-4}$ alkyl;

$R^3$ is $C_{5-10}$aryl$C_{0-3}$alkyl, $C_{5-10}$arylOC$_{0-3}$alkyl, $C_{5-10}$heteroaryl$C_{0-3}$alkyl, $C_{1-4}$alkyl, $C_1$ alkenyl or $C_{1-6}$alkynyl which may be optionally substituted by one or more B;

B is $C_{0-3}$hydroxyalkyl, $C_{1-4}$alkyl, $C_{1-4}$alkoxy, $C_{0-4}$alkylthio$C_{0-4}$alkyl, $C_{3-6}$cycloalkyl$C_{0-4}$thioalkyl, $C_{0-3}$alkylS(O)$_n$ $C_{0-4}$alkyl, $C_{1-6}$haloalkyl, $C_{1-4}$haloalkoxy, halo, nitro, cyano, $C_{1-4}$alkylOC$_{1-4}$alkyl, $C_{1-6}$alkylOC$_{1-4}$alkylOC$_{1-4}$alkyl, $C_{0-6}$alkylC(O)C$_{0-4}$alkyl, $C_{0-4}$alkylC(O)OC$_{0-4}$alkyl, $C_{0-4}$alkylOC(O)C$_{0-4}$alkyl, NR$^5$R$^6$C$_{0-4}$alkyl, NR$^5$R$^6$C(O)C$_{0-4}$alkyl, NR$^5$R$^6$OC(O)C$_{0-4}$alkyl, NR$^5$R$^6$C(O)OC$_{0-4}$alkyl, $R^6$C(O)R$^5$NC$_{0-4}$alkyl, $C_{0-4}$alkylOC(O)C$_{0-4}$alkylNH, $C_{0-4}$alkylC(O)OC$_{0-4}$alkylNH, $C_{0-4}$alkylC(O)C$_{0-4}$alkylNH or NR$^5$R$^6$S(O)$_n$C$_{0-4}$alkyl;

n is 0, 1 or 2;

$R^4$ is hydrogen, hydroxy, halogen, $C_{1-4}$ alkyl or $C_{1-4}$ haloalkyl;

W is hydrogen or phenyl, $C_{3-47}$cycloalkyl, thienyl, isoxazolyl, pyrazolyl, pyridinyl or pyrimidinyl all of which are optionally substituted by one or more halo, $C_{0-3}$hydroxyalkyl, $C_{1-4}$alkyl, $C_{1-4}$alkoxy, $C_{0-4}$alkylthio$C_{0-4}$alkyl, $C_{3-6}$cycloalkyl$C_{0-4}$thioalkyl, $C_{0-4}$alkylS(O)$_n$C$_{0-4}$alkyl, $C_{1-6}$haloalkyl, $C_{1-4}$haloalkoxy, halo, nitro, cyano, $C_{1-4}$alkylOC$_{1-6}$alkyl, $C_{1-6}$alkylOC$_{1-6}$alkylOC$_{1-6}$alkyl, $C_{0-6}$alkylC(O)C$_{0-6}$alkyl, $C_{0-4}$alkylC(O)OC$_{0-4}$alkyl, $C_{0-4}$alkylOC(O)C$_{0-4}$alkyl, NR$^5$R$^6$C$_{0-4}$alkyl, NR$^5$R$^6$C(O) $C_{0-4}$alkyl, NR$^5$R$^6$C(O)OC$_{0-4}$alkyl, NR$^5$R$^6$OC(O)C$_{0-4}$ alkyl, $R^6$C(O)R$^5$NC$_{0-4}$alkyl, $C_{0-4}$alkylOC(O)C$_{0-4}$alkylNH, $C_{0-4}$alkylC(O)OC$_{0-4}$alkylNH, $C_{0-4}$alkylC(O)C$_{0-4}$alkylNH or NR$^5$R$^6$S(O)$_n$C$_{0-4}$alkyl;

X is CH$_2$, O, S, S(O)$_n$, NH or NC$_{1-4}$ alkyl;

Y is hydrogen, halo, $C_{1-4}$alkyl, $C_{1-4}$alkoxy, $C_{1-4}$thioalkyl, $C_4$haloalkyl, $C_{1-4}$alkoxyhalo, nitro, cyano, hydroxy, $R^5$C(O), $R^5$OC(O), $R^5$C(O)O, S(O)$_n$C$_{1-4}$alkyl, $R^5$R$^6$NS(O)$_n$, benzyloxy, imidazolyl, $C_{1-4}$alkylNHC(O), NR$^5$R$^6$C(O), $C_4$alkylC(O)NH or NR$^5$R$^6$;

Z is O or S;

$R^5$ and $R^6$ are independently selected from hydrogen and $C_{1-6}$alkyl; and $R^7$ is $C_{0-6}$alkylC(O)OC$_{0-3}$alkyl, $C_{0-6}$alkylOC(O)C$_{0-3}$alkyl, $C_{5-10}$heteroaryl$C_{0-3}$alkyl, $C_{5-10}$aryl$C_{0-3}$alkylNH or $C_{3-6}$cycloalkyl$C_{0-3}$alkyl;

or a pharmaceutically acceptable salt thereof.

In another aspect the present invention provides the individual compound:

N-[(1R,2S)-1-[1-(4-fluorophenyl)indazol-5-yl]oxy-1-phenyl-propan-2-yl]cyclopropanecarboxamide, 2,2,2-trifluoro-N-[(1R,2S)-1-[1-(4-fluorophenyl)indazol-5-yl]oxy-1-phenyl-propan-2-yl]acetamide, N-[(1R,2S)-1-[1-(4-fluorophenyl)indazol-5-yl]oxy-1-phenyl-propan-2-yl]propanamide, methyl N-[(1R,2S)-1-[1-(4-fluorophenyl)indazol-5-yl]oxy-1-phenyl-propan-2-yl]carbamate, N-[(1R,2S)-1-[1-(4-fluorophenyl)indazol-5-yl]oxy-1-phenyl-propan-2-yl]-2-hydroxy-2-methyl-propanamide, 2,2,2-trifluoro-N-[(1R,2S)-1-[1-(4-fluorophenyl)indazol-5-yl]oxy-1-(3-methoxyphenyl)propan-2-yl]acetamide, N-[(1R,2S)-1-(4-ethylphenyl)-1-[1-(4-fluorophenyl)indazol-5-yl]oxy-propan-2-yl]-2-hydroxy-acetamide, N-[(1R,2S)-1-[1-(4-fluorophenyl)indazol-5-yl]oxy-1-(3-methoxyphenyl)propan-2-yl]-2,2-dimethyl-propanamide, N-[(1R,2S)-1-[1-(4-fluorophenyl)indazol-5-yl]oxy-1-(4-methylsulfanylphenyl)propan-2-yl]-2-methoxy-acetamide,

[(1R,2S)-1-[1-(4-fluorophenyl)indazol-5-yl]oxy-1-(4-methylsulfanylphenyl)propan-2-yl]carbamoylmethyl acetate, N-[(1R,2S)-1-[1-(4-fluorophenyl)indazol-5-yl]oxy-1-(4-methylsulfanylphenyl)propan-2-yl]-2-hydroxy-acetamide, N-[(1R,2S)-1-[1-(4-fluorophenyl)indazol-5-yl]oxy-1-(4-methylsulfonylphenyl)propan-2-yl]-2-hydroxy-acetamide, 2,2,2-trifluoro-N-[(1R,2S)-1-[1-(4-fluorophenyl)indazol-5-yl]oxy-1-(4-methylsulfanylphenyl)propan-2-yl]acetamide, N-[(1R,2S)-1-(4-ethylsulfanylphenyl)-1-[1-(4-fluorophenyl)indazol-5-yl]oxy-propan-2-yl]-2,2,2-trifluoro-acetamide, N-[(1R,2S)-1-(4-cyclopropylsulfanylphenyl)-1-[1-(4-fluorophenyl)indazol-5-yl]oxy-propan-2-yl]-2,2,2-trifluoro-acetamide, N-[(1R,2S)-1-[1-(4-fluorophenyl)indazol-5-yl]oxy-1-phenyl-propan-2-yl]-2-hydroxy-acetamide, N-[(1R,2S)-1-[1-(4-fluorophenyl)indazol-5-yl]oxy-1-(6-methoxypyridin-3-yl)propan-2-yl]cyclopropanecarboxamide, N-[(1R,2S)-1-[1-(4-fluorophenyl)indazol-5-yl]oxy-1-(6-methoxypyridin-3-yl)propan-2-yl]cyclopropanecarboxamide, N-[(1R,2S)-1-(2,5-dioxabicyclo[4.4.0]deca-7,9,11 trien-8-yl)-1-[1-(4-fluorophenyl)indazol-5-yl]oxy-propan-2-yl]-2,2,2-trifluoro-acetamide,
2,2,2-trifluoro-N-[(1R,2S)-1-[1-(4-fluorophenyl)indazol-5-yl]oxy-1-naphthalen-2-yl-propan-2-yl]acetamide,
N-[(1R,2S)-1-[1-(4-fluorophenyl)indazol-5-yl]oxy-1-naphthalen-2-yl-propan-2-yl]-2-hydroxy-acetamide,
N-[(1R,2S)-1-(3-ethylphenyl)-1-[1-(4-fluorophenyl)indazol-5-yl]oxy-propan-2-yl]-2,2,2-trifluoro-acetamide,
N-[(1R,2S)-1-(3-ethylphenyl)-1-[1-(4-fluorophenyl)indazol-5-yl]oxy-propan-2-yl]-2-hydroxy-acetamide,
2,2,2-trifluoro-N-[(1R,2S)-1-[1-(4-fluorophenyl)indazol-5-yl]oxy-1-(3-methylphenyl)propan-2-yl]acetamide,
N-[(1R,2S)-1-[4-(ethylsulfanylmethyl)phenyl]-1-[1-(4-fluorophenyl)indazol-5-yl]oxy-propan-2-yl]-2,2,2-trifluoro-acetamide,
N-[(1R,2S)-1-[4-(ethylsulfinylmethyl)phenyl]-1-[1-(4-fluorophenyl)indazol-5-yl]oxy-propan-2-yl]-2,2,2-trifluoro-acetamide,
N-[(1R,2S)-1-[4-(ethylsulfanylmethyl)phenyl]-1-[1-(4-fluorophenyl)indazol-5-yl]oxy-propan-2-yl]-2-hydroxy-acetamide,
4-amino-N-[(1R,2S)-1-[1-(4-fluorophenyl)indazol-5-yl]oxy-1-phenyl-propan-2-yl]butanamide,
N-[(1R,2S)-1-[1-(4-fluorophenyl)indazol-5-yl]oxy-1-phenyl-propan-2-yl]acetamide,
N-[(1R,2S)-1-[1-(4-fluorophenyl)indazol-5-yl]oxy-1-phenyl-propan-2-yl]-3-methoxy-propanamide,
N-[(1R,2S)-1-[1-(4-fluorophenyl)indazol-5-yl]oxy-1-phenyl-propan-2-yl]-2-methoxy-acetamide,
N-[(1R,2S)-1-[1-(4-fluorophenyl)indazol-5-yl]oxy-1-phenyl-propan-2-yl]benzamide,
N-[(1R,2S)-1-[1-(4-fluorophenyl)indazol-5-yl]oxy-1-phenyl-propan-2-yl]-2-phenyl-acetamide,
[(1R,2S)-1-[1-(4-fluorophenyl)indazol-5-yl]oxy-1-phenyl-propan-2-yl]carbamoylmethyl acetate,
methyl[(1R,2S)-1-[1-(4-fluorophenyl)indazol-5-yl]oxy-1-phenyl-propan-2-yl]carbamoylformate,
[(1R,2S)-1-[1-(4-fluorophenyl)indazol-5-yl]oxy-1-phenyl-propan-2-yl]carbamoylformic acid,
N-[(1R,2S)-1-[1-(4-fluorophenyl)indazol-5-yl]oxy-1-phenyl-propan-2-yl]-2-methyl-propanamide,
2-chloro-N-[(1R,2S)-1-[1-(4-fluorophenyl)indazol-5-yl]oxy-1-phenyl-propan-2-yl]acetamide,
2,2-dichloro-N-[(1R,2S)-1-[1-(4-fluorophenyl)indazol-5-yl]oxy-1-phenyl-propan-2-yl]acetamide,
2,2,2-trichloro-N-[(1R,2S)-1-[1-(4-fluorophenyl)indazol-5-yl]oxy-1-phenyl-propan-2-yl]acetamide,
N-[(1R,2S)-1-[1-(4-fluorophenyl)indazol-5-yl]oxy-1-phenyl-propan-2-yl]butanamide,
N-[(1R,2S)-1-[1-(4-fluorophenyl)indazol-5-yl]oxy-1-phenyl-propan-2-yl]-2,2-dimethyl-propanamide,
N-[(1R,2S)-1-[1-(4-fluorophenyl)indazol-5-yl]oxy-1-phenyl-propan-2-yl]cyclobutanecarboxamide,
2,2-difluoro-N-[(1R,2S)-1-[1-(4-fluorophenyl)indazol-5-yl]oxy-1-phenyl-propan-2-yl]acetamide,
2-fluoro-N-[(1R,2S)-1-[1-(4-fluorophenyl)indazol-5-yl]oxy-1-phenyl-propan-2-yl]acetamide,
N-[(1R,2S)-1-(4-ethylphenyl)-1-[1-(4-fluorophenyl)indazol-5-yl]oxy-propan-2-yl]-2,2,2-trifluoro-acetamide,
2-chloro-2-fluoro-N-[(1R,2S)-1-[1-(4-fluorophenyl)indazol-5-yl]oxy-1-phenyl-propan-2-yl]acetamide,
(2S)—N-[(1R,2S)-1-[1-(4-fluorophenyl)indazol-5-yl]oxy-1-phenyl-propan-2-yl]-2-hydroxy-propanamide,
2,2,2-trifluoro-N-[(1R,2S)-1-[1-(4-fluorophenyl)indazol-5-yl]oxy-1-(3-hydroxyphenyl)propan-2-yl]acetamide,
N-[(1R,2S)-1-(4-ethylphenyl)-1-[1-(4-fluorophenyl)indazol-5-yl]oxy-propan-2-yl]-2-fluoro-acetamide,
N-[(1R,2S)-1-[(4-ethylphenyl)-1-[1-(4-fluorophenyl)indazol-5-yl]oxy-propan-2-yl]-2-methyl-propanamide,
N-[(1R,2S)-1-(4-ethylphenyl)-1-[1-(4-fluorophenyl)indazol-5-yl]oxy-propan-2-yl]-2,2-dimethyl-propanamide,
2-fluoro-N-[(1R,2S)-1-[1-(4-fluorophenyl)indazol-5-yl]oxy-1-(3-methoxyphenyl)propan-2-yl]acetamide,
N-[(1R,2S)-1-[1-(4-fluorophenyl)indazol-5-yl]oxy-1-(3-methoxyphenyl)propan-2-yl]-2-methoxy-acetamide,
N-[(1R,2S)-1-[1-(4-fluorophenyl)indazol-5-yl]oxy-1-(3-methoxyphenyl)propan-2-yl]-2-methyl-propanamide,
N-[(1R,2S)-1-[1-(4-fluorophenyl)indazol-5-yl]oxy-1-(3-methoxyphenyl)propan-2-yl]cyclopentanecarboxamide,
(2R)—N-[(1R,2S)-1-[1-(4-fluorophenyl)indazol-5-yl]oxy-1-(3-methoxyphenyl)propan-2-yl]-2-hydroxy-propanamide,
(2S)—N-[(1R,2S)-1-[1-(4-fluorophenyl)indazol-5-yl]oxy-1-(3-methoxyphenyl)propan-2-yl]-2-hydroxy-propanamide,
N-[(1R,2S)-1-[1-(4-fluorophenyl)indazol-5-yl]oxy-1-[4-(trifluoromethyl)phenyl]propan-2-yl]-2-methoxy-acetamide,
N-[(1R,2S)-1-[1-(4-fluorophenyl)indazol-5-yl]oxy-1-[4-(trifluoromethyl)phenyl]propan-2-yl]-2-hydroxy-acetamide,
N-[(1R,2S)-1-[1-(4-fluorophenyl)indazol-5-yl]oxy-1-[4-(trifluoromethyl)phenyl]propan-2-yl]propanamide,
2,2,2-trifluoro-N-[(1R,2S)-1-[1-(4-fluorophenyl)-6-methyl-indazol-5-yl]oxy-1-phenyl-propan-2-yl]acetamide,
N-[(1R,2S)-1-[1-(4-fluorophenyl)-6-methyl-indazol-5-yl]oxy-1-phenyl-propan-2-yl]-2,2-dimethyl-propanamide,
N-[(1R,2S)-1-[1-(4-fluorophenyl)-6-methyl-indazol-5-yl]oxy-1-phenyl-propan-2-yl]-2-hydroxy-acetamide,
2,2,2-trifluoro-N-[(1R,2S)-1-[1-(4-fluorophenyl)-6-methyl-indazol-5-yl]oxy-1-(3-methoxyphenyl)propan-2-yl]acetamide,
N-[(1R,2S)-1-[1-(4-fluorophenyl)-6-methyl-indazol-5-yl]oxy-1-(3-methoxyphenyl)propan-2-yl]-2,2-dimethyl-propanamide,
N-[(1R,2S)-1-[1-(4-fluorophenyl)-6-methyl-indazol-5-yl]oxy-1-(3-methoxyphenyl)propan-2-yl]-2-hydroxy-acetamide,
2,2,2-trifluoro-N-[(2S,3S)-3-[1-(4-fluorophenyl)indazol-5-yl]oxy-4-phenoxy-butan-2-yl]acetamide,
2,2,2-trifluoro-N-[(2R,3R)-3-[1-(4-fluorophenyl)indazol-5-yl]oxy-4-phenoxy-butan-2-yl]acetamide,
2,2,2-trifluoro-N-[(2S,3R)-3-[1-(4-fluorophenyl)indazol-5-yl]oxy-4-phenoxy-butan-2-yl]acetamide,
N-[(1R,2S)-1-[1-(4-fluorophenyl)indazol-5-yl]oxy-1-(3-methoxyphenyl)propan-2-yl]-2-(2-methoxyethoxy)acetamide,
2,2,2-trifluoro-N-[(2S,3R)-3-[1-(4-fluorophenyl)indazol-5-yl]oxy-4-phenyl-butan-2-yl]acetamide,
N-[(2S,3R)-3-[1-(4-fluorophenyl)indazol-5-yl]oxy-4-phenyl-butan-2-yl]-2,2-dimethyl-propanamide,
N-[(2S,3R)-3-[1-(4-fluorophenyl)indazol-5-yl]oxy-4-phenyl-butan-2-yl]-2-hydroxy-acetamide,
tert-butyl[(1R,2S)-1-[1-(4-fluorophenyl)indazol-5-yl]oxy-1-(3-methoxyphenyl)propan-2-yl]carbamoylformate,
N-[(1R,2S)-1-[1-(4-fluorophenyl)indazol-5-yl]oxy-1-(3-methoxyphenyl)propan-2-yl]oxamide,
propan-2-yl[(1R,2S)-1-[1-(4-fluorophenyl)indazol-5-yl]oxy-1-(3-methoxyphenyl)propan-2-yl]carbamoylformate,
ethyl[(1R,2S)-1-[1-(4-fluorophenyl)indazol-5-yl]oxy-1-(3-methoxyphenyl)propan-2-yl]carbamoylformate, N-[(1R,2S)-1-[1-(4-fluorophenyl)indazol-5-yl]oxy-1-(3-methoxyphenyl)propan-2-yl]-N-methyl-oxamide, N-[(1R,2S)-1-[1-(4-fluorophenyl)indazol-5-yl]oxy-1-(3-methoxyphenyl)propan-2-yl]-N',N'-dimethyl-oxamide, N'-[(1R,2S)-1-[1-(4-fluorophenyl)indazol-5-yl]oxy-1-(3-methoxyphenyl)propan-2-yl]-N-propan-2-yl-oxamide, N-[(1R,2S)-1-[1-(4-fluorophenyl)indazol-5-yl]oxy-1-(3-methoxyphenyl)propan-2-yl]-N'-tert-butyl-oxamide, N-[(1R,2S)-1-[1-(4-fluorophenyl)indazol-5-yl]oxy-1-(3-methoxyphenyl)propan-2-yl]-4-(trifluoromethyl)benzamide, N-[(1R,2S)-1-[1-(4-fluorophenyl)indazol-5-yl]oxy-1-(3-methoxyphenyl)propan-2-yl]1,3-oxazole-2-carboxamide, N-[(1R,2S)-1-[1-(4-fluorophenyl)indazol-5-yl]oxy-1-(3-methoxyphenyl)propan-2-yl]1,3-oxazole-4-carboxamide, N-[(1R,2S)-1-[1-(4-fluorophenyl)indazol-5-yl]oxy-1-(3-methoxyphenyl)propan-2-yl]furan-2-carboxamide, N-[(1R,2S)-1-[1-(4-fluorophenyl)indazol-5-yl]oxy-1-(3-methoxyphenyl)propan-2-yl]thiophene-2-carboxamide, N-[(1R,2S)-1-[1-(4-fluorophenyl)indazol-5-yl]oxy-1-(3-methoxyphenyl)propan-2-yl]pyrimidine-4-carboxamide, N-[(1R,2S)-1-[1-(4-fluorophenyl)indazol-5-yl]oxy-1-(3-methoxyphenyl)propan-2-yl]pyridine-2-carboxamide, N-[(1R,2S)-1-[1-(4-fluorophenyl)indazol-5-yl]oxy-1-(4-methoxyphenyl)propan-2-yl]-2,2-dimethyl-propanamide, N-[(1R,2S)-1-[1-(4-fluorophenyl)indazol-5-yl]oxy-1-phenyl-pentan-2-yl]-2-hydroxy-acetamide, N-[(1R,2S)-1-[1-(4-fluorophenyl)indazol-5-yl]oxy-1-phenyl-pentan-2-yl]-2,2-dimethyl-propanamide, N-[(1R,2S)-1-[1-(4-fluorophenyl)indazol-5-yl]oxy-1-(3-methoxyphenyl)pentan-2-yl]-2-hydroxy-acetamide, N-[(1R,2S)-1-[1-(4-fluorophenyl)indazol-5-yl]oxy-1-(3-methoxyphenyl)pentan-2-yl]-2,2-dimethyl-propanamide, N-[(1R,2S)-1-[1-(4-fluorophenyl)indazol-5-yl]oxy-1-phenyl-butan-2-yl]-2-hydroxy-acetamide, N-[(1R,2S)-1-[1-(4-fluorophenyl)indazol-5-yl]oxy-1-phenyl-butan-2-yl]-2,2-dimethyl-propanamide, N-[(1R,2S)-1-[1-(4-fluorophenyl)indazol-5-yl]oxy-1-(3-methoxyphenyl)butan-2-yl]-2-hydroxy-acetamide, N-[(1R,2S)-1-[1-(4-fluorophenyl)indazol-5-yl]oxy-1-(3-methoxyphenyl)butan-2-yl]-2,2-dimethyl-propanamide, N-[(1R,2S)-1-[6-chloro-1-(4-fluorophenyl)indazol-5-yl]oxy-1-(4-fluorophenyl)propan-2-yl]-2,2,2-trifluoro-acetamide, N-[(1R,2R)-1-[6-chloro-1-(4-fluorophenyl)indazol-5-yl]oxy-1-(4-fluorophenyl)propan-2-yl]acetamide, N-[(1R,2S)-1-[6-chloro-1-(4-fluorophenyl)indazol-5-yl]oxy-1-(4-fluorophenyl)propan-2-yl]acetamide, 2,2,2-trifluoro-N-[(1R,2S)-1-[1-(4-fluorophenyl)indazol-5-yl]sulfanyl-1-phenyl-propan-2-yl]acetamide, 1-(Cyclopentyl)-3-{(1S,2R)-2-[1-(4-fluorophenyl)-1H-indazole-5-yl)oxy]-1-methyl-2-phenyl-ethyl}urea, 1-{(1S,2R)-2-{[1-(4-Fluorophenyl)-1H-indazole-5-yl]oxy}-1-methyl-2-phenylethyl}-3-(2-furylmethyl)urea, Ethyl N-{[(1S,2R)-2-{[1-(4-fluorophenyl)-1H-indazole-5-yl]oxy}-1-methyl-2-phenylethyl]carbamoyl}glycinate, 1-((R)-1,2-Dimethylpropyl)-3-{(1S,2R)-2-[1-(4-fluorophenyl)-1H-indazole-5-yl)oxy]-1-methyl-2-phenylethyl}urea, 1-{(1S,2R)-2-{[1-(4-Fluorophenyl)-1H-indazole-5-yl]oxy}-1-methyl-2-phenylethyl}-3-(2-furylmethyl)thiourea, N-{(1S)-1-[(R)-(3-Fluorophenyl)-{[1-(4-fluorophenyl)-1H-indazole-5-yl]oxy}methyl}-3-methyl-butyl}-2-methoxyacetamide, 2,2,2-Trifluoro-N-{(1S)-1-[(R)-(3-Fluorophenyl)-{[1-(4-fluorophenyl)-1H-indazole-5-yl]oxy}methyl}-3-methyl-butyl}-acetamide, N-[(1S)-(2R)-(3-Fluorophenyl)-2-{[1-(4-fluorophenyl)-1H-indazole-5-yl]oxy}-1-(methoxymethyl)ethyl]-2-methoxyacetamide, N-[(1S)-(2R)-(3-Fluorophenyl)-2-{[1-(4-fluorophenyl)-1H-indazol-5-yl]oxy}-1-(methoxymethyl)ethyl]furan-2-carboxamide, N-[(1S)-2-(3-Fluorophenyl)-2-{[1-(4-fluorophenyl)-1H-indazol-5-yl]oxy}-1-(hydroxymethyl)ethyl]-2-methoxyacetamide, N-[(1S,2R)-1-Methyl-2-phenyl-2-{[1-(3-pyridyl)-1H-indazol-5-yl]oxy}ethyl]furan-2-carboxamide, N-[(1S,2R)-1-Methyl-2-phenyl-2-{[1-(4-pyridyl)-1H-indazol-5-yl]oxy}ethyl]furan-2-carboxamide, Methyl 4-(5-{(1R,2S)-2-[(2-furylcarbonyl)amino]-1-phenylpropoxy}-1H-indazol-1-yl)benzoate, N-{(1R,2S)-1-[1-(4-fluorophenyl)indazol-5-yl]oxy-1-phenylpropan-2-yl}-5-methyl-[1,3,4]oxadiazol-2-carboxamide, 2-methoxy-N-[(1R,2S)-1-phenyl-1-(1-pyridin-2-ylindazol-5-yl)oxy-propan-2-yl]acetamide, N-[(1R,2S)-1-[1-(6-chloropyridazin-3-yl)indazol-5-yl]oxy-1-phenyl-propan-2-yl]-2,2,2-trifluoro-acetamide, 2-methoxy-N-[(1R,2S)-1-phenyl-1-(1-pyrimidin-2-ylindazol-5-yl)oxy-propan-2-yl]acetamide, N-[(1R,2S)-1-[1-(4-fluorophenyl)indazol-5-yl]oxy-1-(3-methoxyphenyl)propan-2-yl]-2-hydroxy-acetamide, 2,2,2-trifluoro-N-[(1R,2S)-1-[1-(4-fluorophenyl)indazol-5-yl]oxy-1-quinolin-3-yl-propan-2-yl]acetamide, N-[(1R,2S)-1-(2,5-dioxabicyclo[4.4.0]deca-7,9,11 trien-8-yl)-1-[1-(4-fluorophenyl)indazol-5-yl]oxy-propan-2-yl]-2-hydroxy-acetamide, N-[(1R,2S)-1-(2,5-dioxabicyclo[4.4.0]deca-7,9,11 trien-8-yl)-1-[1-(4-fluorophenyl)indazol-5-yl]oxy-propan-2-yl]-1-methyl-cyclopropane-1-carboxamide, (2S)—N-[(1R,2S)-1-(2,5-dioxabicyclo[4.4.0]deca-7,9,11-trien-8-yl)-1-[1-(4-fluorophenyl)indazol-5-yl]oxy-propan-2-yl]pyrrolidine-2-carboxamide, N-[(1R,2S)-1-[1-(4-chlorophenyl)indazol-5-yl]oxy-1-(3-methoxyphenyl)propan-2-yl]-2,2,2-trifluoro-acetamide, N-[(1R,2S)-1-(2,5-dioxabicyclo[4.4.0]deca-7,9,11-trien-8-yl)-1-[1-(4-fluorophenyl)indazol-5-yl]oxy-propan-2-yl]-2,2-difluoro-propanamide, N-[(1R,2S)-1-[1-(4-chlorophenyl)indazol-5-yl]oxy-1-(3-methoxyphenyl)propan-2-yl]-2,2-difluoro-propanamide, 2,2,2-trifluoro-N-[(1R,2S)-1-phenyl-1-(1-propan-2-ylindazol-5-yl)oxy-propan-2-yl]acetamide, N-[(1R,2S)-1-(1-cyclopentylindazol-5-yl)oxy-1-phenyl-propan-2-yl]-2,2,2-trifluoro-acetamide, N-[(1R,2S)-1-[1-(4-fluorophenyl)indazol-5-yl]oxy-1-(3-methoxyphenyl)propan-2-yl]-5-methyl-thiophene-2-carboxamide, N-[(1R,2S)-1-[1-(4-fluorophenyl)indazol-5-yl]oxy-1-(3-methoxyphenyl)propan-2-yl]-3-methyl-thiophene-2-carboxamide, N-[(1R,2S)-1-[1-(4-fluorophenyl)indazol-5-yl]oxy-1-(3-methoxyphenyl)propan-2-yl]-1-methyl-pyrrole-2-carboxamide, N-[(1R,2S)-1-[1-(4-fluorophenyl)indazol-5-yl]oxy-1-(3-methoxyphenyl)propan-2-yl]thiophene-3-carboxamide, N-[(1R,2S)-1-[1-(4-fluorophenyl)indazol-5-yl]oxy-1-(3-methoxyphenyl)propan-2-yl]1,3-thiazole-2-carboxamide, N-[(1R,2S)-1-[1-(4-fluorophenyl)indazol-5-yl]oxy-1-(3-methoxyphenyl)propan-2-yl]-5-methyl-1,2-oxazole-3-carboxamide, N-[2-[1-(4-fluorophenyl)indazol-5-yl]oxy-2-phenyl-acetyl]-2-methyl-propanamide, (2R)—N-[(1R,2S)-1-[1-(4-fluorophenyl)indazol-5-yl]oxy-1-[4-(trifluoromethyl)phenyl]propan-2-yl]-2-hydroxy-propanamide,
N-[(1R,2S)-1-[1-(4-fluorophenyl)indazol-5-yl]oxy-1-[4-(trifluoromethyl)phenyl]propan-2-yl]-1-hydroxy-cyclopropane-1-carboxamide,
(2S)—N-[(1R,2S)-1-[1-(4-fluorophenyl)indazol-5-yl]oxy-1-[4-(trifluoromethyl)phenyl]propan-2-yl]-2-hydroxy-propanamide,
2,2,2-trifluoro-N-[(1R,2S)-1-[1-[4-(hydroxymethyl)phenyl]indazol-5-yl]oxy-1-phenyl-propan-2-yl]acetamide,
2,2,2-trifluoro-N-[(1R,2S)-1-[1-[4-(morpholin-4-ylmethyl)phenyl]indazol-5-yl]oxy-1-phenyl-propan-2-yl]acetamide,
N-[(1R,2S)-1-[1-[4-(dimethylaminomethyl)phenyl]indazol-5-yl]oxy-1-phenyl-propan-2-yl]-2,2,2-trifluoro-acetamide,
2,2,2-trifluoro-N-[(1R,2S)-1-[1-[3-(hydroxymethyl)phenyl]indazol-5-yl]oxy-1-phenyl-propan-2-yl]acetamide,
2,2,2-trifluoro-N-[(1R,2S)-1-[1-[3-(morpholin-4-ylmethyl)phenyl]indazol-5-yl]oxy-1-phenyl-propan-2-yl]acetamide,
N-[(1R,2S)-1-[1-[3-(dimethylaminomethyl)phenyl]indazol-5-yl]oxy-1-phenyl-propan-2-yl]-2,2,2-trifluoro-acetamide,
2,2-dimethyl-N-[2,2,2-trifluoro-1-[[1-(4-fluorophenyl)indazol-5-yl]oxy-phenyl-methyl]ethyl]propanamide,
N-[(1S,2R)-1-[1-(4-fluorophenyl)indazol-5-yl]oxy-1-(6-methoxypyridin-3-yl)propan-2-yl]cyclopropanecarboxamide,
N-[(1R,2S)-1-(3,4-dimethylphenyl)-1-[1-(4-fluorophenyl)indazol-5-yl]oxy-propan-2-yl]-2,2,2-trifluoro-acetamide,
N-[(1R,2S)-1-(3,4-difluorophenyl)-1-[1-(4-fluorophenyl)indazol-5-yl]oxy-propan-2-yl]-2,2,2-trifluoro-acetamide,
2,2,2-trifluoro-N-[(1R,2S)-1-(3-fluoro-4-methyl-phenyl)-1-[1-(4-fluorophenyl)indazol-5-yl]oxy-propan-2-yl]acetamide,
2,2,2-trifluoro-N-[(1R,2S)-1-(3-fluorophenyl)-1-[1-(4-fluorophenyl)indazol-5-yl]oxy-propan-2-yl]acetamide,
N-[(1R,2S)-1-(2,5-dimethylphenyl)-1-[1-(4-fluorophenyl)indazol-5-yl]oxy-propan-2-yl]-2,2,2-trifluoro-acetamide,
N-[(1R,2S)-1-(2,4-dimethylphenyl)-1-[1-(4-fluorophenyl)indazol-5-yl]oxy-propan-2-yl]-2,2,2-trifluoro-acetamide,
N-[(1R,2S)-1-(3-chlorophenyl)-1-[1-(4-fluorophenyl)indazol-5-yl]oxy-propan-2-yl]-2,2,2-trifluoro-acetamide,
2,2,2-trifluoro-N-[(1R,2S)-1-(4-fluoro-2-methyl-phenyl)-1-[1-(4-fluorophenyl)indazol-5-yl]oxy-propan-2-yl]acetamide,
2,2,2-trifluoro-N-[(1R,2S)-1-(5-fluoro-2-methyl-phenyl)-1-[1-(4-fluorophenyl)indazol-5-yl]oxy-propan-2-yl]acetamide,
2,2,2-trifluoro-N-[(1R,2S)-1-(5-fluoro-2-methoxy-phenyl)-1-[1-(4-fluorophenyl)indazol-5-yl]oxy-propan-2-yl]acetamide,
2,2,2-trifluoro-N-[(1R,2S)-1-[1-(4-fluorophenyl)indazol-5-yl]oxy-1-(4-methoxy-3,5-dimethyl-phenyl)propan-2-yl]acetamide,
N-[(1R,2S)-1-(4-chlorophenyl)-1-[1-(4-fluorophenyl)indazol-5-yl]oxy-propan-2-yl]-2,2,2-trifluoro-acetamide,
N-[(1R,2S)-1-(3-chloro-5-fluoro-phenyl)-1-[1-(4-fluorophenyl)indazol-5-yl]oxy-propan-2-yl]-2,2,2-trifluoro-acetamide,
2,2,2-trifluoro-N-[(1R,2S)-1-[1-(4-fluorophenyl)indazol-5-yl]oxy-1-(2,4,5-trimethylphenyl)propan-2-yl]acetamide,
2,2,2-trifluoro-N-[(1R,2S)-1-[1-(4-fluorophenyl)indazol-5-yl]oxy-1-(4-tert-butylphenyl)propan-2-yl]acetamide,
2,2,2-trifluoro-N-[(1R,2S)-1-[1-(4-fluorophenyl)indazol-5-yl]oxy-1-(2-methoxyphenyl)propan-2-yl]acetamide,
2,2,2-trifluoro-N-[(1R,2S)-1-[1-(4-fluorophenyl)indazol-5-yl]oxy-1-(4-propylphenyl)propan-2-yl]acetamide,
N-[(1R,2S)-1-benzo[1,3]dioxol-5-yl-1-[1-(4-fluorophenyl)indazol-5-yl]oxy-propan-2-yl]-2,2,2-trifluoro-acetamide,
2,2,2-trifluoro-N-[(1R,2S)-1-(3-fluoro-2-methyl-phenyl)-1-[1-(4-fluorophenyl)indazol-5-yl]oxy-propan-2-yl]acetamide,
N-[(1R,2S)-1-(4-chloro-3-methyl-phenyl)-1-[1-(4-fluorophenyl)indazol-5-yl]oxy-propan-2-yl]-2,2,2-trifluoro-acetamide,
N-[(1R,2S)-1-(4-chloro-2-methyl-phenyl)-1-[1-(4-fluorophenyl)indazol-5-yl]oxy-propan-2-yl]-2,2,2-trifluoro-acetamide,
N-[(1R,2S)-1-(4-chloro-3-fluoro-phenyl)-1-[1-(4-fluorophenyl)indazol-5-yl]oxy-propan-2-yl]-2,2,2-trifluoro-acetamide,
N-[(1R,2S)-1-(3,4-dimethylphenyl)-1-[1-(4-fluorophenyl)indazol-5-yl]oxy-propan-2-yl]-2,2-dimethyl-propanamide,
N-[(1R,2S)-1-(3,4-difluorophenyl)-1-[1-(4-fluorophenyl)indazol-5-yl]oxy-propan-2-yl]-2,2-dimethyl-propanamide,
N-[(1R,2S)-1-(3-fluoro-4-methyl-phenyl)-1-[1-(4-fluorophenyl)indazol-5-yl]oxy-propan-2-yl]-2,2-dimethyl-propanamide,
N-[(1R,2S)-1-(3-fluorophenyl)-1-[1-(4-fluorophenyl)indazol-5-yl]oxy-propan-2-yl]-2,2-dimethyl-propanamide,
N-[(1R,2S)-1-(2,5-dimethylphenyl)-1-[1-(4-fluorophenyl)indazol-5-yl]oxy-propan-2-yl]-2,2-dimethyl-propanamide,
N-[(1R,2S)-1-(2,4-dimethylphenyl)-1-[1-(4-fluorophenyl)indazol-5-yl]oxy-propan-2-yl]-2,2-dimethyl-propanamide,
N-[(1R,2S)-1-(3-fluoro-4-methoxy-phenyl)-1-[1-(4-fluorophenyl)indazol-5-yl]oxy-propan-2-yl]-2,2-dimethyl-propanamide,
N-[(1R,2S)-1-(3-chlorophenyl)-1-[1-(4-fluorophenyl)indazol-5-yl]oxy-propan-2-yl]-2,2-dimethyl-propanamide,
N-[(1R,2S)-1-(4-fluoro-2-methyl-phenyl)-1-[1-(4-fluorophenyl)indazol-5-yl]oxy-propan-2-yl]-2,2-dimethyl-propanamide,
N-[(1R,2S)-1-(5-fluoro-2-methyl-phenyl)-1-[1-(4-fluorophenyl)indazol-5-yl]oxy-propan-2-yl]-2,2-dimethyl-propanamide,
N-[(1R,2S)-1-(5-fluoro-2-methoxy-phenyl)-1-[1-(4-fluorophenyl)indazol-5-yl]oxy-propan-2-yl]-2,2-dimethyl-propanamide,
N-[(1R,2S)-1-[1-(4-fluorophenyl)indazol-5-yl]oxy-1-(4-methoxy-3,5-dimethyl-phenyl)propan-2-yl]-2,2-dimethyl-propanamide,
N-[(1R,2S)-1-(4-chlorophenyl)-1-[1-(4-fluorophenyl)indazol-5-yl]oxy-propan-2-yl]-2,2-dimethyl-propanamide,
N-[(1R,2S)-1-(3-chloro-5-fluoro-phenyl)-1-[1-(4-fluorophenyl)indazol-5-yl]oxy-propan-2-yl]-2,2-dimethyl-propanamide,
N-[(1R,2S)-1-[1-(4-fluorophenyl)indazol-5-yl]oxy-1-(3-methylphenyl)propan-2-yl]-2,2-dimethyl-propanamide,
N-[(1R,2S)-1-[1-(4-fluorophenyl)indazol-5-yl]oxy-1-(4-tert-butylphenyl)propan-2-yl]-2,2-dimethyl-propanamide,
N-[(1R,2S)-1-[1-(4-fluorophenyl)indazol-5-yl]oxy-1-(2-methoxyphenyl)propan-2-yl]-2,2-dimethyl-propanamide,
N-[(1R,2S)-1-[1-(4-fluorophenyl)indazol-5-yl]oxy-1-(4-propylphenyl)propan-2-yl]-2,2-dimethyl-propanamide, N-[(1R,2S)-1-benzo[1,3]dioxol-5-yl-1-[1-(4-fluorophenyl)indazol-5-yl]oxy-propan-2-yl]-2,2-dimethyl-propanamide,
N-[(1R,2S)-1-(3-fluoro-2-methyl-phenyl)-1-[1-(4-fluorophenyl)indazol-5-yl]oxy-propan-2-yl]-2,2-dimethyl-propanamide,
N-[(1R,2S)-1-(4-chloro-3-methyl-phenyl)-1-[1-(4-fluorophenyl)indazol-5-yl]oxy-propan-2-yl]-2,2-methyl-propanamide,
N-[(1R,2S)-1-(3,4-dimethylphenyl)-1-[1-(4-fluorophenyl)indazol-5-yl]oxy-propan-2-yl]-5-methyl-1,3-thiazole-2-carboxamide,
N-[(1R,2S)-1-(3,4-difluorophenyl)-1-[1-(4-fluorophenyl)indazol-5-yl]oxy-propan-2-yl]-5-methyl-1,3-thiazole-2-carboxamide,
N-[(1R,2S)-1-(3-fluoro-4-methyl-phenyl)-1-[1-(4-fluorophenyl)indazol-5-yl]oxy-propan-2-yl]-5-methyl-1,3-thiazole-2-carboxamide,
N-[(1R,2S)-1-(3-fluorophenyl)-1-[1-(4-fluorophenyl)indazol-5-yl]oxy-propan-2-yl]-5-methyl-1,3-thiazole-2-arboxamide,
N-[(1R,2S)-1-(2,5-dimethylphenyl)-1-[1-(4-fluorophenyl)indazol-5-yl]oxy-propan-2-yl]-5-methyl-1,3-thiazole-2-carboxamide,
N-[(1R,2S)-1-(2,4-dimethylphenyl)-1-[1-(4-fluorophenyl)indazol-5-yl]oxy-propan-2-yl]-5-methyl-1,3-thiazole-2-arboxamide,
N-[(1R,2S)-1-(3-fluoro-4-methoxy-phenyl)-1-[1-(4-fluorophenyl)indazol-5-yl]oxy-propan-2-yl]-5-methyl-1,3-thiazole-2-carboxamide,
N-[(1R,2S)-1-(3-chlorophenyl)-1-[1-(4-fluorophenyl)indazol-5-yl]oxy-propan-2-yl]-5-methyl-1,3-thiazole-2-carboxamide,
N-[(1R,2S)-1-(4-fluoro-2-methyl-phenyl)-1-[1-(4-fluorophenyl)indazol-5-yl]oxy-propan-2-yl]-5-methyl-1,3-thiazole-2-carboxamide,
N-[(1R,2S)-1-(5-fluoro-2-methyl-phenyl)-1-[1-(4-fluorophenyl)indazol-5-yl]oxy-propan-2-yl]-5-methyl-1,3-thiazole-2-carboxamide,
N-[(1R,2S)-1-(5-fluoro-2-methoxy-phenyl)-1-[1-(4-fluorophenyl)indazol-5-yl]oxy-propan-2-yl]-5-methyl-1,3-thiazole-2-carboxamide,
N-[(1R,2S)-1-[1-(4-fluorophenyl)indazol-5-yl]oxy-1-(4-methoxy-3,5-dimethyl-phenyl)propan-2-yl]-5-methyl-1,3-thiazole-2-carboxamide,
N-[(1R,2S)-1-(4-chlorophenyl)-1-[1-(4-fluorophenyl)indazol-5-yl]oxy-propan-2-yl]-5-methyl-1,3-thiazole-2-carboxamide,
N-[(1R,2S)-1-(3-chloro-5-fluoro-phenyl)-1-[1-(4-fluorophenyl)indazol-5-yl]oxy-propan-2-yl]-5-methyl-1,3-thiazole-2-carboxamide,
N-[(1R,2S)-1-[1-(4-fluorophenyl)indazol-5-yl]oxy-1-(2,4,5-trimethylphenyl)propan-2-yl]-5-methyl-1,3-thiazole-2-arboxamide,
N-[(1R,2S)-1-[1-(4-fluorophenyl)indazol-5-yl]oxy-1-(3-methylphenyl)propan-2-yl]-5-methyl-1,3-thiazole-2-carboxamide,
N-[(1R,2S)-1-[1-(4-fluorophenyl)indazol-5-yl]oxy-1-(4-tert-butylphenyl)propan-2-yl]-5-methyl-1,3-thiazole-2-carboxamide,
N-[(1R,2S)-1-[1-(4-fluorophenyl)indazol-5-yl]oxy-1-(2-methoxyphenyl)propan-2-yl]-5-methyl-1,3-thiazole-2-carboxamide,
N-[(1R,2S)-1-benzo[1,3]dioxol-5-yl-1-[1-(4-fluorophenyl)indazol-5-yl]oxy-propan-2-yl]-5-methyl-1,3-thiazole-2-carboxamide,
N-[(1R,2S)-1-(3,4-dimethylphenyl)-1-[1-(4-fluorophenyl)indazol-5-yl]oxy-propan-2-yl]-1-methyl-cyclopropane-1-carboxamide,
N-[(1R,2S)-1-(3,4-difluorophenyl)-1-[1-(4-fluorophenyl)indazol-5-yl]oxy-propan-2-yl]-1-methyl-cyclopropane-1-carboxamide,
N-[(1R,2S)-1-(3-fluoro-4-methyl-phenyl)-1-[1-(4-fluorophenyl)indazol-5-yl]oxy-propan-2-yl]-1-methyl-cyclopropane-1-carboxamide,
N-[(1R,2S)-1-(3-fluorophenyl)-1-[1-(4-fluorophenyl)indazol-5-yl]oxy-propan-2-yl]-1-methyl-cyclopropane-1-carboxamide,
N-[(1R,2S)-1-(2,5-dimethylphenyl)-1-[1-(4-fluorophenyl)indazol-5-yl]oxy-propan-2-yl]-1-methyl-cyclopropane-1-carboxamide,
N-[(1R,2S)-1-(2,4-dimethylphenyl)-1-[1-(4-fluorophenyl)indazol-5-yl]oxy-propan-2-yl]-1-methyl-cyclopropane-1-carboxamide,
N-[(1R,2S)-1-(3-fluoro-4-methoxy-phenyl)-1-[1-(4-fluorophenyl)indazol-5-yl]oxy-propan-2-yl]-1-methyl-cyclopropane-1-carboxamide,
N-[(1R,2S)-1-(3 chlorophenyl)-1-[1-(4-fluorophenyl)indazol-5-yl]oxy-propan-2-yl]-1-methyl-cyclopropane-1-carboxamide,
N-[(1R,2S)-1-(4-fluoro-2-methyl-phenyl)-1-[1-(4-fluorophenyl)indazol-5-yl]oxy-propan-2-yl]-1-methyl-cyclopropane-1 carboxamide,
N-[(1R,2S)-1-(5-fluoro-2-methyl-phenyl)-1-[1-(4-fluorophenyl)indazol-5-yl]oxy-propan-2-yl]-1-methyl-cyclopropane-1-carboxamide,
N-[(1R,2S)-1-[1-(4-fluorophenyl)indazol-5-yl]oxy-1-(4-methoxy-3,5-dimethyl-phenyl)propan-2-yl]-1-methyl-cyclopropane-1-carboxamide,
N-[(1R,2S)-1-(4-chlorophenyl)-1-[1-(4-fluorophenyl)indazol-5-yl]oxy-propan-2-yl]-1-methyl-cyclopropane-1-carboxamide,
N-[(1R,2S)-1-(3-chloro-5-fluoro-phenyl)-1-[1-(4-fluorophenyl)indazol-5-yl]oxy-propan-2-yl]-1-methylcyclopropane-1-carboxamide,
N-[(1R,2S)-1-[1-(4-fluorophenyl)indazol-5-yl]oxy-1-(2,4,5-trimethylphenyl)propan-2-yl]-1-methyl-cyclopropane-1-carboxamide,
N-[(1R,2S)-1-[1-(4-fluorophenyl)indazol-5-yl]oxy-1-(3-methylphenyl)propan-2-yl]-1-methyl-cyclopropane-1-carboxamide,
N-[(1R,2S)-1-[1-(4-fluorophenyl)indazol-5-yl]oxy-1-(4-tert-butylphenyl)propan-2-yl]-1-methyl-cyclopropane-1-carboxamide,
N-[(1R,2S)-1-[1-(4-fluorophenyl)indazol-5-yl]oxy-1-(2-methoxyphenyl)propan-2-yl]-1-methyl-cyclopropane-1-carboxamide,
N-[(1R,2S)-1-(3,4-difluorophenyl)-1-[1-(4-fluorophenyl)indazol-5-yl]oxy-propan-2-yl]-2,2-difluoro-propanamide,
2,2-difluoro-N-[(1R,2S)-1-(3-fluoro-4-methyl-phenyl)-1-[1-(4-fluorophenyl)indazol-5-yl]oxy-propan-2-yl]propanamide,
2,2-difluoro-N-[(1R,2S)-1-(3-fluorophenyl)-1-[1-(4-fluorophenyl)indazol-5-yl]oxy-propan-2-yl]propanamide,
2,2-difluoro-N-[(1R,2S)-1-(3-fluoro-4-methoxy-phenyl)-1-[1-(4-fluorophenyl)indazol-5-yl]oxy-propan-2-yl]propanamide,
N-[(1R,2S)-1-(3-chlorophenyl)-1-[1-(4-fluorophenyl)indazol-5-yl]oxy-propan-2-yl]-2,2-difluoro-propanamide,
2,2-difluoro-N-[(1R,2S)-1-(4-fluoro-2-methyl-phenyl)-1-[1-(4-fluorophenyl)indazol-5-yl]oxy-propan-2-yl]propanamide, 2,2-difluoro-N-[(1R,2S)-1-(5-fluoro-2-methyl-phenyl)-1-[1-(4-fluorophenyl)indazol-5-yl]oxy-propan-2-yl]propanamide,
2,2-difluoro-N-[(1R,2S)-1-(5-fluoro-2-methoxy-phenyl)-1-[1-(4-fluorophenyl)indazol-5-yl]oxy-propan-2-yl]propanamide,
2,2-difluoro-N-[(1R,2S)-1-[1-(4-fluorophenyl)indazol-5-yl]oxy-1-(4-methoxy-3,5-dimethyl-phenyl)propan-2-yl]propanamide,
N-[(1R,2S)-1-(4-chlorophenyl)-1-[1-(4-fluorophenyl)indazol-5-yl]oxy-propan-2-yl]-2,2-difluoro-propanamide,
N-[(1R,2S)-1-(3-chloro-5-fluoro-phenyl)-1-[1-(4-fluorophenyl)indazol-5-yl]oxy-propan-2-yl]-2,2-difluoro-propanamide,
2,2-difluoro-N-[(1R,2S)-1-[1-(4-fluorophenyl)indazol-5-yl]oxy-1-(3-methylphenyl)propan-2-yl]propanamide,
N-[(1R,2S)-1-(3,4-dimethylphenyl)-1-[1-(4-fluorophenyl)indazol-5-yl]oxy-propan-2-yl]-2-fluoro-2-methyl-propanamide,
N-[(1R,2S)-1-(3,4-difluorophenyl)-1-[1-(4-fluorophenyl)indazol-5-yl]oxy-propan-2-yl]-2-fluoro-2-methyl-propanamide,
2-fluoro-N-[(1R,2S)-1-(3-fluoro-4-methyl-phenyl)-1-[1-(4-fluorophenyl)indazol-5-yl]oxy-propan-2-yl]-2-methyl-propanamide,
2-fluoro-N-[(1R,2S)-1-(3-fluorophenyl)-1-[1-(4-fluorophenyl)indazol-5-yl]oxy-propan-2-yl]-2-methyl-propanamide,
N-[(1R,2S)-1-(2,5-dimethylphenyl)-1-[1-(4-fluorophenyl)indazol-5-yl]oxy-propan-2-yl]-2-fluoro-2-methyl-propanamide,
N-[(1R,2S)-1-(2,4-dimethylphenyl)-1-[1-(4-fluorophenyl)indazol-5-yl]oxy-propan-2-yl]-2-fluoro-2-methyl-propanamide,
2-fluoro-N-[(1R,2S)-1-(3-fluoro-4-methoxy-phenyl)-1-[1-(4-fluorophenyl)indazol-5-yl]oxy-propan-2-yl]-2-methyl-propanamide,
N-[(1R,2S)-1-(3-chlorophenyl)-1-[1-(4-fluorophenyl)indazol-5-yl]oxy-propan-2-yl]-2-fluoro-2-methyl-propanamide,
2-fluoro-N-[(1R,2S)-1-(4-fluoro-2-methyl-phenyl)-1-[1-(4-fluorophenyl)indazol-5-yl]oxy-propan-2-yl]-2-methyl-propanamide,
2-fluoro-N-[(1R,2S)-1-(5-fluoro-2-methyl-phenyl)-1-[1-(4-fluorophenyl)indazol-5-yl]oxy-propan-2-yl]-2-methyl-propanamide,
2-fluoro-N-[(1R,2S)-1-(5-fluoro-2-methoxy-phenyl)-1-[1-(4-fluorophenyl)indazol-5-yl]oxy-propan-2-yl]-2-methyl-propanamide,
N-[(1R,2S)-1-(3,4-difluorophenyl)-1-[1-(4-fluorophenyl)indazol-5-yl]oxy-propan-2-yl]-3-hydroxy-2,2-dimethyl-propanamide,
N-[(1R,2S)-1-(3-fluoro-4-methyl-phenyl)-1-[1-(4-fluorophenyl)indazol-5-yl]oxy-propan-2-yl]-3-hydroxy-2,2-dimethyl-propanamide,
N-[(1R,2S)-1-(3-fluorophenyl)-1-[1-(4-fluorophenyl)indazol-5-yl]oxy-propan-2-yl]-3-hydroxy-2,2-dimethyl-propanamide,
N-[(1R,2S)-1-(2,5-dimethylphenyl)-1-[1-(4-fluorophenyl)indazol-5-yl]oxy-propan-2-yl]-3-hydroxy-2,2-dimethyl-propanamide,
N-[(1R,2S)-1-(3-chlorophenyl)-1-[1-(4-fluorophenyl)indazol-5-yl]oxy-propan-2-yl]-3-hydroxy-2,2-dimethyl-propanamide,
N-[(1R,2S)-1-(4-fluoro-2-methyl-phenyl)-1-[1-(4-fluorophenyl)indazol-5-yl]oxy-propan-2-yl]-3-hydroxy-2,2-dimethyl-propanamide,
N-[(1R,2S)-1-(3,4-dimethylphenyl)-1-[1-(4-fluorophenyl)indazol-5-yl]oxy-propan-2-yl]-2-methoxy-acetamide,
N-[(1R,2S)-1-(3,4-difluorophenyl)-1-[1-(4-fluorophenyl)indazol-5-yl]oxy-propan-2-yl]-2-methoxy-acetamide,
N-[(1R,2S)-1-(3-fluoro-4-methyl-phenyl)-1-[1-(4-fluorophenyl)indazol-5-yl]oxy-propan-2-yl]-2-methoxy-acetamide,
N-[(1R,2S)-1-(2,5-dimethylphenyl)-1-[1-(4-fluorophenyl)indazol-5-yl]oxy-propan-2-yl]-2-methoxy-acetamide,
N-[(1R,2S)-1-(2,4-dimethylphenyl)-1-[1-(4-fluorophenyl)indazol-5-yl]oxy-propan-2-yl]-2-methoxy-acetamide,
N-[(1R,2S)-1-(3-fluoro-4-methoxy-phenyl)-1-[1-(4-fluorophenyl)indazol-5-yl]oxy-propan-2-yl]-2-methoxy-acetamide,
N-[(1R,2S)-1-(3-fluorophenyl)-1-[1-(4-fluorophenyl)indazol-5-yl]oxy-propan-2-yl]-2-methoxy-acetamide,
2,2,2-trifluoro-N-[(1R,2S)-1-(3-fluoro-4-methoxy-phenyl)-1-[1-(4-fluorophenyl)indazol-5-yl]oxy-propan-2-yl]acetamide,
N-[(1R,2S)-1-[1-(4-fluorophenyl)indazol-5-yl]oxy-1-(4-methoxy-2-methyl-phenyl)propan-2-yl]-1-methyl-cyclopropane-1-carboxamide,
N-[(1R,2S)-1-(2,5-dimethylphenyl)-1-[1-(4-fluorophenyl)indazol-5-yl]oxy-propan-2-yl]-2,2-difluoro-propanamide,
N-[(1R,2S)-1-[1-(4-fluorophenyl)indazol-5-yl]oxy-1-(2,4,5-trimethylphenyl)propan-2-yl]-2,2-dimethyl-propanamide,
N-[(1R,2S)-1-(5-fluoro-2-methoxy-phenyl)-1-[1-(4-fluorophenyl)indazol-5-yl]oxy-propan-2-yl]-1-methyl-cyclopropane-1-carboxamide,
N-[[(1R,2S)-1-[1-(4-fluorophenyl)indazol-5-yl]oxy-1-(3-methoxyphenyl)propan-2-yl]carbamoylmethyl]acetamide,
2-(carbamoylamino)-N-[(1R,2S)-1-[1-(4-fluorophenyl)indazol-5-yl]oxy-1-(3-methoxyphenyl)propan-2-yl]acetamide,
3-[(1R,2S)-1-[1-(4-fluorophenyl)indazol-5-yl]oxy-1-(3-methoxyphenyl)propan-2-yl]imidazolidine-2,4-dione,
5-bromo-N-[(1R,2S)-1-[1-(4-fluorophenyl)indazol-5-yl]oxy-1-(3-methoxyphenyl)propan-2-yl]thiophene-2-carboxamide,
N-[(1R,2S)-1-[1-(4-fluorophenyl)indazol-5-yl]oxy-1-(3-methoxyphenyl)propan-2-yl]-5-methylsulfonyl-thiophene-2-carboxamide,
N-[(1R,2S)-1-[1-(4-fluorophenyl)indazol-5-yl]oxy-1-(3-methoxyphenyl)propan-2-yl]-5-methyl-1,3-thiazole-2-carboxamide,
4-cyano-N-[(1R,2S)-1-[1-(4-fluorophenyl)indazol-5-yl]oxy-1-(3-methoxyphenyl)propan-2-yl]thiophene-2-carboxamide,
5-bromo-N-[(1R,2S)-1-[1-(4-fluorophenyl)indazol-5-yl]oxy-1-(3-methoxyphenyl)propan-2-yl]furan-2-carboxamide,
N-[(1R,2S)-1-[1-(4-fluorophenyl)indazol-5-yl]oxy-1-(3-methoxyphenyl)propan-2-yl]-5-methyl-1,3,4-oxadiazole-2-carboxamide,
N-[(1R,2S)-1-[1-(4-fluorophenyl)indazol-5-yl]oxy-1-(3-methoxyphenyl)propan-2-yl]-1H-imidazole-4-carboxamide,
N-[(1R,2S)-1-[1-(4-fluorophenyl)indazol-5-yl]oxy-1-(3-methoxyphenyl)propan-2-yl]-1H-pyrazole-3-carboxamide,
N-[(1R,2S)-1-[1-(4-fluorophenyl)indazol-5-yl]oxy-1-(3-methoxyphenyl)propan-2-yl]1,2-oxazole-3-carboxamide,
N-[(1R,2S)-1-[1-(4-fluorophenyl)indazol-5-yl]oxy-1-(3-methoxyphenyl)propan-2-yl]-1H-1,2,4-triazole-3-carboxamide, N-[(1R,2S)-1-[1-(4-fluorophenyl)indazol-5-yl]oxy-1-(3-methoxyphenyl)propan-2-yl]-5-methyl-1H-pyrazole-3-carboxamide, N-[(1R,2S)-1-[1-(4-fluorophenyl)indazol-5-yl]oxy-1-(3-methoxyphenyl)propan-2-yl]1-methyl-imidazole-4-carboxamide, N-[(1R,2S)-1-[1-(4-fluorophenyl)indazol-5-yl]oxy-1-(3-methoxyphenyl)propan-2-yl]-5-methyl-1,2-oxazole-4-carboxamide, N-[(1R,2S)-1-[1-(4-fluorophenyl)indazol-5-yl]oxy-1-(3-methoxyphenyl)propan-2-yl]-1-methyl-triazole-4-carboxamide, N-[(1R,2S)-1-[1-(4-fluorophenyl)indazol-5-yl]oxy-1-(3-methoxyphenyl)propan-2-yl]-4,5-dimethyl-furan-2-carboxamide, N-[(1R,2S)-1-[1-(4-fluorophenyl)indazol-5-yl]oxy-1-(3-methoxyphenyl)propan-2-yl]-1,5-dimethyl-pyrazole-3-carboxamide, N-[(1R,2S)-1-[1-(4-fluorophenyl)indazol-5-yl]oxy-1-(3-methoxyphenyl)propan-2-yl]-5-methyl-1,3-thiazole-4-carboxamide, N-[(1R,2S)-1-[1-(4-fluorophenyl)indazol-5-yl]oxy-1-(3-methoxyphenyl)propan-2-yl]-4-methyl-1,3-thiazole-5-carboxamide, N-[(1R,2S)-1-[1-(4-fluorophenyl)indazol-5-yl]oxy-1-(3-methoxyphenyl)propan-2-yl]-4-methyl-1,3-thiazole-2-carboxamide, N-[(1R,2S)-1-[1-(4-fluorophenyl)indazol-5-yl]oxy-1-(3-methoxyphenyl)propan-2-yl]-4,5-dimethyl-thiophene-2-carboxamide, N-[(1R,2S)-1-[1-(4-fluorophenyl)indazol-5-yl]oxy-1-(3-methoxyphenyl)propan-2-yl]-3-methoxy-thiophene-2-carboxamide, N-[(1R,2S)-1-[1-(4-fluorophenyl)indazol-5-yl]oxy-1-(3-methoxyphenyl)propan-2-yl]-1,9-diazabicyclo[4.3.0]nona-2,4,6,8-tetraene-8-carboxamide, N-[(1R,2S)-1-[1-(4-fluorophenyl)indazol-5-yl]oxy-1-(3-methoxyphenyl)propan-2-yl]-1H-benzoimidazole-2-arboxamide, 5-chloro-N-[(1R,2S)-1-[1-(4-fluorophenyl)indazol-5-yl]oxy-1-(3-methoxyphenyl)propan-2-yl]thiophene-2-carboxamide, N-[(1R,2S)-1-[1-(4-fluorophenyl)indazol-5-yl]oxy-1-(3-methoxyphenyl)propan-2-yl]benzothiophene-2-carboxamide, N-[(1R,2S)-1-[1-(4-fluorophenyl)indazol-5-yl]oxy-1-(3-methoxyphenyl)propan-2-yl]benzothiazole-2-carboxamide, N-[(1R,2S)-1-[1-(4-fluorophenyl)indazol-5-yl]oxy-1-(3-methoxyphenyl)propan-2-yl]-3-hydroxy-5-(trifluoromethyl)thiophene-2-carboxamide, N-[(1R,2S)-1-[1-(4-fluorophenyl)indazol-5-yl]oxy-1-(3-methoxyphenyl)propan-2-yl]-5-(methoxymethyl)thiophene-2-carboxamide, N-[(1R,2S)-1-(2-chlorophenyl)-1-[1-(4-fluorophenyl)indazol-5-yl]oxy-propan-2-yl]-2,2-dimethyl-propanamide, tert-butyl 3-[[(1R,2S)-1-[1-(4-fluorophenyl)indazol-5-yl]oxy-1-(3-methoxyphenyl)propan-2-yl]carbamoyl]pyrrolidine-1-carboxylate, 2,2-difluoro-N-[(1R,2S)-1-[1-(4-fluorophenyl)indazol-5-yl]oxy-1-(3-methoxyphenyl)propan-2-yl]propanamide, (2R)-2-amino-N-[(1R,2S)-1-[1-(4-fluorophenyl)indazol-5-yl]oxy-1-(3-methoxyphenyl)propan-2-yl]propanamide, (2R)—N-[(1R,2S)-1-[1-(4-fluorophenyl)indazol-5-yl]oxy-1-(3-methoxyphenyl)propan-2-yl]pyrrolidine-2-carboxamide, N-[(1S,2S)-3-(2,4-difluorophenoxy)-2-[1-(4-fluorophenyl)indazol-5-yl]oxy-1-methyl-propyl]-2,2,2-trifluoro-acetamide, N-[(1S,2R)-2-(2,3-dihydrobenzofuran-6-yl)-2-[1-(4-fluorophenyl)indazol-5-yl]oxy-1-methyl-ethyl]-2,2-difluoropropanamide, N-[(1R,2S)-1-(2,3-dihydrobenzofuran-6-yl)-1-[1-(4-fluorophenyl)indazol-5-yl]oxy-propan-2-yl]-2,2,2-trifluoroacetamide, and 2,2,2-trifluoro-N-[(1R,2S)-1-[1-(4-fluorophenyl)indazol-5-yl]oxy-1-(3-methoxy-4-methylsulfanyl-phenyl)propan-2-yl]acetamide, or a pharmaceutically acceptable salt thereof.

For the avoidance of doubt it is to be understood that where in this specification a group is qualified by 'hereinbefore defined', 'defined hereinbefore' or 'defined above' the said group encompasses the first occurring and broadest definition as well as each and all of the other definitions for that group.

For the avoidance of doubt it is to be understood that in this specification '$C_{1-6}$' means a carbon group having 1, 2, 3, 4, 5 or 6 carbon atoms.

In this specification, unless stated otherwise, the term "alkyl" includes both straight and branched chain alkyl groups and may be, but are not limited to methyl, ethyl, n-propyl, i-propyl, n-butyl, i-butyl, s-butyl, t-butyl, n-pentyl, i-pentyl, neo-pentyl, n-hexyl or i-hexyl. The term $C_{1-4}$ alkyl having 1 to 4 carbon atoms and may be but are not limited to methyl, ethyl, n-propyl, i-propyl or t-butyl. The term "$C_0$" in $C_{0-4}$ alkyl refers to a situation where no carbon atom is present.

The term "alkoxy", unless stated otherwise, refers to radicals of the general formula —O—R, wherein R is selected from a hydrocarbon radical. The term "alkoxy" may include, but is not limited to methoxy, ethoxy, propoxy, isopropoxy, butoxy, t-butoxy, isobutoxy, cyclopropylmethoxy, allyloxy or propargyloxy.

In this specification, unless stated otherwise, the term "cycloalkyl" refers to an optionally substituted, partially or completely saturated monocyclic, bicyclic or bridged hydrocarbon ring system. The term "$C_{1-6}$cycloalkyl" may be, but is not limited to cyclopropyl, cyclobutyl, cyclopentyl or cyclohexyl.

In this specification, unless stated otherwise, the term "heterocycloalkyl" refers to an optionally substituted, partially or completely saturated monocyclic, bicyclic or bridged hydrocarbon ring system having one or more heteroatoms independently selected from O, N or S. The term "$C_{1-6}$heterocycloalkyl" may be, but is not limited to pyrrolidinyl, piperidinyl or tetrahydrofuranyl.

In this specification, unless stated otherwise, the term "A forms together with Rx a 5 to 6 membered azacyclic ring optionally having one or more further heteroatoms independently selected from O, N and S" refers to an optionally substituted, aromatic or partially or completely saturated monocyclic hydrocarbon ring system having one or more heteroatoms independently selected from O, N or S. This term may be, but is not limited to imidazolidine-2,4-dione.

In this specification, unless stated otherwise, the terms "halo" and "halogen" may be fluorine (fluoro), iodine (iodo), chlorine (chloro) or bromine (bromo).

In this specification, unless stated otherwise, the term "haloalkyl" means an alkyl group as defined above, which is substituted with halo as defined above. The term "$C_{1-6}$haloalkyl" may include, but is not limited to fluoromethyl, difluoromethyl, trifluoromethyl, chloromethyl, dichloromethyl, trichloromethyl or fluorochloromethyl.

The term "$C_{1-3}$haloalkylO" or "$C_{1-3}$haloalkoxy" may include, but is not limited to fluoromethoxy, difluoromethoxy, trifluoromethoxy, fluoroethoxy or difluoroethoxy.

In this specification, unless stated otherwise, the term "thioalkyl" means an alkyl group as defined above, which is substituted with sulphur atom. The term "$C_{1-6}$thioalkyl" may include, but is not limited to methylsulfanyl, ethylsulfanyl or propylsulfanyl.

The term "cycloalkylS" means a sulphur atom substituted with a cycloalkyl as defined above such as for instance cyclopropylsulfanyl in example 15.

The term "$C_{1-4}$alkyl$C_{1-4}$thioalkyl" or "$C_{1-4}$alkylS$C_{1-4}$alkyl" means a alkyl group with a sulphur atom between the carbon atoms. The term "$C_{1-4}$alkyl$C_{1-4}$thioalkyl" may include, but is not limited to ethylsulfanylmethyl as in example 25.

In this specification, unless stated otherwise, the term "$C_{5-10}$aryl" refers to an aromatic or partial aromatic group having 5 to 10 carbon atoms such as for example, phenyl or naphthyl. In this specification, unless stated otherwise, the term "$C_{5-10}$heteroaryl" refers to a mono- or bicyclic aromatic or partially aromatic ring with 5 to 10 atoms and containing one or more heteroatoms independently selected from nitrogen, oxygen or sulphur. Example of heteroaryls are oxazolyl, furyl, thiophenyl, pyrrolyl, pyrazolyl, imidazolyl, pyridinyl, pyrimidinyl, indolyl, indazolyl, benzofuryl, benzothienyl or dioxabicyclodecatrienyl as in example 19. Heteroaryl may also be quinolinyl or isoquinolinyl.

When phenyl is substituted by $OCH_2O$, $OCH_2CH_2O$ or $OCH_2CH_2$ these groups link to adjacent carbons on the phenyl ring.

For the avoidance of doubt a group $R^3$ defined as $C_{5-10}$aryl e.g. phenyl, substituted with a group $C_{1-2}$alkylS(O)$_n$ includes a phenyl substituted with methylsulphonyl group as in example 12. And a group $R^7$ defined as $C_{5-10}$heteroaryl-$C_{1-3}$alkyl includes a furylmethyl group as in example 105.

It will be appreciated that throughout the specification, the number and nature of substituents on rings in the compounds of the invention will be selected so as to avoid sterically undesirable combinations.

One embodiment of the invention relates to compounds of formula Ic

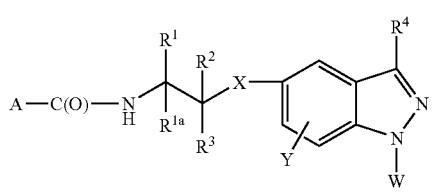

(Ic)

wherein:

A is $C_{1-10}$ alkyl, $C_{1-10}$ alkoxy, $C_{1-10}$ alkylthio, ($C_{1-10}$ alkyl)($R^{11}$)N or $C_{3-7}$ cycloalkyl, all of which are optionally substituted by halogen, cyano, nitro, hydroxy, thio, $C_{1-6}$ alkoxy, $C_{1-6}$ alkylS(O)$_n$, $R^{12}R^{13}$N, ($C_{1-4}$ alkyl)C(O)O, $C_{3-7}$ cycloalkyl, phenyl (itself optionally substituted by halogen, $C_{1-4}$ alkyl, $CF_3$, $C_{1-4}$ alkoxy or $OCF_3$) or heteroaryl (itself optionally substituted by halogen, $C_{1-4}$ alkyl, $CF_3$, $C_{1-4}$ alkoxy or $OCF_3$); and $C_{3-7}$ cycloalkyl may additionally be optionally substituted by $C_{1-4}$ alkyl;

n is 0, 1 or 2;

$R^1$ and $R^{1a}$ are, independently, hydrogen, $C_{1-4}$ alkyl or $C_{1-4}$ haloalkyl;

$R^2$ is hydrogen or $C_{1-4}$ alkyl;

$R^3$ is aryl, ($C_{1-4}$ alkyl)aryl, ($C_{1-4}$ alkoxy)aryl, ($C_{1-4}$ alkylthio)aryl, heteroaryl, ($C_{1-4}$ alkyl)heteroaryl, ($C_{1-4}$ alkoxy)heteroaryl or ($C_{1-4}$ alkylthio)heteroaryl [wherein the phenyl rings are optionally substituted by halo, $C_{1-6}$ alkyl (optionally substituted by $C_{1-6}$alkoxy), $C_{1-6}$ alkoxy, $C_{1-4}$ alkylthio, $C_{3-6}$ cycloalkylthio, $C_{1-4}$ haloalkyl, $C_{1-4}$ haloalkoxy, nitro, cyano, OH, C(O)$_2$H, C(O)$_2$($C_{1-4}$ alkyl), S(O)$_2$($C_{1-4}$ alkyl), S(O)$_2$($C_{3-6}$ cycloalkyl), S(O)$_2$NH$_2$, S(O)$_2$NH($C_{1-4}$ alkyl), S(O)$_2$N($C_{1-4}$ alkyl)$_2$, benzyloxy, imidazolyl, C(O)($C_{1-4}$ alkyl), C(O)NH$_2$, C(O)NH($C_{1-4}$ alkyl), C(O)N($C_{1-4}$ alkyl)$_2$, NHC(O)($C_{1-4}$ alkyl), $NR^5R^6$, $OCH_2O$, $OCH_2CH_2O$ or $OCH_2CH_2$; the heteroaryl ring is optionally substituted by halo, $C_{1-6}$alkyl (optionally substituted by $C_{1-6}$alkoxy), $C_{1-6}$alkoxy, $C_{1-4}$ alkylthio, $C_{3-6}$ cycloalkylthio, $C_{1-4}$ haloalkyl, $C_{1-4}$ haloalkoxy, nitro, cyano, OH, C(O)$_2$H, C(O)$_2$($C_{1-4}$ alkyl), S(O)$_2$($C_{1-4}$ alkyl), S(O)$_2$($C_{3-6}$ cycloalkyl), S(O)$_2$NH$_2$, S(O)$_2$NH($C_{1-4}$ alkyl), S(O)$_2$N($C_{1-4}$ alkyl)$_2$, benzyloxy, imidazolyl, C(O)($C_{1-4}$ alkyl), C(O)NH$_2$, C(O)NH($C_{1-4}$ alkyl), C(O)N($C_{1-4}$ alkyl)$_2$, NHC(O)($C_{1-4}$ alkyl) or $NR^5R^6$];

$R^4$ is hydrogen, hydroxy, halogen, $C_{1-4}$ alkyl or $C_{1-4}$ haloalkyl;

W is hydrogen or phenyl, $C_{3-7}$ cycloalkyl, thienyl, isoxazolyl, pyrazolyl, pyridinyl or pyrimidinyl all of which are optionally substituted by halo, $C_{1-4}$alkyl (optionally substituted by $C_{1-6}$ alkoxy), $C_{1-6}$ alkoxy, $C_{1-4}$ alkylthio, $C_{1-4}$ haloalkyl, $C_{1-4}$ haloalkoxy, nitro, cyano, OH, C(O)$_2$H, C(O)$_2$($C_{1-4}$ alkyl), S(O)$_2$($C_{1-4}$ alkyl), S(O)$_2$NH$_2$, S(O)$_2$NH($C_{1-4}$alkyl), S(O)$_2$N($C_{1-4}$ alkyl)$_2$, benzyloxy, imidazolyl, C(O)($C_{1-4}$ alkyl), C(O)NH$_2$, C(O)NH($C_{1-4}$ alkyl), C(O)N($C_{1-4}$ alkyl)$_2$, NHC(O)($C_{1-4}$ alkyl) or $NR^7R^8$;

X is $CH_2$, O, S, S(O), S(O)$_2$, NH or N($C_{1-4}$ alkyl);

Y is hydrogen, halo, $C_{1-6}$alkyl, $C_{1-6}$alkoxy, $C_{1-4}$ alkylthio, $C_{1-4}$ haloalkyl, $C_{1-4}$ haloalkoxy, nitro, cyano, OH, C(O)$_2$H, C(O)$_2$($C_{1-4}$ alkyl), S(O)$_2$($C_{1-4}$ alkyl), S(O)$_2$NH$_2$, S(O)$_2$NH($C_{1-4}$ alkyl), S(O)$_2$N($C_{1-4}$ alkyl)$_2$, benzyloxy, imidazolyl, C(O)($C_{1-4}$ alkyl), C(O)NH$_2$, C(O)NH($C_{1-4}$ alkyl), C(O)N($C_{1-4}$ alkyl)$_2$, NHC(O)($C_{1-4}$ alkyl) or $NR^9R^{10}$;

$R^5$, $R^6$, $R^7$, $R^8$, $R^9$ and $R^{10}$ are, independently, hydrogen, $C_{1-4}$ alkyl or $C_{3-7}$ cycloalkyl;

$R^{11}$ is hydrogen or $C_{1-10}$ alkyl;

$R^{12}$ and $R^{13}$ are, independently, hydrogen or $C_{1-6}$ alkyl;

or a pharmaceutically acceptable salt thereof.

For the avoidance of doubt, the definitions of groups and substituents for compounds of formula Ic is as follows and is distinct and separate from those for formula I and Ib.

Compounds of formula (Ic) can exist in different isomeric forms (such as enantiomers, diastereomers, geometric isomers or tautomers). The present invention covers all such isomers and mixtures thereof in all proportions.

Suitable salts include acid addition salts such as a hydrochloride, hydrobromide, phosphate, acetate, trifluoroacetate, fumarate, maleate, tartrate, citrate, oxalate, methanesulphonate, p-toluenesulphonate, succinate, glutarate or malonate.

The compounds of formula (Ic) may exist as solvates (such as hydrates) and the present invention covers all such solvates.

Alkyl groups and moieties are straight or branched chain and are, for example, methyl, ethyl, n-propyl, iso-propyl, n-butyl, sec-butyl or tert-butyl.

Haloalkyl comprises, for example, 1 to 6, such as 1, 2, 3, 4 or 5 halogen (such as fluorine or chlorine) atoms. It is, for example, $CHF_2$, $CF_3$, $CH_2CF_3$, $C_2F_5$ or $CH_2Cl$. Further examples are $CH_2F$, $CHFCl$, $CCl_3$ or $CHCl_2$.

Haloalkoxy comprises, for example, 1 to 6, such as 1, 2, 3, 4 or 5 halogen (such as fluorine or chlorine) atoms. It is, for example, $OCHF_2$, $OCF_3$, $OCH_2CF_3$, $OC_2F_5$ or $OCH_2Cl$.

Cycloalkyl is for example, cyclopropyl, cyclopentyl or cyclohexyl. It can also be cyclobutyl.

Aryl is, for example, phenyl or naphthyl. In one aspect of the invention aryl is phenyl. Heteroaryl is, for example, a mono-cyclic, aromatic 5- or 6-membered ring containing 1 or 2 nitrogen atoms, said ring being optionally fused to a benzene ring. Heteroaryl is, for example, pyrrolyl, pyrazolyl, imidazolyl, pyridinyl, pyrimidinyl, indolyl, indazolyl, benzofuryl or benzothienyl. Heteroaryl may also be quinolinyl or isoquinolinyl.

When phenyl is substituted by $OCH_2O$, $OCH_2CH_2O$ or $OCH_2CH_2$ these groups link to adjacent carbons on the phenyl ring.

($C_{1-4}$ Alkyl)aryl is for example benzyl. ($C_{1-4}$ Alkoxy)aryl is, for example, $CH_2O$-phenyl. ($C_{1-4}$ Alkylthio)aryl is, for example, $CH_2S$-phenyl. ($C_{1-4}$ Alkyl)heteroaryl is, for example, $CH_2$-pyridinyl. ($C_{1-4}$Alkoxy)heteroaryl is, for example, $CH_2O$-pyridinyl. ($C_{1-4}$ Alkylthio)heteroaryl is, for example, $CH_2S$-pyridinyl.

In one particular aspect the present invention provides a compound of formula (Ic) wherein: A is $C_{1-10}$ alkyl, $C_{1-10}$ alkoxy, $C_{1-10}$ alkylthio, ($C_{1-10}$ alkyl)($R^{11}$)N or $C_{3-7}$ cycloalkyl, all of which are optionally substituted by halogen, cyano, nitro, hydroxy, thio, $C_{1-6}$ alkoxy, $C_{1-6}$ alkyl$S(O)_n$, $R^{12}R^{13}N$, $C_{3-7}$ cycloalkyl, phenyl (itself optionally substituted by halogen, $C_{1-4}$ alkyl, $CF_3$, $C_{1-4}$ alkoxy or $OCF_3$) or heteroaryl (itself optionally substituted by halogen, $C_{1-4}$ alkyl, $CF_3$, $C_{1-4}$ alkoxy or $OCF_3$); and $C_{3-7}$ cycloalkyl may additionally be optionally substituted by $C_{1-4}$ alkyl; n is 0, 1 or 2; $R^1$ and $R^{1a}$ are, independently, hydrogen, $C_{1-4}$ alkyl or $C_{1-4}$ haloalkyl; $R^2$ is hydrogen or $C_{1-4}$ alkyl; $R^3$ is phenyl or heteroaryl [wherein phenyl and heteroaryl are optionally substituted by halo, $C_{1-6}$ alkyl (optionally substituted by $C_{1-6}$ alkoxy), $C_{1-6}$ alkoxy, $C_{1-4}$ alkylthio, $C_{1-4}$ haloalkyl, $C_{1-4}$ haloalkoxy, nitro, cyano, OH, $C(O)_2H$, $C(O)_2(C_{1-4}$ alkyl), $S(O)_2(C_{1-4}$ alkyl), $S(O)_2NH_2$, $S(O)_2NH(C_{1-4}$ alkyl), $S(O)_2N(C_{1-4}$ alkyl)$_2$, benzyloxy, imidazolyl, $C(O)(C_{1-4}$ alkyl), $C(O)NH_2$, $C(O)NH(C_{1-4}$ alkyl), $C(O)N(C_{1-4}$ alkyl)$_2$, NHC(O)($C_{1-4}$ alkyl) or $NR^5R^6$; and phenyl may additionally be optionally substituted on adjacent carbons by $OCH_2O$, $OCH_2CH_2O$ or $OCH_2CH_2$]; $R^4$ is hydrogen, hydroxy, halogen, $C_{1-4}$ alkyl or $C_{1-4}$ haloalkyl; W is hydrogen, phenyl, $C_{3-7}$ cycloalkyl, thienyl, isoxazolyl, pyrazolyl, pyridinyl or pyrimidinyl all of which are optionally substituted by halo, $C_{1-6}$alkyl (optionally substituted by $C_{1-6}$ alkoxy), $C_{1-6}$ alkoxy, $C_{1-4}$ alkylthio, $C_{1-4}$ haloalkyl, $C_{1-4}$ haloalkoxy, nitro, cyano, OH, $C(O)_2H$, $C(O)_2(C_{1-4}$ alkyl), $S(O)_2(C_{1-4}$ alkyl), $S(O)_2NH_2$, $S(O)_2NH(C_{1-4}$ alkyl), $S(O)_2N(C_{1-4}$ alkyl)$_2$, benzyloxy, imidazolyl, $C(O)(C_{1-4}$ alkyl), $C(O)NH_2$, $C(O)NH(C_{1-4}$ alkyl), $C(O)N(C_{1-4}$ alkyl)$_2$, NHC(O)($C_{1-4}$ alkyl) or $NR^7R^8$; X is $CH_2$, O, S, S(O), $S(O)_2$, NH or $N(C_{1-4}$ alkyl); Y is hydrogen, halo, $C_{1-6}$alkyl, $C_{1-6}$alkoxy, $C_{1-4}$ alkylthio, $C_{1-4}$ haloalkyl, $C_{1-4}$ haloalkoxy, nitro, cyano, OH, $C(O)_2H$, $C(O)_2(C_{1-4}$ alkyl), $S(O)_2(C_{1-4}$ alkyl), $S(O)_2NH_2$, $S(O)_2NH(C_{1-4}$ alkyl), $S(O)_2N(C_{1-4}$ alkyl)$_2$, benzyloxy, imidazolyl, $C(O)(C_{1-4}$ alkyl), $C(O)NH_2$, $C(O)NH(C_{1-4}$ alkyl), $C(O)N(C_{1-4}$ alkyl)$_2$, NHC(O)($C_{1-4}$ alkyl) or $NR^9R^{10}$; $R^5$, $R^6$, $R^7$, $R^8$, $R^9$ and $R^{10}$ are, independently, hydrogen, $C_{1-4}$ alkyl or $C_{3-7}$ cycloalkyl; $R^{11}$ is hydrogen or $C_{1-10}$ alkyl; $R^{12}$ and $R^{13}$ are, independently, hydrogen or $C_{1-4}$ alkyl; or a pharmaceutically acceptable salt thereof.

In a further aspect the present invention provides a compound of formula (Ic) wherein A is $C_{3-7}$ cycloalkyl (optionally substituted by halogen or $C_{1-4}$ alkyl), $C_{1-4}$ alkyl (such as ethyl or tert-butyl), $C_{1-4}$ haloalkyl (such as $CF_3$), $C_{1-4}$ alkoxy (such as methoxy) $C_{1-4}$ hydroxyalkyl (such as $HOCH_2$, $HO(CH_3)CH$ or $HO(CH_3)_2C$), $C_{1-4}$ alkoxy($C_{1-4}$ alkyl) (such as $CH_3OCH_2$) or $C_{1-4}$ alkylC(O)O($C_{1-4}$ alkyl) (such as $CH_3C(O)OCH_2$).

In another aspect the present invention provides a compound of formula (Ic) wherein A is $C_{3-7}$ cycloalkyl (optionally substituted by halogen or $C_{1-6}$ alkyl).

In a further aspect the present invention provides a compound of formula (Ic) wherein A is $C_{1-4}$ alkyl (such as ethyl), $C_{1-4}$ haloalkyl (such as $CF_3$) or $C_{1-4}$ alkoxy (such as methoxy).

In another aspect the present invention provides a compound of formula (Ic) wherein $R^1$ is $C_{1-4}$ alkyl (for example methyl).

In yet another aspect the present invention provides a compound of formula (Ic) wherein $R^{1a}$ is hydrogen.

In a further aspect the present invention provides a compound of formula (Ic) wherein $R^2$ is hydrogen.

In a still further aspect the present invention provides a compound of formula (Ic) wherein $R^3$ is phenyl optionally substituted by halo, $C_{1-6}$ alkyl (optionally substituted by $C_{1-6}$ alkoxy), $C_{1-6}$alkoxy, $C_{1-4}$ alkylthio, $C_{1-4}$ haloalkyl, $C_{1-4}$ haloalkoxy, nitro, cyano, OH, $C(O)_2H$, $C(O)_2(C_{1-4}$ alkyl), $S(O)_2(C_{1-4}$ alkyl), $S(O)_2NH_2$, $S(O)_2NH(C_{1-4}$ alkyl), $S(O)_2N(C_{1-4}$ alkyl)$_2$, benzyloxy, imidazolyl, $C(O)(C_{1-4}$ alkyl), $C(O)NH_2$, $C(O)NH(C_{1-4}$ alkyl), $C(O)N(C_{1-4}$ alkyl)$_2$, NHC(O)($C_{1-4}$ alkyl) or $NR^5R^6$; wherein $R^5$ and $R^6$ are, independently, hydrogen, $C_{1-4}$ alkyl or $C_{3-7}$ cycloalkyl.

In a further aspect the present invention provides a compound of formula (Ic) wherein $R^3$ is phenyl optionally substituted by halo, $C_{1-6}$ alkyl (such as ethyl), $C_{1-6}$ alkoxy (such as methoxy), $C_{1-4}$ alkylthio (such as $CH_3S$ or $C_2H_5S$), $C_{3-6}$ cycloalkylthio (such as cyclopropylthio), $C_{1-4}$ haloalkyl (such as $CF_3$) or $S(O)_2(C_{1-4}$ alkyl) (such as $S(O)_2CH_3$).

In a still further aspect the present invention provides a compound of formula (Ic) wherein Y is hydrogen.

In another aspect the present invention provides a compound of formula (Ic) wherein $R^4$ is hydrogen.

In yet another aspect the present invention provides a compound of formula (Ic) wherein W is phenyl optionally substituted by halo, $C_{1-6}$ alkyl (optionally substituted by $C_{1-6}$ alkoxy), $C_{1-6}$ alkoxy, $C_{1-4}$ alkylthio, $C_{1-4}$ haloalkyl, $C_{1-4}$ haloalkoxy, nitro, cyano, OH, $C(O)_2H$, $C(O)_2(C_{1-4}$ alkyl), $S(O)_2(C_{1-4}$ alkyl), $S(O)_2NH_2$, $S(O)_2NH(C_{1-4}$ alkyl), $S(O)_2N(C_{1-4}$ alkyl)$_2$, benzyloxy, imidazolyl, $C(O)(C_{1-4}$ alkyl), $C(O)NH_2$, $C(O)NH(C_{1-4}$ alkyl), $C(O)N(C_{1-4}$ alkyl)$_2$, NHC(O)($C_{1-4}$ alkyl) or $NR^7R^8$; wherein $R^7$ and $R^8$ are, independently, hydrogen, $C_{1-4}$ alkyl or $C_{3-7}$ cycloalkyl.

In another aspect the present invention provides a compound of formula (Ic) wherein W is phenyl optionally substituted by halo (such as fluoro), $C_{1-6}$ alkyl, $C_1$ alkoxy, $C_{1-4}$ haloalkyl or $C_{1-4}$ haloalkoxy.

In a further aspect the present invention provides a compound of formula (Ic) wherein X is O, S, S(O) or $S(O)_2$.

In a still further aspect the present invention provides a compound of formula (Ic) wherein X is O.

In a further aspect the present invention provides a compound of formula (Ic) wherein A is $C_{3-7}$ cycloalkyl (optionally substituted by halogen or $C_{1-6}$ alkyl), $C_{1-4}$ alkyl (such as ethyl or tert-butyl), $C_{1-4}$ haloalkyl (such as $CF_3$), $C_{1-4}$ alkoxy (such as methoxy) $C_{1-4}$ hydroxyalkyl (such as $HOCH_2$, $HO(CH_3)CH$ or $HO(CH_3)_2C$), $C_{1-4}$ alkoxy($C_{1-4}$ alkyl) (such as $CH_3OCH_2$) or $C_{1-4}$ alkylC(O)O($C_{1-4}$ alkyl) (such as $CH_3C(O)OCH_2$); $R^1$ is $C_{1-4}$ alkyl (for example methyl); $R^{1a}$ is hydrogen; $R^2$ is hydrogen; $R^3$ is phenyl optionally substituted by halo, $C_{1-6}$alkyl (such as ethyl), $C_1$ alkoxy (such as methoxy), $C_{1-4}$ alkylthio (such as $CH_3S$ or $C_2H_5S$), $C_{3-6}$ cycloalkylthio (such as cyclopropylthio), $C_{1-4}$ haloalkyl (such as $CF_3$) or $S(O)_2(C_{1-4}$ alkyl) (such as $S(O)_2CH_3$); Y is hydrogen; $R^4$ is hydrogen; W is phenyl optionally substituted by halo (such as fluoro), $C_{1-6}$ alkyl, $C_{1-6}$ alkoxy, $C_{1-4}$ haloalkyl or $C_{1-4}$ haloalkoxy; and X is O.

In a further aspect the present invention provides a compound of formula (Ic) having the stereochemistry shown in the structure immediately below:

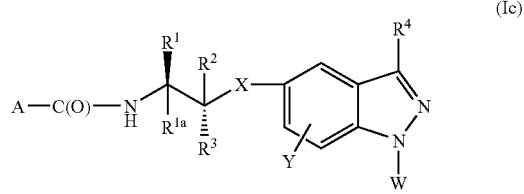

In another aspect the present invention provides the individual compound:
N-((1S,2R)-2-{[1-(4-fluorophenyl)-1H-indazol-5-yl]oxy}-1-methyl-2-phenylethyl)cyclopropanecarboxamide;
2,2,2-Trifluoro-N-((1S,2R)-2-{[1-(4-fluorophenyl)-1H-indazol-5-yl]oxy}-1-methyl-2-phenylethyl)acetamide;
N-((1S,2R)-2-{[1-(4-fluorophenyl)-1H-indazol-5-yl]oxy}-1-methyl-2-phenylethyl)propanamide;
Methyl ((1S,2R)-2-{[1-(4-fluorophenyl)-1H-indazol-5-yl]oxy}-1-methyl-2-phenylethyl)carbamate;
N-[(1R,2S)-1-[1-(4-fluorophenyl)indazol-5-yl]oxy-1-phenyl-propan-2-yl]-2-hydroxy-2-methyl-propanamide;
2,2,2-trifluoro-N-[(1R,2S)-1-[1-(4-fluorophenyl)indazol-5-yl]oxy-1-(3-methoxyphenyl)propan-2-yl]acetamide;
N-[(1R,2S)-1-(4-ethylphenyl)-1-[1-(4-fluorophenyl)indazol-5-yl]oxy-propan-2-yl]-2-hydroxy-acetamide;
N-{2-[1-(4-Fluoro-phenyl)-1H-indazo-5-yloxy]-2-(3-methoxy-phenyl)-1-methyl-ethyl}-2,2-dimethyl-propionamide;
N-[(1R,2S)-1-[1-(4-fluorophenyl)indazol-5-yl]oxy-1-(4-methylsulfanylphenyl)propan-2-yl]-2-methoxy-acetamide;
N-[(1R,2S)-1-[1-(4-fluorophenyl)indazol-5-yl]oxy-1-(4-methylsulfanylphenyl)propan-2-yl]carbamoylmethyl acetate;
N-[(1R,2S)-1-[1-(4-fluorophenyl)indazol-5-yl]oxy-1-(4-methylsulfanylphenyl)propan-2-yl]-2-hydroxy-acetamide;
N-[(1R,2S)-1-[1-(4-fluorophenyl)indazol-5-yl]oxy-1-(4-methylsulfonylphenyl)propan-2-yl]-2-hydroxy-acetamide;
2,2,2-trifluoro-N-[(1R,2S)-1-[1-(4-fluorophenyl)indazol-5-yl]oxy-1-(4-methylsulfanylphenyl)propan-2-yl]acetamide;
N-[(1R,2S)-1-(4-Ethylsulfanylphenyl)-1-[1-(4-fluorophenyl)indazol-5-yl]oxy-propan-2-yl]-2,2,2-trifluoro-acetamide; or,
N-[(1R,2S)-1-(4-cyclopropylsulfanylphenyl)-1-[1-(4-fluorophenyl)indazol-5-yl]oxy-propan-2-yl]-2,2,2-trifluoro-acetamide;

or a pharmaceutically acceptable salt thereof.

Compounds of the present invention have been named with the aid of computer software (ACDLabs 8.0/Name(IUPAC)).

Compounds of formula (I), (Ib) or (Ic) may include an asymmetric centre and be chiral in nature. Where the compound is chiral, it may be in the form of a single stereoisomer, such as a enantiomer, or it may be in the form of mixtures of these stereoisomers in any proportions, including racemic mixtures. Therefore, all enantiomers, diastereomers, racemates and mixtures thereof are included within the scope of the invention. The various optical isomers may be isolated by separation of a racemic mixture of the compounds using conventional techniques, for example, fractional crystallisation, or HPLC. Alternatively the optical isomers may be obtained by asymmetric synthesis, or by synthesis from optically active starting materials.

Compounds of formula (I), (Ib) or (Ic) above may be converted to a pharmaceutically acceptable salt thereof, preferably an acid addition salt such as a hydrochloride, hydrobromide, phosphate, sulphate, acetate, ascorbate, benzoate, fumarate, hemifumarate, furoate, succinate, maleate, tartrate, citrate, oxalate, xinafoate, methanesulphonate, p-toluenesulphonate, benzenesulphonate, ethanesulphonate, 2-naphthalenesulfonate, mesytilenesulfonate, nitric acid, 1,5-naphthalene-disulphonate, p-xylenesulphonate, aspartate or glutamate.

They may also include basic addition salts such as an alkali metal salt for example sodium or potassium salts, an alkaline earth metal salt for example calcium or magnesium salts, a transition metal salt such as a zinc salt, an organic amine salt for example a salt of triethylamine, diethylamine, morpholine, N-methylpiperidine, N-ethylpiperidine, piperazine, procaine, dibenzylamine, N,N-dibenzylethylamine, choline or 2-aminoethanol or amino acids for example lysine or arginine.

The compounds of formula (I), (Ib) or (Ic) and pharmaceutically acceptable salts thereof may exist in solvated, for example hydrated, as well as unsolvated forms, or as cocrystals and the present invention encompasses all such forms.

Process

The compounds of formula (I) can be prepared using or adapting methods disclosed in the art, or by using or adapting the method disclosed in the Example below. Starting materials for the preparative methods are either commercially available or can be prepared by using or adapting literature methods.

One embodiment relates to a process for the preparation of compounds of formula (I) by coupling a compound of formula (II):

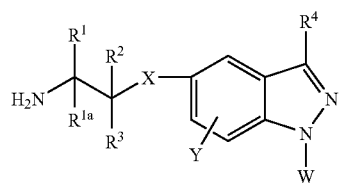

with acylation reagents of formula (IIIa) or formula (IIIb)

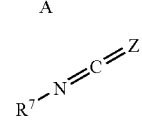

wherein $R^1$, $R^{1a}$, $R^2$, $R^3$, $R^4$, $R^7$, A, W, X, Y and Z are defined as in compounds of formula (I), and $L^1$ is a leaving group (such as halogen (for example chloro) or, when $L^1$=OH, a leaving group generated by reaction of a coupling reagent (such as HATU with a carboxylic acid). The reaction may be performed in a suitable solvent (such as pyridine, THF or DMF), in the presence of a suitable base (such as a tri($C_{1-6}$ alkyl)amine, for example diisopropylethylamine, or pyridine) and at a suitable temperature (such as −10° to 50° C.).

Another embodiment relates to a process for the preparation of compounds of formula (II) according to steps a, b or c.

a) A compound of formula (II), wherein X is O, S or NH, may be prepared by coupling a compound of formula (IV)

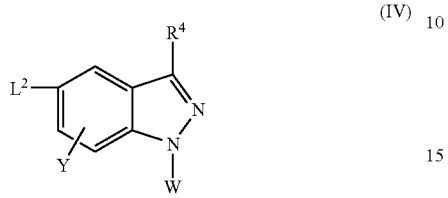

(IV)

wherein $R^4$, W and Y are defined as in compounds of formula (I) and $L^2$ is a leaving group (such as halogen or triflate) with a compound of formula (V)

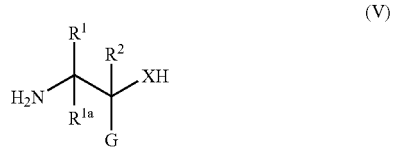

(V)

wherein $R^1$, $R^{1a}$, $R^2$ and $R^3$ are defined as in compounds of formula (I) and G corresponds to $R^3$ or a protected precurser to $R^3$.

The reaction can be performed in a suitable solvent (such as an aromatic solvent, for example toluene) or a polar, aprotic solvent, such as DMF or butyronitril, in the presence of a suitable base (such as a alkali metal alkoxide (for example sodium tert-butoxide) or, cesium carbonate, preferable mediated by a suitable metal catalyst such as Copper(I) iodide at a suitable temperature (for example in the range 80° to 120° C.).

Or, b) A compound of formula (II) may be prepared by reacting a compound of formula (VII)

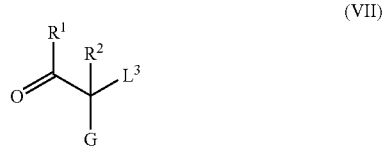

(VII)

with a compound of formula (VIII)

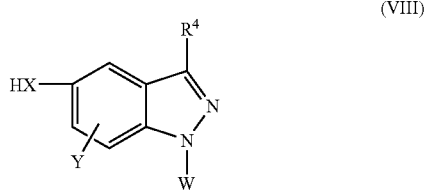

(VIII)

wherein $R^1$, $R^2$, $R^4$, $R^3$, X, W and Y are defined as in compounds of formula (I), G corresponds to $R^3$ or a protected precurser to $R^3$ and $L^3$ is a leaving group (such as halogen, mesylate or tosylate).

The reaction can be performed in a suitable solvent (such as DCM, DMF or acetonitrile), in the presence of a suitable base (such as an alkali metal carbonate, for example cesium carbonate or potassium carbonate) at a suitable temperature (for example in the range −10 to 50° C.), followed by a subsequent reductive amination step using or adopting literature methods.

Or, c) a compound of formula (II) may be prepared by reacting a compound of formula (VIII) with a compound of formula (IX)

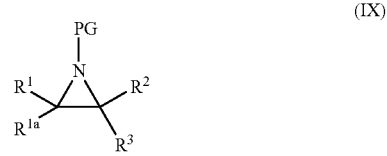

(IX)

wherein $R^1$, $R^{1a}$, $R^2$ and $R^3$ are defined as in compounds of formula (I) and PG is a suitable protecting group such as BOC, Ms, Ns, Ts or related carbonyl- or sulfonyl residues.

The reaction can be performed in a suitable solvent such as DCM or toluene in the presence of a suitable base such as NaH or KOtBu, followed by a deprotection step using or adopting literature methods.

As a specific case of a compound of formula (V), a compound of formula (X) might be used to prepare a compound of formula (II)

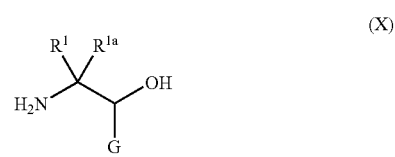

(X)

wherein $R^1$, $R^{1a}$ and G are defined as in compounds of formula (V).

Compounds of formula (X) may be prepared by reacting a nucleophile G-M with a carbonyl compound of formula (XI) followed reduction and subsequent deprotection of the intermediate of formula (XII)

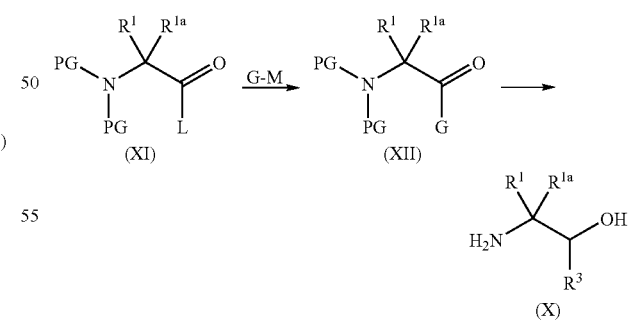

wherein $R^1$, $R^{1a}$ and $R^3$ are defined as in compounds of formula (I) and G corresponds to $R^3$ or a protected precurser to $R^3$ and L is a leaving group (such as alkoxy, methoxy(methyl) amino). M is a metal such as $L^1$ or Mg-halide.

The addition of the nucleophile may be performed in a suitable aprotic solvent such as THF at moderate temperature between −10 and 50° C. The following reduction and deprotection steps might be carried out by using or adopting literature methods.

Alternatively, compounds of formula (X) may be prepared by a reaction of a nuceophile G-M with an aldehyde of formula (XIII) and a subsequent deprotection.

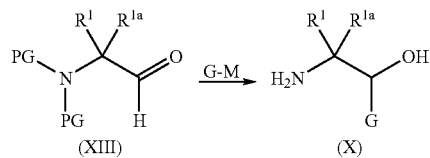

wherein $R^1$, $R^{1a}$ and $R^3$ are defined as in compounds of formula (I) and G corresponds to $R^3$ or a protected precurser to $R^3$ and PG is a protecting group or hydrogen. M is a metal such as an alkali metal (e.g. Li) or Mg-halide.

The reaction may be performed by following disclosed protocols for addition of carbanions to aldehydes.

Another way to prepare a compound of formula (X) is the reaction of nitroalkyles of formula (XIV) with aldehydes of formula (XV), followed by reduction of the nitro function

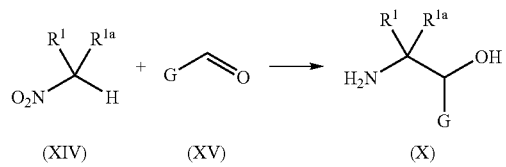

wherein $R^1$ and $R^{1a}$ and $R^3$ are defined as in compounds of formula (I), G corresponds to $R^3$ or a protected precurser to $R^3$ and PG is a protecting group or hydrogen.

Both steps may be carried out by following or adopting literature methods.

Medical Use

Because of their ability to bind to the glucocorticoid receptor the compounds of formula (I), (Ib) or (Ic) are useful as anti-inflammatory agents, and can also display antiallergic, immunosuppressive and anti-proliferative actions. Thus, a compound of formula (I), (Ib) or (Ic), or a pharmaceutically acceptable salt thereof can be used as a medicament for the treatment or prophylaxis of one or more of the following pathologic conditions (disease states) in a mammal (such as a human):

(i) Lung diseases, which coincide with inflammatory, allergic and/or proliferative processes:
chronically obstructive lung diseases of any origin, mainly bronchial asthma, chronic obstructive pulmonary disease
bronchitis of different origins
Adult respiratory distress syndrome (ARDS), acute respiratory distress syndrome
Bronchiectases
all forms of restrictive lung diseases, mainly allergic alveolitis
all forms of pulmonary edema, mainly toxic pulmonary edema
sarcoidoses and granulomatoses, such as Boeck's disease (ii) Rheumatic diseases/auto-immune diseases/degenerative joint diseases, which coincide with inflammatory, allergic and/or proliferative processes:
all forms of rheumatic diseases, especially rheumatoid arthritis, acute rheumatic fever, polymyalgia rheumatica, collagenoses, Behçet's disease
reactive arthritis
inflammatory soft-tissue diseases of other origins
arthritic symptoms in degenerative joint diseases (arthroses)
traumatic arthritides
collagen diseases of other origins, for example systemic lupus erythematodes, discoid lupus erythematosus, sclerodermia, polymyositis, dermatomyositis, polyarteritis nodosa, temporal arteritis
Sjögren's syndrome, Still syndrome, Felty's syndrome
Vitiligo
Soft-tissue rheumatism (iii) Allergies, which coincide with inflammatory, allergic and/or proliferative processes:
All forms of allergic reactions, for example Quincke's edema, insect bites, allergic reactions to pharmaceutical agents, blood derivatives, contrast media, etc., anaphylactic shock, urticaria, contact dermatitis (e.g. allergic and irritative), allergic vascular diseases
Allergic vasculitis
inflammatory vasculitis (iv) Vascular inflammations (vasculitides)
Panarteritis nodosa, temporal arteritis, erythema nodosum
Polyarteris nodosa
Wegner's granulomatosis
Giant-cell arteritis (v) Dermatological diseases, which coincide with inflammatory, allergic and/or proliferative processes:
atopic dermatitis (mainly in children)
exfoliative dermatitis,
psoriasis
erythematous diseases, triggered by different noxae, for example radiation, chemicals, burns, etc.
acid burns
bullous dermatoses, such as, for example, autoimmune pemphigus vulgaris, bullous pemphigoid
diseases of the lichenoid group
itching (for example of allergic origins)
all forms of eczema, such as, for example, atopic eczema or seborrheal eczema rosacea
pemphigus vulgaris
eiythema exudativum multiforme
erythema nodosum
balanitis
Pruritis, such as, for example, allergic origin)
Manifestation of vascular diseases
vulvitis
inflammatory hair loss, such as alopecia areata
cutaneous T-cell lymphoma
Rashes of any origin or dermatoses
Psoriasis and parapsoriasis groups
Pityriasis rubra pilaris (vi) Nephropathies, which coincide with inflammatory, allergic and/or proliferative processes:
nephrotic syndrome
all nephritides, such as, for example, glomerulonephritis (vii) Liver diseases, which coincide with inflammatory, allergic and/or proliferative processes:
acute liver cell decomposition
acute hepatitis of different origins, for example virally-, toxically- or pharmaceutical agent-induced
chronically aggressive and/or chronically intermittent hepatitis (viii) Gastrointestinal diseases, which coincide with inflammatory, allergic and/or proliferative processes:
regional enteritis (Crohn's disease)
Gastritis
Reflux esophagitis
ulcerative colitis
gastroenteritis of other origins, for example native sprue (ix) Proctological diseases, which coincide with inflammatory, allergic and/or proliferative processes:
anal eczema
fissures
haemorrhoids
idiopathic proctitis (x) Eye diseases, which coincide with inflammatory, allergic and/or proliferative processes:
allergic keratitis, uvenitis iritis
conjunctivitis
blepharitis
optic neuritis
chorioiditis
sympathetic ophthalmia (xi) Diseases of the ear-nose-throat area, which coincide with inflammatory, allergic and/or proliferative processes:
allergic rhinitis, hay fever
otitis extema, for example caused by contact dermatitis, infection, etc.
otitis media (xii) Neurological diseases, which coincide with inflammatory, allergic and/or proliferative processes:
cerebral edema, mainly tumor-induced cerebral edema
multiple sclerosis
acute encephalomyelitis
different forms of convulsions, for example infantile nodding spasms
Meningitis
spinal cord injury
Stroke (xiii) Blood diseases, which coincide with inflammatory, allergic and/or proliferative processes:
acquired haemolytic anemia
thrombocytopenia such as for example idiopathic thrombocytopenia
M. Hodgkins or Non-Hodgkins lymphomas,
thrombocythemias,
erythrocytoses (xiv) Tumor diseases, which coincide with inflammatory, allergic and/or proliferative processes:
acute lymphatic leukaemia
malignant lymphoma
lymphogranulomatoses
lymphosarcoma
extensive metastases, mainly in breast and prostate cancers (xv) Endocrine diseases, which coincide with inflammatory, allergic and/or proliferative processes:
endocrine orbitopathy
thyrotoxic crisis
de Quervain's thyroiditis
Hashimoto's thyroiditis
Hyperthyroidism
Basedow's disease
Granulomatous thyroiditis
Lymphadenoid goiter (xvi) Transplants, which coincide with inflammatory, allergic and/or proliferative processes;

(xvii) Severe shock conditions, which coincide with inflammatory, allergic and/or
proliferative processes, for example anaphylactic shock (xviii) Substitution therapy, which coincides with inflammatory, allergic and/or
proliferative processes, with:
innate primary suprarenal insufficiency, for example congenital adrenogenital syndrome acquired primary suprarenal insufficiency, for example Addison's disease, autoimmune adrenalitis, meta-infective, tumors, metastases, etc.
innate secondary suprarenal insufficiency, for example congenital hypopituitarism acquired secondary suprarenal insufficiency, for example meta-infective, tumors, etc.

(xix) Emesis, which coincides with inflammatory, allergic and/or proliferative processes:
for example in combination with a 5-HT3-antagonist in cytostatic-agent-induced vomiting.

(xx) Pains of inflammatory origins, e.g., lumbago
Without prejudice to the foregoing, the compounds of formula (I), (Ib) or (Ic) can also be used to treat disorders such as: diabetes type I (insulin-dependent diabetes), Guillain-Barrésyndrome, restenoses after percutaneous transluminal angioplasty, Alzheimer's disease, acute and chronic pain, arteriosclerosis, reperfusion injury, thermal injury, multiple organ injury secondary to trauma, acute purulent meningitis, necrotizing enterocolitis and syndromes associated with hemodialysis, leukopheresis, granulocyte transfusion, Conies Syndrome, primary and secondary hyperaldosteronism, increased sodium retention, increased magnesium and potassium excretion (diuresis), increased water retention, hypertension (isolated systolic and combined systolic/diastolic), arrhythmias, myocardial fibrosis, myocardial infarction, Bartter's Syndrome, disorders associated with excess catecholamine levels, diastolic and systolic congestive heart failure (CHF), peripheral vascular disease, diabetic nephropathy, cirrhosis with edema and ascites, oesophageal varicies, muscle weakness, increased melanin pigmentation of the skin, weight loss, hypotension, hypoglycemia, Cushing's Syndrome, obesity, glucose intolerance, hyperglycemia, diabetes mellitus, osteoporosis, polyuria, polydipsia, inflammation, autoimmune disorders, tissue rejection associated with organ transplant, malignancies such as leukemias and lymphomas, rheumatic fever, granulomatous polyarteritis, inhibition of myeloid cell lines, immune proliferation/apoptosis, HPA axis suppression and regulation, hypercortisolemia, modulation of the Th1/Th2 cytokine balance, chronic kidney disease, hypercalcemia, acute adrenal insufficiency, chronic primary adrenal insufficiency, secondary adrenal insufficiency, congenital adrenal hyperplasia, Little's syndrome, systemic inflammation, inflammatory bowel disease, Wegener's granulomatosis, giant cell arthritis, osteoarthritis, angioneurotic edema, tendonitis, bursitis, autoimmune chronic active hepatitis, hepatitis, cinhosis, panniculitis, inflamed cysts, pyoderma gangrenosum, eosinophilic fasciitis, relapsing polychondritis, sarcoidosis Sweet's disease, type 1 reactive leprosy, capillary hemangiomas, lichen planus, erythema nodosum acne, hirsutism, toxic epidermal necrolysis, erythema multiform, psychoses, cognitive disorders (such as memory disturbances) mood disorders (such as depression and bipolar disorder), anxiety disorders and personality disorders.

As used herein the term "congestive heart failure" (CHF) or "congestive heart disease" refers to a disease state of the cardiovascular system whereby the heart is unable to efficiently pump an adequate volume of blood to meet the requirements of the body's tissues and organ systems. Typically, CHF is characterized by left ventricular failure (systolic dysfunction) and fluid accumulation in the lungs, with the underlying cause being attributed to one or more heart or cardiovascular disease states including coronary artery disease, myocardial infarction, hypertension, diabetes, valvular heart disease, and cardiomyopathy. The term "diastolic congestive heart failure" refers to a state of CHF characterized by impairment in the ability of the heart to properly relax and fill with blood. Conversely, the term "systolic congestive heart failure" refers to a state of CHF characterized by impairment in the ability of the heart to properly contract and eject blood.

As will be appreciated by one of skill in the art, physiological disorders may present as a "chronic" condition, or an "acute" episode. The term "chronic", as used herein, means a condition of slow progress and long continuance. As such, a chronic condition is treated when it is diagnosed and treatment continued throughout the course of the disease. Conversely, the term "acute" means an exacerbated event or attack, of short course, followed by a period of remission. Thus, the treatment of physiological disorders contemplates both acute events and chronic conditions. In an acute event, compound is administered at the onset of symptoms and discontinued when the symptoms disappear.

In another aspect the present invention provides the compounds or formula (I), (Ib) or (Ic), or a pharmaceutically acceptable salt thereof, for use in therapy (such as a therapy described above).

In yet another aspect the present invention provides the use of a compound of formula (I), (Ib) or (Ic), or a pharmaceutically acceptable salt thereof, in the manufacture of a medicament for use in the treatment of a glucocorticoid receptor mediated disease state (such as a disease state described above).

In a further aspect the invention provides the use of a compound of formula (I), (Ib) or (Ic), or a pharmaceutically acceptable salt thereof, in the manufacture of a medicament for use in the treatment of an inflammatory condition (such as an arthritic).

In a still further aspect the invention provides the use of a compound of formula (I), (Ib) or (Ic), or a pharmaceutically acceptable salt thereof, in the manufacture of a medicament for use in the treatment of asthma.

In another aspect the invention provides the use of a compound of formula (I), (Ib) or (Ic), or a pharmaceutically acceptable salt thereof, in the manufacture of a medicament for use in the treatment of COPD.

In another aspect the present invention provides the compounds or formula (I), (Ib) or (Ic), or a pharmaceutically acceptable salt thereof, for use in treating an inflammatory condition, asthma and/or COPD.

The present invention further provides a method of treating a glucocorticoid receptor mediated disease state (such as a disease state described above), an inflammatory condition, asthma and/or COPD, in a mammal (such as man), which comprises administering to a mammal in need of such treatment an effective amount of a compound of formula (I), (Ib) or (Ic), or a pharmaceutically acceptable salt thereof.

In the context of the present specification, the term "therapy" and "treatment" also includes prophylaxis and prevention unless there are specific indications to the contrary. The terms "therapeutic" and "therapeutically" should be construed accordingly. In this specification, unless stated otherwise, the terms "inhibitor" and "antagonist" mean a compound that by any means, partly or completely, blocks the transduction pathway leading to the production of a response by the agonist. An agonist may be a full or partial agonist. The term "disorder", unless stated otherwise, means any condition and disease associated with glucocorticoid receptor activity.

Pharmaceutical Composition

In order to use a compound of formula (I), (Ib) or (Ic), or a pharmaceutically acceptable salt thereof, for the therapeutic treatment of a mammal, said active ingredient is normally formulated in accordance with standard pharmaceutical practice as a pharmaceutical composition.

Therefore another aspect the present invention provides a pharmaceutical composition comprising a compound of formula (I), (Ib) or (Ic), or a pharmaceutically acceptable salt thereof, (active ingredient) and a pharmaceutically acceptable adjuvant, diluent or carrier. One embodiment relates to the use of a pharmaceutical composition comprising a compound of formula (I), (Ib) or (Ic), or a pharmaceutically acceptable salt thereof, for treating a glucocorticoid receptor mediated disease state (such as a disease state described above), an inflammatory condition, asthma and/or COPD.

A further aspect the present invention provides a process for the preparation of said composition comprising mixing the active ingredient with a pharmaceutically acceptable adjuvant, diluent or carrier. Depending on the mode of administration, the pharmaceutical composition can comprise from 0.05 to 99% w (percent by weight), for example from 0.05 to 80% w, such as from 0.10 to 70% w (for example from 0.10 to 50% w), of active ingredient, all percentages by weight being based on total composition.

A pharmaceutical composition of the present invention can be administered in a standard manner for the disease condition that it is desired to treat, for example by topical (such as to the lung and/or airways or to the skin), oral, rectal or parenteral administration. Thus, a compound of formula (I), (Ib) or (Ic), or a pharmaceutically acceptable salt thereof, may be formulated into the form of, for example, an aerosol, a powder (for example dry or dispersible), a tablet, a capsule, a syrup, a granule, an aqueous or oily solution or suspension, an (lipid) emulsion, a suppository, an ointment, a cream, drops, or a sterile injectable aqueous or oily solution or suspension.

A suitable pharmaceutical composition of this invention is one suitable for oral administration in unit dosage form, for example a tablet or capsule containing between 0.1 mg and 10 g of active ingredient.

In another aspect a pharmaceutical composition of the invention is one suitable for intravenous, subcutaneous, intraarticular or intramuscular injection.

In one embodiment the compounds of formula (I), (Ib) or (Ic), or a pharmaceutically acceptable salt thereof, are administered orally.

In another embodiment the compounds of formula (I), (Ib) or (Ic), or a pharmaceutically acceptable salt thereof, are administered by inhalation.

Buffers, pharmaceutically-acceptable cosolvents such as polyethylene glycol, polypropylene glycol, glycerol or ethanol or complexing agents such as hydroxy-propyl β-cyclodextrin may be used to aid formulation.

The above formulations may be obtained by conventional procedures well known in the pharmaceutical art. Tablets may be enteric coated by conventional means, for example to provide a coating of cellulose acetate phthalate.

The invention further relates to combination therapies or compositions wherein the compounds of formula (I), (Ib) or (Ic), or a pharmaceutically acceptable salt thereof, or a pharmaceutical composition comprising the compounds of formula (I), (Ib) or (Ic), or a pharmaceutically acceptable salt thereof, is administered concurrently (possibly in the same composition) or sequentially with one or more agents for the treatment of any of the above disease states.

For example, for the treatment of rheumatoid arthritis, osteoarthritis, COPD, asthma or allergic rhinitis a compounds of formula (I), (Ib) or (Ic), or a pharmaceutically acceptable salt thereof, can be combined with one or more agents for the treatment of such a condition. Where such a combination is to be administered by inhalation, then the one or more agents is selected from the list comprising:
- a PDE4 inhibitor including an inhibitor of the isoform PDE4D;
- a selective β.sub2. adrenoceptor agonist such as metaproterenol, isoproterenol, isoprenaline, albuterol, salbutamol, formoterol, salmeterol, terbutaline, orciprenaline, bitolterol mesylate, pirbuterol or indacaterol;
- a muscarinic receptor antagonist (for example a M1, M2 or M3 antagonist, such as a selective M3 antagonist) such as ipratropium bromide, tiotropium bromide, oxitropium bromide, pirenzepine or telenzepine;
- a steroid (such as budesonide);
- a modulator of chemokine receptor function (such as a CCR1 receptor antagonist);
- an inhibitor of p38 kinase function;
- an inhibitor of matrix metalloproteases, most preferably targeting MMP-2, -9 or MMP-12; or,
- an inhibitor of neutrophil serine proteases, most preferably neutrophil elastase or proteinase 3.

In another embodiment of the invention where such a combination is for the treatment of COPD, asthma or allergic rhinitis, the compounds of formula (I), (Ib) or (Ic), or a pharmaceutically acceptable salt thereof, can be administered by inhalation or by the oral route and the other agent, e.g. xanthine (such as aminophylline or theophylline) can be administered by inhalation or by the oral route. The compounds of formula (I), (Ib) or (Ic), or a pharmaceutically acceptable salt thereof, and the other agent, e.g xanthine may be administered together. They may be administered sequentially. Or they may be administered separately.

EXAMPLES

The following Examples illustrate the invention. The following abbreviations are used in the Examples:
TFA Trifluoroacetic acid;
THF Tetrahydrofuran
DCM Dichloromethane
HPLC High Performance Liquid Chromatography;
LC/MS Liquid Column Chromatography/Mass Spectroscopy;
GC Gas Chromatography
DMSO Dimethylsulfoxide;
APCI-MS Atmospheric Pressure Chemical Ionisation Mass Spectroscopy;
NMP 1-methyl-2-pyrrolidinone
DIEA N,N-diisopropylethylamine
HATU O-(7-azabenzotriazol-1-yl)-N,N,N',N'-tetramethyluronium hexafluorophosphate
r.t. Room temperature, which is a temperature in the range from of 16° C. to 25° C.

General Methods

NMR spectra were recorded on a Varian Mercury-VX 300 MHz instrument or a Varian Inova 400 MHz instrument. The central peaks of chloroform-d (H 7.27 ppm), acetone (H 2.05 ppm), dichloromethane-d2 (H 5.32 ppm) or DMSO-$d_6$ (H 2.50 ppm) were used as internal references. Alternativly, NMR spectra were recorded on a Varian Inova Unity 500 MHz instrument. Proton-NMR experiments were acquired using dual suppression of residual solvent peak and $H_2O$.

The following method was used for LC/MS analysis:
Instrument Agilent 1100; Column Waters Symmetry 2.1×30 mm; Mass APCI; Flow rate 0.7 mL/min; Wavelength 254 nm; Solvent A: water+0.1% TFA; Solvent B: acetonitrile+ 0.1% TFA; Gradient 15-95%/B 2.7 min, 95% B 0.3 min.

The following method was used for GC-MS analysis:
Low resolution mass spectra and accurate mass determination were recorded on a Hewlett-Packard GC. MS system equipped with EI ionisation chamber, 70 eV.

The following method was used for LC analysis:
Method A. Instrument Agilent 1100; Column: Kromasil C18 100×3 mm, 5μ particle size, Solvent A: 0.1% TFA/water, Solvent B: 0.08% TFA/acetonitrile Flow: 1 mL/min, Gradient 10-100%/B 20 min, 100% B 1 min. Absorption was measured at 220, 254 and 280 nm.

A Kromasil KR-100-5-C18 column (250×20 mm, Akzo Nobel) and mixtures of acetonitrile/water (0.1% TFA) at a flow rate of 10 mL/min was used for preparative HPLC.

Unless stated otherwise, starting materials were commercially available. All solvents and commercial reagents were of laboratory grade and were used as received.

Example 1

N-((1S,2R)-2-{[1-(4-fluorophenyl)-1H-indazol-5-yl]oxy}-1-methyl-2-phenylethyl)cyclopropanecarboxamide

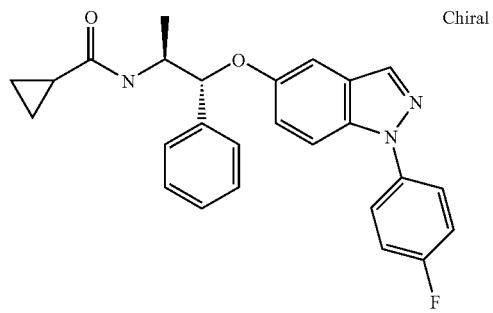

To a stirred solution of (1S,2R)-1-{[1-(4-fluorophenyl)-1H-indazol-5-yl]oxy}-1-phenylpropan-2-amine (18 mg, 50 μmol) in dichloromethane (2 ml) was added triethylamine (100 μl), followed by cyclopropanecarbonyl chloride (15 mg, 150 μmol). The stirring was continued for 20 min at r.t., then the solvent was removed under reduced pressure, and the product purified by semi-preparative HPLC. Yield 20 mg (95%).

APCI-MS: m/z 430 [MH$^+$]1H NMR (400 MHz, $d_6$-acetone) δ 8.04 (d, J=0.5 Hz, 1H), 7.77 (m, 2H), 7.71 (d, J=9.2 Hz, 1H), 7.58 (br.d, J=7.8 Hz, 1H), 7.46 (d, J=7.3 Hz, 2H), 7.35 (m, 4H), 7.28 (d, J=7.4 Hz, 1H), 7.25 (dd, J=9.2, 2.3 Hz, 1H), 7.10 (d, J=2.3 Hz, 1H), 5.51 (d, J=3.5 Hz, 1H), 4.32 (m, 1H), 1.58 (septet, J=4.2 Hz, 1H), 1.19 (d, J=6.9 Hz, 3H), 0.79 (m, 1H), 0.71 (m, 1H), 0.67-0.53 (m, 2H).

(1R,2S)-1-[1-(4-fluorophenyl)indazol-5-yl]oxy-1-phenyl-propan-2-amine (1a)

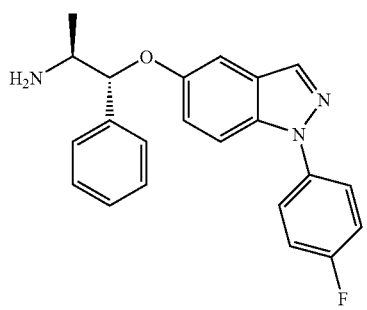

The title compound was prepared essentially by the method described by Job & Buchwald: Org. Lett. 2002, 4 (21), 3703-3706.

1-(Fluorophenyl)-5-iodoindazole (43 mg, 0.12 mmol), (1R,2S)-norephedrine (16 mg, 0.1 mmol), copper (I) iodide (2.2 mg, 5 mol %) and caesium carbonate (84 mg, 0.26 mmol) were suspended in butyronitrile (1 mL). The reaction vessel was capped and the mixture was stirred at 125° C. The progress of the reaction was followed by HPLC (R.P. C-18, 20-90% gradient of CH$_3$CN in water, 0.1% TFA). After 7.5 h additional (1R,2S)-norephedrine (70 mg), copper (I) iodide (16 mg) and caesium carbonate (136 mg) were added and the stirring was continued at 125° C. After 2 h all 1-(fluorophenyl)-5-iodoindazole was consumed and the mixture was cooled, filtered and evaporated. Flash chromatography (SiO$_2$, gradient of 0-30% MeOH in EtOAc) gave the title compound (19 mg, 41%).

APCI-MS m/z: 362.2 [MH$^+$]. $^1$H-NMR (300 MHz, DMSO-d$_6$+D$_2$O, TfA added): 8.16 (1H, d), 7.76-7.68 (3H, m), 7.43-7.28 (8H, m), 7.12 (1H, d), 5.64 (1H, d), 3.70 (1H, qd), 1.16 (3H, d). $^{19}$F-NMR (DMSO-d$_6$): −115.97 (tt, unresolved).

Example 2

2,2,2-Trifluoro-N-((1S,2R)-2-{[1-(4-fluorophenyl)-1H-indazol-5-yl]oxy}-1-methyl-2-phenylethyl)acetamide

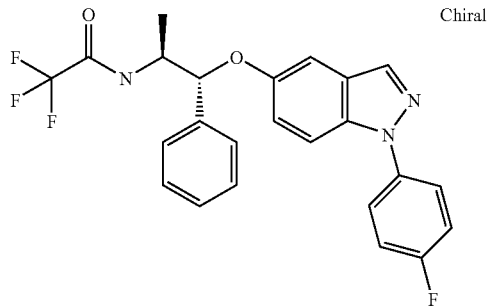

Prepared as described in Example 1 using (1S,2R)-1-{[1-(4-fluorophenyl)-1H-indazol-5-yl]oxy}-1-phenylpropan-2-amine (1a, 18 mg, 50 μmol) and trifluoroacetic anhydride (31 mg, 150 μmol). Yield 18 mg (78%).

APCI-MS: m/z 458 [MH$^+$]$^1$H NMR (400 MHz, d$_6$-acetone) δ 8.62 (br.d, J=7.8 Hz, 1H), 8.03 (d, J=0.7 Hz, 1H), 7.77 (m, 3H), 7.70 (d, J=9.2 Hz, 1H), 7.49 (d, J=7.3 Hz, 2H), 7.34 (m, 4H), 7.24 (dd, J=9.1, 2.4 Hz, 1H), 7.15 (d, J=2.3 Hz, 1H), 5.51 (d, J=4.8 Hz, 1H), 4.44 (m, 1H), 1.38 (d, J=6.9 Hz, 3H).

Example 3

N-((1S,2R)-2-{[1-(4-fluorophenyl)-1H-indazol-5-yl]oxy}-1-methyl-2-phenylethyl)propanamide

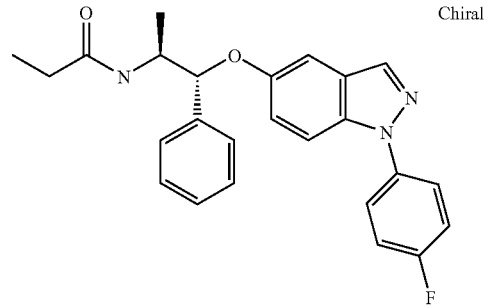

Prepared as described in Example 1 using (1S,2R)-1-{[1-(4-fluorophenyl)-1H-indazol-5-yl]oxy}-1-phenylpropan-2-amine (1a, 14 mg, 38 μmol) and propanoyl chloride (10 mg, 114 μmol). Yield 14 mg (90%).

APCI-MS: m/z 418 [MH$^+$]1H NMR (400 MHz, d$_6$-acetone) δ 8.03 (d, J=0.7 Hz, 1H), 7.77 (m, 2H), 7.70 (d, J=9.0 Hz, 1H), 7.46 (d, J=7.1 Hz, 2H), 7.38-7.26 (m, 5H), 7.23 (dd, J=9.2, 2.5 Hz, 1H), 7.11 (d, J=2.3 Hz, 1H), 5.48 (d, J=3.9 Hz, 1H), 4.33 (m, 1H), 2.13 (m, 2H), 1.19 (d, J=6.9 Hz, 3H), 0.99 (t, J=7.6 Hz, 3H).

Example 4

Methyl ((1S,2R)-2-{[1-(4-fluorophenyl)-1H-indazol-5-yl]oxy}-1-methyl-2-phenylethyl)carbamate

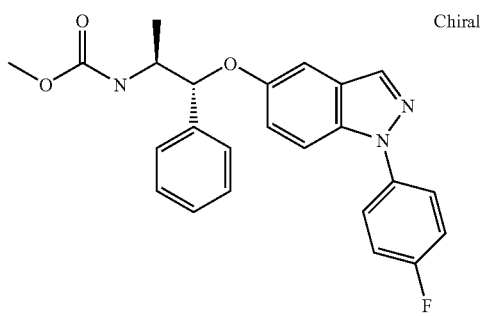

Prepared as described in Example 1 using (1S,2R)-1-{[1-(4-fluorophenyl)-1H-indazol-5-yl]oxy}-1-phenylpropan-2-amine (1a, 14 mg, 38 μmol) and methyl chlorocarbonate (11 mg, 114 μmol). Yield 14 mg (90%).

APCI-MS: m/z 420 [MH$^+$]1H NMR (400 MHz, d$_6$-acetone) δ 8.03 (s, 1H), 7.77 (m, 2H), 7.70 (d, J=9.0 Hz, 1H), 7.46 (d, J=7.3 Hz, 2H), 7.40-7.26 (m, 5H), 7.24 (dd, J=9.1, 2.4 Hz, 1H), 7.10 (d, J=2.1 Hz, 1H), 6.43 (br.d, J=7.8 Hz, 1H), 5.46 (d, J=3.5 Hz, 1H), 4.06 (m, 1H), 3.54 (s, 3H), 1.23 (d, J=6.9 Hz, 3H).

Example 5

N-[(1R,2S)-1-[1-(4-fluorophenyl)indazol-5-yl]oxy-1-phenyl-propan-2-yl]-2-hydroxy-2-methyl-propanamide

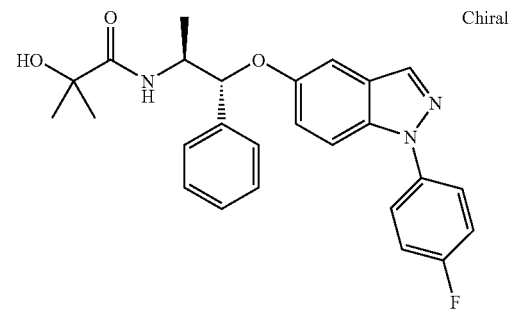

To a stirred solution of (1S,2R)-1-{[1-(4-fluorophenyl)-1H-indazol-5-yl]oxy}-1-phenylpropan-2-amine (18 mg, 50 μmol) in dichloromethane (2 ml) was added triethylamine (100 μl), followed by 2-chloro-1,1-dimethyl-2-oxoethyl acetate (24 mg, 150 μmol). The stirring was continued for 20 min at r.t., then the solvent was removed under reduced pressure, and the residue dissolved in ethanol (1 ml). Aqueous sodium hydroxide solution (1 M, 1 ml) was added, and the mixture was stirrer at 80° C. for 30 min. Then it was cooled to r.t., acidified with TFA, and concentrated under reduced pressure. The product was purified by semi-prep. HPLC. Yield 22 mg (96%).

APCI-MS: m/z 448 [MH+]1H NMR (400 MHz, $d_6$-acetone) δ 8.04 (d, J=0.7 Hz, 1H), 7.77 (m, 2H), 7.70 (d, J=9.0 Hz, 1H), 7.49 (d, J=7.4 Hz, 2H), 7.43-7.27 (m, 5H), 7.25 (dd, J=9.1, 2.4 Hz, 1H), 7.15 (d, J=2.3 Hz, 1H), 5.48 (d, J=4.6 Hz, 1H), 4.33 (m, 1H), 1.30 (s, 3H), 1.23 (d, J=6.7 Hz, 3H), 1.20 (s, 3H).

Example 6

2,2,2-Trifluoro-N-[(1R,2S)-1-[1-(4-fluorophenyl)indazol-5-yl]oxy-1-(3-methoxyphenyl)propan-2-yl]acetamide

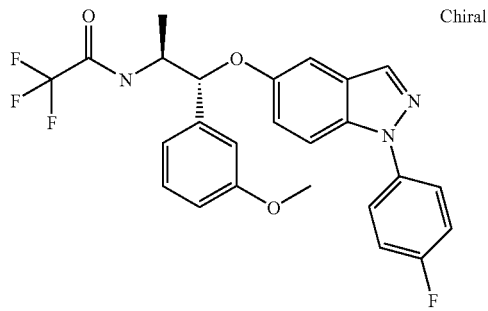

Chiral

Prepared as described in Example 1 using (1R,2S)-1-{[1-(4-fluorophenyl)-1H-indazol-5-yl]oxy}-1-(3-methoxyphenyl)propan-2-amine (90 mg, 230 μmol) and trifluoroacetic anhydride (98 mg, 460 μmol). Yield 101 mg (90%).

APCI-MS: m/z 488 [MH+]1H NMR (400 MHz, $d_6$-acetone) δ 8.60 (br.d, J=8.1 Hz, 1H), 8.05 (d, J=0.9 Hz, 1H), 7.77 (m, 2H), 7.71 (d, J=9.0 Hz, 1H), 7.32 (m, 3H), 7.24 (dd, J=9.1, 2.4 Hz, 1H), 7.16 (d, J=2.1 Hz, 1H), 7.06 (m, 2H), 6.87 (m, 1H), 5.48 (d, J=4.8 Hz, 1H), 4.44 (m, 1H), 3.78 (s, 3H), 1.38 (d, J=6.9 Hz, 3H).

(1R,2S)-1-{[1-(4-fluorophenyl)-1H-indazol-5-yl]oxy}-1-(3-methoxyphenyl)propan-2-amine (6a)

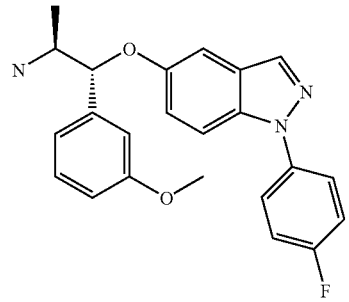

1-(Fluorophenyl)-5-iodo-1H-indazole (338 mg, 1 mmol), (1R,2S)-2-amino-1-(3-methoxyphenyl)propan-1-ol (220 mg, 1.2 mmol), copper (I) iodide (19 mg, 100 μmol, 10 mol %), and cesium carbonate (764 mg, 2 mmol) were suspended in butyronitrile (2 ml). The reaction vessel was capped and the mixture was stirred at 125° C. for 5 h. Then the mixture was cooled, the precipitate removed by filtration and washed with ethyl acetate (10 ml). The combined organic solutions were concentrated under reduced pressure. The product was isolated by flash chromatography on silica gel (gradient of 0-30% MeOH in EtOAc) to afford the subtitle compound (148 mg, 38%).

APCI-MS m/z: 392 [MH+]. 1H-NMR (400 MHz, CD3OD): 7.88 (d, J=1.8 Hz, 1H), 7.54 (m, 2H), 7.46 (d, J=8.8 Hz, 1H), 7.24-7.12 (m, 4H), 7.02 (d, J=1.6 Hz, 1H), 6.95 (m, 2H), 6.78 (m, 1H), 5.04 (d, J=5.1 Hz, 1H), 3.70 (s, 3H), 3.22 (quintet, J=6.1 Hz, 1H), 1.15 (d, J=6.7 Hz, 3H)

(1R,2S)-2-amino-1-(3-methoxyphenyl)propan-1-ol (6b)

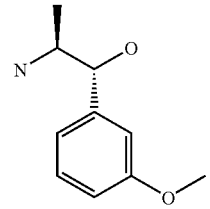

To a stirred solution of tert-butyl[(1S,2R)-2-hydroxy-2-(3-methoxyphenyl)-1-methylethyl]carbamate (317 mg, 1.13 mmol) in dichloromethane (3 ml) was added water (3 ml), and TFA (5 ml), so that a clear solution has been obtained. The mixture was stirred at r.t. for 1 h, than poured into water (30 ml). The aqueous layer was washed with dichloromethane (30 ml), and made alkaline (pH≈10) by addition of 10 N aqueous NaOH. Brine (20 ml) was added, and the solution was extracted with dichloromethane (3×30 ml). The extracts were dried with $Na_2SO_4$, and the solvent was removed under reduced pressure to afford the subtitle compound as colourless oil. Yield 179 mg (88%).

APCI-MS m/z: 182 [MH+]. 1H-NMR (400 MHz, CDCl3): δ 7.24 (d, J=8.3 Hz, 1H), 6.90 (m, 2H), 6.81 (m, 1H), 4.53 (d, J=4.6 Hz, 1H), 3.81 (s, 3H), 3.19 (dt, J=11.3, 6.5 Hz, 1H), 0.98 (d, J=6.5 Hz, 3H)

tert-Butyl[(1S,2R)-2-hydroxy-2-(3-methoxyphenyl)-1-methylethyl]carbamate (6c)

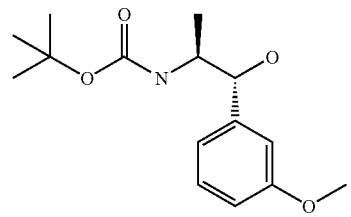

Synthesized analogously to the method described by J. Yin et al, *J. Org. Chem.*, 71, 840-843 (2006).

A mixture of tert-butyl[(1S)-2-(3-methoxyphenyl)-1-methyl-2-oxoethyl]carbamate (13.6 g, 48.7 mmol), aluminium isopropoxide (1.99 g, 9.70 mmol), 2-propanol (41 mL, 535 mmol) in toluene (63 mL) was stirred under an atmosphere of argon at 50° C. overnight. LC/MS showed complete conversion into the alcohol. The mixture was partitioned between ethyl acetate (200 mL) and hydrochloric acid (1M, 200 mL).

The organic phase was washed with water (200 mL), dried over magnesium sulfate and concentrated to give the subtitle compound as a syrup (13.5 g). The compound was used in the next step without further purification.

¹H-NMR (400 MHz, CDCl₃): δ 7.27 (t, J=8.0 Hz, 1H), 6.93 (m, 2H), 6.83 (dd, J=8.0, 2.2 Hz, 1H), 4.85 (d, J=2.8 Hz, 1H), 4.00 (br.s, 1H), 3.83 (s, 3H), 3.04 (br.s, 1H), 1.48 (s, 9H), 1.01 (d, J=6.9 Hz, 3H).

tert-Butyl[(1S)-2-(3-methoxyphenyl)-1-methyl-2-oxoethyl]carbamate (6d)

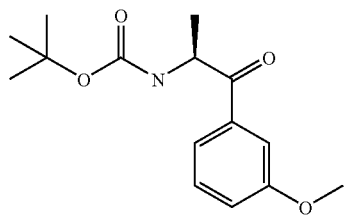

To a stirred solution of N²-(tert-butoxycarbonyl)-N-methoxy-N-methyl-L-alaninamide (777 mg, 3.3 mmol) in dry THF (50 ml) was added a solution of bromo(3-methoxyphenyl)magnesium (1M in THF, 10 ml, 10 mmol). The mixture was stirred at r.t. for 5 h, then quenched with saturated aqueous NH₄Cl (50 ml). After stirring for 30 min, the layers were separated, the aqueous layer extracted with ethyl acetate (50 ml). The combined organic layers were dried with Na₂SO₄, and the solvent was removed in vacuo. The subtitle compound was isolated by flash chromatography on silica gel (n-heptane/ethyl acetate, gradient from 20 to 50% ethyl acetate). Yield 471 mg (94%).

¹H-NMR (400 MHz, CDCl₃): δ 7.55 (d, J=7.6 Hz, 1H), 7.49 (t, J=1.9 Hz, 1H), 7.39 (t, J=8.0 Hz, 1H), 7.15 (dd, J=8.2, 2.0 Hz, 1H), 5.56 (d, J=6.9 Hz, 1H), 5.28 (quintet, J=7.2 Hz, 1H), 3.86 (s, 3H), 1.47 (s, 9H), 1.41 (d, J=7.1 Hz, 3H).

Example 7

N-[(1R,2S)-1-(4-ethylphenyl)-1-[1-(4-fluorophenyl)indazol-5-yl]oxy-propan-2-yl]-2-hydroxy-acetamide

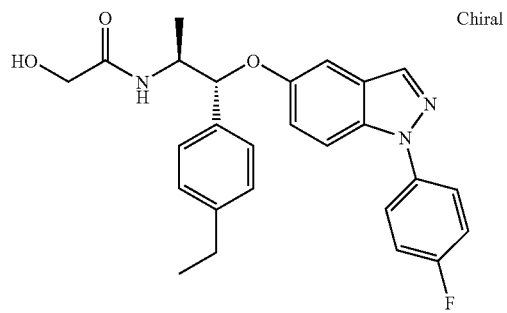

Prepared as described in Example 5 using (1R,2S)-1-(4-ethylphenyl)-1-{[1-(4-fluorophenyl)-1H-indazol-5-yl]oxy}propan-2-amine (20 mg, 50 μmol) and 2-chloro-2-oxoethyl acetate (21 mg, 150 μmol). Yield 21 mg (91%).

APCI-MS: m/z 448 [MH⁺]1H NMR (400 MHz, d₆-acetone) δ 8.04 (d, J=0.5 Hz, 1H), 7.77 (m, 2H), 7.70 (d, J=9.2 Hz, 1H), 7.41-7.30 (m, 5H), 7.23 (m, 3H), 7.13 (d, J=2.1 Hz, 1H), 5.48 (d, J=3.9 Hz, 1H), 4.39 (m, 1H), 3.91 (dd, J=16.8, 15.9 Hz, 2H), 2.62 (q, J=7.5 Hz, 2H), 1.21 (d, J=6.9 Hz, 3H), 1.19 (t, J=7.6 Hz, 3H)

(1R,2S)-1-(4-ethylphenyl)-1-{[1-(4-fluorophenyl)-1H-indazol-5-yl]oxy}propan-2-amine (7a)

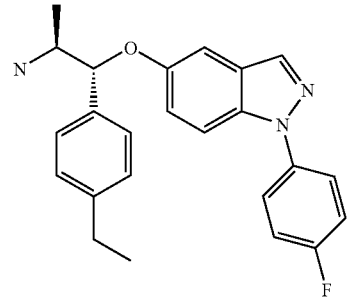

Prepared as described in Example 6 (Step 6a), using (1R,2S)-2-amino-1-(4-ethylphenyl)propan-1-ol (440 mg, 1.3 mmol). Yield 239 mg (47%).

APCI-MS: m/z 390 [MH⁺]1H NMR (400 MHz, d₆-DMSO) δ 8.16 (s, 1H), 7.71 (m, 3H), 7.38 (t, J=8.8 Hz, 2H), 7.30 (m, 3H), 7.23 (d, J=8.0 Hz, 2H), 7.13 (d, J=2.3 Hz, 1H), 5.59 (d, J=3.0 Hz, 1H), 3.65 (m, 1H), 2.56 (q, J=7.5 Hz, 2H), 1.14 (m, 6H)

(1R,2S)-2-Amino-1-(4-ethylphenyl)propan-1-ol (7b)

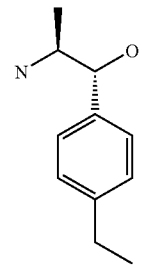

To a stirred solution of tert-butyl[(1S,2R)-2-(4-ethylphenyl)-2-hydroxy-1-methylethyl]carbamate (450 mg, 1.51 mmol) in acetonitrile (10 ml) was added aq. HCl (6 N, 3 ml), and stirring was continued for 3.5 h. Then the mixture was diluted with water (10 ml), and acetonitrile was removed in vacuo. The mixture was washed with dichloromethane (20 ml). The aqueous layer was then made alkaline (pH≈10) by addition of aq. NaOH (10 N), and extracted with dichloromethane (3×20 ml). The combined organic extracts were dried with Na₂SO₄, the solvent was removed in vacuo to afford white solid, 280 mg (97%).

APCI-MS: m/z 180 [MH⁺]1H NMR (400 MHz, d₆-DMSO) δ 7.20 (d, J=8.0 Hz, 3H), 7.14 (d, J=8.1 Hz, 3H), 5.05 (br.s, 1H), 4.26 (d, J=4.8 Hz, 1H), 2.85 (quintet, J=6.1 Hz, 1H), 2.58 (q, J=7.6 Hz, 2H), 1.17 (t, J=7.6 Hz, 3H), 0.85 (d, J=6.4 Hz, 3H).

tert-Butyl[(1S,2R)-2-(4-ethylphenyl)-2-hydroxy-1-methylethyl]carbamate (7c)

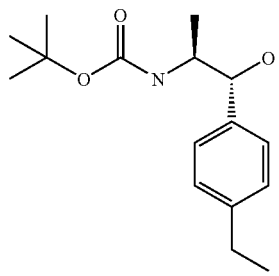

The procedure described by J. Yin et al., *J. Org. Chem.* 2006, 71, 840-843) was used. A mixture of tert-butyl[(1S)-2-(4-ethylphenyl)-1-methyl-2-oxoethyl]carbamate (555 mg, 2 mmol), Al(iPr)$_3$ (81 mg, 0.4 mmol), 2-propanol (1.32 g, 22 mmol), and toluene (2.6 ml, 1.3 ml/mmol) was heated in a sealed vial at 50° C. overnight. Then the reaction mixture was cooled to r.t., quenched with aqueous HCl (1 N, 10 ml), and diluted with ethyl acetate (10 ml). The layers were separated, the organic layer was washed with water (80 ml), dried with Na$_2$SO$_4$, and concentrated. Trituration with n-heptane (30 ml) afforded the subtitle compound as colourless precipitate, 137 mg. n-Heptane solution was concentrated under reduced pressure, and the residue purified by flash chromatography in silica gel to give the second crop of the subtitle compound, 318 mg. Overall yield 455 mg (81%).

1H NMR (400 MHz, CDCl$_3$) δ 7.26 (d, J=8.1 Hz, 2H, partially covered with the signal of solvent), 7.19 (d, J=8.1 Hz, 2H), 4.83 (d, J=2.7 Hz, 1H), 4.62 (br.s, 1H), 4.01 (br.s, 1H), 2.65 (q, J=7.5 Hz, 2H), 1.47 (s, 9H), 1.24 (t, J=7.6 Hz, 3H), 1.01 (d, J=6.9 Hz, 3H).

tert-Butyl[(1S)-2-(4-ethylphenyl)-1-methyl-2-oxoethyl]carbamate (7d)

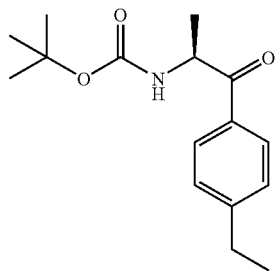

To a stirred suspension of magnesium turnings (243 mg, 10 mmol) in dry THF (10 ml) was added a solution of 1-bromo-4-ethylbenzene (1.85 g, 10 mmol) in dry THF (10 ml), followed by a small crystal of iodine. The reaction mixture was heated with reflux for 4 h, then cooled to r.t. A solution of N$^2$-(tert-butoxycarbonyl)-N-methoxy-N-methyl-L-alaninamide (464 mg, 2 mmol) in dry THF (15 ml) was added dropwise, and the stirring was continued for 5 h at r.t. Then the reaction mixture was quenched with sat. aqueous NH$_4$Cl (25 ml) stirred for 30 min, and the layers were separated. The aqueous layer extracted with ethyl acetate (50 ml). The combined organic layers were dried with Na$_2$SO$_4$, and the solvent was removed under reduced pressure to give the subtitle compound as colourless oil, 718 mg, 70% purity (as determined by NMR). Used in the next step without further purification.

1H NMR (400 MHz, CDCl$_3$) δ 7.90 (d, J=8.1 Hz, 2H), 7.32 (d, J=8.1 Hz, 2H), 5.60 (br.d, J=5.8 Hz, 1H), 5.28 (quintet, J=7.0 Hz, 1H), 2.73 (q, J=7.6 Hz, 2H), 1.47 (s, 9H), 1.41 (d, J=7.1 Hz, 3H), 1.27 (t, J=7.6 Hz, 3H).

Example 8

N-{2-[1-(4-Fluoro-phenyl)-1H-indazo-5-yl]oxy]-2-(3-methoxy-phenyl)-1-methyl-ethyl}-2,2-dimethyl-propionamide

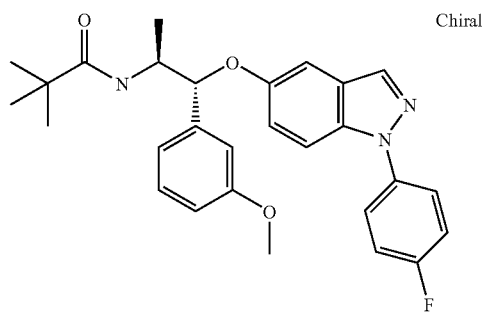

Prepared as described in Example 1 using (1S,2R)-1-{[1-(4-fluorophenyl)-1H-indazol-5-yl]oxy}-1-phenylpropan-2-amine (6a, 110 mg, 200 μmol) and pyvaloyl chloride (0.070 ml, 560 μmol).

Yield 86 mg (90%). APCI-MS: m/z 476.1 [MH$^+$]1H NMR (400 MHz, d$_6$-DMSO) δ 8.18 (br, 1H), 7.76-7.62 (m, 3H), 7.39 (t, J=8.7 Hz, 2H), 7.33 (d, J=8.5 Hz 1H), 7.27-7.18 (m, 2H), 7.10 (d, J=2 Hz, 1H), 7.0-6.94 (m, 2H), 6.81 (d, J=8.6 Hz 1H), 5.26 (d, J=6.2 Hz, 1H), 4.18 (m, 1H), 3.73 (s, 3H), 1.22 (d, J=6.7 Hz, 3H), 0.95 (s, 9H).

Example 9

N-[(1R,2S)-1-[1-(4-fluorophenyl)indazol-5-yl]oxy-1-(4-methylsulfanylphenyl)propan-2-yl]-2-methoxy-acetamide

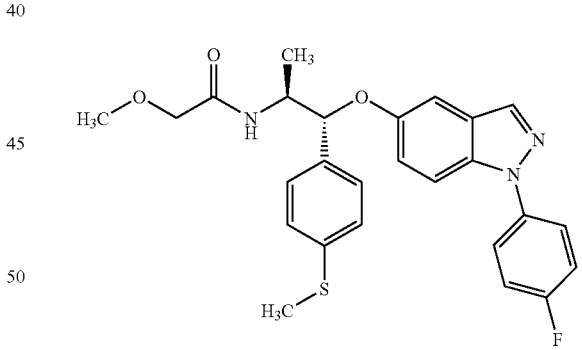

Methoxyacetyl chloride (10 μL, 0.11 mmol) was added to a suspension of (1R,2S)-1-{[1-(4-fluorophenyl)-1H-indazol-5-yl]oxy}-1-[4-(methylthio)phenyl]propan-2-amine hydrochloride (40 mg, 0.09 mmol) and triethylamine (42 μL, 0.3 mmol) in THF (1 mL). The reaction was stirred at r.t. for 30 min and then quenched by adding water, the mixture was diluted with a small volume of MeCN so that a solution was obtained. This crude mixture was purified by semi-preparative HPLC using a Kromasil® C18 250×20 mm, 5 μm column. Flow 10 mL/min, 20 min gradient of 20%-90% MeCN in water followed by isocratic final concentration until product had eluted. UV=254 nm was used for detection. Fractions with product was combined and lyophilized to afford the title compound as a colourless solid. Yield 30 mg (69%).

APCI-MS: m/z 480.1 [MH+]¹H-NMR (300 MHz, DMSO-d₆): δ 8.17 (d, J=0.8 Hz, 1H), 7.80-7.70 (m, 3H), 7.68 (d, J=9.16 Hz, 1H), 7.45-7.30 (m, 4H), 7.25-7.16 (m, 3H), 7.10 (d, J=2.12 Hz, 1H), 5.33 (d, J=5.97 Hz, 1H), 4.23 (m, 1H), 3.70 (dd, 2H), 3.20 (s, 3H), 2.43 (s, 3H), 1.21 (d, J=6.77 Hz, 3H).

(1R,2S)-1-{[1-(4-fluorophenyl)-1H-indazol-5-yl]oxy}-1-[4-(methylthio)phenyl]propan-2-amine hydrochloride (9a)

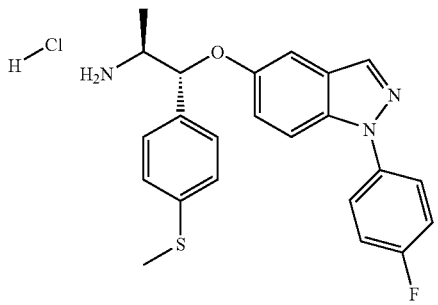

(1R,2S)-2-Amino-1-[4-(methylthio)phenyl]propan-1-ol (595 mg, 3 mmol), 1-(fluorophenyl)-5-iodoindazole (913 mg, 2.7 mmol), CuI (28 mg, 0.15 mmol) and Cs₂CO₃ (1.95 g, 6 mmol) was suspended in butyronitrile (5 mL) and toluene (2 mL). The reaction vessel was sealed and the mixture was stirred at +125° C. for 6 h. The reaction mixture was cooled down and partitioned between EtOAc and water, the water phase was extracted once with EtOAc. The combined organic phases was concentrated and purified by semi-preparative HPLC using a Kromasil® C18 250×20 mm, 5 μm column. Flow 10 mL/min, 20 min gradient of 20%-90% MeCN in water. UV=254 nm was used for detection. Fractions with product was combined and solvents removed by evaporation. This material was further purified by dissolving it in EtOAc and applying it onto a short silica column, the impurity could be washed out using EtOAc as eluent, the desired product was eluted by using an 0.35 N NH₃ in 5% MeOH/EtOAc solution, (prepared by diluting 1 volume of commercially available 7 N NH₃ in MeOH with 19 volumes of EtOAc). The solvents were evaporated and the residual material was evaporated from MeOH several times. The residual sticky material was dissolved in MeCN and 5-6N HCl in 2-propanol was added, the solvent was then removed by evaporation to afford the subtitle compound as a beige solid salt. Yield 300 mg (25%).

APCI-MS: m/z 408.1 [MH⁺—HCl]¹H-NMR (300 MHz, DMSO-d₆): δ 8.40 (brs, 3H), 8.20 (d, J=0.93 Hz, 1H), 7.79-7.71 (m, 3H), 7.45-7.24 (m, 7H), 7.14 (d, J=2.26 Hz), 5.69 (d, J=2.92 Hz, 1H), 3.65 (brm, 1H), 2.45 (s, 3H), 1.19 (d, J=6.77 Hz, 3H).

(1R,2S)-2-amino-1-[4-(methylthio)phenyl]propan-1-ol (9b)

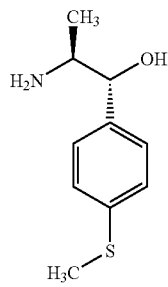

The subtitle compound was prepared following a procedure described by: M. Osorio-Olivares et al. Bioorg. Med. Chem. 12 (2004) 4055-4066.

(S)-2-Trifluoroacetamido-1-(4-methylthiophenyl)-1-propanone (1.9 g, 6.6 mmol; M. Osorio-Olivares et al. Tetrahedron: Asymmetry 14 (2003) 1473-1477) was dissolved in 99.5% EtOH (65 mL). NaBH₄ (1.24 g, 33 mmol) was added and the mixture was stirred at r.t. for 19 h. The solvents were removed by evaporation, water (75 mL) was added, the mixture was extracted with DCM (2×75 mL), the organic phase was dried over Na₂SO₄, filtered and concentrated. The residual oil was dissolved in Et₂O and 5-6N HCl in 2-propanol (10 mL) was added, the precipitated salt was collected and washed with ether. Obtained 1.46 g (96% yield) as the hydrochloride salt. NMR showed an 84:16 mixture of the two possible diastereomers. The major diastereomer was isolated by preparative HPLC using an XTerra® Prep MS C₁₈ OBD™ Column, 5 μm, 19×50 mm. 20 min gradient of 10-30% MeCN in (Water+2 mL NH₃/L). The purest fractions was combined and lyophilized to afford the subtitle compound as a colourless solid. Yield 595 mg (45%).

APCI-MS: m/z 198.1 [MH⁺]¹H-NMR (300 MHz, CD₃OD): δ 7.33-7.24 (m, 4H), 4.54 (d, J=4.91 Hz, 1H), 3.13 (m, 1H), 2.47 (s, 3H), 1.05 (d, J=6.63 Hz, 3H).

Example 10

N-[(1R,2S)-1-[1-(4-fluorophenyl)indazol-5-yl]oxy-1-(4-methylsulfanylphenyl)propan-2-yl]carbamoylmethyl acetate

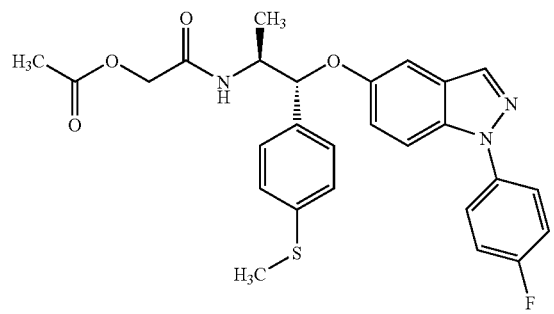

Acetoxyacetyl chloride (32 μL, 0.3 mmol) was added to a solution of (1R,2S)-1-{[1-(4-fluorophenyl)-1H-indazol-5-yl]oxy}-1-[4-(methylthio)phenyl]propan-2-amine hydrochloride (9a) (97 mg, 0.22 mmol) and N-ethyldiisopropylamine (120 μL, 0.7 mmol) in THF (2 mL). The reaction mixture was stirred at r.t. for 1 h, another portion of reagents was added, N-ethyldiisopropylamine (120 μL, 0.7 mmol) and acetoxyacetyl chloride (32 μL, 0.3 mmol), after another 15 min the reaction was quenced by addition of water. The reaction mixture was concentrated and purified by semi-preparative HPLC using a Kromasil® C18 250×20 mm, 5 μm column. Flow 10 mL/min, 20 min gradient of 20%-90% MeCN in water followed by isocratic final concentration until product had eluted. UV=254 nm was used for detection. Fractions with product was combined and lyophilized to afford the title compound as a colourless solid. Yield 67 mg (60%).

APCI-MS: m/z 508.1 [MH⁺]¹H-NMR (300 MHz, DMSO-d₆): δ 8.17 (d, J=7.2 Hz, 1H), 8.16 (d, J=0.92 Hz, 1H), 7.78-7.66 (m, 3H), 7.44-7.17 (m, 7H), 7.09 (d, J=2.12 Hz, 1H), 5.31 (d, J=4.77 Hz, 1H), 4.40 (dd, 2H), 4.15 (m, 1H), 2.44 (s, 3H), 2.06 (s, 3H), 1.17 (d, J=6.9 Hz, 3H).

Example 11

N-[(1R,2S)-1-[1-(4-fluorophenyl)indazol-5-yl]oxy-1-(4-methylsulfanylphenyl)propan-2-yl]-2-hydroxy-acetamide

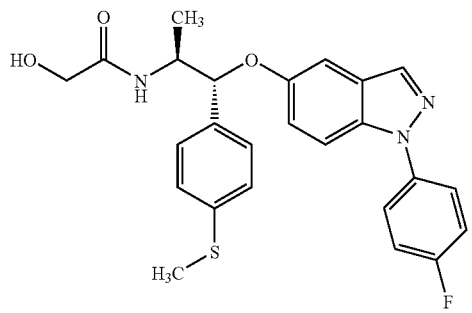

N-[(1R,2S)-1-[1-(4-fluorophenyl)indazol-5-yl]oxy-1-(4-methylsulfanylphenyl)propan-2-yl]carbamoylmethyl acetate (10) (47 mg, 0.09 mmol) was dissolved in MeOH (5 mL), water (1 mL) and 28% NH$_3$ (aq) (1 mL). The solution was stirred at r.t. for 1 h. MeOH was removed by evaporation and the residual material was diluted with water, the formed slurry was lyophilized to afford the title compound as a colourless solid. Yield 36 mg (89%)

APCI-MS: m/z 465.9 [MH$^+$]$^1$H-NMR (300 MHz, DMSO-d$_6$): δ 8.16 (d, J=0.80 Hz, 1H), 7.78-7.66 (m, 3H), 7.63 (d, J=8.89 Hz, 1H), 7.44-7.30 (m, 4H), 7.25-7.16 (m, 3H), 7.10 (d, J=2.12 Hz, 1H), 5.51 (t, J=5.7 Hz, 1H), 5.38 (d, J=5.31 Hz, 1H), 4.24 (m, 1H), 3.74 (m, 2H), 2.43 (s, 3H), 1.19 (d, J=6.77 Hz, 3H).

Example 12

N-[(1R,2S)-1-[1-(4-fluorophenyl)indazol-5-yl]oxy-1-(4-methylsulfonylphenyl)propan-2-yl]-2-hydroxy-acetamide

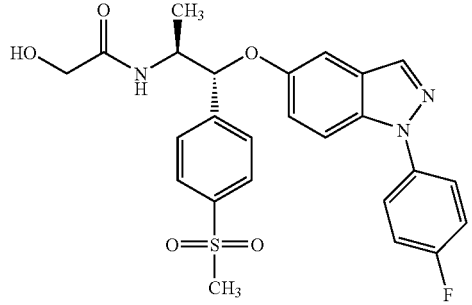

N-[(1R,2S)-1-[1-(4-fluorophenyl)indazol-5-yl]oxy-1-(4-methylsulfanylphenyl)propan-2-yl]-2-hydroxy-acetamide (11) (80 mg, 0.17 mmol) was dissolved in AcOH (1 mL), hydrogen peroxide, 35% (1 mL, 12.14 mmol) was added and the mixture was stirred at +60° C. for 1.5 h. The reaction mixture was lyophilized to give a crude product as an sticky oil. The crude product was further purified by HPLC using an XBridge™ Prep C18 5 μm OBD™ 30×150 mm column [Flow=20 mL/min, 30 min gradient of 10-60% MeCN in (H2O+2 mL NH$_3$/L), UV=220 nm was used for detection]. The fractions containing the product was combined and lyophilized to afford the title compound as an colourless solid. Yield 26 mg (30%)

APCI-MS: m/z 498.1 [MH$^+$]$^1$H-NMR (400 MHz, DMSO-d$_6$): δ 8.17 (d, J=0.61 Hz, 1H), 7.91 (d, J=8.31 Hz, 2H), 7.78-7.65 (m, 6H), 7.40 (m, 2H), 7.24 (dd, J=9.2, 2.48 Hz, 1H), 7.13 (d, J=2.3 Hz, 1H), 5.55 (d, J=5.48 Hz, 1H), 5.51 (t, J=4.95 Hz, 1H), 4.28 (m, 1H), 3.72 (m, 2H), 3.19 (s, 3H), 1.21 (d, J=6.72 Hz, 3H).

Example 13

2,2,2-trifluoro-N-[(1R,2S)-1-[1-(4-fluorophenyl)indazol-5-yl]oxy-1-(4-methylsulfanylphenyl)propan-2-yl]acetamide

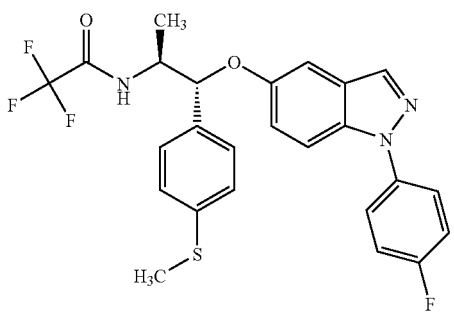

(1R,2S)-1-{[1-(4-Fluorophenyl)-1H-indazol-5-yl]oxy}-1-[4-(methylthio)phenyl]propan-2-amine hydrochloride (9a) (150 mg, 0.34 mmol) was dissolved in MeOH (2 mL). 1,1,3,3-tetramethylguanidine (128 μL, 1.02 mmol) was added and the mixture was stirred for 5 min, ethyl trifluoroacetate (83 μL, 0.7 mmol) was added and the reaction mixture was stirred at r.t. for 2.5 h. The reaction mixture was evaporated and the residual material was purified by semi-preparative HPLC using a Kromasil® C18 250×20 mm, 5 μm column. Flow 10 mL/min, 20 min gradient of 20%-90% MeCN in water followed by isocratic final concentration until product had eluted. UV=254 nm was used for detection. Fractions with product was combined and lyophilized to afford the title compound as a colourless solid. Yield 128 mg (74%)

APCI-MS: m/z 504.1 [MH$^+$]$^1$H-NMR (300 MHz, DMSO-d$_6$): δ 9.51 (d, J=8.36 Hz, 1H), 8.17 (d, J=0.79 Hz, 1H), 7.78-7.66 (m, 3H), 7.44-7.30 (m, 4H), 7.26-7.16 (m, 3H), 7.11 (d, J=2.13 Hz, 1H), 5.27 (d, J=6.37 Hz, 1H), 4.23 (m, 1H), 2.43 (s, 3H), 1.32 (d, J=6.77 Hz, 3H).

Example 14

N-[(1R,2S)-1-(4-Ethylsulfanylphenyl)-1-[1-(4-fluorophenyl)indazol-5-yl]oxy-propan-2-yl]-2,2,2-trifluoro-acetamide

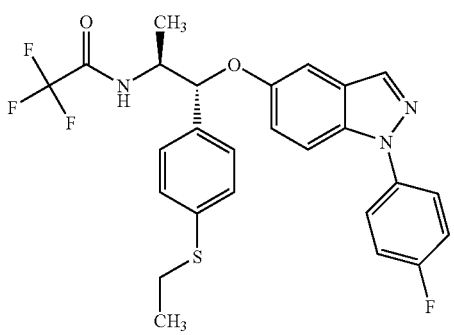

(1R,2S)-2-Amino-1-[4-(ethylthio)phenyl]propan-1-ol (526 mg, 2.49 mmol), 1-(fluorophenyl)-5-iodoindazole (676 mg, 2 mmol), CuI (24 mg, 0.13 mmol) and Cs$_2$CO$_3$ (1.6 g, 5 mmol) was suspended in butyronitrile (5 mL) and toluene (0.5 mL). The reaction vessel was sealed and the mixture was stirred at +125° C. for 6 h. The reaction mixture was cooled down and partitioned between EtOAc and water, the water phase was extracted once with EtOAc. The organic phase was filtered through a short silica column and impurities was washed out with EtOAc, the crude intermediate product was eluted using a 0.35N NH$_3$ 5% MeOH/EtOAc (prepared by diluting 1 volume of commercially available 7 N NH$_3$ in MeOH with 19 volumes of EtOAc). Solvents were removed by evaporation to give 515 mg of crude intermediate amine (1R,2S)-1-{[1-(4-fluorophenyl)-1H-indazol-5-yl]oxy}-1-[4-(ethylthio)phenyl]propan-2-amine.

APCI-MS: m/z 422.1 [MH$^+$], the major impurity being unreacted (1R,2S)-2-amino-1-[4-(ethylthio)phenyl]propan-1-ol.

The crude amine was dissolved in MeOH (15 mL) and treated with excess 1,1,3,3-tetramethylguanidine (629 µL, 5 mmol) and ethyl trifluoroacetate (595 µL, 5 mmol). The reaction mixture was stirred at r.t. for 1 h, concentrated and purified by HPLC using a Kromasil® 100-10-C18 250×50 mm column. Flow 40 mL/min, 10 min gradient of 50%-90% MeCN in water followed by isocratic final concentration for 30 min until product had eluted. UV=254 nm was used for detection. Fractions with product was combined and lyophilized to afford the title compound as a colourless solid. Yield 380 mg (36%).

APCI-MS: m/z 518.1 [MH$^+$] $^1$H-NMR (300 MHz, DMSO-d$_6$): δ 9.49 (d, J=8.63 Hz, 1H), 8.17 (d, J=0.8 Hz, 1H), 7.78-7.66 (m, 3H), 7.46-7.23 (m, 6H), 7.19 (dd, J=9.16, 2.52 Hz, 1H), 7.12 (d, J=2.13 Hz, 1H), 5.25 (d, J=6.5 Hz, 1H), 4.23 (m, 1H), 2.94 (q, J=7.29 Hz, 2H), 1.33 (d, J=6.77 Hz, 3H), 1.18 (t, J=7.17 Hz, 3H)

(1R,2S)-2-amino-1-[4-(ethylthio)phenyl]propan-1-ol
(14a)

The subtitle compound was prepared following a procedure described by: M. Osorio-Olivares et al. Bioorg. Med. Chem. 12 (2004) 4055-4066.

(S)-2-Trifluoroacetamido-1-(4-ethylthiophenyl)-1-propanone (1.08 g, 3.5 mmol; M. Osotio-Olivares et al *Tetrahedron: Asymmetry* 14 (2003) 1473-1477) was dissolved in 99.5% EtOH (35 mL). NaBH$_4$ (0.67 g, 17.7 mmol) was added and the mixture was stirred at r.t. for 19 h. Solvents were removed by evaporation and the residual material was suspended in water (50 mL) and extracted with DCM (2×50 mL). The organic phase was dried over Na$_2$SO$_4$, filtered and concentrated, the residual oil was dissolved in Et$_2$O, addition of 5-6N HCl in 2-propanol resulted in the precipitation of an hydrochloride salt, this salt was collected by filtration, washed with ether and dried to constant weight. Obtained 845 mg (97%) of the subtitle compound as the hydrochloride salt and as a 85:15 mixture of the two possible diastereomers.

The major diastereomer was isolated by preparative HPLC using an XTerra® Prep MS C$_{18}$ OBD™ Column, 5 µm, 19×50 mm. 20 min gradient of 10-30% MeCN in (Water+2 mL NH$_3$/L). The purest fractions was combined and lyophilized to afford the subtitle compound as a colourless solid. Yield 526 mg (71%)

APCI-MS: m/z 212.1 [MH$^+$] $^1$H-NMR (300 MHz, CD$_3$OD): δ 7.36-7.26 (m, 4H), 4.46 (d, J=5.44 Hz, 1H), 3.05 (m, 1H), 2.94 (q, J=7.3 Hz, 2H), 1.28 (t, J=7.3 Hz, 3H), 1.04 (d, J=6.64 Hz, 3H).

Example 15

N-[(1R,2S)-1-(4-cyclopropylsulfanylphenyl)-1-[1-(4-fluorophenyl)indazol-5-yl]oxy-propan-2-yl]-2,2,2-trifluoro-acetamide

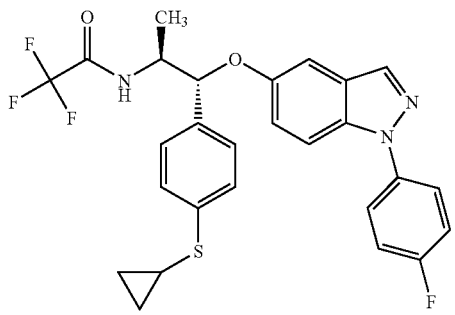

(1R,2S)-1-{[1-(4-Fluorophenyl)-1H-indazol-5-yl]oxy}-1-[4-(cyclopropylthio)phenyl]propan-2-amine (62 mg, 0.14 mmol) was dissolved in MeOH (2 mL), 1,1,3,3-tetramethylguanidine (100 µL, 0.8 mmol) and ethyl trifluoroacetate (83 µL, 0.7 mmol) was added. The mixture was stirred at r.t. for 2 h, the solvents was removed by evaporation and the residual material was treated with water and a few drops of dilute HCl(aq) until slightly acidic. The formed slurry was extracted with DCM and EtOAc, the combined organic phases was concentrated and purified by semi-preparative HPLC using a Kromasil® C18 250×20 mm, 5 µm column. Flow 10 mL/min, 15 min gradient of 50%-90% MeCN in water followed by isocratic final concentration until product had eluted. UV=254 nm was used for detection. Fractions with product was combined and lyophilized to afford the title compound as a colourless solid.

Yield 59 mg (79%). APCI-MS: m/z 530.1 [MH$^+$] $^1$H-NMR (300 MHz, DMSO-d$_6$): δ 9.51 (brs, 1H), 8.18 (d, J=0.79 Hz, 1H), 7.78-7.66 (m, 3H), 7.44-7.28 (m, 6H), 7.19 (dd, J=9.02, 2.39 Hz, 1H), 7.13 (d, J=1.99 Hz, 1H), 5.28 (d, J=6.24 Hz, 1H), 4.24 (m, 1H), 2.23 (m, 1H), 1.32 (d, J=6.77 Hz, 3H), 1.12-0.98 (m, 2H), 0.60-0.46 (m, 2H)

(1R,2S)-1-([1-(4-Fluorophenyl)-1H-indazol-5-yl]oxy)-1-[4-(cyclopropylthio)phenyl]propan-2-amine
(15a)

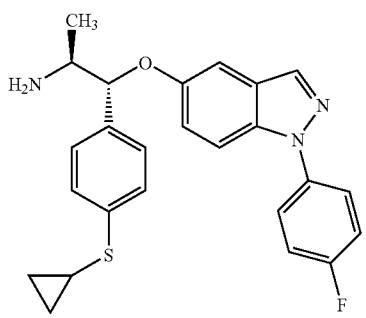

(1R,2S)-2-Amino-1-[4-(cyclopropylthio)phenyl]propan-1-ol (103 mg, 0.46 mmol), 1-(fluorophenyl)-5-iodoindazole (170 mg, 0.5 mmol), CuI (5 mg, 0.03 mmol) and Cs$_2$CO$_3$ (325 mg, 1 mmol) was suspended in butyronitrile (1 mL) and toluene (0.5 mL). The reaction vessel was sealed and the mixture was stirred at +125° C. for 18 h. The reaction mixture was cooled down and diluted with EtOAc (5 mL), washed with water (2×1 mL). The organic phase was filtered through a short silica column and impurities was washed out with EtOAc, the crude product was eluted using a 0.35N NH$_3$ 5% MeOH/EtOAc (prepared by diluting 1 volume of commercially available 7 N NH$_3$ in MeOH with 19 volumes of EtOAc). Solvents was removed by evaporation and the material was further purified by preparative HPLC using an XTerra® Prep MS Cl, OBD™ Column, 5 μm, 19×50 mm. 15 min gradient of 20-80% MeCN in (Water+2 mL NH$_3$/L). The fractions containing product was combined and lyophilized afford the subtitle compound as a hygroscopic solid. Yield 62 mg (31%)

APCI-MS: m/z 434.1 [MH$^+$]$^1$H-NMR (300 MHz, CD$_3$OD): δ 8.00 (d, J=0.93 Hz, 1H), 7.70-7.62 (m, 2H), 7.57 (dt, 1H), 7.39-7.20 (m, 7H), 7.09 (d, J=1.99 Hz, 1H), 5.11 (d, J=5.04 Hz, 1H), 3.27 (m, 1H), 2.20 (m, 1H), 1.20 (d, J=6.63 Hz, 3H), 1.06 (m, 2H), 0.59 (m, 2H)

(1R,2S)-2-amino-1-[4-(cyclopropylthio)phenyl]propan-1-ol (15b)

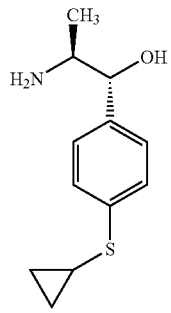

The subtitle compound was prepared in two steps following the procedure described by: M. Osorio-Olivares et al. Tetrahedron: Asymmetry 14 (2003) 1473-1477, and M. Osorio-Olivares et al. Bioorg. Med. Chem. 12 (2004) 4055-4066.

To a stirred solution of N-(trifluoroacetyl)-L-alanyl chloride (6.5 g, 32 mmol) and cyclopropyl phenyl sulfide (5 g, 33.28 mmol) in DCM (30 mL) was added AlCl$_3$ (4.27 g, 32 mmol). The reaction mixture was stirred at r.t. 17 h, cooled down in an ice-water batch and slowly quenched by addition of 1 N HCl (aq) (50 mL). The mixture was extracted with DCM (2×50 mL), the organic phase was dried over MgSO$_4$, filtered and evaporated to give a crude product as an oil. Addition of heptane failed to give a solid, the oil was dissolved in DCM and filtered through a short silica gel to remove some impurities.

The crude product showed some traces of the desired (S)-2-Trifluoroacetamido-1-(4-cyclopropylthiophenyl)-1-propanone by GC/MS, m/z=317.

The crude material was dissolved in 99.5% EtOH (100 mL), NaBH$_4$ (1.95 g, 51.5 mmol) was added, the mixture was stirred at r.t. for 19 h. LC/MS analysis showed traces of desired product APCI-MS: m/z 224 [MH$^+$]. The solvents were removed by evaporation, water (100 mL) was added, the formed slurry was extracted with DCM. The organic phase was concentrated and the residue was purified by preparative HPLC using an XTerra® Prep MS C$_{18}$ OBD™ Column, 5 μm, 19×50 mm. 20 min gradient of 10-40% MeCN in (Water+2 mL NH$_3$/L). The fractions containing product was combined and the purification was repeated one more time as above. The purest fractions were combined and lyophilized to afford the subtitle compound as a colourless hygroscopic solid. Yield 103 mg (1.4%).

APCI-MS: m/z 224.1 [MH$^+$]$^1$H-NMR (300 MHz, CD$_3$OD): δ 7.36 (d, J=8.49 Hz, 2H), 7.29 (d, J=8.36 Hz, 2H), 4.44 (d, J=5.44 Hz, 1H), 3.04 (m, 1H), 2.23 (m, 1H), 1.12-1.02 (m, 2H), 1.05 (d, J=6.64 Hz, 3H), 0.64-0.57 (m, 2H)

Example 16

N-[(1R,2S)-1-[1-(4-fluorophenyl)indazol-5-yl]oxy-1-phenyl-propan-2-yl]-2-hydroxy-acetamide

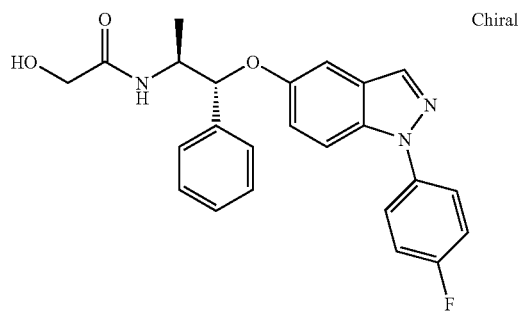

Prepared as described in Example 7 using (1S,2R)-1-{[1-(4-fluorophenyl)-1H-indazol-5-yl]oxy}-1-phenylpropan-2-amine (1a, 149 mg, 0.41 mmol) and 2-chloro-2-oxoethyl acetate (49 μL, 0.45 mmol). Yield 125 mg (72%).

APCI-MS: m/z 420.1 [MH$^+$]$^1$H NMR (400 MHz, DMSO-d6): δ 8.16 (s, 1H), 7.74 (m, 2H), 7.69 (d, J=9.2 Hz, 1H), 7.63 (d, J=8.8 Hz, 1H), 7.44-7.32 (m, 6H), 7.26 (m 1H), 7.22 (dd, J=9.2, 2.3 Hz, 1H), 7.10 (d, J=2.1 Hz, 1H), 5.42 (d, J=5.0 Hz, 1H), 4.25 (m 1H), 3.73 (m, 2H), 2.55 (s, 1H), 1.18 (d, J=6.7 Hz, 3H).

Example 17

N-[(1R*,2S*)-1-[1-(4-fluorophenyl)indazol-5-yl]oxy-1-(6-methoxypyridin-3-yl)propan-2-yl]cyclopropanecarboxamide

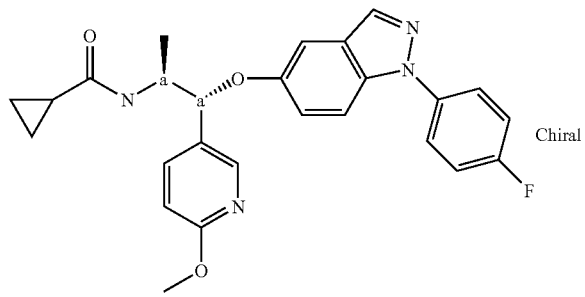

a = relative mixture

Prepared as described in Example 1 with corresponding starting material.

APCI-MS: m/z 461.1 [MH$^+$]$^1$H-NMR (400 MHz, acetone-d$_6$) δ 8.22 (1H, d); 8.06 (1H, s); 7.80-7.69 (4H, m); 7.52 (1H, d); 7.34 (2H, dd); 7.23 (2H, dd); 7.19 (1H, d); 6.74 (1H, d);

5.45 (1H, d); 4.37-4.27 (1H, m); 3.85 (3H, s); 1.54 (1H, ddd); 1.27 (3H, d); 0.79-0.73 (1H, m); 0.69-0.53 (3H, m).

(1R*,2S*)-1-[1-(4-fluorophenyl)indazol-5-yl]oxy-1-(6-methoxypyridin-3-yl)propan-2-amine (17a)

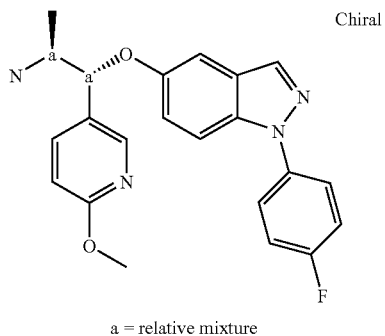

a = relative mixture

Prepared as described in Example 1 with corresponding starting material.

APCI-MS: m/z 393.1 [MH+] ¹H-NMR (400 MHz, acetone-d₆) δ 8.21 (1H, d); 8.04 (1H, d); 7.78-7.70 (3H, m); 7.65 (1H, d); 7.38-7.14 (4H, m); 6.68 (1H, d); 5.23 (1H, d); 3.98 (1H, q); 3.82 (3H, s); 1.85-1.79 (1H, m); 1.65-1.58 (1H, m); 1.27 (3H, d)

(1R*,2S*)-2-amino-1-(6-methoxypyridin-3-yl)propan-1-ol 1-(6-methoxypyridin-3-yl)-2-nitro-propan-1-ol (17b)

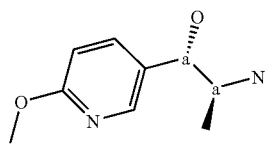

a = relative mixture 1-(6-methoxypyridin-3-yl)-2-nitro-propan-1-ol (17c) (2.20 g, 10.37 mmol) was dissolved in methanol (410 mL) and hydrogenated using a H-Cube™ hydrogenation reactor (THALES nanotechnology) equipped with a cartridge of 10% Pd/C. The flow rate was set to 0.8 mL/min, temperature 80° C. and full the hydrogen production at full mode. After evaporation of the solution diastereomers were separated on preparative HPLC (XTerrra C₁₈, 19×50 mm) using a gradient of 5-30% acetonitrile in water (+1% NH₃) gave the subtitle compound 17b (448 mg, 24%).

¹H-NMR (400 MHz, DMSO-d₆): δ 8.05 (1H, d); 7.63 (1H, dd); 6.76 (1H, d); 4.29 (1H, d); 3.82 (3H, s); 2.90 (1H, quintet); 0.87 (3H, d).

APCI-MS: m/z 183.0 [MH+].

1-(6-methoxypyridin-3-yl)-2-nitro-propan-1-ol (17c)

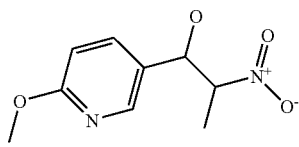

To a round bottom flask was added anhydrous magnesium sulphate (4.77 g, 40 mmol) and nitroethane (15 ml) The flask was evacuated and filled with argon. The reaction mixture was stirred vigorously to get a homogeneous suspension before 6-methoxynicotinaldehyde (2.37 g, 18 mmol in 5 mL nitroethane) was added. After stirring in 5 min 2,5,8,9-tetraaza-1-phosphabicyclo[3.3.3]undecane, 2,8,9-tris(1-methylethyl) (1082 mg, 3.6 mmol) was added. The reaction mixture was stirred overnight at r.t. before it was purified by flash chromatography (SiO₂, heptane-ethylacetate). Yield 2.22 g, 58%.

APCI-MS: m/z 213.1 [MH+].

(1R*,2S*)-1-[1-(4-fluorophenyl)indazol-5-yl]oxy-1-(6-methoxypyridin-3-yl)propan-2-amine

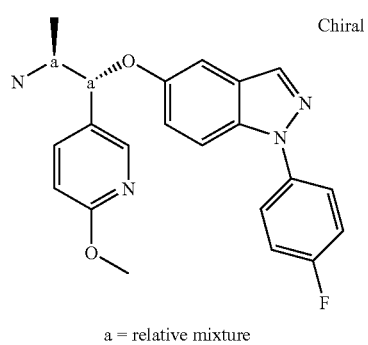

a = relative mixture

Prepared as described in Example 1 with corresponding starting material.

APCI-MS: m/z 393.1 [MH+] ¹H-NMR (400 MHz, acetone-d₆) δ 8.21 (1H, d); 8.04 (1H, d); 7.78-7.70 (3H, m); 7.65 (1H, d); 7.38-7.14 (4H, m); 6.68 (1H, d); 5.23 (1H, d); 3.98 (1H, q); 3.82 (3H, s); 1.85-1.79 (1H, m); 1.65-1.58 (1H, m); 1.27 (3H, d).

Example 18

N-[(1R,2S)-1-[1-(4-fluorophenyl)indazol-5-yl]oxy-1-(6-methoxypyridin-3-yl)propan-2-yl]cyclopropanecarboxamide

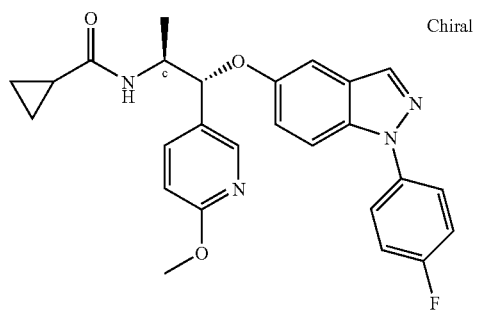

ISOMER 2
c = relative absolute

The racemic mixture of N-[(1R,2S)-1-[1-(4-fluorophenyl)indazol-5-yl]oxy-1-(6-methoxypyridin-3-yl)propan-2-yl] cyclopropanecarboxamide (16) were separated on Thales SFC, Chiralpak IA column (75% CO₂, 25% MeOH) collecting the second eluating peak.

¹H-NMR (400 MHz, Acetone-d₆) δ 8.22 (1H, d); 8.06 (1H, s); 7.80-7.69 (4H, m); 7.52 (1H, d); 7.34 (2H, dd); 7.23 (2H, dd); 7.19 (1H, d); 6.74 (1H, d); 5.45 (1H, d); 4.37-4.27 (1H, m); 3.85 (3H, s); 1.54 (1H, ddd); 1.27 (3H, d); 0.79-0.73 (1H, m); 0.69-0.53 (3H, m). APCI-MS: m/z 461.1 [MH+].

Example 19

N-[(1R,2S)-1-(2,5-dioxabicyclo[4.4.0]deca-7,9,11-trien-8-yl)-1-[1-(4-fluorophenyl)indazol-5-yl]oxy-propan-2-yl]-2,2,2-trifluoro-acetamide

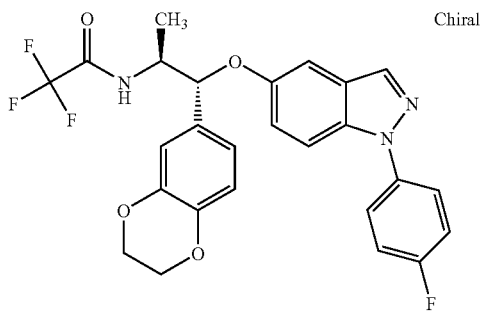

Trifluoroacetic anhydride (0.095 mL, 0.67 mmol) was added to (1R,2S)-1-(2,3-dihydrobenzo[b][1,4]dioxin-6-yl)-1-(1-(4-fluorophenyl)-1H-indazol-5-yloxy)propan-2-amine 2,2,2-trifluoroacetate (300 mg, 0.56 mmol) and triethylamine (0.235 mL, 1.69 mmol) in THF (6 mL) at r.t. After 20 min another portion of triethylamine (0.103 mL, 0.74 mmol) and Trifluoroacetic anhydride (0.050 mL, 0.35 mmol) was added. The reaction mixture was stirred for another 20 min, concentrated, diluted with 10% NaHSO$_4$ (aq) and extracted with EtOAc. The organic phase was washed with 10% NaHSO$_4$ (aq). The crude product was further purified by HPLC. Yield 230 mg (79%)

Chiral analysis was made using a CHIRALPAK® IB, 150×0.46 mm column, 15% EtOH/iso-Hexane, 0.5 mL/min, UV=254 nm: >99% ee, Rt=15.57 min.

APCI-MS: m/z 516.1 [MH+] $^1$H-NMR (300 MHz, DMSO-d$_6$): δ 9.47 (d, 1H), 8.19 (d, 1H), 7.74 (m, 2H), 7.69 (d, 1H), 7.40 (m, 2H), 7.18 (dd, 1H), 7.12 (d, 1H), 6.89-6.79 (m, 3H), 5.19 (d, 1H), 4.18 (s+m, 4H+1H), 1.31 (d, 3H).

(1R,2S)-J-(2,3-dihydrobenzo[b][1,4]dioxin-6-yl)-1-(1-(4-fluorophenyl)-1H-indazol-5-yloxy)propan-2-amine 2,2,2-trifluoroacetate. (19a)

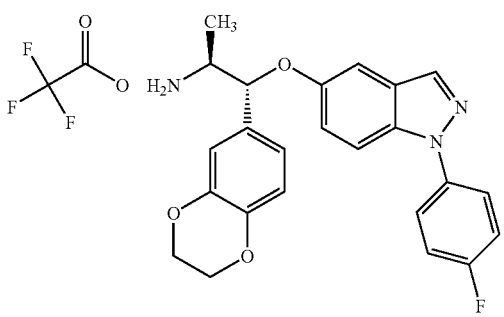

The subtitle compound was prepared essentially by the method described by Job & Buchwald: Org. Lett. 2002, 4 (21), 3703-3706.

A mixture of (1R,2S)-2-amino-1-(2,3-dihydrobenzo[b][1,4]dioxin-6-yl)propan-1-ol hydrochloride (246 mg, 1.00 mmol), 1-(4-fluorophenyl)-5-iodo-1H-indazole (406 mg, 1.20 mmol), copper(I) iodide (38.1 mg, 0.20 mmol) and Cs$_2$CO$_3$ (979 mg, 3.00 mmol) in butyronitrile (3 mL) was heated for 5 h at +100° C. in a sealed reaction tube flushed with Argon. The reaction mixture was cooled down, partitioned between DCM (20 mL) and water (5 mL), brine (5 mL) was added. The water phase was extracted with another portion of DCM (20 mL). The combined DCM phases (40 mL) was filtered through a 10 g silica column, EtOAc (40 mL) was used to wash the column. The crude product was washed out from the column using 0.35 M NH$_3$ in 5% MeOH/EtOAc (150 mL). The solvents was removed by evaporation. The crude product was further purified by HPLC. The fractions containing product were freeze dried to give the TFA salt of the desired product. NMR showed 4 mol % of second set of signals originating from diastereomer. Yield 125 mg (23%)

APCI-MS: m/z 420.1 [MH+-TFA] $^1$H-NMR (300 MHz, DMSO-d$_6$): δ 8.22 (d, 1H), 8.11 (brs, 3H), 7.80-7.70 (m, 3H), 7.41 (m, 2H), 7.27 (dd, 1H), 7.15 (d, 1H), 6.92-6.85 (m, 3H), 5.51 (d, 1H), 4.21 (s, 4H), 3.68 (bnn, 1H), 1.18 (d, 3H).

(1R,2S)-2-amino-1-(2,3-dihydrobenzo[b][1,4]dioxin-6-yl)propan-1-ol hydrochloride. (19b)

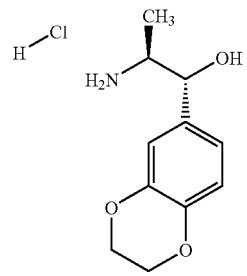

5-6 N HCl in 2-Propanol (8 mL, 40-48 mmol) was added to tert-butyl (1R,2S)-1-(2,3-dihydrobenzo[b][1,4]dioxin-6-yl)-1-hydroxypropan-2-ylcarbamate (3.1 g, 10.02 mmol) in ethyl acetate (40 mL) at +40° C. and stirred at for 3 h. The reaction mixture was allowed to reach r.t. and concentrated by evaporation. Ether was added and the salt was collected by filtration and washed with ether. The salt was found to be hygroscopic. Yield 2.10 g (85%)

APCI-MS: m/z 210 [MH+—HCl] $^1$H-NMR (300 MHz, DMSO-d$_6$): δ 8.01 (brs, 3H), 6.87-6.76 (m, 3H), 5.93 (brd, 1H), 4.79 (brt, 1H), 4.22 (s, 4H), 3.32 (bnm, 1H), 0.94 (d, 3H).

tert-butyl (1R,2S)-1-(2,3-dihydrobenzo[b][1,4]dioxin-6-yl)-1-hydroxypropan-2-ylcarbamate (19c)

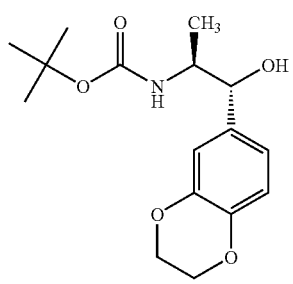

The diastereoselective catalytic Meerwein-Ponndorf-Verley reduction was made by the method described by Jingjun Yin et. al. J. Org. Chem. 2006, 71, 840-843. (S)-tert-butyl 1-(2,3-dihydrobenzo[b][1,4]dioxin-6-yl)-1-oxopropan-2-ylcarbamate (3.76 g, 12.23 mmol), aluminium isopropoxide (0.5 g, 2.45 mmol) and 2-propanol (12 mL, 157.75 mmol) in toluene (22 mL) was stirred at +50° C. under argon for 16 h.

The reaction mixture was poured into 1M HCl (150 mL), the mixture was extracted with EtOAc (250 mL). The organic phase was washed with water (2×50 mL) and brine (100 mL), dried over $Na_2SO_4$, filtered and concentrated. The crude product was purified by flash-chromatography on silica using EtOAc:Hexane (1:2) as eluent. Fractions containing product was combined. Solvent was removed by evaporation to give the desired product as a colourless solid. Yield 3.19 g (84%)

APCI-MS: m/z 236, 210, 192 [MH+-tBu-18, MH+—BOC, MH+—BOC-18] $^1$H-NMR (300 MHz, DMSO-$d_6$): δ 6.80-6.70 (m, 3H), 6.51 (d, 1H), 5.17 (d, 1H), 4.36 (t, 1H), 4.19 (s, 4H), 3.49 (m, 1H), 1.31 (s, 9H), 0.93 (d, 3H).

(S)-tert-butyl 1-(2,3-dihydrobenzo[b][1,4]dioxin-6-yl)-1-oxopropan-2-ylcarbamate (19d)

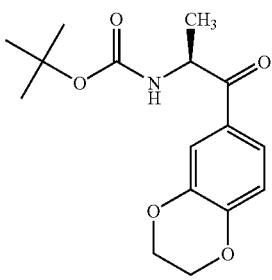

A suspension of (S)-tert-butyl 1-(methoxy(methyl) amino)-1-oxopropan-2-ylcarbamate (3 g, 12.92 mmol) in THF (30 mL) was placed under a protective atmosphere of Argon and cooled down to −15 to −20° C., isopropylmagnesium chloride, 2M in THF (6.5 mL, 13.00 mmol) was added keeping the temperature below −10° C. The slurry started to dissolve, temperature was allowed to reach 0° C., a freshly prepared solution of (2,3-dihydrobenzo[b][1,4]dioxin-6-yl) magnesium bromide, 0.7M in THF (20 mL, 14.00 mmol) was added. The temperature was allowed to reach r.t., the reaction mixture was stirred for 17 h. 1N HCl (300 mL) was cooled on icebath to +10° C., the reaction mixture was poured into the acidic water solution, TBME=tert-butyl methyl ether (300 mL) was added and the mixture was transferred to a separation funnel. The waterphase was backextracted with TBME (200 mL). The ether phases were washed with water, brine and dried ($Na_2SO_4$).

The crude product was purified by flash chromatography using TBME:Heptane=1:2 as eluent. Fractions containing the product was combined and solvents was removed by evaporation to give the subtitle compound as a slightly yellow sticky oil/gum. Yield 3.76 g (95%)

APCI-MS: m/z 208.1 [MH+—BOC] $^1$H-NMR (300 MHz, DMSO-$d_6$): δ 7.50 (dd, 1H), 7.46 (d, 1H), 7.24 (d, 1H), 6.97 (d, 1H), 4.97 (m, 1H), 4.30 (m, 4H), 1.36 (s, 9H), 1.19 (d, 3H).

Example 20

2,2,2-trifluoro-N-[(1R,2S)-1-[1-(4-fluorophenyl) indazol-5-yl]oxy-1-naphthalen-2-yl-propan-2-yl] acetamide

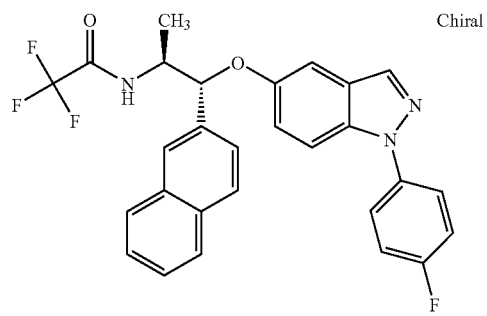

(1R,2S)-1-(1-(4-fluorophenyl)-1H-indazol-5-yloxy)-1-(naphthalen-2-yl)propan-2-amine hydrochloride (50 mg, 0.11 mmol), 1,1,3,3-tetramethylguanidine (100 μl, 0.79 mmol) and Ethyl trifluoroacetate (200 μl, 1.68 mmol) in MeOH (2.5 mL) was stirred at r.t. for 1 h. The reaction mixture was concentrated by evaporation. The residual material was purified by HPLC. Yield 37 mg (65%)

APCI-MS: m/z 508.1 [MH+] $^1$H-NMR (400 MHz, DMSO-$d_6$): 9.58 (d, 1H), 8.13 (d, 1H), 7.94-7.85 (m, 4H), 7.76-7.66 (m, 3H), 7.56 (dd, 1H), 7.50 (m, 2H), 7.38 (m, 2H), 7.25 (dd, 1H), 7.17 (d, 1H), 5.46 (d, 1H), 4.36 (m, 1H), 1.38 (d, 3H).

(1R,2S)-1-(1-(4-fluorophenyl)-1H-indazol-5-yloxy)-1-(naphthalen-2-yl)propan-2-amine hydrochloride (20a)

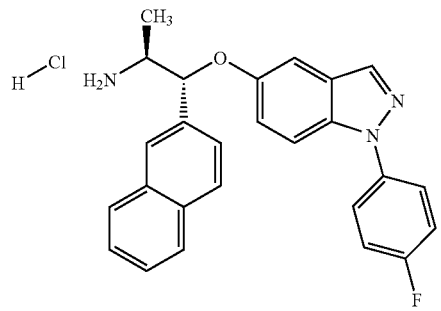

The subtitle compound was prepared analogous to the method described in Example 19 (step 19a). (1R,2S)-2-amino-1-(naphthalen-2-yl)propan-1-ol hydrochloride (238 mg, 1.00 mmol), 1-(4-fluorophenyl)-5-iodo-1H-indazole (406 mg, 1.20 mmol), Cesium carbonate (979 mg, 3.00 mmol) and copper(I) iodide (38.1 mg, 0.20 mmol) in Butyronitrile (3 mL) was heated for 19 h at +125° C. in a sealed reactiontube flushed with Argon. After final purification by HPLC the obtained material was isolated as a brownish coloured hydrochloride salt from tert-butylmethylether/HCl.

Yield 171 mg (38%) APCI-MS: m/z 412.9 [MH+—HCl] $^1$H-NMR (400 MHz, DMSO-$d_6$) 8.45 (brs, 3H), 8.16 (s, 1H), 8.00-7.88 (m, 4H), 7.73 (m, 3H), 7.58 (dd, 1H), 7.53 (m, 2H), 7.39 (m, 3H), 7.20 (d, 1H), 5.88 (d, 1H), 3.80 (m, 1H) 1.24 (d, 3H).

(1R,2S)-2-amino-1-(naphthalen-2-yl)propan-1-ol hydrochloride (20b)

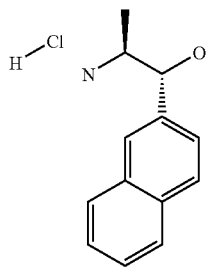

tert-butyl (1R,2S)-1-hydroxy-1-(naphthalen-2-yl)propan-2-ylcarbamate (588 mg, 1.95 mmol) was dissolved in Ethyl acetate (20 mL). To the clear solution was added 1.5 N HCl/EtOAc (10 mL, 15.00 mmol), the reaction mixture was stirred at +40° C. for 2 h. The resulting slurry was allowed to cool to r.t., the salt was removed by filtration, washed with ether and dried by suction in the filtration funnel.

Yield 588 mg (85%). APCI-MS: m/z 202 [MH$^+$—HCl] $^1$H-NMR (300 MHz, DMSO-d$_6$): δ 8.13 (brs, 3H), 7.96-7.88 (m, 4H), 7.56-7.47 (m, 3H), 6.20 (d, J=4.11 Hz, 1H), 5.11 (t, 1H), 3.50 (m, 1H), 0.98 (d, 3H).

tert-butyl (1R,2S)-1-hydroxy-1-(naphthalen-2-yl)propan-2-ylcarbamate (20c)

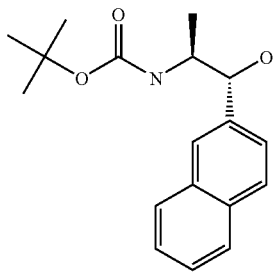

The title compound was prepared analogous to the method described in Example 19 (step 19c), starting from tert-butyl [(1S)-1-methyl-2-(2-naphthyl)-2-oxoethyl]carbamate (350 mg, 1.17 mmol). In contrast the reaction mixture was stirred at +50° C. for 19 h, crude material was purified by flash chromatography on silica using a gradient of 0% to 30% EtOAc in Heptane.

Yield 309 mg (87%) APCI-MS: m/z 202 [MH$^+$—BOC] $^1$H-NMR (300 MHz, DMSO-d$_6$): δ 7.92-7.77 (m, 4H), 7.53-7.41 (m, 3H), 6.65 (d, 1H), 5.44 (d, 1H), 4.68 (t, 1H), 3.69 (m, 1H), 1.25 (s, 9H), 0.99 (d, 3H).

tert-butyl[(1S)-1-methyl-2-(2-naphthyl)-2-oxoethyl]carbamate (20d)

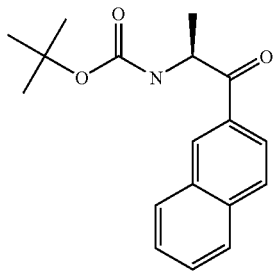

The subtitle compound was prepared analogous to the method described in Example 19 (step 19d), starting from (S)-tert-butyl 1-(methoxy(methyl)amino)-1-oxopropan-2-ylcarbamate (1.86 g, 8 mmol) and a freshly prepared 2-Naphthylmagnesiumbromide 1M solution in THF (8 mL, 8 mmol). The obtained material was crystallised from Heptane. Yield 350 mg (14%).

APCI-MS: m/z 200 [MH$^+$—BOC] $^1$H-NMR (300 MHz, DMSO-d$_6$): δ 8.70 (s 1H), 8.11 (d, 1H), 8.00 (m, 3H), 7.65 (m, 2H), 7.38 (d, 1H), 5.24 (m, 1H), 1.35 (s, 9H), 1.29 (d, 3H).

Example 21

N-[(1R,2S)-1-[1-(4-fluorophenyl)indazol-5-yl]oxy-1-naphthalen-2-yl-propan-2-yl]-2-hydroxy-acetamide

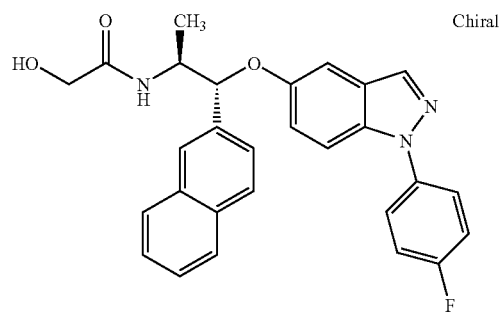

Acetoxyacetyl chloride (13 μL, 0.12 mmol) was added to a stirred mixture of (1R,2S)-1-(1-(4-fluorophenyl)-1H-indazol-5-yloxy)-1-(naphthalen-2-yl)propan-2-amine hydrochloride (20a) (50 mg, 0.11 mmol) and N,N-diisopropylethylamine (60 μL, 0.34 mmol) in THF (2 mL). The reaction mixture was stirred at r.t. 45 min. Water (0.5 mL), 28% (aq) NH3 (0.5 mL) and MeOH (0.5 mL) was added to give a clear one-phase solution, the mixture was stirred over night at r.t.

The reaction mixture was concentrated, the residual material was purified by HPLC. Yield 32 mg (61%)

APCI-MS: m/z 470.1 [MH$^+$] $^1$H-NMR (400 MHz, DMSO-d$_6$): δ 8.13 (d, 1H), 7.94-7.86 (m, 4H), 7.76-7.66 (m, 4H), 7.58 (dd, 1H), 7.49 (m, 2H), 7.38 (m, 2H), 7.27 (dd, 1H), 7.15 (d, 1H), 5.57 (d, 1H), 5.51 (brs, 1H), 4.37 (m, 1H), 3.71 (q, 2H), 1.24 (d, 3H).

Example 22

N-[(1R,2S)-1-(3-ethylphenyl)-1-[1-(4-fluorophenyl)indazol-5-yl]oxy-propan-2-yl]-2,2,2-trifluoro-acetamide

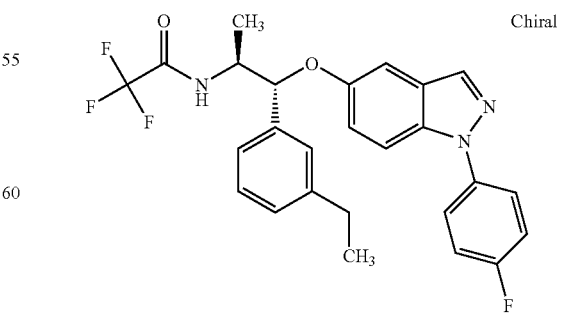

(1R,2S)-1-(3-ethylphenyl)-1-(1-(4-fluorophenyl)-1H-indazol-5-yloxy)propan-2-amine hydrochloride (50 mg, 0.12 mmol), 1,1,3,3-tetramethylguanidine (100 µl, 0.79 mmol) and ethyl trifluoroacetate (200 µl, 1.68 mmol) in MeOH (2.5 mL) was stirred at r.t. for 1 h. The reaction mixture was concentrated by evaporation, the residual material was purified by HPLC. Yield 41 mg (72%).

APCI-MS: m/z 486.1 [MH+]$^1$H-NMR (400 MHz, DMSO-d$_6$): δ 9.49 (d, 1H), 8.18 (s, 1H), 7.77-7.66 (m, 3H), 7.39 (m 2H), 7.28-7.17 (m, 4H), 7.15-1.08 (m, 2H), 5.26 (d, 1H), 4.22 (m, 1H), 2.58 (q, 2H), 1.33 (d, 3H), 1.14 (t, 3H).

(1R,2S)-1-(3-ethylphenyl)-1-(1-(4-fluorophenyl)-1H-indazol-5-yloxy)propan-2-amine hydrochloride (22a)

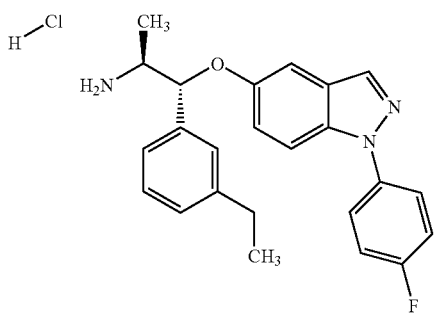

The subtitle compound was prepared analogous to the method described in Example 19 (step 19a). A mixture of (1R,2S)-2-amino-1-(3-ethylphenyl)propan-1-ol hydrochloride (22b, 216 mg, 1.00 mmol), 1-(4-fluorophenyl)-5-iodo-1H-indazole (406 mg, 1.20 mmol), cesium carbonate (979 mg, 3.00 mmol) and copper(I) iodide (38.1 mg, 0.20 mmol) in butyronitrile (3 mL) was heated for 19 h at +125° C. in a sealed reactiontube flushed with Argon. After final purification by HPLC the obtained material was dissolved in tert-Butyl methyl ether, and precipitated as the hydrochloride salt by adding a solution of 6-7 N HCl in 2-propanol. Yield 199 mg (46%)

APCI-MS: m/z 390.1 [MH+—HCl]$^1$H-NMR (400 MHz, DMSO-d$_6$): δ 8.39 (brs, 3H), 8.21 (s, 1H), 7.75 (m, 3H), 7.44-7.14 (m, 8H), 5.70 (d, 1H), 3.67 (m, 1H), 2.61 (q, 2H), 1.17 (d, 3H), 1.16 (t, 3H).

(1R,2S)-2-amino-1-(3-ethylphenyl)propan-1-ol hydrochloride (22b)

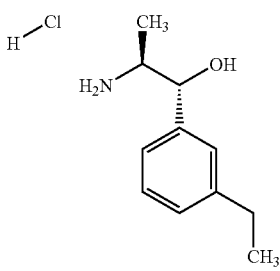

The subtitle compound was prepared in two steps analogous to the method described in Example 19 (step 19b+19c). Starting from (S)-tert-butyl 1-(3-ethylphenyl)-1-oxopropan-2-ylcarbamate (22c, 700 mg, 2.52 mmol). Yield 425 mg (78%)

APCI-MS: m/z 180 [MH+—HCl]$^1$H-NMR (300 MHz, DMSO-d$_6$): δ 8.12 (brs, 3H), 7.28 (t, 1H), 7.22-7.09 (m, 3H), 5.98 (d, 1H), 4.93 (t, 1H), 3.35 (m, 1H), 2.61 (q, 2H), 1.18 (t, 3H), 0.94 (d, 3H).

(S)-tert-butyl 1-(3-ethylphenyl)-1-oxopropan-2-ylcarbamate (22c)

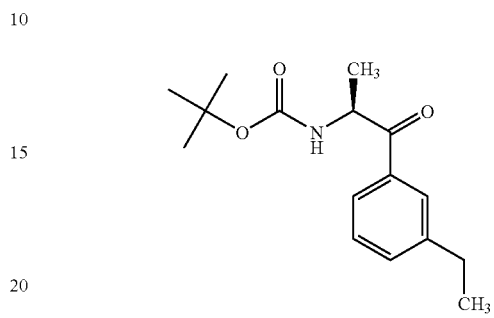

The subtitle compound was prepared analogous to the method described in Example 19 (step 19d). Starting from (S)-tert-butyl 1-(methoxy(methyl)amino)-1-oxopropan-2-ylcarbamate (0.7 g, 3.01 mmol) and freshly made (3-ethylphenyl)magnesium bromide 0.9M solution in THF (5 mL, 4.50 mmol). Yield 817 mg (97%)

GC/MS: m/z=221 (M-tBu) $^1$H-NMR (300 MHz, DMSO-d$_6$): δ 7.82-7.74 (m, 2H), 7.51-7.38 (m, 2H), 7.30 (d, 1H), 5.04 (m, 1H), 2.67 (q, 2H), 1.35 (s, 9H), 1.22 (d, 3H), 1.20 (t, 3H).

Example 23

N-[(1R,2S)-1-(3-ethylphenyl)-1-[1-(4-fluorophenyl)indazol-5-yl]oxy-propan-2-yl]-2-hydroxy-acetamide

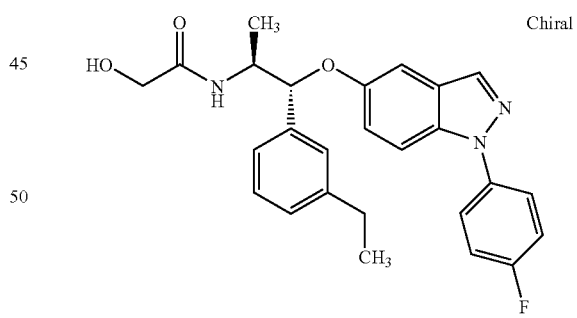

The title compound was prepared analogous to the method described in Example 21 starting from (1R,2S)-1-(3-ethylphenyl)-1-(1-(4-fluorophenyl)-1H-indazol-5-yloxy)propan-2-amine hydrochloride (22a) (50 mg, 0.12 mmol), and Acetoxyacetyl chloride (14 µL, 0.13 mmol).

Yield 37 mg (70%). APCI-MS: m/z 448.1 [MH+]$^1$H-NMR (400 MHz, DMSO-d$_6$): δ 8.17 (d, 1H), 7.74 (m, 2H), 7.69 (d, 1H), 7.60 (d, 1H), 7.40 (m, 2H), 7.29-7.18 (m, 4H), 7.11 (m, 2H), 5.50 (t, 1H), 5.40 (d, 1H), 4.24 (m, 1H), 3.74 (m, 2H), 2.59 (q, 2H), 1.16 (d, 3H), 1.15 (t, 3H).

Example 24

2,2,2-trifluoro-N-[(1R,2S)-1-[1(4-fluorophenyl)indazol-5-yl]oxy-1-(3-methylphenyl)propan-2-yl]acetamide

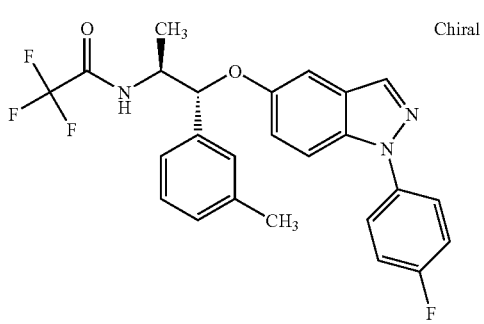

Trifluoroacetic anhydride (42 µl, 0.30 mmol) was added to a stirred solution of (1R,2S)-1-(1-(4-fluorophenyl)-1H-indazol-5-yloxy)-1-m-tolylpropan-2-amine 2,2,2-trifluoroacetate (120 mg, 0.25 mmol) and triethylamine (103 µl, 0.74 mmol) in THF (6 mL) at r.t., after 20 min another portion of triethylamine (103 µl, 0.74 mmol) and trifluoroacetic anhydride (42 µl, 0.30 mmol) was added. The reaction mixture was stirred for another 80 min, concentrated, diluted with 10% NaHSO$_4$ (aq) and extracted with EtOAc, the organic phase was washed with another portion of 10% NaHSO$_4$ (aq) and concentrated. The crude product was further purified by preparative HPLC. Yield 89 mg (77%)

APCI-MS: m/z 472.1 [MH$^+$]$^1$H-NMR (400 MHz, DMSO-d$_6$): δ 9.52 (d, 1H), 8.17 (d, 1H), 7.78-7.66 (m, 3H), 7.44-7.34 (m, 2H), 7.27-7.16 (m, 4H), 7.12-7.05 (m, 2H), 5.25 (d, 1H), 4.21 (m, 1H), 2.28 (s, 3H), 1.32 (d, 3H).

(1R,2S)-1-(1-(4-fluorophenyl)-1H-indazol-5-yloxy)-1-m-tolylpropan-2-amine 2,2,2-trifluoroacetate. (24a)

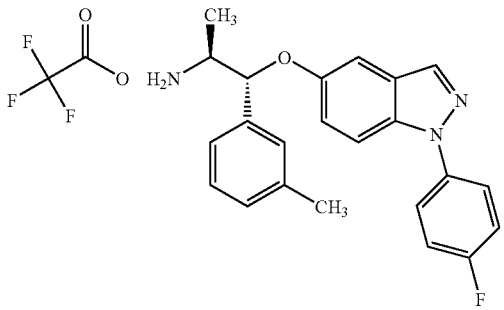

The subtitle compound was prepared analogous to the method described in Example 19a, starting from (1R,2S)-2-amino-1-m-tolylpropan-1-ol hydrochloride (202 mg, 1.00 mmol).

Yield 125 mg (25%). APCI-MS: m/z 376.1 [MH$^+$-TFA] $^1$H-NMR (400 MHz, DMSO-d$_6$): δ 8.21 (d, 1H), 8.19 (brs, 3H), 7.80-7.70 (m, 3H), 7.41 (m, 2H), 7.35-7.10 (m, 6H), 5.60 (d, 1H), 3.71 (brm, 1H), 2.31 (s, 3H), 1.16 (d, 3H).

(1R,2S)-2-amino-1-m-tolylpropan-1-ol hydrochloride (24b)

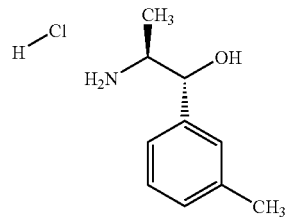

tert-butyl (1R,2S)-1-hydroxy-1-m-tolylpropan-2-ylcarbamate (2.31 g, 8.71 mmol) was dissolved in ethyl acetate (30 mL), 1.5 M HCl in EtOAc (20 ml, 30.00 mmol) was added and the mixture was stirred at +50° C. for 90 min. The reaction mixture was allowed to assume r.t. while stirring for 30 min, the solvents was removed by evaporation. The residual material was treated with EtOAc (5-10 mL), ether was added (60-70 mL) and the formed slurry was stirred for 30 min at r.t.

The solid HCl salt was collected by filtration and washed with ether, the salt was found to be hygroscopic and was transferred to a desiccator and dried under reduced pressure at +40° C.

Yield 1.68 g (95%) APCI-MS: m/z 166 [MH$^+$—HCl]$^1$H-NMR (300 MHz, DMSO-d$_6$): δ 8.10 (brs, 3H), 7.31-7.02 (m, 4H), 5.98 (d, 1H), 4.91 (t, 1H), 3.35 (brs, 1H+ water), 2.31 (s, 3H), 0.93 (d, 3H).

tert-butyl (1R,2S)-1-hydroxy-1-m-tolylpropan-2-ylcarbamate (24c)

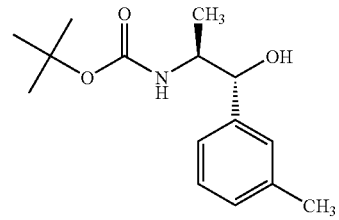

The subtitle compound was prepared in two steps analogous to the methods described in Example 19 (step 19c+19d). Starting from (S)-tert-butyl 1-(methoxy(methyl)amino)-1-oxopropan-2-ylcarbamate (2.323 g, 10 mmol), and m-tolylmagnesium bromide 1.0M solution in THF (12.00 mL, 12.00 mmol). Yield 2.33 g (88%)

APCI-MS: m/z 166.1 [MH$^+$—BOC]$^1$H-NMR (300 MHz, DMSO-d$_6$): δ 7.22-6.96 (m, 4H), 6.56 (d, 1H), 5.22 (d, 1H), 4.49 (t, 1H), 3.56 (m, 1H), 2.29 (s, 3H), 1.32 (s, 9H), 0.92 (d, 3H).

Example 25

N-[(1R,2S)-1-[4-(ethylsulfanylmethyl)phenyl]-1-[1-(4-fluorophenyl)indazol-5-yl]oxy-propan-2-yl]-2,2,2-trifluoro-acetamide

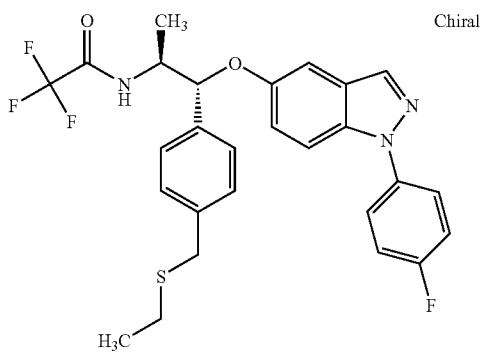

(1R,2S)-1-(4-(ethylthiomethyl)phenyl)-1-(1-(4-fluorophenyl)-1H-indazol-5-yloxy)propan-2-amine hydrochloride (50 mg, 0.11 mmol), 1,1,3,3-tetramethylguanidine (100 μl, 0.79 mmol) and ethyl trifluoroacetate (200 μl, 1.68 mmol) in MeOH (2.5 mL) was stirred at r.t. for 1 h. The reaction mixture was concentrated by evaporation and the residual material was purified by HPLC. Yield 35 mg (62%).

APCI-MS: m/z 532 [MH$^+$] $^1$H-NMR (300 MHz, DMSO-d$_6$): δ 9.49 (d, 1H), 8.17 (d, 1H), 7.73 (m, 2H), 7.69 (d, 1H), 7.44-7.24 (m, 6H), 7.19 (dd, 1H), 7.12 (d, 1H), 5.26 (d, 1H), 4.24 (m, 1H), 3.68 (s, 2H), 2.31 (q, 2H), 1.33 (d, 3H), 1.09 (t, 3H).

(1R,2S)-1-(4-(ethylthiomethyl)phenyl)-1-(1-(4-fluorophenyl)-1H-indazol-5-yloxy)propan-2-amine hydrochloride (25a)

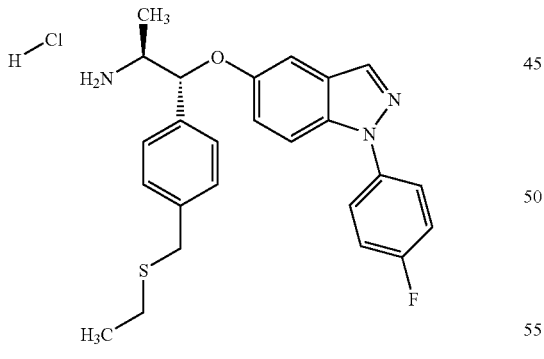

The subtitle compound was prepared analogous to the method described in Example 19a, starting from (1R,2S)-2-amino-1-(4-(ethylthiomethyl)phenyl)propan-1-ol (225 mg, 1.00 mmol). In contrast the reaction mixture was heated at +125° C. for 19 h, after final purification by HPLC the obtained material was dissolved in tert-Butyl methyl ether, and precipitated as the hydrochloride salt by adding a solution of 6-7 N HCl in 2-propanol. The obtained material was found to contain approximately 5 mol % oxidized material (1R,2S)-1-(4-(ethylsulfinylmethyl)phenyl)-1-(1-(4-fluorophenyl)-1H-indazol-5-yloxy)propan-2-amine hydrochloride. The material was not repurified. Yield 180 mg (38%).

APCI-MS: m/z 436 [MH$^+$—HCl], m/z 452 [MH$^+$—HCl] for oxidized impurity. $^1$H-NMR (400 MHz, DMSO-d$_6$): δ 8.38 (brs, 3H), 8.20 (s, 1H), 7.78-7.70 (m, 3H), 7.45-7.29 (m, 7H), 7.14 (d, 1H), 5.71 (d, 1H), 3.72 (s, 2H), 3.67 (brm, 1H), 2.39 (q, 2H), 1.17 (d, 3H), 1.13 (t, 3H).

(1R,2S)-2-amino-1-(4-(ethylthiomethyl)phenyl)propan-1-ol (25b)

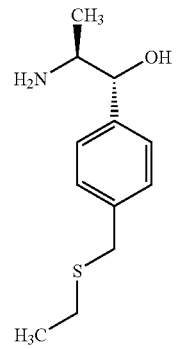

The subtitle compound was prepared in two steps analogous to the method described in Example 19 (step 19b+c). Starting from (S)-tert-butyl 1-(4-(ethylthiomethyl)phenyl)-1-oxopropan-2-ylcarbamate (750 mg, 2.32 mmol). In contrast after final deprotection the obtained hydrochloride salt was hygroscopic, compound was instead isolated as the free base.

Yield 330 mg (63%). APCI-MS: m/z 226 [MH$^+$] $^1$H-NMR (400 MHz, CD$_3$OD): δ 7.32 (m, 4H), 4.48 (d, 1H), 3.73 (s, 2H), 3.07 (m, 1H), 2.42 (q, 2H), 1.20 (t, 3H), 1.05 (d, 3H).

(S)-tert-butyl 1-(4-(ethylthiomethyl)phenyl)-1-oxopropan-2-ylcarbamate (25c)

Magnesium turnings (0.150 g, 6.17 mmol), (4-bromobenzyl)(ethyl)sulfane (1.160 g, 5.02 mmol) and one small crystal of iodine in dry THF (5 mL) was heated to +60° C. for 1 h, the reaction mixture was allowed to reach r.t.

In a separate vessel was placed (S)-tert-butyl 1-(methoxy(methyl)amino)-1-oxopropan-2-ylcarbamate (0.705 g, 3.04 mmol) in dry THF (3 mL), the formed slurry was placed under Argon and cooled on an acetone/ice bath to −10° C. Isopropylmagnesium chloride 2.0M solution in THF (1.500 mL, 3 mmol) was slowly added, to the formed solution was thereafter slowly added the previously made Grignard reagent, after addition the mixture was allowed to reach r.t. and stirred for 1.5 h. The reaction mixture was poured into an icecold mixture of EtOAc (100 mL) and 1M HCl (30 mL) and stirred for a few min. The organic phase was washed with water (30 mL) and brine (30 mL), dried (Na₂SO₄), filtered and evaporated. The residual crude material was purified by flash chromatography on silica and a gradient of 5% to 30% EtOAc/Heptane. Fractions containing product was combined and solvent removed by evaporation to give the subtitle compound as a colourless solid. Yield 750 mg (76%)

APCI-MS: m/z 224.1 [MH⁺—BOC]¹H-NMR (300 MHz, DMSO-d₆): 7.91 (d, 2H), 7.45 (d, 2H), 7.31 (d, 1H), 5.01 (m, 1H), 3.80 (s, 2H), 2.39 (q, 2H), 1.34 (s, 9H), 1.22 (d, 3H), 1.15 (t, 3H).

Example 26

N-[(1R,2S)-1-[4-(ethylsulfinylmethyl)phenyl]-1-[1-(4-fluorophenyl)indazol-5-yl]oxy-propan-2-yl]-2,2,2-trifluoro-acetamide

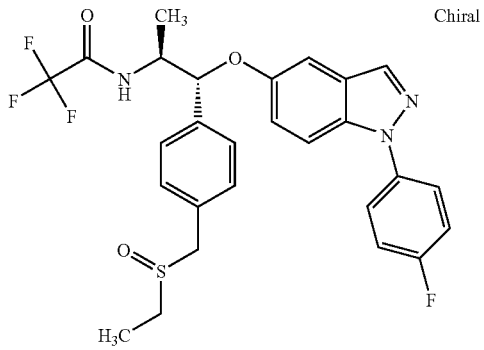

The title compound was formed as a sideproduct during the preparation of N-[(1R,2S)-1-[4-(ethylsulfanylmethyl)phenyl]-1-[1-(4-fluorophenyl)indazol-5-yl]oxy-propan-2-yl]-2,2,2-trifluoro-acetamide. Yield 3.4 mg (5.9%)

APCI-MS: m/z 548 [MH⁺]¹H-NMR (300 MHz, DMSO-d₆): δ 9.52 (d, 1H), 8.17 (d, 1H), 7.74 (m, 2H), 7.69 (d, 1H), 7.44-7.26 (m, 6H), 7.20 (dd, 1H), 7.13 (d, 1H), 5.29 (d, 1H), 4.24 (m, 1H), 3.97 (dd, 2H), 2.60 (m, 2H), 1.33 (d, 3H), 1.14 (t, 3H).

Example 27

N-[(1R,2S)-1-[4-(ethylsulfanylmethyl)phenyl]-1-[1-(4-fluorophenyl)indazol-5-yl]oxy-propan-2-yl]-2-hydroxy-acetamide

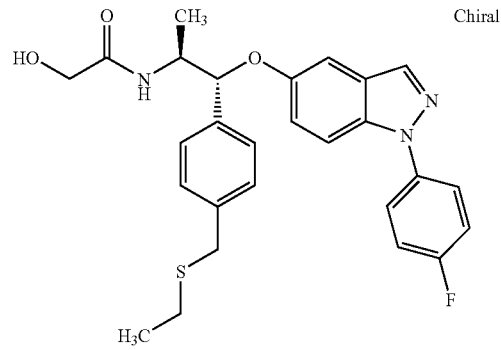

The title compound was prepared analogous to the method described in Example 21 starting from (1R,2S)-1-(4-(ethylthiomethyl)phenyl)-1-(1-(4-fluorophenyl)-1H-indazol-5-yloxy)propan-2-amine hydrochloride (25a) (50 mg, 0.11 mmol), and acetoxyacetyl chloride (13 μL, 0.12 mmol). Yield 33 mg (63%).

APCI-MS: m/z 494.1 [MH⁺]¹H-NMR (400 MHz, DMSO-d₆): δ 8.16 (d, 1H), 7.74 (m, 2H), 7.69 (d, 1H), 7.62 (d, 1H), 7.44-7.26 (m, 6H), 7.21 (dd, 1H), 7.10 (d, 1H), 5.52 (brs, 1H), 5.40 (d, 1H), 4.24 (m, 1H), 3.72 (dd, 2H), 3.70 (s, 2H), 2.36 (q, 2H), 1.17 (d, 3H), 1.11 (t, 3H).

Example 28

4-Amino-N-[(1R,2S)-1-[1-(4-fluorophenyl)indazol-5-yl]oxy-1-phenyl-propan-2-yl]butanamide

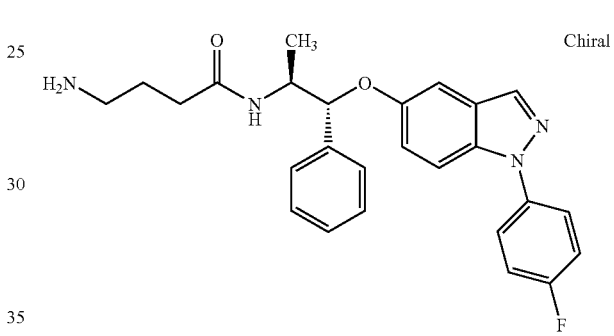

In a 5 mL Vial, AZ12671597 (60.0 mg, 0.17 mmol), 4-(tert-butoxycarbonylamino)butyric acid (33.7 mg, 0.17 mmol), O-benzotriazol-1-yl-N,N,N',N'-tetramethyl-uronium hexafluorophosphate (69.3 mg, 0.18 mmol) and triethylamine (0.028 mL, 0.20 mmol) were dissolved in DMF (0.5 mL) and stirred at r.t. over night. Then the mixture was diluted with ethyl acetate (30 mL), washed with water and sat. sodium bicarbonate and dried over sodium sulfate. The crude was purified by flash chromatography on silica gel (ethyl acetate/heptane=4:1) and a pale yellow oil (75 mg) was obtained. The intermediate was dissolved in acetonitrile (5 mL). 6M aq. HCl (1 mL) was added and the solution was stirred for 1 h at 50 C. Small impurities were removed by purification on reversed phase HPLC. The hygroscopic salt obtained after freezedrying was taken up with ethyl acetate and washed with sat. bicarbonate and brine. Removal of the solvent yielded and freeze drying from acetonitril/water 19 mg (26%).

¹H-NMR (400 MHz, CDCl₃): δ 8.09 (s, 1H), 7.67 (d, J=4.6, 2.3 Hz, 2H), 7.60 (d, J=9.0 Hz, 1H), 7.44 (d, J=7.3 Hz, 2H), 7.35 (t, J=7.5 Hz, 2H), 7.32-7.26 (m, 3H), 7.24 (dd, J=9.2, 2.5 Hz, 1H), 7.04 (d, J=2.3 Hz, 1H), 5.34 (d, J=4.6 Hz, 1H), 4.32 (dd, J=6.9, 4.6 Hz, 1H), 2.58 (t, J=7.3 Hz, 2H), 2.21 (td, J=7.3, 4.4 Hz, 2H), 1.69 (t, J=7.3 Hz, 2H), 1.24 (d, J=6.9 Hz, 3H). APCI-MS: m/z 447.2 [MH⁺]

Example 29

N-[(1R,2S)-1-[1-(4-fluorophenyl)indazol-5-yl]oxy-1-phenyl-propan-2-yl]acetamide

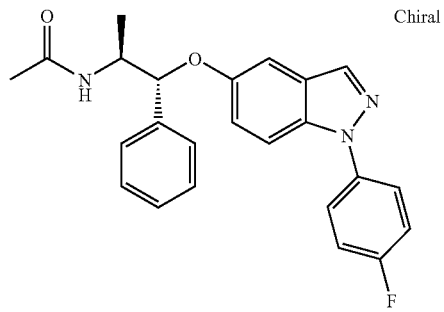

Prepared as described in Example 1 using (1S,2R)-1-{[1-(4-fluorophenyl)-1H-indazol-5-yl]oxy}-1-phenylpropan-2-amine (1a, 36 mg, 100 μmol) and acetic anhydride (30 mg, 300 μmol). Yield 37 mg (92%).

APCI-MS: m/z 404 [MH$^+$]$^1$H NMR (400 MHz, d$_6$-acetone) δ 8.03 (d, J=0.5 Hz, 1H), 7.77 (m, 2H), 7.70 (d, J=9.2 Hz, 1H), 7.45 (d, J=7.4 Hz, 2H), 7.41-7.26 (m, 5H), 7.23 (dd, J=9.1, 2.4 Hz, 1H), 7.10 (d, J=2.3 Hz, 1H), 5.49 (d, J=3.5 Hz, 1H), 4.31 (m, 1H), 1.85 (s, 3H), 1.17 (d, J=6.9 Hz, 3H).

Example 30

N-[(1R,2S)-1-[1-(4-fluorophenyl)indazol-5-yl]oxy-1-phenyl-propan-2-yl]-3-methoxy-propanamide

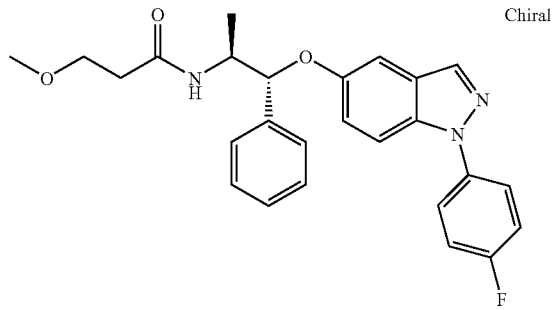

Prepared as described in Example 1 using (1S,2R)-1-{[1-(4-fluorophenyl)-1H-indazol-5-yl]oxy}-1-phenylpropan-2-amine (1a, 18 mg, 50 μmol) and 3-methoxypropanoyl chloride (18 mg, 150 μmol). Yield 17 mg (74%).

APCI-MS: m/z 448 [MH$^+$]$^1$H NMR (400 MHz, d$_6$-acetone) δ 8.04 (d, J=0.7 Hz, 1H), 7.77 (m, 2H), 7.71 (d, J=9.0 Hz, 1H), 7.47 (d, J=7.4 Hz, 2H), 7.39-7.28 (m, 5H), 7.25 (dd, J=9.1, 2.4 Hz, 1H), 7.12 (d, J=2.3 Hz, 1H), 5.49 (d, J=3.5 Hz, 1H), 4.33 (m, 1H), 3.53 (m, 2H), 3.18 (s, 3H), 2.36 (t, J=6.3 Hz, 2H), 1.17 (d, J=7.1 Hz, 3H).

Example 31

N-[(1R,2S)-1-[1-(4-fluorophenyl)indazol-5-yl]oxy-1-phenyl-propan-2-yl]-2-methoxy-acetamide

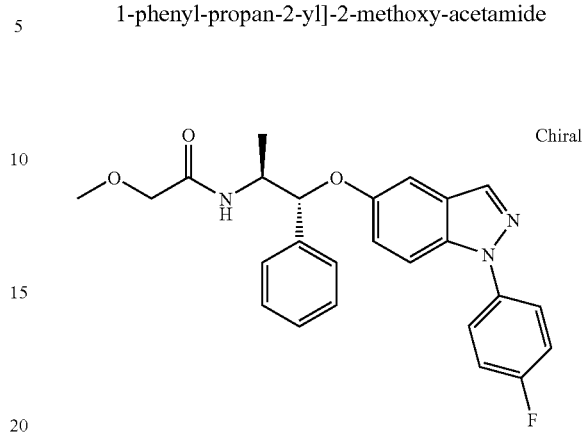

Prepared as described in Example 1 using (1S,2R)-1-{[1-(4-fluorophenyl)-1H-indazol-5-yl]oxy}-1-phenylpropan-2-amine (1a, 18 mg, 50 μmol) and methoxyacetyl chloride (16 mg, 150 μmol). Yield 18 mg (86%).

APCI-MS: m/z 434 [MH$^+$]$^1$H NMR (400 MHz, d$_6$-acetone) δ 8.04 (d, J=0.5 Hz, 1H), 7.77 (m, 2H), 7.70 (d, J=9.2 Hz, 1H), 7.48 (d, J=7.3 Hz, 2H), 7.40-7.29 (m, 4H), 7.26 (dd, J=9.1, 2.4 Hz, 1H), 7.18 (br. d, J=8.3 Hz, 1H), 7.14 (d, J=2.3 Hz, 1H), 5.50 (d, J=4.4 Hz, 1H), 4.41 (m, 1H), 3.76 (dd, J=37.2, 15.0 Hz, 2H), 3.28 (s, 3H), 1.24 (d, J=6.9 Hz, 3H).

Example 32

N-[(1R,2S)-1-[1-(4-fluorophenyl)indazol-5-yl]oxy-1-phenyl-propan-2-yl]benzamide

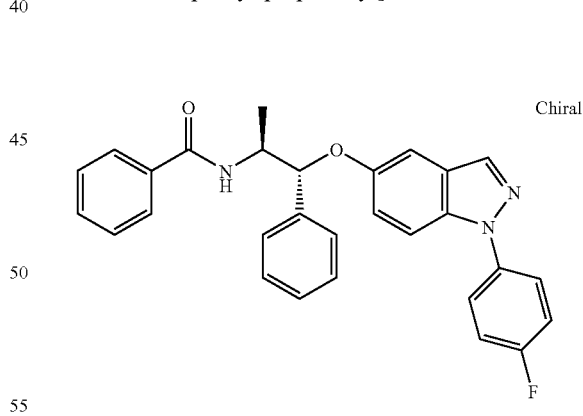

Prepared as described in Example 1 using (1S,2R)-1-{[1-(4-fluorophenyl)-1H-indazol-5-yl]oxy}-1-phenylpropan-2-amine (1a, 18 mg, 50 μmol) and benzoyl chloride (21 mg, 150 μmol). Yield 19 mg (82%).

APCI-MS: m/z 465 [MH$^+$]$^1$H NMR (400 MHz, d$_6$-acetone) δ 8.02 (d, J=0.7 Hz, 1H), 7.83 (m, 3H), 7.75 (m, 2H), 7.68 (d, J=9.2 Hz, 1H), 7.54 (d, J=7.3 Hz, 2H), 7.47 (m, 1H), 7.42-7.24 (m, 8H), 7.14 (d, J=2.1 Hz, 1H), 5.64 (d, J=4.1 Hz, 1H), 4.57 (m, 1H), 1.36 (d, J=6.9 Hz, 3H).

Example 33

N-[(1R,2S)-1-[1-(4-fluorophenyl)indazol-5-yl]oxy-1-phenyl-propan-2-yl]-2-phenyl-acetamide

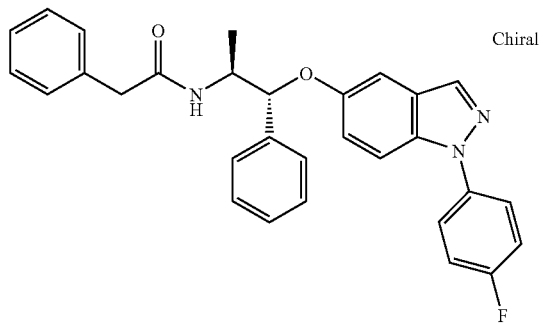

Prepared as described in Example 1 using (1S,2R)-1-{[1-(4-fluorophenyl)-1H-indazol-5-yl]oxy}-1-phenylpropan-2-amine (1a, 18 mg, 50 µmol) and phenylacetyl chloride (23 mg, 150 µmol). Yield 22 mg (80%).

APCI-MS: m/z 480 [MH+] $^1$H NMR (400 MHz, $d_6$-acetone) δ 8.03 (d, J=0.7 Hz, 1H), 7.78 (m, 2H), 7.69 (d, J=9.2 Hz, 1H), 7.45-7.13 (m, 13H), 7.06 (d, J=2.3 Hz, 1H), 5.46 (d, J=3.5 Hz, 1H), 4.32 (m, 1H), 3.47 (dd, J=19.5, 14.3 Hz, 2H), 1.18 (d, J=7.1 Hz, 3H).

Example 34

[(1R,2S)-1-[1-(4-fluorophenyl)indazol-5-yl]oxy-1-phenyl-propan-2-yl]carbamoylmethyl acetate

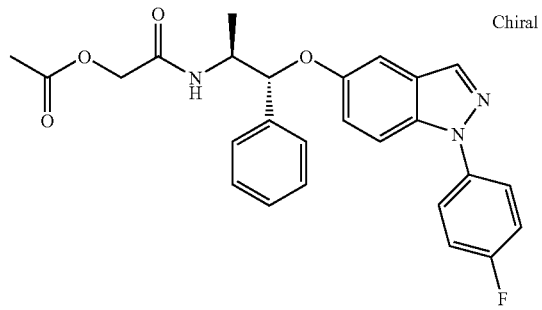

Prepared as described in Example 1 using (1S,2R)-1-{[1-(4-fluorophenyl)-1H-indazol-5-yl]oxy}-1-phenylpropan-2-amine (1a, 18 mg, 50 µmol) and 2-chloro-2-oxoethyl acetate (20 mg, 150 µmol). Yield 16 mg (70%).

APCI-MS: m/z 462 [MH+] $^1$H NMR (400 MHz, $d_6$-acetone) δ 8.05 (d, $J_1$=0.7 Hz, 1H), 7.77 (m, 2H), 7.71 (d, J=9.0 Hz, 1H), 7.48 (d, J=7.3 Hz, 2H), 7.43-7.28 (m, 5H), 7.25 (dd, J=9.1, 2.4 Hz, 1H), 7.14 (d, J=2.3 Hz, 1H), 5.48 (d, J=3.9 Hz, 1H), 4.46 (s, 2H), 4.38 (m, 1H), 1.21 (d, J=6.9 Hz, 3H).

Example 35

Methyl[(1R,2S)-1-[1-(4-fluorophenyl)indazol-5-yl]oxy-1-phenyl-propan-2-yl]carbamoylformate

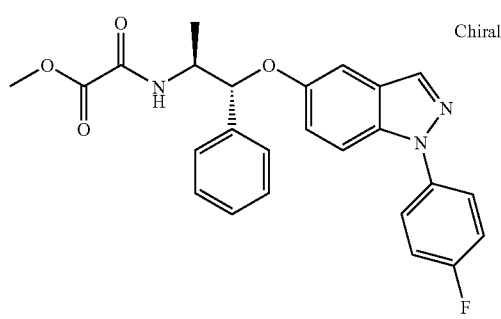

Prepared as described in Example 1 using (1S,2R)-1-{[1-(4-fluorophenyl)-1H-indazol-5-yl]oxy}-1-phenylpropan-2-amine (1a, 18 mg, 50 µmol) and methyl cloro(oxo)acetate (18 mg, 150 µmol). Yield 18 mg (82%).

APCI-MS: m/z 448 [MH+] $^1$H NMR (400 MHz, $d_6$-acetone) δ 8.09 (br.d, J=8.7 Hz, 1H), 8.04 (d, J=0.7 Hz, 1H), 7.77 (m, 2H), 7.71 (d, J=9.0 Hz, 1H), 7.49 (d, J=7.3 Hz, 2H), 7.42-7.28 (m, 5H), 7.26 (dd, J=9.1, 2.4 Hz, 1H), 7.14 (d, J=2.3 Hz, 1H), 5.53 (d, J=4.4 Hz, 1H), 4.39 (m, 1H), 3.76 (s, 3H), 1.32 (d, J=6.9 Hz, 3H).

Example 36

[(1R,2S)-1-[1-(4-fluorophenyl)indazol-5-yl]oxy-1-phenyl-propan-2-yl]carbamoylformic acid

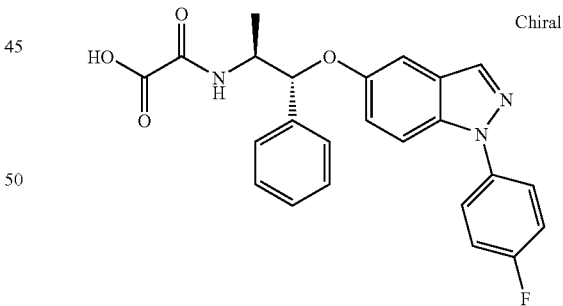

Prepared as described in Example 5 using (1S,2R)-1-{[1-(4-fluorophenyl)-1H-indazol-5-yl]oxy}-1-phenylpropan-2-amine (1a, 18 mg, 50 µmol) and methyl cloro(oxo)acetate (18 mg, 150 µmol). Yield 19 mg (88%).

APCI-MS: m/z 434 [MH+] $^1$H NMR (400 MHz, $d_6$-acetone) δ 8.21 (br. d, J=8.8 Hz, 1H), 8.03 (s, 1H), 7.77 (m, 2H), 7.70 (d, J=9.0 Hz, 1H), 7.50 (d, J=7.3 Hz, 2H), 7.40-7.29 (m, 4H), 7.26 (dd, J=9.2, 2.3 Hz, 1H), 7.15 (d, J=2.3 Hz, 1H), 5.53 (d, J=5.0 Hz, 1H), 4.39 (m, 1H), 1.37 (d, J=6.7 Hz, 3H).

Example 37

N-[(1R,2S)-1-[1-(4-fluorophenyl)indazol-5-yl]oxy-1-phenyl-propan-2-yl]-2-methyl-propanamide

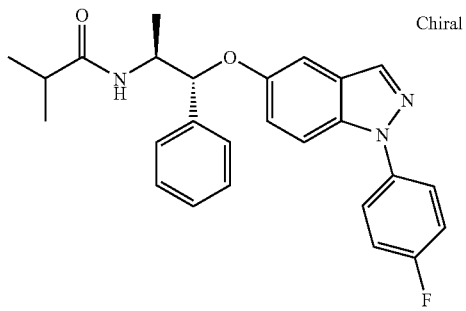

Prepared as described in Example 1 using (1S,2R)-1-{[1-(4-fluorophenyl)-1H-indazol-5-yl]oxy}-1-phenylpropan-2-amine (1a, 18 mg, 50 µmol) and 2-methylpropanoyl chloride (21 mg, 150 µmol). Yield 18 mg (84%).

APCI-MS: m/z 432 [MH+] $^1$H NMR (400 MHz, d$_6$-acetone) δ 8.04 (d, J=0.7 Hz, 1H), 7.77 (m, 2H), 7.70 (d, J=9.2 Hz, 1H), 7.47 (d, J=7.3 Hz, 2H), 7.40-7.26 (m, 5H), 7.24 (dd, J=9.2, 2.5 Hz, 1H), 7.17 (br. d, J=7.6 Hz, 1H), 7.11 (d, J=2.3 Hz, 1H), 5.47 (d, J=4.2 Hz, 1H), 4.31 (septet, J=6.9 Hz, 1H), 1.20 (d, J=6.9 Hz, 3H), 1.02 (d, J=6.7 Hz, 3H), 0.92 (d, J=6.9 Hz, 3H).

Example 38

2-Chloro-N-[(1R,2S)-1-[1-(4-fluorophenyl)indazol-5-yl]oxy-1-phenyl-propan-2-yl]acetamide

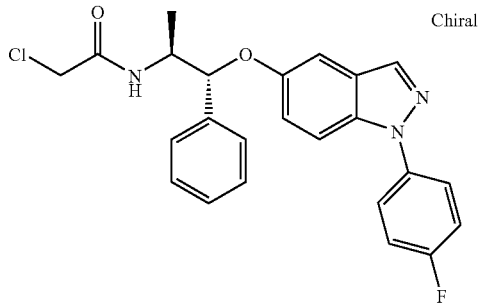

Prepared as described in Example 1 using (1S,2R)-1-{[1-(4-fluorophenyl)-1H-indazol-5-yl]oxy}-1-phenylpropan-2-amine (1a, 18 mg, 50 µmol) and chloroacetyl chloride (17 mg, 150 µmol). Yield 22 mg (73%).

APCI-MS: m/z 438 [MH+] $^1$H NMR (400 MHz, d$_6$-acetone) δ 8.04 (d, J=0.7 Hz, 1H), 7.77 (m, 2H), 7.71 (d, J=9.2 Hz, 1H), 7.59 (d, J=8.0 Hz, 1H), 7.48 (br. d, J=7.3 Hz, 2H), 7.41-7.27 (m, 5H), 7.25 (dd, J=9.1, 2.4 Hz, 1H), 7.13 (d, J=2.3 Hz, 1H), 5.51 (d, J=4.1 Hz, 1H), 4.37 (m, 1H), 4.03 (dd, J=17.2, 13.7 Hz, 2H), 1.24 (d, J=6.9 Hz, 3H).

Example 39

2,2-Dichloro-N-[(1R,2S)-1-[1-(4-fluorophenyl)indazol-5-yl]oxy-1-phenyl-propan-2-yl]acetamide

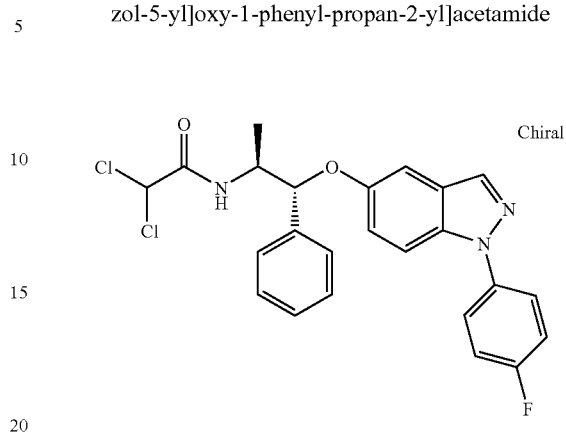

Prepared as described in Example 1 using (1S,2R)-1-{[1-(4-fluorophenyl)-1H-indazol-5-yl]oxy}-1-phenylpropan-2-amine (1a, 18 mg, 50 µmol) and dichloroacetyl chloride (22 mg, 150 µmol). Yield 20 mg (83%).

APCI-MS: m/z 473 [MH+] $^1$H NMR (400 MHz, d$_6$-acetone) δ 8.04 (d, J=0.5 Hz, 1H), 7.94 (br. d, J=7.8 Hz, 1H), 7.77 (m, 2H), 7.71 (d, J=9.0 Hz, 1H), 7.49 (d, J=7.3 Hz, 2H), 7.41-7.27 (m, 5H), 7.25 (dd, J=9.1, 2.4 Hz, 1H), 7.15 (d, J=2.3 Hz, 1H), 6.30 (s, 1H), 5.54 (d, J=4.1 Hz, 1H), 4.36 (m, 1H), 1.28 (d, J=6.9 Hz, 3H).

Example 40

2,2,2-Trichloro-N-[(1R,2S)-1-[1-(4-fluorophenyl)indazol-5-yl]oxy-1-phenyl-propan-2-yl]acetamide

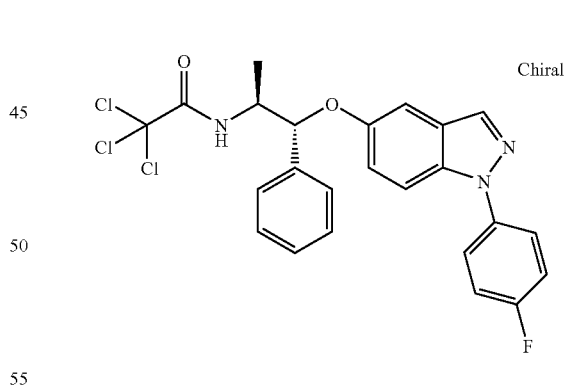

Prepared as described in Example 1 using (1S,2R)-1-{[1-(4-fluorophenyl)-1H-indazol-5-yl]oxy}-1-phenylpropan-2-amine (1a, 18 mg, 50 µmol) and trichloroacetyl chloride (27 mg, 150 µmol). Yield 21 mg (84%).

APCI-MS: m/z 507 [MH+] $^1$H NMR (400 MHz, d$_6$-acetone) δ 8.11 (br. d, J=8.0 Hz, 1H), 8.04 (d, J=0.7 Hz, 1H), 7.76 (m, 1H), 7.70 (d, J=9.0 Hz, 1H), 7.53 (d, J=7.4 Hz, 2H), 7.42-7.29 (m, 5H), 7.26 (dd, J=9.1, 2.4 Hz, 1H), 7.18 (d, J=2.3 Hz, 1H), 5.55 (d, J=5.3 Hz, 1H), 4.39 (m, 1H), 1.41 (d, J=6.9 Hz, 3H).

Example 41

N-[(1R,2S)-1-[1-(4-fluorophenyl)indazol-5-yl]oxy-1-phenyl-propan-2-yl]butanamide

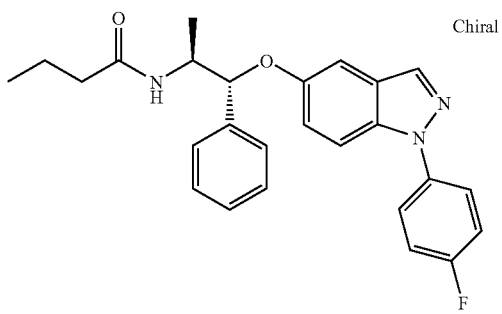

Prepared as described in Example 1 using (1S,2R)-1-{[1-(4-fluorophenyl)-1H-indazol-5-yl]oxy}-1-phenylpropan-2-amine (1a, 18 mg, 50 μmol) and butanoyl chloride (16 mg, 150 μmol). Yield 18 mg (82%).

APCI-MS: m/z 432 [MH$^+$]$^1$H NMR (400 MHz, d$_6$-acetone) δ 8.03 (d, J=0.7 Hz, 1H), 7.77 (m, 2H), 7.70 (d, J=9.2 Hz, 1H), 7.46 (d, J=7.3 Hz, 2H), 7.38-7.25 (m, 5H), 7.23 (dd, J=9.1, 2.4 Hz, 1H), 7.10 (d, J=2.3 Hz, 1H), 5.49 (d, J=3.9 Hz, 1H), 4.33 (m, 1H), 2.09 (td, J=7.4, 2.8 Hz, 2H), 1.53 (sextet, J=7.3 Hz, 2H), 1.19 (d, J=6.9 Hz, 3H), 0.79 (t, J=7.4 Hz, 3H).

Example 42

N-[(1R,2S)-1-[1-(4-fluorophenyl)indazol-5-yl]oxy-1-phenyl-propan-2-yl]-2,2-dimethyl-propanamide

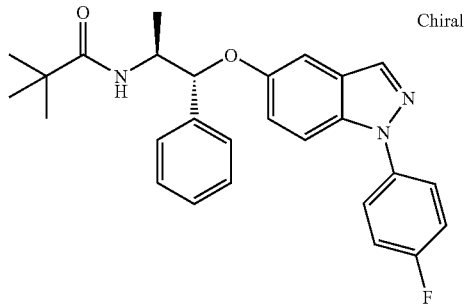

Prepared as described in Example 1 using (1S,2R)-1-{[1-(4-fluorophenyl)-1H-indazol-5-yl]oxy}-1-phenylpropan-2-amine (1a, 18 mg, 50 μmol) and 2,2-dimethylpropanoyl chloride (18 mg, 150 μmol). Yield 17 mg (74%).

APCI-MS: m/z 446 [MH$^+$]$^1$H NMR (400 MHz, d$_6$-acetone) δ 8.04 (d, J=0.7 Hz, 1H), 7.77 (m, 2H), 7.70 (d, J=9.0 Hz, 1H), 7.48 (d, J=7.4 Hz, 2H), 7.38-7.26 (m, 5H), 7.25 (dd, J=9.1, 2.4 Hz, 1H), 7.13 (d, J=2.1 Hz, 1H), 6.78 (br. d, J=8.3 Hz, 1H), 5.46 (d, J=5.0 Hz, 1H), 4.34 (m, 1H), 1.23 (d, J=6.9 Hz, 3H), 1.05 (s, 9H).

Example 43

N-[(1R,2S)-1-[1-(4-fluorophenyl)indazol-5-yl]oxy-1-phenyl-propan-2-yl]cyclobutanecarboxamide

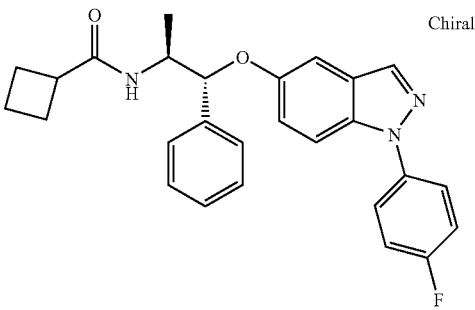

Prepared as described in Example 1 using (1S,2R)-1-{[1-(4-fluorophenyl)-1H-indazol-5-yl]oxy}-1-phenylpropan-2-amine (1a, 18 mg, 50 μmol) and cyclobutanecarbonyl chloride (18 mg, 150 μmol). Yield 18 mg (82%).

APCI-MS: m/z 444 [MH$^+$]$^1$H NMR (400 MHz, d$_6$-acetone) δ 8.03 (d, J=0.5 Hz, 1H), 7.77 (m, 2H), 7.70 (d, J=9.2 Hz, 1H), 7.46 (d, J=7.3 Hz, 2H), 7.39-7.25 (m, 5H), 7.22 (dd, J=9.1, 2.4 Hz, 1H), 7.11 (d, J=2.3 Hz, 1H), 7.09 (br. d, J=8.9 Hz, 1H), 5.47 (d, J=4.1 Hz, 1H), 4.32 (m, 1H), 3.03 (quintet, J=8.2 Hz, 1H), 2.21 (m, 1H), 2.13-1.68 (m, 5H, partially covered with the signal of solvent), 1.18 (d, J=6.9 Hz, 3H).

Example 44

2,2-Difluoro-N-[(1R,2S)-1-[1-(4-fluorophenyl)indazol-5-yl]oxy-1-phenyl-propan-2-yl]acetamide

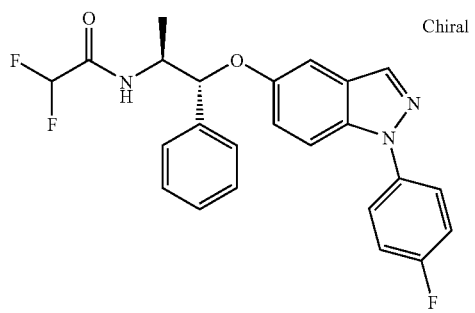

Prepared as described in Example 1 using (1S,2R)-1-{[1-(4-fluorophenyl)-1H-indazol-5-yl]oxy}-1-phenylpropan-2-amine (1a, 18 mg, 50 μmol) and difluoroacetyl chloride (23 mg, 150 μmol). Yield 21 mg (95%).

APCI-MS: m/z 440 [MH$^+$]$^1$H NMR (400 MHz, d$_6$-acetone) δ 8.08 (br. d, J=7.8 Hz, 1H), 8.03 (d, J=0.7 Hz, 1H), 7.77 (m, 2H), 7.71 (d, J=9.2 Hz, 1H), 7.49 (d, J=7.3 Hz, 2H), 7.40-7.27 (m, 5H), 7.24 (dd, J=9.2, 2.5 Hz, 1H), 7.13 (d, J=2.3 Hz, 1H), 6.06 (t, J=54.0 Hz, 1H), 5.51 (d, J=4.4 Hz, 1H), 4.41 (m, 1H), 1.31 (d, J=6.9 Hz, 3H).

Example 45

2-Fluoro-N-[(1R,2S)-1-[1-(4-fluorophenyl)indazol-5-yl]oxy-1-phenyl-propan-2-yl]acetamide

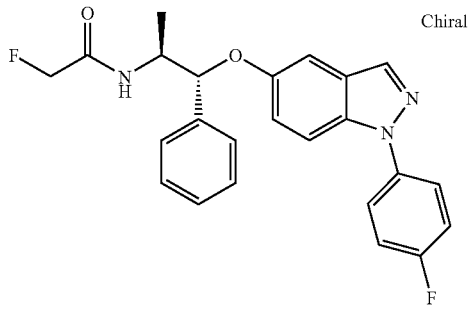

Prepared as described in Example 1 using (1S,2R)-1-{[1-(4-fluorophenyl)-1H-indazol-5-yl]oxy}-1-phenylpropan-2-amine (1a, 36 mg, 100 μmol) and difluoroacetyl chloride (29 mg, 300 μmol). Yield 40 mg (95%).

APCI-MS: m/z 422 [MH+] $^1$H NMR (400 MHz, $d_6$-acetone) δ 8.04 (s, 1H), 7.77 (m, 2H), 7.71 (d, J=9.2 Hz, 1H), 7.48 (d, J=7.3 Hz, 2H), 7.44 (br. d, J=7.6 Hz, 1H), 7.41-7.28 (m, 5H), 7.25 (dd, J=9.1, 2.4 Hz, 1H), 7.13 (d, J=2.3 Hz, 1H), 5.50 (d, J=4.4 Hz, 1H), 4.78 (q, J=14.0 Hz, 1H), 4.66 (q, J=14.0 Hz, 1H), 4.44 (m, 1H), 1.29 (d, J=6.9 Hz, 3H).

Example 46

N-[(1R,2S)-1-(4-ethylphenyl)-1-[1-(4-fluorophenyl)indazol-5-yl]oxy-propan-2-yl]-2,2,2-trifluoro-acetamide

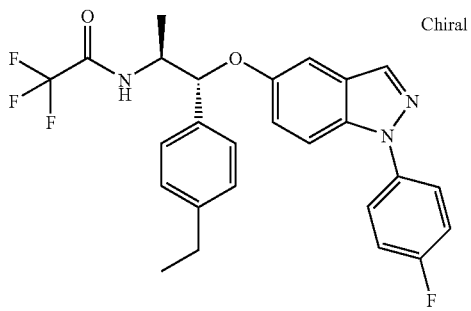

Prepared as described in Example 1 using (1R,2S)-1-(4-ethylphenyl)-1-{[1-(4-fluorophenyl)-1H-indazol-5-yl]oxy}propan-2-amine (7a, 39 mg, 100 μmol) and trifluoroacetic anhydride (63 mg, 300 μmol). Yield 44 mg (90%).

APCI-MS: m/z 484 [MH+] $^1$H NMR (400 MHz, $d_6$-acetone) δ 8.59 (br. d, J=7.8 Hz, 1H), 8.04 (s, 1H), 7.77 (m, 2H), 7.70 (d, J=9.0 Hz, 1H), 7.40 (d, J=8.1 Hz, 2H), 7.33 (m, 2H), 7.23 (m, 3H), 7.15 (d, J=2.3 Hz, 1H), 5.49 (d, J=4.6 Hz, 1H), 4.41 (m, 1H), 2.62 (q, J=7.6 Hz, 2H), 1.37 (d, J=6.9 Hz, 3H), 1.18 (t, J=7.6 Hz, 3H).

Example 47

2-Chloro-2-fluoro-N-[(1R,2S)-1-[1-(4-fluorophenyl)indazol-5-yl]oxy-1-phenyl-propan-2-yl]acetamide

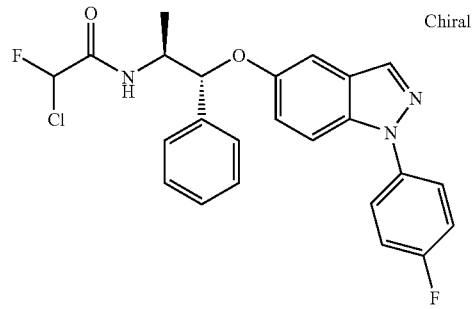

Prepared as described in Example 1 using (1S,2R)-1-{[1-(4-fluorophenyl)-1H-indazol-5-yl]oxy}-1-phenylpropan-2-amine (1a, 18 mg, 50 μmol) and chlorofluoroacetyl chloride (19 mg, 150 μmol). Yield 16 mg (70%).

APCI-MS: m/z 456 [MH+] $^1$H NMR (400 MHz, $d_6$-acetone) δ 8.04 (s, 1H), 7.98 (br. t, J=7.1 Hz, 1H), 7.77 (m, 2H), 7.71 (d, J=9.0 Hz, 1H), 7.49 (dd, J=7.4, 2.8 Hz, 2H), 7.41-7.27 (m, 5H), 7.25 (dt, J=9.1, 2.2 Hz, 1H), 7.14 (dd, J=5.1, 2.3 Hz, 1H), 6.55 (dd, J=50.0, 9.8 Hz, 1H), 5.52 (dd, J=7.3, 4.4 Hz, 1H), 4.39 (m, 1H), 1.31 (dd, J=6.9, 2.7 Hz, 3H).

Example 48

(2S)—N-[(1R,2S)-1-[1-(4-fluorophenyl)indazol-5-yl]oxy-1-phenyl-propan-2-yl]-2-hydroxy-propanamide

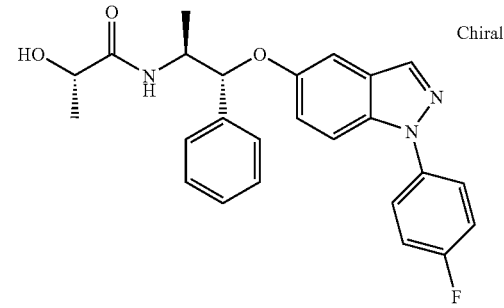

Prepared as described in Example 5 using (1S,2R)-1-{[1-(4-fluorophenyl)-1H-indazol-5-yl]oxy}-1-phenylpropan-2-amine (1a, 18 mg, 50 μmol) and methyl (1S)-2-chloro-1methyl-2-oxoethyl acetate (22 mg, 150 μmol). Yield 20 mg (91%).

APCI-MS: m/z 434 [MH+] $^1$H NMR (400 MHz, $d_6$-acetone) δ 8.04 (d, J=0.7 Hz, 1H), 7.77 (m, 2H), 7.70 (d, J=9.2 Hz, 1H), 7.48 (d, J=7.3 Hz, 2H), 7.40-7.28 (m, 5H), 7.25 (dd, J=9.2, 2.5 Hz, 1H), 7.13 (d, J=2.3 Hz, 1H), 5.49 (d, J=4.1 Hz, 1H), 4.35 (m, 1H), 4.06 (q, J=6.8 Hz, 1H), 1.25 (d, J=6.7 Hz, 3H), 1.22 (d, J=6.9 Hz, 3H).

Example 49

2,2,2-Trifluoro-N-[(1R,2S)-1-[1-(4-fluorophenyl) indazol-5-yl]oxy-1-(3-hydroxyphenyl)propan-2-yl] acetamide

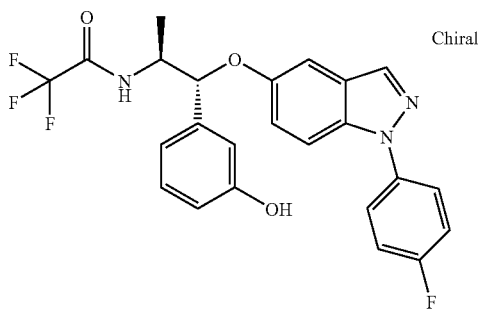

To a stirred solution of 2,2,2-trifluoro-N-((1R,2S)-1-(1-(4-fluorophenyl)-1H-indazol-5-yloxy)-1-(3-methoxyphenyl)propan-2-yl)acetamide (Example 6, 10 mg, 20 μmol) in methylbenzene (1 ml) was added dodecanethiole (1 ml), followed with anhydrous aluminium chloride (5.3 mg, 40 μmol). The mixture was stirred at 40° C. for 1 h. Methylbenzene was removed in vacuo, the solution in dodecanethiole was diluted with n-heptane (10 ml). Oily precipitate has formed, which was washed with heptane, dried in vacuo, and dissolved in acetonitrile/water mixture. The crude product was purified by preparative HPLC afforded 4 mg of product as a white solid (42%).

APCI-MS: m/z 474 [MH$^+$]$^1$H NMR (400 MHz, d$_6$-acetone) δ 8.60 (d, J=8.0 Hz, 1H), 8.06 (d, J=0.5 Hz, 1H), 7.77 (m, 2H), 7.71 (d, J=9.2 Hz, 1H), 7.34 (m, 2H), 7.23 (dd, J=6.9, 2.1 Hz, 1H), 7.19 (m, 1H), 7.14 (d, J=2.1 Hz, 1H), 6.95 (m, 2H), 6.77 (dd, J=8.0, 1.5 Hz, 1H), 5.44 (d, J=4.6 Hz, 1H), 4.41 (m, 1H), 1.37 (d, J=6.9 Hz, 3H).

Example 50

N-[(1R,2S)-1-(4-ethylphenyl)-1-[1-(4-fluorophenyl) indazol-5-yl]oxy-propan-2-yl]-2-fluoro-acetamide

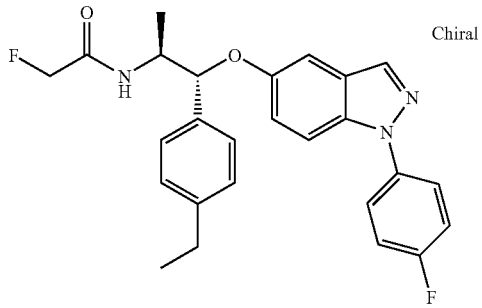

Prepared as described in Example 1 using (1R,2S)-1-(4-ethylphenyl)-1-{[1-(4-fluorophenyl)-1H-indazol-5-yl]oxy}propan-2-amine (7a, 20 mg, 50 μmol) and fluoroacetyl chloride (14 mg, 150 μmol). Yield 15 mg (65%).

APCI-MS: m/z 450 [MH$^+$]$^1$H NMR (400 MHz, d$_6$-acetone) δ 8.04 (d, J=0.5 Hz, 1H), 7.77 (m, 2H), 7.70 (d, J=9.2 Hz, 1H), 7.44-7.30 (m, 4H), 7.23 (m, 3H), 7.13 (d, J=2.3 Hz, 1H), 5.48 (d, J=4.2 Hz, 1H), 4.78 (dd, J=26.4, 14.0 Hz, 1H), 4.67 (dd, J=26.4, 14.0 Hz, 1H), 4.42 (m, 1H), 2.62 (q, J=7.6 Hz, 2H), 1.28 (d, J=6.9 Hz, 3H), 1.19 (t, J=7.6 Hz, 3H).

Example 51

N-[(1R,2S)-1-(4-ethylphenyl)-1-[1-(4-fluorophenyl) indazol-5-yl]oxy-propan-2-yl]-2-methyl-propanamide

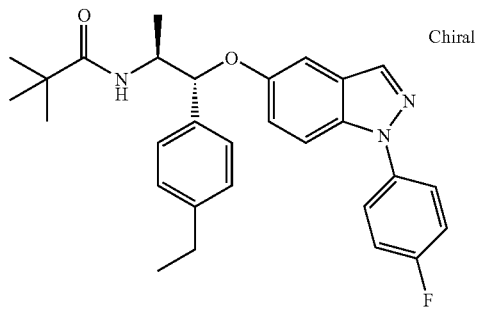

Prepared as described in Example 1 using (1R,2S)-1-(4-ethylphenyl)-1-{[1-(4-fluorophenyl)-1H-indazol-5-yl]oxy}propan-2-amine (7a, 20 mg, 50 μmol) and 2-methylpropanoyl chloride (16 mg, 150 nmol). Yield 18 mg (78%).

APCI-MS: m/z 460 [MH$^+$]$^1$H NMR (400 MHz, d$_6$-acetone) δ 8.04 (d, J=0.7 Hz, 1H), 7.77 (m, 2H), 7.70 (d, J=9.0 Hz, 1H), 7.39-7.30 (m, 4H), 7.22 (m, 3H), 7.15 (br. d, J=8.1 Hz, 1H), 7.12 (d, J=2.3 Hz, 1H), 5.44 (d, J=4.1 Hz, 1H), 4.29 (m, 1H), 2.61 (q, J=7.6 Hz, 2H), 2.37 (septet, J=6.9 Hz, 1H), 1.18 (m, 6H), 1.02 (d, J=6.9 Hz, 3H), 0.92 (d, J=6.9 Hz, 3H).

Example 52

N-[(1R,2S)-1-(4-ethylphenyl)-1-[1-(4-fluorophenyl) indazol-5-yl]oxy-propan-2-yl]-2,2-dimethyl-propanamide Prepared as described in Example 1 using (1R,2S)-1-(4-ethylphenyl)-1-{[1-(4-fluorophenyl)-1H-indazol-5-yl]oxy}propan-2-amine (7a, 20 mg, 50 μmol) and 2,2-dimethylpropanoyl chloride (18 mg, 150 μmol). Yield 17 mg (71%)

APCI-MS: m/z 474 [MH$^+$]$^1$H NMR (400 MHz, d$_6$-acetone) δ 8.04 (s, 1H), 7.77 (m, 2H), 7.69 (d, J=9.2 Hz, 1H), 7.40-7.30 (m, 4H), 7.24 (dd, J=9.1, 2.4 Hz, 1H), 7.21 (d, J=8.1 Hz, 2H), 7.14 (d, J=2.1 Hz, 1H), 6.75 (d, J=8.1 Hz, 1H), 5.42 (d, J=4.8 Hz, 1H), 4.33 (m, 1H), 2.61 (q, J=7.5 Hz, 2H), 1.22 (d, J=6.7 Hz, 3H), 1.18 (t, J=7.6 Hz, 3H), 1.05 (s, 9H).

Example 53

2-Fluoro-N-[(1R,2S)-1-[1-(4-fluorophenyl)indazol-5-yl]oxy-1-(3-methoxyphenyl)propan-2-yl]acetamide

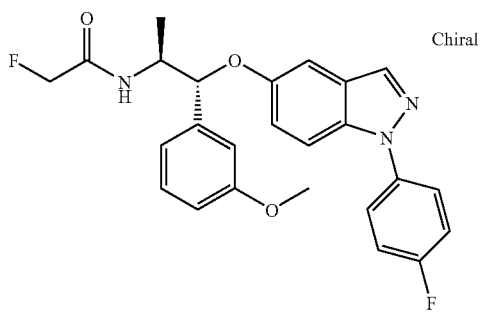

Prepared as described in Example 1 using (1R,2S)-1-{[1-(4-fluorophenyl)-1H-indazol-5-yl]oxy}-1-(3-methoxyphenyl)propan-2-amine (6a, 19 mg, 50 μmol) and fluoroacetyl chloride (14 mg, 150 μmol). Yield 16 mg (71%).

APCI-MS: m/z 452 [MH$^+$] $^1$H NMR (400 MHz, d$_6$-acetone) δ 8.05 (d, J=0.9 Hz, 1H), 7.77 (m, 1H), 7.71 (d, J=9.2 Hz, 1H), 7.42 (br. d, J=8.7 Hz, 1H), 7.37-7.23 (m, 3H), 7.15 (d, J=2.1 Hz, 1H), 7.05 (d, J=7.4 Hz, 2H), 6.86 (m, 1H), 5.47 (d, J=4.2 Hz, 1H), 4.79 (dd, J=26.3, 13.9 Hz, 1H), 4.67 (dd, J=26.3, 13.9 Hz, 1H), 4.44 (m, 1H), 3.78 (s, 3H), 1.30 (d, J=6.9 Hz, 3H).

Example 54

N-[(1R,2S)-1-[1-(4-fluorophenyl)indazol-5-yl]oxy-1-(3-methoxyphenyl)propan-2-yl]-2-methoxy-acetamide

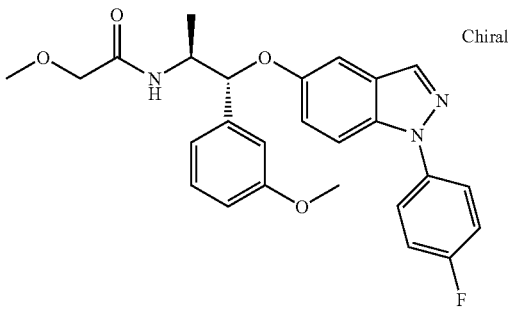

Prepared as described in Example 1 using (1R,2S)-1-{[1-(4-fluorophenyl)-1H-indazol-5-yl]oxy}-1-(3-methoxyphenyl)propan-2-amine (6a, 19 mg, 50 μmol) and methoxyacetyl chloride (16 mg, 150 μmol). Yield 23 mg (99%).

APCI-MS: m/z 464 [MH$^+$] $^1$H NMR (400 MHz, d$_6$-acetone) δ 8.05 (d, J=0.7 Hz, 1H), 7.78 (m, 2H), 7.71 (d, J=9.2 Hz, 1H), 7.37-7.24 (m, 4H), 7.16 (d, J=2.3 Hz, 1H), 7.14 (br. d, J=9.5 Hz, 1H), 7.05 (m, 2H), 6.85 (dd, J=8.2, 1.7 Hz, 1H), 5.47 (d, J=4.2 Hz, 1H), 4.41 (m, 1H), 3.78 (s, 3H), 3.76 (q, J=17.1 Hz, 2H), 3.29 (s, 3H), 1.25 (d, J=6.9 Hz, 3H).

Example 55

N-[(1R,2S)-1-[1-(4-fluorophenyl)indazol-5-yl]oxy-1-(3-methoxyphenyl)propan-2-yl]-2-methyl-propanamide

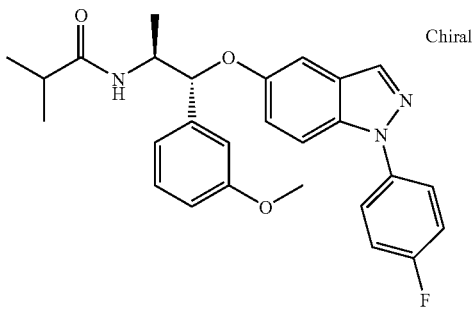

Prepared as described in Example 1 using (1R,2S)-1-{[1-(4-fluorophenyl)-1H-indazol-5-yl]oxy}-1-(3-methoxyphenyl)propan-2-amine (6a, 19 mg, 50 μmol) and 2-methylpropanoyl chloride (16 mg, 150 μmol). Yield 17 mg (74%).

APCI-MS: m/z 462 [MH$^+$] $^1$H NMR (400 MHz, d$_6$-acetone) δ 8.05 (d, J=0.7 Hz, 1H), 7.77 (m, 2H), 7.70 (d, J=9.2 Hz, 1H), 7.37-7.25 (m, 3H), 7.24 (dd, J=9.1, 2.4 Hz, 1H), 7.16 (br. d, J=7.8 Hz, 1H), 7.13 (d, J=2.3 Hz, 1H), 7.03 (m, 2H), 6.84 (m, 1H), 5.44 (d, J=4.1 Hz, 1H), 4.31 (m, 1H), 3.78 (s, 3H), 2.38 (septet, J=6.8 Hz, 1H), 1.20 (d, J=6.9 Hz, 3H), 1.02 (d, J=6.7 Hz, 3H), 0.93 (d, J=6.9 Hz, 3H).

Example 56

N-[(1R,2S)-1-[1-(4-fluorophenyl)indazol-5-yl]oxy-1-(3-methoxyphenyl)propan-2-yl]cyclopentanecarboxamide

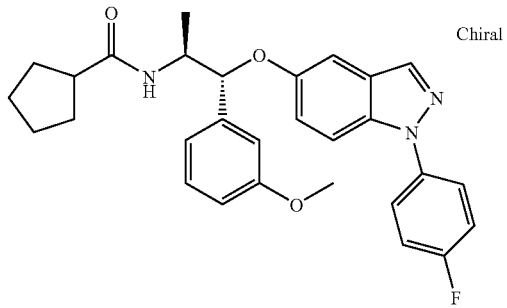

To a stirred solution of 1,1-carbonyldiimidazole (12 mg, 70 μmol) in dichloromethane (1 ml) was added cyclopentanecarboxylic acid (11 μl, 100 μmol) to give a colorless solution. The reaction mixture was stirred for 1 h at r.t. Then a solution of (1R,2S)-1-{[1-(4-fluorophenyl)-1H-indazol-5-yl]oxy}-1-(3-methoxyphenyl)propan-2-amine (6a, 19 mg, 50 μmol) in dichloromethane (0.5 ml) was added, and the stirring was continued at r.t. overnight. The solvent was removed in vacuo, the residue dissolved in acetonitrile/water mixture, and the crude product purified by preparative HPLC. Yield 18 mg (76%).

APCI-MS: m/z 488 [MH$^+$] $^1$H NMR (400 MHz, d$_6$-acetone) δ 8.05 (s, 1H), 7.77 (m, 2H), 7.70 (d, J=9.2 Hz, 1H), 7.38-7.21 (m, 4H), 7.19 (br. d, J=8.1 Hz, 1H), 7.13 (d, J=2.3 Hz, 1H), 7.03 (m, 2H), 6.84 (m, 1H), 5.45 (d, J=4.1 Hz, 1H), 4.32 (m, 1H), 3.78 (s, 3H), 2.59 (quintet, J=7.7 Hz, 1H), 1.78-1.40 (m, 8H), 1.20 (d, J=6.9 Hz, 3H).

Example 57

(2R)-N-[(1R,2S)-1-[1-(4-fluorophenyl)indazol-5-yl]oxy-1-(3-methoxyphenyl)propan-2-yl]-2-hydroxy-propanamide

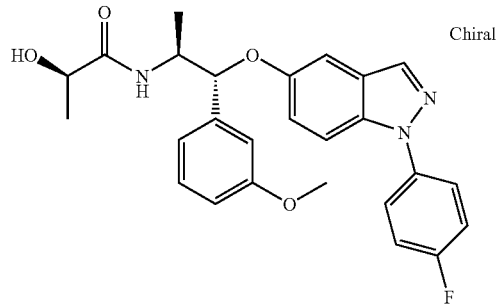

To a stirred solution of 1,1-carbonyldiimidazole (31 mg, 190 μmol) in THF (1 ml) was added (2R)-2-hydroxypropanoic acid (18 mg, 20 μmol) to give a colorless solution. The reaction mixture was stirred for 1 h at r.t. Then a solution of (1R,2S)-1-{[1-(4-fluorophenyl)-1H-indazol-5-yl]oxy}-1-(3-methoxyphenyl)propan-2-amine (6a, 39 mg, 100 μmol) in THF (0.5 ml) was added, and the stirring was continued at r.t. overnight. The solvent was removed in vacuo, the residue dissolved in acetonitrile/water mixture, and the crude product purified by preparative HPLC. Yield 16 mg (35%).

APCI-MS: m/z 464 [MH$^+$]$^1$H NMR (400 MHz, d$_6$-acetone) δ 8.05 (d, J=0.5 Hz, 1H), 7.77 (m, 2H), 7.71 (d, J=9.2 Hz, 1H), 7.38-7.23 (m, 4H), 7.16 (d, J=2.3 Hz, 1H), 7.05 (m, 2H), 6.85 (dd, J=8.2, 1.9 Hz, 1H), 5.45 (d, J=4.4 Hz, 1H), 4.37 (m, 1H), 4.07 (q, J=6.8 Hz, 1H), 3.78 (s, 3H), 1.24 (d, J=6.9 Hz, 3H), 1.18 (d, J=6.9 Hz, 3H).

Example 58

(2S)-N-[(1R,2S)-1-[1-(4-fluorophenyl)indazol-5-yl]oxy-1-(3-methoxyphenyl)propan-2-yl]-2-hydroxy-propanamide

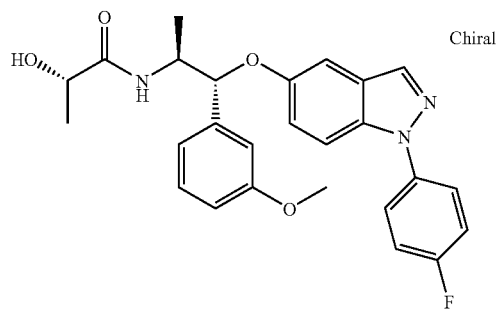

Prepared as described in Example 110 using (1R,2S)-1-{[1-(4-fluorophenyl)-1H-indazol-5-yl]oxy}-1-(3-methoxyphenyl)propan-2-amine (6a, 39 mg, 1000 μmol) and (2S)-2-hydroxypropanoic acid (18 mg, 20 μmol). Yield 17 mg (37%).

APCI-MS: m/z 464 [MH$^+$]$^1$H NMR (400 MHz, d$_6$-acetone) δ 8.05 (d, J=0.5 Hz, 1H), 7.77 (m, 2H), 7.70 (d, J=9.2 Hz, 1H), 7.39-7.23 (m, 4H), 7.15 (d, J=2.3 Hz, 1H), 7.04 (m, 2H), 6.85 (m, 1H), 5.46 (d, J=4.1 Hz, 1H), 4.36 (m, 1H), 4.06 (q, J=6.7 Hz, 1H), 3.78 (s, 3H), 1.26 (d, J=6.7 Hz, 3H), 1.23 (d, J=6.9 Hz, 3H).

Example 59

N-[(1R,2S)-1-[1-(4-fluorophenyl)indazol-5-yl]oxy-1-[4-(trifluoromethyl)phenyl]propan-2-yl]-2-methoxy-acetamide

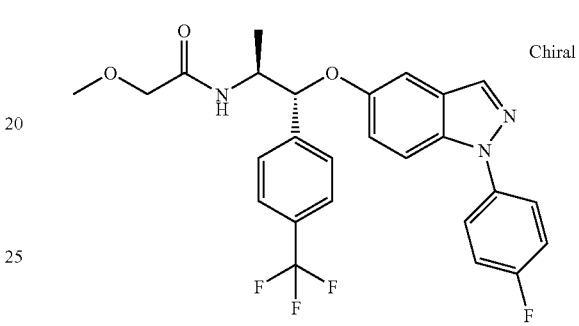

Prepared as described in Example 1 using (1R,2S)-1-{[1-(4-fluorophenyl)-1H-indazol-5-yl]oxy}-1-[4-(trifluoromethyl)phenyl]propan-2-amine (59a, 21 mg, 50 μmol) and methoxyacetyl chloride (16 mg, 150 μmol). Yield 17 mg (69%).

APCI-MS: m/z 502 [MH$^+$]$^1$H NMR (400 MHz, d$_6$-acetone) δ 8.05 (d, J=0.5 Hz, 1H), 7.70-7.80 (m, 6H), 7.34 (m, 2H), 7.28 (dd, J=9.2, 2.5 Hz, 1H), 7.25 (br. d, J=8.5 Hz, 1H), 7.17 (d, J=2.3 Hz, 1H), 5.61 (d, J=4.8 Hz, 1H), 4.44 (m, 1H), 3.80 (d, J=15.0 Hz, 1H), 3.70 (d, J=15.0 Hz, 1H), 3.28 (s, 3H), 1.28 (d, J=6.9 Hz, 3H).

(1R,2S)-1-{[1-(4-fluorophenyl)-1H-indazol-5-yl]oxy}-1-[4-(trifluoromethyl)phenyl]propan-2-amine (59a)

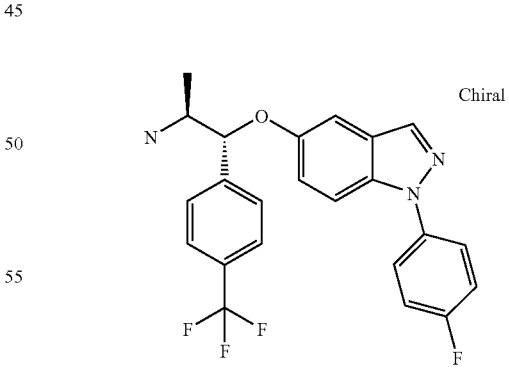

Prepared as described in Example 6 (step 6a), using (1R,2S)-2-amino-1-[4-(trifluoromethyl)phenyl]propan-1-ol (136 mg, 0.62 mmol). Yield 70 mg (32%).

APCI-MS: m/z 430 [MH$^+$]$^1$H NMR (400 MHz, d$_6$-DMSO+D$_2$O, TFA added) δ 8.18 (s, 1H), 7.69-7.81 (m, 3H), 7.65 (d, J=8.1 Hz, 2H), 7.39 (t, J=8.8 Hz, 2H), 7.32 (dd, J=9.2, 2.3 Hz, 1H), 7.15 (d, J=2.1 Hz, 1H), 5.77 (d, J=2.7 Hz, 1H), 3.78 (m, 1H), 1.16 (d, J=6.9 Hz, 3H).

(1R,2S)-2-amino-1-[4-(trifluoromethyl)phenyl]propan-1-ol (59b)

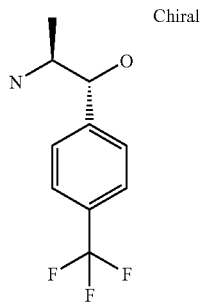

Prepared from tert-butyl {(1S,2R)-2-hydroxy-1-methyl-2-[4-(trifluoromethyl)phenyl]ethyl}carbamate (59c, 279 mg, 0.87 mmol) as described in Example 7, Step 7b. Yield 175 mg (91%).

APCI-MS: m/z 220 [MH$^+$]

$^1$H NMR (400 MHz, d$_6$-DMSO) δ 7.66 (d, J=8.1 Hz, 2H), 7.53 (d, J=8.1 Hz, 2H), 5.36 (s, 1H), 4.43 (s, 1H), 2.92 (dd, J=6.5, 5.0 Hz, 1H), 1.39 (s, 2H), 0.83 (d, J=6.4 Hz, 3H).

tert-Butyl {(1S,2R)-2-hydroxy-1-methyl-2-[4-(trifluoromethyl)phenyl]ethyl}carbamate (59c)

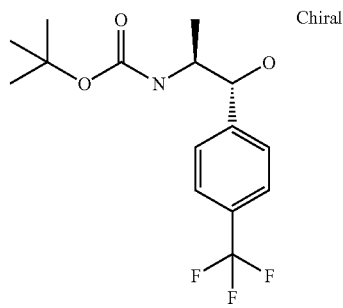

Prepared from tert-butyl {(1S)-1-methyl-2-oxo-2-[4-(trifluoromethyl)phenyl]ethyl}carbamate (58c, 385 mg, 1.21 mmol) as described in Example 7, Step 7c. Yield 279 mg (72%).

$^1$H NMR (400 MHz, CDCl$_3$) δ 7.62 (d, J=8.1 Hz, 2H), 7.48 (d, J=8.5 Hz, 2H), 4.93 (s, 1H), 4.56 (br.s, 1H), 4.04 (br.s, 1H), 3.52 (br.s, 1H), 1.48 (s, 9H), 1.00 (d, J=6.9 Hz, 3H).

tert-Butyl {(1S)-1-methyl-2-oxo-2-[4-(trifluoromethyl)phenyl]ethyl}carbamate (59c)

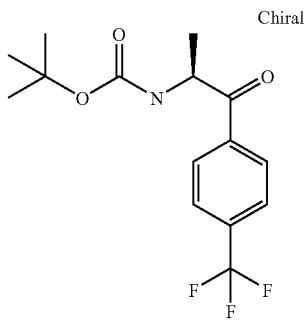

To a stirred mixture of isopropylmagnesium chloride-lithium chloride complex (14% wt 1 M solution, 726 mg, 5 mmol, 5 ml) and THF (5 ml) was added 1-bromo-4-(trifluoromethyl)benzene (1.125 g, 5 mmol) under argon. The stirring was continued at r.t. for 4 h. A solution of N$^2$-(tert-butoxycarbonyl)-N-methoxy-N-methyl-L-alaninamide (232 mg, 1 mmol) in THF (10 ml) was added dropwise, and the stirring was continued overnight at r.t. Then the reaction mixture was quenched with sat. aq. NH$_4$Cl (20 ml), and stirring was continued for 30 min. The layers were separated, the aqueous layer extracted with ethyl acetate (20 ml). The combined organic extracts were dried over Na$_2$SO$_4$, and the solvent was evaporated to give yellow partly crystalline product. Purification by flash chromatography on silica gel with n-heptane/ethyl acetate afforded colourless solid, 260 mg (82%).

$^1$H NMR (400 MHz, CDCl$_3$) δ 8.09 (d, J=8.0 Hz, 2H), 7.77 (d, J=8.1 Hz, 2H), 5.46 (d, J=7.1 Hz, 1H), 5.29 (quintet, J=7.2 Hz, 1H), 1.46 (s, 9H), 1.41 (d, J=7.1 Hz, 3H).

Example 60

N-[(1R,2S)-1-[1-(4-fluorophenyl)indazol-5-yl]oxy-1-[4-(trifluoromethyl)phenyl]propan-2-yl]-2-hydroxy-acetamide

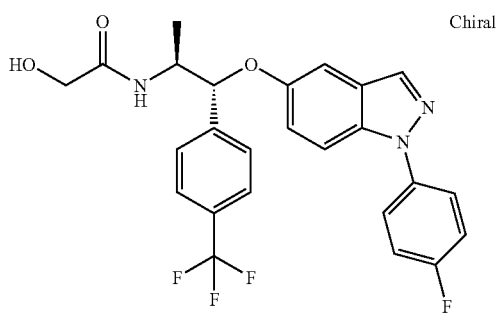

Prepared as described in Example 5 using (1R,2S)-1-{[1-(4-fluorophenyl)-1H-indazol-5-yl]oxy}-1-[4-(trifluoromethyl)phenyl]propan-2-amine (59a, 21 mg, 50 μmol) and 2-chloro-2-oxoethyl acetate (21 mg, 150 μmol). Yield 18 mg (76%).

APCI-MS: m/z 488 [MH$^+$]$^1$H NMR (400 MHz, d$_6$-acetone) δ 8.04 (d, J=0.7 Hz, 1H), 7.70-7.80 (m, 6H), 7.43 (d, J=8.7 Hz, 1H), 7.34 (m, 2H), 7.28 (dd, J=9.2, 2.5 Hz, 1H), 7.17 (d, J=2.3 Hz, 1H), 5.62 (d, J=4.2 Hz, 1H), 4.44 (m, 1H), 3.90 (dd, J=21.0, 15.8 Hz, 2H), 1.27 (d, J=6.9 Hz, 3H).

Example 61

N-[(1R,2S)-1-[1-(4-fluorophenyl)indazol-5-yl]oxy-1-[4-(trifluoromethyl)phenyl]propan-2-yl]propanamide

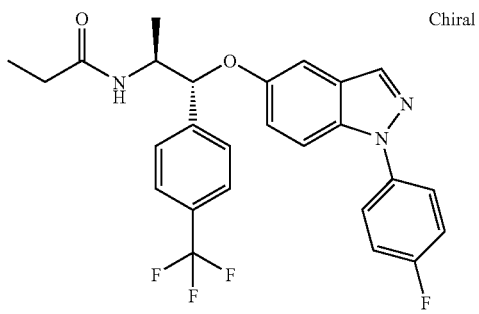

Prepared as described in Example 1 using (1R,2S)-1-{[1-(4-fluorophenyl)-1H-indazol-5-yl]oxy}-1-[4-(trifluoromethyl)phenyl]propan-2-amine (59a, 21 mg, 50 μmol) and propanoyl chloride (14 mg, 150 μmol). Yield 17 mg (72%).

APCI-MS: m/z 486 [MH+] 1H NMR (400 MHz, d6-acetone) δ 8.04 (d, J=0.7 Hz, 1H), 7.68-7.80 (m, 6H), 7.34 (m, 2H), 7.30 (d, J=8.3 Hz, 1H), 7.25 (dd, J=9.1, 2.4 Hz, 1H), 7.14 (d, J=2.3 Hz, 1H), 5.58 (d, J=4.1 Hz, 1H), 4.35 (m, 1H), 2.12 (m, 2H), 1.21 (d, J=6.9 Hz, 3H), 0.98 (t, J=7.6 Hz, 3H).

Example 62

2,2,2-Trifluoro-N-[(1R,2S)-1-[1-(4-fluorophenyl)-6-methyl-indazol-5-yl]oxy-1-phenyl-propan-2-yl]acetamide

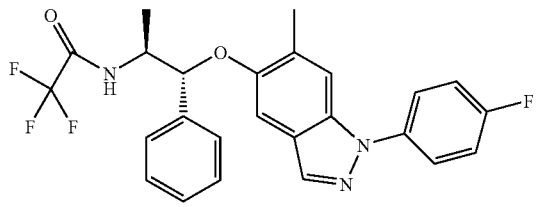

Prepared as described in Example 1 using (1R,2S)-1-[1-(4-fluorophenyl)-6-methyl-indazol-5-yl]oxy-1-phenyl-propan-2-amine (50 mg, 0.13 mmol) and trifluoroacetic anhydride (0.075 mL, 0.53 mmol). Yield 54 mg (86%).

APCI-MS: m/z 472.3 [MH+] 1H-NMR (400 MHz, CD3OD): δ 7.91 (s, 1H), 7.66 (m, 2H), 7.49 (s, 1H), 7.44-7.40 (m, 2H), 7.35 (m, 2H), 7.32-7.26 (m, 3H), 6.89 (s, 1H), 5.41 (d, J=5.5 Hz, 1H), 4.44 (m, 1H), 2.51 (s, 3H), 1.40 (d, J=6.9 Hz, 3H).

(1R,2S)-1-[1-(4-Fluorophenyl)-6-methyl-indazol-5-yl]oxy-1-phenyl-propan-2-amine (62a)

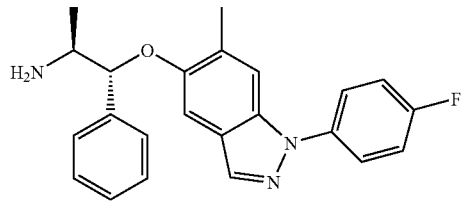

Prepared as described in Example 1 from (1R,2S)-2-amino-1-phenylpropan-1-ol (257 mg, 1.70 mmol), and 1-(4-fluorophenyl)-5-iodo-6-methylindazole (200 mg, 0.57 mmol). Yield 169 mg (79%).

1H-NMR (400 MHz, CD3OD): δ 7.90 (s, 1H), 7.65 (m, 2H), 7.49 (s, 1H), 7.43-7.33 (m, 4H), 7.29 (m, 3H), 6.91 (s, 1H), 5.23 (d, J=4.8 Hz, 1H), 2.51 (s, 3H), 1.22 (d, J=6.5 Hz, 3H).

1-(4-Fluorophenyl)-5-iodo-6-methylindazole (62b)

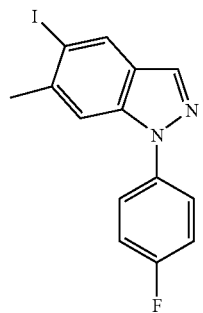

5-Iodo-6-methylindazole (1.3 g, 5.0 mmol), p-fluorobenzeneboronic acid (1.4 g, 10 mmol), anhydrous copper(II) acetate (1.4 g, 7.5 mmol) and pyridine (0.80 mL, 10 mmol) were stirred in dichloromethane (30 mL) overnight. Additional portions of p-fluorobenzeneboronic acid (0.47 g, 3.4 mmol), anhydrous copper(II) acetate (0.45 g, 2.5 mmol) and pyridine (0.27 mL, 3.4 mmol) were added. The mixture was filtered through celite after stirring for an additional night. The filtrate was concentrated and purified by column chromatography (SiO2, toluene) to give the subtitle compound (0.90 g, 51%) as a light orange powder.

APCI-MS: m/z 353.1 [MH+] 1H-NMR (400 MHz, CD2Cl2): δ 8.29 (s, 1H), 8.06 (s, 1H), 7.66 (m, 2H), 7.61 (s, 1H), 7.26 (m, 2H), 2.57 (s, 3H).

5-Iodo-6-methylindazole (62c)

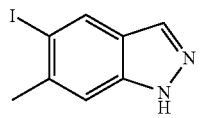

1-Acetyl-5-iodo-6-methylindazole (1.5 g, 5.0 mmol) was stirred with ammonia (7 M in methanol, 4 mL) in methanol/THF (2/1, 15 mL) for 1 h. The solution was evaporated to give the subtitle compound (1.3 g, 100%) as an off-white powder.

APCI-MS: m/z 259.1 [MH+]

1-Acetyl-5-iodo-6-methylindazole (62d)

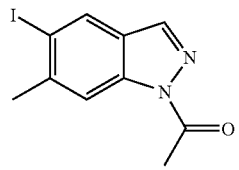

Acetic acid anhydride (6.9 mL, 72 mmol) was added to a slurry of 2,5-dimethyl-4-iodoaniline (6.0 g, 24 mmol) and potassium acetate (2.4 g, 24 mmol) in benzene (50 mL). The mixture was heated to 80° C. and isopentylnitrit (4.8 mL, 36 mmol) was added during 20 min. The mixture was stirred at 80° C. overnight, then cooled and filtered. The filtrate was evaporated and purified by column chromatography (SiO2, dichloromethane). Product containing fractions were pooled and concentrated. The subtitle compound (1.5 g, 21%) was obtained as crystals from ethyl acetate.

1H-NMR (400 MHz, CD2Cl2): δ 8.37 (s, 1H), 8.24 (s, 1H), 8.02 (s, 1H), 2.73 (s, 3H), 2.61 (s, 3H).

Example 63

N-[(1R,2S)-1-[1-(4-Fluorophenyl)-6-methyl-indazol-5-yl]oxy-1-phenyl-propan-2-yl]-2,2-dimethyl-propanamide

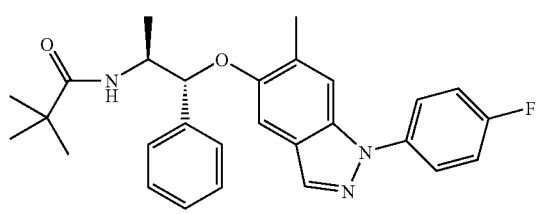

Prepared as described in Example 1 using (1R,2S)-1-[1-(4-fluorophenyl)-6-methyl-indazol-5-yl]oxy-1-phenyl-propan-2-amine (50 mg, 0.13 mmol) and pivaloyl chloride (0.065 mL, 0.53 mmol). Yield 53 mg (87%).

APCI-MS: m/z 460.4 [MH+] $^1$H-NMR (400 MHz, CD$_3$OD): δ 7.92 (s, 1H), 7.66 (m, 2H), 7.49 (s, 1H), 7.46-7.42 (m, 2H), 7.37-7.20 (m, 5H), 6.90 (s, 1H), 5.39 (d, J=5.7 Hz, 1H), 4.41 (m, 1H), 2.52 (s, 3H), 1.32 (d, J=6.9 Hz, 3H), 1.04 (s, 9H).

Example 64

N-[(1R,2S)-1-[1-(4-Fluorophenyl)-6-methyl-indazol-5-yl]oxy-1-phenyl-propan-2-yl]-2-hydroxy-acetamide

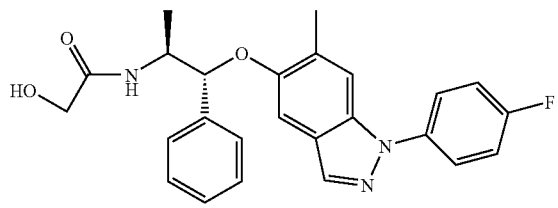

Acetoxyacetyl chloride (0.071 mL, 0.66 mmol) was added to a solution of (1R,2S)-1-(1-(4-fluorophenyl)-6-methyl-1H-indazol-5-yloxy)-1-phenylpropan-2-amine (62 mg, 0.17 mmol) and triethylamine (0.18 mL, 1.3 mmol) in THF (2.5 mL) at r.t. The mixture was stirred overnight and concentrated. The residue was dissolved in methanol (2 mL) and 28% ammonia (2 mL) and stirred at r.t. overnight. The title compound (57 mg, 80%) was obtained after purification by semi-preparative HPLC.

APCI-MS: m/z 434.3-[MH+] $^1$H-NMR (400 MHz, CD$_3$OD): δ 7.90 (s, 1H), 7.66 (m, 2H), 7.51 (s, 1H), 7.45-7.41 (m, 2H), 7.37 (m, 2H), 7.33-7.26 (m, 3H), 6.86 (s, 1H), 5.46 (d, J=4.3 Hz, 1H), 4.46 (m, 1H), 3.93 (m, 2H), 2.53 (s, 3H), 1.27 (d, J=6.9 Hz, 3H).

Example 65

2,2,2-Trifluoro-N-[(1R,2S)-1-[1-(4-fluorophenyl)-6-methyl-indazol-5-yl]oxy-1-(3-methoxyphenyl)propan-2-yl]acetamide

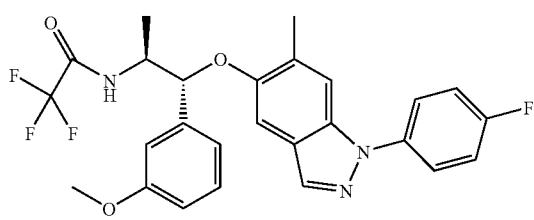

Prepared as described in Example 1 using (1R,2S)-1-[1-(4-fluorophenyl)-6-methyl-indazol-5-yl]oxy-1-(3-methoxyphenyl)-propan-2-amine (73 mg, 0.18 mmol) and trifluoroacetic anhydride (0.102 ml, 0.72 mmol). Yield 69 mg (76%).

APCI-MS: m/z 502.4 [MH+] $^1$H-NMR (400 MHz, CD$_3$OD): δ 7.93 (s, 1H), 7.66 (m, 2H), 7.49 (s, 1H), 7.33-7.23 (m, 3H), 7.02-6.95 (m, 2H), 6.91 (s, 1H), 6.85 (dd, J$_1$=8.1 Hz, J$_2$=2.3 Hz, 1H), 5.37 (d, J=5.5 Hz, 1H), 4.44 (m, 1H), 3.77 (s, 3H), 2.51 (s, 3H), 1.40 (d, J=6.9 Hz, 3H).

(1R,2S)-1-[1-(4-Fluorophenyl)-6-methyl-indazol-5-yl]oxy-1-(3-methoxyphenyl)-propan-2-amine (65a)

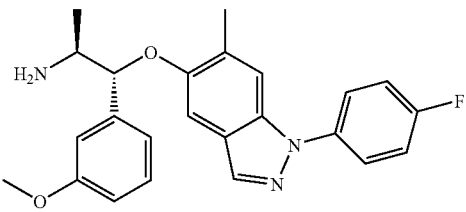

Prepared as described in Example 1 from (1R,2S)-1-hydroxy-1-(3-methoxyphenyl)propan-2-aminium chloride (185 mg, 0.85 mmol) and 1-(4-fluorophenyl)-5-iodo-6-methylindazole (300 mg, 0.85 mmol). Yield 224 mg (65%).

$^1$H-NMR (400 MHz, CD$_3$OD): δ 7.92 (s, 1H), 7.66 (m, 2H), 7.49 (s, 1H), 7.33-7.25 (m, 3H), 7.01-6.95 (m, 2H), 6.93 (s, 1H), 6.85 (dd, J=7.8 Hz, J$_2$=2.1 Hz, 1H), 5.18 (d, J=5.0 Hz, 1H), 3.77 (s, 3H), 2.51 (s, 3H), 1.23 (d, J=6.5 Hz, 3H).

Example 66

N-[(1R,2S)-1-[1-(4-Fluorophenyl)-6-methyl-indazol-5-yl]oxy-1-(3-methoxyphenyl)propan-2-yl]-2,2-dimethyl-propanamide

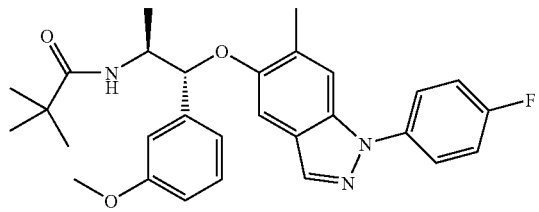

Prepared as described in Example 1 using (1R,2S)-1-[1-(4-fluorophenyl)-6-methyl-indazol-5-yl]oxy-1-(3-methoxyphenyl)-propan-2-amine (73 mg, 0.18 mmol) and pivaloyl chloride (0.088 ml, 0.72 mmol). Yield 75 mg (85%).

APCI-MS: m/z 490.4 [MH+] $^1$H-NMR (400 MHz, CD$_3$OD): δ 7.93 (s, 1H), 7.66 (m, 2H), 7.49 (s, 1H), 7.32-7.22 (m, 3H), 7.03-6.98 (m, 2H), 6.92 (s, 1H), 6.83 (dd, J=8.5 Hz, J$_2$=2.1 Hz, 1H), 5.35 (d, J=5.7 Hz, 1H), 4.40 (m, 1H), 3.77 (s, 3H), 2.52 (s, 3H), 1.32 (d, J=6.9 Hz, 3H), 1.06 (s, 9H).

Example 67

N-[(1R,2S)-1-[1-(4-Fluorophenyl)-6-methyl-indazol-5-yl]oxy-1-(3-methoxyphenyl)propan-2-yl]-2-hydroxy-acetamide

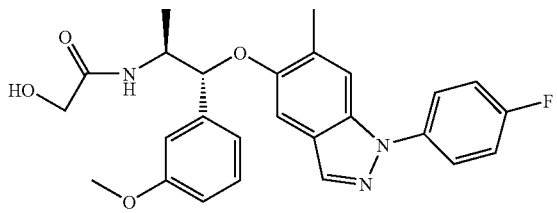

Prepared as described in Example 102 using (1R,2S)-1-[1-(4-fluorophenyl)-6-methyl-indazol-5-yl]oxy-1-(3-methoxyphenyl)-propan-2-amine (73 mg, 0.18 mmol) and acetoxyacetyl chloride (0.077 ml, 0.72 mmol). Yield 67 mg (80%).

APCI-MS: m/z 464.3 [MH+]¹H-NMR (400 MHz, CD₃OD): δ 7.92 (s, 1H), 7.67 (m, 2H), 7.50 (s, 1H), 7.33-7.25 (m, 3H), 7.03-6.97 (m, 2H), 6.89-6.84 (m, 2H), 5.43 (d, J=4.2 Hz, 1H), 4.46 (m, 1H), 3.93 (m, 2H), 3.77 (s, 3H), 2.53 (s, 3H), 1.27 (d, J=6.9 Hz, 3H).

Example 68

2,2,2-Trifluoro-N-[(2S*,3S*)-3-[1-(4-fluorophenyl) indazol-5-yl]oxy-4-phenoxy-butan-2-yl]acetamide

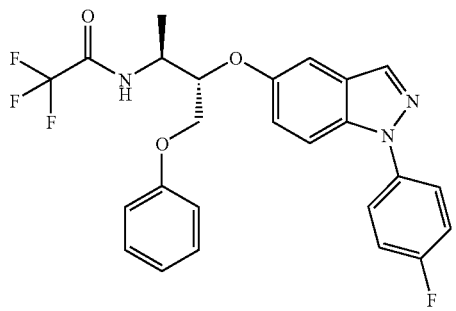

The racemate was prepared as described in Example 1 using (2RS,3RS)-3-[1-(4-fluorophenyl)indazol-5-yl]oxy-4-phenoxy-butan-2-amine (0.13 g, 0.33 mmol) and trifluoroacetic anhydride (0.14 ml, 1.0 mmol). Yield 155 mg (96%). The two enantiomers were separated by semi-preparative HPLC (ChiralpakIA, 21×250 mm, 5 μm, 20% isopropanole/80% iso-hexane). Yield of the faster eluting compound was 57 mg.

APCI-MS: m/z 488.3 [MH+]¹H-NMR (400 MHz, CD₃OD): δ 8.14 (s, 1H), 7.71 (m, 2H), 7.64 (d, J=9.0 Hz, 1H), 7.43 (d, J=2.1 Hz, 1H), 7.32 (m, 2H), 7.28-7.23 (m, 3H), 6.96-6.89 (m, 3H), 4.79 (m, 1H), 4.51 (m, 1H), 4.24 (m, 2H), 1.43 (d, J=6.9 Hz, 3H).

(2RS, 3RS)-3-[1-(4-fluorophenyl)indazol-5-yl]oxy-4-phenoxy-butan-2-amine (68a)

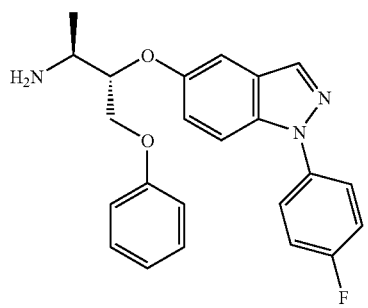

Prepared as described in Example 1 from (2RS,3RS)-3-amino-1-phenoxy-butan-2-ol (250 mg, 1.37 mmol), and 1-(4-fluorophenyl)-5-iodoindazole (557 mg, 1.64 mmol). Yield 157 mg (29

¹H-NMR (400 MHz, CD₃OD): δ 8.14 (s, 1H), 7.71 (m, 2H), 7.64 (d, J=9.0 Hz, 1H), 7.46 (m, 1H), 7.35-7.21 (m, 5H), 6.95-6.88 (m, 3H), 4.59 (m, 1H), 4.28 (m, 2H), 3.41 (m, 1H), 1.29 (d, J=6.7 Hz, 3H).

(2RS,3RS)-3-Amino-1-phenoxy-butan-2-ol (68b)

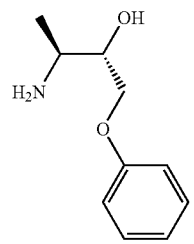

3-Nitro-1-phenoxy-butan-2-ol (1.7 g, 8.0 mmol) in methanol (50 mL) was hydrogenated over platinum oxide (300 mg) at atmospheric pressure overnight. The mixture was filtered through celite and purified by semi-preparative HPLC (XBridge, C18, 5 μm, 19×50 mm, 12 min gradient of 5-20% acetonitrile in (water+2 mL NH3/L). Fractions containing the faster eluting peak were pooled and concentrated to give the subtitle compound (409 mg).

¹H-NMR (400 MHz, CD₃OD): δ 7.26 (m, 2H), 6.98-6.89 (m, 3H), 4.01 (m, 2H), 3.80 (m, 1H), 3.07 (m, 1H), 1.15 (d, J=6.5 Hz, 3H). The coupling constant between the methine protons was measured to 4.95 Hz. Comparison with the coupling constant of norephedrine, with known stereochemistry, indicated that the first eluting racemate has the (2R,3R)/(2S, 3S)-configuration and the secondly eluting racemate has the (2R,3S)/(2S,3R)-configuration.

3-Nitro-1-phenoxy-butan-2-ol (68c)

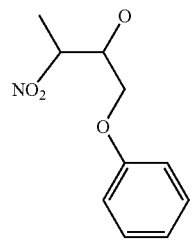

Synthesized analogously to the method described by P. B. Kisanga and J. G. Verkade, *J. Org. Chem.*, 64, 4298-4303 (1999).

2-Phenoxyacetaldehyde (1.36 g, 10 mmol) was added to a suspension of anhydrous magnesium sulfate (2.65 g, 22 mmol) in nitroethane (7.0 mL) under an argon atmosphere. After 5 min a solution of 2,8,9-triisopropyl-2,5,8,9-tetraaza-1-phosphabicyclo[3,3,3]undecane (0.30 g, 1.0 mmol) in nitromethane (3.0 mL) was added. The mixture was vigorously stirred for 5 days at r.t., filtered through celite and concentrated. Purification by column chromatography (SiO₂, dichloromethane/t-butyl methyl ether) gave the subtitle compound as an oil (1.7 g, 81%).

¹H-NMR (400 MHz, CDCl₃): δ 7.32 (m, 2H), 7.02 (m, 1H), 6.92 (m, 2H), 4.92 (m, 0.6H), 4.84 (m, 0.4H), 4.6 (m, 0.4H), 4.33 (m, 0.6H), 4.17 (m, 0.6H), 4.12-4.06 (m, 1H), 4.01 (m, 0.4H), 2.78 (d, J=7.6 Hz, 0.6H), 2.70 (d, J=5.3 Hz, 0.4H), 1.68 (d, J=6.9 Hz, 1.2H), 1.63 (d, J=6.9 Hz, 1.8H).

2-Phenoxyacetaldehyde (68d)

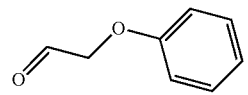

Synthesized analogously to the method described by M. Daumas et al, *Synthesis*, 64-65 (1989).

Sodium periodate (0.65 M in water, 20 mL) was added to a vigorously stirred suspension of silica gel (20 g) in dichloromethane (160 mL), followed by a solution of 3-phenoxy-1,2-propanediol (1.68 g, 10.0 mmol) in dichloromethane (20 mL). After stirring for 10 min the mixture was filtered and the filtrate was concentrated to give the subtitle compound (1.36 g, 100%).

$^1$H-NMR (400 MHz, CDCl$_3$): δ 9.89 (s, 1H9, 7.33 (m, 2H), 7.04 (m, 1H), 6.92 (m, 2H), 4.59 (s, 2H).

Example 69

2,2,2-trifluoro-N-[2R*,3R*-3-[1-(4-fluorophenyl)indazol-5-yl]oxy-4-phenoxy-butan-2-yl]acetamide

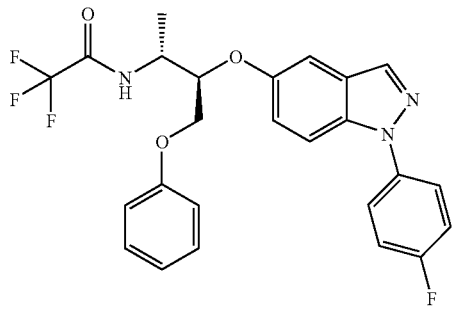

Obtained as the slower eluting compound (49 mg) in the chiral separation in Example 68.

APCI-MS: m/z 488.3 [MH$^+$]$^1$H-NMR (400 MHz, CD$_3$OD): δ 8.13 (s, 1H), 7.71 (m, 2H), 7.64 (d, J=9.2 Hz, 1H), 7.43 (d, J=2.1 Hz, 1H), 7.31 (m, 2H), 7.28-7.22 (m, 3H), 6.96-6.89 (m, 3H), 4.79 (m, 1H), 4.51 (m, 1H), 4.24 (m, 2H), 1.43 (d, J=7.1, 3H).

Example 70

2,2,2-Trifluoro-N-[(2RS,3SR)-3-[1-(4-fluorophenyl)indazol-5-yl]oxy-4-phenoxy-butan-2-yl]acetamide

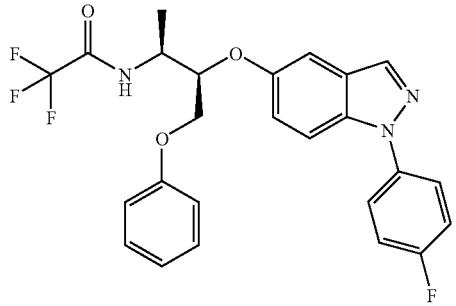

Prepared as described in Example 1 using (2RS,3SR)-3-[1-(4-fluorophenyl)indazol-5-yl]oxy-4-phenoxy-butan-2-amine (38 mg, 0.097 mmol) and trifluoroacetic anhydride (0.041 ml, 0.29 mmol). Yield 40 mg (85%).

APCI-MS: m/z 488.3 [MH$^+$]$^1$H-NMR (400 MHz, CD$_3$OD): δ 8.15 (s, 1H), 7.71 (m, 2H), 7.64 (d, J=9.2 Hz, 1H), 7.50 (d, J=2.3 Hz, 1H), 7.35-7.22 (m, 5H), 6.96-6.89 (m, 3H), 4.76 (m, 1H), 4.60 (m, 1H), 4.29 (m, 1H), 4.21 (m, 1H), 1.39 (d, J=6.9, 3H).

(2RS,3SR)-3-[1-(4-fluorophenyl)indazol-5-yl]oxy-4-phenoxy-butan-2-amine (70a)

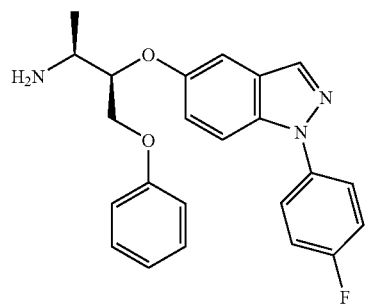

Prepared as described in Example 1 from (2RS,3SR)-3-amino-1-phenoxy-butan-2-ol (319 mg, 1.75 mmol), and 1-(4-fluorophenyl)-5-iodoindazole (710 mg, 2.10 mmol). Yield 244 mg (36%).

$^1$H-NMR (400 MHz, CD$_2$Cl2): δ 8.06 (s, 1H), 7.67 (m, 2H), 7.59 (d, J=9.2 Hz, 1H), 7.37 (d, J=2.1 Hz, 1H), 7.30-7.20 (m, 5H), 6.97-6.88 (m, 3H), 4.39 (m, 1H), 4.29 (m, 1H), 4.19 (m, 1H), 3.43 (m, 1H), 1.25 (d, J=6.6 Hz, 3H).

(2RS,3SR)-3-Amino-1-phenoxy-butan-2-ol (70b)

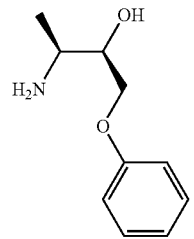

The subtitle compound (319 mg) was obtained as the secondly eluting peak in the chromatographic purification in Example 68b.

$^1$H-NMR (400 MHz, CD$_3$OD): δ 7.27 (m, 2H), 6.98-6.89 (m, 3H), 4.02 (m, 2H), 3.67 (m, 1H), 3.08 (m, 1H), 1.17 (d, J=6.6 Hz, 3H). The coupling constant between the methine protons was measured to 6.0 Hz. Comparison with the coupling constant of norephedrine, with known stereochemistry, indicated that the first eluting racemate has the (2R,3R)/(2S,3S)-configuration and the secondly eluting racemate has the (2R,3S)/(2S,3R)-configuration.

Example 71

N-[(1R,2S)-1-[1-(4-Fluorophenyl)indazol-5-yl]oxy-1-(3-methoxyphenyl)propan-2-yl]-2-(2-methoxyethoxy)acetamide

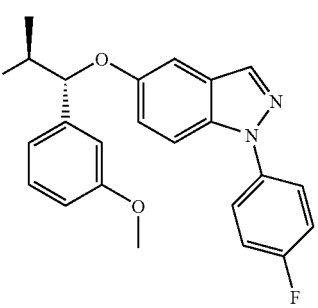

Prepared as described in Example 1 using (1R,2S)-1-[1-(4-fluorophenyl)-indazol-5-yl]oxy-1-(3-methoxyphenyl)-propan-2-amine (50 mg, 0.13 mmol) and 2-(2-methoxyethoxy)acetyl chloride (0.039 mL, 0.38 mmol). Yield 52 mg (80%).

APCI-MS: m/z 508.4 [MH+] $^1$H-NMR (400 MHz, CD$_3$OD): δ 8.01 (s, 1H), 7.67 (m, 2H), 7.59 (d, J=9.2 Hz, 1H), 7.32-7.21 (m, 4H), 7.08 (d, J=2.3 Hz, 1H), 7.04-7.00 (m, 2H), 6.84 (m, 1H), 5.34 (d, J=4.6 Hz, 1H), 4.41 (m, 1H), 3.92 (m, 2H), 3.77 (s, 3H), 3.59-3.55 (m, 2H), 3.53-3.49 (m, 2H), 3.34 (s, 3H), 1.27 (d, J=6.9 Hz, 3H).

Example 72

2,2,2-Trifluoro-N-[(2S,3R)-3-[1-(4-fluorophenyl)indazol-5-yl]oxy-4-phenyl-butan-2-yl]acetamide

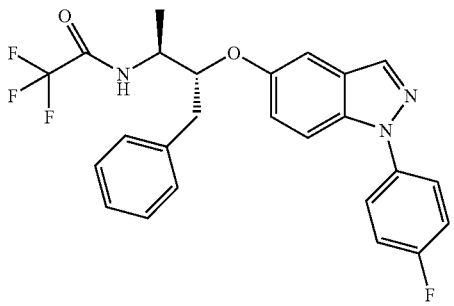

Prepared as described in Example 1 using (2S,3R)-3-[1-(4-fluorophenyl)indazol-5-yl]oxy-4-phenyl-butan-2-amine (60 mg, 0.16 mmol) and trifluoroacetic anhydride (0.090 mL, 0.64 mmol). Yield 45 mg (60%).

APCI-MS: m/z 472.3 [MH+] $^1$H-NMR (400 MHz, CD$_3$OD): δ 9.23 (dd, J=7.6 Hz, 1H), 8.05 (s, 1H), 7.67 (m, 2H), 7.54 (d, J=9.2 Hz, 1H), 7.34-7.22 (m, 6H), 7.20-7.15 (m, 1H), 7.12 (d, J=2.0 Hz, 1H), 7.02 (dd, J$_1$=9.2 Hz, J$_2$=2.1 Hz, 1H), 4.71 (m, 1H), 4.23 (m, 1H), 3.01 (d, J=6.4 Hz, 2H), 1.39 (d, J=6.9 Hz, 3H).

(2S,3R)-3-[1-(4-Fluorophenyl)indazol-5-yl]oxy-4-phenyl-butan-2-amine (72a)

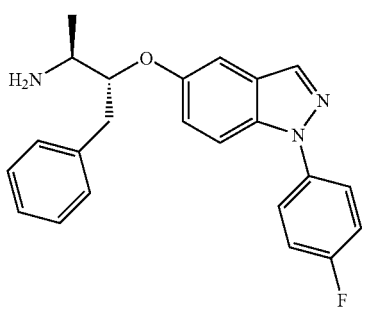

Prepared as described in Example 1 from (2S,3R)-3-hydroxy-4-phenylbutan-2-aminium chloride (290 mg, 1.44 mmol) and 1-(4-fluorophenyl)-5-iodoindazole (583 mg, 1.73 mmol). Yield 340 mg (63%).

$^1$H-NMR (400 MHz, CD$_3$OD): δ 8.07 (s, 1H), 7.68 (m, 2H), 7.56 (d, J=9.0 Hz, 1H), 7.34-7.12 (m, 8H), 7.09 (dd, J$_1$=9.2 Hz, J$_2$=2.3 Hz, 1H), 4.52 (m, 1H), 3.15 (m, 1H), 3.05 (m, 1H), 2.94 (m, 1H), 1.27 (d, J=6.5 Hz, 3H).

(2S,3R)-3-Hydroxy-4-phenylbutan-2-aminium chloride (72b)

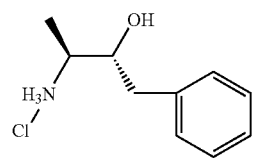

Hydrochloric acid (5 to 6 M in isopropanol, 4 mL) was added to a solution of tert-butyl (2S,3R)-3-hydroxy-4-phenylbutan-2-ylcarbamate (640 mg, 2.41 mmol) in ethyl acetate (4 mL). The mixture was stirred at 50° C. for 2.5 h and then concentrated. The solid was dissolved in warm ethanol (4-5 mL). Diethyl ether (ca 15 mL) was added under stirring to give the subtitle compound as a light lilic precipitate (290 mg, 60%).

$^1$H-NMR (400 MHz, CD$_3$OD): δ 7.35-7.20 (m, 5H), 4.00 (m, 1H), 3.23 (m, 1H), 2.79 (m, 2H), 1.32 (d, J=6.9 Hz, 3H).

tert-Butyl N-[(2S,3R)-3-hydroxy-4-phenyl-butan-2-yl]carbamate (72c)

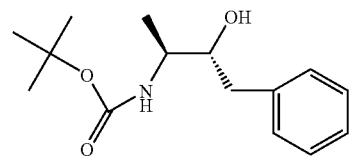

Prepared as described in Example 6 from tert-butyl N-[(2S)-3-oxo-4-phenyl-butan-2-yl]carbamate (650 mg, 2.47 mmol). Yield 646 mg (99%; containing 15% of the (2S,3S)-diastereoisomer).

$^1$H-NMR (400 MHz, CD$_2$Cl$_2$): δ 7.34-7.28 (m, 2H), 7.25-7.20 (m, 3H), 4.81 (broad s, 1H), 3.84 (m, 1H), 3.71 (m, 1H), 2.70 (m, 2H), 1.42 (s, 9H), 1.16 (d, J=6.7 Hz, 3H).

tert-Butyl N-[(2S)-3-oxo-4-phenyl-butan-2-yl]carbamate (72d)

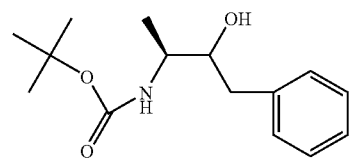

Prepared as described in Example 6 from (S)-tert-butyl 1-(methoxy(methyl)amino)-1-oxopropan-2-ylcarbamate (600 mg, 2.58 mmol) and benzylmagnesium chloride (2.0 M in THF, 3.87 mL, 7.75 mmol). Yield 653 mg (96%).

¹H-NMR (400 MHz, CD₂Cl₂): δ 7.36-7.30 (m, 2H), 7.29-7.24 (m, 1H), 7.21-7.17 (m, 2H), 5.18 (broad s, 1H), 4.35 (m, 1H), 3.81 (m, 2H), 1.42 (s, 9H), 1.32 (d, J=7.1 Hz, 3H).

Example 73

N-[(2S,3R)-3-[1-(4-Fluorophenyl)indazol-5-yl]oxy-4-phenyl-butan-2-yl]-2,2-dimethyl-propanamide

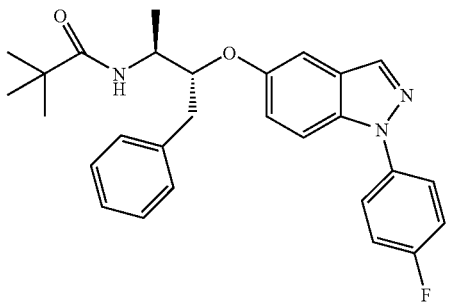

Prepared as described in Example 1 using (2S,3R)-3-[1-(4-fluorophenyl)indazol-5-yl]oxy-4-phenyl-butan-2-amine (60 mg, 0.16 mmol) and pivaloyl chloride (0.078 mL, 0.64 mmol). Yield 53 mg (72%).

APCI-MS: m/z 460.4 [MH⁺] ¹H-NMR (400 MHz, CD₃OD): δ 8.02 (s, 1H), 7.66 (m, 2H), 7.53 (d, J=9.0 Hz, 1H), 7.34-7.21 (m, 6H), 7.19-7.13 (m, 1H), 7.07 (d, J=2.1 Hz, 1H), 7.02 (dd, J₁=9.0 Hz, J₂=2.3 Hz, 1H), 4.74 (m, 1H), 4.14 (m, 1H), 2.99 (d, J=6.4 Hz, 2H), 1.33 (d, J=6.9 Hz, 3H), 1.02 (s, 9H).

Example 74

N-[(2S,3R)-3-[1-(4-Fluorophenyl)indazol-5-yl]oxy-4-phenyl-butan-2-yl]-2-hydroxy-acetamide

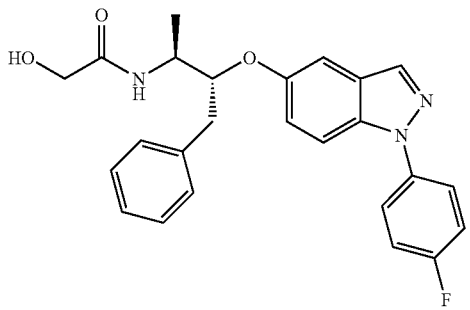

Prepared as described in Example 64 using (2S,3R)-3-[1-(4-fluorophenyl)indazol-5-yl]oxy-4-phenyl-butan-2-amine (60 mg, 0.16 mmol) and acetoxyacetyl chloride (0.069 mL, 0.64 mmol). Yield 60 mg (87%).

APCI-MS: m/z 434.3 [MH⁺] ¹H-NMR (400 MJz, CD₃OD): δ 8.06 (s, 1H), 7.68 (m, 2H), 7.55 (d, J=9.0 Hz, 1H), 7.35-7.22 (m, 6H), 7.19-7.14 (m, 2H), 7.06 (dd, J₁=9.0 Hz, J₂=2.3 Hz, 1H), 4.70 (m, 1H), 4.22 (m, 1H), 3.89 (s, 2H), 3.02 (m, 2H), 1.35 (d, J=6.7 Hz, 3H).

Example 75 tert-Butyl[(1R,2S)-1-[1-(4-fluorophenyl)indazol-5-yl]oxy-1-(3-methoxyphenyl)propan-2-yl]carbamoyl-formate

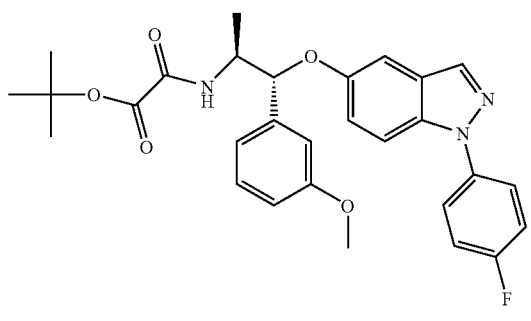

Prepared as described in Example 1 using (1R,2S)-1-[1-(4-fluorophenyl)-indazol-5-yl]oxy-1-(3-methoxyphenyl)-propan-2-amine (50 mg, 0.13 mmol) and tert-butyl 2-chloro-2-oxoacetate (0.064 mL, 0.40 mmol) [prepared according to G. Bucher at al, *Eur J Org Chem*, 545-552 (2001); b.p. 54-55° C., 21 mmHg]. Yield 44 mg (66%).

APCI-MS: m/z 520.4 [MH⁺] ¹H-NMR (400 MHz, CD₃OD): δ 8.01 (s, 1H), 7.66 (m, 2H), 7.59 (d, J=9.2 Hz, 1H), 7.33-7.20 (m, 4H), 7.09 (m, 1H), 7.04-6.98 (m, 2H), 6.84 (broad d, J=8.3 Hz, 1H), 5.32 (d, J=5.3 Hz, 1H), 4.35 (m, 1H), 3.77 (s, 3H), 1.50 (s, 9H), 1.33 (d, J=6.9 Hz, 3H).

Example 76

N-[(1R,2S)-1-[1-(4-Fluorophenyl)indazol-5-yl]oxy-1-(3-methoxyphenyl)propan-2-yl]oxamide

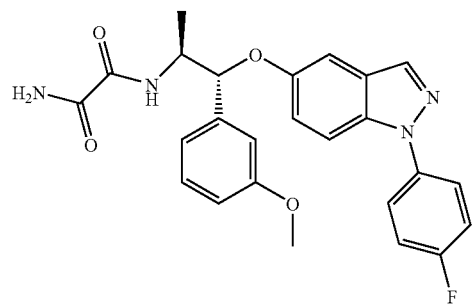

N,N-Diisopropylamine (0.049 mL, 0.30 mmol) was added to a suspension of (1R,2S)-1-(1-(4-fluorophenyl)indazol-5-yloxy)-1-(3-methoxyphenyl)propan-2-amine (53 mg, 0.14 mmol), 2-amino-2-oxoacetic acid (12 mg, 0.14 mmol) and HBTU (62 mg, 0.16 mmoL) in dichloromethane (2 mL). The mixture was stirred at r.t. overnight. The clear solution was concentrated and purified by HPLC to give the title compound (43 mg, 69%).

APCI-MS: m/z 463.3 [MH⁺] ¹H-NMR (400 MHz, CD₃OD): δ 8.00 (s, 1H), 7.66 (m, 2H), 7.59 (d, J=9.2 Hz, 1H), 7.33-7.21 (m, 4H), 7.08 (d, J=2.3 Hz, 1H), 7.04-6.99 (m, 2H), 6.83 (m, 1H), 5.34 (d, J=5.1 Hz, 1H), 4.35 (m, 1H), 3.77 (s, 3H), 1.31 (d, J=6.9 Hz, 3H).

Example 77

Propan-2-yl[(1R,2S)-1-[1-(4-fluorophenyl)indazol-5-yl]oxy-1-(3-methoxyphenyl)propan-2-yl]carbamoylformate

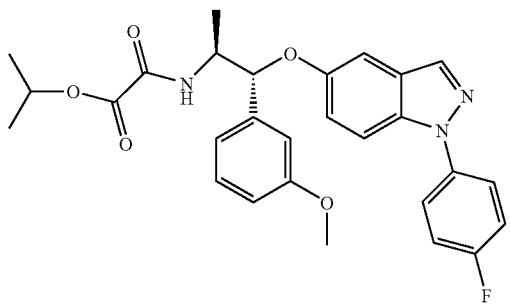

Prepared as described in Example 1 using (1R,2S)-1-[1-(4-fluorophenyl)-indazol-5-yl]oxy-1-(3-methoxyphenyl)-propan-2-amine (53 mg, 0.14 mmol) and isopropyl 2-chloro-2-oxoacetate (0.035 mL, 0.27 mmol) [prepared according to G. Bucher at al, *Eur J Org Chem*, 545-552 (2001); b.p. 54-55° C., 30 mmHg]. Yield 54 mg (79%).

APCI-MS: m/z 506.4 [MH+] $^1$H-NMR (400 MHz, CD$_3$OD): δ 8.00 (s, 1H), 7.66 (m, 2H), 7.58 (d, J=9.2 Hz, 1H), 7.32-7.21 (m, 4H), 7.08 (d, J=2.1 Hz, 1H), 7.04-6.99 (m, 2H), 6.83 (m, 1H), 5.32 (d, J=5.3 Hz, 1H), 5.06 (m, 1H), 4.37 (m, 1H), 3.77 (s, 3H), 1.34 (d, J=6.9 Hz, 3H), 1.29 (t, J=5.8 Hz, 6H).

Example 78

Ethyl[(1R,2S)-1-[1-(4-fluorophenyl)indazol-5-yl]oxy-1-(3-methoxyphenyl)propan-2-yl]carbamoylformate

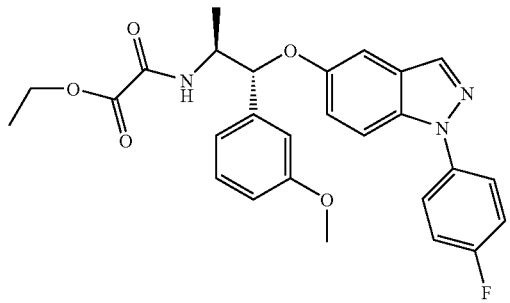

Prepared as described in Example 1 using (1R,2S)-1-[1-(4-fluorophenyl)-indazol-5-yl]oxy-1-(3-methoxyphenyl)-propan-2-amine (52 mg, 0.13 mmol) and ethyl 2-chloro-2-oxoacetate (0.030 mL, 0.27 mmol). Yield 53 mg (81%).

APCI-MS: m/z 492.4 [MH+] $^1$H-NMR (400 MHz, CD$_3$OD): δ 8.00 (s, 1H), 7.65 (m, 2H), 7.58 (d, J=9.2 Hz, 1H), 7.32-7.20 (m, 4H), 7.07 (d, J=2.0 Hz, 1H), 7.04-6.98 (m, 2H), 6.83 (m, 1H), 5.33 (d, J=5.1 Hz, 1H), 4.38 (m, 1H), 4.27 (m, 2H), 3.76 (s, 3H), 1.34 (d, J=6.9 Hz, 3H), 1.31 (t, J=7.2 Hz, 3H).

Example 79

N-[(1R,2S)-1-[1-(4-Fluorophenyl)indazol-5-yl]oxy-1-(3-methoxyphenyl)propan-2-yl]-N'-methyl-oxamide

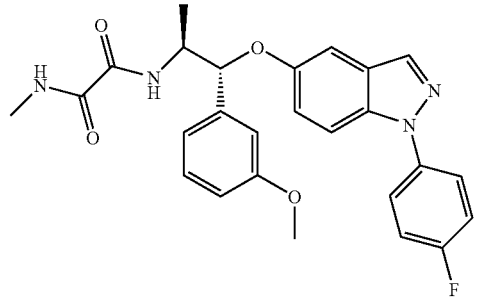

Prepared as described in Example 76 using (1R,2S)-1-[1-(4-fluorophenyl)-indazol-5-yl]oxy-1-(3-methoxyphenyl)-propan-2-amine (51 mg, 0.13 mmol) and 2-(methylamino)-2-oxoacetic acid (13 mg, 0.13 mmol). Yield 34 mg (55%).

APCI-MS: m/z 477.4 [MH+] $^1$H-NMR (400 MHz, CD$_3$OD): δ 8.01 (s, 1H), 7.67 (m, 2H), 7.59 (d, J=9.2 Hz, 1H), 7.32-7.21 (m, 4H), 7.07 (d, J=2.3 Hz, 1H), 7.03-6.99 (m, 2H), 6.83 (m, 1H), 5.34 (d, J=5.0 Hz, 1H), 4.35 (m, 1H), 3.76 (s, 3H), 2.78 (s, 3H), 1.31 (d, J=6.9 Hz, 3H).

Example 80

N-[(1R,2S)-1-[1-(4-Fluorophenyl)indazol-5-yl]oxy-1-(3-methoxyphenyl)propan-2-yl]-N',N'-dimethyl-oxamide

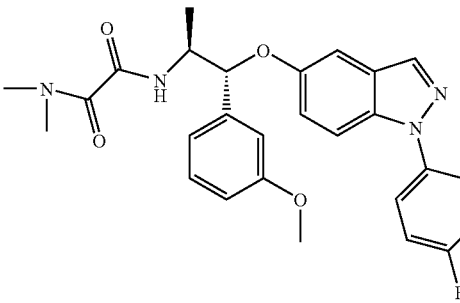

Prepared as described in Example 76 using (1R,2S)-1-[1-(4-fluorophenyl)-indazol-5-yl]oxy-1-(3-methoxyphenyl)-propan-2-amine (51 mg, 0.13 mmol) and 2-(dimethylamino)-2-oxoacetic acid (13 mg, 0.13 mmol). Yield 44 mg (69%).

APCI-MS: m/z 491.4 [MH+] $^1$H-NMR (400 MHz, CD$_3$OD): δ 8.02 (s, 1H), 7.67 (m, 2H), 7.60 (d, J=9.2 Hz, 1H), 7.33-7.21 (m, 4H), 7.10 (d, J=2.1 Hz, 1H), 7.06-7.01 (m, 2H), 6.84 (m, 1H), 5.32 (d, J=5.1 Hz, 1H), 4.43 (m, 1H), 3.77 (s, 3H), 2.90 (s, 3H), 2.78 (s, 3H), 1.32 (d, J=6.9 Hz, 3H).

Example 81

N'-[(1R,2S)-1-[1-(4-Fluorophenyl)indazol-5-yl]oxy-1-(3-methoxyphenyl)propan-2-yl]-N-propan-2-yl-oxamide

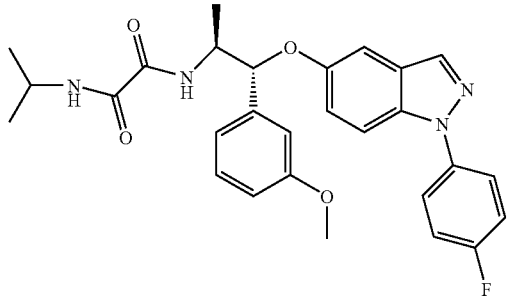

Prepared as described in Example 76 using (1R,2S)-1-[1-(4-fluorophenyl)-indazol-5-yl]oxy-1-(3-methoxyphenyl)-propan-2-amine (53 mg, 0.14 mmol) and 2-(isopropylamino)-2-oxoacetic acid (18 mg, 0.14 mmol). Yield 42 mg (62%).

APCI-MS: m/z 505.4 [MH+] $^1$H-NMR (400 MHz, CD$_3$OD): δ 8.01 (s, 1H), 7.67 (m, 2H), 7.60 (d, J=9.2 Hz, 1H), 7.33-7.22 (m, 4H), 7.08 (d, J=2.1 Hz, 1H), 7.04-6.99 (m, 2H), 6.84 (m, 1H), 5.34 (d, J=5.1 Hz, 1H), 4.35 (m, 1H), 3.97 (m, 1H), 3.77 (s, 3H), 1.31 (d, J=6.9 Hz, 3H), 1.18 (d, J=6.6 Hz, 3H), 1.15 (d, J=6.7 Hz, 3H).

Example 82

N-[(1R,2S)-1-[1-(4-Fluorophenyl)indazol-5-yl]oxy-1-(3-methoxyphenyl)propan-2-yl]-N'-tert-butyl-oxamide

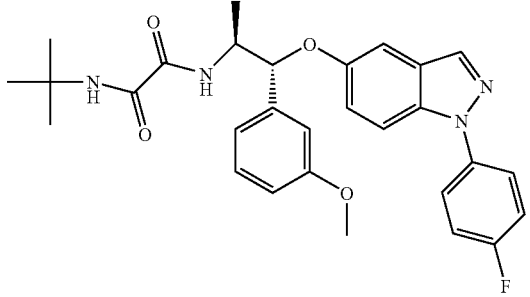

Prepared as described in Example 76 using (1R,2S)-1-[1-(4-fluorophenyl)-indazol-5-yl]oxy-1-(3-methoxyphenyl)-propan-2-amine (51 mg, 0.13 mmol) and 2-(tert-butylamino)-2-oxoacetic acid (19 mg, 0.13 mmol). Yield 53 mg (78%).

APCI-MS: m/z 519.4 [MH+] $^1$H-NMR (400 MHz, CD$_3$OD): δ 8.01 (s, 1H), 7.67 (m, 2H), 7.60 (d, J=9.2 Hz, 1H), 7.33-7.22 (m, 4H), 7.08 (d, J=2.1 Hz, 1H), 7.03-6.98 (m, 2H), 6.84 (m, 1H), 5.33 (d, J=5.0 Hz, 1H), 4.33 (m, 1H), 3.77 (s, 3H), 1.35 s, 9H), 1.31 (d, J=6.9 Hz, 3H).

Example 83

N-((1R,2S)-1-(1-(4-fluorophenyl)-1H-indazol-5-yloxy)-1-(3-methoxyphenyl)propan-2-yl)-4-(trifluoromethyl)benzamide

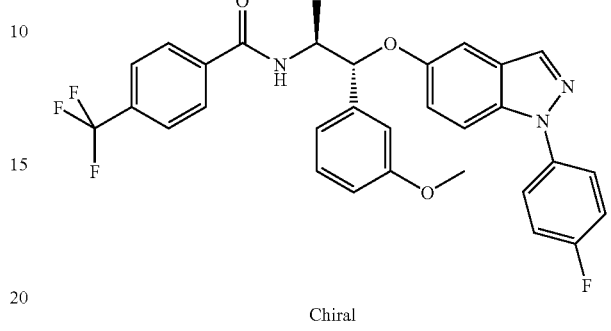

Chiral (1R,2S)-1-(1-(4-fluorophenyl)-1H-indazol-5-yloxy)-1-(3-methoxyphenyl)propan-2-amine (6a, 28 mg, 0.07 mmol) and 4-(trifluoromethyl)benzoic acid (14 mg, 0.07 mmol) were dissolved in DMF (0.265 ml). HBTU (30 mg, 0.08 mmol) and N,N-diisopropyl-ethylamine (0.026 ml, 0.16 mmol) were added and the mixture was stirred over night at r.t. Then it was diluted with acetonitrile and purified by semi-preparative HPLC. Yield 24 mg (59%).

APCI-MS: m/z 564 [MH+]1H NMR (300 MHz, d$_6$-dmso) δ 8.77 (d, J=8.2 Hz, 1H), 8.16 (d, J=0.8 Hz, 1H), 7.98-7.78 (m, 4H), 7.77-7.65 (m, 3H), 7.45-7.34 (m, 2H), 7.30-7.19 (m, 2H), 7.12 (d, J=2.3 Hz, 1H), 7.07-6.97 (m, 2H), 6.84-6.78 (m, 1H), 5.41 (d, J=5.6 Hz, 1H), 4.47-4.34 (m, 1H), 3.70 (s, 3H), 1.33 (d, J=6.8 Hz, 3H).

Example 84

N-((1R,2S)-1-(1-(4-fluorophenyl)-1H-indazol-5-yloxy)-1-(3-methoxyphenyl)propan-2-yl)oxazole-2-carboxamide

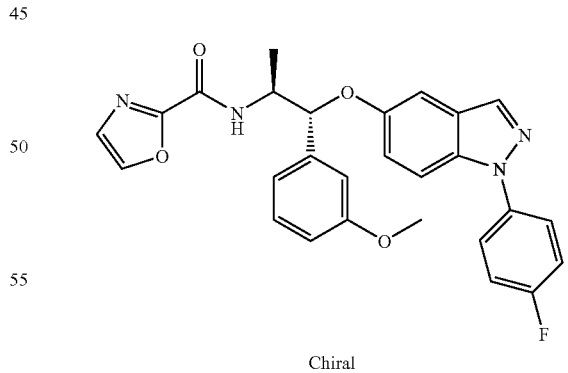

Chiral

Prepared as described in Example 83 using (1R,2S)-1-(1-(4-fluorophenyl)-1H-indazol-5-yloxy)-1-(3-methoxyphenyl)propan-2-amine (6a, 28 mg, 0.07 mmol) and oxazole-2-carboxylic acid (8 mg, 0.07 mmol). Yield 24 mg (69%).

APCI-MS: m/z 487 [MH+]1H NMR (400 MHz, d$_6$-dmso) δ 8.83 (d, J=8.8 Hz, 1H), 8.28 (s, 1H), 8.18 (s, 1H), 7.77-7.66 (m, 3H), 7.44-7.36 (m, 3H), 7.26-7.18 (m, 2H), 7.11 (d, J=2.3

Hz, 1H), 7.04-6.96 (m, 2H), 6.80 (dd, J=8.1, 2.1 Hz, 1H), 5.39 (d, J=6.5 Hz, 1H), 4.43-4.31 (m, 1H), 3.69 (s, 3H), 1.34 (d, J=6.7 Hz, 3H).

Example 85

N-((1R,2S)-1-(1-(4-fluorophenyl)-1H-indazol-5-yloxy)-1-(3-methoxyphenyl)propan-2-yl)oxazole-4-carboxamide

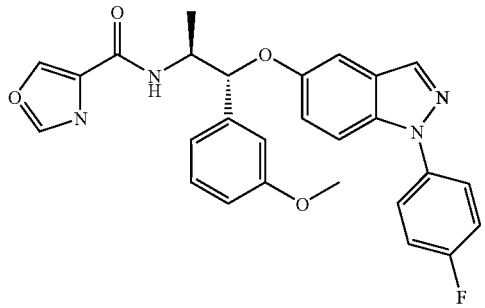

Chiral

Prepared as described in Example 83 using (1R,2S)-1-(1-(4-fluorophenyl)-1H-indazol-5-yloxy)-1-(3-methoxyphenyl)propan-2-amine (6a, 28 mg, 0.07 mmol) and oxazole-4-carboxylic acid (8 mg, 0.07 mmol). Yield 26 mg (75%).

APCI-MS: m/z 487 [MH$^+$]1H NMR (300 MHz, d$_6$-DMSO) δ 8.58 (d, J=1.1 Hz, 1H), 8.50 (d, J=0.9 Hz, 1H), 8.17 (d, J=0.8 Hz, 1H), 8.11 (d, J=9.0 Hz, 1H), 7.78-7.66 (m, 3H), 7.44-7.34 (m, 2H), 7.28-7.18 (m, 2H), 7.12 (d, J=2.1 Hz, 1H), 7.04-6.97 (m, 2H), 6.83-6.77 (m, 1H), 5.45 (d, J=6.1 Hz, 1H), 4.47-4.33 (m, 1H), 3.70 (s, 3H), 1.30 (d, J=6.8 Hz, 3H).

Example 86

N-((1R,2S)-1-(1-(4-fluorophenyl)-1H-indazol-5-yloxy)-1-(3-methoxyphenyl)propan-2-yl)furan-2-carboxamide

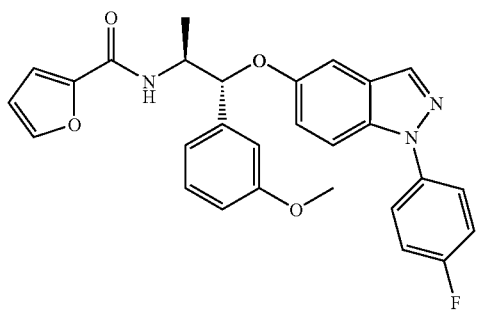

Chiral

Prepared as described in Example 83 using (1R,2S)-1-(1-(4-fluorophenyl)-1H-indazol-5-yloxy)-1-(3-methoxyphenyl)propan-2-amine (6a, 28 mg, 0.07 mmol) and furan-2-carboxylic acid (8 mg, 0.07 mmol). Yield 27 mg (78%).

APCI-MS: m/z 486 [MH$^+$]1H NMR (299.946 MHz, d$_6$-dmso) δ 8.33 (d, J=8.5 Hz, 1H), 8.16 (d, J=0.8 Hz, 1H), 7.82-7.65 (m, 4H), 7.44-7.35 (m, 2H), 7.28-7.18 (m, 2H), 7.12-7.05 (m, 2H), 7.03-6.95 (m, 2H), 6.80 (dd, J=8.2, 1.8 Hz, 1H), 6.58 (dd, J=3.4, 1.7 Hz, 1H), 5.38 (d, J=5.8 Hz, 1H), 4.41-4.28 (m, 1H), 3.70 (s, 3H), 1.30 (d, J=6.9 Hz, 3H).

Example 87

N-((1R,2S)-1-(1-(4-fluorophenyl)-1H-indazol-5-yloxy)-1-(3-methoxyphenyl)propan-2-yl)thiophene-2-carboxamide

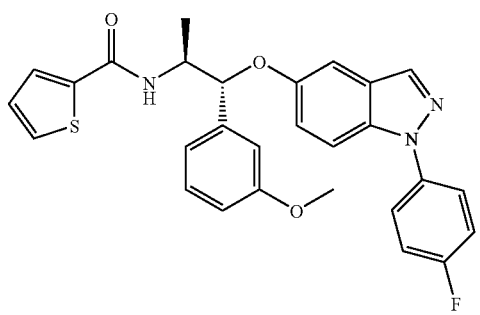

Chiral

Prepared as described in Example 83 using (1R,2S)-1-(1-(4-fluorophenyl)-1H-indazol-5-yloxy)-1-(3-methoxyphenyl)propan-2-amine (6a, 28 mg, 0.07 mmol) and thiophene-2-carboxylic acid (9 mg, 0.07 mmol). Yield 26 mg (72%).

APCI-MS: m/z 502 [MH$^+$]1H NMR (300 MHz, d$_6$-dmso) δ 8.54 (d, J=8.2 Hz, 1H), 8.16 (d, J=0.8 Hz, 1H), 7.80-7.66 (m, 5H), 7.44-7.34 (m, 2H), 7.29-7.20 (m, 2H), 7.14-7.08 (m, 2H), 7.04-6.96 (m, 2H), 6.81 (dd, J=8.2, 1.9 Hz, 1H), 5.40 (d, J=5.3 Hz, 1H), 4.39-4.26 (m, 1H), 3.70 (s, 3H), 1.31 (d, J=6.9 Hz, 3H).

Example 88

N-((1R,2S)-1-(1-(4-fluorophenyl)-1H-indazol-5-yloxy)-1-(3-methoxyphenyl)propan-2-yl)pyrimidine-4-carboxamide

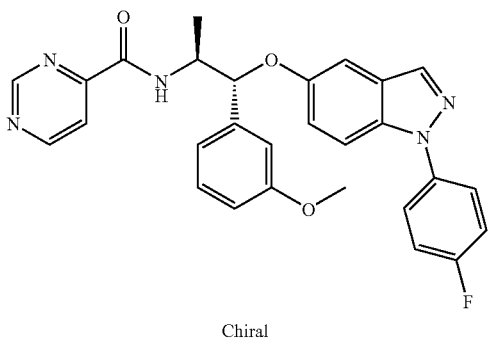

Chiral

Prepared as described in Example 83 using (1R,2S)-1-(1-(4-fluorophenyl)-1H-indazol-5-yloxy)-1-(3-methoxyphenyl)propan-2-amine (6a, 28 mg, 0.07 mmol) and pyrimidine-4-carboxylic acid (9 mg, 0.07 mmol). Yield 12 mg (34%).

APCI-MS: m/z 498 [MH$^+$]1H NMR (300 MHz, d$_6$-dmso) δ 9.32 (d, J=1.3 Hz, 1H), 9.04 (d, J=5.0 Hz, 1H), 8.88 (d, J=9.0 Hz, 1H), 8.17 (d, J=0.8 Hz, 1H), 7.94 (dd, J=5.0, 1.3 Hz, 1H), 7.78-7.65 (m, 3H), 7.45-7.34 (m, 2H), 7.26-7.19 (m, 2H), 7.14 (d, J=2.3 Hz, 1H), 7.04-6.98 (m, 2H), 6.83-6.76 (m, 1H), 5.51 (d, J=6.0 Hz, 1H), 4.53-4.39 (m, 1H), 3.68 (s, 3H), 1.34 (d, J=6.6 Hz, 3H).

Example 89

N-((1R,2S)-1-(1-(4-fluorophenyl)-1H-indazol-5-yloxy)-1-(3-methoxyphenyl)propan-2-yl)picolinamide

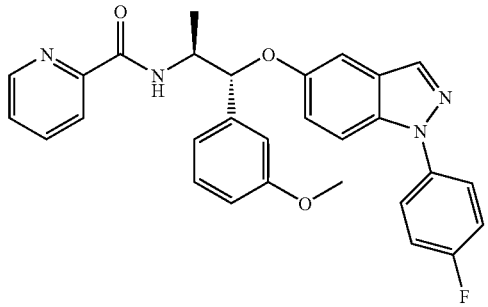

Chiral

Prepared as described in Example 83 using (1R,2S)-1-(1-(4-fluorophenyl)-1H-indazol-5-yloxy)-1-(3-methoxyphenyl)propan-2-amine (6a, 28 mg, 0.07 mmol) and picolinic acid (9 mg, 0.07 mmol). Yield 14 mg (39%).

APCI-MS: m/z 497 [MH$^+$]1H NMR (300 MHz, d$_6$-dmso) δ 8.69-8.59 (m, 2H), 8.16 (d, J=0.9 Hz, 1H), 8.01-7.96 (m, 2H), 7.77-7.65 (m, 3H), 7.63-7.55 (m, 1H), 7.44-7.34 (m, 2H), 7.28-7.20 (m, 2H), 7.15 (d, J=2.1 Hz, 1H), 7.05-6.99 (m, 2H), 6.83-6.77 (m, 1H), 5.54 (d, J=5.4 Hz, 1H), 4.53-4.40 (m, 1H), 3.68 (s, 3H), 1.31 (d, J=6.8 Hz, 3N).

Example 90

N-((1R,2S)-1-(1-(4-fluorophenyl)-1H-indazol-5-yloxy)-1-(4-methoxyphenyl)propan-2-yl)pivalamide

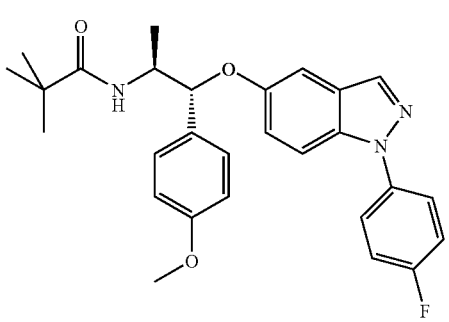

Chiral

Prepared as described in Example 83 using (1R,2S)-1-(1-(4-fluorophenyl)-1H-indazol-5-yloxy)-1-(4-methoxyphenyl)propan-2-amine (90a, 20 mg, 0.05 mmol) and Pivaloyl chloride (19 μl, 0.15 mmol). Yield 13 mg (55%).

APCI-MS: m/z 476 [MH$^+$]1H NMR (300 MHz, d$_6$-dmso) δ 8.17 (d, J=0.8 Hz, 1H), 7.79-7.64 (m, 3H), 7.44-7.26 (m, 5H), 7.17 (dd, J=9.2, 2.4 Hz, 1H), 7.09 (d, J=2.3 Hz, 1H), 6.91-6.85 (m, 2H), 5.23 (d, J=6.5 Hz, 1H), 4.23-4.09 (m, 1H), 3.70 (s, 3H), 1.22 (d, J=6.8 Hz, 3H), 0.94 (s, 9H).

(1R,2S)-1-(1-(4-fluorophenyl)-1H-indazol-5-yloxy)-1-(4-methoxyphenyl)propan-2-amine (90a)

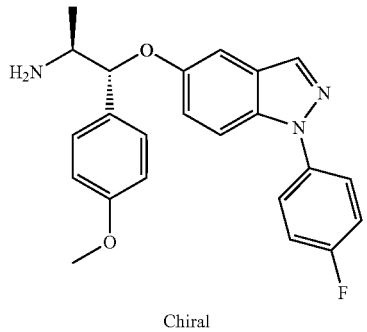

Chiral

Prepared as described in Example 6 using (1R,2S)-2-amino-1-(4-methoxy-phenyl)propan-1-ol hydrochloride (87 mg, 0.40 mmol). Yield 43 mg (28%).

APCI-MS: m/z 392 [MH$^+$]

(1R,2S)-2-amino-1-(4-methoxy-phenyl)propan-1-ol hydrochloride (90b)

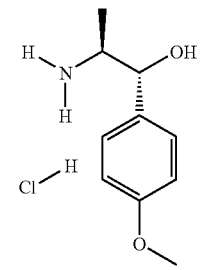

Prepared as described in Example 6 using tert-butyl (1R,2S)-1-hydroxy-1-(4-methoxyphenyl)propan-2-ylcarbamate (130 mg, 0.46 mmol). Yield 87 mg (86%).

APCI-MS: m/z 182 [MH$^+$]

tert-butyl (1R,2S)-1-hydroxy-1-(4-methoxyphenyl)propan-2-ylcarbamate (90c)

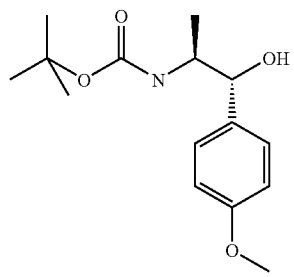

Prepared as described in Example 6 using (S)-tert-butyl 1-(4-methoxyphenyl)-1-oxopropan-2-ylcarbamate (0.45 g, 1.61 mmol). Yield 389 mg (86%).

1H NMR (300 MHz, d$_6$-dmso) δ 7.24-7.18 (m, 2H), 6.88-6.82 (m, 2H), 6.51 (d, J=8.8 Hz, 1H), 5.17 (d, J=4.6 Hz, 1H), 4.47-4.40 (m, 1H), 3.72 (s, 3H), 3.58-3.46 (m, 1H), 1.30 (s, 9H), 0.93 (d, J=6.8 Hz, 3H).

(S)-tert-butyl 1-(4-methoxyphenyl)-1-oxopropan-2-ylcarbamate (90d)

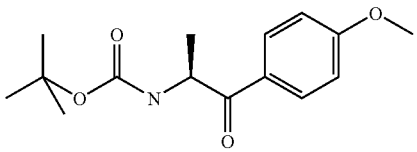

Prepared as described in Example 6 using tert-butyl{(1S)-2-[methoxy(methyl)amino]-1-methyl-2-oxoethyl}carbamate (0.462 g, 2.0 mmol) and 4-methoxymethylmagnesium-bromide (0.5M in THF, 12 ml, 6.0 mmol). Yield 0.45 g (80%).

1H NMR (300 MHz, $d_6$-dmso) δ 7.99-7.92 (m, 2H), 7.23 (d, J=7.6 Hz, 1H), 7.07-7.01 (m, 2H), 5.07-4.96 (m, 1H), 3.84 (s, 3H), 1.36 (s, 9H), 1.21 (d, J=7.2 Hz, 3H).

Example 91

N-((1R,2S)-1-(1-(4-fluorophenyl)-1H-indazol-5-yloxy)-1-phenylpentan-2-yl)-2-hydroxyacetamide

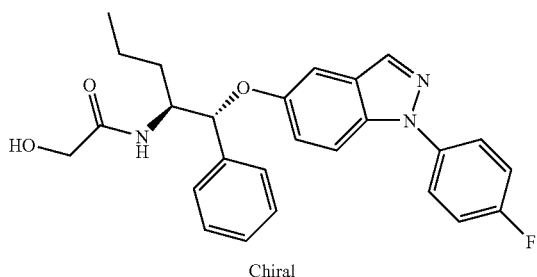

To a stirred solution of (1R,2S)-1-(1-(4-fluorophenyl)-1H-indazol-5-yloxy)-1-phenylpentan-2-amine (91a, 13 mg, 0.03 mmol) in dry THF (1 ml) were added, at r.t., triethylamine (28 µl, 0.2 mmol) and 2-chloro-2-oxoethyl acetate (10.8 µl, 0.1 mmol). The reaction was stirred over night. The solvent was removed under reduced pressure. To the crude solid was added Methanol (300 µl) and ammonium hydroxide (100 µl, 28%). The solution was stirred over night.

The product was purified by preparative HPLC.

Yield. 14 mg (94%) APCI-MS: m/z 448 [MH$^+$]$^1$H NMR (399.99 MHz, dmso) δ 8.15 (s, 1H), 7.77-7.71 (m, 2H), 7.67 (d, J=26.2 Hz, 1H), 7.48 (d, J=26.2 Hz, 1H), 7.43-7.36 (m, 4H), 7.33 (t, J=13.1 Hz, 2H), 7.29-7.16 (m, 2H), 7.16-7.03 (m, 1H), 5.38 (d, J=51.8 Hz, 1H), 4.19 (m, 1H), 3.76 (d, J=15.7 Hz, 1H), 3.68 (d, J=15.7 Hz, 1H), 1.63 (m, 2H), 1.38 (m, 1H), 1.16 (m, 1H), 0.82 (t, J=7.3 Hz, 3H)

(1R,2S)-(1-(4-fluorophenyl)-1H-indazol-5-yloxy)-1-phenylpentan-2-amine (91a)

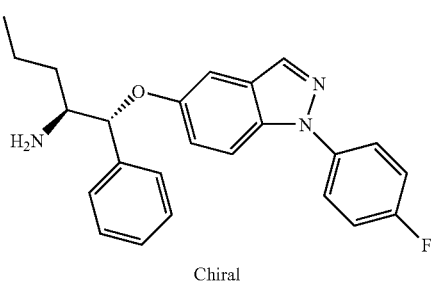

In a vial under argon (1R,2S)-2-amino-1-phenylpentan-1-ol hydrochloride (91b, 46 mg, 0.21 mmol), 1-(4-fluorophenyl)-5-iodo-1H-indazole (87 mg, 0.26 mmol), copper(I)iodide (8.12 mg, 0.04 mmol) and cesium carbonate (278 mg, 0.85 mmol) were mixed in butyronitrile (0.6 mL). The vial was sealed and heated to 125° C. for 16 h. The mixture was filtered through celite. The celite was washed with ethyl acetate. The collected organic phases were evaporated and the crude product was purified by preparative HPLC. The pure fractions were collected, ethyl acetate and a saturated sodium carbonate were added and the mixture was shaken. The organic layer was separated and the water layer was washed twice with ethyl acetate. The combined organic layers were dried over sodium sulphate and finally evaporated to give the pure product.

Yield: 30 mg, 36% APCI-MS: m/z 390 [MH$^+$]$^1$H NMR (400 MHz, DMSO-$d_6$) δ 8.14 (s, 1H), 7.76 (m, 2H), 7.66 (d, J=9.2 Hz, 2H), 7.45-7.29 (m, 5H), 7.28-7.17 (m, 2H), 7.14 (d, J=2.1 Hz, 1H), 5.14 (d, J=5.5 Hz, 1H), 3.03 (m, 1H), 1.61 (m, 2H), 1.44-1.14 (m, 4H), 0.85 (t, J=6.9 Hz, 3H)

(1R,2S)-2-amino-1-phenylpentan-1-ol hydrochloride (91b)

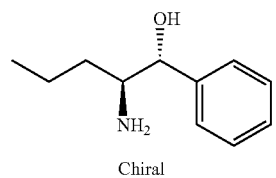

(S)-tert-butyl 1-oxo-1-phenylpentan-2-ylcarbamate (91c, 190 mg, 0.69 mmol) was dissolved in toluene under argon. Triisopropoxyaluminum (28.0 mg, 0.14 mmol) was added followed by 2-propanol (0.573 ml, 7.54 mmol). The reaction was stirred at 50° C. over night. The solution was evaporated. Ethyl acetate was added, the suspension was stirred and finally filtered through celite. The eluent was evaporated and the crude product was purified by Flash chromatography.

The pure tert-butyl (1R,2S)-1-hydroxy-1-phenylpentan-2-ylcarbamate was dissolved in ethyl acetate (1.2 ml). Water (50 µl) and hydrochloric acid in ethyl acetate (1.0 ml, 1.5 M) were added. The solution was stirred at 50° C. for 90 min. A precipitation was formed. The volume was reduced to ⅔ by heavy stirring and a stream of argon gas. The stirring was continued for 1 h at r.t. The suspension was filtered and the solid was dried at 50° C. under reduced pressure for 2 h.

Yield 59 mg, 39% APCI-MS: m/z 180 [MH$^+$]$^1$H NMR (400 MHz, DMSO-$d_6$) δ 8.04 (s, 3H), 7.43-7.23 (m, 5H), 6.03 (d, J=4.1 Hz, 1H), 4.99 (t, J=3.4 Hz, 1H), 3.25 (m, 1H), 1.31 (m, 3H), 1.03 (m, 1H), 0.72 (t, J=7.1 Hz, 3H)

(S)-tert-butyl 1-oxo-1-phenylpentan-2-ylcarbamate (91c)

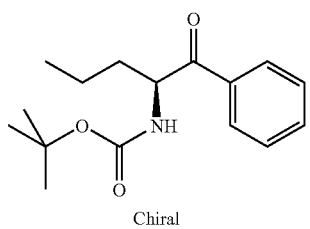

In a 50 mL round-bottomed flask was (S)-tert-butyl 1-(methoxy(methyl)amino)-1-oxopentan-2-ylcarbamate (91d, 250 mg, 0.96 mmol) dissolved in THF (9.6 ml). Phenylmagnesium bromide (2.88 ml, 2.88 mmol) 1.0 M in THF was added. The reaction was stirred at r.t. for 5 h. The reaction was poured into a mixture of saturated ammonium chloride and ethyl acetate. The mixture was shaken and the layers separated. The water layer was washed twice with ethyl acetate. The combined organic layers were washed once with a small portion of water and dried over sodium sulphate. The solvent was evaporated and the crude product was purified by flash chromatography.

Yield: 190 mg, 71% APCI-MS: m/z 178 [MH$^+$–BOC]$^1$H NMR (400 MHz, DMSO-d$_6$) δ 7.95 (m, 2H), 7.65 (t, J=21.4 Hz, 1H), 7.53 (t, J=7.6 Hz, 2H), 7.28 (d, J=7.8 Hz, 1H), 4.95 (m, 1H), 1.61 (m, 1H), 1.50 (m, 1H), 1.36 (m, 1H), 0.86 (t, J=7.3 Hz, 3H)

(S)-tert-butyl 1-(methoxy(methyl)amino)-1-oxopentan-2-ylcarbamate (91d)

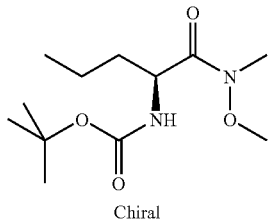

Chiral

Commercially available (2S)-2-[(tert-butoxycarbonyl)amino]pentanoic acid (1.0 g, 4.6 mmol) and N,O-dimethylhydroxylamine hydrochloride (0.47 g, 4.8 mmol) were dissolved in DMF (18 ml). O-benzotriazole-1-yl-N,N,N',N'-tetramethyl-uronium hexafluorophosphate (1.92 g, 5.06 mmol) and N,N-diisopropylethylamine (2.47 ml, 14.5 mmol) were added. The reaction was stirred at r.t. over night. The reaction was poured into a mixture of water and ethyl acetate. The mixture was shaken, the layers separated and the water layer washed twice with ethyl acetate. The collected organic phase was washed with a small portion of water and dried over sodium sulphate. The solvent was removed under educed pressure and the crude product was purified by flash chromatography.

Yield. 1.02 g, 85% APCI-MS: m/z 261 [MH$^+$]$^1$H NMR (400 MHz, DMSO-d$_6$) δ 6.96 (d, J=8.3 Hz, 1H), 4.37 (m, 1H), 3.72 (s, 3H), 3.09 (s, 3M), 1.36 (m, 13H), 0.85 (t, J=7.3 Hz, 3H)

Example 92

N-((1R,2S)-1-(1-(4-fluorophenyl)-1H-indazol-5-yloxy)-1-phenylpentan-2-yl)pivalamide

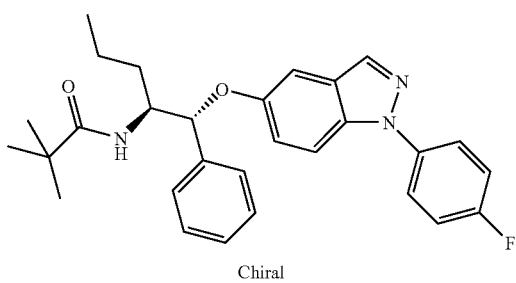

Chiral

To a stirred solution of (1R,2S)-1-(1-(4-fluorophenyl)-1H-indazol-5-yloxy)-1-phenylpentan-2-amine (91a, 13 mg, 0.03 mmol) dissolved in dry THF (150 μmol) were added, at r.t., triethylamine (27.8 μl, 0.20 mmol) and pivaloyl chloride (12.3 ul, 0.1 mmo). The reaction was stirred over night. The solvent was removed under reduced pressure, and the product purified by preparative HPLC.

Yield. 13 mg, 0.027 mmol, 91% APCI-MS: m/z 474 [MH$^+$] $^1$H NMR (400 MHz, DMSO-d$_6$) δ 8.16 (s, 1H), 7.73 (m, 2H), 7.66 (d, J=37.5 Hz, 1H), 7.42-7.36 (m, 4H), 7.31 (t, J=7.5 Hz, 2H), 7.25-7.16 (m, 3H), 7.11-7.07 (m, 1H), 5.25 (d, J=33.3 Hz, 1H), 4.16 (m, 1H), 1.70 (m, 2H), 1.36 (m, 1H), 1.18 (m, 1H), 1.02 (s, 9H), 0.84 (t, J=7.3 Hz, 3H)

Example 93

N-((1R,2S)-1-(1-(4-fluorophenyl)-1H-indazol-5-yloxy)-1-(3-methoxyphenyl)pentan-2-yl)-2-hydroxyacetamide

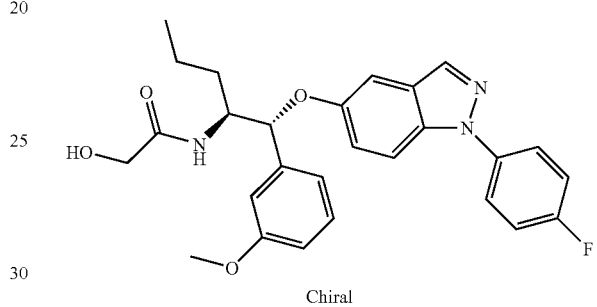

Chiral was synthesised in the same way as example 131 from (1R,2S)-1-(1-(4-fluorophenyl)-1H-indazol-5-yloxy)-1-(3-methoxyphenyl)pentan-2-amine (93a, 11 mg, 0.03 mmol).

The product was purified by preparative HPLC.

Yield. 12 mg, 92% APCI-MS: m/z 478 [MH$^+$]$^1$H NMR (400 MHz, DMSO-d$_6$) δ 8.17 (s, 1H), 7.74 (m, 2H), 7.68 (d, J=9.2 Hz, 1H), 7.48 (d, J=9.6 Hz, 1H), 7.39 (m, 2H), 7.28-7.18 (m, 2H), 7.12-7.07 (m, 1H), 6.99-6.93 (m, 2H), 5.35 (d, J=5.5 Hz, 1H), 4.20 (m, 1H), 3.77 (d, J=15.7 Hz, 1H), 3.72 (s, 3H), 3.70 (d, J=16.6 Hz, 1H), 1.64 (m, 2H), 1.40 (m, 1H), 1.13 (m, 1H), 0.83 (t, J=7.3 Hz, 3H)

(1R,2S)-1-(1-(4-fluorophenyl)-1H-indazol-5-yloxy)-1-(3-methoxyphenyl)pentan-2-amine (93a)

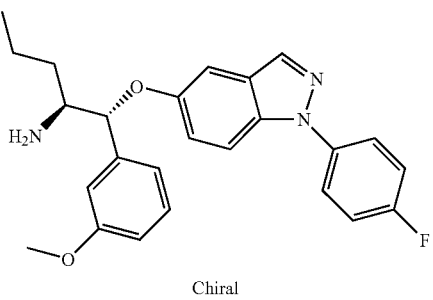

Chiral was synthesised in the same way as (91a) from (1R,2S)-2-amino-1-(3-methoxyphenyl)pentan-1-ol hydrochloride (93b, 50 mg, 0.20 mmol).

The product was purified by preparative HPLC.

Yield. 26 mg, 31% APCI-MS: m/z 420 [MH$^+$]$^1$H NMR (400 MHz, DMSO-d$_6$) δ 8.15 (d, J=0.7 Hz, 1H), 7.74 (m, 2H), 7.66 (d, J=9.2 Hz, 2H), 7.39 (t, J=8.8 Hz, 2H), 7.25 (m, 2H), 7.15 (d, J=2.1 Hz, 1H), 7.00 (m, 2H), 6.82 (m, 1H), 5.10 (d, J=5.3 Hz, 1H), 3.72 (s, 3H), 3.02 (m, 1H), 1.62-1.13 (m, 6H), 0.86 (t, J=7.0 Hz, 3H)

(1R,2S)-2-amino-1-(3-methoxyphenyl)pentan-1-ol hydrochloride (93b)

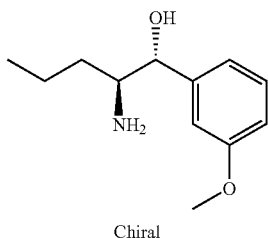

Chiral was synthesised in the same way as 91b from (S)-tert-butyl 1-(3-methoxyphenyl)-1-oxopentan-2-ylcarbamate (213 mg, 0.693 mmol).

Yield. 102 mg, 59% APCI-MS: m/z 210 [MH+] $^1$H NMR (400 MHz, DMSO-d$_6$) δ 7.98 (s, 3H), 7.29 (t, J=7.9 Hz, 3H), 6.94 (m, 6H), 6.85 (m, 2H), 6.03 (d, J=4.1 Hz, 1H), 4.93 (s, 1H), 3.76 (s, 3H), 3.28 (m, 1H), 1.44-1.20 (m, 3H), 1.19-1.05 (m, 1H), 0.74 (t, J=7.0 Hz, 3H)

(S)-tert-butyl 1-(3-methoxyphenyl)-1-oxopentan-2-ylcarbamate (93c)

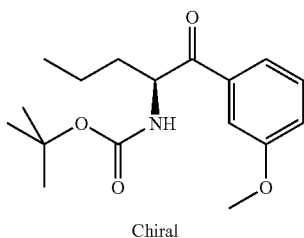

Chiral was synthesised in the same way as (91c) from (S)-tert-butyl 1-(methoxy(methyl)amino)-1-oxopentan-2-ylcarbamate (91d, 250 mg, 0.96 mmol).

Yield. 213 mg, 72% APCI-MS: m/z 208 [MH+–BOC] $^1$H NMR (400 MHz, DMSO-d$_6$) δ 7.55 (d, J=7.6 Hz, 1H), 7.44 (m, 2H), 7.27 (d, J=8.0 Hz, 1H), 7.21 (m, 1H), 4.93 (m, 1H), 3.81 (s, 3H), 1.61 (m, 1H), 1.49 (m, 1H), 1.35 (m, 1H), 0.86 (t, J=7.3 Hz, 3H)

Example 94

N-((1R,2S)-1-(1-(4-fluorophenyl)-1H-indazol-5-yloxy)-1-(3-methoxyphenyl)pentan-2-yl)pivalamide

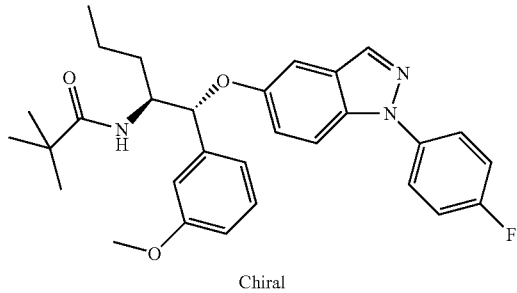

Chiral was synthesised in the same way as example 92 from (1R,2S)-1-(1-(4-fluorophenyl)-1H-indazol-5-yloxy)-1-(3-methoxyphenyl)pentan-2-amine (93a, 11 mg, 0.03 mmol)

The product was purified by preparative HPLC.

Yield. 13 mg, 98% APCI-MS: m/z 504 [MH+] $^1$H NMR (400 MHz, DMSO-d$_6$) δ 8.18 (s, 1H), 7.74 (m, 2H), 7.68 (d, J=9.0 Hz, 1H), 7.39 (t, J=8.8 Hz, 2H), 7.25-7.16 (m, 3H), 7.10 (m, 1H), 6.99-6.92 (m, 2H), 5.21 (d, J=6.9 Hz, 1H), 4.14 (m, 1H), 3.72 (s, 3H), 1.69 (m, 2H), 1.34 (m, 1H), 1.19 (m, 1H), 0.94 (s, 9H), 0.85 (t, J=7.3 Hz, 3H)

Example 95

N-((1R,2S)-1-(1-(4-fluorophenyl)-1H-indazol-5-yloxy)-1-phenylbutan-2-yl)-2-hydroxyacetamide

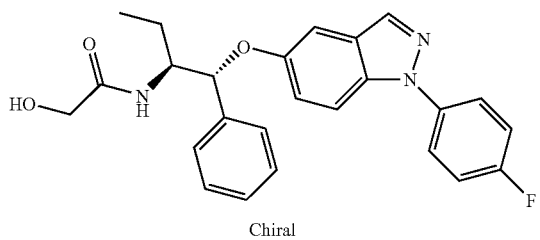

Chiral was synthesised in the same way as example 131 from (1R,2S)-1-(1-(4-fluorophenyl)-1H-indazol-5-yloxy)-1-phenylbutan-2-amine (95a, 10 mg, 0.03 mmol). The product was purified by preparative HPLC.

Yield. 12 mg, 100% APCI-MS: m/z 434 [MH+] $^1$H NMR (400 MHz, DMSO-d$_6$) δ 8.15 (s, 1H), 7.73 (m, 2H), 7.68 (d, J=9.0 Hz, 1H), 7.48 (d, J=31.2 Hz, 1H), 7.43-7.36 (m, 4H), 7.33 (t, J=7.5 Hz, 2H), 7.27-7.17 (m, 2H), 7.11-7.07 (m, 1H), 5.38 (d, J=5.7 Hz, 1H), 4.13 (m, 1H), 3.77 (d, J=15.7 Hz, 1H), 3.69 (d, J=15.7 Hz, 1H), 1.73 (m, 1H), 1.58 (m, 1H), 0.83 (t, J=7.3 Hz, 3H).

(1R,2S)-1-(1-(4-fluorophenyl)-1H-indazol-5-yloxy)-1-phenylbutan-2-amine (95a)

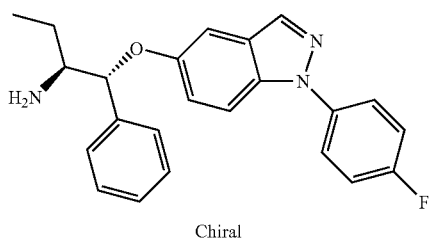

Chiral was synthesised in the same way as (91a) from (1R,2S)-2-amino-1-phenylbutan-1-ol hydrochloride (95b, 53 mg, 0.26 mmol).

The product was purified by preparative HPLC.

Yield. 23 mg, 24% APCI-MS: m/z 376 [MH+] $^1$H NMR (400 MHz, DMSO-d) δ 8.14 (s, 1H), 7.75 (m, 2H), 7.66 (d, J=9.2 Hz, 1H), 7.46-7.30 (m, 6H), 7.25 (m, 1H), 7.19 (m, 1>, 7.14 (d, J=2.1 Hz, 1H), 5.14 (d, J=5.5 Hz, 1H), 2.95 (m, 1H), 1.67 (m, 1H), 1.29 (m, 3H), 0.95 (t, J=7.3 Hz, 3H)

(1R,2S)-2-amino-1-phenylbutan-1-ol (95b)

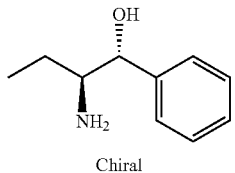

was synthesised in the same way as 90b from (S)-tert-butyl 1-oxo-1-phenylbutan-2-ylcarbamate (95c, 209 mg, 0.795 mmol).

Yield. 60 mg, 38% APCI-MS: m/z 166 [MH$^+$]$^1$H NMR (400 MHz, DMSO-d$_6$) δ 8.01 (s, 3H), 7.33 (m, 5H), 6.03 (d, J=4.2 Hz, 1H), 4.97 (t, J=3.6 Hz, 1H), 3.20 (quintet, J=4.0 Hz, 1H), 1.51-1.27 (m, 2H), 0.79 (t, J=7.5 Hz, 3H).

(S)-tert-butyl 1-oxo-1-phenylbutan-2-ylcarbamate (95c)

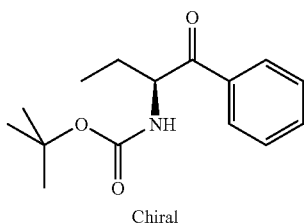

was synthesised in the same way as (91c) from (S)-tert-butyl 1-(methoxy(methyl)amino)-1-oxobutan-2-ylcarbamate (95d, 250 mg, 1.02 mmol).

Yield. 209 mg, 78% APCI-MS: m/z 164 [MH$^+$–BOC]$^1$H NMR (400 MHz, DMSO-d$_6$) δ 7.96 (d, J=7.3 Hz, 2H), 7.64 (t, J=7.3 Hz, 1H), 7.53 (t, J=7.7 Hz, 2H), 7.26 (d, J=7.8 Hz, 1H), 4.89 (m, 1H), 1.72 (m, 1H), 1.53 (m, 1H), 1.37 (s, 8H), 0.90 (t, J=7.3 Hz, 3H).

(S)-tert-Butyl 1-(methoxy(methyl)amino)-1-oxobutan-2-ylcarbamate (95d)

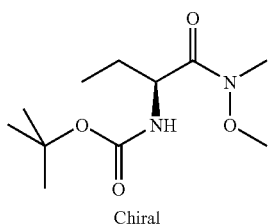

was synthesised in the same way as (91d) from commercially available (2S)-2-[(tert-butoxycarbonyl)amino]butanoic acid (0.935 g, 4.60 mmol).

Yield. 0.987 g, 87% APCI-MS: m/z 191[MH$^+$–56]$^1$H NMR (400 MHz, DMSO-d$_6$) δ 6.96 (d, J=8.0 Hz, 1H), 4.29 (m, 1H), 3.72 (s, 3H), 3.10 (s, 3H), 1.53 (m, 2H), 1.37 (s, 9H), 0.86 (t, J=7.3 Hz, 3H)

Example 96

N-((1R,2S)-1-(1-(4-fluorophenyl)-1H-indazol-5-yloxy)-1-phenylbutan-2-yl)pivalamide

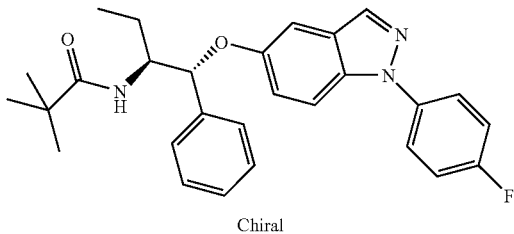

Was synthesised in the same way as example 132 from (1R,2S)-1-(1-(4-fluorophenyl)-1H-indazol-5-yloxy)-1-phenylbutan-2-amine (96a, 10 mg, 0.03 mmol). The product was purified by preparative HPLC.

Yield. 11 mg, 90% APCI-MS: m/z 460 [MH$^+$]$^1$H NMR (399.99 MHz, dmso) δ 8.16 (s, 1H), 7.76-7.70 (m, 2H), 7.67 (d, J=9.2 Hz, 1H), 7.43-7.36 (m, 4H), 7.31 (t, J=7.4 Hz, 2H), 7.25-7.16 (m, 3H), 7.09 (m, 1H), 5.24 (d, J=7.3 Hz, 1H), 4.07 (m, 1H), 1.82 (m, 1H), 1.67 (m, 1H), 0.93 (s, 9H), 0.83 (t, J=7.4 Hz, 3H)

Example 97

N-((1R,2S)-1-(1-(4-fluorophenyl)-1H-indazol-5-yloxy)-1-(3-methoxyphenyl)butan-2-yl)-2-hydroxy-acetamide

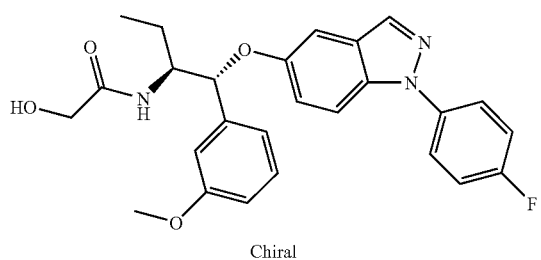

was synthesised in the same way as example 131 from (1R,2S)-1-(1-(4-fluorophenyl)-1H-indazol-5-yloxy)-1-(3-methoxyphenyl)butan-2-amine (97a, 13 mg, 0.03 mmol)

The product was purified by preparative HPLC.

Yield. 11 mg, 74% APCI-MS: m/z 464 [MH$^+$]$^1$H NMR (400 MHz, DMSO-d$_6$) δ 8.17 (s, 1H), 7.82 (m, 2H), 7.68 (d, J=9.2 Hz, 1H), 7.48 (d, J=9.4 Hz, 1H), 7.39 (m, 2H), 7.29-7.17 (m, 2H), 7.10 (m, 1H), 6.98 (m, 2H), 6.82 (m, 1H), 5.36 (d, J=5.7 Hz, 1H), 4.12 (m, 1H), 3.78 (d, J=15.7 Hz, 1H), 3.72 (s, 3H), 3.71 (d, J=14.0 Hz, 1H), 1.72 (m, 1H), 1.59 (m, 1H), 0.84 (t, J=7.3 Hz, 3H)

117

(1R,2S)-1-(1-(4-fluorophenyl)-1H-indazol-5-yloxy)-1-(3-methoxyphenyl)butan-2-amine (97a)

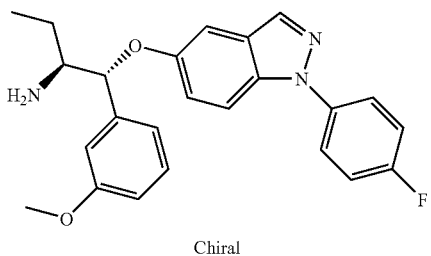

Chiral was synthesised in the same way as (91a) from (1R,2S)-2-amino-1-(3-methoxyphenyl)butan-1-ol hydrochloride (97b, 50 mg, 0.22 mmol).

The product was purified by preparative HPLC. Yield. 30 mg, 34%

APCI-MS: m/z 406 [MH$^+$]$^1$H NMR (400 MHz, DMSO-d$_6$) δ 8.15 (s, 1H), 7.73 (m, 2H), 7.66 (d, J=9.0 Hz, 2H), 7.39 (t, J=8.8 Hz, 2H), 7.29-7.17 (m, 4H), 7.15 (d, J=2.1 Hz, 2H), 6.97 (m, 2H), 6.82 (m, 1H), 5.10 (d, J=5.7 Hz, 1H), 3.72 (s, 4H), 2.93 (m, 1H), 1.63 (m, 1H), 1.24 (m, 1H), 0.95 (t, J=7.4 Hz, 3H).

(1R,2S)-2-amino-1-(3-methoxyphenyl)butan-1-ol (97b)

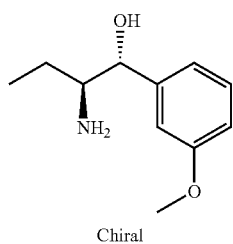

Chiral was synthesised in the same way as 90b from (S)-tert-butyl 1-oxo-1-phenylbutan-2-ylcarbamate (97c, 225 mg, 0.768 mmol).

Yield. 115 mg, 65% APCI-MS: m/z 196 [MH$^+$]$^1$H NMR (400 MHz, DMSO-d$_6$) δ 7.99 (s, 3H), 7.28 (t, J=7.8 Hz, 1H), 6.95 (m, 2H), 6.85 (m, 1H), 6.03 (d, J=4.1 Hz, 1H), 4.93 (t, J=3.5 Hz, 1H), 3.76 (s, 3H), 3.21 (m, 1H), 1.38 (m, 2H), 0.81 (t, J=7.5 Hz, 3H).

(S)-tert-butyl 1-(3-methoxyphenyl)-1-oxobutan-2-ylcarbamate (97c)

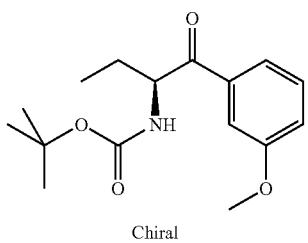

Chiral was synthesised in the same way as 91c from (S)-tert-butyl 1-(methoxy(methyl)amino)-1-oxobutan-2-ylcarbamate (95d, 250 mg, 1.02 mmol).

118

Yield. 225 mg, 75% APCI-MS: m/z 194 [MH$^+$–BOC]$^1$H NMR (400 MHz, DMSO-d$_6$) δ 7.56 (d, J=7.8 Hz, 1H), 7.45 (m, 2H), 7.23 (m, 2H), 4.88 (m, 1H), 3.81 (s, 3H), 1.71 (m, 1H), 1.52 (m, 1H), 1.36 (s, 9H), 0.89 (t, J=7.3 Hz, 3H).

Example 98

N-((1R,2S)-1-(1-(4-fluorophenyl)-1H-indazol-5-yloxy)-1-(3-methoxyphenyl)butan-2-yl)pivalamide

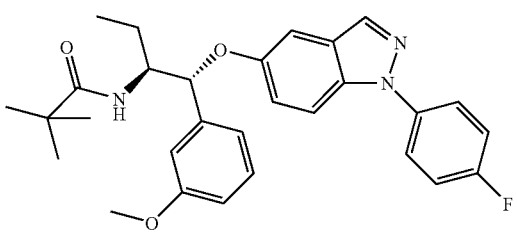

Chiral was synthesised in the same way as example 92 from (1R,2S)-1-(1-(4-fluorophenyl)-1H-indazol-5-yloxy)-1-(3-methoxyphenyl)butan-2-amine (97a, 13 mg, 0.03 mmol). The product was purified by preparative HPLC. Yield. 12 mg, 76%.

APCI-MS: m/z 490 [MH$^+$]$^1$H NMR (400 MHz, DMSO-d$_6$) δ 8.18 (s, 1H), 7.74 (m, 2H), 7.68 (d, J=9.2 Hz, 1H), 7.39 (m, 2H), 7.20 (m, 3H), 7.09 (m, 1H), 6.97 (m, 2H), 6.79 (m, 1H), 5.21 (d, J=7.1 Hz, 1H), 4.05 (m, 1H), 3.72 (s, 3H), 1.79 (m, 1H), 1.66 (m, 1H), 0.95 (s, 9H), 0.83 (t, J=7.3 Hz, 3H)

Example 99

N-[(1RS,2SR)-1-[6-chloro-1-(4-fluorophenyl)indazol-5-yl]oxy-1-(4-fluorophenyl)propan-2-yl]-2,2,2-trifluoro-acetamide

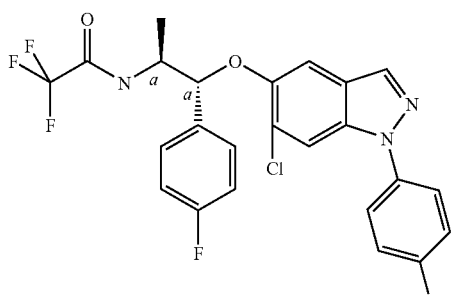

Chiral a = relative mixture (1RS,2SR)-1-[6-chloro-1-(4-fluorophenyl)indazol-5-yl]oxy-1-(4-fluorophenyl)propan-2-amine (99a-rac-2, 10 mg, 0.02 mmol) and TEA (100 μl) in MeCN (1 ml) were mixed and trifluoroacetic anhydride (10 μl, 0.07 mol) was added. The mixture was stirred at r.t. over night. The title compound (10 mg, 82%) was obtained by preparative HPLC (water/MeCN/1% TFA).

$^1$H NMR (400 MHz, CD$_3$OD) δ 9.29 (d, J=8.3 Hz, 1H), 8.02 (s, 1H), 7.78 (s, 1H), 7.67 (dd, J=8.9, 4.7 Hz, 2H), 7.47 (dd, J=8.7, 5.3 Hz, 2H), 7.31 (t, J=8.7 Hz, 2H), 7.16 (s, 1H), 7.09 (t, J=8.8 Hz, 2H), 5.44 (d, J=6.0 Hz, 1H), 4.47-4.39 (m, 1H), 1.44 (d, J=6.7 Hz, 3H). APCI-MS: 510 m/z [MH$^+$].

1-[6-chloro-1-(4-fluorophenyl)indazol-5-yl]oxy-1-(4-fluorophenyl)propan-2-amine (99a)

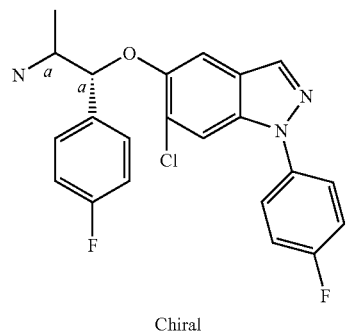

Chiral
a = relative mixture

1-{[6-Chloro-1-(4-fluorophenyl)-1H-indazol-5-yl]oxy}-1-(4-fluorophenyl)acetone (500 mg, 1.21 mmol), ammonium acetate (934 mg, 12.11) and cyanoborohydride on polymer support (1.82 g, 3.63 mmol) were mixed in methanol (3 ml) and heated in micro at 140° C. for 10 min. The mixture was concentrated and treated with NaHCO$_3$ and DCM. The organic phase was concentrated and the crude product was purified by flash chromatography (EtOAc/heptane followed by EtOAc/methanol). The diasteromers were separated on preparative HPLC (Kromasil column, water buffered with 2 g NH$_4$OAc/l, pH set to 5.5 with HOAc, and MeCN, 25%-75%) to give the syn-isomer (1RS,2RS)-1-[6-chloro-1-(4-fluorophenyl)indazol-5-yl]oxy-1-(4-fluorophenyl)propan-2-amine (98a-rac-1) as first eluated isomer (assignment by 1H-NMR).

$^1$H NMR (400 MHz, CD$_3$OD) δ 8.05 (d, J=0.9 Hz, 1H), 7.75 (s, 1H), 7.65 (tt, J=4.6, 2.3 Hz, 2H), 7.53 (dd, J=12.0, 1.9 Hz, 2H), 7.34-7.26 (m, 3H), 7.13 (t, J=8.8 Hz, 2H), 5.28 (d, J=8.3 Hz, 1H), 3.69 (dd, J=8.2, 6.8 Hz, 1H), 1.17 (d, J=6.7 Hz, 3H). APCI-MS: 414 m/z [MH$^+$].

The anti-isomer (1RS,2SR)-1-[6-chloro-1-(4-fluorophenyl)indazol-5-yl]oxy-1-(4-fluorophenyl)propan-2-amine (99a-rac-2) was eluated secondly.

$^1$H NMR (400 MHz, CD$_3$OD) δ 8.02 (s, 1H), 7.79 (s, 1H), 7.69-7.64 (m, 2H), 7.48-7.43 (m, 2H), 7.31 (dd, J=20.8, 3.4 Hz, 2H), 7.18-7.10 (m, 3H), 5.41 (d, J=4.6 Hz, 1H), 3.46 (dt, J=11.1, 6.6 Hz, 1H), 1.27 (d, J=6.5 Hz, 3H). APCI-MS: 414 m/z [MH$^+$].

1-{[6-chloro-1-(4-fluorophenyl)-1H-indazol-5-yl]oxy}-1-(4-fluorophenyl)acetone (99b)

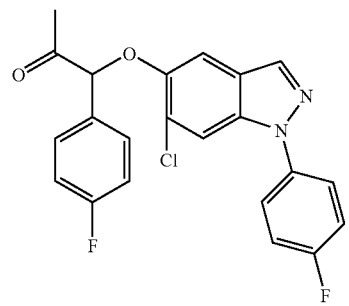

4-Fluorophenylacetone (388 μl, 2.9 mmol) in DCM (12 ml) was cooled to 0° C. and bromine (672 mg, 2.9 mmol) was slowly added. The mixture was stirred for 30 min and then concentrated in vacuo. The crude intermediate was added to a mixture of 6-chloro-1-(4-fluorophenyl)-1H-indazol-5-ol, (99c) (762 mg, 2.9 mmol) and potassium carbonate (804 mg, 5.8 mmol) in THF (12 ml). The mixture was stirred for 4 h, filtrated and concentrated. The crude product was purified by flash chromatography (EtOAc/heptane, product eluted at 40% EtOAc) to give the title compound (1.06 g, 88%).

APCI-MS: 413 m/z [MH$^+$].

6-Chloro-1-(4-fluorophenyl)-1H-indazol-5-ol (99c)

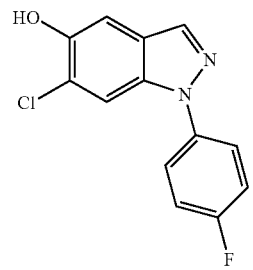

1-(4-Fluorophenyl)-6-chloro-5-methoxy-1H-indazole (99d) (0.91 mmol, 253 mg) was dissolved in dichloromethane (4 mL) and BBr$_3$ (4 mL, 1 M/CH$_2$Cl$_2$) was added. The reaction mixture was stirred in room temperature overnight before it was quenched with water (20 mL). The product was extracted with dichloromethane (2×20 mL) and washed with sat NaHCO$_3$. The organic phase was dried over Na$_2$SO$_4$, concentrated and purified by flash chromatography on silica gel (heptane-ethyl acetate). Yield: 219 mg (91%).

$^1$H NMR (500 MHz, CDCl$_3$) δ 8.09 (d, J=0.7 Hz, 1H), 7.70 (s, 1H), 7.67-7.60 (m, 2H), 7.37 (s, 1H), 7.28-7.23 (m, 2H), 5.43 (s, 1H). APCI-MS m/z (method A): 360.0 [MH$^+$].

1-(4-Fluorophenyl)-6-chloro-5-methoxy-1H-indazole (99d)

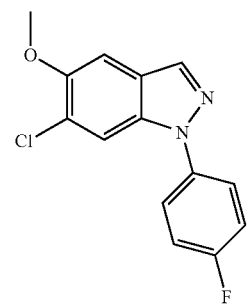

4-Chloro-2-fluoro-5-methoxy benzaldehyde (204 mg, 1.1 mmol) and 4-fluorophenylhydrazine (176 mg, 1.1 mmol) were dissolved in N-methylpyrrolidine (5 mL). After addition of cesium carbonate (1.15 g, 3.3 mmol) the mixture was heated in a microwave reactor (CEM Discovery, 150 Watt) to 150° C. for 20 min. After dilution with DCM the mixture was washed with sat. NaHCO$_3$, brine and the organic phase was evaporated. After purification of the crude by flash chromatography on silica gel 253 mg (84%) of the subtitle compound were obtained.

APCI-MS: 277.0 m/z [MH$^+$].

Example 100

N-[(1RS,2SR)-1-[6-chloro-1-(4-fluorophenyl)indazol-5-yl]oxy-1-(4-fluorophenyl)propan-2-yl]acetamide

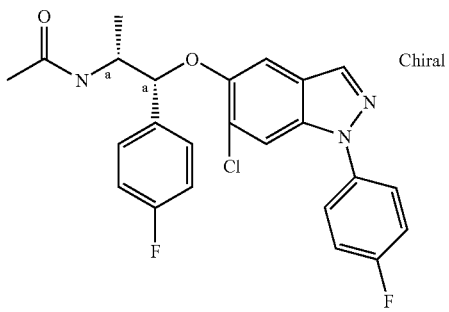

a = relative mixture

The title compound was made from (1RS,2RS)-1-[6-chloro-1-(4-fluorophenyl)indazol-5-yl]oxy-1-(4-fluorophenyl)propan-2-amine (99a-rac-1) and purified on preparative HPLC (water/MeCN/1% TFA).

$^1$H NMR (400 MHz, CD$_3$OD) δ 8.02 (d, J=0.7 Hz, 1H), 7.75 (s, 1H), 7.65 (tt, J=4.6, 2.3 Hz, 2H), 7.45 (dd, J=8.7, 5.5 Hz, 2H), 7.30 (t, J=8.9 Hz, 2H), 7.24 (s, 1H), 7.10 (t, J=8.8 Hz, 2H), 5.44 (d, J=5.3 Hz, 1H), 4.48 (dd, J=6.7, 5.7 Hz, 1H), 1.96 (s, 3H), 1.18 (d, J=6.9 Hz, 3H). APCI-MS: 456 m/z [MH$^+$].

Example 101

N-[(1S*,2R*)-1-[6-chloro-1-(4-fluorophenyl)indazol-5-yl]oxy-1-(4-fluorophenyl)propan-2-yl]acetamide

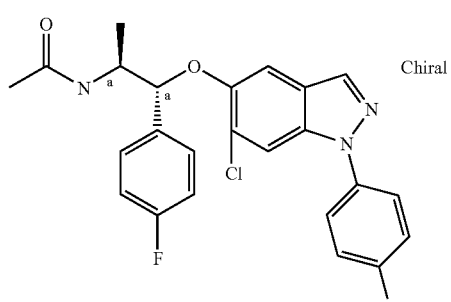

a = relative absolute

The title compound was obtained by acylation of (1RS, 2SR)-1-[6-chloro-1-(4-fluorophenyl)indazol-5-yl]oxy-1-(4-fluorophenyl)propan-2-amine (99a-rac-2) followed by separation using chiral HPLC (Chiralpak IA; isohexane/ethanol 4:1) The title compound was obtained as the first eluated enantiomer.

APCI-MS: 456 m/z [MH$^+$] $^1$H NMR (400 MHz, CD$_3$OD) δ 8.01 (d, J=0.9 Hz, 1H), 7.78 (s, 1H), 7.69-7.64 (m, 2H), 7.45 (dd, J=12.0, 1.9 Hz, 2H), 7.31 (t, J=8.7 Hz, 2H), 7.12-7.06 (m, 3H), 5.49 (d, J=4.4 Hz, 1H), 4.31 (dt, J=11.4, 6.9 Hz, 1H), 1.89 (s, 3H), 1.30 (d, J=6.9 Hz, 3H)

Example 102

N-[(1R*,2S*)-1-[6-chloro-1-(4-fluorophenyl)indazol-5-yl]oxy-1-(4-fluorophenyl)propan-2-yl]acetamide

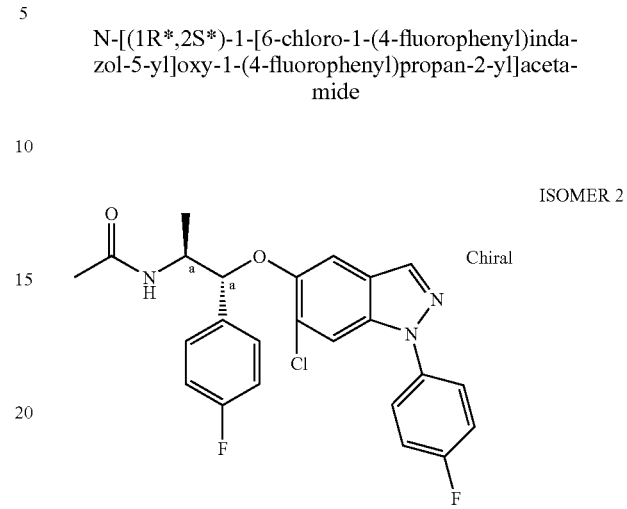

a = relative absolute

Obtained from the separation described in Example 101 as the secondly eluated enantiomer.

$^1$H NMR (400 MHz, CD$_3$OD) δ 8.01 (d, J=0.9 Hz, 1H), 7.78 (s, 1H), 7.66 (dd, J=17.2, 3.5 Hz, 2H), 7.45 (dd, J=12.0, 1.9 Hz, 2H), 7.31 (ddd, J=12.3, 8.5, 3.7 Hz, 2H), 7.12-7.06 (m, 3H), 5.49 (d, J=4.6 Hz, 1H), 4.31 (dt, J=11.3, 6.9 Hz, 1H), 1.89 (s, 3H), 1.30 (d, J=6.9 Hz, 3H). APCI-MS: 456 m/z [MH$^+$].

Example 103

2,2,2-trifluoro-N-((1R,2S)-1-(1-(4-fluorophenyl)-1H-indazol-5-ylthio)-1-phenylpropan-2-yl)acetamide

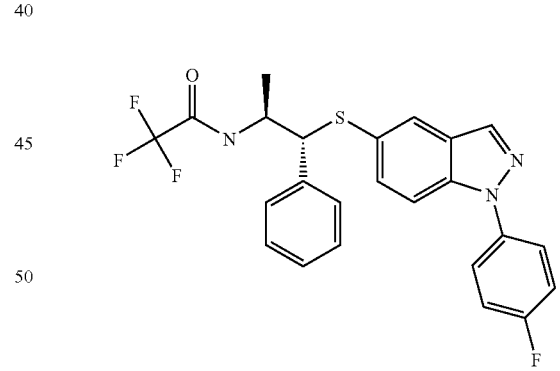

To (1R,2S)-1-(1-(4-fluorophenyl)-1H-indazol-5-ylthio)-1-phenylpropan-2-amine (0.024 g, 0.06 mmol) in MeOH (2.5 mL), 1,1,3,3-tetramethylguanidine (0.056 mL, 0.45 mmol) and ethyl trifluoroacetate (0.114 mL, 0.95 mmol) was added and the mixture was stirred at rt O/N and than submitted to purification on HPLC. The relevant fractions were collected freezdried to give 16 mg of product (53% yield) which was analysed by LC/MS and NMR.

APCI-MS: m/z 474 [MH$^+$]. $^1$H NMR (400 MHz, d$_6$-DMSO) δ 9.34 (s, 1H), 8.30 (s, 1H), 7.79-7.73 (m, 3H), 7.68 (d, J=8.8 Hz, 1H), 7.42 (t, J=8.8 Hz, 2H), 7.32 (d, J=9.3 Hz, 1H), 7.21 (dd, J=11.5, 6.9 Hz, 4H), 4.40 (s, 1H), 4.38-4.28 (m, 1H), 1.42 (d, J=6.5 Hz, 3H).

123

(1R,2S)-1-(1-(4-fluorophenyl)-1H-indazol-5-ylthio)-1-phenylpropan-2-amine (103a)

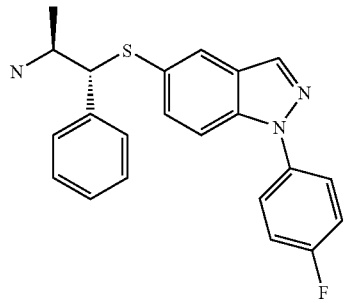

To N-((1R,2S)-1-(1-(4-fluorophenyl)-1H-indazol-5-ylthio)-1-phenylpropan-2-yl)-2-(trimethylsilyl)ethanesulfonamide (103a, 0.042 g, 0.08 mmol) in DMF (2 mL) cesium fluoride (8.60 µL, 0.23 mmol) was added and the mixture was stirred at 95° C. Stirring was continued at that temperature O/N. Cooled at rt the solvent was removed and the mixture was partitioned between EtOAc/water the organic phase was than purified with HPLC The relevant fractions were collected freezdried to give 24 mg of product (84% yield) which was analysed by LC/MS.

APCI-MS: m/z 378 [MH+]

N-((1R,2S)-1-(1-(4-fluorophenyl)-1H-indazol-5-ylthio)-1-phenylpropan-2-yl)-2-(trimethylsilyl)ethanesulfonamide (103b)

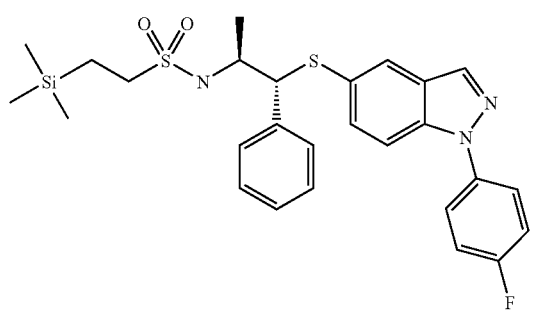

To (2R,3R)-2-methyl-3-phenyl-1-(2-(trimethylsilyl)ethylsulfonyl)aziridine (103c, 0.068 g, 0.23 mmol) in THF (2 mL) 1-(4-fluorophenyl)-1H-indazole-5-thiol (0.056 g, 0.23 mmol) and sodium hydride dispertion, 55-60% in oil (10.97 mg, 0.46 mmol) was added and the mixture was stirred at r.t. LC/MS after 2 h showed product, stirring was continued at 40 C for 4 h than this mixture was stirred O/N at r.t. The mixture was separated between water and EtOAc and the organic phase was purified with HPLC. The relevant fractions were collected freezdried to give 12 mg of product (10% yield) which was analysed by LC/MS.

APCI-MS: m/z 543.1 [MH+]

124

(2R,3R)-2-methyl-3-phenyl-1-(2-(trimethylsilyl)ethylsulfonyl)aziridine (103c)

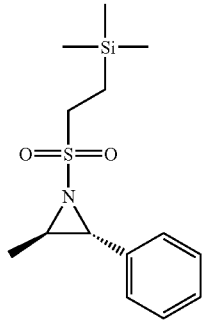

To (2R,3R)-2-methyl-3-phenylaziridine (103d, 0.05 g, 0.38 mmol) in THF (3 mL) at −10° C. N,N-diisopropylamine (0.124 mL, 0.75 mmol) was added and stirred for 5 min before (2R,3R)-2-methyl-3-phenyl-1-(2-(trimethylsilyl)ethylsulfonyl)aziridine (8.00 mg, 7.16%) in THF (1 ml) was added in small portions. The acetone/ice bath was than removed and the mixture was stirred for 1 hr at r.t. before the solvent was removed the mixture was dilute in MeCN an purified on HPLC. The relevant fractions were collected freezdried to give 8 mg (7%) of product which was analysed by LC/MS.

APCI-MS: m/z 339.1 [MH++MeCN]

S-1-(4-fluorophenyl)-1H-indazol-5-yl benzothioate (103d)

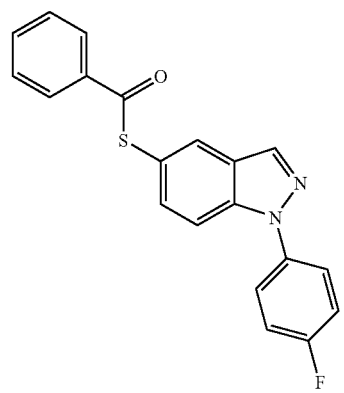

To a solution of 1-(4-fluorophenyl)-5-iodo-1H-indazole (103e, 0.224 g, 0.66 mmol), thiobenzoic acid (0.093 ml, 0.79 mmol), 3,4,7,8-tetramethyl-1,10-phenantroline (0.031 g, 0.13 mmol) and N,N-diisopropylamine (0.220 ml, 1.32 mmol) in toluene (2.5 ml) was added copper(I) iodine (2.245 µl, 0.07 mmol). The resulting mixture was stirred at 110 C O/N. The reaction mixture was cooled to r.t. diluted with EtOAc and washed with water. The organic phase was the dried the solvent evaporated and then purified on HPLC. The relevant fractions were collected freezdried to give 45 mg of product (20% yield) which was analysed by LC/MS.

APCI-MS: m/z 349 [MH+]

1-(4-fluorophenyl)-1H-indazole-5-thiol (103e)

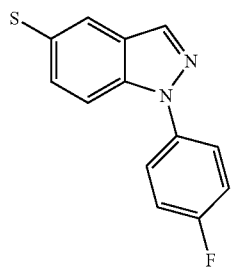

To S-1-(4-fluorophenyl)-1H-indazol-5-yl benzothioate (0.046 g, 0.13 mmol) in methanol (3 mL), potassium carbonate (0.011 mL, 0.20 mmol) was added and the mixture was stirred at r.t. for 2 h. water was than added, 1N HCl (2 ml) and extracted with EtOAc (2*20 ml), dried, evaporated and then purified on HPLC. The relevant fractions were collected freeze dried and analysed by LC/MS.

APCI-MS: m/z 245 [MH$^+$].

Example 104

1-(Cyclopentyl)-3-{(1S,2R)-2-[1-(4-fluorophenyl)-1H-indazole-5-yl)oxy]-1-methyl-2-phenyl-ethyl}urea

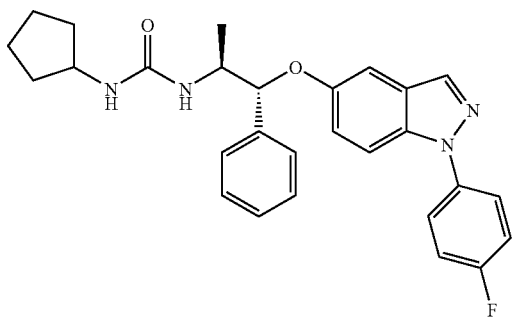

(αS,βR)-β-{[1-(4-Fluorophenyl)-1H-indazole-5-yl]oxy}-α-methylbenzeneethanamine (100 mg, 0.28 mmol), as described in Example 1, is dissolved in 1.77 mL dichloromethane and cyclopentylisocyanate (0.031 mL, 0.28 mmol) is dropwise added. After stirring for 45 min at r.t. the solvent is removed and the residue purified by chromatography (silicagel, eluents: hexane/ethyl acetate). 94.8 mg (72.5%) of the title compound are obtained.

MS (CI): 473 (M+) $^1$H-NMR (300 MHz, CDCl$_3$): δ=1.17 (3H), 1.22-1.45 (2H), 1.49-1.72 (4H), 1.82-2.03 (2H), 3.90-4.02 (1H), 4.19-4.80 (3H), 5.42 (1H), 6.98 (1H), 7.10-7.49 (8H), 7.50-7.70 (3H), 7.97 (1H).

Example 105

1-{(1S,2R)-2-{[1-(4-Fluorophenyl)-1H-indazole-5-yl]oxy}-1-methyl-2-phenylethyl}-3-(2-furylmethyl) urea

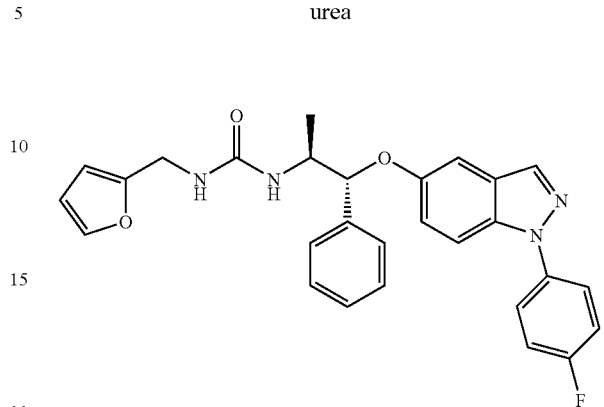

(αS,βR)-β-{[1-(4-Fluorophenyl)-1H-indazole-5-yl]oxy}-α-methylbenzeneethanamine (100 mg, 0.28 mmol), as described in Example 1, is dissolved in 1.77 mL dichloromethane and furylmethylisocyanate (34.1 mg, 0.28 mmol) is dropwise added. After stirring for 45 min at r.t. the solvent is removed and the residue purified by chromatography (silicagel, eluents: hexane/ethylacetate). 116.2 mg (86.7%) of the title compound are obtained.

MS (EI+): 484 (M) $^1$H-NMR (400 MHz, CDCl$_3$): δ=1.13 (3H), 4.22-4.45 (3H), 4.70-4.95 (broad, 2H), 5.43 (1H), 6.19 (1H), 6.29 (1H), 6.93 (1H), 7.12 (1H), 7.16-7.44 (8H), 7.52 (1H), 7.57-7.68 (2H), 7.95 (1H).

Example 106

Ethyl N-{[(1S,2R)-2-{[1-(4-fluorophenyl)-1H-indazole-5-yl]oxy}-1-methyl-2-phenylethyl] carbamoyl}glycinate

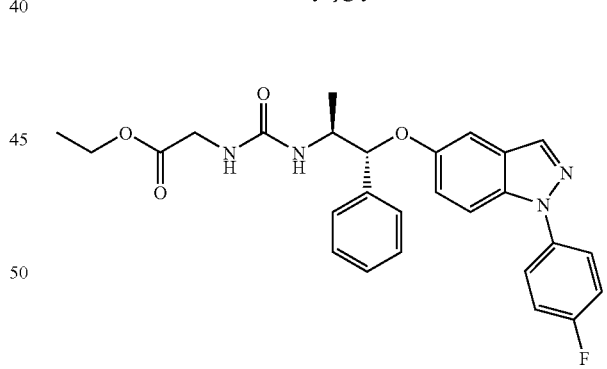

(αS,βR)-β-{[1-(4-Fluorophenyl)-1H-indazole-5-yl]oxy}-α-methylbenzeneethanamine (80 mg, 0.22 mmol), as described in Example 1, is dissolved in 1.42 mL dichloromethane and ethylisocyanatoacetate (28.6 mg, 0.22 mmol) is dropwise added. After stirring for 45 min at r.t. the solvent is removed and the residue purified by chromatography (silicagel, eluents: hexane/ethylacetate). 85.4 mg (78.6%) of the title compound are obtained.

MS (CI+): 491 (M+) $^1$H-NMR (400 MHz, CDCl$_3$): δ=1.19 (3H), 1.29 (3H), 3.89-4.32 (5H), 4.82-5.12 (broad, 2H), 5.42 (1H), 6.96 (1H), 7.12-7.45 (8H), 7.55 (1H), 7.58-7.65 (2H), 7.96 (1H).

Example 107

1-((R)-1,2-Dimethylpropyl)-3-{(1S,2R)-2-[1-(4-fluorophenyl)-1H-indazole-5-yl]oxy]-1-methyl-2-phenylethyl}urea

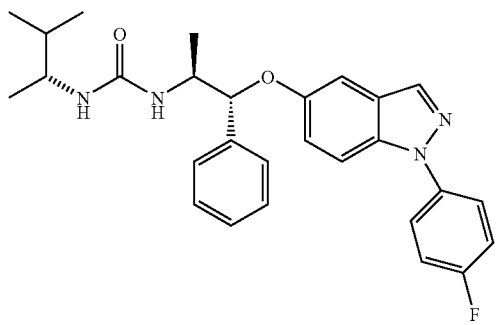

(αS,βR)-β-{[1-(4-Fluorophenyl)-1H-indazole-5-yl]oxy}-α-methylbenzeneethanamine (50 mg, 0.14 mmol), as described in Example 1, is dissolved in 0.89 mL dichloromethane and (R)-(−)-3-methyl-2-butylisocyanate (15.7 mg, 0.14 mmol) is dropwise added. After stirring for 90 min at r.t. the solvent is removed and the residue purified by chromatography (silicagel, eluents: hexane/ethylacetate). 50.6 mg (77.1%) of the title compound are obtained.

MS (CI): 475 (M+) $^1$H-NMR (300 MHz, CDCl$_3$): δ=0.85-0.95 (6H), 1.10 (3H), 1.29 (3H), 1.69 (1H), 3.67 (1H), 4.00-4.70 (extremely broad, 2H), 4.30 (1H), 5.50 (1H), 7.03 (1H), 7.17-7.49 (8H), 7.58 (1H), 7.61-7.70 (2H), 8.00 (1H).

Example 108

1-{(1S,2R)-2-{[1-(4-Fluorophenyl)-1H-indazole-5-yl]oxy}-1-methyl-2-phenylethyl}-3-(2-furylmethyl)thiourea

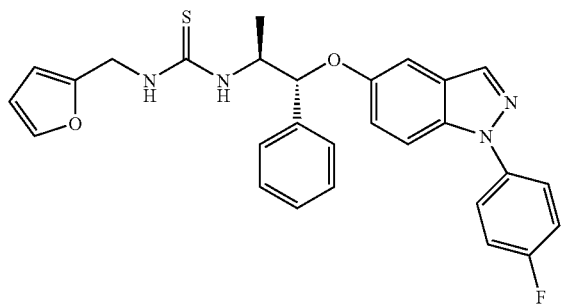

(αS,βR)-O-{[1-(4-Fluorophenyl)-1H-indazole-5-yl]oxy}-α-methylbenzeneethanamine (50 mg, 0.14 mmol), as described in Example 1, is dissolved in 0.89 mL dichloromethane and furylmethylisothiocyanate (19.3 mg, 0.14 mmol) is dropwise added. After stirring for 90 min at r.t. water (5 mL) is added and the reaction mixture extracted once with ethyl acetate (50 mL). The organic phase is washed with water (10 mL) and dried over Na$_2$SO$_4$. After filtration the solvent is removed and the residue purified by chromatography (silicagel, eluents: hexane/ethylacetate). 53.8 mg (77.7%) of the title compound are obtained.

MS (CI+): 501 (M+) $^1$H-NMR (300 MHz, CDCl$_3$): δ=1.28 (3H), 4.52-4.92 (3H), 5.60 (1H), 6.08-6.68 (4H), 6.97 (1H), 7.19 (1H), 7.18-7.50 (8H), 7.55 (1H), 7.58-7.70 (2H), 8.00 (1H).

Example 109

N-{(1S)-1-[(R)-(3-Fluorophenyl)-{[1-(4-fluorophenyl)-1H-indazole-5-yl]oxy}methyl]-3-methyl-butyl}-2-methoxyacetamide

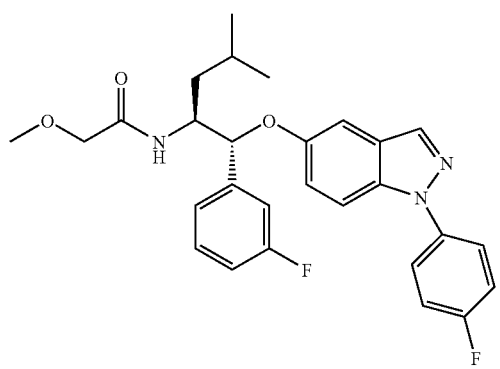

N-(tert.-Butoxycarbonyl)-L-leucinal

Lithiumaluminiumhydride (863.5 mg, 22.8 mmol) is added in portions at 10° C. to N-(tert.-butoxycarbonyl)-L-leucine-N'-methoxy-N'-methylamide (5 g, 18.2 mmol), dissolved in diethylether (500 mL). After stirring of the reaction mixture for 1 h at r.t., a solution of 4.34 g KHSO$_4$ in 91 mL water is added carefully at 10° C. Afterwards the reaction mixture is vigorously stirred for 30 min and the organic phase separated. After twice extraction of the aqueous phase with diethylether the combined organic phases are washed with water and brine and dried over Na$_2$SO$_4$. The solvent is removed and the residue (4.3 g, >100%) is used without further purification in the next step.

MS (CI+): 216 (M+) $^1$H-NMR (300 MHz, CDCl$_3$): δ= 0.85-1.02 (6H), 1.32-1.86 (12H), 4.24 (1H), 4.91 (1H), 9.59 (1H).

{(S)-1-[(3-Fluorophenyl)-hydroxymethyl]-3-methyl-butyl}-carbamic acid tert.-butylester An 1M 3-Fluorophenylgrignard solution (58.5 mL, 58.5 mmol) is added dropwise under nitrogen and water bath cooling to N-(tert.-butoxycarbonyl)-L-leucinal (4.2 g, 19.5 mmol), dissolved in 50.5 mL diethylether (the temperature rises to 30° C.). The reaction mixture is stirred for 2 h at r.t. and then poured on NH$_4$Cl/ice. After extraction with diethylether (three times) the combined organic phases are washed with water and brine. The solvent is dried over Na$_2$SO$_4$ and evaporated. The residue is finally purified by chromatography (silicagel, eluents: ethylacetate/hexane). 4.7 g (77.4%) of the title compound as a mixture of two stereoisomers are obtained.

MS (CI+): 312 (M+) $^1$H-NMR (300 MHz, CDCl$_3$): δ= 0.80-1.02 (6H), 1.28-1.55 (12H), 3.78 (1H), 4.64 (1H), 6.52-6.66 (1H), 6.98 (1H), 7.01-7.13 (1H), 7.22-7.38 (1H).

(2S)-2-Amino-1-(3-fluorophenyl)-4-methyl-pentane-1-ol hydrochloride

The aforementioned described {(S)-1-[(3-fluorophenyl)-hydroxymethyl]-3-methylbutyl}-carbamic acid tert.-butylester (4.7 g, 15.1 mmol) is dissolved in dioxane (37 mL). After addition of HCl in dioxane (37.7 mL of a 4M solution) the reaction mixture is stirred for 4 h. After evaporation of the solvent the crude product (3.7 g, 99.5%) is used in the next step without further purification.

(2S)-2-Amino-1-(3-fluorophenyl)-4-methyl-pentane-1-ol (2S)-2-Amino-1-(3-fluorophenyl)-4-methyl-pentane-1-ol hydrochloride (1.6 g, 6.46 mmol) is stirred overnight in a mixture of 1N NaOH (12.92 mL) and ethyl acetate (20 mL). The organic phase is separated and the aqueous phase is washed twice with ethyl acetate. The combined organic extracts are washed with brine, dried over $Na_2SO_4$ and the solvent is evaporated. After purification of the residue by chromatography (silicagel, eluents: dichloromethane/methanol) 694 mg (50.9%) of the title compound as mixture of stereoisomers is obtained.

MS (CI+): 212 (M+) $^1$H-NMR (300 MHz, $CDCl_3$): δ= 0.80-1.08 (6H), 1.20-1.35 (2H), 1.62-1.88 (1H), 1.90-2.55 (broad, 2H), 2.96 and 3.16 (combined 1H), 4.33 and 4.63 (combined 1H), 7.02 (1H), 7.08-7.20 (2H), 7.29-7.41 (1H).

(αS)-3-Fluoro-β-[[1-(4-fluorophenyl)-1H-indazole-5-yl]oxy]-α-(2-methylpropyl)benzeneethanamine (2S)-2-Amino-1-(3-fluorophenyl)-4-methyl-pentane-1-ol (350 mg, 1.66 mmol), 5-iodo-1-(4-fluorophenyl)-1H-indazole (672.2 mg, 1.99 mmol), cesiumcarbonate (1.08 g, 3.31 mmol), copper (I)-iodide (157.8 mg, 0.83 mmol) and isobutyronitrile (1.75 mL) are stirred in a glass pressure tube at 120° C. for 20 h. The reaction mixture is filtered via a glass microfibre filter, the solvent evaporated and the residue purified by chromatography (silicagel, eluents: ethylacetate/methanol). 162.8 mg (23.3%) of the title compound are obtained.

MS (EI+): 421 (M) $^1$H-NMR (300 MHz, $CDCl_3$): δ=0.75-1.02 (6H), 1.25-1.90 (3H), 3.18 (broad, 1H), 4.95 (broad, 1H), 6.88-7.40 (8H), 7.53 (1H), 7.55-7.70 (2H), 7.99 (1H).

N-{(1S)-1-[(R)-(3-Fluorophenyl)-{[1-(4-fluorophenyl)-1H-indazole-5-yl]oxy}methyl}-3-methyl-butyl}-2-methoxyacetamide (αS)-3-Fluoro-β-[[1-(4-fluorophenyl)-1H-indazole-5-yl]oxy]-α-(2-methylpropyl)benzeneethanamine (76.4 mg, 0.18 mmol) is dissolved in 7 mL dichloromethane. Triethylamine (0.06 mL, 0.44 mmol) and 2-methoxyacetyl chloride (0.02 mL, 0.22 mmol) are added. After stirring overnight the reaction mixture is diluted with dichloromethane, washed with water and brine and dried over $Na_2SO_4$. After filtration the solvent is evaporated and the residue is purified by chromatography (silicagel, eluents: ethylacetate/hexane). The obtained mixture of the two stereoisomers is separated by HPLC (Chiralpak AD-H 5 μm, eluents: hexane/ethanol) yielding 3.7 mg (10.2%) of the title stereoisomer and 24.7 mg (68%) of the stereoisomer N-{(1S)-1-[(S)-(3-fluorophenyl)-{[1-(4-fluorophenyl)-1H-indazole-5-yl]oxy}methyl}-3-methyl-butyl}-2-methoxyacetamide.

MS (EI+): 421 (M) $^1$H-NMR (300 MHz, $CDCl_3$): δ=0.79 (3H), 0.93 (3H), 1.16-1.34 (2H), 1.55-1.76 (1H), 3.38 (3H), 3.79-3.98 (2H), 4.45 (1H), 5.39 (1H), 6.70 (1H), 6.93 (1H), 7.00 (1H), 7.09-7.40 (6H), 7.55 (1H), 7.58-7.69 (2H), 7.98 (1H).

Example 110

2,2,2-Trifluoro-N-{(1S)-1-[(R)-(3-Fluorophenyl)-{[1-(4-fluorophenyl)-1H-indazole-5-yl]oxy}methyl}-3-methylbutyl}-acetaminde

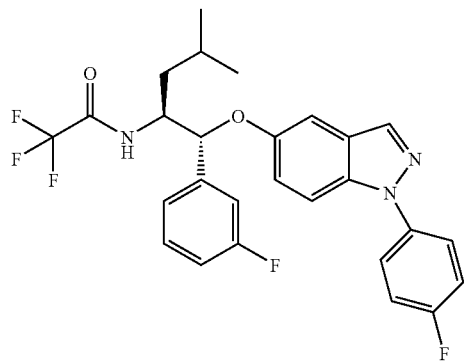

(αS)-3-Fluoro-β-[[1-(4-fluorophenyl)-1H-indazole-5-yl]oxy]-α-(2-methylpropyl)benzeneethanamine described in Example 1 (76.4 mg, 0.18 mmol) is dissolved in 7 mL dichloromethane. Triethylamine (0.06 mL, 0.44 mmol) and trifluoroacetanhydride (0.03 mL, 0.22 mmol) are added. The reaction mixture is stirred overnight and then diluted with dichloromethane, washed with water and brine and dried over $Na_2SO_4$. After filtration the solvent is evaporated and the residue is purified by chromatography (silicagel, eluents: ethyl acetate/hexane). The obtained mixture of the two stereoisomers is separated by HPLC (Chiralcel OJ-H 5μ, eluents: hexane/ethanol) yielding 3.8 mg (18.3%) of the title stereoisomer and 14.2 mg (68%) of the stereoisomer 2,2,2-trifluoro-N-{(1S)-1-[(S)-(3-fluorophenyl)-{[1-(4-fluorophenyl)-1H-indazole-5-yl]oxy}methyl}-3-methylbutyl}-acetamide.

MS (EI+): 517 (M) $^1$H-NMR (400 MHz, $CDCl_3$): δ=0.81 (3H), 0.93 (3H), 1.23-1.39 (2H), 1.65-1.77 (1H), 4.49 (1H), 5.39 (1H), 6.41 (1H), 6.94 (1H), 7.04 (1H), 7.08-7.30 (5H), 7.39 (1H), 7.56 (1H), 7.59-7.68 (2H), 7.99 (1H).

Example 111

N-[(1)-(2R)-(3-Fluorophenyl)-2-{[1-(4-fluorophenyl)-1H-indazole-5-yl]oxy}-1-(methoxymethyl)ethyl]-2-methoxyacetamide

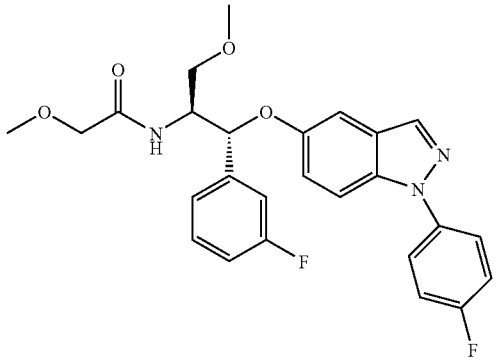

(αS)-3-Fluoro-γ-[[1-(4-fluorophenyl)-1H-indazole-5-yl]oxy]-α-(methoxymethyl))benzeneethanamine is synthesized in analogy to the sequence described in example 1: commercially available Boc-Ser(Me)-OH is transformed into its Weinreb-amide. Reduction to the aldehyde with LiAlH₄, followed by reaction with 3-fluorophenylgrignard, cleavage of the protecting group, liberation of the amine from the hydrochloride and etherification with 1-(4-fluorophenyl)-5-iodo-1H-indazole. This amine (66.4 mg, 0.16 mmol) is dissolved in 7 mL of dichloromethane. Triethylamine (0.054 mL, 0.39 mmol) and 0.018 mL (0.19 mmol) 2-methoxyacetylchloride are added. The reaction mixture is stirred for four h at r.t. and then diluted with dichloromethane, washed with water and brine and dried over Na₂SO₄. After filtration the solvent is evaporated and the residue purified by chromatography (silicagel, eluents: ethyl acetate/hexane). The mixture of stereoisomers is separated by HPLC (Chiralpak AD-H 5μ, eluents: hexane/ethanol) providing 3 mg (3.8%) of the title compound and 6 mg (7.6%) of the stereoisomer N-[(1S)-(2S)-(3-fluorophenyl)-2-{[1-(4-fluorophenyl)-1H-indazole-5-yl]oxy}-1-(methoxymethyl)ethyl]-2-methoxyacetamide.

MS (CI+): 482 (M+) ¹H-NMR (400 MHz, CDCl₃): δ= 3.32-3.42 (1H), 3.38 (3H), 3.41 (3H), 3.53-3.62 (1H), 3.78-3.98 (2H), 4.57 (1H), 5.52 (1H), 6.94-7.02 (2H), 7.06 (1H), 7.10-7.25 (5H), 7.29-7.38 (1H), 7.57 (1H), 7.59-7.68 (2H), 8.01 (1H).

Example 112

N-[(1S)-(2R)-(3-Fluorophenyl)-2-{[1-(4-fluorophenyl)-1H-indazol-5-yl]oxy}-1-(methoxymethyl)ethyl]furan-2-carboxamide

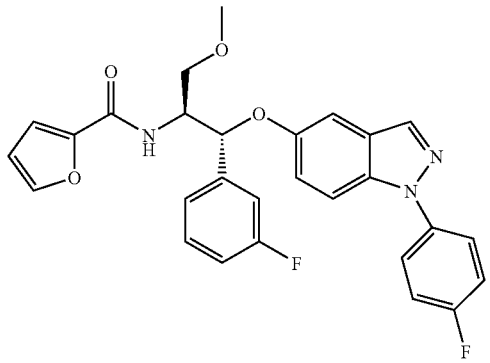

(αS)-3-Fluoro-β-[[1-(4-fluorophenyl)-1H-indazole-5-yl]oxy]-α-(methoxymethyl)]benzeneethanamine (66.4 mg, 0.16 mmol) is dissolved in 7 mL of dichloromethane. Triethylamine (0.054 mL, 0.39 mmol) and 25 mg (0.19 mmol) 2-furoylchloride are added. The reaction mixture is stirred for 4 h at r.t., diluted with dichloromethane, washed with water and brine and dried over Na₂SO₄. After filtration the solvent is evaporated and the residue purified by chromatography (silicagel, eluents: ethyl acetate/hexane). The mixture of stereoisomers is separated by HPLC (Chiralpak AD-H 5μ, eluents: hexane/ethanol) providing 5 mg (6.1%) of the title compound and 2 mg (2.5%) of the stereoisomer N-[(1S)-(2S)-(3-fluorophenyl)-2-{[1-(4-fluorophenyl)-1H-indazole-5-yl]oxy}-1-(methoxymethyl)ethyl]furan-2-carboxamide.

MS (CI+): 504 (M+) ¹H-NMR (400 MHz, CDCl₃): δ=3.38 (3H), 3.42-3.51 (1H), 3.60-3.69 (1H), 4.69 (1H), 5.58 (1H), 6.51 (1H), 6.83 (1H), 6.91-7.39 (9H), 7.48 (1H), 7.55 (1H), 7.59-7.69 (2H), 8.01 (1H).

Example 113

N-[(1S)-2-(3-Fluorophenyl)-2-{[1-(4-fluorophenyl)-1H-indazol-5-yl]oxy}-1-(hydroxymethyl)ethyl]-2-methoxyacetamide

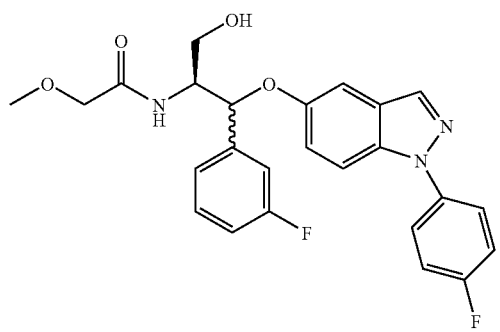

N-[(1S)-2-(3-Fluorophenyl)-2-{[1-(4-fluorophenyl)-1H-indazole-5-yl]oxy}-1-(benzyloxymethyl)ethyl]-2-methoxyacetamide (αS)-3-Fluoro-β-[[1-(4-fluorophenyl)-1H-indazole-5-yl]oxy]-α-[[(phenylmethoxy)methyl]benzeneethanamine is synthesized in analogy to the sequence previously described in example 1: commercially available Boc-Ser(Bn)-OH is transformed into its Weinreb-amide. Reduction to the aldehyde with LiAlH₄, reaction with 3-fluorophenylgrignard, cleavage of the tert.-butyloxycarbonyl protecting group, liberation of the amine from the hydrochloride and etherification with 1-(4-fluorophenyl)-5-iodo-1H-indazole gives the desired amine. This amine (123.3 mg, 0.25 mmol) is dissolved in 10 mL of dichloromethane. Triethylamine (0.084 mL, 0.61 mmol) and 0.028 mL (0.3 mmol) 2-methoxyacetylchloride are added. The reaction mixture is stirred overnight at r.t., then diluted with dichloromethane, washed with water and brine and dried over Na₂SO₄. After filtration the solvent is evaporated and the residue purified by chromatography (silicagel, eluents: ethyl acetate/hexane). 79.1 mg (55.9%) of the title compound as a mixture of stereoisomers are isolated.

MS (CI+): 559 (M+) ¹H-NMR (300 MHz, CDCl₃): δ=3.40 and 3.43 (combined 3H), 3.49-3.61 (1H), 3.65-3.78 (1H), 3.79-4.00 (2H), 4.49-4.73 (3H), 5.48 and 5.61 (combined 1H), 6.95-7.43 (14H), 7.58 (1H), 7.62-7.73 (2H), 8.04 (1H).

N-[(1S)-2-(3-Fluorophenyl)-2-{[1-(4-fluorophenyl)-1H-indazole-5-yl]oxy}-1-(hydroxymethyl)ethyl]-2-methoxyacetamide N-[(1S)-2-(3-Fluorophenyl)-2-{[1-(4-fluorophenyl)-1H-indazole-5-yl]oxy}-1-(benzyloxymethyl)ethyl]-2-methoxyacetamide (15 mg, 0.027 mmol) is dissolved in 10 mL ethanol and Pd (10% on charcoal, 0.29 mg, 0.0027 mmol) is added. The reaction mixture is charged with hydrogen and stirred for 2 h at r.t. After filtration of the reaction mixture via a glass microfibre filter, the solvent evaporated and the residue purified by chromatography (silicagel, eluents: ethylacetate/hexane). 7.5 mg (59.6%) of the title compound as a mixture of stereoisomers are obtained.

MS (CI+): 468 (M+) ¹H-NMR (300 MHz, CDCl₃): δ=2.20 (broad, 1H), 3.41 and 3.45 (combined 3H), 3.70-4.03 and 4.05-4.21 (combined 4H), 4.31-4.47 (1H), 5.57-5.65 (1H), 6.99-7.12 (2H), 7.13-7.47 (7H), 7.53-7.71 (3H), 8.04 (1H).

Example 114

N-[(1S,2R)-1-Methyl-2-phenyl-2-{[1-(3-pyridyl)-1H-indazol-5-yl]oxy}ethyl]furan-2-carboxamide

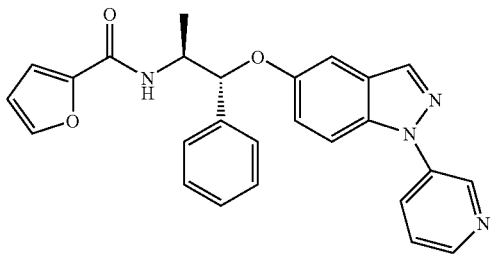

5-Iodo-1-(3-pyridyl)-1H-indazole

Cesiumcarbonate (26.84 g, 82.38 mmol) is added to a suspension of 2-fluoro-5-iodobenzaldehyde (6.87 g, 27.46 mmol) and 3-pyridylhydrazine dihydrochloride (5 g, 27.46 mmol) in 136 mL N-methylpyrrolidon. The reaction mixture is stirred overnight at r.t. After checking that the hydrazone has been formed ($^1$H-NMR) the reaction mixture is heated for 4 h at 160° C. The reaction mixture is allowed to cool down and the darkbrown suspension is poured on 1000 mL ice water. After vigorously stirring at r.t. for 45 min, the precipitated product is sucked off via a glass microfibre filter, washed with water and dried at the evaporator at 45° C. 8.28 g (93.9%) of the title compound are obtained.

MS (CI+): 322 (M+) $^1$H-NMR (400 MHz, DMSO [d6]): δ=7.62 (1H), 7.72 (2H), 8.20 (1H), 8.32 (1H), 8.49 (1H), 8.61 (1H), 9.01 (1H).

(αS,βR)-β-{[1-(3-Pyridyl)-1H-indazole-5-yl]oxy}-α-methylbenzeneethanamine (1R,2S)-Norephedrine (500 mg, 3.31 mmol), 5-iodo-1-(3-pyridyl)-1H-indazole (1.08 g, 33.37 mmol), cesiumcarbonate (2.15 g, 6.61 mmol), copper (I)-iodide (314.9 mg, 1.65 mmol) and butyronitrile (2 mL) are stirred in a glass pressure tube at 120° C. for 20 h. The reaction mixture is filtered via a glass microfibre filter, the solvent evaporated and the residue purified by chromatography (silicagel, eluents: dichloromethane/methanol). 307.8 mg (27%) of the title compound are obtained.

MS (CI+): 345 (M+) $^1$H-NMR (300 MHz, CDCl$_3$): δ=1.27 (3H), 3.52 (1H), 5.05 (1H), 7.08 (1H), 7.15-7.60 (7H), 7.68 (1H), 7.99-8.12 (2H), 8.62 (1H), 9.08 (1H).

N-[(1S,2R)-1-Methyl-2-phenyl-2-{[1-(3-pyridyl)-1H-indazole-5-yl]oxy}ethyl]furan-2-carboxamide (αS,βR)-β-{[1-(3-Pyridyl)-1H-indazole-5-yl]oxy}-α-methylbenzeneethanamine (75 mg, 0.22 mmol) is dissolved in 8 mL of dichloromethane. Triethylamine (0.072 mL, 0.52 mmol) and 2-furoylchloride (28.4 mg, 0.22 mmol) are added. After 4 h stirring at r.t. the reaction mixture is diluted with dichloromethane, washed with water and brine and dried over Na$_2$SO$_4$. The reaction mixture is filtered, the solvent evaporated and the residue purified by chromatography (silicagel, eluents: ethyl acetate/hexane). 46.4 mg (48.6%) of the title compound are obtained.

MS (CI+): 439 (M+) $^1$H-NMR (300 MHz, CDCl$_3$): δ=1.29 (3H), 4.62 (1H), 5.51 (1H), 6.51 (1H), 6.78 (1H), 6.99 (1H), 7.13 (1H), 7.19-7.54 (8H), 7.63 (1H), 7.96-8.08 (2H), 8.59 (1H), 9.03 (1H).

Example 115

N-[(1S,2R)-1-Methyl-2-phenyl-2-{[1-(4-pyridyl)-1H-indazol-5-yl]oxy}ethyl]furan-2-carboxamide

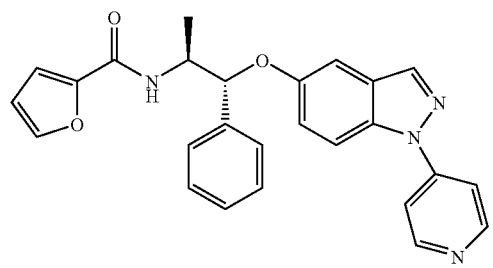

5-Iodo-1-(4-pyridyl)-1H-indazole

Cesiumcarbonate (26.84 g, 82.38 mmol) is added to a suspension of 2-fluoro-5-iodobenzaldehyde (6.87 g, 27.46 mmol) and 4-pyridylhydrazine dihydrochloride (5 g, 27.46 mmol) in 136 mL N-methylpyrrolidon. The reaction mixture is stirred overnight at r.t. After checking that the hydrazone has been formed ($^1$H-NMR) the reaction mixture is heated for 4 h at 160° C. The reaction mixture is allowed to cool down and the darkbrown suspension is poured on 1000 mL ice water. After vigorously stirring at r.t. for 45 min, the precipitated product is sucked off via a glass microfibre filter, washed with water and dried at the evaporator at 45° C. The title compound is obtained with a yield of 92.3% (8.14 g).

$^1$H-NMR (300 MHz, DMSO [d6]): δ=7.83 (1H), 7.89-7.92 (2H), 7.99 (1H), 8.39 (1H), 8.48 (1H), 8.70-8.78 (2H).

(αS,8R)-β-{[1-(4-Pyridyl)-1H-indazole-5-yl]oxy}-α-methylbenzeneethanamine (1R,2S)-Norephedrine (500 mg, 3.31 mmol), 5-iodo-1-(4-pyridyl)-1H-indazole (1.08 g, 3.37 mmol), cesiumcarbonate (2.15 g, 6.61 mmol), copper (I)-iodide (314.9 mg, 1.65 mmol) and butyronitrile (2 mL) are stirred in a glass pressure tube at 120° C. for 20 h. The reaction mixture is filtered via a glass microfibre filter, the solvent evaporated and the residue purified by chromatography (silicagel, eluents: dichloromethane/methanol). 257.2 mg (22.6%) of the title compound are obtained.

MS (CI+): 345 (M+) $^1$H-NMR (300 MHz, CDCl$_3$): δ=1.29 (3H), 3.45 (1H), 5.08 (1H), 7.05 (1H), 7.18-7.50 (6H), 7.62-7.83 (3H), 8.08 (1H), 8.63-8.82 (2H).

N-[(1S,2R)-1-Methyl-2-phenyl-2-{[1-(4-pyridyl)-1H-indazole-5-yl]oxy}ethyl]furan-2-carboxamide (αS,βR)-β{[1-(4-Pyridyl)-1H-indazole-5-yl]oxy}-α-methylbenzeneethanamine (64.3 mg, 0.19 mmol) is dissolved in 7.1 mL of dichloromethane. Triethylamine (0.062 mL, 0.45 mmol) and 2-furoylchloride (24.3 mg, 0.19 mmol) are added. After 4 h stirring at r.t. the reaction mixture is diluted with dichloromethane, washed with water and brine and dried over Na$_2$SO$_4$. The reaction mixture is filtered, the solvent evaporated and the residue purified by chromatography (silicagel, eluents: ethyl acetate/hexane). 53.7 mg (65.6%) of the title compound are obtained.

MS (CI+): 439 (M+) $^1$H-NMR (300 MHz, CDCl$_3$): δ=1.29 (3H), 4.62 (1H), 5.52 (1H), 6.50 (1H), 6.75 (1H), 7.00 (1H), 7.13 (1H), 7.19-7.50 (8H), 7.65-7.82 (3H), 8.02 (1H), 8.72 (1H).

Example 116

Methyl 4-(5-{(1R,2S)-2-[(2-furylcarbonyl)amino]-1-phenylpropoxy}-1H-indazol-1-yl)benzoate

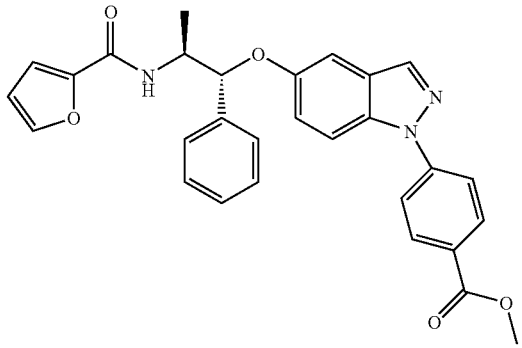

Methyl-4-(5-iodoindazole-1-yl)-benzoate

4-Hydrazinobenzoic acid (11.32 g, 60 mmol) and cesiumcarbonate (58.65 g, 180 mmol) are added to 2-fluoro-5-iodobenzaldehyde (15 g, 60 mmol) in 300 mL N-methylpyrrolidon. After 1 h stirring at r.t., the reaction is heated for 4 h at 150° C. The reaction mixture is allowed to cool off and poured on 1 L ice water. The reaction mixture is acidified with citric acid and vigorously stirred at r.t. for 30 min. The precipitate is filtered off and given in ethyl acetate. The slurry is vigorously stirred for 1 h and sucked off. The filter residue (few material) is discarded and the filtrate evaporated. This residue which is contaminated with N-methylpyrrolidine is treated with 300 mL of a mixture of ethyl acetate/hexane (1:3) and stirred overnight. The precipitated crystals are sucked off and dried. 17.11 g (78.32%) of 4-(5-iodoindazole-1-yl)-benzoic acid are obtained.

K$_2$CO$_3$ (7.35 g, 53.2 mmol) is suspended in 110 mL DMF. 4-(5-iodoindazole-1-yl)-benzoic acid (17.6 g, 48.33 mmol), dissolved in 25 mL DMF, is added dropwise. The reaction mixture is stirred for 30 min at r.t. Subsequently CH$_3$I (3.31 mL, 53.2 mmol) is added dropwise (temperature rises to 30° C.). The reaction mixture is stirred overnight at r.t. and then poured on ice water. It is three times extracted with ethyl acetate. The combined organic extracts are washed twice with water and brine. After drying over Na$_2$SO$_4$ and filtration the solvent is evaporated. The residue is purified by chromatography (silicagel, eluents: ethyl acetate/hexane) yielding 14.03 g (76.8%) of the title compound.

MS (CI+): 496 (M+) $^1$H-NMR (300 MHz, DMSO [d6]): δ=3.92 (3H), 7.75-7.92 (2H), 7.93-8.03 (2H), 8.10-8.25 (2H), 8.38 (1H), 8.44 (1H).

Methyl 4-{5-[(1R,2S)-2-amino-1-phenylpropoxy]-1H-indazole-1-yl}benzoate (1R,2S)-Norephedrine (500 mg, 3.31 mmol), methyl-4-(5-iodoindazole-1-yl)-benzoate (1.28 g, 3.37 mmol), cesiumcarbonate (2.15 g, 6.61 mmol), copper (I)-iodide (314.9 mg, 1.65 mmol) and butyronitrile (2 mL) are stirred in a glass pressure tube at 120° C. for 20 h. The reaction mixture is filtered via a glass microfibre filter, the solvent evaporated and the residue purified by chromatography (silicagel, eluents: dichloromethane/methanol). 217.9 mg (16.4%) of the title compound are obtained.

MS (CI+): 402 (M+) $^1$H-NMR (300 MHz, CDCl$_3$): δ=1.29 (3H), 4.00 (3H), 5.05 (1H), 5.42 (1H), 7.04 (1H), 7.23 (1H), 7.28-7.55 (5H), 7.22 (1H), 7.78-7.90 (2H), 8.08 (1H), 8.18-8.30 (2H).

Methyl 4-(5-{(1R,2S)-2-[(2-furylcarbonyl)amino]-1-phenylpropoxy}-1H-indazole-1-yl)benzoate Methyl 4-{5-[(1R,2S)-2-amino-1-phenylpropoxy]-1H-indazole-1-yl}benzoate (64.3 mg, 0.16 mmol) is dissolved in 6.1 mL of dichloromethane. Triethylamine (0.053 mL, 0.38 mmol) and 2-furoylchloride (20.9 mg, 0.16 mmol) are added. After 4 h stirring at r.t. the reaction mixture is diluted with dichloromethane, washed with water and brine and dried over Na$_2$SO$_4$. The reaction mixture is filtered, the solvent evaporated and the residue purified by chromatography (silicagel, eluents: ethyl acetate/hexane). 38.2 mg (48.1%) of the title compound are obtained.

MS (CI+): 496 (M+) $^1$H-NMR (300 MHz, CDCl$_3$): δ=1.32 (3H), 4.01 (3H), 4.69 (1H), 5.58 (1H), 6.53 (1H), 6.79 (1H), 7.04 (1H), 7.19 (1H), 7.23-7.55 (7H), 7.75 (1H), 7.79-7.89 (2H), 8.06 (1H), 8.19-8.29 (2H).

Example 117

N-{(1R,2S)-1-[1-(4-fluorophenyl)indazol-5-yl]oxy-1-phenylpropan-2-yl}-5-methyl-[1,3,4]oxadiazol-2-carboxamide

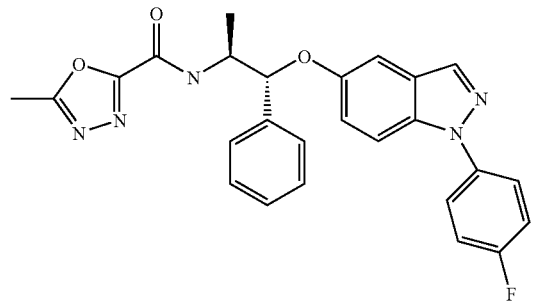

To a stirred solution of HATU (630 mg, 1.66 mmol) in DMF (1 ml) was added ethyldiisopropylamine (570 μl, 3.3 mmol), followed by 5-methyl-[1,3,4]oxadiazol carboxylic acid potassium salt (138 mg, 830 μmol) and stirred for 20 min. Then (1S,2R)-1-{[1-(4-fluorophenyl)-1H-indazol-5-yl]oxy}-1-phenylpropan-2-amine (300 mg, 830 mmol) in DMF (1 ml) was added to the brown/red solution and the stirring was continued for 24 h at r.t. The mixture was diluted by dichloromethane and filtrated through a path of silica gel. Solvent was removed under reduced pressure, and the residue was purified by preparative TLC on silica gel (hexane/acetone 50%). Yield 82 mg (21%).

ES$^+$-MS: m/z=472 [MH$^+$] $^1$H-NMR (300 MHz, CDCl$_3$) δ=7.95 (d, 1H), 7.62 (dd, 2H), 7.55 (d, 1H), 7.46-7.32 (m, 6H), 7.21 (dd, 2H), 7.18 (d, 1H), 6.95 (d, 1H), 5.46 (d, 1H), 4.63 (ddq, 1H), 2.62 (s, 3H), 1.30 (d, 3H).

Example 118

2-Methoxy-N-[1-methyl-2-phenyl-2-(1-pyridin-2-yl-1H-indazol-5-yloxy)-ethyl]acetamide

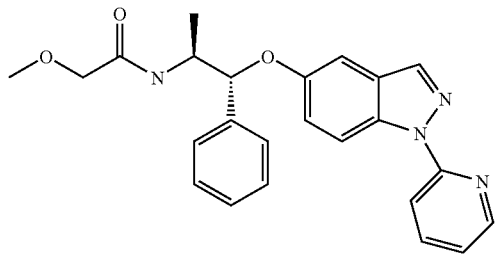

1-Methyl-2-phenyl-2-(1-pyridin-2-yl-1H-indazol-5-yloxy)-ethylamine (118a, 14 mg, 0.041 mmol), DIPEA (12 ul, 0.070 mmol) and acetonitrile (2 ml) were charged in a 7 ml vial. Methoxyacetyl chloride (12 ul, 0.13 mmol) was added, the vial was sealed and the solution stirred (magnetic bar) at r.t. for 1 h. Concentration and purification on C18 (Kromasil) with acetonitrile:water:TFA, 45:55:0.1 to 90:10:0.1 over 30 min, afforded 5 mg (29%) of 2-methoxy-N-[1-methyl-2-phenyl-2-(1-pyridin-2-yl-1H-indazol-5-yloxy)-ethyl]acetamide.

APCI-MS $^m$/z: 417.1 [MH$^+$] $^1$H NMR (300 MHz, (CD$_3$)$_2$CO) δ 8.58 (bs, 1H), 8.51-8.37 (m, 1H), 8.17-7.87 (m, 3H), 7.40 (s, 1H), 7.42-7.35 (m, 4H) 7.35-7.22 (m, 3H), 6.97 (s, 1H), 5.39 (d, 1H), 4.57-4.47 (m, 1H), 4.01 (q, 2H), 3.40 (s, 3H), 1.24 (d, 3H)

1-Methyl-2-phenyl-2-(1-pyridin-2-yl-1H-indazol-5-yloxy)-ethylamine (118a)

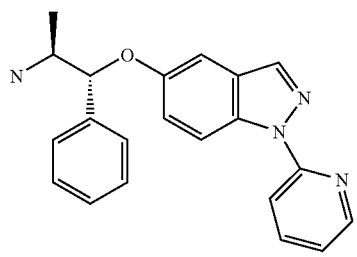

5-Iodo-1-pyridin-2-yl-1H-indazole (118b, 81 mg, 0.25 mmol), (1R,2S)-(−)-norephedrine (119 mg, 0.79 mmol) and butyronitrile (3 ml) were charged in a 7 ml vial. Copper(I) iodide (5.8 mg, 0.1 mol %) and cesium carbonate (261 mg, 0.8 mmol) were added, the vial was sealed and the solution was stirred (magnetic bar) at 125° C. for 2 h. Inorganic material was filtered off, and washed with ethyl acetate. The ethyl acetate phase was collected and concentrated and purified on silica with methanol:ethyl acetate 0:100 to 30:70 over 45 min. Pure fractions were pooled and concentrated to give 14 mg (16%) of 1-methyl-2-phenyl-2-(1-pyridin-2-yl-1H-indazol-5-yloxy)-ethylamine.

APCI-MS $^m$/z: 345.1 [MH$^+$]

5-Iodo-1-pyridin-2-yl-1H-indazole (118b)

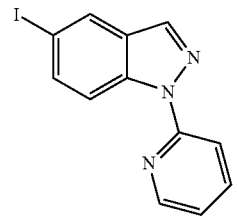

2-Fluoro-5-iodobenzaldehyde (527 mg, 2.11 mmol), 2-hydrazinopyridine (237 mg, 2.17 mmol), cesium carbonate (2.06 g, 6.32 mmol) and NMP (10 ml) werer charged in a 10 ml vial which was sealed and stirred (magnetic bar) over night at 100° C. Water and ethylacetate were added and the phases was separated. The organic layer was washed three times with brine and concentrated. Purification on silica with ethylacetate:heptane 5:95 to 10:90 over 15 min, 10 ml/min, followed by evaporation afforded 31 mg (5%) of 5-iodo-1-pyridin-2-yl-1H-indazole.

APCI-MS $^m$/z: 321.8 [MH$^+$] $^1$H NMR (300 MHz, CDCl$_2$) δ 8.64 (dt, 1H), 8.50 (dq, 1H), 8.13 (dd, 1H), 8.11 (d, 1H), 7.87-7.81 (m, 1H), 7.74 (dd, 1H).

Example 119

N-{2-[1-(6-Chloro-pyridazin-3-yl)-1H-indazol-5-yloxy]-1-methyl-2-phenyl-ethyl}-2,2,2-trifluoro-acetamide

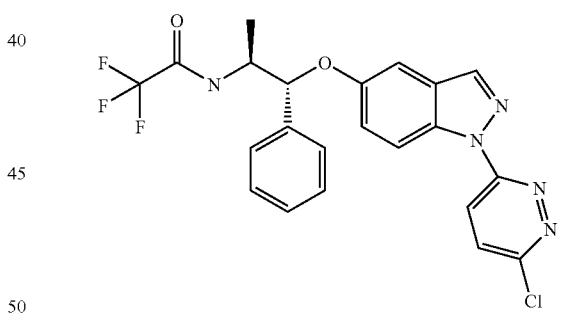

2-[1-(6-Chloro-pyridazin-3-yl)-1H-indazol-5-yloxy]-1-methyl-2-phenyl-ethylamine (119a, 29 mg, 0.076 mmol), trifluoroacetic anhydride (185 ul, 1.31 mmol), triethylamine (25 ul, 0.18 mmol) and dichloromethane (3 ml) were charged in a 7 ml vial. The vial was sealed and the solution stirred (magnetic bar) at r.t. for 18 h. Concentration and purification on C18 (Kromasil) with acetonitrile:water, 32:68 to 75:25 over 30 min, afforded 12 mg (33%) of N-{2-[1-(6-Chloro-pyridazin-3-yl)-1H-indazol-5-yloxy]-1-methyl-2-phenyl-ethyl}-2,2,2-trifluoro-acetamide.

APCI-MS $^m$/z: 475.9 [MH$^+$] $^1$H NMR (300 MHz, (CD$_3$CN) δ 8.59 (dt, 1H), 8.20 (d, 1H), 8.12 (d, 1H), 7.70 (d, 1H), 7.66 (bd, 1H) 7.45-7.25 (m, 6H), 7.10 (d, 1H), 5.39 (d, 1H), 4.46-4.32 (m, 1H), 1.31 (d, 3H).

2-[1-(6-Chloro-pyridazin-3-yl)-1H-indazol-5-yloxy]-1-methyl-2-phenyl-ethylamine (119a)

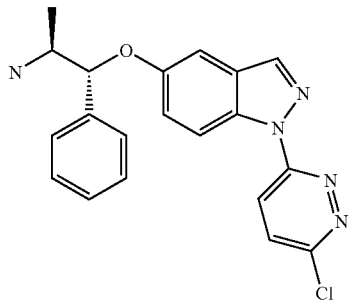

Prepared as described for 118a using 1-(6-Chloro-pyridazin-3-yl)-5-iodo-1H-indazole (119b). Yield 35 mg (7%). APCI-MS $^m$/z: 380.1 [MH$^+$]

1-(6-Chloro-pyridazin-3-yl)-5-iodo-1H-indazole (119b)

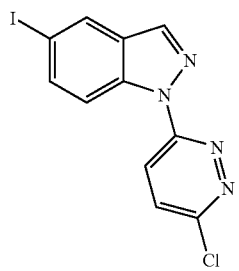

Prepared as described for 118b using 3-chloro-6-hydrazinopyridazine. Yield 687 mg (45%).
$^1$H NMR (300 MHz, (CD$_3$)$_2$SO) δ 8.55 (s, 1H), 8.49 (d, 1H), 8.37 (d, 1H), 8.34 (d, 1H), 8.08 (d, 1H), 7.93 (dd, 1H). APCI-MS $^m$/z: 356.8 (MH$^+$)

Example 120

2-Methoxy-N-[1-methyl-2-phenyl-2-(1-pyrimidin-2-yl-1H-indazol-5-yloxy)-ethyl]-acetamide

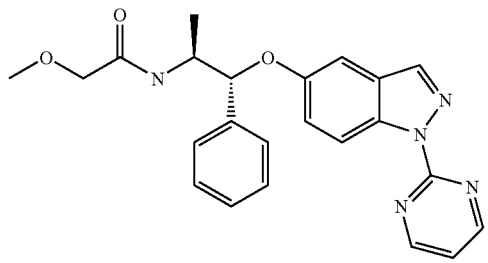

Prepared as in Example 118 using 1-methyl-2-phenyl-2-(1-pyrimidin-2-yl-1H-indazol-5-yloxy)-ethylamine (120a). Yield 7 mg (9%).
APCI-MS $^m$/z: 418.0 [MH+]$^1$H NMR (300 MHz, (CD$_3$CN) δ 8.80 (d, 2H), 8.61 (d, 1H), 8.10 (s, 1H), 7.47-7.24 (m, 7H), 7.11 (d, 1H), 6.91 (bd, 1H), 5.41 (d, 1H), 4.45-4.35 (m, 1H), 3.75 (q, 2H), 3.29 (s, 3H), 1.23 (d, 3H).

1-Methyl-2-phenyl-2-(1-pyrimidin-2-yl-1H-indazol-5-yloxy)-ethylamine (120a)

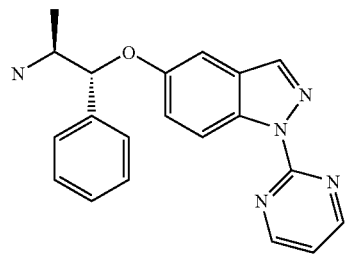

Prepared as described for 118a using 5-Iodo-1-pyrimidin-2-yl-1H-indazole (120b). Yield 66 mg (20%).
APCI-MS $^m$/z: 346.0 (MH$^+$)

5-Iodo-1-pyrimidin-2-yl-1H-indazole (120b)

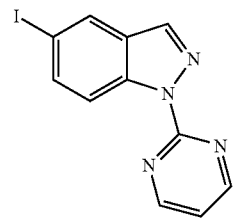

Prepared as described for 118b using 2-hydrazinopyrimidine. Yield 296 mg (24%).
APCI-MS $^m$/z: 322.9 [MH+]$^1$H NMR (300 MHz, (CD$_3$)$_2$SO) δ 8.94 (d, 2H), 8.50 (dt, 1H), 8.44 (d, 1H), 8.33 (dd, 1H), 7.87 (dd, 1H), 7.47 (t, 1H).

Example 121

N-[(1R,2S)-1-[1-(4-fluorophenyl)indazol-5-yl]oxy-1-(3-methoxyphenyl)propan-2-yl]-2-hydroxy-acetamide

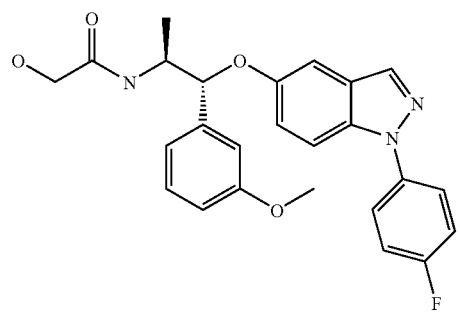

The title compound was prepared analogous to the method described in Example 21 starting from (1R,2S)-1-{[1-(4-fluorophenyl)-1H-indazol-5-yl]oxy}-1-(3-methoxyphenyl)

propan-2-amine (6a) (511 mg, 1.31 mmol), and Acetoxyacetyl chloride (155 μL, 1.44 mmol). Yield 429 mg (73%).

APCI-MS: m/z 450.1 [MH+]1H-NMR (300 MHz, DMSO-d6): δ 8.17 (d, 1H), 7.78-7.67 (m, 3H), 7.62 (d, 1H), 7.40 (t, 2H), 7.27 (t, 1H), 7.22 (dd, 1H), 7.11 (d, 1H), 7.00-6.94 (m, 2H), 6.83 (dd, 1H), 5.51 (t, 1H), 5.39 (d, J=5.04 Hz, 1H), 4.25 (m, 1H), 3.75 (m, 2H), 3.73 (s, 3H), 1.18 (d, 3H) ppm.

Example 122

2,2,2-trifluoro-N-((1R,2S)-1-(1-(4-fluorophenyl)-1H-indazol-5-yloxy)-1-(quinolin-3-yl)propan-2-yl)acetamide

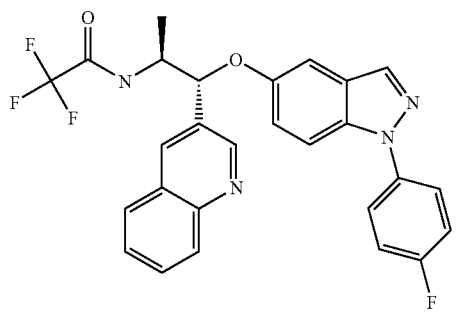

(1R,2S)-1-(1-(4-fluorophenyl)-1H-indazol-5-yloxy)-1-(quinolin-3-yl)propan-2-amine bis(2,2,2-trifluoroacetate) (65 mg, 0.10 mmol) was dissolved in MeOH (1.5 mL), 1,1,3,3-tetramethylguanidine (0.064 mL, 0.51 mmol) and ethyl trifluoroacetate (0.242 mL, 2.03 mmol) was added, the reaction mixture was stirred at r.t. for 2.5 h. Solvent was removed by evaporation and the residual material was purified by HPLC. Fractions was freezedried to give the product as a colourless powder. Yield 35 mg (67%)

APCI-MS: m/z 509.1 [MH+]1H-NMR (300 MHz, DMSO-d6): δ 9.64 (brs, 1H), 8.96 (d, 1H), 8.35 (d, 1H), 8.14 (d, 1H), 7.98 (m, 2H), 7.79-7.66 (m, 4H), 7.60 (m, 1H), 7.38 (m, 2H), 7.27 (m, 2H), 5.56 (d, 1H), 4.45 (m, 1H), 1.42 (d, 3H)

(1R,2S)-1-(1-(4-fluorophenyl-1H-indazol-5-yloxy)-1-(quinolin-3-propan-2-amine bis(2,2,2-trifluoroacetate) (122a)

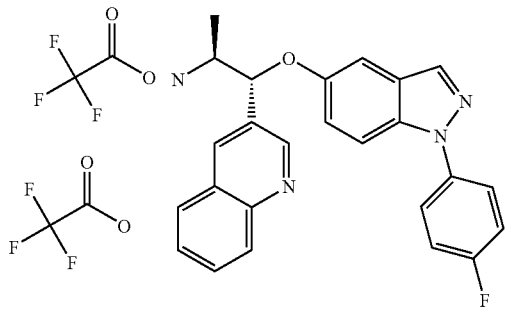

Following the procedure described in Example 19 (step 19a). Starting from (1R,2S)-2-amino-1-(quinolin-3-yl)propan-1-ol dihydrochloride (250 mg, 0.80 mmol), 1-(4-fluorophenyl)-5-iodo-1H-indazole (340 mg, 1.01 mmol), Cs2CO3 (1070 mg, 3.28 mmol) and CuI (36 mg, 0.19 mmol) in butyronitrile (4 mL), the reaction vessel was sealed and flushed with argon, the resulting slurry was stirred at +125° C. for 5 h, the temperature was then lowered to 100° C. and the mixture was stirred over night 16 h. Workup and purification by HPLC afforded the subtitle compound as a hygroscopic yellow powder. Yield 200 mg (39%)

APCI-MS m/z: 413.1 [MH+-2TFA]1H-NMR (300 Mhz, DMSO-d6): δ 9.01 (d, 1H), 8.41 (d, 1H), 8.26 (brs, 3H), 8.17 (d, 1H), 8.02 (t, 2H), 7.84-7.68 (m, 4H), 7.64 (m, 1H), 7.44-7.34 (m, 3H), 7.28 (d, 1H), 5.89 (d, J=3.32 Hz, 1H), 3.95 (m, 1H), 1.26 (d, 3H)

(1R,2S)-2-amino-1-(quinolin-3-yl)propan-1-ol dihydrochloride (122b)

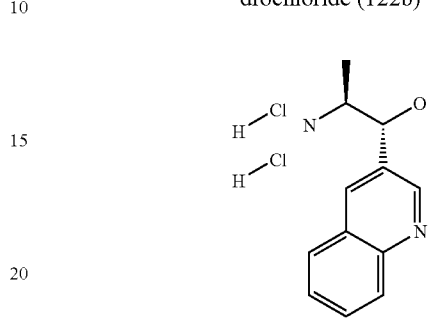

Following the procedure described in Example 19 (step 19b+19c). Starting from (S)-tert-butyl 1-oxo-1-(quinolin-3-yl)propan-2-ylcarbamate (1.6 g, 5.33 mmol), Aluminum isopropoxide (0.68 g, 3.33 mmol) and 2-propanol (4.5 mL, 59.16 mmol) in toluene (7 mL) stirred at +50° C. in sealed reaction tube flushed with argon for 16 h. Work up and deprotection of the intermediate BOC-protected amine afforded the subtitle compound as a colourless solid. Yield 1.29 g (88%).

APCI-MS m/z: 203 [MH+-2HCl]1H-NMR (400 Mhz, DMSO-d6): δ 9.23 (d, 1R), 8.97 (s, 1H), 8.42-8.24 (m, 5H), 8.06 (t, 1H), 7.89 (t, 1H), 6.68 (vbrs, 1H), 5.28 (d, J=3.72 Hz, 1H), 3.68 (m, 1H), 1.10 (d, 3H)

(S)-tert-butyl 1-oxo-1-(quinolin-3-yl)propan-2-ylcarbamate (122c)

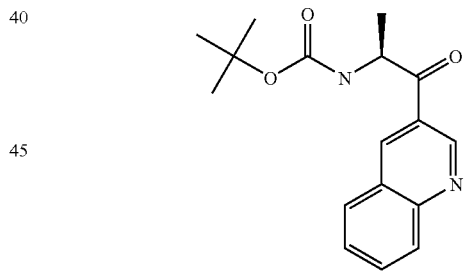

(S)-tert-butyl 1-(methoxy(methyl)amino)-1-oxopropan-2-ylcarbamate (2.5 g, 10.76 mmol) was suspended in THF (5 mL) and stirred at −10° C., isopropylmagnesium chloride 2.0M solution in THF (5.4 ml, 10.80 mmol) was added and a solution was formed. To this solution was added a solution of Lithium tri(3-quinolinyl)magnesiate in THF/Hexane, prepared from 3-bromoquinoline (1.471 ml, 10.81 mmol) according to the procedure described by Sylvain Dumouchel et-al. in *Tetrahedron* 59 (2003) 8629-8640. The mixture was stirred at −10° C. for 30 min and was the allowed to reach r.t. and stirred over night, 15 h. The reaction mixture, a clear red solution, was slowly poured into ice-cooled 1M HCl (aq) (100 mL). EtOAc (150 mL) was added and the mixture was stirred for a few min, the water phase was extracted once with EtOAc, the combined EtOAc solutions was further washed with saturated NaHCO3 (aq) and brine. The crude material was purified by flash-chromatography on silica using a gradient of 0% to 40% EtOAc in Heptane. The obtained material was the further purified by HPLC to afford the subtitle compound as a yellow sticky oil. Yield 1.6 g (49%)

APCI-MS m/z: 301.1 [MH$^+$]$^1$H-NMR (400 Mhz, CDCl$_3$): δ 9.44 (d, 1H), 8.81 (s, 1H), 8.20 (d, 1H), 7.98 (d, 1H), 7.89 (t, 1H), 7.67 (t, 1H), 5.53 (brd, 1H), 5.42 (m, 1H), 1.48 (d, 3H), 1.47 (s, 9H)

Example 123

N-((1R,2S)-1-(2,3-dihydrobenzo[b][1,4]dioxin-6-yl)-1-(1-(4-fluorophenyl)-1H-indazol-5-yloxy)propan-2-yl)-2-hydroxyacetamide

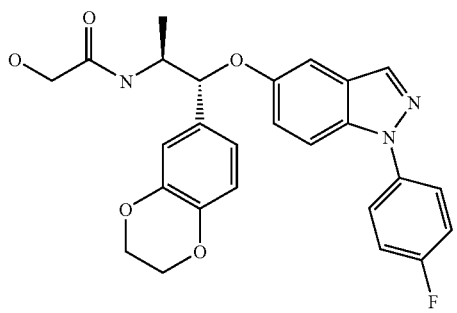

(1R,2S)-1-(2,3-dihydrobenzo[b][1,4]dioxin-6-yl)-1-(1-(4-fluorophenyl)-1H-indazol-5-yloxy)propan-2-amine 2,2,2-trifluoroacetate. (19a) (0.16 g, 0.30 mmol) and N,N-diisopropylethylamine (0.16 mL, 0.92 mmol) in THF (3 mL) was treated with acetoxyacetyl chloride (0.04 mL, 0.37 mmol). The mixture was stirred at ambient temperature for 1 h. LC/MS showed formation of intermediate hydroxyacetyl compound, MH+=520, no unreacted amine remained. To the reaction mixture was added water (1 mL), 28% ammonia solution in water (1 mL) and MeOH (0.5 mL. The mixture was stirred at r.t. over night. The solvents was removed by evaporation and the residual material was purified by HPLC. Fractions with product was freezedried. Yield 79 mg (55%)

APCI-MS: m/z 478.1 [MH$^+$]$^1$H-NMR (400 MHz, DMSO-d$_6$): δ 8.18 (d, 1H), 7.74 (m, 2H), 7.69 (d, 1H), 7.58 (d, 1H), 7.40 (t, 2H), 7.19 (dd, 1H), 7.11 (d, 1H), 6.89-6.69 (m, 3H), 5.51 (t, 1H), 5.32 (d, 1H), 4.19 (m+s, 1H+4H), 3.75 (m, 2H), 1.17 (d, 3H)

Example 124

N-((1R,2S)-1-(2,3-dihydrobenzo[b][1,4]dioxin-6-yl)-1-(1-(4-fluorophenyl)-1H-indazol-5-yloxy)propan-2-yl)-1-methylcyclopropanecarboxamide

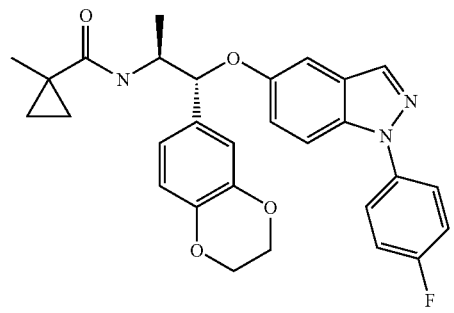

1-methylcyclopropanecarboxylic acid (39 mg, 0.39 mmol), HATU (150 mg, 0.39 mmol) and DIPEA (170 μl, 0.97 mmol) in NMP (2 mL) was stirred at r.t. for 5 min until a solution had formed. To this solution was added (1R,2S)-1-(2,3-dihydrobenzo[b][1,4]dioxin-6-yl)-1-(1-(4-fluorophenyl)-1H-indazol-5-yloxy)propan-2-amine (19a) (102 mg, 0.24 mmol) dissolved in NMP (1 mL). The reaction mixture was stirred for 2 h at r.t. The reaction mixture was diluted with water (10 mL) and extracted with EtOAc (2×10 mL), the organic phases was then washed with brine, dried over Na2SO4, filtered and evaporated. The remaining oily residue was purified by HPLC. Fractions containing product was freezedried. Yield 68 mg (55%10).

APCI-MS: m/z 502.2 [MH$^+$]$^1$H-NMR (300 MHz, DMSO-d$_6$): δ 8.19 (d, 1H), 7.79-7.65 (m, 3H), 7.40 (m, 2H), 7.27 (d, 1H), 7.18 (dd, 1H), 7.09 (d, 1H), 6.88-6.77 (m, 3H), 5.19 (d, 1H), 4.19 (s, 4H), 4.12 (m, 1H), 1.21 (d, 3H), 1.18 (s, 3H), 0.80 (m, 2H), 0.41 (m, 2H) ppm.

Example 125

(S)-N-((1R,2S)-1-(2,3-dihydrobenzo[b][1,4]dioxin-6-yl)-1-(1-(4-fluorophenyl)-1H-indazol-5-yloxy)propan-2-yl)pyrrolidine-2-carboxamide

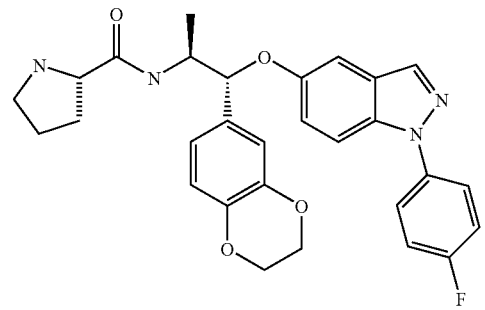

(1R,2S)-1-(2,3-dihydrobenzo[b][1,4]dioxin-6-yl)-1-(1-(4-fluorophenyl)-1H-indazol-5-yloxy)propan-2-amine (19a) (102 mg, 0.24 mmol) dissolved in NMP (1 mL) was added to a solution of (S)-1-(tert-butoxycarbonyl)pyrrolidine-2-carboxylic acid (77 mg, 0.36 mmol), HATU (150 mg, 0.39 mmol) and DIPEA (170 μl, 0.97 mmol) in NMP (2 mL). The mixture was stirred at r.t. for 1 h. The reaction mixture was diluted with water (10 mL) and extracted with EtOAc (2×10 mL), the organic solution was washed with brine, dried (Na2SO4), filtered and evaporated to give an oily residue. The obtained material was dissolved in EtOAc (20 mL) and treated with 5-6N HCl in 2-Propanol (5 mL), the solution was stirred at +40° C. for 1 h. Solvents was removed by evaporation. The crude material was purified by HPLC, relevant fractions was freezedried to give the title compound as a colourless solid. Yield 21 mg (16%)

APCI-MS: m/z 517.0 [MH$^+$]$^1$H-NMR (300 MHz, DMSO-d$_6$): δ 8.18 (d, 1H), 8.02 (d, 1H), 7.74 (m, 2H), 7.68 (d, 1H), 7.40 (m, 1H), 7.19 (dd, 1H), 7.13 (d, 1H), 6.88-8.78 (m, 3H), 5.28 (d, 1H), 4.19 (s, 4H), 4.10 (m, 1H), 3.43 (m, 1H), 3.20-2.60 (vbrs, 1H), 2.73 (m, 2H), 1.85 (m, 1H), 1.52 (m, 3H), 1.13 (d, 3H) ppm.

Example 126

N-((1R,2S)-1-(1-(4-chlorophenyl)-1H-indazol-5-yloxy)-1-(3-methoxyphenyl)propan-2-yl)-2,2,2-trifluoroacetamide

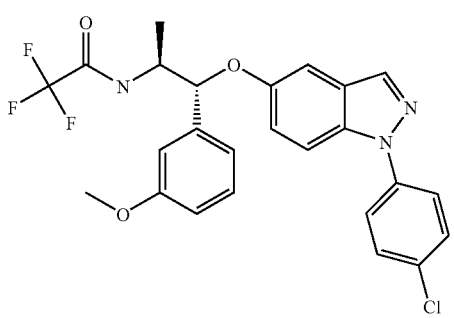

(1R,2S)-1-(1-(4-chlorophenyl)-1H-indazol-5-yloxy)-1-(3-methoxyphenyl)propan-2-amine (250 mg, 0.61 mmol) was dissolved in THF (5 mL), N,N-diisopropylethylamine (255 µl, 1.54 mmol) was added. Trifluoroacetic anhydride (105 µl, 0.74 mmol) was added and the mixture was stirred at r.t. for 30 min. The reaction mixture was concentrated and the residual material was purified by HPLC, C-18, 50-90% MeCN/water gradient, the pure fractions was combined and freeze dried. Yield: 187 mg (60%).

APCI-MS: m/z 504.1 [MH+] $^1$H-NMR (300 MHz, DMSO-$d_6$): δ 9.51 (brd, 1H), 8.21 (d, 1H), 7.76 (m, 3H), 7.61 (m, 2H), 7.29-7.19 (m, 2H), 7.14 (d, 1H), 7.00-6.93 (m, 2H), 6.84 (m, 1H), 5.27 (d, 1H), 4.24 (m, 1H), 3.72 (s, 3H), 1.33 (d, 3H) ppm.

(1R,2S)-1-(1-(4-chlorophenyl)-1H-indazol-5-yloxy)-1-(3-methoxyphenyl)propan-2-amine (126a)

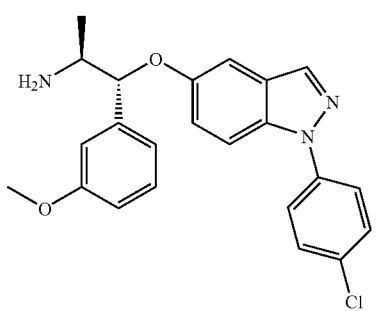

The subtitle compound was prepared analogous to the method described in Example 6 (step 6a). Starting from the hydrochloride salt of (1R,2S)-2-amino-1-(3-methoxyphenyl)propan-1-ol (6b) (0.88 g, 4.04 mmol), 1-(4-chlorophenyl)-5-iodo-1H-indazole (1.720 g, 4.85 mmol), CuI (0.154 g, 0.81 mmol) and cesium carbonate (3.95 g, 12.13 mmol) in butyronitrile (14 mL) stirred at +110° C. for 16 h. Work up and final purification by HPLC was followed by extraction of product into EtOAc from basic water solution, evaporation of solvents gave the subtitle compound as a sticky oil. Yield 490 mg (29%)

APCI-MS: m/z 408.1 [MH+] $^1$H-NMR (400 MHz, CD$_3$OD): δ 8.01 (d, 1H), 7.66 (d, 2H), 7.62 (d, 1H), 7.53 (d, 2H), 7.27 (t, 1H), 7.23 (dd, 1H), 7.09 (d, 1H), 7.02-6.96 (m, 2H), 6.84 (ddd, 1H), 5.10 (d, 1H), 3.76 (s, 3H), 3.27 (m, 1H), 1.20 (d, 3H)

1-(4-chlorophenyl)-5-iodo-1H-indazole (126b)

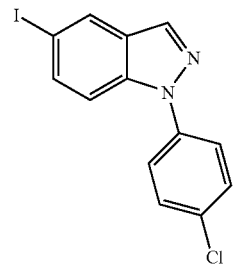

4-chlorophenylhydrazine hydrochloride (5.24 g, 29.27 mmol), 2-fluoro-5-iodobenzaldehyde (7.5 g, 30.00 mmol) and cesium carbonate (22.8 g, 69.98 mmol) was suspended in NMP (120 mL) and stirred at ambient temperature for 45 min. The temperature was raised to +160° C. and the reaction mixture was stirred for 1 h, the now black suspension was allowed to reach r.t. Water was added, the slurry was extracted with EtOAc (500 mL. The organic phase was washed with brine (2×). The brine fractions and waterphase were combined and backextracted once with EtOAc. This second EtOAc phase was washed with brine (2×) before combined with the previous EtOAc phase. The organic phases were dried over Na$_2$SO$_4$, filtered and evaporated. The black residue were dissolved in DCM/Heptane (=1/1) and filtered through a silica column, and the column was then further eluted with DCM/Heptane (=1/1) solvent mixture. The fractions containing product was evaporated, residue was dissolved in EtOAc and Heptane was added, evaporation and diluting with Heptane afforded a slurry, the solid material was collected by filtration and washed with Heptane. Yield 2.82 g (27%)

APCI-MS: m/z 354.9 [MH+] $^1$H-NMR (300 MHz, DMSO-$d_6$): δ 8.36 (d, J=0.79 Hz, 1H), 8.32 (dd, J=0.66 Hz, 1.46 Hz, 1H), 7.80 (m, 2H), 7.73 (d, J=1.54 Hz, 1H), 7.71 (t, unresolved, 1H), 7.65 (m, 2H)

Example 127

N-((1R,2S)-1-(2,3-dihydrobenzo[b][1,4]dioxin-6-yl)-1-(1-(4-fluorophenyl)-1H-indazol-5-yloxy)propan-2-yl)-2,2-difluoropropanamide

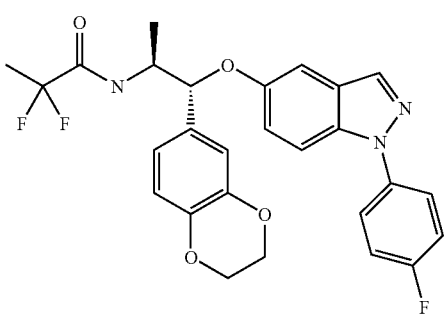

(1R,2S)-1-(2,3-dihydrobenzo[b][1,4]dioxin-6-yl)-1-(1-(4-fluorophenyl)-1H-indazol-5-yloxy)propan-2-amine 2,2,2-trifluoroacetate. (19a) (316 mg, 0.59 mmol) was partitioned between EtOAc and 1M NaOH (aq) solution. The organic phase was washed with brine, dried (MgSO₄), filtered and evaporated to give 256 mg of the free amine as a sticky oil. This material was dissolved in NMP (3.5 mL) and added to a stirred solution of 2,2-difluoropropanoic acid (104 mg, 0.95 mmol), HATU (360 mg, 0.95 mmol) and DIPEA (0.414 mL, 2.37 mmol) in NMP (1.5 mL). The reaction mixture was stirred at r.t. for 2 h. Additional 2,2-difluoropropanoic acid (80 mg, 0.73 mmol), HATU (278 mg, 0.73 mmol) and DIPEA (0.25 mL, 1.4 mmol) in NMP (1.5 mL) was added. The reaction mixture was stirred at r.t. for one more h. Water (50 mL) was added, the mixture was extracted with EtOAc (2×50 mL), the organic phase was washed with 10% NaHSO₄ (aq), brine, dried over MgSO₄, filtered and evaporated to give a crude product that was purified by HPLC. The fractions containing the product was combined and freeze dried. Yield 155 mg (51%).

APCI-MS: m/z 512.0 [MH⁺] ¹H-NMR (400 MHz, DMSO-d₆): δ 8.65 (d, J=8.49 Hz, 1H), 8.19 (d, J=0.53 Hz, 1H), 7.74 (m, 2H), 7.69 (d, 1H), 7.40 (t, 2H), 7.18 (dd, 1H), 7.11 (d, 1H), 6.89-6.78 (m, 3H), 5.16 (d, J=6.72 Hz, 1H), 4.18 (s, 4H), 4.17 (m, 1H), 1.55 (t, J=19.46 Hz, 3H), 1.29 (d, J=6.72 Hz, 3H) ppm.

Example 128

N-((1R,2S)-1-(1-(4-chlorophenyl)-1H-indazol-5-yloxy)-1-(3-methoxyphenyl)propan-2-yl)-2,2-difluoropropanamide

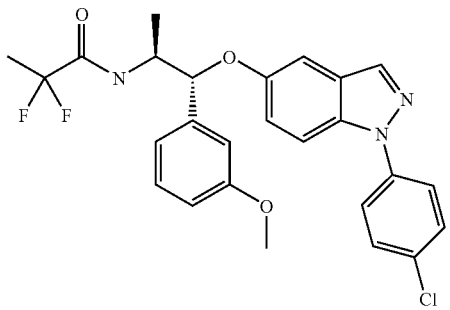

(1R,2S)-1-(1-(4-chlorophenyl)-1H-indazol-5-yloxy)-1-(3-methoxyphenyl)propan-2-amine (126a) (256 mg, 0.63 mmol) dissolved in NMP (3.5 mL) was added to a solution of 2,2-difluoropropanoic acid (111 mg, 1.00 mmol), HATU (382 mg, 1.00 mmol) and DIPEA (0.438 mL, 2.51 mmol) in NMP (1.5 mL). The reaction mixture was stirred at r.t. for 2 h. Additional 2,2-difluoropropanoic acid (80 mg, 0.73 mmol), HATU (278 mg, 0.73 mmol) and DIPEA (0.25 mL, 1.4 mmol) in NMP (1.5 mL) was added. The reaction mixture was stirred at r.t. for another h. Water (50 mL) was added, the mixture was extracted with EtOAc (2×50 mL), the organic phase was washed with 10% NaHSO4 (aq), brine, dried over MgSO₄, filtered and evaporated to give a crude product that was purified by HPLC. The fractions containing the product was combined and freeze dried. Yield 197 mg (62%).

APCI-MS: m/z 500.3 [MH⁺] ¹H-NMR (400 MHz, DMSO-d₆): δ 8.69 (d, 1H), 8.21 (d, 1H), 7.76 (d, 3H), 7.60 (d, 2H), 7.28-7.19 (m, 2H), 7.13 (d, 1H), 7.00-6.93 (m, 2H), 6.82 (dd, 1H), 5.24 (d, 1H), 4.21 (m, 1H), 3.72 (s, 3H), 1.52 (t, 3H), 1.31 (d, 3H) ppm.

Example 129

2,2,2-Trifluoro-N-[(1R,2S)-1-phenyl-1-(1-propan-2-ylindazol-5-yl)oxy-propan-2-yl]acetamide

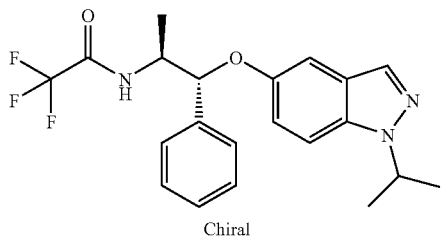

The title compound was prepared from (1R,2S)-1-[(1-isopropyl-1H-indazol-5-yl)oxy]-1-phenylpropan-2-amine (129b, 31 mg, 100 μmol) and trifluoroacetic anhydride (63 mg, 300 μmol) as described in Example 1. Yield 28 mg (70%).

APCI-MS: m/z 406 [MH⁺] ¹H NMR (400 MHz, d₆-acetone) δ 8.57 (d, J=6.7 Hz, 1H), 7.74 (s, 1H), 7.49 (dd, J=10.5, 9.1 Hz, 3H), 7.37 (t, J=7.5 Hz, 2H), 7.28 (m, 1H), 7.12 (dd, J=9.1, 2.4 Hz, 1H), 7.01 (d, J=2.3 Hz, 1H), 5.44 (d, J=5.0 Hz, 1H), 4.88 (septet, J=6.6 Hz, 1H), 4.41 (sextet, J=6.8 Hz, 1H), 1.47 (dd, J=6.5, 3.5 Hz, 6H), 1.37 (d, J=6.9 Hz, 3H).

(1R,2S)-1-[(1-isopropyl-1H-indazol-5-yl)oxy]-1-phenylpropan-2-amine (129b)

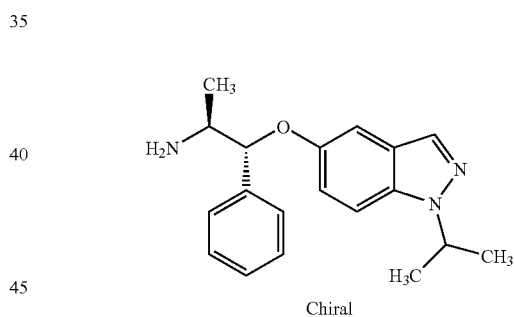

A mixture of 5-iodo-1-isopropyl-1H-indazole (129c, 461 mg, 1.26 mmol), (1R,2S)-2-amino-1-phenylpropan-1-ol (286 mg, 1.89 mmol), copper (I) iodide (25 mg, 130 μmol), and cesium carbonate (1.45 g, 3.8 mmol) in butyronitrile (5 ml) was stirred at 125° C. for 2 h. Then the mixture was cooled to r.t., the inorganic material was removed by filtration and washed with ethyl acetete. The combined organic solutions were concentrated in vacuo, and the product purified by flash chromatography on silica gel (ethyl acetate/methanol). Yield 200 mg (51%) of a brown oil.

APCI-MS: m/z 310 [MH⁺] ¹H NMR (400 MHz, DMSO-d₆/D₂O/TFA) δ 7.80 (s, 1H), 7.53 (d, J=9.0 Hz, 1H), 7.40 (d, J=7.1 Hz, 2H), 7.33 (t, J=7.5 Hz, 2H), 7.24 (m, 1H), 7.08 (dd, J=9.0, 2.3 Hz, 1H), 6.98 (d, J=2.1 Hz, 1H), 5.75 (s, 1H), 5.03 (d, J=5.3 Hz, 1H), 4.86 (septet, J=6.7 Hz, 1H), 3.15 (quintet, J=6.0 Hz, 1H), 1.41 (dd, J=6.4, 5.5 Hz, 6H), 1.06 (d, J=6.5 Hz, 3H).

5-Iodo-1-isopropyl-1H-indazole (129c)

A mixture of 5-iodo-1H-indazole (488 mg, 2 mmol), isopropyl bromide (244 mg, 2 mmol), and KOtBu (336 mg, 3 mmol) in dry DMF (4 ml) was stirred at r.t. overnight. Then it was diluted with ethyl acetate (50 ml), washed with water (2×50 ml), and dried with $Na_2SO_4$. Evaporation of solvent and purification by flash chromatography on silica gel (n-heptane/ethyl acetate) afforded the subtitle compound (298 mg, 52%) along with 5-iodo-2-isopropyl-2H-indazole (227 mg, 40%).

APCI-MS: m/z 287 [MH$^+$]$^1$H NMR (400 MHz, CDCl$_3$) δ 8.11 (d, J=0.9 Hz, 1H), 7.94 (s, 1H), 7.60 (dd, J=8.8, 1.5 Hz, 1H), 7.26 (d, J=8.8 Hz, 1H), 4.83 (septet, J=6.8 Hz, 1H), 1.61 (d, J=6.7 Hz, 6H)

Example 130

N-[(1R,2S)-1-(1-cyclopentylindazol-5-yl)oxy-1-phenyl-propan-2-yl]-2,2,2-trifluoro-acetamide

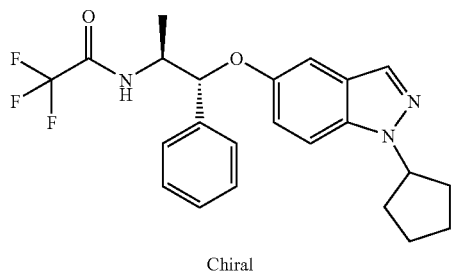
Chiral

The title compound was prepared from (1R,2S)-1-[(1-cyclopentyl-1H-indazol-5-yl)oxy]-1-phenylpropan-2-amine (130b, 17 mg, 51 µmol) and trifluoroacetic anhydride (32 mg, 153 µmol) as described in Example 1. Yield 14 mg (64%).

APCI-MS: m/z 432 [MH$^+$]$^1$H NMR (400 MHz, d$_6$-acetone) δ 8.57 (d, J=7.4 Hz, 1H), 7.73 (s, 1H), 7.49 (m, 3H), 7.37 (t, J=7.5 Hz, 2H), 7.28 (t, J=7.3 Hz, 1H), 7.12 (dd, J=9.1, 2.4 Hz, 1H), 7.01 (d, J=2.1 Hz, 1H), 5.44 (d, J=5.0 Hz, 1H), 5.05 (quintet, J=7.0 Hz, 1H), 4.41 (sextet, J=6.8 Hz, 1H), 2.07-2.16 (m, 4H, partially covered with the signal of solvent), 1.83-1.93 (m, 2H), 1.65-1.76 (m, 2H), 1.37 (d, J=6.9 Hz, 3H).

(1R,2S)-1-[(1-cyclopentyl-1H-indazol-5-yl)oxy]-1-phenylpropan-2-amine (130b)

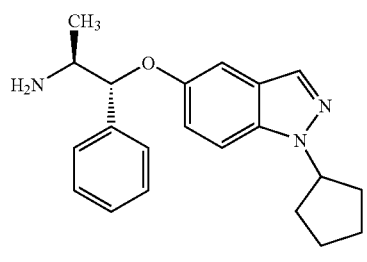
Chiral

Prepared from 1-cyclopentyl-5-iodo-1H-indazole (130c, 158 mg, 500 µmol) as described for 129b. Yield 34 mg (20%).
APCI-MS: m/z 336 [MH$^+$]

1-Cyclopentyl-5-iodo-1H-indazole (130c)

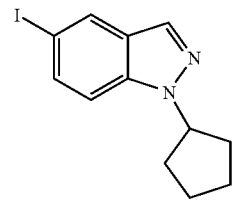

A mixture of 2-fluoro-5-iodobenzaldehyde (500 mg, 2 mmol), cyclopentylhydrazine (273 mg, 2 mmol), and cesium carbonate (1.91 g, 5 mmol) in NMP (5 ml) was stirred at 100° C. overnight. Then KOtBu (560 mg, 5 mmol) and DMF (10 ml) were added, and the mixture was stirred at 150° C. for 5 h. After cooling to r.t., the mixture was diluted with ethyl acetate (100 ml), and washed with water (3×50 ml), and dried. Evaporation of solvent afforded batch residue, which was dissolved in acetonitrile (50 ml), and the insoluble material was removed by filtration. Flash chromatography on silica gel (n-heptane/ethyl acetate) afforded yellow oil, 158 mg (25%).

APCI-MS: m/z 313 [MH$^+$]$^1$H NMR (400 MHz, CDCl$_3$) δ 8.08 (d, J=0.9 Hz, 1H), 7.91 (s, 1H), 7.59 (dd, J=8.8, 1.5 Hz, 1H), 7.26 (d, J=9.4 Hz, 1H, partially covered with the signal of solvent), 4.95 (quintet, J=7.4 Hz, 1H), 2.17 (m, 4H), 1.98 (m, 2H), 1.75 (m, 2H).

Example 131

N-[(1R,2S)-1-[1-(4-fluorophenyl)indazol-5-yl]oxy-1-(3-methoxyphenyl)propan-2-yl]-5-methyl-thiophene-2-carboxamide

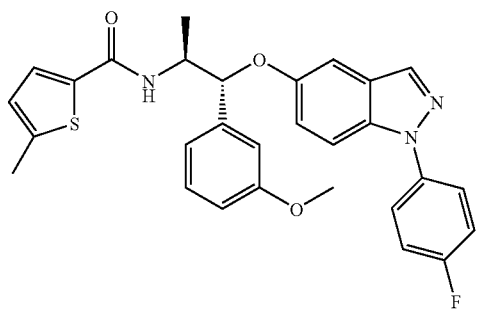
Chiral

Prepared as described in Example 105 using (1R,2S)-1-{[1-(4-fluorophenyl)-1H-indazol-5-yl]oxy}-1-(3-methoxyphenyl)propan-2-amine (6a, 39 mg, 100 µmol) and 5-methyl-2-thiophenecarboxylic acid (28 mg, 200 µmol). Yield 42 mg (81%).

APCI-MS: m/z 516 [MH$^+$]$^1$H NMR (400 MHz, d$_6$-acetone) δ 8.02 (d, J=0.7 Hz, 1H), 7.75 (m, 2H), 7.68 (d, J=9.2 Hz, 2H), 7.47 (d, J=3.7 Hz, 1H), 7.23-7.36 (m, 4H), 7.14 (d, J=2.3 Hz, 1H), 7.08 (m, 2H), 6.84 (m, 1H), 6.73 (dd, J=3.7, 1.1 Hz, 1H), 5.56 (d, J=3.9 Hz, 1H), 4.49 (m, 1H), 3.77 (s, 3H), 2.45 (s, 3H), 1.32 (d, J=7.1 Hz, 3H).

Example 132

N-[(1R,2S)-1-[1-(4-fluorophenyl)indazol-5-yl]oxy-1-(3-methoxyphenyl)propan-2-yl]-3-methyl-thiophene-2-carboxamid

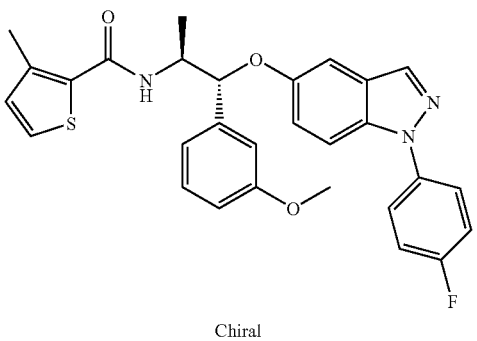

Chiral

Prepared as described in Example 105 using (1R,2S)-1-{[1-(4-fluorophenyl)-1H-indazol-5-yl]oxy}-1-(3-methoxyphenyl)propan-2-amine (6a, 39 mg, 100 µmol) and 3-methyl-2-thiophenecarboxylic acid (28 mg, 200 µmol). Yield 43 mg (98%).

APCI-MS: m/z 516 [MH$^+$] $^1$H NMR (400 MHz, d$_6$-acetone) δ 8.04 (d, J=0.7 Hz, 1H), 7.77 (m, 2H), 7.70 (d, J=9.2 Hz, 1H), 7.41 (d, J=5.0 Hz, 1H), 7.26-7.37 (m, 4H), 7.18 (d, J=2.3 Hz, 1H), 7.08-7.14 (m, 3H), 6.88 (d, J=5.0 Hz, 1H), 6.86 (m, 1H), 5.59 (d, J=4.4 Hz, 1H), 4.53 (m, 1H), 3.78 (s, 3H), 2.38 (s, 3H), 1.34 (d, J=6.9 Hz, 3H).

Example 133

N-[(1R,2S)-1-[1-(4-fluorophenyl)indazol-5-yl]oxy-1-(3-methoxyphenyl)propan-2-yl]-1-methyl-pyrrole-2-carboxamide

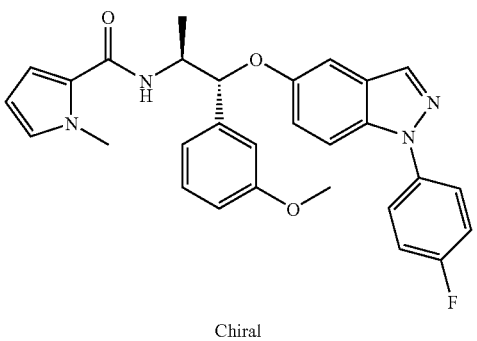

Chiral

Prepared as described in Example 105 using (1R,2S)-1-{[1-(4-fluorophenyl)-1H-indazol-5-yl]oxy}-1-(3-methoxyphenyl)propan-2-amine (6a, 39 mg, 100 mmol) and 1-methyl-2-pyrrolecarboxylic acid (25 mg, 200 µmol). Yield 35 mg (70%).

APCI-MS: m/z 499 [MH$^+$] $^1$H NMR (400 MHz, d$_6$-acetone) δ 8.03 (d, J=0.7 Hz, 1H), 7.76 (m, 2H), 7.69 (d, J=9.0 Hz, 1H), 7.24-7.36 (m, 4H), 7.14 (d, J=2.3 Hz, 1H), 7.09 (m, 2H), 6.84 (m, 1H), 6.78 (t, J=2.0 Hz, 1H), 6.68 (dd, J=3.9, 1.6 Hz, 1H), 5.95 (dd, J=3.9, 2.7 Hz, 1H), 5.53 (d, J=4.2 Hz, 1H), 4.49 (m, 1H), 3.87 (s, 3H), 3.77 (s, 3H), 1.31 (d, J=6.9 Hz, 3H).

Example 134

N-[(1R,2S)-1-[1-(4-fluorophenyl)indazol-5-yl]oxy-1-(3-methoxyphenyl)propan-2-yl]thiophene-3-carboxamide

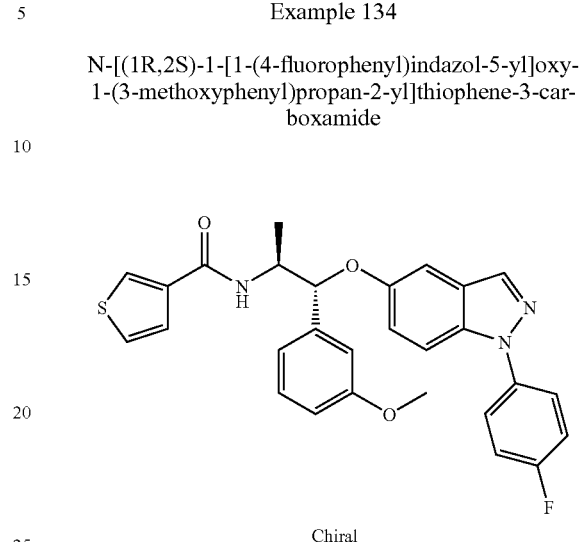

Chiral

Prepared as described in Example 105 using (1R,2S)-1-{[1-(4-fluorophenyl)-1H-indazol-5-yl]oxy}-1-(3-methoxyphenyl)propan-2-amine (6a, 39 mg, 100 µmol) and 3-thiophenecarboxylic acid (38 mg, 300 µmol). Yield 47 mg (94%).

APCI-MS: m/z 502 [MH$^+$] $^1$H NMR (400 MHz, d$_6$-acetone) δ 8.04 (dd, J=2.9, 1.1 Hz, 12H), 8.02 (d, J=0.7 Hz, 1H), 7.66-7.79 (m, 4H), 7.50 (dd, J=5.1, 1.2 Hz, 1H), 7.45 (dd, J=5.1, 3.0 Hz, 1H), 7.24-7.36 (m, 4H), 7.14 (d, J=2.3 Hz, 1H), 7.09 (m, 1H), 6.84 (m, 1H), 5.58 (d, J=4.1 Hz, 1H), 4.52 (m, 1H), 3.78 (s, 3H), 1.33 (d, J=6.9 Hz, 3H).

Example 135

N-[(1R,2S)-1-[1-(4-fluorophenyl)indazol-5-yl]oxy-1-(3-methoxyphenyl)propan-2-yl]1,3-thiazole-2-carboxamide

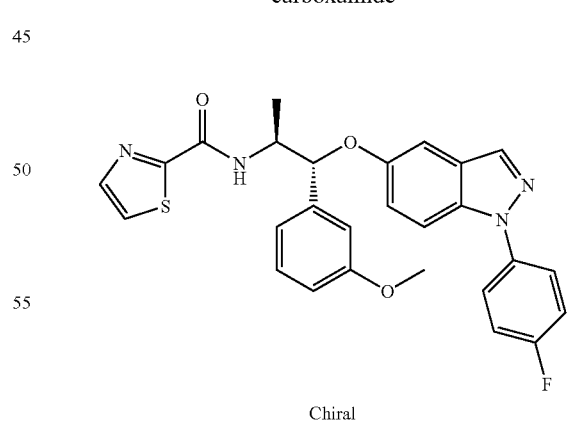

Chiral

Prepared as described in Example 1 using (1R,2S)-1-{[1-(4-fluorophenyl)-1H-indazol-5-yl]oxy}-1-(3-methoxyphenyl)propan-2-amine (6a, 20 mg, 50 µmol) and 1,3-thiazole-2carbonyl chloride (23 mg, 150 µmol). Yield 25 mg (97%).

APCI-MS: m/z 503 [MH$^+$] $^1$H NMR (400 MHz, d$_6$-acetone) δ 8.03 (d, J=0.7 Hz, 1H), 7.98 (d, J=8.8 Hz, 1H), 7.91

(d, J=3.2 Hz, 1H), 7.87 (d, J=3.2 Hz, 1H), 7.76 (m, 2H), 7.69 (d, J=9.2 Hz, 1H), 7.26-7.36 (m, 4H), 7.19 (d, J=2.3 Hz, 1H), 7.10 (m, 2H), 6.85 (m, 1H), 5.61 (d, J=4.4 Hz, 1H), 4.57 (m, 1H), 3.77 (s, 3H), 1.40 (d, J=6.7 Hz, 3H).

Example 136

N-[(1R,2S)-1-[1-(4-fluorophenyl)indazol-5-yl]oxy-1-(3-methoxyphenyl)propan-2-yl]-5-methyl-1,2-oxazole-3-carboxamide

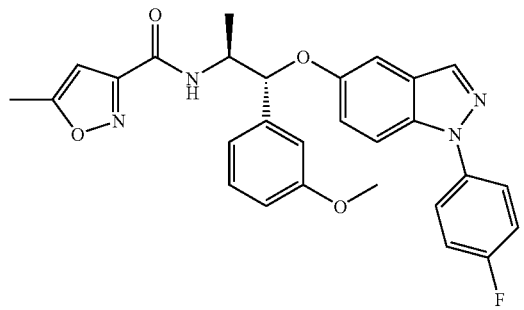

Chiral

Prepared as described in Example 1 using (1R,2S)-1-{[1-(4-fluorophenyl)-1H-indazol-5-yl]oxy}-1-(3-methoxyphenyl)propan-2-amine (6a, 20 mg, 50 µmol) and 5-methylisoxazole-3-carbonyl chloride (22 mg, 150 µmol). Yield 19 mg (74%).

APCI-MS: m/z 501 [MH+] $^1$H NMR (400 MHz, d$_6$-acetone) δ 8.04 (d, J=0.5 Hz, 1H), 7.77 (m, 2H), 7.70 (d, J=9.2 Hz, 2H), 7.25-7.37 (m, 4H), 7.17 (d, J=2.1 Hz, 1H), 7.09 (m, 2H), 6.85 (dd, J=8.2, 1.9 Hz, 1H), 6.41 (d, J=0.7 Hz, 1H), 5.56 (d, J=4.6 Hz, 1H), 4.56 (m, 1H), 3.78 (s, 3H), 2.44 (d, J=0.5 Hz, 3H), 1.37 (d, J=6.9 Hz, 3H).

Example 137

N-[2-[1-(4-fluorophenyl)indazol-5-yl]oxy-2-phenylacetyl]-2-methyl-propanamide

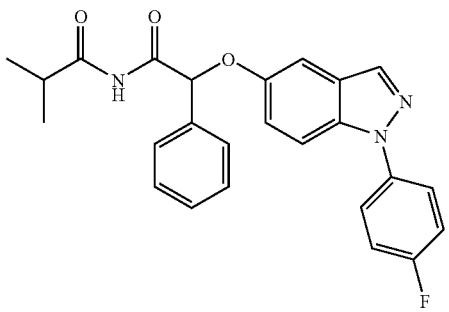

A stirred solution of 2-(1-(4-fluorophenyl)-1H-indazol-5-yloxy)-2-phenylacetamide (137b, 20 mg, 60 µmol) in THF (2 ml) was cooled to 0° C., and potassium 2-methylpropan-2-olate (18.6 mg, 170 µmol) was added. The mixture was stirred at 0° C. for 10 min, and a solution of 2-methylpropanoyl chloride (30 mg, 280 µmol) in THF (0.5 ml) was added. Stirring was continued for 30 min at 0° C. Then the sample was concentrated in vacuo and purified by semi-prep. HPLC go give white solid material, 14 mg (59%).

APCI-MS: m/z 432 [MH+] $^1$H NMR (400 MHz, d$_6$-DMSO) δ 10.98 (s, 1H), 8.28 (d, J=0.7 Hz, 1H), 7.77 (m, 3H), 7.60 (m, 2H), 7.47-7.36 (m, 5H), 7.26 (m, 2H), 6.24 (s, 1H), 2.89 (septet, J=6.9 Hz, 1H), 1.02 (d, J=6.7 Hz, 3H), 0.96 (d, J=6.7 Hz, 3H).

2-(1-(4-Fluorophenyl)-1H-indazol-5-yloxy)-2-phenylacetamide (137b)

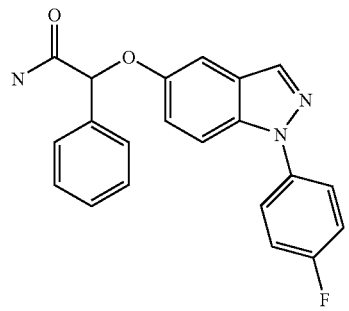

A suspension of methyl 2-(1-(4-fluorophenyl)-1H-indazol-5-yloxy)-2-phenylacetate (137c, 75 mg, 200 µmol) in methanolic NH$_3$ (7 M, 1 ml) was stirred at r.t. overnight to give a clear solution. Then the solvent was removed in vacuo, and the crude product was freeze-dried go give white solid material, 60 mg (83%).

APCI-MS: m/z 362 [MH+]

2-(1-(4-Fluorophenyl)-1H-indazol-5-yloxy)-2-phenylacetate (137c)

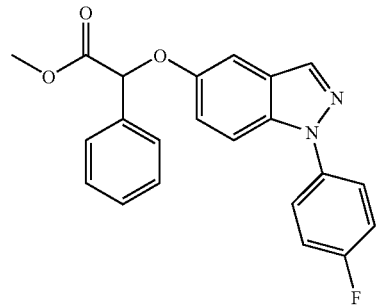

A mixture of 1-(4-fluorophenyl)-1H-indazol-5-ol (137d, 0.228 g, 1 mmol), methyl 2-bromo-2-phenylacetate (230 mg, 1 mmol), and cesium carbonate (652 mg, 2 mmol) in DMF (3 ml) was stirred at r.t. overnight. Then the reaction mixture was diluted with ethyl acetate (50 ml), and washed with water (2×25 ml). The organic layer was dried over sodium sulfate, and the solvent was removed in vacuo The residue purified by flash chromatography on silica gel (ethyl acetate/n-heptane=1:4). White solid, 252 mg (67%).

APCI-MS: m/z 377 [MH+] $^1$H NMR (400 MHz, CD$_3$OD) δ 8.07 (d, J=0.7 Hz, 1H), 7.68-7.57 (m, 5H), 7.46-7.36 (m, 4H), 7.22 (m, 2H), 7.15 (d, J=2.1 Hz, 1H), 5.71 (s, 1H), 3.77 (s, 3H).

1-(4-Fluorophenyl)-1H-indazol-5-ol (137d)

1-(4-Fluorophenyl)-5-methoxy-1H-indazole (137e, 1.0 mmol, 242 mg) was dissolved in dichloromethane (4 ml) and BBr$_3$ (4 ml, 1 M in dichloromethane) was added. The reaction mixture was stirred in r.t. overnight before it was quenched with water (20 ml). The product was extracted with dichloromethane (2×20 ml) and washed with sat. NaHCO$_3$. The organic phase was dried over Na$_2$SO$_4$, concentrated and purified by flash chromatography on silica gel (heptane-ethyl acetate).

APCI-MS: m/z 229 [MH$^+$] $^1$H NMR (400 MHz, CD$_3$OD) δ 8.08 (s, 1H), 7.73-7.65 (m, 2H), 7.57 (d, J=9.0 Hz, 1H), 7.30 (t, J=18.7 Hz, 2H), 7.13-7.02 (m, 2H), 3.33 (s, 1H).

1-(4-Fluorophenyl)-5-methoxy-1H-indazole (137e)

A mixture of 2-fluoromethoxybenzaldehyde (2.1 mmol, 320 mg), 4-fluorophenylhydrazine hydrochloride (2.1 mmol, 340 mg) and cesium carbonate (3 mmol, 2.0 g) in NMP (6 ml) was heated in a microwave reactor (300 W, 20 min, 150° C.). After cooling to r.t. the reaction mixture was diluted with dichloromethane (20 ml) and washed with 1M HCl, and sat. NaHCO$_3$. The organic layer was dried over Na$_2$SO$_4$, concentrated, and purified by flash chromatography on silica gel (heptane-ethyl acetate).

APCI-MS: m/z 243 [MH$^+$] $^1$H NMR (400 MHz, CDCl$_3$) δ 8.17 (s, 1H), 7.76-7.67 (m, 2H), 7.61 (d, J=27.3 Hz, 1H), 7.33-7.22 (m, 2H), 7.21-7.12 (m, 2H), 3.93 (s, 3H).

Example 138

(2R)-N-[(1R,2S)-1-[1-(4-fluorophenyl)indazol-5-yl]oxy-1-[4-(trifluoromethyl)phenyl]propan-2-yl]-2-hydroxy-propanamide

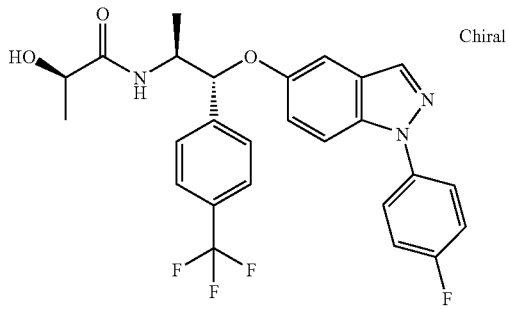

Prepared as described in Example 105 using (1R,2S)-1-{[1-(4-fluorophenyl)-1H-indazol-5-yl]oxy}-1-[4-(trifluoromethyl)phenyl]propan-2-amine (59a, 21 mg, 50 µmol) and (R)-2-hydroxypropanoic acid (12 mg, 150 µmol). Yield 14 mg (60%).

APCI-MS: m/z 502 [MH$^+$] $^1$H NMR (400 MHz, d$_6$-acetone) δ 8.05 (d, J=0.7 Hz, 1H), 7.70-7.80 (m, 7H), 7.40 (br.d, J=8.7 Hz, 1H), 7.34 (m, 2H), 7.27 (dd, J=9.1, 2.4 Hz, 1H), 7.19 (d, J=2.3 Hz, 1H), 5.58 (d, J=5.0 Hz, 1H), 4.41 (m, 1H), 4.05 (q, J=7.1 Hz, 1H), 1.28 (d, J=6.9 Hz, 3H), 1.12 (d, J=6.7 Hz, 3H).

Example 139

N-[(1R,2S)-1-[1-(4-fluorophenyl)indazol-5-yl]oxy-1-[4-(trifluoromethyl)phenyl]propan-2-yl]-1-hydroxy-cyclopropane-1-carboxamide

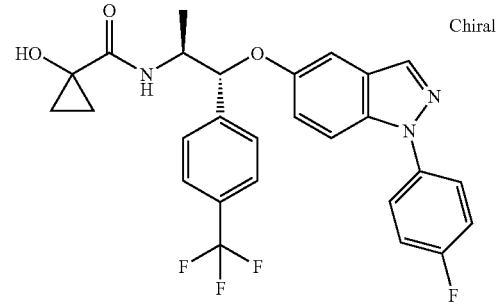

Prepared as described in Example 105 using (1R,2S)-1-{[1-(4-fluorophenyl)-1H-indazol-5-yl]oxy}-1-[4-(trifluoromethyl)phenyl]propan-2-amine (59a, 21 mg, 50 µmol) and 1-hydroxycyclopropanecarboxylic acid (14 mg, 150 µmol). Yield 10 mg (42%).

APCI-MS: m/z 514 [MH$^+$] $^1$H NMR (400 MHz, d$_6$-acetone) δ 8.05 (8.05 (d, J=0.9 Hz, 1H), 7.81-7.70 (m, 7H), 7.57 (br.d, J=8.7 Hz, 1H), 7.34 (m, 2H), 7.30 (dd, J=3.9, 9.3 Hz, 2H), 7.17 (d, J=2.3 Hz, 1H), 5.61 (d, J=4.4 Hz, 1H), 4.40 (m, 1H), 1.28 (d, J=6.9 Hz, 3H), 1.12 (m, 1H), 1.00 (m, 1H), 0.85 (m, 2H).

Example 140

(2S)N-[(1R,2S)-1-[1-(4-fluorophenyl)indazol-5-yl]oxy-1-[4-(trifluoromethyl)phenyl]propan-2-yl]-2-hydroxy-propanamide

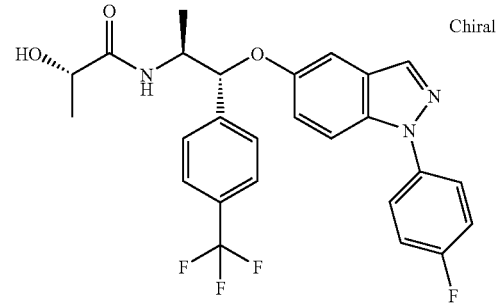

Prepared as described in Example 105 using (1R,2S)-1-{[1-(4-fluorophenyl)-1H-indazol-5-yl]oxy}-1-[4-(trifluoromethyl)phenyl]propan-2-amine (59a, 21 mg, 50 µmol) and (S)-2-hydroxypropanoic acid (12 mg, 150 µmol). Yield 13 mg (56%).

APCI-MS: m/z 502 [MH$^+$] $^1$H NMR (400 MHz, d$_6$-acetone) δ 8.04 (d, J=0.9 Hz, 1H), 7.80-7.70 (m, 7H), 7.42 (br.d, J=7.8 Hz, 1H), 7.34 (m, 2H), 7.28 (dd, J=9.1, 2.4 Hz, 1H), 7.17 (d, J=2.1 Hz, 1H), 5.60 (d, J=4.6 Hz, 1H), 4.38 (m, 1H), 4.03 (m, 1H), 1.25 (t, J=6.9 Hz, 6H).

Example 141

2,2,2-trifluoro-N-((1R,2S)-1-(1-(4-(hydroxymethyl)phenyl)-1H-indazol-5-yloxy)-1-phenylpropan-2-yl)acetamide

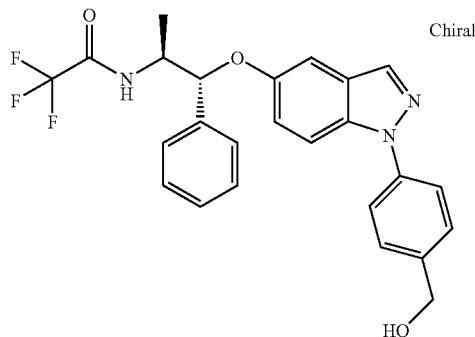

To a stirred suspension of (4-(5-((1R,2S)-2-amino-1-phenylpropoxy)-1H-indazol-1-yl)phenyl)methanol (141a, 462 mg, 1.2 mmol) in dichloromethane (50 ml) was added triethylamine (2.45 mL, 17.6 mmol), followed by trifluoroacetic anhydride (1.0 mL, 7.1 mmol). The suspension dissolved when TFA-anhydride was added. The mixture was stirred at ambient temperature for 1.5 h. and water (1 mL) was then added. The stirring was continued for 30 min and the mixture was then evaporated.

Chromatography (SiO$_2$, 0-80% EtOAc in Heptane) afforded slightly impure 2,2,2-trifluoro-N-((1R,2S)-1-(1-(4-(hydroxymethyl)phenyl)-1H-indazol-5-yloxy)-1-phenylpropan-2-yl)acetamide (443 mg) as a beige amorphous solid.

A sample (50 mg) of the material thus obtained was subjected to preparative HPLC (Kromasil C-18, 2.5×20 cm, 50-90% acetonitrile in water/40 min, 0.1% TfA) to afford pure 2,2,2-trifluoro-N-((1R,2S)-1-(1-(4-(hydroxymethyl)phenyl)-1H-indazol-5-yloxy)-1-phenylpropan-2-yl)acetamide (41 mg, 62%)

APCI-MS: m/z 470 [MH$^+$]$^1$H-NMR (400 MHz, DMSO-d$_6$): δ 9.52 (d, J=8.6 Hz, 1H), 8.15, d, J=0.7 Hz, 1H), 7.72 (d, J=9.3 Hz, 1H), 7.66 (d, J=8.4 Hz, further coupled, 2H), 7.49 (d, J=8.4 Hz, 2H), 7.43-7.39 (2H), 7.35 (t, J=7.3 Hz, further coupled, 2H), 7.27 (t, J=7.3 Hz, further coupled, 1H), 7.19 (dd, J=9.2 and 2.3 Hz, 1H), 7.12 (d, J=2.3 Hz, 1H), 5.29 (d, J=6.5 Hz, 1H), 4.56 (s, 2H), 4.25 (dq, J=14.9 and 6.8 Hz, 1H), 1.33 (d, J=6.8 Hz, 3H).

(4-(5-((1R,2S)-2-amino-1-phenylpropoxy)-1H-indazol-1-yl)phenyl)methanol (141a)

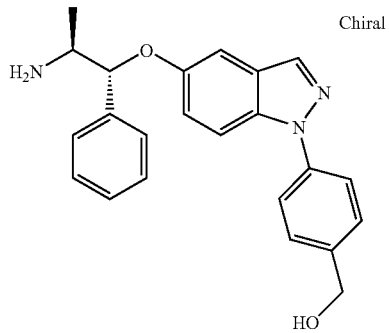

(4-(5-iodo-1H-indazol-1-yl)phenyl)methanol (141b, 1.06 g, 3 mmol), (2R,3S-norephedrine (1.39 g, 9.2 mmol), CuI (206 mg, 1 mmol) and was stirred under argon atmosphere in butyronitrile (14 mL) at 125° C. Caesium carbonate (5.1 g, 15.7 mmol) was added and the mixture was vigorously stirred for 50 min, cooled, filtered and evaporated. Chromatography (SiO$_2$, 040% MeOH in EtOAc) afforded (4-(5-((1R,2S)-2-amino-1-phenylpropoxy)-1H-indazol-1-yl)phenyl)methanol (516 mg, 45%).

APCI-MS: m/z 374 [MH$^+$]$^1$H-NMR (400 MHz, DMSO-d$_6$, D$_2$O, added): δ 8.12 (d, J=0.6 Hz, 1H), 7.69 (d, J=9.2 Hz, 1H), 7.64 (d, J=8.4 Hz, further coupled, 2H), 7.48 (d, J=8.4 Hz, 2H), 7.43-7.39 (2H), 7.38-7.31 (3H), 7.26 (t, further coupled, J=7.3 Hz, 1H), 7.21 (dd, J=9.1 and 1.8 Hz, 1H), 7.12 (d, J=1.8 Hz, 1H), 5.18 (d, J=3.7 Hz, 1H), 4.55, (s, 2H), 3.23 (b, 1H), 1.08 (d, J=6.2 Hz, 3H).

(4-(5-iodo-1H-indazol-1-yl)phenyl)methanol (141b)

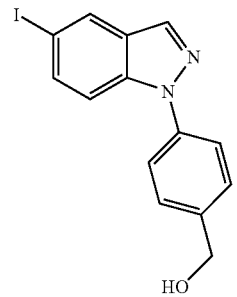

Crude 4-(5-iodo-1H-indazol-1-yl)benzoic acid (141c, 3.05 g, 8.4 mmol) was dissolved in THF (60 mL, dried over 4 Å MS) under argon atmosphere and cooled in an ice bath. Borane-THF complex (1M, 11 mL, 11 mmol) was added during 5 min. The ice bath was then removed and the mixture was allowed to reach r.t. and was finally heated at reflux for 40 min. The reaction mixture was then cooled to r.t. and sat. aqueous NH$_4$Cl (25 mL) was added. After being diluted with EtOAc the reaction mixture was extracted trice with water and finally with brine and evaporated. The residue was subjected to chromatography (SiO$_2$, 10-80% EtOAc in Heptane) to give (4-(5-iodo-1H-indazol-1-yl)phenyl)methanol (2.1 g, 71%).

APCI-MS: m/z 351 [MH$^+$]$^1$H-NMR (400 MHz, DMSO-d$_6$): δ 8.31 (m, 2H), 7.73-7.64 (4H), 7.53 (d, J=8.6 Hz, 2H), 5.31 (t, J=5.7 Hz, 1H), 4.59 (d, J=5.5 Hz, 2H).

4-(5-iodo-1H-indazol-1-yl)benzoic acid (141c)

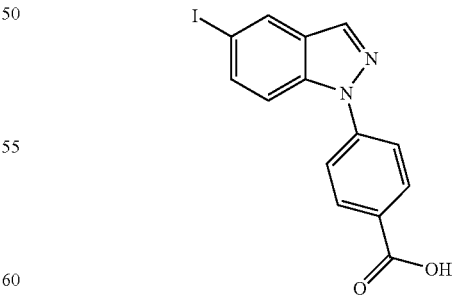

4-(2-(2-fluoro-5-iodobenzylidene)hydrazinyl)benzoic acid (141d, 3.42 g, 8.9 mmol) and potassium tert-butoxide (2.29 g, 20.5 mmol) was stirred under argon atmosphere in NMP (45 mL) at 150° C. for 15 min. The mixture was then cooled, diluted with water and acidified with aqueous HCl (1.7 M). The precipitate that formed was collected by filtration and dried in vacuo to give crude 4-(5-iodo-1H-indazol-1-yl)benzoic acid (3.05 g, 94%)

APCI-MS: m/z 365 [MH+] $^1$H-NMR (300 MHz, DMSO-$d_6$): δ 13.0 (b, 1H), 8.40 (d, J=0.6 Hz, 1H), 8.33 (d, J=1 Hz, further coupled, 1H), 8.14 (d, J=8.5 Hz, further coupled, 2H), 7.92 (d, J=8.5 Hz, further coupled, 2H), 7.83 (d, J=8.9 Hz, further coupled, 1H), 7.76 (dd, J=8.9 and 1.6 Hz, 1H).

4-(2-(2-fluoro-5-iodobenzylidene)hydrazinyl)benzoic acid (141d)

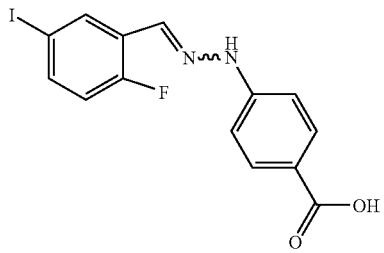

4-hydrazinylbenzoic acid (1.54 g, 10 mmol), 2-fluoro-5-iodobenzaldehyde (2.52 g, 10 mmol) and caesium carbonate (3.27 g, 10 mmol) was stirred in DMF (10 mL) at r.t. for 70 min. Water (40 mL) was then added and the clear solution was acidified with aqueous HCl (1.7 M). The light yellow precipitate that formed was collected by filtration, washed with water and dried in vacuo to give 4-(2-(2-fluoro-5-iodobenzylidene)hydrazinyl)benzoic acid (3.77 g, 98%)

APCI-MS: m/z 385 [MH+] $^1$H-NMR (300 MHz, DMSO-$d_6$): δ 13-10 (b, 1H), 11.1 (s, 1H), 8.21 (dd, J=6.9 and 2.3 Hz, 1H), 8.01 (s, 1H), 7.84 (d, further coupled, J=8.8 Hz, 2H), 7.67 (qd, J=8.6, 5.0 and 2.3 Hz, 1H), 7.16-7.05 (3H). $^{19}$F-NMR (300 MHz, DMSO-$d_6$): δ−123.3 (m).

Example 142

2,2,2-trifluoro-N-((1R,2S)-1-(1-(4-(morpholinomethyl)phenyl)-1H-indazol-5-yloxy)-1-phenylpropan-2-yl)acetamide

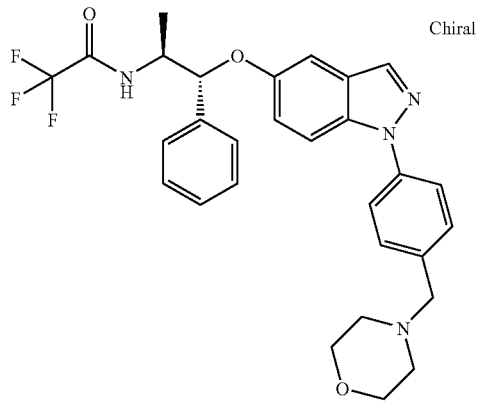

To a stirred, ice-cooled solution of 2,2,2-trifluoro-N-((1R,2S)-1-(1-(4-(hydroxymethyl)phenyl)-1H-indazol-5-yloxy)-1-phenylpropan-2-yl)acetamide (141, 115 mg, 0.24 mmol) and triethylamine (0.35 mL, 2.5 mmol) in dichloromethane (10 mL) was added methanesulfonyl chloride (38 uL, 0.49 mmol). The mixture was stirred at 0° C. Additional portions of methanesulfonyl chloride (38 and 60 uL) were added after 35 and 60 min respectively. After a total time of 1.5 h, the cooling bath was removed. Brine and dichloromethane (10 mL) were added and the mixture was washed with 1M aqueous. $KHSO_4$ followed by sat. $NaHCO_3$. To the organic phase was added morpholine (1 mL, 11.5 mmol) and the mixture was stirred overnight.

Evaporation followed by preparative HPLC (Kromasil C-18, 2.5×20 cm, 30-90% $CH_3CN$ in water/60 min (0.1% TfA) afforded the title product as a TfA salt. This material was dissolved in MeOH and absorbed on a plug of acidic ion exchange resin (SCX, 5 g, pre-washed with MeOH). Elution with methanol followed by methanolic ammonia (2M) and lyophilization afforded 2,2,2-trifluoro-N-((1R,2S)-1-(1-(4-(morpholinomethyl)phenyl)-1H-indazol-5-yloxy)-1-phenylpropan-2-yl)acetamide (45 mg; 34%) as an amorphous solid. APCI-MS: m/z 539 [MH+] $^1$H-NMR (400 MHz, DMSO-$d_6$,): δ 9.52 (d, J=8.5 Hz, 1H), 8.16 (d, J=0.7 Hz, 1H), 7.74 (d, J=9.1 Hz, 1H), 7.66 (d, J=8.5 Hz, further coupled, 2H), 7.48 (d, J=8.3 Hz, further coupled, 2H), 7.43-7.39 (2H), 7.35 (t, J=7.5 Hz, further coupled, 1H), 7.27 (t, J=7.4 Hz, further coupled, 1H), 7.19 (dd, J=9.2 and 2.5 Hz, 1H), 7.11 (d, J=2.4 Hz, 1H), 5.29 (d, J=6.4 Hz, 1H), 4.25 (dq, J=14.8 and 6.7 Hz, 1H), 3.59 (m, 4H), 3.52 (s, 2H), 2.39 (m, 4H), 1.33 (d, J=6.8 Hz, 3H). $^{19}$F-NMR (300 MHz, DMSO-$d_6$): δ−74.3 (s).

Example 143

N-((1R,2S)-1-(1-(4-((dimethylamino)methyl)phenyl)-1H-indazol-5-yloxy)-1-phenylpropan-2-yl)-2,2,2-trifluoroacetamide

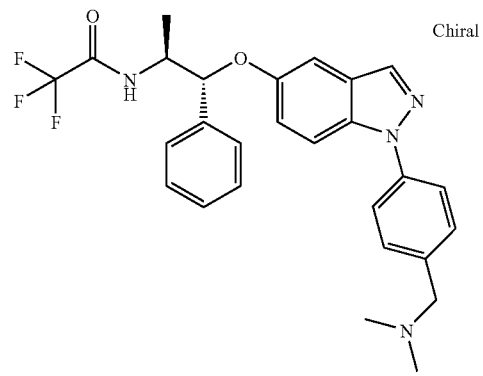

To a stirred, ice-cooled suspension of 2,2,2-trifluoro-N-((1R,2S)-1-(1-(4-(hydroxymethyl)phenyl)-1H-indazol-5-yloxy)-1-phenylpropan-2-yl)acetamide (141, 118 mg, 0.25 mmol) and triethylamine (0.35 mL, 2.5 mmol) was added methanesulfonyl chloride (140 μL, 1.8 mmol). After stirring for 50 min at 0° C. brine and dichloromethane (10 mL) were added. The mixture was washed with aqueous $KHSO_4$ (1M) and sat. aqueous $NaHCO_3$. To the organic phase was added dimethylamine (0.75 mL, 11.3 mmol). The mixture was stirred at ambient temperature for 40 min and was then evaporated. Preparative HPLC (Kromasil C-18, 2.5×20 cm, 30-90% $CH_3CN$ in water/40 min (0.1% TfA) afforded slightly impure title compound as a TfA-salt. The material was dissolved in MeOH and absorbed on a plug of acidic ion exchange resin (SCX, 5 g, pre-washed with MeOH). Eluting subsequently with MeOH and methanolic ammonia (2M) gave somewhat impure title compound. Purification by preparative HPLC on an XBridge C-18 column using a gradient of 50-90% acetonitrile in water containing 0.1% aqueous ammonia (28%). afforded pure N-((1R,2S)-1-(1-(4-((dimethylamino)methyl)phenyl)-1H-indazol-5-yloxy)-1-phenyl-propan-2-yl)-2,2,2-trifluoroacetamide (77 mg, 61%).

APCI-MS: m/z 497 [MH+] $^1$H-NMR (400 MHz, DMSO-d$_6$,): δ 9.53 (d, J=8.3 Hz, 1H), 8.16 (d, J=0.6 Hz, 1H), 7.74 (d, J=9.2 Hz, 1H), 7.65 (d, J=8.5 Hz, further coupled, 2H), 7.45 (d, J=8.5 Hz, further coupled, 2H), 7-43-7-39 (2H), 7.35 (t, J=7.5 Hz, 1H), 7.27 (t, J=7.5 Hz, further coupled, 1H), 7.19 (dd, J=6.7 and 2.5 Hz, 1H), 7.12 (d, J=2.3 Hz, 1H), 5.29 (d, J=6.6 Hz, 1H), 4.25 (dq, J=13.5 and 7 Hz, 1H), 3.44 (s, 2H), 2.17 (s, 6H), 1.33 (d, J=6.8 Hz, 1H) $^{19}$F-NMR (300 MHz, DMSO-d$_6$): δ−74.3 (s)

Example 144

2,2,2-trifluoro-N-((1R,2S)-1-(1-(3-(hydroxymethyl)phenyl)-1H-indazol-5-yloxy)-1-phenylpropan-2-yl)acetamide

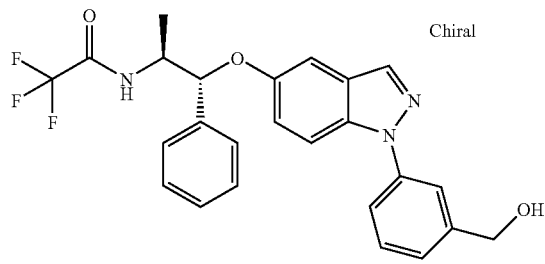

To a stirred suspension of (3-(5-((1R,2S)-2-amino-1-phenylpropoxy)-1H-indazol-1-yl)phenyl)methanol (144a, 38 mg, 0.1 mmol) in dichloromethane (4 ml) was added triethylamine (200 μl, 1.4 mmol) followed by trifluoroacetic anhydride (85 uL, 0.6 mmol). The mixture was stirred for 90 min and water (8 drops) was then added. The mixture was evaporated and the residue was subjected to preparative HPLC (Kromasil C-18, 2.5×20 cm) using a gradient (holding 0.1% TfA) of 30-90% acetonitrile in water/30 min Fractions containing the title compound was combined and lyophilized to afford 2,2,2-trifluoro-N-((1R,2S)-1-(1-(3-(hydroxymethyl)phenyl)-1H-indazol-5-yloxy)-1-phenylpropan-2-yl)acetamide (32.5 mg, 68%)

APCI-MS: m/z 470 [MH+] $^1$H-NMR (300 MHz, DMSO-d$_6$, D$_2$O added): δ 9.60 (d, J=8.5 Hz, 1H), 8.14 (d, J=0.8 Hz, 1H), 7.72 (d, J=9.3 Hz, further coupled, 1H), 7.62 (m, 1H), 7.54 (d, J=8.2 Hz, further coupled, 1H), 7.50 (d, J=7.3 Hz, 1H), 7.48 (d, J=7.9 Hz, 1H), 7.42-7.22 (6H), 7.20 (dd, J=9.2 and 2.3 Hz, 1H), 7.13 (d, J=2.3 Hz, 1H), 5.26 (d, J=6.9 Hz, 1H), 4.57 (s, 2H), 4.24 (m, 1H), 1.33 (d, J=6.9 Hz, 3H).

(3-(5-((1R,2S)-2-amino-1-phenylpropoxy)-1H-indazol-1-yl)phenyl)methanol (144a)

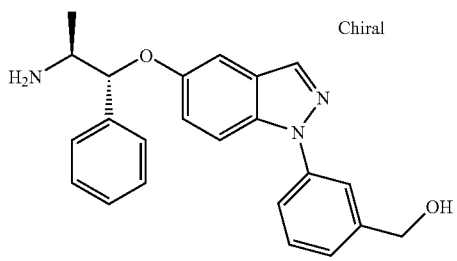

(1R,2S)-2-amino-1-phenylpropan-1-ol (133 mg, 1.22 mmol) was dissolved in butyronitrile (2.5 mL) under argon atmosphere in a vial. CuI (20 mg, 0.17 mmol), (3-(144, 5-iodo-1H-indazol-1-yl)phenyl)methanol (92 mg, 0.26 mmol) and caesium carbonate (250 mg, 1.63 mmol) was added in one portion with stirring. The vial was closed and the mixture stirred at 125° C. for 5 h. Additional (1R,2S)-2-amino-1-phenylpropan-1-ol (90 mg, 0.6 mmol), CuI (13 mg, 0.07 mmol) and caesium carbonate (280 mg, 0.86 mmol) was added in one portion with stirring at 125° C. After a total heating time of 5.5 h all 5-iodo-1H-indazol-1-yl)phenyl)methanol was consumed. The mixture was cooled, filtered and evaporated. The residue was subjected to chromatography (SiO$_2$, 0-40% MeOH in EtOAc) to afford (3-(5-((1R,2S)-2-amino-1-phenylpropoxy)-1H-indazol-1-yl)phenyl)methanol (48 mg, 49%).

APCI-MS: m/z 374 [MH+] $^1$H-NMR (300 MHz, DMSO-d$_6$, D$_2$O, added): δ 8.12 (s, 1H), 7.71 (d, J=9.1 Hz, 1H), 7.63 (bs, 1H), 7.54 (d, J=8.3 Hz, further coupled, 1H), 7.50 (d, J=7.3 Hz, 1H), 7.48 (d, J=7.9 Hz, 1H), 7.43-7.19 (7H), 7.13 (d, J=2.3 Hz, 1H), 5.15 (s, 1H), 4.57, (s, 2H), 1.07 (d, J=6.0 Hz, 3H).

(3-(5-iodo-1H-indazol-1-yl)phenyl)methanol (144b)

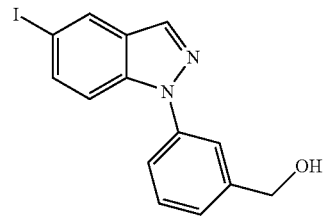

Crude 3-(5-iodo-1H-indazol-1-yl)benzoic acid (144c, 3.5 g, 9.6 mmol) was dissolved in THF (70 mL, dried over 4 Å MS) under argon atmosphere and cooled in an ice bath. Borane-THF complex (1M, 12 mL, 12 mmol) was added during 2 min. The cooling bath was removed and the mixture was stirred at r.t. for 15 min, then heated at reflux for 35 min. Additional borane reagent was added and the heating was continued for 20 min, at which time all starting material had been consumed. Sat. aqueous NR$_4$Cl (25 mL) was added followed by ethyl acetate. The phases were separated and the organic phase was washed trice with water and finally with brine. Evaporation left a residue that was subjected to chromatography (SiO$_2$, 10-80% EtOAc in Heptane) to afford a material that was crystallized from ethyl acetate-Heptane to give (3-(5-iodo-1H-indazol-1-yl)phenyl)methanol (1.69 g) as off white crystals. From the mother liquor was obtained in the same way additional 223 mg of the title compound. Total yield 60% over two steps.

APCI-MS: m/z 351 [MH+] $^1$H-NMR (300 MHz, DMSO-d$_6$): δ 8.33 (d, J=0.7 Hz, 1H), 8.31 (dd, J=1.4 and 0.7 Hz, 1H), 7.73 (dd, J=8.9 and 1.6 Hz, 1H), 7.71-7.66 (2H), 7.61 (d, J=9.9 Hz, further coupled, 1H), 7.54 (t, J=7.4 Hz, 1H), 7.36 (7, J=7.4 Hz, 1H), 5.37 (t, J=5.8 Hz, 1H), 4.62 (d, J=5.7 Hz, 2H).

3-(5-iodo-1H-indazol-1-yl)benzoic acid (144c)

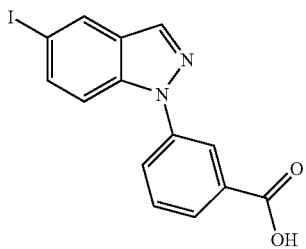

3-(2-(2-fluoro-5-iodobenzylidene)hydrazinyl)benzoic acid (3.47 g, 9 mmol) and potassium tert. butoxide (2.3 g, 20.5 mmol) was stirred under argon atmosphere in NMP (45 mL) at 150° C. for 30 min. After cooling, the mixture was diluted with water (100 mL), acidified with aqueous HCl (1.7 M) and extracted trice with EtOAc. The combined organic phases were washed twice with water and then with brine. Evaporation of the organic phase afforded crude title compound (3.52 g, quant.) as a light brown, amorphous, gummy solid.

APCI-MS: m/z 365 [MH$^+$]$^1$H-NMR (300 MHz, DMSO-d$_6$): δ 13.2 (b, 1H), 8.38 (s, 1H), 8.33 (s, 1H), 8.24 (bs, 1H), 7.97 (d, J=8.2 Hz, further coupled, 1H), 7.81-7.68 (3H).

3-(2-(2-fluoro-5-iodobenzylidene)hydrazinyl)benzoic acid (144d)

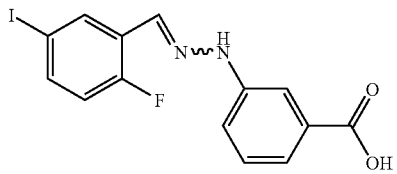

3-hydrazinylbenzoic acid (1.52 g, 10 mmol)), 2-fluoro-5-iodobenzaldehyde (2.5 g, 10 mmol) and caesium carbonate (3.26 g, 10 mmol) were stirred in DMF (10 mL) at r.t. under argon atmosphere for 2.5 h. Water (40 mL) was added and the clear solution was acidified with aqueous HCl (1.7 M). The beige-orange precipitate that formed was collected by, filtration, washed with water and dried in vacuo to give the title compound (3.75 g, 98%).

APCI-MS: m/z 385 [MH$^+$]$^1$H-NMR (300 MHz, DMSO-d$_6$): δ 12.9 (b, 1H), 8.17 (dd, J=6.9 and 2.3 Hz, 1H), 7.94 (s, 1H), 7.65 (qd, J=8.7, 5.0 and 2.3 Hz, 1H), 7.63-7.60 (m, 1H), 7.40-7.31 (3H), 7.09 (dd, J=10.8 and 8.7 Hz, 1H) $^{19}$F-NMR (300 MHz, DMSO-d$_6$, D$_2$O added): δ–123.4 (m)

Example 145

2,2,2-trifluoro-N-((1R,2S)-1-(1-(3-(morpholinomethyl)phenyl)-1H-indazol-5-yloxy)-1-phenylpropan-2-yl)acetamide

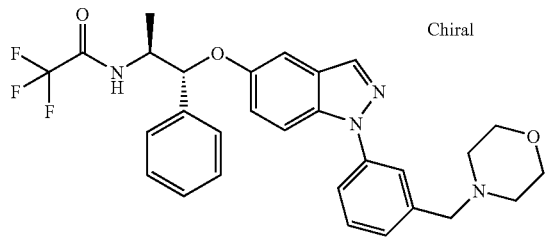

To a stirred, ice-cooled solution of 2,2,2-trifluoro-N-((1R,2S)-1-(1-(3-(hydroxymethyl)phenyl)-1H-indazol-5-yloxy)-1-phenylpropan-2-yl)acetamide (144, 119 mg, 0.35 mmol) and triethylamine (0.35 mL, 2.5 mmol) was added methanesulfonyl chloride (140 μL, 1.8 mmol). The mixture was stirred for 55 min at 0° C. and brine was then added followed by dichloromethane (10 mL) and aqueous KHSO$_4$ (1M). The phases were separated and the organic phase washed with sat aqueous NaHCO$_3$. To the organic phase was the added morpholine (1 mL, 11.5 mmol). The mixture was stirred at ambient temperature for 16 h and was then evaporated. The residue was subjected to preparative HPLC (Kromasil C-18, 2.5×20 cm) using a gradient (holding 0.1% TfA) of 30-90% acetonitrile in water/60 min. Fractions containing the title compound were combined and evaporated. The residue, comprising the TfA-salt of the title compound was dissolved in MeOH and absorbed on a plug of acidic ion exchange resin (SCX, 5 g, pre-washed with MeOH). Eluting with MeOH and methanolic ammonia (2M) subsequently afforded after evaporation, re-dissolving in water and lyophilization 2,2,2-trifluoro-N-((1R,2S)-1-(1-(3-(morpholinomethyl)phenyl)-1H-indazol-5-yloxy)-1-phenylpropan-2-yl)acetamide (105 mg, 77%).

APCI-MS: m/z 539 [MH$^+$]$^1$H-NMR (300 MHz, DMSO-d$_6$,): δ 9.52 (d, J=8.5 Hz, 1H), 8.17 (d, J=0.8H1H), 7.72 (d, J=9.2 Hz, further coupled, 1H), 7.65-7-58 (3H), 7.51 (d, J=7.6 Hz, 1H), 7.49 (d, J=7.8 Hz, 1H), 7.44-7.23 (6H), 7.21 (dd, J=9.2 and 2.4 Hz), 1H), 7.13 (d, J=2.4 Hz), 5.30 (d, J=6.5 Hz, 1H, 4.25 (m, 1H), 3.60-3.54 (6H), 2.42-2.36 (4H), 1.34 (d, J=6.8 Hz). $^{19}$F-NMR (300 MHz, DMSO-d$_6$): δ–74.3 (s).

Example 146

N-((1R,2S)-1-(1-(3-((dimethylamino)methyl)phenyl)-1H-indazol-5-yloxy)-1-phenylpropan-2-yl)-2,2,2-trifluoroacetamide

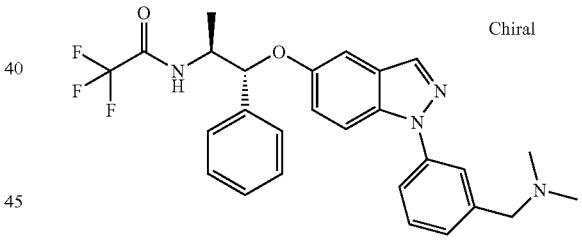

To a stirred ice-cooled solution of 2,2,2-trifluoro-N-((1R,2S)-1-(1-(3-(hydroxymethyl)phenyl)-1H-indazol-5-yloxy)-1-phenylpropan-2-yl)acetamide (144, 118 mg, 0.25 mmol) and triethylamine (0.35 mL, 2.5 mmol) was added methanesulfonyl chloride (140 μL, 1.8 mmol). The mixture was stirred at 0° C. for 65 min and brine was then added, followed by dichloromethane (10 mL).

The phases were separated and the organic phase was washed with aqueous KHSO$_4$ (1 M) and sat aqueous NaHCO$_3$ subsequently. To the organic phase was then added dimethylamine (0.75 mL, 11.3 mmol) and the mixture was stirred at ambient temperature for 70 min. After evaporation, the residue was subjected to preparative HPLC (Kromasil C-18, 2.5×20 cm) using a gradient (holding 0.1% TfA) of 30-90% acetonitrile in water/40 min to afford the TfA salt of the title compound. This material was dissolved in MeOH and absorbed on a plug of acidic ion exchange resin (SCX, 5 g, pre-washed with MeOH). Eluting with MeOH and methanolic ammonia (2M) subsequently gave, after lyophilization from water, a residue that was subjected to preparative HPLC under basic conditions using an XBridge C-18 column and a gradient of 50-90% actonitrile in water containing 0.1% aqueous ammonia (28%). This afforded after lyophilization N-((1R,2S)-1-(1-(3-((dimethylamino)methyl)phenyl)-1H-indazol-5-yloxy)-1-phenylpropan-2-yl)-2,2,2-trifluoroacetamide (75 mg, 60%)

APCI-MS: m/z 497 [MH$^+$]$^1$H-NMR (400 MHz, DMSO-d$_6$,): δ 9.53 (d, J=8.1 Hz, 1H), 8.17 (d, J=0.7 Hz, 1H), 7.72 (d, J=9.2 Hz, 1H), 7.63-7.57 (2H), 7.50 (t, J=7.7 Hz, 1H) 7.43-7.39 (2H), 7.37-7.32 (2H), 7.30-7.24 (2H), 7.21 (dd, J=9.2 and 2.5 Hz, 1H), 7.13 (d, J=2.3 Hz, 1H), 5.29 (d, J=6.8 Hz, 1H), 4.25 (m, 1H), 3.48 (s, 2H), 2.18 (s, 6H), 1.34 (d, J=6.7 Hz, 1H) $^{19}$F-NMR (300 MHz, DMSO-d$_6$): δ−74.3 (s)

Example 147

N-(1,1,1-trifluoro-3-(1-(4-fluorophenyl)-1H-indazol-5-yloxy)-3-phenylpropan-2-yl)pivalamide

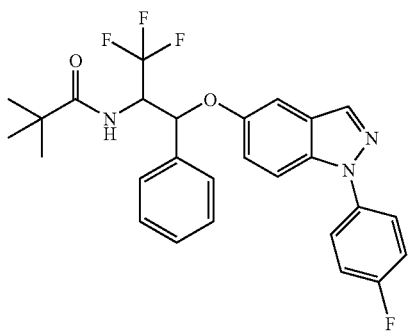

N-(1,1,1-trifluoro-3-(1-(4-fluorophenyl)-1H-indazol-5-yloxy)-3-phenylpropan-2-yl)pivalamide (147D1E1)

Racemic 147D1 (198 mg) was subjected to chiral separation on a Chiralpak fA 2×20 cm. Mobile phase: iso-Hexane-dichloromethane-methanol; 500-100-5. 147D1E1 was isolated as the first eluted enantiomer: 87 mg (ee 100%).

[α]$_D$=+63° (c 0.9, MeOH) APCI-MS: m/z 500 [MH$^+$]$^1$H-NMR (300 MHz, DMSO-d$_6$): δ 8.18 (d, J=0.8 Hz, 1H), 7.94 (d, J=9.5 Hz, 1H), 7.81-7.67 (3H), 7.52-7.47 (2H), 7.44-7.23 (6H), 7.21 (d, J=2.1 Hz, 1H), 5.86 (d, J=4.4 Hz, 1H), 5.12 (m, 1H), 1.09 (s, 9H). $^{19}$F-NMR (300 MHz, DMSO-d$_6$): δ−70.1 (d, J=8.5 Hz), −115.8 (m).

N-(1,1,1-trifluoro-3-(1-(4-fluorophenyl)-1H-indazol-5-yloxy)-3-phenylpropan-2-yl)pivalamide (147D1E2)

The title compound was isolated as the second eluted enantiomer from the chiral HPLC separation described for 147D1E1. Yield: 86 mg (ee 98%)

[α]$_D$=−65° (c 0.9, MeOH) APCI-MS and NMR spectral properties as for enantiomer 1

N-(1,1,1-trifluoro-3-(1-(4-fluorophenyl)-1H-indazol-5-yloxy)-3-phenylpropan-2-yl)pivalamide (147D2E1)

100 mg of racemic 147D2 were subjected to HPLC on a chiral column as described for 147D1. 147D2E1 was isolated as the first eluted enantiomer. Yield: 40 mg (ee 100%).

[α]$_D$=−82° (c 0.9, MeOH) APCI-MS: m/z 500 [MH$^+$]$^1$H-NMR (300 MHz, DMSO-d$_6$): δ 8.22 (d, J=0.9 Hz, 1H), 7.95 (d, J=9.8 Hz, 1H), 7.77-7.65 (3H), 7.57-7.51 (2H), 7.44-7.24 (5H), 7.18 (d, J=2.2 Hz, 1H), 7.13 (dd, J=9.0 and 2.4 Hz, 1H), 5.64 (d, J=10.0 Hz, 1H), 5.00 (m, 1H), 0.86 (s, 9H) $^{19}$F-NMR (300 MHz, DMSO-d$_6$): δ−69.16 (d, J=7.4 Hz), −115.8 (m)

N-(1,1,1-trifluoro-3-(1-(4-fluorophenyl)-1H-indazol-5-yloxy)-3-phenylpropan-2-yl)pivalamide (147D2E2)

The subtitle compound was isolated as the second eluted enantiomer from the chiral HPLC separation of 147D2 described for 147D2E1. Yield: 46 mg (ee 88%)

[α]$_D$=+71° (c 1, MeOH) APCI-MS and NMR spectral properties as for enantiomer 1

N-(1,1,1-trifluoro-3-(1-(4-fluorophenyl)-1H-indazol-5-yloxy)-3-phenylpropan-2-yl)pivalamide (147D1)

1,1,1-trifluoro-3-(1-(4-fluorophenyl)-1H-indazol-5-yloxy)-3-phenylpropan-2-amine, (147aD1, 160 mg, approx. 0.39 mmol) was dissolved in dichloromethane (10 mL). Pivaloyl chloride (70 uL, 0.57 mmol) was added followed by triethylamine (80 uL, 0.57 mmol). The mixture was stirred at ambient temperature for 100 min.

Additional pivaloyl chloride (20 uL) and triethylamine 15 uL was then added and the stirring was continued for 70 min. Water was added and the mixture was stirred for 15 min. Dichloromethane was then added and the phases were separated. The aqueous phase was extracted once with dichloromethane and the combined organic phases were evaporated. Chromatography (SiO$_2$, gradient of 0-40% ethyl acetate in Heptane) afforded pure racemic N-(1,1,1-trifluoro-3-(1-(4-fluorophenyl)-1H-indazol-5-yloxy)-3-phenylpropan-2-yl)pivalamide (diastereomer 1, 170 mg, approx. 88%)

N-(1,1,1-trifluoro-3-(1-(4-fluorophenyl)-1H-indazol-5-yloxy)-3-phenylpropan-2-yl)pivalamide (147D2)

Pivaloylation and isolation of racemic 1,1,1-trifluoro-3-(1-(4-fluorophenyl)-1H-indazol-5-yloxy)-3-phenylpropan-2-amine (147aD2), was performed in an analogous manner as described for 147D1. From 135 mg of amine 147aD2 was obtained 84 mg of pure racemic pivaloyl ester 147D2.

1,1,1-trifluoro-3-(1-(4-fluorophenyl)-1H-indazol-5-yloxy)-3-phenylpropan-2-amine (147aD1)

A solution of 1,1,1-trifluoro-3-(1-(4-fluorophenyl)-1H-indazol-5-yloxy)-3-phenylpropan-2-one oxime (147b, slightly impure, 1.08 g, 2.5 mmol) in THF (40 mL, dried over 4 A MS) was added during 10 min to a mixture of Red-Al® (2.5 mL of a 3.5 M solution in toluene) in THF (60 mL). After the addition was complete the mixture was heated at reflux temperature for 1 h and was then cooled to r.t. Sat. aqueous ammonium chloride solution (10 mL) was added. The mixture was stirred for additional 10 min and was then partitioned between ethyl acetate and water. The turbid aqueous phase was extracted once with ethyl acetate. The combined organic phases were washed twice with water, once with brine and evaporated. The residue was subjected to extensive chromatography (SiO$_2$, gradients of ethyl acetate in Heptane) to afford the separated diastereomeric amine products, both however contaminated by unidentified side products. 160 mg of the first eluted diastereomer (147aD1) were obtained after evaporation of the solvents.

APCI-MS: m/z 416 [MH$^+$]

1,1,1-trifluoro-3-(1-(4-fluorophenyl)-1H-indazol-5-yloxy)-3-phenylpropan-2-amine (147aD2)

521 mg of diastereomer 147aD2 were obtained as the second eluted diastereomer from the separation on silica gel described for 147aD1

APCI-MS: m/z 416 [MH+]

1,1,1-trifluoro-3-(1-(4-fluorophenyl)-1H-indazol-5-yloxy)-3-phenylpropan-2-one oxime (147b)

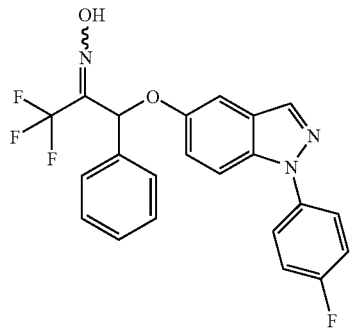

1,1,1-trifluoro-3-(1-(4-fluorophenyl)-1H-indazol-5-yloxy)-3-phenylpropane-2,2-diol (147c) 1.22 g, 2.8 mmol) and hydroxylamine hydrochloride (3.32 g, 48 mmol) was mixed in pyridine (85 mL, dried over 4 Å MS). The mixture was stirred at 115° C. for 30 min, after which time HPLC analysis showed complete reaction. Solvent was evaporated and the residue partitioned between ethyl acetate and water. The phases were separated and the organic phase washed twice with water, followed by brine and then evaporated. The residue was subjected to chromatography (SiO$_2$, gradient of 10-60% Ethyl acetate in Heptane) to afford somewhat impure 1,1,1-trifluoro-3-(1-(4-fluorophenyl)-1H-indazol-5-yloxy)-3-phenylpropan-2-one oxime as a 3:7 mixture of diastereomers (0.99 g, 82%).

APCI-MS: m/z 430 [MH+] $^1$H-NMR (300 & 600 MHz, DMSO-d$_6$): δ 13.08 (b, 1H), 8.27 (d, J=Hz, 0.3H), 8.24 (d, J=Hz, 0.7H), 7.82-7.70 (3H), 7.55-7.49 (2H), 7.48-7.24 (7H), 6.49 (s, 1H) $^{19}$F-NMR (300 MHz, DMSO-d$_6$): δ− 63.9 (s), −115.7 (m)

1,1,1-trifluoro-3-(1-(4-fluorophenyl)-1H-indazol-5-yloxy)-3-phenylpropane-2,2-diol (147c)

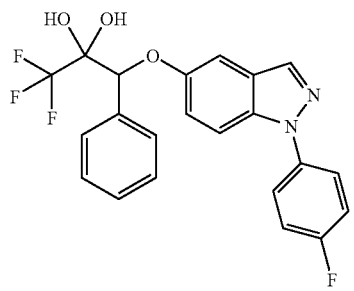

Methyl 2-(1-(4-fluorophenyl)-1H-indazol-5-yloxy)-2-phenylacetate (147d, 2.5 g, 6.6 mmol) was dissolved in THF (15 mL, dried over 4 Å MS) under Argon atmosphere and cooled in an ice-bath. Trimethyl(trifluoromethyl)silane (1.18 mL, 8 mmol) was added followed by Caesium fluoride (100 mg, 0.66 mmol). The cooling bath was removed and the stirring was continued at r.t. for 4 h. A solution of tetrabutylammonium fluoride in THF (1M, 7 mL, 7 mmol) followed by water (4 mL) was then added and the mixture was stirred for additional 1 h and then partitioned between ethyl acetate and water. The organic phase was washed twice with water, then brine and evaporated to afford 1,1,1-trifluoro-3-(1-(4-fluorophenyl)-1H-indazol-5-yloxy)-3-phenylpropane-2,2-diol (2.74 g, 95%)

APCI-MS: m/z 433 [M+] $^1$H-NMR (600 MHz, DMSO-d$_6$): δ 8.15 (d, J=0.9 Hz, 1H), 7.77-7.69 (m, 2H), 7.66 (d, J=9.3 Hz, further coupled, 1H), 7.57-7.51 (2H), 7.43-7.23 (5H), 7.21-7.13 (3H), 5.40 (s, 1H) $^{13}$C-NMR (400 MHz, DMSO-d$_6$): δ 160.2 (d, J=243.0 Hz), 152.4, 136.1 (d, J=2.6 Hz), 135.3, 135.0, 134.1, 129.1 (2C), 127.9, 127.5 (2C), 125.2, 123.9 (d, J=8.5 Hz), 123.8 (q, J=291 Hz), 111.4, 104.2, 92.2 (q, J=28.9 Hz), 80.5 $^{19}$F-NMR (300 MHz, DMSO-d$_6$): δ− 79.5 (s), −115.9 (m)

Methyl 2-(1-(4-fluorophenyl)-1H-indazol-5-yloxy)-2-phenylacetate (147d)

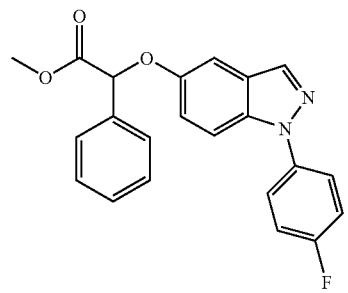

1-(4-fluorophenyl)-1H-indazol-5-ol (147e, 912 mg, 4 mmol), methyl 2-bromo-2-phenylacetate (0.65 mL, 4.1 mmol) and Caesium carbonate (2.64 g, 8.1 mmol) were stirred in DMF (12 mL) at ambient temp. for 55 min. and the mixture was then poured into water and extracted trice with ethyl acetate. The combined organic phases were washed with water and brine subsequently, and evaporated to afford crude methyl 2-(1-(4-fluorophenyl)-1H-indazol-5-yloxy)-2-phenylacetate (1.59 g). The product was combined with additional crude methyl 2-(1-(4-fluorophenyl)-1H-indazol-5-yloxy)-2-phenylacetate (2.03 g obtained in the same way as above from 1.2 g of methyl 2-bromo-2-phenylacetate) and crystallized from methanol to afford pure methyl 2-(1-(4-fluorophenyl)-1H-indazol-5-yloxy)-2-phenylacetate (2.94 g) as off-white, small needles. The mother liquor was subjected to chromatography (SiO$_2$, gradient of 0-70% Ethyl acetate in Heptane) to give, after crystallization from methanol, additional methyl 2-(1-(4-fluorophenyl)-1H-indazol-5-yloxy)-2-phenylacetate (272 mg). Total yield 3.2 g (92%)

APCI-MS: m/z 377 [MH+] $^1$H-NMR (300 MHz, DMSO-d$_6$,): δ 8.26 (d, J=0.9 Hz, 1H), 7.81-7.70 (3H), 7.62-7.56 (2H), 7.48-7.36 (5H), 7.35 (d, J=2.4 Hz, 1H), 7.26 (dd, J=9.1 and 2.4 Hz, 1H), 6.1 (s, 1H), 3.67 (s, 3H) $^{13}$C-NMR (400 MHz, DMSO-d$_6$): δ 170.0, 160.3 (d, J=243.3 Hz), 152.1, 136.1 (d, J=2.6 Hz), 135.5, 135.1, 134.3, 129.0, 128.7 (2C), 127.4 (2C), 125.3, 124.0 (d, J=8.6 Hz), 119.7, 116.4 d, J=22.9 Hz), 111.5, 103.7, 77.8, 52.4. $^{19}$F-NMR (300 MHz, DMSO-d$_6$): δ–115.8 (m)

1-(4-fluorophenyl)-1H-indazol-5-ol (147e)

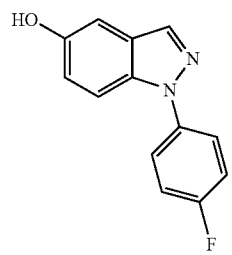

1-(4-fluorophenyl)-5-methoxy-1H-indazole (147f, 3.32 g, 13.7 mmol) in CH$_2$Cl$_2$ (40 mL, dried over 4 Å mol sieves). Borontribromide solution (1M in dichloromethane, 35 mL, 35 mmol) was added and the mixture was stirred at 50° C. for 80 min. The reaction mixture was cooled to r.t., diluted with dichloromethane and washed with ice-cold sat. aqueous NaHCO$_3$. Crude title compound crystallised from the organic phase at 8° C. Re-crystallization from methanol-water afforded 1-(4-fluorophenyl)-1H-indazol-5-ol as light grey needles (1.88 g). From the mother liquor was obtained by crystallization (methanol-water) additional title compound (0.7 g). Total yield 2.58 g (82%).

APCI-MS: m/z 229 [MH$^+$] $^1$H-NMR (300 MHz, DMSO-d$_6$,): δ 9.41 (s, 1H), 8.16 (d, J=0.9 Hz. 1H), 7.80-7.72 (m, 2H), 7.64 (d, J=9.1 Hz, further coupled, 1H), 7.44-7.35 (m, 2H), 7.10 (dd, J=2.3 and 0.6 and Hz, 1H), 7.02 (dd, J=9.1 and 2.4 Hz, 1H)

1-(4-fluorophenyl)-5-methoxy-1H-indazole (147f)

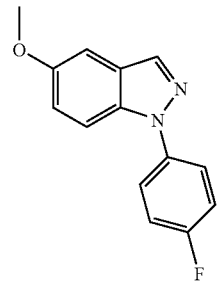

Step 1)

1-(2-fluoro-5-methoxybenzylidene)-2-(4-fluorophenyl)hydrazine

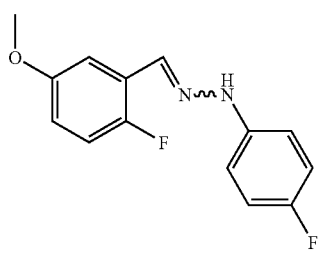

(4-fluorophenyl)hydrazine (6.5 g, 40 mmol), 2-fluoro-5-methoxybenzaldehyde (6.2 g, 40 mmol) and cesium carbonate (13 g, 40 mmol) were stirred in DMF (40 mL) at r.t. under argon atmosphere for 1.5 h and was then poured with stirring into water and extracted with ethyl acetate. The organic phase was washed trice with water, then brine and evaporated. The residue crystallized slowly to afford the subtitle compound as a beige-light brown crystal mass (10.21 g).

APCI-MS: m/z 263 [MH$^+$]

Step 2)

1-(2-fluoro-5-methoxybenzylidene)-2-(4-fluorophenyl)hydrazine (10 g, 38 mmol) and potassium tert. butoxide (5 g, 46 mmol) was stirred under argon atmosphere in NMP (50 mL) at 150° C. for 45 min. The reaction mixture was then cooled and poured with stirring into ice-water and extracted trice with ethyl acetate. The combined organic phases were washed with water and brine, and were then evaporated. The residue crystallized slowly from methanol-water to afford 1-(4-fluorophenyl)-5-methoxy-1H-indazole as beige crystals (3.32 g, 36%)

$^1$H-NMR (300 MHz, DMSO-d$_6$,): δ 8.25 (d, J=0.9 Hz, 1H), 7.81-7.74 (m, 2H), 7.71 (d, J=9.2 Hz, further coupled, 1H), 7.45-7.37 (m, 2H), 7.31 (d, J=2.4 Hz, 1H), 7.13 (dd, J=9.2 and 2.5 Hz, 1H), 3.82 (s, 3H) $^{19}$F-NMR (300 MHz, DMSO-d$_6$): δ–115.9 (m).

Example 148

N-[(1 S,2R)-1-[1-(4-fluorophenyl)indazol-5-yl]oxy-1-(6-methoxypyrdin-3-ylpropan-2-yl]cyclopropanecarboxamide

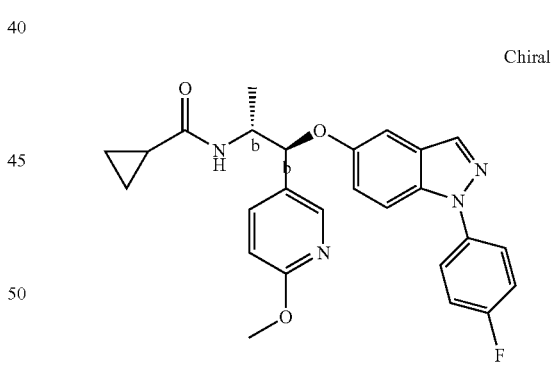

ISOMER 1
b = relative absolute

The racemic mixture of N-[(1R,2S)-1-[1-(4-fluorophenyl)indazol-5-yl]oxy-1-(6-methoxypyridin-3-yl)propan-2-yl] cyclopropanecarboxamide (16) were separated on Thales SFC, Chiralpak IA column (75% CO$_2$, 25% MeOH) collecting the first eluting peak.

$^1$H-NMR (400 MHz, Acetone-d$_6$) δ 8.22 (1H, d); 8.06 (1H, s); 7.80-7.69 (4H, m); 7.52 (1H, d); 7.34 (2H, dd); 7.23 (2H, dd); 7.19 (1H, d); 6.74 (1H, d); 5.45 (1H, d); 4.37-4.27 (1H, m); 3.85 (3H, s); 1.54 (1H, ddd); 1.27 (3H, d); 0.79-0.73 (1H, m); 0.69-0.53 (3H, m). APCI-MS: m/z 461.1 [MH$^+$].

Example 149

N-[(1R,2S)-1-(3,4-dimethylphenyl)-1-[1-(4-fluorophenyl)indazol-5-yl]oxy-propan-2-yl]-2,2,2-trifluoro-acetamide

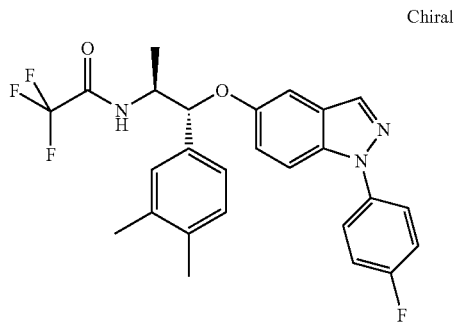

Prepared as described in Example 6 using corresponding starting material.

APCI-MS: m/z 486.2 [MH+] $^1$H-NMR (500 MHz, DMSO-d6): δ 9.51 (1H, d); 8.12 (1H, d); 7.70-7.67 (2H, m); 7.64 (1H, d); 7.37-7.33 (2H, m); 7.15 (1H, dd); 7.11 (1H, s); 7.07-7.04 (3H, m); 5.18 (1H, d); 4.18-4.11 (1H, m); 2.14-2.11 (6H, m); 1.26 (3H, d).

Example 150

N-[(1R,2S)-1-(3,4-difluorophenyl)-1-[1-(4-fluorophenyl)indazol-5-yl]oxy-propan-2-yl]-2,2,2-trifluoro-acetamide

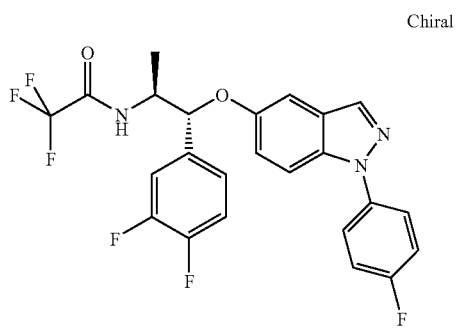

Prepared as described in Example 6 using corresponding starting material.

APCI-MS: m/z 494.1 [MH+] $^1$H-NMR (500 MHz, DMSO-d6): δ 9.50 (1H, d); 8.14 (1H, d); 7.71-7.65 (3H, m); 7.42-7.34 (4H, m); 7.23-7.14 (3H, m); 5.22 (1H, d); 4.25-4.19 (1H, m); 1.31 (3H, d).

Example 151

2,2,2-trifluoro-N-[(1R,2S)-1-(3-fluoro-4-methylphenyl)-1-[1-(4-fluorophenyl)indazol-5-yl]oxy-propan-2-yl]acetamide

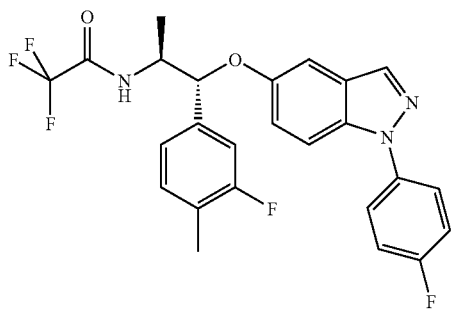

Prepared as described in Example 6 using corresponding starting material.

APCI-MS: m/z 490.1 [MH+] $^1$H-NMR (500 MHz, DMSO-d6): δ 9.52 (1H, d); 8.13 (1H, d); 7.70-7.64 (3H, m); 7.37-7.34 (2H, m); 7.21 (1H, t); 7.16 (1H, dd); 7.11-7.07 (3H, m); 5.21 (1H, d); 4.23-4.17 (1H, m); 1.29 (3H, d).

Example 152

2,2,2-trifluoro-N-[(1R,2S)-1-(3-fluorophenyl)-1-[1-(4-fluorophenyl)indazol-5-yl]oxy-propan-2-yl]acetamide

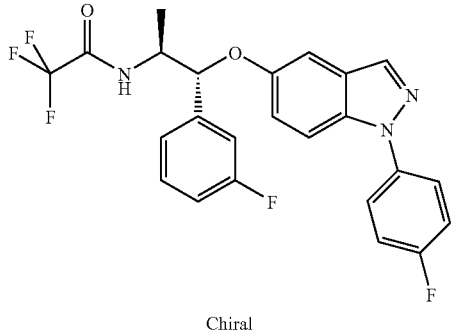

Prepared as described in Example 6 using corresponding starting material.

APCI-MS: m/z 476.1 [MH+] $^1$H-NMR (500 MHz, DMSO-d6): δ 9.53 (1H, d); 8.14 (1H, d); 7.70-7.64 (3H, m); 7.38-7.32 (3H, m); 7.22-7.12 (4H, m); 7.06 (1H, td); 5.25 (1H, d); 4.26-4.18 (1H, m); 1.31 (3H, d).

Example 153

N-[(1R,2S)-1-(2,5-dimethylphenyl)-1-[1-(4-fluorophenyl)indazol-5-yl]oxy-propan-2-yl]-2,2,2-trifluoro-acetamide

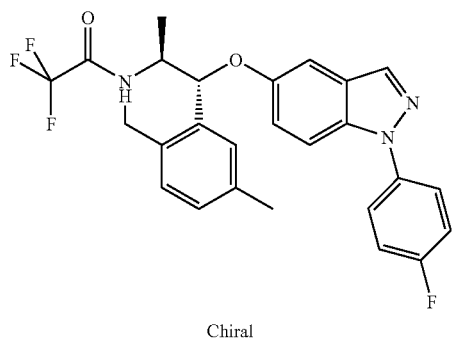

Chiral

Prepared as described in Example 6 using corresponding starting material.

APCI-MS: m/z 486.2 [MH+] $^1$H-NMR (500 MHz, DMSO-d6): δ 9.64 (1H, d); 8.13 (1H, d); 7.70-7.64 (3H, m); 7.37-7.33 (2H, m); 7.16 (1H, dd); 7.12 (1H, s); 7.04 (1H, d); 6.96-6.93 (2H, m); 5.38 (1H, d); 4.24-4.18 (1H, m); 2.15 (3H, s); 1.26 (3H, d).

Example 154

N-[(1R,2S)-1-(2,4-dimethylphenyl)-1-[1-(4-fluorophenyl)indazol-5-yl]oxy-propan-2-yl]-2,2,2-trifluoro-acetamide

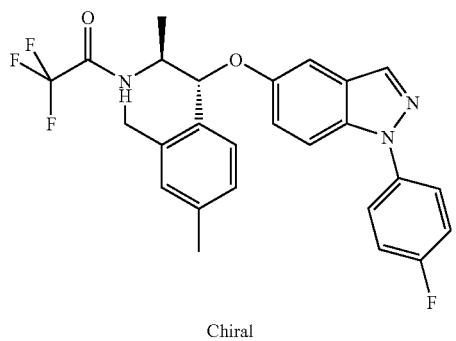

Chiral

Prepared as described in Example 6 using corresponding starting material.

APCI-MS: m/z 486.2 [MH+] $^1$H-NMR (500 MHz, DMSO-d6): δ 9.65 (1H, d); 8.11 (1H, d); 7.70-7.63 (3H, m); 7.37-7.33 (2H, m); 7.18 (1H, d); 7.14 (1H, dd); 6.96 (1H, s); 6.94 (1H, d); 6.90 (1H, d); 5.40 (1H, d); 4.24-4.19 (1H, m); 2.16 (3H, s); 1.25 (3H, d).

Example 155

N-[(1R,2S)-1-(3-chlorophenyl)-1-[1-(4-fluorophenyl)indazol-5-yl]oxy-propan-2-yl]-2,2,2-trifluoro-acetamide

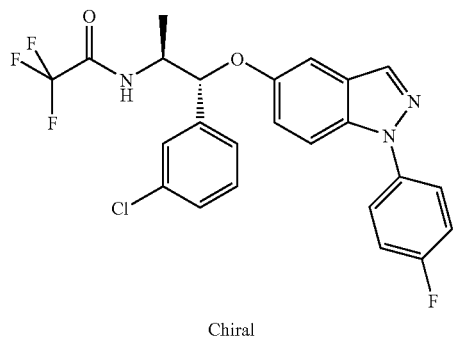

Chiral

Prepared as described in Example 6 using corresponding starting material.

APCI-MS: m/z 492.1 [MH+] $^1$H-NMR (500 MHz, DMSO-d6): δ 9.56 (1H, d); 8.13 (1H, s); 7.70-7.64 (3H, m); 7.38-7.27 (6H, m); 7.17 (1H, dd); 7.12 (1H, d); 5.22 (1H, d); 4.24-4.17 (1H, m); 1.30 (3H, d).

Example 156

2,2,2-trifluoro-N-[(1R,2S)-1-(4-fluoro-2-methylphenyl)-1-[1-(4-fluorophenyl)indazol-5-yl]oxy-propan-2-yl]acetamide

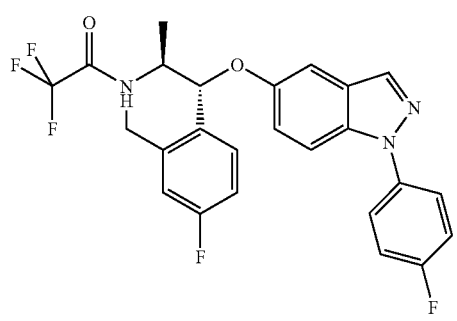

Chiral

Prepared as described in Example 6 using corresponding starting material.

APCI-MS: m/z 490.2 [MH+] $^1$H-NMR (500 Hz, DMSO-d6): δ 9.65 (1H, d); 8.13 (1H, d); 7.70-7.64 (3H, m); 7.37-7.32 (3H, m); 7.15 (1H, dd); 7.02-6.98 (2H, m); 6.93 (1H, td); 5.39 (1H, d); 4.27-4.22 (1H, m); 1.27 (2H, d).

Example 157

2,2,2-trifluoro-N-[(1R,2S)-1-(5-fluoro-2-methyl-phenyl)-1-[1-(4-fluorophenyl)indazol-5-yl]oxy-propan-2-yl]acetamide

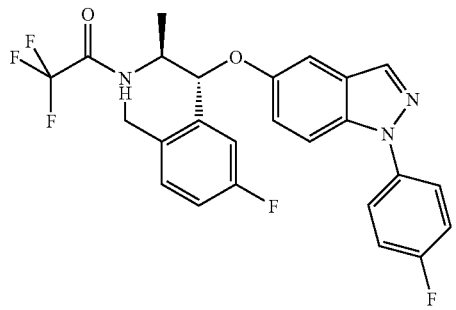

Chiral

Prepared as described in Example 6 using corresponding starting material.

APCI-MS: m/z 490.2 [MH+] $^1$H-NMR (500 MHz, DMSO-d6): δ 9.68 (1H, d); 8.14 (1H, d); 7.71-7.65 (3H, m); 7.35 (2H, dd); 7.21-7.16 (2H, m); 7.07 (1H, dd); 7.01-6.94 (2H, m); 5.40 (1H, d); 4.29-4.24 (1H, m); 1.28 (3H, d).

Example 158

2,2,2-trifluoro-N-[(1R,2S)-1-(5-fluoro-2-methoxy-phenyl)-1-[1-(4-fluorophenyl)indazol-5-yl]oxy-propan-2-yl]acetamide

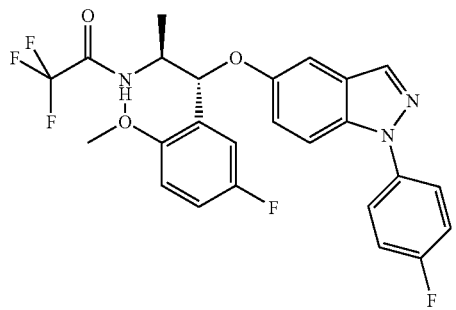

Chiral

Prepared as described in Example 6 using corresponding starting material.

APCI-MS: m/z 506 [MH+] $^1$H-NMR (500 MHz, DMSO-d6): δ 9.46 (1H, d); 8.15 (1H, d); 7.71-7.65 (3H, m); 7.37-7.33 (2H, m); 7.15 (1H, dd); 7.07-6.99 (4H, m); 5.51 (1H, d); 4.37-4.30 (1H, m); 3.82 (3H, s); 1.25 (3H, d).

Example 159

2,2,2-trifluoro-N-[(1R,2S)-1-[1-(4-fluorophenyl)indazol-5-yl]oxy-1-(4-methoxy-3,5-dimethyl-phenyl)propan-2-yl]acetamide

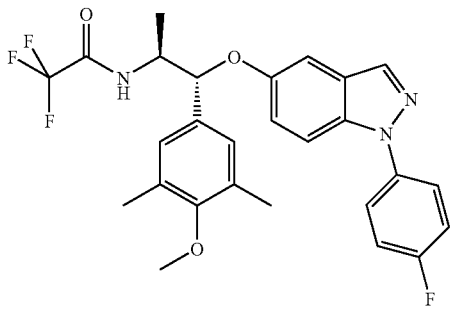

Chiral

Prepared as described in Example 6 using corresponding starting material.

APCI-MS: m/z 516.2 [MH+] $^1$H-NMR (500 MHz, DMSO-d6): δ 9.48 (1H, d); 8.14 (1H, d); 7.71-7.64 (3H, m); 7.37-7.34 (2H, m); 7.16 (1H, dd); 7.09 (1H, d); 7.01 (2H, s); 5.13 (1H, d); 4.14-4.07 (1H, m); 2.13 (6H, s); 1.26 (3H, d).

Example 160

N-[(1R,2S)-1-(4-chlorophenyl)-1-[1-(4-fluorophenyl)indazol-5-yl]oxy-propan-2-yl]-2,2,2-trifluoro-acetamide

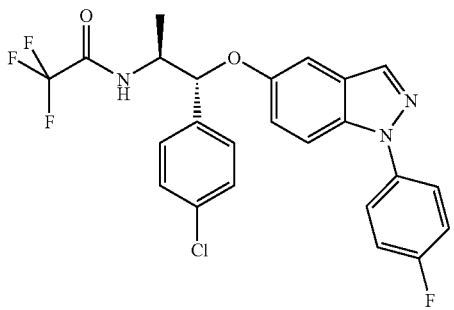

Chiral

Prepared as described in Example 6 using corresponding starting material.

APCI-MS: m/z 492.1 [MH+] $^1$H-NMR (500 MHz, DMSO-d6): δ 9.53 (1H, d); 8.13 (1H, d); 7.70-7.63 (3H, m); 7.40-7.33 (6H, m); 7.15 (1H, dd); 7.09 (1H, d); 5.23 (1H, d); 4.23-4.18 (1H, m); 1.29 (3H, d).

Example 161

N-[(1R,2S)-1-(3-chloro-5-fluoro-phenyl)-1-[1-(4-fluorophenyl)indazol-5-yl]oxy-propan-2-yl]-2,2,2-trifluoro-acetamide

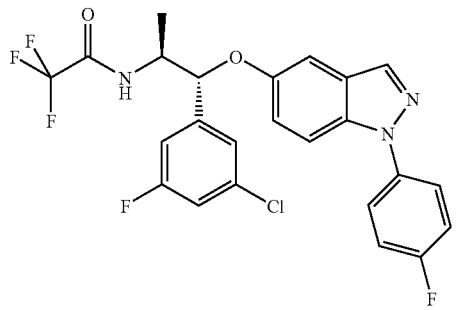

Chiral

Prepared as described in Example 6 using corresponding starting material.

APCI-MS: m/z 510.1 [MH+] $^1$H-NMR (500 MHz, DMSO-d6): δ 9.53 (1H, d); 8.16 (1H, d); 7.71-7.66 (3H, m); 7.38-7.34 (2H, m); 7.31 (1H, dt); 7.27 (1H, s); 7.20-7.16 (3H, m); 5.24 (1H, d); 4.25-4.19 (1H, m); 1.31 (3H, d).

Example 162

2,2,2-trifluoro-N-[(1R,2S)-1-[1-(4-fluorophenyl)indazol-5-yl]oxy-1-(2,4,5-trimethylphenyl)propan-2-yl]acetamide

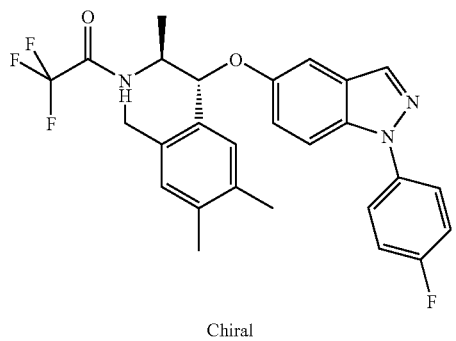

Chiral

Prepared as described in Example 6 using corresponding starting material.

APCI-MS: m/z 500.2 [MH+] $^1$H-NMR (500 MHz, DMSO-d6): δ 9.63 (1H, d); 8.12 (1H, t); 7.70-7.63 (3H, m); 7.37-7.33 (2H, m); 7.15 (1H, dd); 7.05 (1H, s); 6.94-6.91 (2H, m); 5.35 (1H, d); 4.21-4.16 (1H, m); 2.08 (3H, s); 2.05 (3H, s); 1.25 (3H, d).

Example 163

2,2,2-trifluoro-N-[(1R,2S)-1-[1-(4-fluorophenyl)indazol-5-yl]oxy-1-(4-tert-butylphenyl)propan-2-yl]acetamide

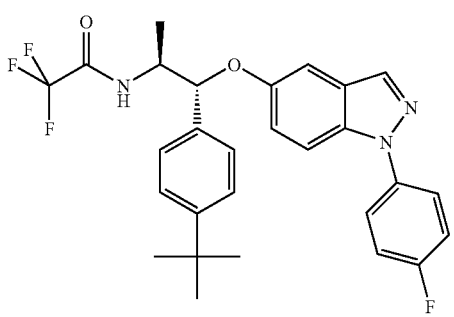

Chiral

Prepared as described in Example 6 using corresponding starting material.

APCI-MS: m/z 514.2 [MH+]

$^1$H-NMR (500 MHz, DMSO-d6): δ 9.51 (1H, d); 8.13 (1H, d); 7.70-7.63 (3H, m); 7.37-7.27 (5H, m); 7.17 (1H, dd); 7.10 (1H, d); 5.26 (1H, d); 4.21-4.14 (1H, m); 1.26 (3H, d); 1.18 (9H, s).

Example 164

2,2,2-trifluoro-N-[(1R,2S)-1-[1-(4-fluorophenyl)indazol-5-yl]oxy-1-(2-methoxyphenyl)propan-2-yl]acetamide

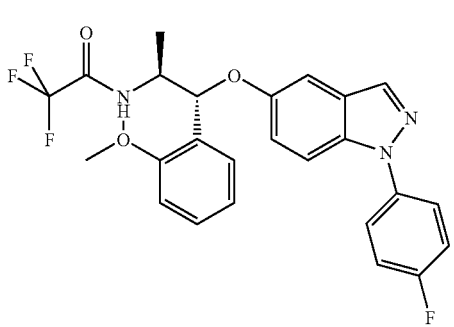

Chiral

Prepared as described in Example 6 using corresponding starting material.

APCI-MS: m/z 488.2 [MH+]

$^1$H-NMR (500 MHz, DMSO-d6): δ 9.42 (1H, d); 8.13 (1H, d); 7.70-7.64 (3H, m); 7.37-7.33 (2H, m); 7.27-7.20 (2H, m); 7.14 (1H, dd); 7.00 (1H, d); 6.97 (1H, d); 6.85 (1H, t); 5.54 (1H, d); 4.36-4.30 (1H, m); 3.84 (3H, s); 1.23 (3H, d).

Example 165

2,2,2-trifluoro-N-[(1R,2S)-1-[1-(4-fluorophenyl)indazol-5-yl]oxy-1-(4-propylphenyl)propan-2-yl]acetamide

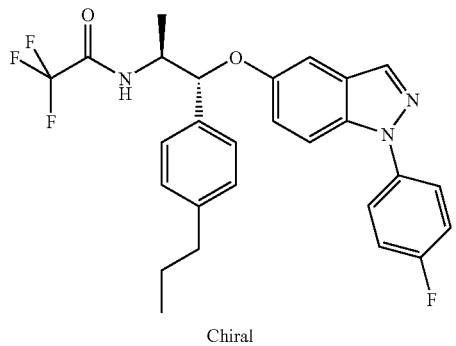

Chiral

Prepared as described in Example 6 using corresponding starting material

APCI-MS: m/z 500.2 [MH+]

$^1$H-NMR (500 MHz, DMSO-d6): δ 9.49 (1H, d); 8.12 (1H, d); 7.70-7.67 (2H, m); 7.64 (1H, d); 7.37-7.33 (2H, m); 7.26 (2H, d); 7.15 (1H, dd); 7.12-7.08 (3H, m); 5.21 (1H, d); 4.18 (1H, dd); 1.49 (2H, sextet); 1.28 (3H, d); 0.78 (3H, t).

Example 166

N-[(1R,2S)-1-benzo[1,3]dioxol-5-yl-1-[1-(4-fluorophenyl)indazol-5-yl]oxy-propan-2-yl]-2,2,2-trifluoro-acetamide

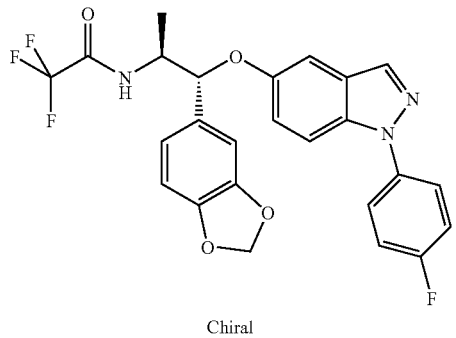

Chiral

Prepared as described in Example 6 using corresponding starting material.

APCI-MS: m/z 502.1 [MH+]

$^1$H-NMR (500 MHz, DMSO-d6): δ 9.46 (1H, d); 8.14 (1H, d); 7.71-7.63 (3H, m); 7.37-7.34 (2H, m); 7.15 (1H, dd); 7.11 (1H, d); 6.85-6.81 (3H, m); 5.92 (2H, dd); 5.14 (1H, d); 4.21-4.14 (1H, m); 1.29 (3H, d).

Example 167

2,2,2-trifluoro-N-[(1R,2S)-1-(3-fluoro-2-methyl-phenyl)-1-[1-(4-fluorophenyl)indazol-5-yl]oxy-propan-2-yl]acetamide

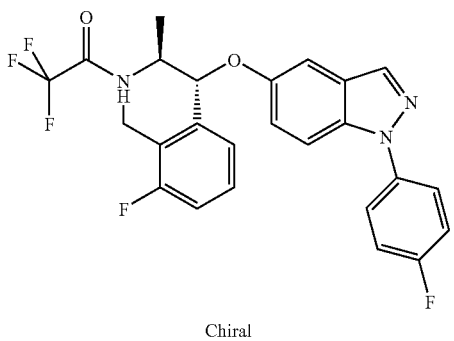

Chiral

Prepared as described in Example 6 using corresponding starting material.

APCI-MS: m/z 490.1 [MH+]

$^1$H-NMR (500 MHz, DMSO-d6): δ 9.68 (1H, d); 8.13 (1H, d); 7.70-7.64 (3H, m); 7.37-7.33 (2H, m); 7.18-7.12 (3H, m); 7.05-6.99 (2H, m); 5.44 (1H, d); 4.30-4.23 (1H, m); 1.27 (3H, d).

Example 168

N-[(1R,2S)-1-(4-chloro-3-methyl-phenyl)-1-[1-(4-fluorophenyl)indazol-5-yl]oxy-propan-2-yl]-2,2,2-trifluoro-acetamide

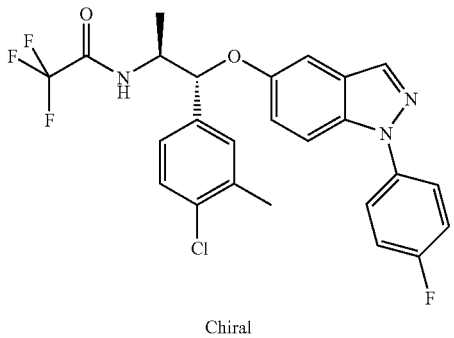

Chiral

Prepared as described in Example 6 using corresponding starting material.

APCI-MS: m/z 506.1 [MH+]

$^1$H-NMR (500 MHz, DMSO-d6): δ 9.53 (1H, d); 8.13 (1H, d); 7.70-7.64 (3H, m); 7.37-7.32 (4H, m); 7.20 (1H, dd); 7.16 (1H, dd); 7.09 (1H, d); 5.19 (1H, d); 4.21-4.14 (1H, m); 2.25 (3H, s); 1.28 (3H, d).

Example 169

N-[(1R,2S)-1-(4-chloro-2-methyl-phenyl)-1-[1-(4-fluorophenyl)indazol-5-yl]oxy-propan-2-yl]-2,2,2-trifluoro-acetamide

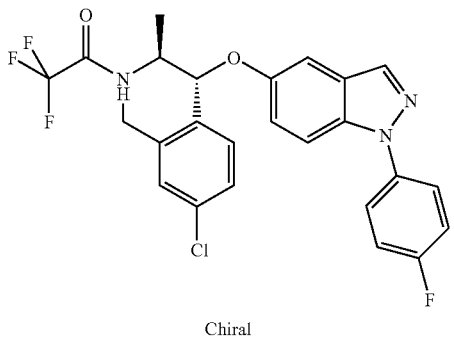

Chiral

Prepared as described in Example 6 using corresponding starting material.

APCI-MS: m/z 506.1 [MH+]

Example 170

N-[(1R,2S)-1-(4-chloro-3-fluoro-phenyl)-1-[1-(4-fluorophenyl)indazol-5-yl]oxy-propan-2-yl]-2,2,2-trifluoro-acetamide

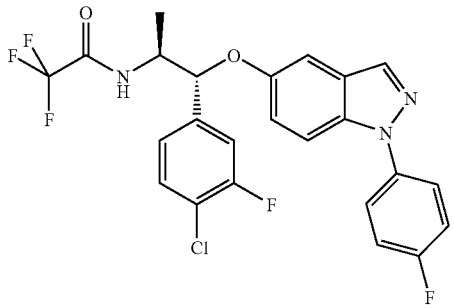

Chiral

Prepared as described in Example 6 using corresponding starting material.

APCI-MS: m/z 510.1 [MH+]

$^1$H-NMR (500 MHz, DMSO-d6): δ 9.52 (1H, d); 8.14 (1H, d); 7.70-7.64 (3H, m); 7.53 (1H, t); 7.39-7.33 (3H, m); 7.24 (1H, s); 7.18-7.14 (2H, m); 5.24 (1H, d); 4.26-4.20 (1H, m); 1.30 (3H, d).

Example 171

N-[(1R,2S)-1-(3,4-dimethylphenyl)-1-[1-(4-fluorophenyl)indazol-5-yl]oxy-propan-2-yl]-2,2-dimethyl-propanamide

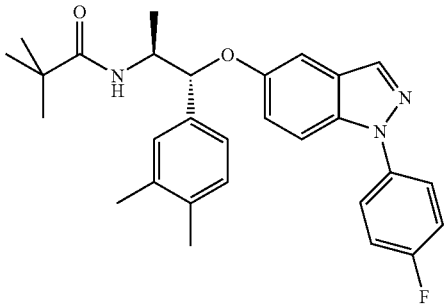

Chiral

Prepared as described in Example 8 using corresponding starting material.

APCI-MS: m/z 474.3 [MH+]

$^1$H-NMR (500 MHz, DMSO-d6): δ 8.12 (1H, d); 7.70-7.67 (2H, m); 7.63 (1H, d); 7.37-7.33 (2H, m); 7.30 (1H, d); 7.15 (1H, dd); 7.11 (1H, s); 7.07-7.02 (3H, m); 5.18 (1H, d); 4.12-4.05 (1H, m); 2.13 (3H, s); 2.11 (3H, s); 1.15 (3H, d); 0.91 (9H, s).

Example 172

N-[(1R,2S)-1-(3,4-difluorophenyl)-1-[1-(4-fluorophenyl)indazol-5-yl]oxy-propan-2-yl]-2,2-dimethyl-propanamide

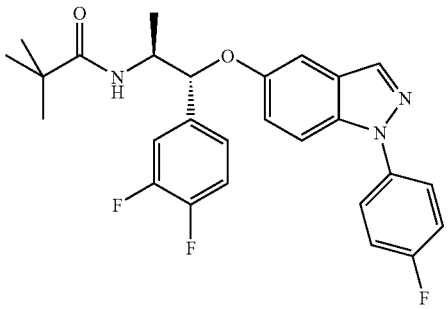

Chiral

Prepared as described in Example 8 using corresponding starting material.

APCI-MS: m/z 482.2 [MH+]

$^1$H-NMR (500 MHz, DMSO-d6): δ 8.14 (1H, d); 7.70-7.67 (2H, m); 7.65 (1H, d); 7.40-7.30 (5H, m); 7.23-7.19 (1H, m); 7.16 (1H, dd); 7.12 (1H, d); 5.19 (1H, d); 4.20-4.12 (1H, m); 1.22 (3H, d); 0.88 (9H, s).

Example 173

N-[(1R,2S)-1-(3-fluoro-4-methyl-phenyl)-1-[1-(4-fluorophenyl)indazol-5-yl]oxy-propan-2-yl]-2,2-dimethyl-propanamide

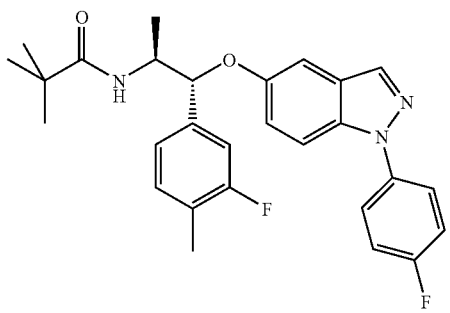

Chiral

Prepared as described in Example 8 using corresponding starting material.

APCI-MS: m/z 478.2 [MH+]

$^1$H-NMR (500 MHz, DMSO-d6): δ 8.13 (1H, d); 7.70-7.67 (2H, m); 7.64 (1H, d); 7.37-7.33 (3H, m); 7.20-7.14 (2H, m); 7.10-7.05 (3H, m); 5.20 (1H, d); 4.17-4.10 (1H, m); 2.12 (3H, s); 1.19 (3H, d); 0.90 (9H, s).

Example 174

N-[(1R,2S)-1-(3-fluorophenyl)-1-[1-(4-fluorophenyl)indazol-5-yl]oxy-propan-2-yl]-2,2-dimethyl-propanamide Prepared as described in Example 8 using corresponding starting material.

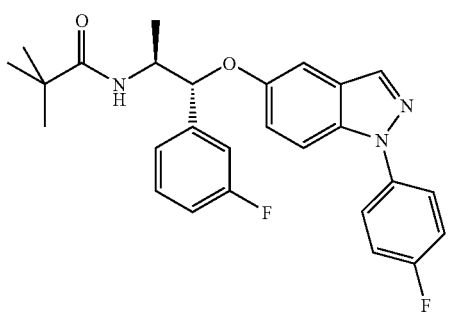

Chiral

APCI-MS: m/z 464.2 [MH+]

$^1$H-NMR (500 MHz, DMSO-d6): δ 8.13 (1H, dd); 7.70-7.63 (3H, m); 7.38-7.30 (4H, m); 7.21 (1H, d); 7.18-7.13 (2H, m); 7.10 (1H, d); 7.02 (1H, td); 5.24 (1H, d); 4.20-4.13 (1H, m); 1.23-1.19 (3H, m); 0.88 (9H, s).

Example 175

N-[(1R,2S)-1-(2,5-dimethylphenyl)-1-[1-(4-fluorophenyl)indazol-5-yl]oxy-propan-2-yl]-2,2-dimethyl-propanamide

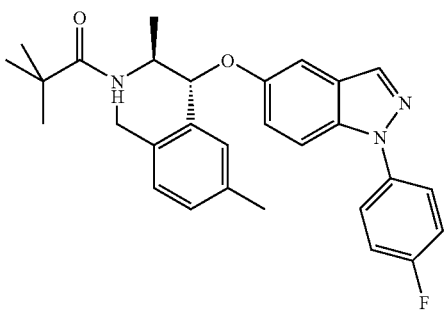

Chiral

Prepared as described in Example 8 using corresponding starting material.

APCI-MS: m/z 474.3 [MH+]

$^1$H-NMR (500 MHz, DMSO-d6): δ 8.12 (1H, d); 7.70-7.63 (3H, m); 7.37-7.33 (3H, m); 7.16 (1H, dd); 7.11 (1H, s); 7.01 (1H, d); 6.94-6.90 (2H, m); 5.37 (1H, d); 4.18-4.11 (1H, m); 2.15 (3H, s); 1.15 (3H, d); 0.92 (9H, s).

Example 176

N-[(1R,2S)-1-(2,4-dimethylphenyl)-1-[1-(4-fluorophenyl)indazol-5-yl]oxy-propan-2-yl]-2,2-dimethyl-propanamide

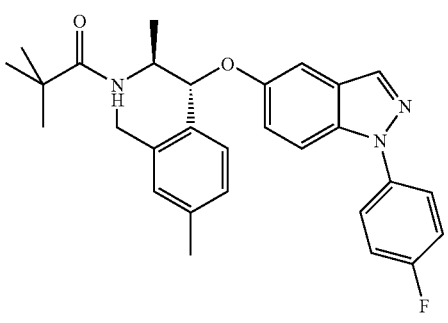

Chiral

Prepared as described in Example 8 using corresponding starting material.

APCI-MS: m/z 474.2 [MH+]

$^1$H-NMR (500 MHz, DMSO-d6): δ 8.11 (1H, d); 7.70-7.66 (2H, m); 7.63 (1H, d); 7.38-7.33 (3H, m); 7.18-7.13 (2H, m); 6.95-6.87 (3H, m); 5.38 (1H, d); 4.16-4.11 (1H, m); 2.16 (3H, s); 1.14 (3H, d); 0.94 (9H, s).

Example 177

N-[(1R,2S)-1-(3-fluoro-4-methoxy-phenyl)-1-[1-(4-fluorophenyl)indazol-5-yl]oxy-propan-2-yl]-2,2-dimethyl-propanamide

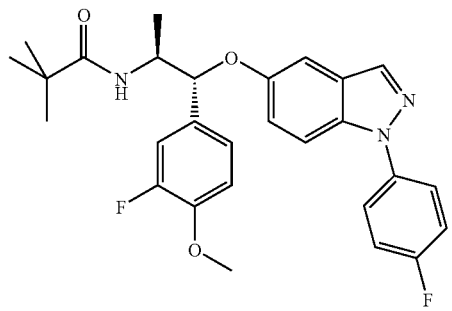

Chiral

Prepared as described in Example 8 using corresponding starting material.

APCI-MS: m/z 494.2 [MH+]

$^1$H-NMR (500 MHz, DMSO-d6): δ 8.14 (1H, d); 7.71-7.67 (2H, m); 7.64 (1H, d); 7.37-7.31 (3H, m); 7.16-7.03 (5H, m); 5.16 (1H, d); 4.16-4.10 (1H, m); 1.21-1.18 (6H, m); 0.89 (9H, s).

Example 178

N-[(1R,2S)-1-(3-chlorophenyl)-1-[1-(4-fluorophenyl)indazol-5-yl]oxy-propan-2-yl]-2,2-dimethyl-propanamide

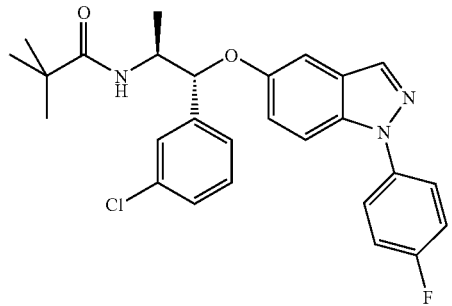

Chiral

Prepared as described in Example 8 using corresponding starting material.

APCI-MS: m/z 480.2 [MH+]

$^1$H-NMR (500 MHz, DMSO-d6): δ 8.14 (1H, t); 7.70-7.67 (2H, m); 7.65 (1H, d); 7.39-7.29 (7H, m); 7.25 (1H, dt); 7.16 (1H, dd); 7.09 (1H, d); 5.21 (1H, d); 4.19-4.11 (1H, m); 1.21 (3H, d); 0.89 (9H, s).

Example 179

N-[(1R,2S)-1-(4-fluoro-2-methyl-phenyl)-1-[1-(4-fluorophenyl)indazol-5-yl]oxy-propan-2-yl]-2,2-dimethyl-propanamide

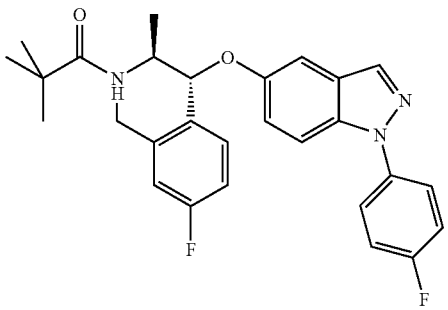

Chiral

Prepared as described in Example 8 using corresponding starting material.

APCI-MS: m/z 478.2 [MH+]

$^1$H-NMR (500 MHz, DMSO-d6): δ 8.12 (1H, d); 7.70-7.67 (2H, m); 7.64 (1H, d); 7.41-7.31 (4H, m); 7.14 (1H, dd); 6.99-6.95 (2H, m); 6.91 (1H, td); 5.37 (1H, d); 4.22-4.15 (1H, m); 1.17 (3H, d); 0.91 (9H, s).

Example 180

N-[(1R,2S)-1-(5-fluoro-2-methyl-phenyl)-1-[1-(4-fluorophenyl)indazol-5-yl]oxy-propan-2-yl]-2,2-dimethyl-propanamide

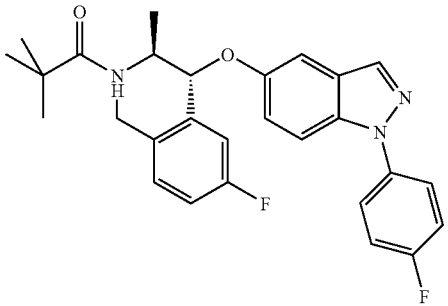

Chiral

Prepared as described in Example 8 using corresponding starting material.

APCI-MS: m/z 478.2 [MH+]

$^1$H-NMR (500 MHz, DMSO-d6): δ 8.13 (1H, d); 7.70-7.64 (3H, m); 7.43 (1H, d); 7.37-7.33 (2H, m); 7.18-7.14 (2H, m); 7.05 (1H, dd); 6.98 (1H, d); 6.95-6.91 (1H, m); 5.38 (1H, d); 4.23-4.16 (1H, m); 1.17 (3H, d); 0.92 (9H, s).

Example 181

N-[(1R,2S)-1-(5-fluoro-2-methoxy-phenyl)-1-[1-(4-fluorophenyl)indazol-5-yl]oxy-propan-2-yl]-2,2-dimethyl-propanamide

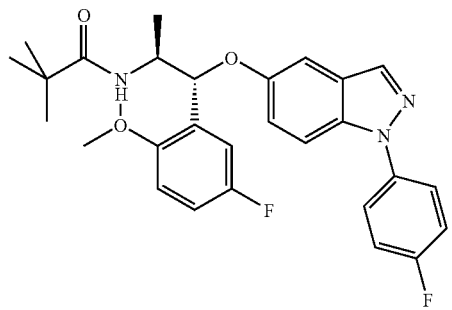

Chiral

Prepared as described in Example 8 using corresponding starting material.

APCI-MS: m/z 494.2 [MH+]

$^1$H-NMR (500 MHz, DMSO-d6): δ 8.14 (1H, d); 7.70-7.67 (2H, m); 7.65 (1H, d); 7.37-7.33 (2H, m); 7.16-7.12 (2H, m); 7.03-6.96 (4H, m); 5.47 (1H, d); 4.37-4.30 (1H, m); 3.84 (3H, s); 1.16 (3H, d); 0.89 (9H, s).

Example 182

N-[(1R,2S)-1-[1-(4-fluorophenyl)indazol-5-yl]oxy-1-(4-methoxy-3,5-dimethyl-phenyl)propan-2-yl]-2,2-dimethyl-propanamide

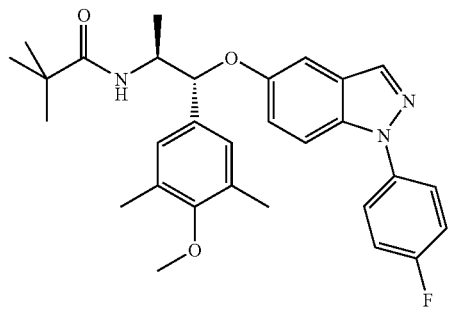

Chiral

Prepared as described in Example 8 using corresponding starting material.

APCI-MS: m/z 504.3 [MH+]

$^1$H-NMR (500 MHz, DMSO-d6): δ 8.14 (1H, d); 7.69 (2H, dd); 7.64 (1H, d); 7.35 (2H, t); 7.28 (1H, d); 7.16 (1H, dd); 7.07 (1H, d); 7.01 (2H, s); 5.13 (1H, d); 4.09-4.02 (1H, m); 2.13 (6H, s); 1.16 (3H, d); 0.89 (9H, s).

Example 183

N-[(1R,2S)-1-(4-chlorophenyl)-1-[1-(4-fluorophenyl)indazol-5-yl]oxy-propan-2-yl]-2,2-dimethyl-propanamide

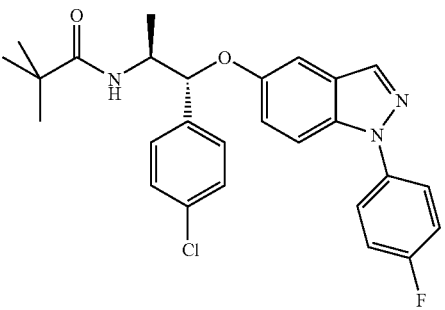

Chiral

Prepared as described in Example 8 using corresponding starting material.

APCI-MS: m/z 480.2 [MH+]

$^1$H-NMR (500 MHz, DMSO-d6): δ 8.13 (1H, d); 7.70-7.67 (2H, m); 7.64 (1H, d); 7.40-7.32 (7H, m); 7.15 (1H, dd); 7.07 (1H, d); 5.22 (1H, d); 4.19-4.12 (1H, m); 1.20 (3H, d); 0.88 (9H, s).

Example 184

N-[(1R,2S)-1-(3-chloro-5-fluoro-phenyl)-1-[1-(4-fluorophenyl)indazol-5-yl]oxy-propan-2-yl]-2,2-dimethyl-propanamide

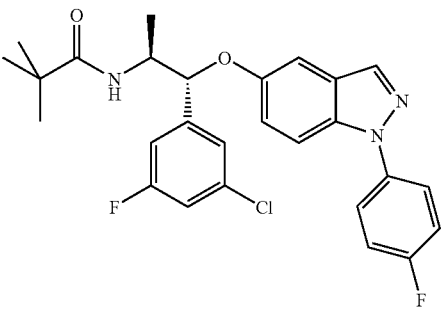

Chiral

Prepared as described in Example 8 using corresponding starting material.

APCI-MS: m/z 498.2 [MH+]

$^1$H-NMR (500 MHz, DMSO-d6): δ 8.16 (1H, d); 7.71-7.65 (3H, m); 7.40 (1H, d); 7.38-7.34 (2H, m); 7.27-7.24 (2H, m); 7.19-7.15 (2H, m); 7.13 (1H, d); 5.20 (1H, d); 4.18-4.12 (1H, m); 1.23 (3H, d); 0.90 (9H, s).

Example 185

N-[(1R,2S)-1-[1-(4-fluorophenyl)indazol-5-yl]oxy-1-(3-methylphenyl)propan-2-yl]-2,2-dimethyl-propanamide

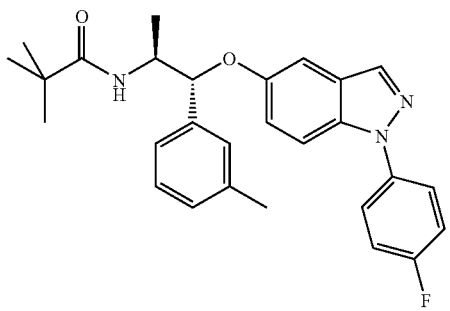

Chiral

Prepared as described in Example 8 using corresponding starting material.

APCI-MS: m/z 460.2 [MH+]

$^1$H-NMR (500 MHz, DMSO-d6): δ 8.12 (1H, d); 7.70-7.62 (3H, m); 7.37-7.31 (3H, m); 7.18-7.15 (4H, m); 7.05 (1H, d); 7.02-7.00 (1H, m); 5.21 (1H, d); 4.15-4.08 (1H, m); 2.23 (3H, s); 1.17 (3H, d); 0.89 (9H, s).

Example 186

N-[(1R,2S)-1-[1-(4-fluorophenyl)indazol-5-yl]oxy-1-(4-tert-butylphenyl)propan-2-yl]-2,2-dimethyl-propanamide

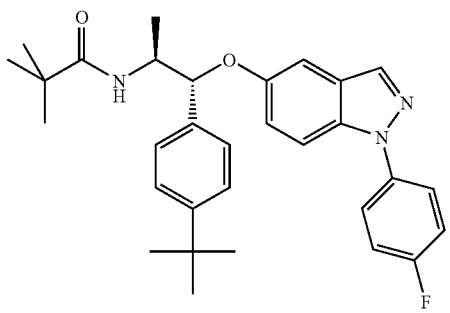

Chiral

Prepared as described in Example 8 using corresponding starting material.

APCI-MS: m/z 502.3 [MH+]

$^1$H-NMR (500 MHz, DMSO-d6): δ 8.13 (1H, d); 7.69-7.62 (3H, m); 7.37-7.33 (2H, m); 7.29-7.26 (5H, m); 7.16 (1H, dd); 7.09 (1H, d); 5.22 (1H, d); 4.19-4.11 (1H, m); 1.19-1.17 (12H, m); 0.85 (9H, s).

Example 187

N-[(1R,2S)-1-[1-(4-fluorophenyl)indazol-5-yl]oxy-1-(2-methoxyphenyl)propan-2-yl]-2,2-dimethyl-propanamide

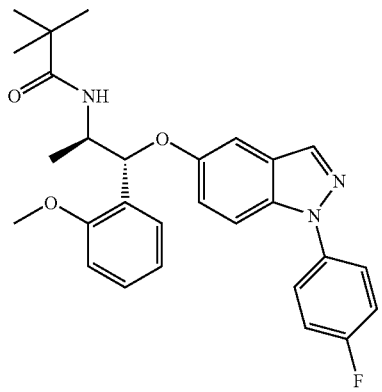

Chiral

Prepared as described in Example 8 using corresponding starting material.

APCI-MS: m/z 476.2 [MH+]

$^1$H-NMR (500 MHz, DMSO-d6): δ 8.12 (1H, t); 7.70-7.66 (2H, m); 7.63 (1H, d); 7.37-7.33 (2H, m); 7.26 (1H, dd); 7.19 (1H, dddd); 7.14 (1H, dd); 7.05 (1H, d); 7.00-6.97 (2H, m); 6.84 (1H, t); 5.50 (1H, d); 4.35-4.30 (1H, m); 3.85 (3H, s); 1.13 (3H, d); 0.89 (9H, d).

Example 188

N-[(1R,2S)-1-[1-(4-fluorophenyl)indazol-5-yl]oxy-1-(4-propylphenyl)propan-2-yl]-2,2-dimethyl-propanamide

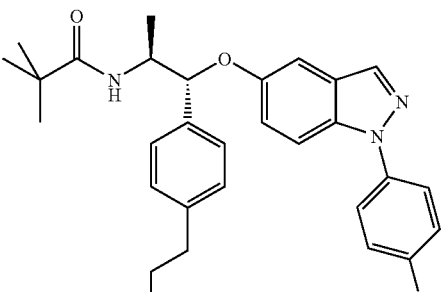

Chiral

Prepared as described in Example 8 using corresponding starting material.

APCI-MS: m/z 488.3 [MH+]

$^1$H-NMR (500 MHz, DMSO-d6): δ 8.12 (1H, d); 7.69-7.66 (2H, m); 7.63 (1H, d); 7.37-7.33 (2H, m); 7.30-7.25 (3H, m); 7.15 (1H, dd); 7.09-7.06 (3H, m); 5.20 (1H, d); 4.17-4.12 (1H, m); 1.47 (2H, quintet); 1.18 (3H, d); 0.87 (9H, s); 0.79 (3H, t).

Example 189

N-[(1R,2S)-1-benzo[1,3]dioxol-5-yl-1-[1-(4-fluorophenyl)indazol-5-yl]oxy-propan-2-yl]-2,2-dimethyl-propanamide

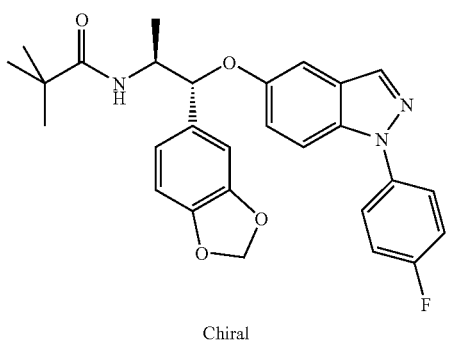

Chiral

Prepared as described in Example 8 using corresponding starting material.
APCI-MS: m/z 490.2 [MH+]
$^1$H-NMR (500 MHz, DMSO-d6): δ 8.14 (1H, d); 7.70-7.67 (2H, m); 7.64 (1H, d); 7.37-7.33 (2H, m); 7.29 (1H, d); 7.14 (1H, dd); 7.09 (1H, d); 6.87-6.79 (3H, m); 5.90 (2H, d); 5.14 (1H, d); 4.15-4.08 (1H, m); 1.19 (3H, d); 0.90 (9H, d).

Example 190

N-[(1R,2S)-1-(3-fluoro-2-methyl-phenyl)-1-[1-(4-fluorophenyl)indazol-5-yl]oxy-propan-2-yl]-2,2-dimethyl-propanamide

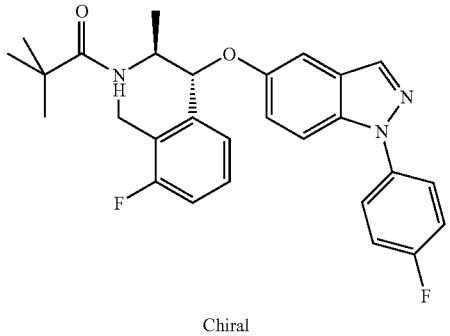

Chiral

Prepared as described in Example 8 using corresponding starting material.
APCI-MS: m/z 478.2 [MH+]
$^1$H NMR (499.875 MHz, DMSO-d6) δ8.12 (1H, d); 7.71-7.63 (3H, m); 7.43 (1H, d); 7.38-7.32 (2H, m); 7.18-7.10 (3H, m); 7.02-6.96 (2H, m); 5.43 (1H, d); 4.19 (1H, td); 1.15 (3H, t); 0.92 (9H, s);

Example 191

N-[(1R,2S)-1-(4-chloro-3-methyl-phenyl)-1-[1-(4-fluorophenyl)indazol-5-yl]oxy-propan-2-yl]-2,2-dimethyl-propanamide

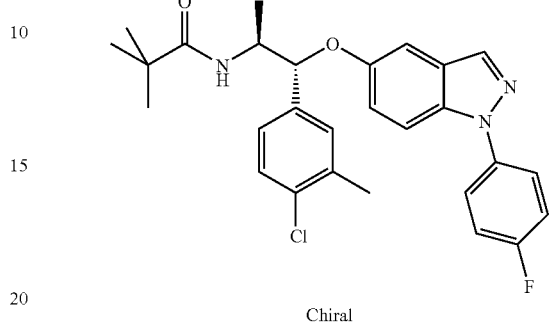

Chiral

Prepared as described in Example 8 using corresponding starting material.
APCI-MS: m/z 494.2 [MH+]
$^1$H-NMR (500 MHz, DMSO-d6): δ 8.13 (1H, d); 7.70-7.67 (2H, m); 7.64 (1H, d); 7.37-7.29 (5H, m); 7.20 (1H, dd); 7.15 (1H, dd); 7.07 (1H, d); 5.18 (1H, d); 4.16-4.08 (1H, m); 2.24 (3H, s); 1.19 (3H, d); 0.89 (9H, s).

Example 192

N-[(1R,2S)-1-(3,4-dimethylphenyl)-1-[1-(4-fluorophenyl)indazol-5-yl]oxy-propan-2-yl]-5-methyl-1,3-thiazole-2-carboxamide 5-methyl-1,3-thiazole-2-carboxylic acid (29 mg, 0.2 mmol) was dissolved in NMP (1 mL) together with HATU (76 mg, 0.2 mmol) and DIEA (133 uL, 0.8 mmol). The mixture was stirred in r.t. for 5 min before (1R,2S)-1-(3,4-dimethylphenyl)-1-(1-(4-fluorophenyl)-1H-indazol-5-yloxy)propan-2-amine (58 mg, 0.15 mmol, prepared analogously to Example 6a with corresponding starting material) was added. The reaction mixture was stirred in r.t. overnight before it was evaporated under reduced pressure and purified by semi-prep. HPLC.
APCI-MS: m/z 515.2 [MH+]
$^1$H-NMR (500 MHz, DMSO-d6): δ 8.47 (1H, d); 8.11 (1H, d); 7.69-7.66 (2H, m); 7.63 (1H, d); 7.51 (1H, d); 7.37-7.33 (2H, m); 7.18-7.15 (2H, m); 7.11-7.02 (3H, m); 5.39 (1H, d); 4.34-4.28 (1H, m); 2.10 (6H, d); 1.26 (3H, d).

Example 193

N-[(1R,2S)-1-(3,4-difluorophenyl)-1-[1-(4-fluorophenyl)indazol-5-yl]oxy-propan-2-yl]-5-methyl-1,3-thiazole-2-carboxamide

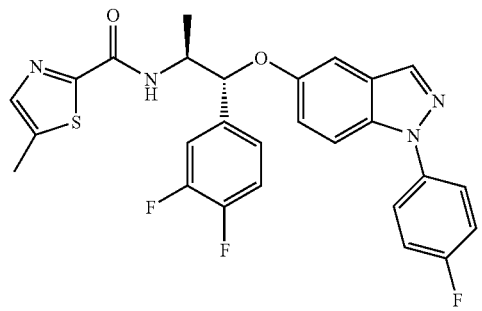

Chiral

Prepared as described in Example 192 using corresponding starting material.

APCI-MS: m/z 523.1 [MH+]

$^1$H-NMR (500 MHz, DMSO-d6): δ 8.64 (1H, d); 8.13 (1H, d); 7.70-7.64 (3H, m); 7.51 (1H, d); 7.44-7.28 (4H, m); 7.25-7.21 (1H, m); 7.18 (1H, dd); 7.13 (1H, d); 5.39 (1H, d); 4.37-4.30 (1H, m); 1.33 (3H, d).

Example 194

N-[(1R,2S)-1-(3-fluoro-4-methyl-phenyl)-1-[1-(4-fluorophenyl)indazol-5-yl]oxy-propan-2-yl]-5-methyl-1,3-thiazole-2-carboxamide

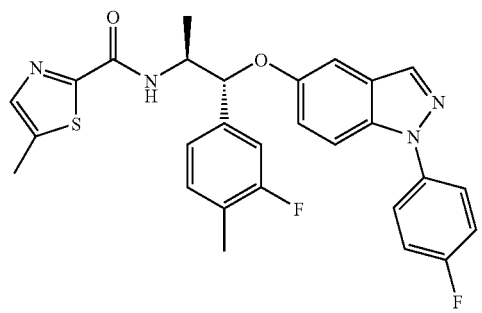

Chiral

Prepared as described in Example 192 using corresponding starting material.

APCI-MS: m/z 519.2 [MH+]

$^1$H-NMR (500 MHz, DMSO-d6): δ 8.60 (1H, d); 8.12 (1H, d); 7.70-7.63 (3H, m); 7.51 (1H, d); 7.37-7.33 (2H, m); 7.19-7.10 (5H, m); 5.41 (1H, d); 4.37-4.30 (1H, m); 2.10 (3H, d); 1.31 (3H, d).

Example 195

N-[(1R,2S)-1-(3-fluorophenyl)-1-[1-(4-fluorophenyl)indazol-5-yl]oxy-propan-2-yl]-5-methyl-1,3-thiazole-2-carboxamide

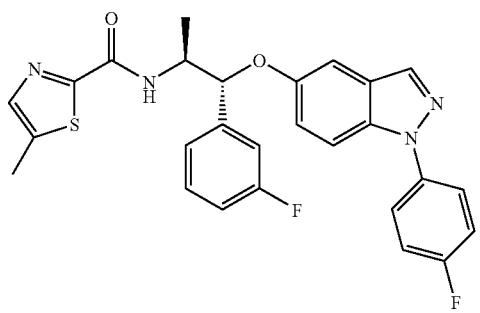

Chiral

Prepared as described in Example 192 using corresponding starting material.

APCI-MS: m/z 505.2 [MH+]

$^1$H-NMR (500 MHz, DMSO-d6): δ 8.63 (1H, d); 8.13 (1H, d); 7.70-7.64 (3H, m); 7.50 (1H, d); 7.37-7.33 (2H, m); 7.33-7.28 (1H, m); 7.24 (1H, d); 7.20-7.17 (2H, m); 7.12 (1H, d); 7.03-6.99 (1H, m); 5.44 (1H, d); 4.39-4.32 (1H, m); 1.32 (3H, d).

Example 196

N-[(1R,2S)-1-(2,5-dimethylphenyl)-1-[1-(4-fluorophenyl)indazol-5-yl]oxy-propan-2-yl]-5-methyl-1,3-thiazole-2-carboxamide

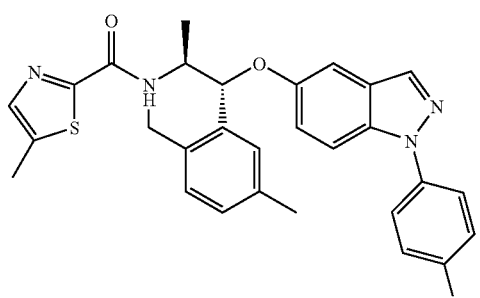

Chiral

Prepared as described in Example 192 using corresponding starting material.

APCI-MS: m/z 515.2 [MH+] $^1$H-NMR (500 MHz, DMSO-d6): δ 8.53 (1H, d); 8.10 (1H, d); 7.69-7.62 (3H, m); 7.51 (1H, d); 7.51 (1H, d); 7.36-7.32 (2H, m); 7.18 (1H, dd); 7.13 (1H, s); 7.03 (1H, d); 6.95-6.91 (2H, m); 5.54 (1H, d); 4.37-4.31 (1H, m); 2.13 (3H, s); 1.28 (3H, d).

Example 197

N-[(1R,2S)-1-(2,4-dimethylphenyl)-1-[1-(4-fluorophenyl)indazol-5-yl]oxy-propan-2-yl]-5-methyl-1,3-thiazole-2-carboxamide

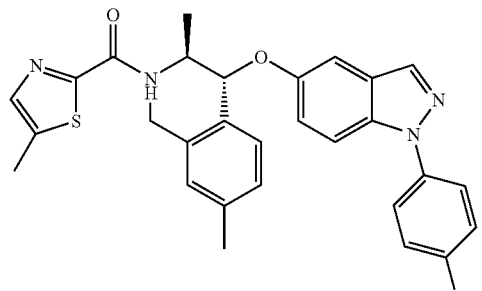

Chiral

Prepared as described in Example 192 using corresponding starting material.

APCI-MS: m/z 515.2 [MH+] $^1$H-NMR (500 MHz, DMSO-d6): δ 8.55 (1H, d); 8.09 (1H, d); 7.69-7.61 (3H, m); 7.51 (1H, d); 7.36-7.32 (2H, m); 7.20-7.15 (2H, m); 6.96-6.93 (2H, m); 6.89 (1H, d); 5.55 (1H, d); 4.38-4.31 (1H, m); 2.15 (3H, s); 1.28 (3H, d).

Example 198

N-[(1R,2S)-1-(3-fluoro-4-methoxy-phenyl)-1-[1-(4-fluorophenyl)indazol-5-yl]oxy-propan-2-yl]-5-methyl-1,3-thiazole-2-carboxamide

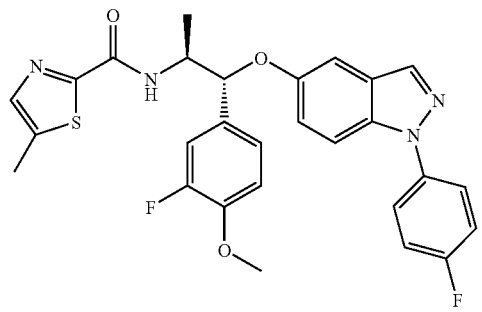

Chiral

Prepared as described in Example 192 using corresponding starting material.

APCI-MS: m/z 535.2 [MH+] $^1$H-NMR (500 MHz, DMSO-d6): δ 8.58 (1H, d); 8.13 (1H, t); 7.70-7.63 (3H, m); 7.51 (1H, d); 7.37-7.33 (2H, m); 7.21-7.11 (4H, m); 7.04 (1H, t); 5.37 (1H, d); 4.35-4.29 (1H, m); 3.71 (3H, s); 1.31 (3H, d).

Example 199

N-[(1R,2S)-1-(3-chlorophenyl)-1-[1-(4-fluorophenyl)indazol-5-yl]oxy-propan-2-yl]-5-methyl-1,3-thiazole-2-carboxamide

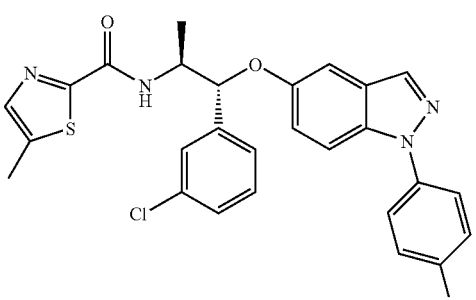

Chiral

Prepared as described in Example 192 using corresponding starting material.

APCI-MS: m/z 521.1 [MH+]

$^1$H-NMR (500 MHz, DMSO-d6): δ 8.63 (1H, d); 8.13 (1H, d); 7.70-7.64 (3H, m); 7.50 (1H, d); 7.42 (1H, s); 7.37-7.33 (2H, m); 7.29 (1H, t); 7.25-7.23 (1H, m); 7.19 (1H, dd); 7.11 (1H, d); 5.42 (1H, d); 4.37-4.30 (1H, m); 1.32 (3H, d).

Example 200

N-[(1R,2S)-1-(4-fluoro-2-methyl-phenyl)-1-[1-(4-fluorophenyl)indazol-5-yl]oxy-propan-2-yl]-5-methyl-1,3-thiazole-2-carboxamide

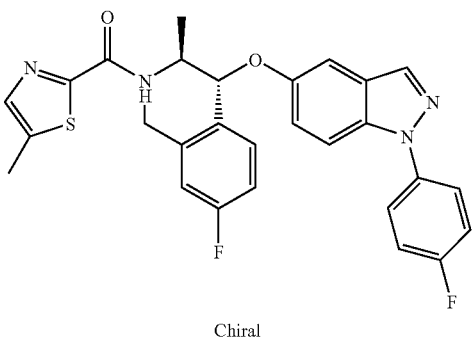

Chiral

Prepared as described in Example 192 using corresponding starting material.

APCI-MS: m/z 519.2 [MH+]

$^1$H-NMR (500 MHz, DMSO-d6): δ 8.62 (1H, d); 8.11 (1H, d); 7.69-7.62 (3H, m); 7.50 (1H, d); 7.36-7.32 (3H, m); 7.17 (1H, dd); 6.99-6.96 (2H, m); 6.93-6.89 (1H, m); 5.54 (1H, d); 4.39-4.34 (1H, m); 1.30 (3H, d).

Example 201

N-[(1R,2S)-1-(5-fluoro-2-methyl-phenyl)-1-[1-(4-fluorophenyl)indazol-5-yl]oxy-propan-2-yl]-5-methyl-1,3-thiazole-2-carboxamide

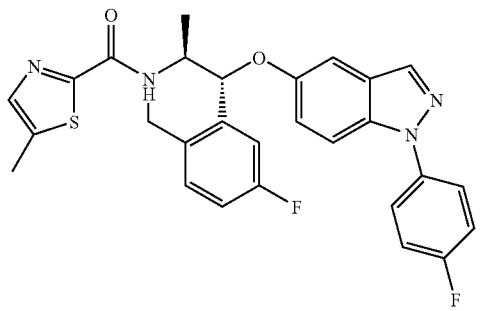

Chiral

Prepared as described in Example 192 using corresponding starting material.

APCI-MS: m/z 519.2 [MH+]

$^1$H-NMR (500 MHz, DMSO-d6): δ 8.64 (1H, d); 8.11 (1H, d); 7.69-7.64 (3H, m); 7.51 (1H, d); 7.37-7.33 (2H, m); 7.20-7.15 (2H, m); 7.07 (1H, dd); 6.99 (1H, d); 6.95-6.91 (1H, m); 5.55 (1H, d); 4.41-4.36 (1H, m); 1.31 (3H, d).

Example 202

N-[(1R,2S)-1-(5-fluoro-2-methoxy-phenyl)-1-[1-(4-fluorophenyl)indazol-5-yl]oxy-propan-2-yl]-5-methyl-1,3-thiazole-2-carboxamide

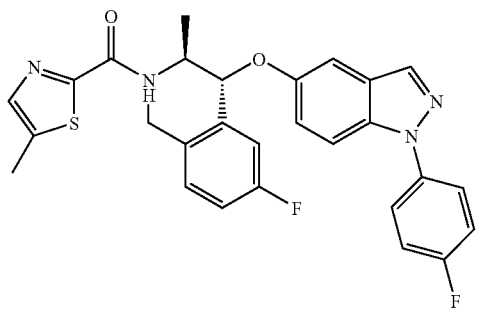

Chiral

Prepared as described in Example 192 using corresponding starting material.

APCI-MS: m/z 535.2 [MH+]

$^1$H-NMR (500 MHz, DMSO-d6): δ 8.32 (1H, d); 8.14 (1H, d); 7.70-7.65 (3H, m); 7.51 (1H, d); 7.37-7.33 (2H, m); 7.19 (1H, dd); 7.07-6.96 (4H, m); 5.64 (1H, d); 4.48-4.40 (1H, m); 3.81 (3H, s); 1.28 (3H, d).

Example 203

N-[(1R,2S)-1-[1-(4-fluorophenyl)indazol-5-yl]oxy-1-(4-methoxy-3,5-dimethyl-phenyl)propan-2-yl]-5-methyl-1,3-thiazole-2-carboxamide

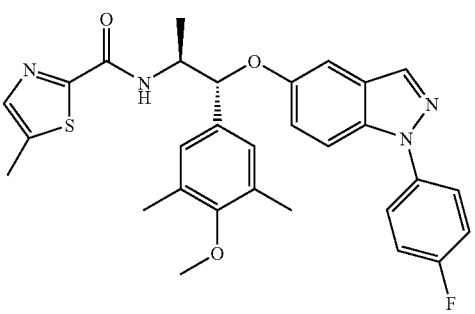

Chiral

Prepared as described in Example 192 using corresponding starting material.

APCI-MS: m/z 545.2 [MH+]

$^1$H-NMR (500 MHz, DMSO-d6): δ 8.43 (1H, d); 8.13 (1H, d); 7.70-7.63 (3H, m); 7.51 (1H, d); 7.37-7.33 (2H, m); 7.18 (1H, dd); 7.09 (1H, d); 7.04 (2H, s); 5.34 (1H, d); 4.30-4.23 (1H, m); 2.09 (6H, s); 1.26 (3H, d).

Example 204

N-[(1R,2S)-1-(4-chlorophenyl)-1-[1-(4-fluorophenyl)indazol-5-yl]oxy-propan-2-yl]-5-methyl-1,3-thiazole-2-carboxamide

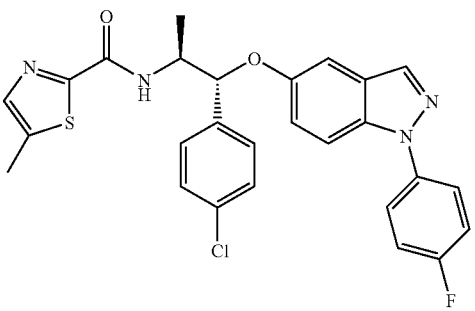

Chiral

Prepared as described in Example 192 using corresponding starting material.

APCI-MS: m/z 521.1 [MH+]

$^1$H-NMR (500 MHz, DMSO-d6): δ 8.62 (1H, d); 8.12 (1H, d); 7.70-7.63 (3H, m); 7.50 (1H, d); 7.42-7.40 (2H, m); 7.37-7.31 (4H, m); 7.17 (1H, dd); 7.09 (1H, d); 5.42 (1H, d); 4.36-4.31 (1H, m); 1.32 (3H, d).

Example 205

N-[(1R,2S)-1-(3-chloro-5-fluoro-phenyl)-1-[1-(4-fluorophenyl)indazol-5-yl]oxy-propan-2-yl]-5-methyl-1,3-thiazole-2-carboxamide

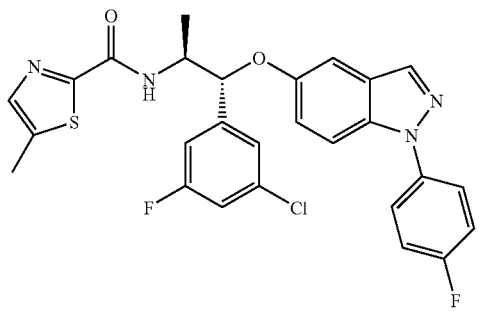

Chiral

Prepared as described in Example 192 using corresponding starting material.

APCI-MS: m/z 539.1 [MH+]

$^1$H-NMR (500 MHz, DMSO-d6): δ 8.67 (1H, d); 8.15 (1H, d); 7.71-7.65 (3H, m); 7.51 (1H, d); 7.38-7.34 (2H, m); 7.29 (1H, s); 7.25-7.19 (2H, m); 7.15 (1H, d); 5.41 (1H, d); 4.37-4.30 (1H, m); 1.34 (3H, d).

Example 206

N-[(1R,2S)-1-[1-(4-fluorophenyl)indazol-5-yl]oxy-1-(2,4,5-trimethylphenyl)propan-2-yl]-5-methyl-1,3-thiazole-2-carboxamide

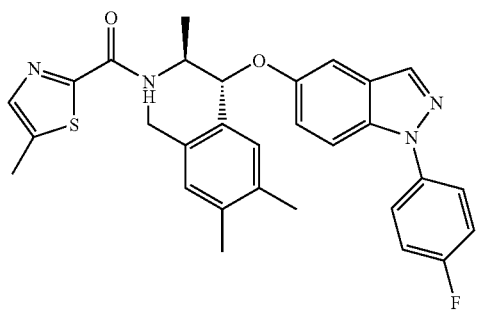

Chiral

Prepared as described in Example 192 using corresponding starting material.

APCI-MS: m/z 529.2 [MH+]

$^1$H-NMR (500 MHz, DMSO-d6): δ 8.50 (1H, d); 8.10 (1H, d); 7.69-7.62 (3H, m); 7.51 (1H, d); 7.36-7.32 (2H, m); 7.17 (1H, dd); 7.06 (1H, s); 6.93 (1H, d); 6.91 (1H, s); 5.51 (1H, d); 4.35-4.30 (1H, m); 2.07 (3H, s); 2.04 (3H, s); 1.27 (3H, d).

Example 207

N-[(1R,2S)-1-[1-(4-fluorophenyl)indazol-5-yl]oxy-1-(3-methylphenyl)propan-2-yl]-5-methyl-1,3-thiazole-2-carboxamide

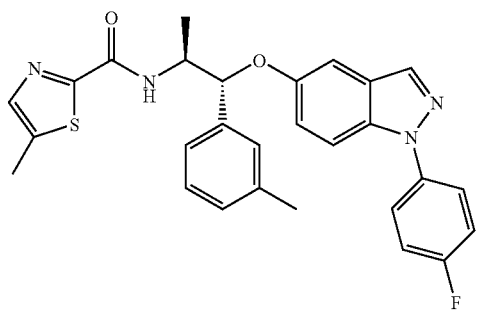

Chiral

Prepared as described in Example 192 using corresponding starting material.

APCI-MS: m/z 501.2 [MH+]

$^1$H-NMR (500 MHz, DMSO-d6): δ 8.50 (1H, d); 8.11 (1H, d); 7.70-7.62 (3H, m); 7.50 (1H, d); 7.37-7.33 (2H, m); 7.22-7.13 (4H, m); 7.08 (1H, d); 7.01 (1H, d); 5.41 (1H, d); 4.35-4.29 (1H, m); 2.19 (3H, s); 1.28 (3H, d).

Example 208

N-[(1R,2S)-1-[1-(4-fluorophenyl)indazol-5-yl]oxy-1-(4-tert-butylphenyl)propan-2-yl]-5-methyl-1,3-thiazole-2-carboxamide

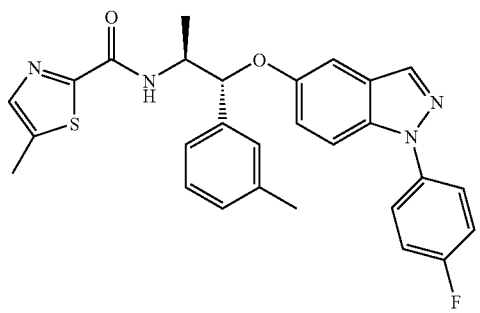

Chiral

Prepared as described in Example 192 using corresponding starting material.

APCI-MS: m/z 543.2 [MH+]

$^1$H-NMR (500 MHz, DMSO-d6): δ 8.51 (1H, d); 8.11 (1H, d); 7.69-7.63 (3H, m); 7.50 (1H, d); 7.37-7.28 (6H, m); 7.19 (1H, dd); 7.10 (1H, d); 5.47 (1H, d); 4.34-4.28 (1H, m); 1.27 (3H, d); 1.17 (9H, s).

Example 209

N-[(1R,2S)-1-[1-(4-fluorophenyl)indazol-5-yl]oxy-1-(2-methoxyphenyl)propan-2-yl]-5-methyl-1,3-thiazole-2-carboxamide

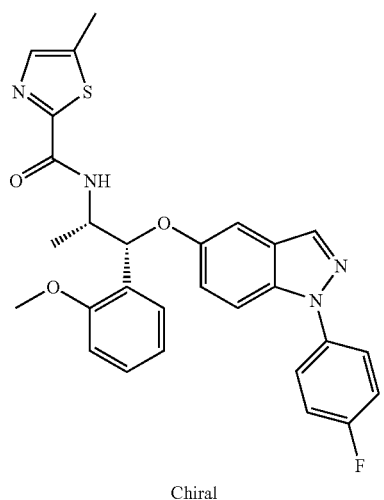

Chiral

Prepared as described in Example 192 using corresponding starting material.

APCI-MS: m/z 517.2 [MH+]

$^1$H-NMR (500 MHz, DMSO-d6): δ 8.25 (1H, d); 8.12 (1H, d); 7.69-7.63 (3H, m); 7.51 (1H, t); 7.37-7.33 (2H, m); 7.28 (1H, dd); 7.22-7.17 (2H, m); 7.01-6.97 (2H, m); 6.85 (1H, t); 5.67 (1H, d); 4.46-4.40 (1H, m); 3.85 (3H, s); 1.26 (3H, d).

Example 210

N-[(1R,2S)-1-benzo[1,3]dioxol-5-yl-1-[1-(4-fluorophenyl)indazol-5-yl]xy-propan-2-yl]-5-methyl-1,3-thiazole-2-carboxamide

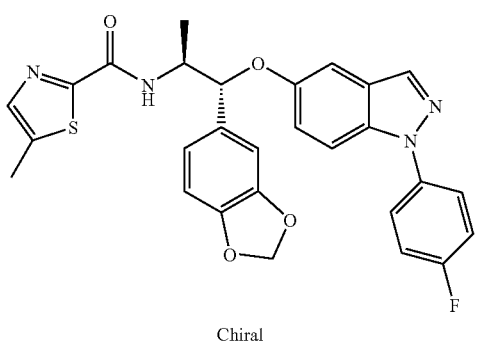

Chiral

Prepared as described in Example 192 using corresponding starting material.

APCI-MS: m/z 531.2 [MH+]

$^1$H-NMR (500 MHz, DMSO-d6): δ 8.53 (1H, d); 8.13 (1H, d); 7.70-7.67 (2H, m); 7.64 (1H, d); 7.50 (1H, d); 7.37-7.33 (2H, m); 7.16 (1H, dd); 7.11 (1H, d); 6.91 (1H, d); 6.87 (1H, dd); 6.78 (1H, d); 5.89 (2H, d); 5.35 (1H, d); 4.35-4.28 (1H, m); 1.30 (3H, d).

Example 211

N-[(1R,2S)-1-(3,4-dimethylphenyl)-1-[1-(4-fluorophenyl)indazol-5-yl]oxy-propan-2-yl]-1-methyl-cyclopropane-1-carboxamide

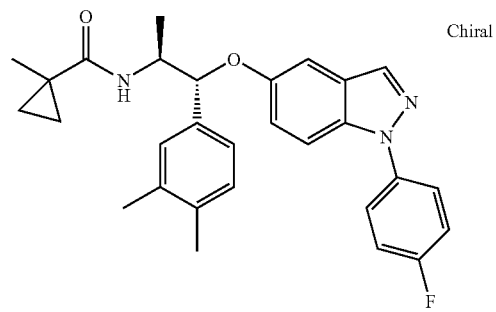

Chiral

Prepared as described in Example 192 using corresponding starting material.

APCI-MS: m/z 472.2 [MH+]

$^1$H-NMR (500 MHz, DMSO-d6): δ 8.11 (1H, s); 7.70-7.67 (2H, m); 7.64 (1H, d); 7.37-7.33 (2H, m); 7.28 (1H, d); 7.16 (1H, dd); 7.11 (2H, s); 7.07-7.02 (2H, m); .19 (1H, d); 4.12-4.05 (1H, m); 2.13 (6H, d); 1.15 (3H, d); 1.12 (3H, s); 0.75 (2H, d); 0.37 (2H, ddd)

Example 212

N-[(1R,2S)-1-(3,4-difluorophenyl)-1-[1-(4-fluorophenyl)indazol-5-yl]oxy-propan-2-yl]-1-methyl-cyclopropane-1-carboxamide

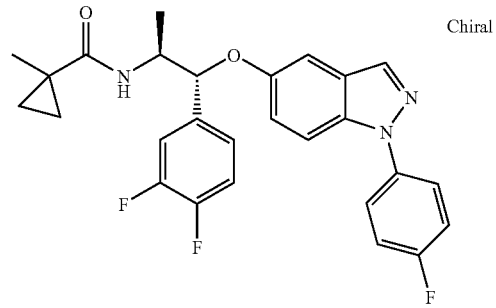

Chiral

Prepared as described in Example 192 using corresponding starting material.

APCI-MS: m/z 480.2 [MH+]

$^1$H-NMR (500 MHz, DMSO-d6): δ 8.14 (1H, d); 7.70-7.67 (2H, m); 7.65 (1H, ); 7.39-7.30 (5H, m); 7.22-7.15 (2H, m); 7.10 (1H, d); 5.20 (1H, d); 4.18-4.12 (1H, m); 1.22 (3H, d); 1.11 (3H, s); 0.76-0.71 (1H, m); 0.65-0.60 (1H, m); 0.42-0.37 (1H, m); 0.35-0.31 (1H, m).

Example 213

N-[(1R,2S)-1-(3-fluoro-4-methyl-phenyl)-1-[1-(4-fluorophenyl)indazol-5-yl]xy-propan-2-yl]-1-methyl-cyclopropane-1-carboxamide

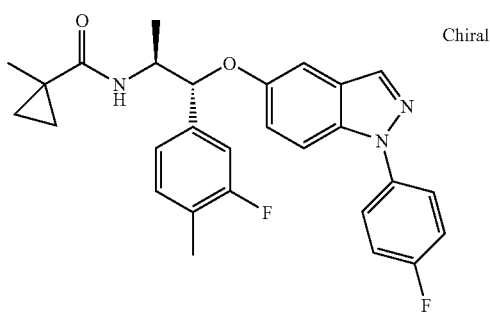

Prepared as described in Example 192 using corresponding starting material.

APCI-MS: m/z 476.2 [MH+]

$^1$H-NMR (500 MHz, DMSO-d6): δ 8.13 (1H, d); 7.70-7.67 (2H, m); 7.64 (1H, d); 7.37-7.33 (3H, m); 7.20-7.15 (3H, m); 7.09-7.05 (3H, m); 5.21 (1H, d); 4.16-4.10 (1H, m); 2.13 (3H, s); 1.19 (3H, d); 1.12 (3H, s); 0.76-0.66 (2H, m); 0.42-0.31 (2H, m).

Example 214

N-[(1R,2S)-1-(3-fluorophenyl)-1-[1-(4-fluorophenyl)indazol-5-yl]oxy-propan-2yl]-1-methyl-cyclopropane-1-carboxamide

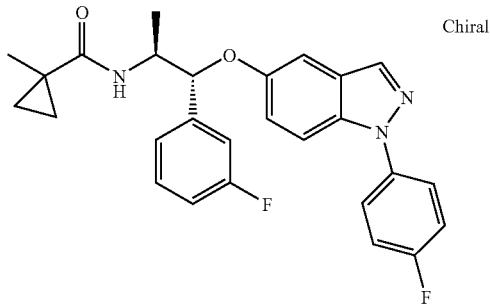

Prepared as described in Example 192 using corresponding starting material.

APCI-MS: m/z 462.2 [MH+]

$^1$H-NMR (500 MHz, DMSO-d6): δ 8.13 (1H, d); 7.70-7.67 (2H, m); 7.65 (1H, ); 7.40-7.30 (4H, m); 7.20 (1H, d); 7.19-7.12 (2H, m); 7.08 (1H, d); 7.03 (1H, td); 5.25 (14, d); 4.20-4.12 (1H, m); 1.21 (3H, d); 1.12 (3H, d); 0.76-0.71 (1H, m); 0.68-0.64 (1H, m); 0.41-0.37 (1H, m); 0.34-0.30 (1H, m).

Example 215

N-[(1R,2S)-1-(2,5-dimethylphenyl)-1-[1-(4-fluorophenyl)indazol-5-yl]oxy-propan-2-yl]-1-methyl-cyclopropane-1-carboxamide

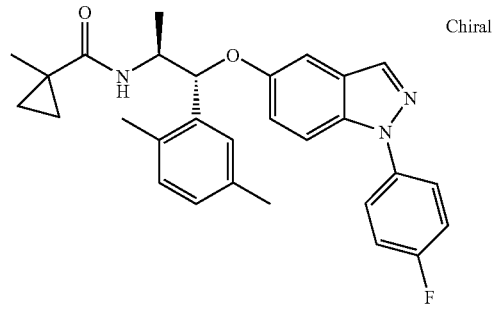

Prepared as described in Example 192 using corresponding starting material.

APCI-MS: m/z 472.2 [MH+]

$^1$H-NMR (500 MHz, DMSO-d6): δ 8.12 (1H, d); 7.70-7.67 (2H, m); 7.65 (1H, d); 7.37-7.32 (3H, m); 7.16 (1H, dd); 7.11 (1H, s); 7.02 (1H, d); 6.94-6.90 (2H, m); 5.36 (1H, d); 4.19-4.12 (1H, m); 2.15 (3H, s); 1.16 (3H, d); 1.13 (3H, s); 0.81-0.75 (2H, m); 0.42-0.33 (2H, m).

Example 216

N-[(1R,2S)-1-(2,4-dimethylphenyl)-1-[1-(4-fluorophenyl)indazol-5-yl]oxy-propan-2-yl]-1-methyl-cyclopropane-1-carboxamide

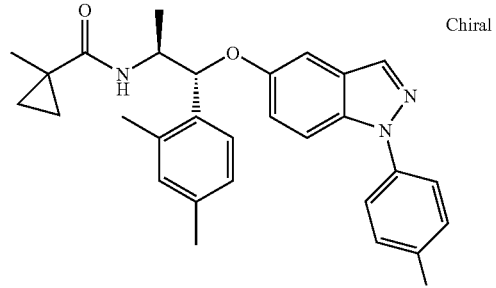

Prepared as described in Example 192 using corresponding starting material.

APCI-MS: m/z 472.2 [MH+]

$^1$H-NMR (500 MHz, DMSO-d6): δ 8.11 (1H, d); 7.70-7.62 (3H, m); 7.37-7.33 3H, m); 7.17-7.14 (2H, m); 6.95-6.87 (3H, m); 5.37 (1H, d); 4.18-4.12 (1H, m); 2 16 (3H, s); 1.16-1.13 (6H, m); 0.82-0.77 (2H, m); 0.43-0.34 (2H, m).

Example 217

N-[(1R,2S)-1-(3-fluoro-4-methoxy-phenyl)-1-[1-(4-fluorophenyl)indazol-5-yl]oxy propan-2-yl]-1-methyl-cyclopropane-1 carboxamide

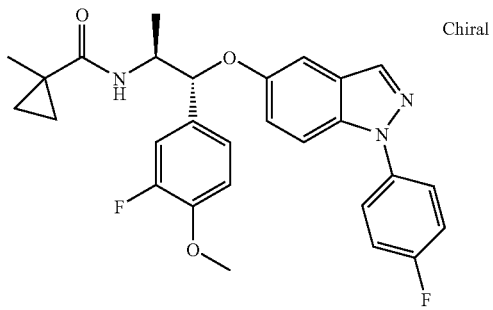

Prepared as described in Example 192 using corresponding starting material.

APCI-MS: m/z 492.2 [MH+]

$^1$H-NMR (500 MHz, DMSO-d6): δ 8.13 (1H, d); 7.71-7.67 (2H, m); 7.64 (1H, ); 7.37-7.31 (3H, m); 7.17-7.04 (5H, m); 5.17 (1H, d); 4.16-4.09 (1H, m); 3.74 (3H, s); 1.20 (3H, d); 1.12 (3H, s); 0.76-0.65 (2H, m); 0.42-0.32 (2H, m).

Example 218

N-[(1R,2S)-1-(3-chlorophenyl)-1-[1-(4-fluorophenyl)indazol-5-yl]oxy-propan-2-y ]-1-methyl-cyclopropane-1-carboxamide

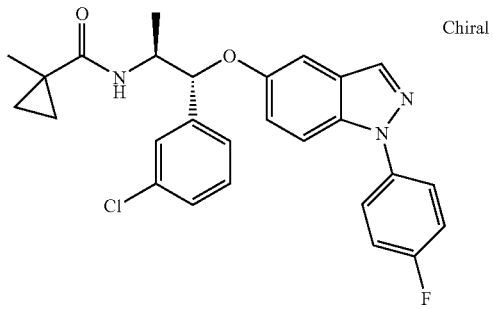

Prepared as described in Example 192 using corresponding starting material.

APCI-MS: m/z 478.2 [MH+]

$^1$H-NMR (500 MHz, DMSO-d6): δ 8.14 (1H, d); 7.71-7.64 (3H, m); 7.40-7.25 7H, m); 7.17 (1H, dd); 7.08 (1H, d); 5.23 (1H, d); 4.18-4.10 (1H, m); 1.21 (3H, d); 1.12 (3H, s); 0.76-0.71 (1H, m); 0.68-0.63 (1H, m); 0.41-0.37 (1H, m); 0.35-0.31 (1H, m).

Example 219

N-[(1R,2S)-1-(4-fluoro-2-methyl-phenyl)-1-[1-(4-fluorophenyl)indazol-5-yl]oxy propan-2-yl]-1-methyl-cyclopropane-1-carboxamide

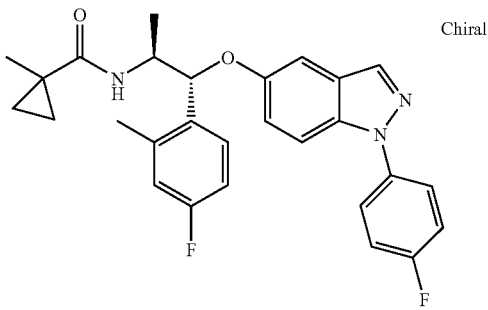

Prepared as described in Example 192 using corresponding starting material.

APCI-MS: m/z 476.2 [MH+]

$^1$H-NMR (500 MHz, DMSO-d6): δ 8.12 (1H, t); 7.70-7.63 (3H, m); 7.39-7.30 4H, m); 7.15 (1H, dd); 6.99-6.95 (2H, m); 6.91 (1H, td); 5.37 (1H, d); 4.22-4.15 1H, m); 1.17 (3H, d); 1.13 (3H, s); 0.80-0.73 (2H, m); 0.42-0.32 (2H, m).

Example 220

N-[(1R,2S)-1-(5-fluoro-2-methyl-phenyl)-1-[1-(4-fluorophenyl)indazol-5-yl]oxy propan-2-yl]-1-methyl-cyclopropane-1-carboxamide

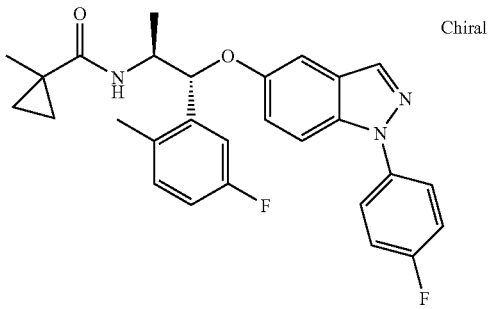

Prepared as described in Example 192 using corresponding starting material.

APCI-MS: m/z 476.2 [MH+]

$^1$H-NMR (500 MHz, DMSO-d6): δ 8.13 (1H, d); 7.70-7.65 (3H, m); 7.41 (1H, d); 7.37-7.33 (2H, m); 7.18-7.15 (2H, m); 7.04 (1H, dd); 6.98 (1H, d); 6.93 (1H, td); 5.38 (1H, d); 4.24-4.17 (1H, m); 1.18 (3H, d); 1.13 (3H, s); 0.80-0.73 (2H, m); 0.43-0. 2 (2H, m).

Example 221

N-[(1R,2S)-1-[1-(4-fluorophenyl)indazol-5-yl]oxy-1-(4-methoxy-3,5-dimethyl phenyl)propan-2-yl]-1-methyl-cyclopropane-1-carboxamide

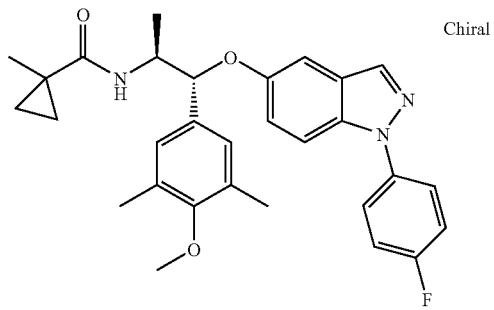

Prepared as described in Example 192 using corresponding starting material.

APCI-MS: m/z 502.2 [MH+]

$^1$H-NMR (500 MHz, DMSO-d6): δ 8.14 (1H, d); 7.71-7.67 (2H, m); 7.65 (1H, ); 7.38-7.33 (2H, m); 7.27 (1H, d); 7.17 (1H, dd); 7.05 (1H, d); 7.00 (2H, s); 5.14 1H, d); 4.09-4.02 (1H, m); 1.16 (3H, d); 1.12 (3H, s); 0.76-0.68 (2H, m); 0.41-0.31 (2H, m).

Example 222

N-[(1R,2S)-1-(4-chlorophenyl)-1-[1-(4-fluorophenyl)indazol-5-yl]oxy-propan-2yl]-1-methyl-cyclopropane-1-carboxamide

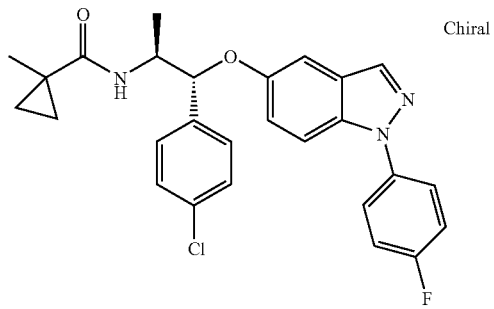

Prepared as described in Example 192 using corresponding starting material.

APCI-MS: m/z 478.2 [MH+]

$^1$H-NMR (500 MHz, DMSO-d6): δ 8.12 (1H, d); 7.70-7.67 (2H, m); 7.64 (1H, d); 7.39-7.33 (7H, m); 7.16 (1H, dd); 7.06 (1H, d); 5.23 (1H, d); 4.17-4.12 (1H, m); 1.20 (3H, d); 1.11 (3H, s); 0.75-0.64 (2H, m); 0.41-0.30 (2H, m).

Example 223

N-[(1R,2S)-1-(3-chloro-5-fluoro-phenyl)-1-[1-(4-fluorophenyl)indazol-5-yl]oxy propan-2-yl]-1-methyl-cyclopropane-1-carboxamide

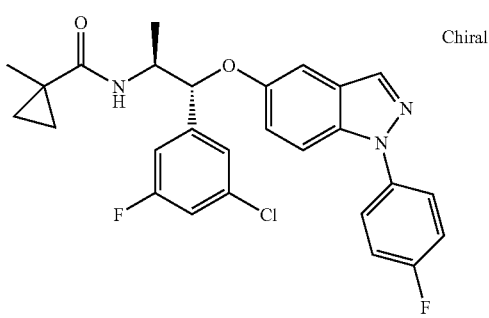

Prepared as described in Example 192 using corresponding starting material.

APCI-MS: m/z 496.2 [MH+]

$^1$H-NMR (500 MHz, DMSO-d6): δ 8.15 (1H, d); 7.71-7.65 (3H, m); 7.42 (1H, ); 7.37-7.34 (2H, m); 7.27-7.24 (2H, m); 7.18 (1H, dd); 7.16-7.13 (1H, m); 7.12 (1H, d); 5.21 (1H, d); 4.18-4.11 (1H, m); 1.24 (3H, d); 1.13 (3H, s); 0.77-0.72 (1H, m); 0.640.59 (1H, m); 0.42-0.32 (2H, m).

Example 224

N-[(1R,2S)-1-[1-(4-fluorophenyl)indazol-5-yl]oxy-1-(2,4,5-trimethylphenyl)propan 2-yl]-1-methyl-cyclopropane-1-carboxamide

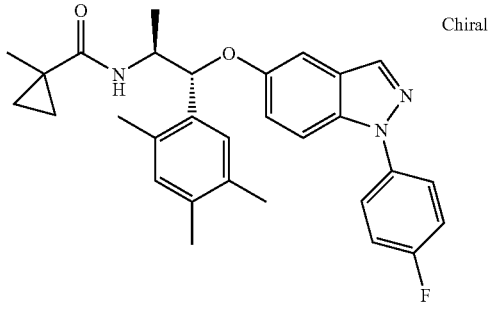

Prepared as described in Example 192 using corresponding starting material.

APCI-MS: m/z 486.3 [MH+]

$^1$H-NMR (500 MHz, DMSO-d6): δ 8.11 (1H, s); 7.69 (2H, dd); 7.64 (1H, d); 7. 8-7.29 (3H, m); 7.15 (1H, dd); 7.03 (1H, s); 6.91 (1H, d); 6.89 (1H, s); 5.33 (1H, d); 4 18-4.06 (1H, m); 2.08 (3H, s); 2.05 (3H, s); 1.22-1.12 (6H, m); 0.83-0.74 (2H, m); 0.44-0.32 2H, m);

Example 225

N-[(1R,2S)-1-[1-(4-fluorophenyl)indazol-5-yl]oxy-1-(3-methylphenyl)propan-2yl]-1-methyl-cyclopropane-1-carboxamide

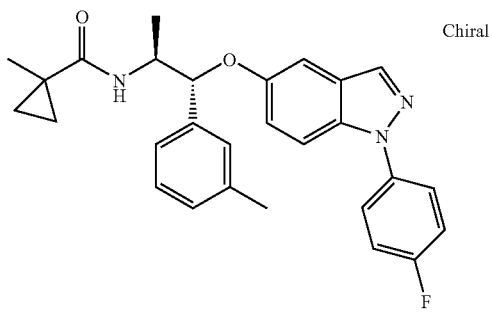

Prepared as described in Example 192 using corresponding starting material.

APCI-MS: m/z 458.2 [MH+]

$^1$H NMR (499.875 MHz, dmso) δ 8.12 (1H, t); 7.71-7.66 (2H, m); 7.64 (1H, d); 7.8-7.29 (3H, m); 7.19-7.12 (4H, m); 7.05-7.03 (1H, m); 7.03-7.00 (1H, m); 5.22 (1H, d); 4.11 (1H, dt); 2.23 (3H, s); 1.17 (3H, d); 1.12 (3H, s); 0.73 (2H, t); 0.36 (2H, ddd);

Example 226

N-[(1R,2S)-1-[1-(4-fluorophenyl)indazol-5-yl]oxy-1-(4-tert-butylphenyl)propan-2-yl]-1-methyl-cyclopropane-1 carboxamide

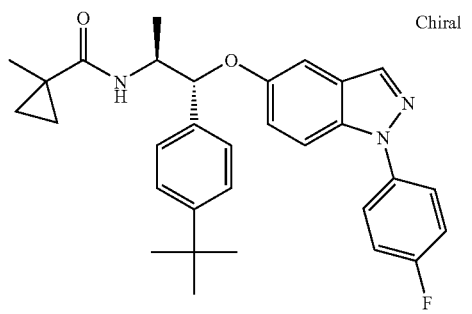

Prepared as described in Example 192 using corresponding starting material.

APCI-MS: m/z 500.3 [MH+]

$^1$H-NMR (500 MHz, DMSO-d6): δ 8.13 (1H, d); 7.70-7.63 (3H, m); 7.37-7.33 2H, m); 7.31-7.26 (5H, m); 7.17 (1H, dd); 7.07 (1H, d); 5.24 (1H, d); 4.16-4.10 1H, m); 1.19-1.16 (12H, m); 1.10 (3H, s).

Example 227

N-[(1R,2S)-1-[1-(4-fluorophenyl)indazol-5-yl]oxy-1-(2-methoxyphenyl)propan-2-y ]-1-methyl-cyclopropane-1-carboxamide

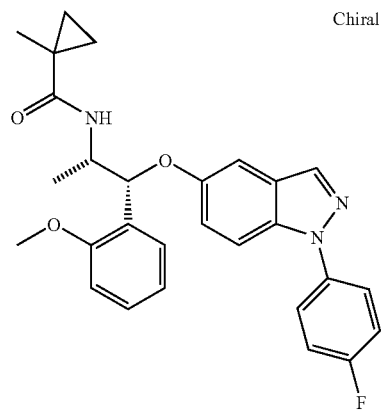

Prepared as described in Example 192 using corresponding starting material.

APCI-MS: m/z 474.2 [MH+]

$^1$H-NMR (500 MHz, DMSO-d6): δ 8.12 (1H, d); 7.70-7.63 (3H, m); 7.37-7.33 2H, m); 7.26 (1H, dd); 7.22-7.18 (1H, m); 7.15 (1H, dd); 7.05 (1H, d); 7.01-6.98 2H, m); 6.84 (1H, t); 5.50 (1H, d); 4.34-4.26 (1H, m); 3.85 (3H, s); 1.14 (3H, d); 1.11 (3H, ); 0.76-0.71 (2H, m); 0.41-0.31 (2H, m).

Example 228

N-[(1R,2S)-1-(3,4-difluorophenyl)-1-[1-(4-fluorophenyl)indazol-5-yl]oxy-propan-2-yl]-2,2-difluoro-propanamide

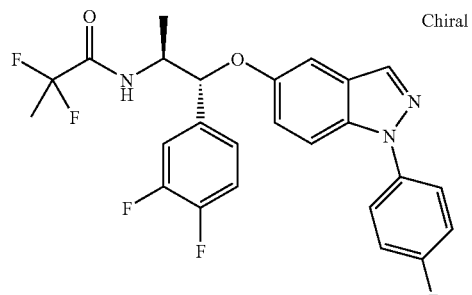

Ethyl 2,2-difluoropropanoate (200 uL) was heated neat together with (1R,2S)-1-(3,4-dimethylphenyl)-1-(1-(4-fluorophenyl)-1H-indazol-5-yloxy)propan-2-amine (58 mg, 0.15 mmol, prepared analogously to Example 6a with corresponding starting material) to 140° C. for 40 min. After cooling the compound was purified by semi-prep. HPLC.

APCI-MS: m/z 490.1 [MH+]

$^1$H-NMR (500 MHz, DMSO-d6): δ 8.75 (1H, d); 8.12 (1H, d); 7.68-7.62 (3H, ); 7.39-7.29 (4H, m); 7.22-7.12 (3H, m); 5.17 (1H, d); 4.20-4.14 (1H, m); 1.47 (3H, t); 1.28 (3H, d).

Example 229

2,2-difluoro-N-[(1R,2S)-1-(3-fluoro-4-methyl-phenyl)-1-[1-(4-fluorophenyl)ndazol-5-yl]oxy-propan-2-yl]propanamide

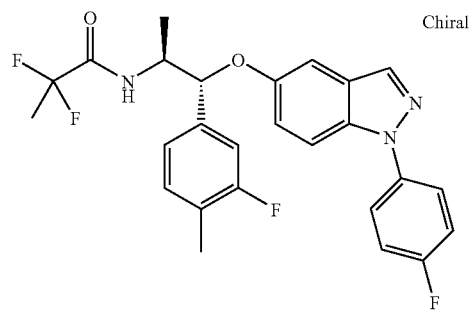

Prepared as described in Example 228 using corresponding starting material.

APCI-MS: m/z 486.2 [MH+]

$^1$H-NMR (500 MHz, DMSO-d6): δ 8.74 (1H, d); 8.11 (1H, d); 7.67-7.61 (3H, ); 7.36-7.32 (2H, m); 7.19-7.14 (2H, m); 7.10-7.04 (3H, m); 5.17 (1H, d); 4.19-4.13 (1H, m); 2.10 (3H, s); 1.46 (3H, t); 1.26 (3H, d).

Example 231

2,2-difluoro-N-[(1R,2S)-1-(3-fluoro-4-methoxy-phenyl)-1-[1-(4-fluorophenyl)ndazol-5-yl]oxy-propan-2-yl]propanamide

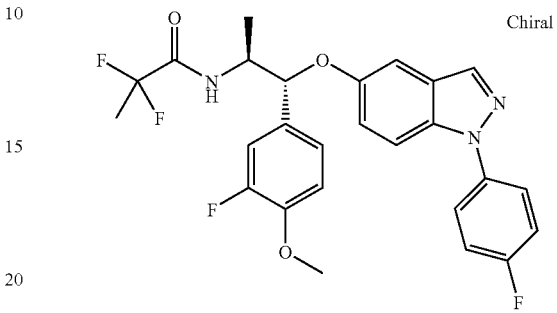

Prepared as described in Example 228 using corresponding starting material.

APCI-MS: m/z 502.2 [MH+]

$^1$H-NMR (500 MHz, DMSO-d6): δ 8.71 (1H, d); 8.12 (1H, d); 7.68-7.65 (2H, m); 7.63 (1H, d); 7.36-7.32 (2H, m); 7.16-7.10 (4H, m); 7.04 (1H, t); 5.13 (1H, d); 4.18 4.12 (1H, m); 1.46 (3H, t); 1.27 (3H, d).

Example 230

2,2-difluoro-N-[(1R,2S)-1-(3-fluorophenyl)-1-[1-(4-fluorophenyl)indazol-5-yl]xy-propan-2-yl]propanamide

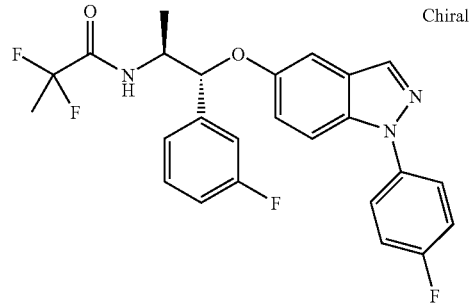

Prepared as described in Example 228 using corresponding starting material.

APCI-MS: m/z 472.2 [MH+]

$^1$H-NMR (500 MHz, DMSO-d6): δ 8.76 (1H, d); 8.11 (1H, d); 7.68-7.62 (3H, ); 7.36-7.29 (3H, m); 7.21-7.10 (4H, m); 7.04-7.00 (1H, m); 5.21 (1H, d); 4.21-4.15 (1H, m); 1.44 (3H, t); 1.28 (3H, d).

Example 232

N-[(1R,2S)-1-(3-chlorophenyl)-1-[1-(4-fluorophenyl)indazol-5-yl]oxy-propan-2yl]-2,2-difluoro-propanamide

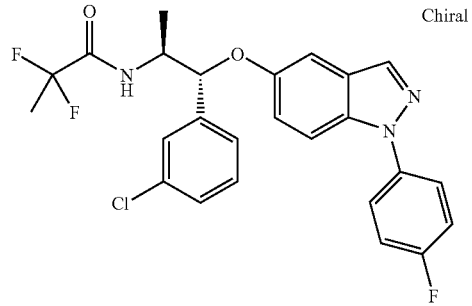

Prepared as described in Example 228 using corresponding starting material.

APCI-MS: m/z 488.1 [MH+]

$^1$H-NMR (500 MHz, DMSO-d6): δ 8.76 (1H, d); 8.12 (1H, s); 7.68-7.63 (3H, m); 7.38-7.25 (5H, m); 7.17 (1H, dd); 7.11 (1H, d); 5.19 (1H, d); 4.20-4.13 (1H, m); .45 (3H, t); 1.28 (3H, d).

Example 233

2,2-difluoro-N-[(1R,2S)-1-(4-fluoro-2-methyl-phenyl)-1-[1-(4-fluorophenyl) ndazol-5-yl]oxy-propan-2-yl]propanamide

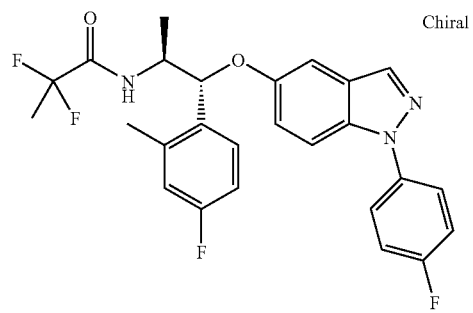

Prepared as described in Example 228 using corresponding starting material.

APCI-MS: m/z 486.2 [MH+]

$^1$H-NMR (500 MHz, DMSO-d6): δ 8.82 (1H, d); 8.11 (1H, s); 7.68-7.62 (3H, ); 7.36-7.31 (3H, m); 7.15-7.13 (1H, m); 6.98-6.88 (3H, m); 5.34 (1H, d); 4.24-4.19(1H, m); 1.50 (3H, t); 1.25 (3H, d).

Example 234

2,2-difluoro-N-[(1R,2S)-1-(5-fluoro-2-methyl-phenyl)-1-[1-(4-fluorophenyl) ndazol-5-yl]oxy-propan-2-yl]propanamide

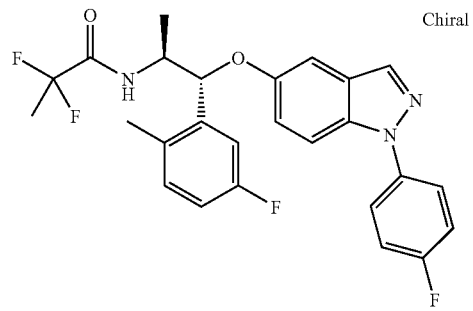

Prepared as described in Example 228 using corresponding starting material.

APCI-MS: m/z 486.2 [MH+]

$^1$H-NMR (500 MHz, DMSO-d6): δ 8.85 (1H, d); 8.12 (1H, s); 7.68-7.63 (3H, m); 7.36-7.32 (2H, m); 7.18-7.15 (2H, m); 7.07-7.03 (1H, m); 6.99 (1H, d); 6.95-6.91(1H, m); 5.36 (1H, d); 4.25-4.21 (1H, m); 1.50 (3H, t); 1.25 (3H, d).

Example 235

2,2-difluoro-N-[(1R,2S)-1-(5-fluoro-2-methoxy-phenyl)-1-[1-(4-fluorophenyl) ndazol-5-yl]oxy-propan-2-yl]propanamide

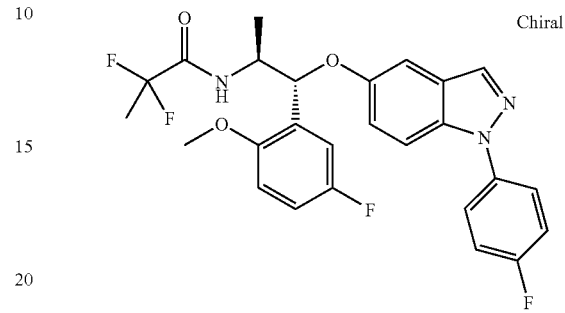

Prepared as described in Example 228 using corresponding starting material.

APCI-MS: m/z 502.2 [MH+]

$^1$H-NMR (500 MHz, DMSO-d6): δ 8.56 (1H, d); 8.15 (1H, d); 7.71-7.65 (3H, m); 7.37-7.33 (2H, m); 7.15 (1H, dd); 7.04-7.00 (4H, m); 5.50 (1H, d); 4.35-4.30 (H, m); 3.83 (3H, s); 1.52 (3H, t); 1.22 (3H, d).

Example 236

2,2-difluoro-N-[(1R,2S)-1-[1-(4-fluorophenyl)indazol-5-yl]oxy-1-(4-methoxy-3,5-dimethyl-phenyl) propan-2-yl]propanamide

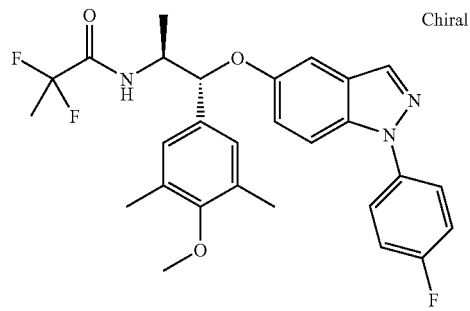

Prepared as described in Example 228 using corresponding starting material.

APCI-MS: m/z 512.2 [MH+]

$^1$H-NMR (500 MHz, DMSO-d6): δ 8.65 (1H, d); 8.14 (1H, s); 7.71-7.67 (2H, m); 7.65 (1H, d); 7.38-7.33 (2H, m); 7.17-7.14 (1H, m); 7.08 (1H, d); 7.01 (2H, s); 5.11 1H, d); 4.11-4.06 (1H, m); 2.13 (6H, s); 1.46 (3H, t); 1.24 (3H, d)

Example 237

N-[(1R,2S)-1-(4-chlorophenyl)-1-[1-(4-fluorophenyl)indazol-5-yl]oxy-propan-2yl]-2,2-difluoro-propanamide

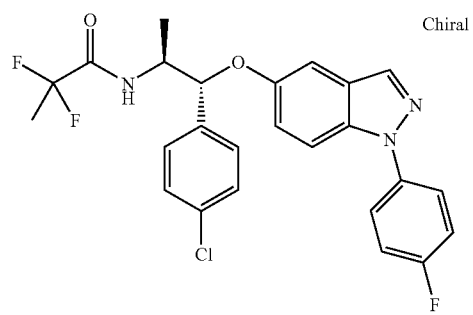

Prepared as described in Example 228 using corresponding starting material.

APCI-MS: m/z 488.1 [MH+]

$^1$H-NMR (500 MHz, DMSO-d6): δ 8.72 (1H, d); 8.13 (1H, d); 7.70-7.67 (2H, m); 7.64 (1H, d); 7.39-7.33 (5H, m); 7.15 (1H, dd); 7.08 (1H, d); 5.21 (1H, d); 4.20-4.13 1H, m); 1.48 (3H, t); 1.28 (3H, d).

Example 238

N-[(1R,2S)-1-(3-chloro-5-fluoro-phenyl)-1-[1-(4-fluorophenyl)indazol-5-yl]oxy propan-2-yl]-2,2-difluoro-propanamide

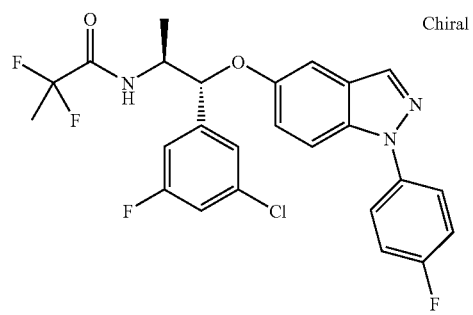

Prepared as described in Example 228 using corresponding starting material.

APCI-MS: m/z 506.1 [MH+]

$^1$H-NMR (500 MHz, DMSO-d6): δ 8.75 (1H, d); 8.16 (1H, d); 7.71-7.65 (3H, ); 7.36 (2H, t); 7.30-7.26 (2H, m); 7.19-7.14 (3H, m); 5.20 (1H, d); 4.21-4.15 (1H, m); 1.50 (2H, t); 1.30 (3H, d).

Example 239

2,2-difluoro-N-[(1R,2S)-1-[1-(4-fluorophenyl)indazol-5-yl]oxy-1-(3methylphenyl)propan-2-yl]propanamide

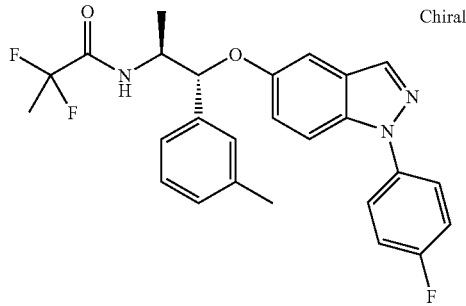

Prepared as described in Example 228 using corresponding starting material.

APCI-MS: m/z 468.2 [MH+]

$^1$H-NMR (500 MHz, DMSO-d6): δ 8.69 (1H, d); 8.12 (1H, d); 7.70-7.67 (2H, ); 7.64 (1H, d); 7.37-7.33 (2H, m); 7.18-7.14 (5H, m); 7.06 (1H, d); 7.02 (1H, d); 5.18 (1H, d); 4.17-4.12 (1H, m); 2.22 (3H, s); 1.46 (3H, t); 1.25 (3H, d).

Example 240

N-[(1R,2S)-1-(3,4-dimethylphenyl)-1-[1-(4-fluorophenyl)indazol-5-yl]oxy-propan-2-yl]-2-fluoro-2-methyl-propanamide

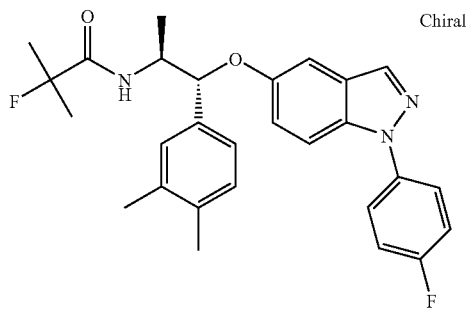

Prepared as described in Example 192 using corresponding starting material.

APCI-MS: m/z 478.2 [MH+]

$^1$H-NMR (500 MHz, DMSO-d6): δ 8.09 (1H, s); 7.90 (1H, dd); 7.66-7.63 (2H, m); 7.61 (1H, d); 7.35-7.31 (2H, m); 7.14 (1H, dd); 7.09 (1H, s); 7.07-7.04 (2H, m); 7.01 (1H, d); 5.17 (1H, d); 4.16-4.09 (1H, m); 2.10 (3H, s); 2.08 (3H, s); 1.30 (3H, d); 1.20 (3H, d); 1.07 (3H, d).

Example 241

N-[(1R,2S)-1-(3,4-difluorophenyl)-1-[1-(4-fluorophenyl)indazol-5-yl]oxy-propan--yl]-2-fluoro-2-methyl-propanamide

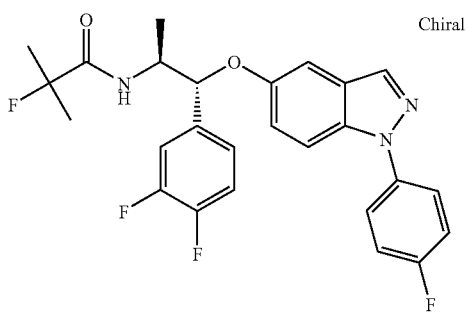

Prepared as described in Example 192 using corresponding starting material.

APCI-MS: m/z 486.2 [MH+]

$^1$H-NMR (500 MHz, DMSO-d6): δ 8.11 (1H, d); 8.07 (1H, dd); 7.67-7.61 (3H, ); 7.39-7.27 (4H, m); 7.23-7.19 (1H, m); 7.17-7.13 (2H, m); 5.17 (1H, d); 4.21-4.13 (1H, m); 1.32-1.25 (6H, m); 1.05 (3H, d).

Example 242

2-fluoro-N-[(1R,2S)-1-(3-fluoro-4-methyl-phenyl)-1-[1-(4-fluorophenyl)indazol-5-yl]oxy-propan-2-yl]-2-methyl-propanamide

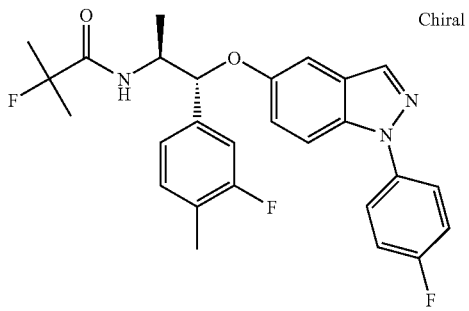

Prepared as described in Example 192 using corresponding starting material.

APCI-MS: m/z 482.2 [MH+]

$^1$H-NMR (500 MHz, DMSO-d6): δ 8.10 (1H, d); 8.01 (1H, dd); 7.67-7.60 (3H, m); 7.35-7.31 (2H, m); 7.17-7.04 (5H, m); 5.18 (1H, d); 4.18-4.13 (1H, m); 2.09 (3, s); 1.32-1.23 (6H, m); 1.05 (3H, d).

Example 243

2-fluoro-N-[(1R,2S)-1-(3-fluorophenyl)-1-[1-(4-fluorophenyl)indazol-5-yl]oxy propan-2-yl]-2-methyl-propanamide

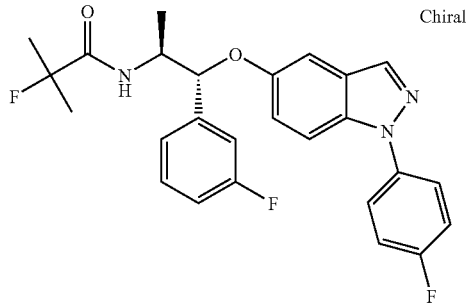

Prepared as described in Example 192 using corresponding starting material.

APCI-MS: m/z 468.2 [MH+]

$^1$H-NMR (500 MHz, DMSO-d6): δ 8.11 (1H, s); 8.06 (1H, dd); 7.67-7.61 (3H, m); 7.35-7.28 (3H, m); 7.22-7.11 (4H, m); 7.00 (1H, td); 5.22 (1H, d); 4.21-4.15 (1H, m); 1.32-1.24 (H, m); 1.32-1.24 (6H, m); 1.03 (3H, d).

Example 244

N-[(1R,2S)-1-(2,5-dimethylphenyl)-1-[1-(4-fluorophenyl)indazol-5-yl]oxy-propan-2-yl]-2-fluoro-2-methyl-propanamide

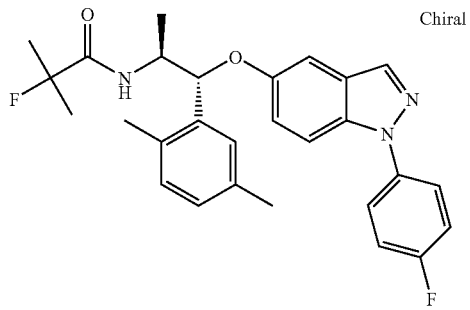

Prepared as described in Example 192 using corresponding starting material.

APCI-MS: m/z 478.2 [MH+]

$^1$H-NMR (500 MHz, DMSO-d6): δ 8.09 (1H, d); 7.96 (1H, dd); 7.66-7.60 (3H, ); 7.35-7.31 (2H, m); 7.14 (1H, dd); 7.10 (1H, s); 6.99-6.96 (2H, m); 6.89 (1H, d); .33 (1H, d); 4.23-4.17 (1H, m); 2.12 (3H, s); 1.32 (3H, d); 1.21 (3H, d); 1.08 (3H, d).

Example 245

N-[(1R,2S)-1-(2,4-dimethylphenyl)-1-[1-(4-fluorophenyl)indazol-5-yl]oxy-propan--yl]-2-fluoro-2-methyl-propanamide

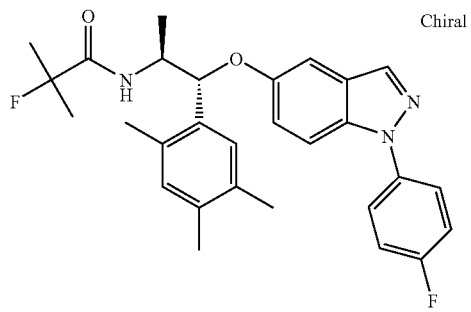

Prepared as described in Example 192 using corresponding starting material.

APCI-MS: m/z 478.2 [MH+]

$^1$H-NMR (500 MHz, DMSO-d6): δ 8.08 (1H, d); 7.95 (1H, dd); 7.66-7.59 (3H, m); 7.34-7.30 (2H, m); 7.17-7.12 (2H, m); 6.95 (1H, d); 6.90 (1H, s); 6.87 (1H, d); .35 (1H, d); 4.23-4.16 (1H, m); 2.12 (3H, s); 1.32 (3H, d); 1.20 (3H, d); 1.10 (3H, d).

Example 246

2-fluoro-N-[(1R,2S)-1-(3-fluoro-4-methoxy-phenyl)-1-[1-(4-fluorophenyl)indazol 5-yl]oxy-propan-2-yl]-2-methyl-propanamide Prepared as described in Example 192 using corresponding starting material.

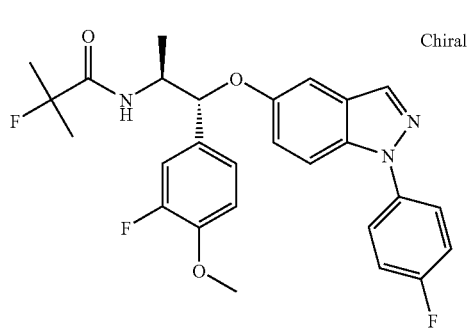

Prepared as described in Example 192 using corresponding starting material.

APCI-MS: m/z 498.2 [MH+]

$^1$H-NMR (500 MHz, DMSO-d6): δ 8.10 (1H, d); 8.00 (1H, dd); 7.67-7.64 (2H, m); 7.61 (1H, d); 7.35-7.31 (2H, m); 7.16-7.11 (4H, m); 7.02 (1H, t); 5.14 (1H, d); 4.18-4.12 (1H, m); 1.30 (3H, d); 1.24 (3H, d); 1.05 (3H, d).

Example 247

N-[(1R,2S)-1-(3-chlorophenyl)-1-[1-(4-fluorophenyl)indazol-5-yl]oxy-propan-2yl]-2-fluoro-2-methyl-propanamide

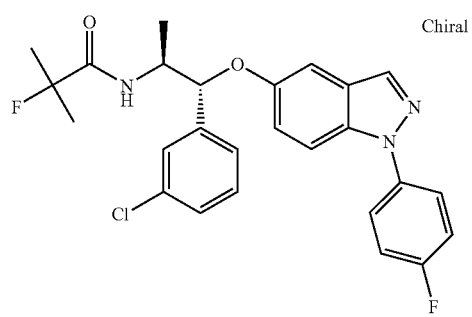

Prepared as described in Example 192 using corresponding starting material.

APCI-MS: m/z 484.1 [MH+]

$^1$H-NMR (500 MHz, DMSO-d6): δ 8.11 (1H, s); 8.07 (1H, dd); 7.67-7.61 (3H, m); 7.38-7.27 (4H, m); 7.25-7.22 (1H, m); 7.16 (1H, dd); 7.11 (1H, d); 5.20 (1H, d); 4.20-4.13 (1H, m); 1.32-1.25 (6H, m); 1.04 (3H, d).

Example 248

2-fluoro-N-[(1R,2S)-1-(4-fluoro-2-methyl-phenyl)-1-[1-(4-fluorophenyl)indazol-5-yl]oxy-propan-2-yl]-2-methyl-propanamide

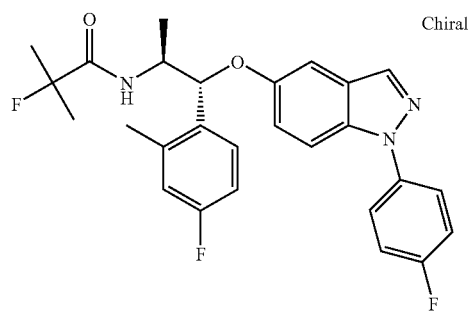

Prepared as described in Example 192 using corresponding starting material.

APCI-MS: m/z 482.2 [MH+]

$^1$H-NMR (500 MHz, DMSO-d6): δ 8.10 (1H, d); 8.03 (1H, dd); 7.67-7.61 (3H, m); 7.35-7.31 (2H, m); 7.13 (1H, dd); 6.99 (2H, d); 6.95-6.86 (2H, m); 5.33 (1H, d); 4.27-4.20 (1H, m); 1.31 (3H, d); 1.24 (3H, d); 1.07 (3H, d).

Example 249

2-fluoro-N-[(1R,2S)-1-(5-fluoro-2-methyl-phenyl)-1-[1-(4-fluorophenyl)indazol-5-yl]oxy-propan-2-yl]-2-methyl-propanamide

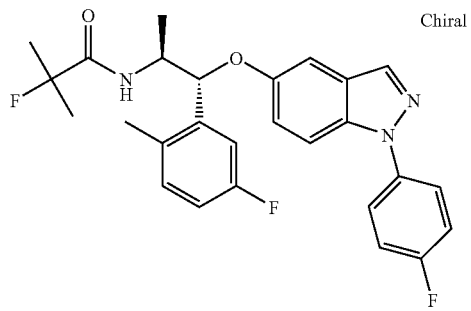

Prepared as described in Example 192 using corresponding starting material.

APCI-MS: m/z 482.2 [MH+]

$^1$H-NMR (500 MHz, DMSO-d6): δ 8.11 (1H, d); 8.06 (1H, dd); 7.67-7.62 (3H, m); 7.35-7.31 (2H, m); 7.17-7.11 (2H, m); 7.05 (1H, dd); 7.00 (1H, d); 6.90 (1H, td); 5.34 (1H, d); 4.27-4.22 (1H, m); 1.32 (3H, d); 1.24 (3H, d); 1.07 (3H, d); 1.07 (3H, d).

Example 250

2-fluoro-N-[(1R,2S)-1-(5-fluoro-2-methoxy-phenyl)-1-[1-(4-fluorophenyl)indazol 5-yl]oxy-propan-2-yl]-2-methyl-propanamide

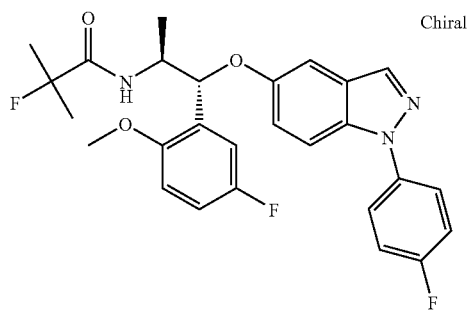

Prepared as described in Example 192 using corresponding starting material.

APCI-MS: m/z 498.2 [MH+]

$^1$H-NMR (500 MHz, DMSO-d6): δ 8.12 (1H, s); 7.74 (1H, dd); 7.68-7.62 (3H, ); 7.35-7.32 (2H, m); 7.14 (1H, dd); 7.03-6.98 (4H, m); 5.48 (1H, d); 4.33-4.27 (1H, m); 1.32 (3H, d); 1.20 (3H, d); 1.08 (3H, d).

Example 251

N-[(1R,2S)-1-(3,4-difluorophenyl)-1-[1-(4-fluorophenyl)indazol-5-yl]oxy-propan-2-yl]-3-hydroxy-2,2-dimethyl-propanamide

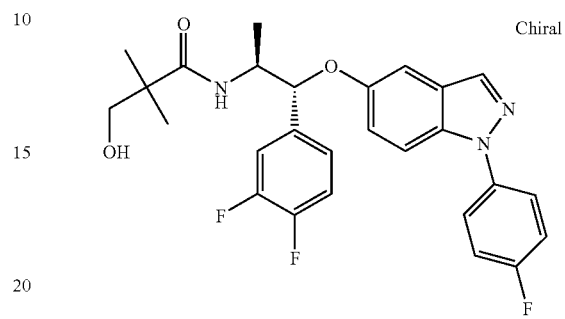

Prepared as described in Example 192 using corresponding starting material.

APCI-MS: m/z 498.2 [MH+]

$^1$H-NMR (500 MHz, DMSO-d6): δ 8.11 (1H, s); 7.67-7.61 (3H, m); 7.50 (1H, d); 7.39-7.27 (4H, m); 7.22-7.18 (1H, m); 7.16 (1H, dd); 7.13 (1H, d); 5.22 (1H, d); .21-4.13 (1H, m); 3.19 (2H, dd); 1.16 (3H, d); 0.84 (3H, s); 0.79 (3H, s).

Example 252

N-[(1R,2S)-1-(3-fluoro-4-methyl-phenyl)-1-[1-(4-fluorophenyl)indazol-5-yl]oxy propan-2-yl]-3-hydroxy-2,2-dimethyl-propanamide

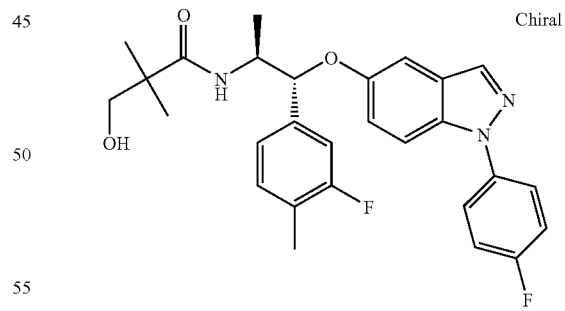

Prepared as described in Example 192 using corresponding starting material.

APCI-MS: m/z 494.2 [MH+]

$^1$H-NMR (500 MHz, DMSO-d6): δ 8.09 (1H, s); 7.67-7.60 (3H, m); 7.51 (1H, ); 7.35-7.31 (2H, m); 7.19-7.14 (2H, m); 7.10-7.04 (3H, m); 5.23 (1H, d); 4.19-4.12 (1H, m); 3.21 (2H, q); 2.10 (3H, s); 1.12 (3H, d); 0.83 (6H, d).

Example 253

N-[(1R,2S)-1-(3-fluorophenyl)-1-[1-(4-fluorophenyl)indazol-5-yl]oxy-propan-2yl]-3-hydroxy-2,2-dimethyl-propanamide

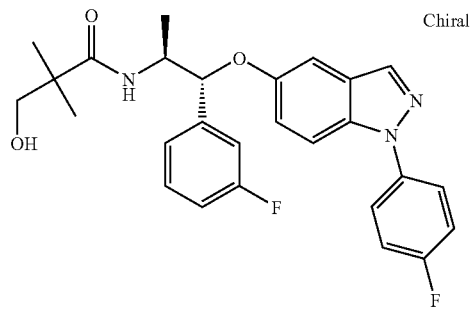

Prepared as described in Example 192 using corresponding starting material.

APCI-MS: m/z 480.2 [MH+]

$^1$H-NMR (500 MHz, DMSO-d6): δ 8.10 (1H, s); 7.67-7.61 (3H, m); 7.53 (1H, d); 7.35-7.29 (3H, m); 7.22-7.10 (4H, m); 7.01 (1H, td); 5.27 (1H, d); 4.22-4.15 (1H, m); 3.19 (2H, dd); 1.14 (3H, d); 0.84 (3H, s); 0.79 (3H, s).

Example 254

N-[(1R,2S)-1-(2,5-dimethylphenyl)-1-[1-(4-fluorophenyl)indazol-5-yl]oxy-propan-2-yl]-3-hydroxy-2,2-dimethyl-propanamide

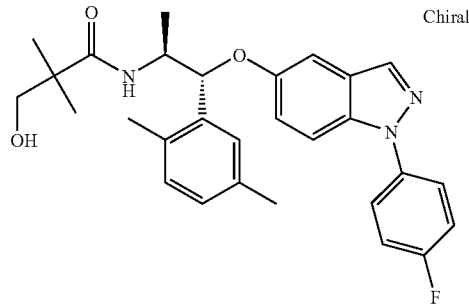

Prepared as described in Example 192 using corresponding starting material.

APCI-MS: m/z 490.2 [MH+]

$^1$H-NMR (500 MHz, DMSO-d6): δ 8.09 (1H, d); 7.68-7.61 (3H, m); 7.56 (1H, ); 7.35-7.32 (2H, m); 7.15 (1H, dd); 7.09 (1H, s); 7.02 (1H, d); 6.95 (1H, d); 6.91 (1H, d); 5.37 (1H, d); 4.18-4.12 (1H, m); 3.23 (2H, dd); 2.13 (3H, s); 1.10 (3H, d); 0.85 (6H, d).

Example 255

N-[(1R,2S)-1-(3-chlorophenyl)-1-[1-(4-fluorophenyl)indazol-5yl]oxy-propan-2-yl 9 -3-hydroxy-2,2-dimethyl-propanamide

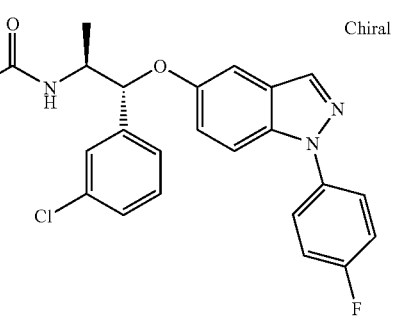

Prepared as described in Example 192 using corresponding starting material.

APCI-MS: m/z 496.2 [MH+]

$^1$H-NMR (500 MHz, DMSO-d6): δ 8.10 (1H, d); 7.67-7.61 (3H, m); 7.52 (1H, ); 7.37-7.28 (4H, m); 7.24 (1H, dt); 7.17 (1H, dd); 7.10 (1H, d); 5.25 (1H, d); 4.204.13 (1H, m); 3.19 (2H, dd); 1.14 (3H, d); 0.84 (3H, s); 0.78 (3H, s).

Example 256

N-[(1R,2S)-1-(4-fluoro-2-methyl-phenyl)-1-[1-(4-fluorophenyl)indazol-5-yl]oxy propan-2-yl]-3-hydroxy-2,2-dimethyl-propanamide

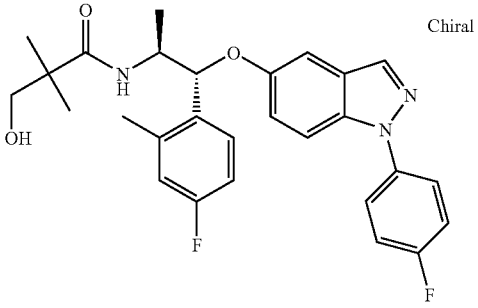

Prepared as described in Example 192 using corresponding starting material.

APCI-MS: m/z 494.2 [MH+]

$^1$H-NMR (500 MHz, DMSO-d6): δ 8.09 (1H, s); 7.67-7.63 (2H, m); 7.61 (1H, ); 7.57 (1H, d); 7.35-7.29 (3H, m); 7.14 (1H, dd); 6.98-6.95 (2H, m); 6.89 (1H, td); 5.38 (1H, d); 4.19-4.14 (1H, m); 3.22 (2H, dd); 1.12 (3H, d); 0.83 (6H, d).

Example 257

N-[(1R,2S)-1-(3,4-dimethylphenyl)-1-[1-(4-fluorophenyl)indazol-5-yl]oxy-propan-2-yl]-2-methoxy-acetamide

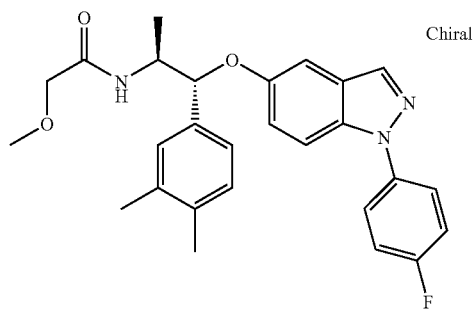

Prepared as described in Example 192 using corresponding starting material.

APCI-MS: m/z 462.2 [MH+]

$^1$H-NMR (500 MHz, DMSO-d6): δ 8.11 (1H, d); 7.70-7.62 (3H, m); 7.37-7.33 2H, m); 7.16 (1H, dd); 7.12 (2H, s); 7.07-7.03 (3H, m); 5.26 (1H, d); 4.20-4.13 (1H, m); 3.15 (3H, d); 2.14 (3H, s); 2.12 (3H, s); 1.14 (3H, d).

Example 258

N-[(1R,2S)-1-(3,4-difluorophenyl)-1-[1-(4-fluorophenyl)indazol-5-yl]oxy-propan-2-yl]-2-methoxy-acetamide

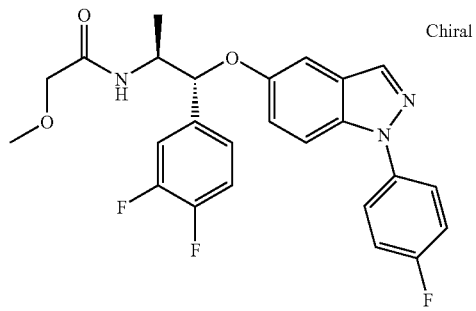

Prepared as described in Example 192 using corresponding starting material.

APCI-MS: m/z 470.2 [MH+]

$^1$H-NMR (500 MHz, DMSO-d6): δ 8.13 (1H, d); 7.79 (1H, d); 7.70-7.67 (2H, m); 7.65 (1H, d); 7.41-7.32 (4H, m); 7.23-7.20 (1H, m); 7.17 (1H, dd); 7.12 (1H, d); 5.28 (1H, d); 4.24-4.17 (1H, m); 3.69 (2H, d); 3.15 (3H, s); 1.20 (3H, d).

Example 259

N-[(1R,2S)-1-(3-fluoro-4-methyl-phenyl)-1-[1-(4-fluorophenyl)indazol-5-yl]oxy propan-2-yl]-2-methoxy-acetamide

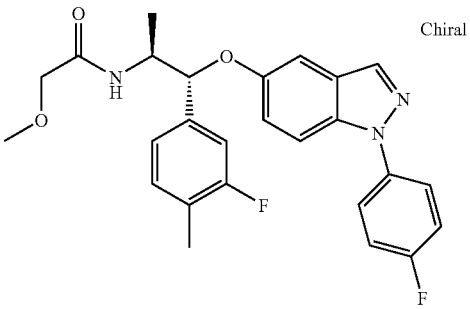

Prepared as described in Example 192 using corresponding starting material.

APCI-MS: m/z 466.2 [MH+]

$^1$H-NMR (500 MHz, DMSO-d6): δ 8.12 (1H, d); 7.76 (1H, d); 7.70-7.67 (2H, m); 7.64 (1H, d); 7.37-7.33 (2H, m); 7.22-7.15 (2H, m); 7.11-7.07 (3H, m); 5.29 (1H, d); 4.23-4.16 (1H, m); 3.70 (2H, d); 3.15 (3H, s); 2.12 (3H, s); 1.17 (3H, d).

Example 260

N-[(1R,2S)-1-(2,5-dimethylphenyl)-1-[1-(4-fluorophenyl)indazol-5-yl]oxy-propan-2-yl]-2-methoxy-acetamide

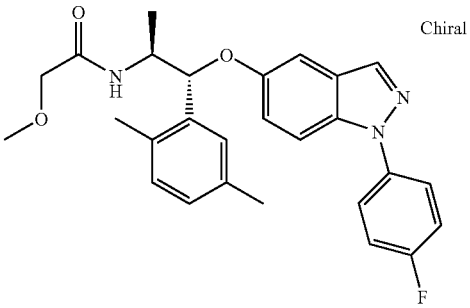

Prepared as described in Example 192 using corresponding starting material.

APCI-MS: m/z 462.2 [MH+]

$^1$H-NMR (500 MHz, DMSO-d6): δ 8.11 (1H, d); 7.76 (1H, d); 7.70-7.64 (3H, m); 7.37-7.33 (2H, m); 7.16 (1H, dd); 7.09 (2H, s); 7.04 (1H, d); 6.94-6.92 (2H, m); 5.41 (1H, d); 4.21-4.17 (1H, m); 3.74 (1H, d); 3.66 (2H, d); 3.15 (3H, s); 2.14 (3H, s); 1.15 (H, d).

Example 261

N-[(1R,2S)-1-(2,4-dimethylphenyl)-1-[1-(4-fluorophenyl)indazol-5-yl]oxy-propan--yl]-2-methoxy-acetamide

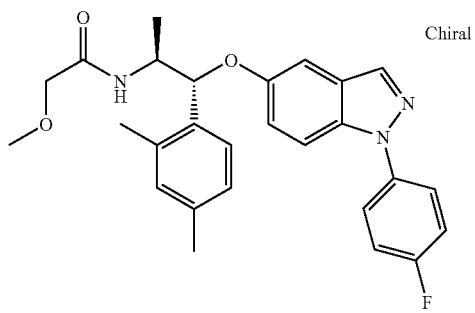

Prepared as described in Example 192 using corresponding starting material.

APCI-MS: m/z 462.2 [MH+]

$^1$H-NMR (500 MHz, DMSO-d6): δ 8.10 (1H, d); 7.77 (1H, d); 7.69-7.66 (2H, m); 7.64 (1H, d); 7.37-7.33 (2H, m); 7.16-7.13 (2H, m); 6.97 (1H, s); 6.92 (1H, d); 6.89 (1H, d); 5.42 (1H, d); 4.21-4.17 (1H, m); 3.76-3.66 (2H, m); 3.16 (3H, s); 2.16 (3H, s); 1.14 (3H, d).

Example 262

N-[(1R,2S)-1-(3-fluoro-4-methoxy-phenyl)-1-[1-(4-fluorophenyl)indazol-5-yl]oxy propan-2-yl]-2-methoxy-acetamide

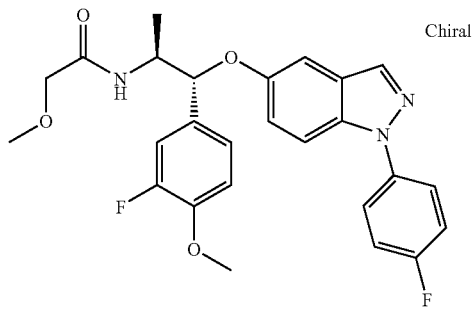

Prepared as described in Example 192 using corresponding starting material.

APCI-MS: m/z 482.2 [MH+]

$^1$H-NMR (500 MHz, DMSO-d6): δ 8.13 (1H, d); 7.73 (1H, d); 7.70-7.67 (2H, ); 7.64 (1H, d); 7.37-7.33 (2H, m); 7.18-7.05 (5H, m); 5.24 (1H, d); 4.22-4.15 (1H, m); 3.74 (3H, s); 3.70 (2H, d); 3.15 (3H, s); 1.18 (3H, d).

Example 263

N-[(1R,2S)-1-(3-fluorophenyl)-1-[1-(4-fluorophenyl)indazol-5-yl]oxy-propan-2yl]-2-methoxy-acetamide

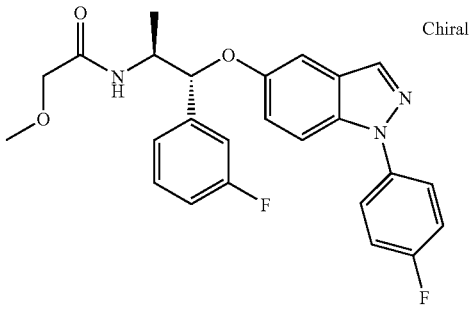

Prepared as described in Example 192 using corresponding starting material.

APCI-MS: m/z 452.2 [MH+]

$^1$H-NMR (500 MHz, DMSO-d6): δ 8.13 (1H, d); 7.79 (1H, d); 7.70-7.64 (3H, m); 7.37-7.32 (2H, m); 7.22 (2H, d); 7.19-7.14 (2H, m); 7.10 (1H, d); 7.04 (1H, d); 5.33 (1H, d); 4.25-4.18 (1H, m); 3.70 (1H, d); 3.14 (3H, s); 1.19 (3H, d).

Example 264

2,2,2-trifluoro-N-[(1R,2S)-1-(3-fluoro-4-methoxy-phenyl)-1-[1-(4-fluorophenyl) ndazol-5-yl]oxy-propan-2-yl]acetamide

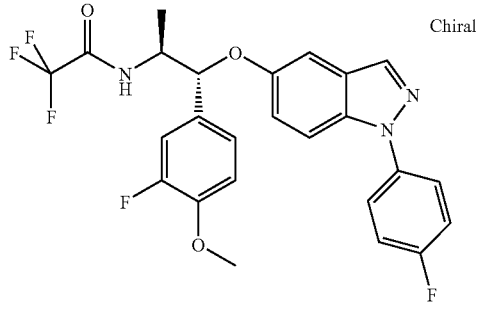

Prepared as described in Example 6 using corresponding starting material.

APCI-MS: m/z 506.1 [MH+]

$^1$H-NMR (500 MHz, DMSO-d6): δ 9.48 (1H, d); 8.14 (1H, d); 7.70-7.63 (3H, m); 7.37-7.33 (2H, m); 7.18-7.06 (5H, m); 5.17 (1H, d); 4.22-4.16 (1H, m); 3.74 (3H, s); 1.30 (3H, d).

Example 265

N-[(1R,2S)-1-[1-(4-fluorophenyl)indazol-5-yl]oxy-1-(4-methoxy-2-methyl-phenyl) ropan-2-yl]-1-methyl-cyclopropane-1-carboxamide

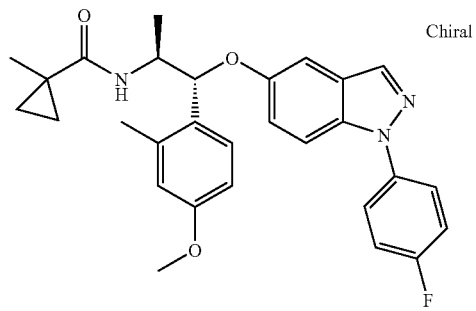

Prepared as described in Example 192 using corresponding starting material.

APCI-MS: m/z 488.2 [MH+]

$^1$H-NMR (500 MHz, DMSO-d6): δ 8.14 (1H, d); 7.70-7.66 (2H, m); 7.62 (1H, d); 7.37-7.32 (3H, m); 7.24 (1H, d); 7.09 (1H, dd); 7.04 (1H, d); 6.71-6.68 (2H, m); 5.47 (1H, d); 4.32-4.25 (1H, m); 1.18 (3H, s); 0.95 (3H, d); 0.91-0.81 (2H, m); 0.47-.40 (2H, m).

Example 266

N-[(1R,2S)-1-(2,5-dimethylphenyl)-1-[1-(4-fluorophenyl)indazol-5-yl]oxy-propan--yl]-2,2-difluoro-propanamide

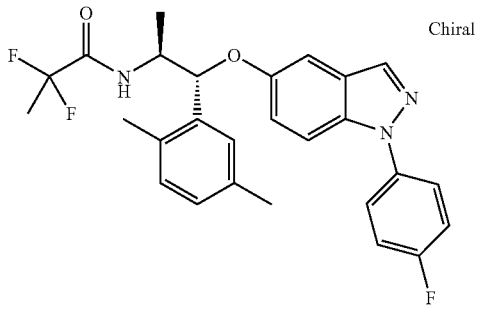

Prepared as described in Example 228 using corresponding starting material.

APCI-MS: m/z 482.2 [MH+]

$^1$H-NMR (500 MHz, DMSO-d6): δ 8.79 (1H, d); 8.10 (1H, d); 7.68-7.62 (3H, m); 7.34 (2H, dd); 7.15 (1H, dd); 7.10 (1H, s); 7.01 (1H, d); 6.95-6.90 (2H, m); 5.34 (1, d); 4.21-4.16 (1H, m); 2.13 (3H, s); 1.49 (3H, t); 1.23 (3H, d).

Example 267

N-[(1R,2S)-1-[1-(4-fluorophenyl)indazol-5-yl]oxy-1-(2,4,5-trimethylphenyl)propan-2-yl]-2,2-dimethyl-propanamide

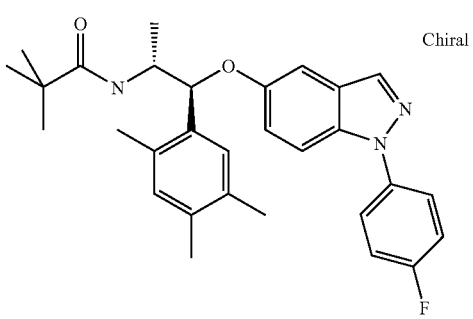

Prepared as described in Example 8 using corresponding starting material.

APCI-MS: m/z 488.2 [MH+]

$^1$H-NMR (500 MHz, DMSO-d6): δ 8.12 (1H, d); 7.70-7.67 (2H, m); 7.64 (1H, d); 7.37-7.33 (4H, m); 7.15 (1H, dd); 7.04 (1H, s); 6.91 (1H, d); 6.89 (1H, s); 5.34 (1H, d); 4.13-4.09 (1H, m); 2.08 (3H, s); 2.06 (3H, s); 1.14 (3H, d); 0.93 (9H, s).

Example 268

N-[(1R,2S)-1-(5-fluoro-2-methoxy-phenyl)-1-[1-(4-fluorophenyl)indazol-5-yl]oxy propan-2-yl]-1-methyl-cyclopropane-1-carboxamide

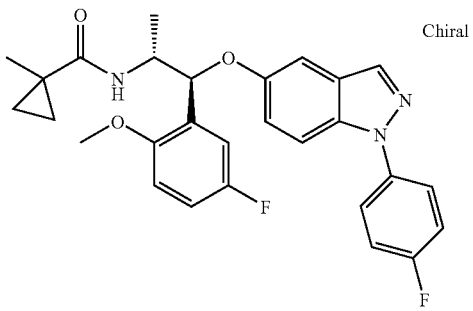

Prepared as described in Example 192 using corresponding starting material.

APCI-MS: m/z 492.2 [MH+]

$^1$H-NMR (500 MHz, DMSO-d6): δ 8.14 (1H, s); 7.70-7.64 (3H, m); 7.35 (2H, d); 7.17-7.12 (2H, m); 7.03-6.99 (4H, m); 5.47 (1H, d); 4.34-4.28 (1H, m); 3.84 (3, s); 1.17 (3H, d); 1.11 (3H, s); 0.76-0.67 (2H, m); 0.41-0.30 (2H, m).

Example 269

N-[[(1R,2S)-1-[1-(4-fluorophenyl)indazol-5-yl]oxy-1-(3-methoxyphenyl)propan--yl]carbamoylmethyl]acetamide

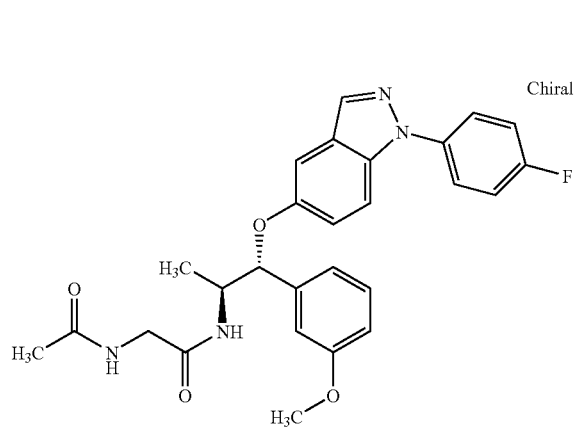

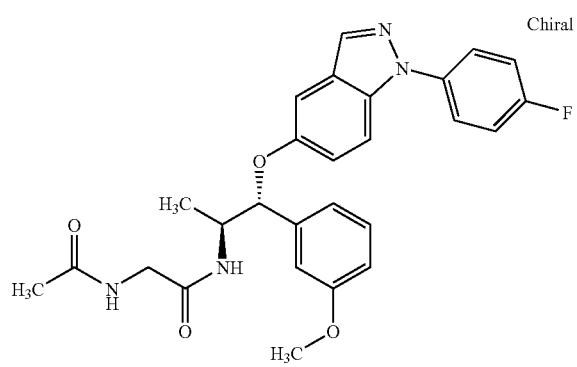

(1R,2S)-1-[1-(4-fluorophenyl)-1H-indazol-5-yl]oxy)-1-(3-methoxyphenyl)propan-2-amine (6a, 200 mg, 0.51 mmol) (1) and N-acetylglycine (59.8 mg, 0.51 mmol) were dissolved in dry DMF (2 ml). O-benzotriazol-1-yl-N,N,N',N'-tetramethyl-uronium hexafluorophosphate (213 mg, 0.56 mmol) was added followed by N,N-diisopropylethylamine (270 µL, 1.53 mmol). The reaction was stirred at r.t. over night. The crude solution was diluted by MeCN/H$_2$O and the product was purified on preparative HPLC.

Yield: 250 mg (98%).

APCI-MS: m/z 491.1 [MH$^+$]

$^1$H-NMR (400 MHz, DMSO-d$_6$) δ 8.17 (s, 1H), 8.02 (m, 2H), 7.77-7.67 (m, 3), 7.40 (t, J=8.5 Hz, 2H), 7.29-7.20 (m, 2H), 7.11-7.08 (m, 1H), 6.97-6.91 (m, 2H), 6.3 (dd, J=8.3, 2.3 Hz, 1H), 5.32 (d, J=4.1 Hz, 1H), 4.15 (m, 1H), 3.73 (s, 3H), 3.69 (dd, J=16.7, 5.9 Hz, 1H), 3.58 (dd, J=16.7, 5.6 Hz, 1H), 1.82 (s, 3H), 1.14 (d, J=7.3 Hz, 3H).

Example 270

2-(carbamoylamino)-N-[(1R,2S)-1-[1-(4-fluorophenyl)indazol-5-yl]oxy-1-(3-methoxyphenyl)propan-2-yl]acetamide

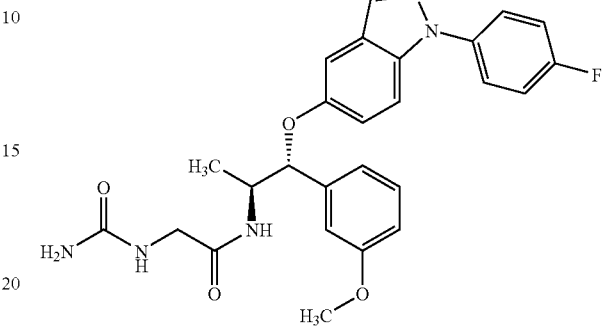

Prepared as described in Example 269 from (1R,2S)-1-(1-(4-fluorophenyl)-1H-indazol-5-yloxy) 1-(3-methoxyphenyl)propan-2-amine (6a, 200 mg, 0.51 mmol) and hydantoic acid (60 mg, 0.51 mmol).

Yield: 220 mg (88%).

APCI-MS: m/z 492.1 [MH$^+$]

$^1$H-NMR (400 MHz, DMSO-d$_6$) δ 8.16 (s, 1H), 8.02 (d, J=7.7 Hz, 1H), 7.76-.68 (m, 3H), 7.40 (t, J=8.6 Hz, 2H), 7.29-7.20 (m, 2H), 7.11-7.07 (m, 1H), 6.97-6.93 m, 2H), 6.83 (dd, J=7.9, 2.4 Hz, 1H), 6.11 (s, 1H), 5.61 (s, 2H), 5.31 (d, J=4.4 Hz, 1H), 4. 7 (m, 1H), 3.73 (s, 3H), 3.62 (d, J=17.1 Hz, 1H), 3.51 (d, J=18.6 Hz, 1H), 1.13 (d, J=7.5 Hz, 3H).

Example 271

3-[(1R,2S)-1-[1-(4-fluorophenyl)indazol-5-yl]oxy-1-(3-methoxyphenyl)propan-2-yl]imidazolidine-2,4-dione

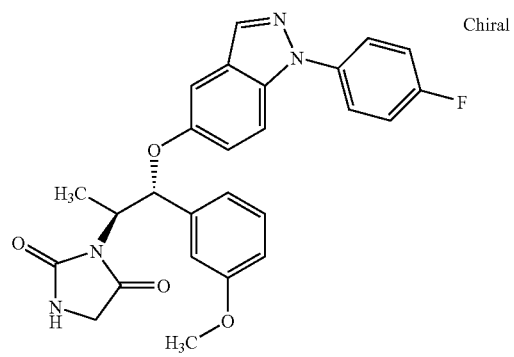

2-(carbamoylamino)-N-[(1R,2S)-1-[1-(4-fluorophenyl)indazol-5-yl]oxy-1-(3-methoxyphenyl)propan-2-yl]acetamide (270, 141 mg, 0.29 mmol) was dissolved in acetic acid (3 mL). The reaction was heated at 120° C. with stirring for 20 h. The HOAc was evaporated and the product was purified by preparative HPLC.

Yield: 37 mg, (27%).

APCI-MS: m/z 475.1 [MH$^+$]

¹H-NMR (400 MHz, DMSO-d₆) δ 8.18 (s, 1H), 7.96 (s, 1H), 7.73 (m, 2H), 7.67 (d, J=8.7 Hz, 1H), 7.39 (t, J=8.5 Hz, 2H), 7.24-7.18 (m, 3H), 6.95-6.90 (m, 2H), 6.81 (dd, J=8.3, 2.6 Hz, 1H), 5.61 (d, J=11.0 Hz, 1H), 4.36 (m, 1H), 3.70 (s, 3H), 3.65 (dd, J=26.0, 17.7 Hz, 2H), 1.59 (t, J=3.7 Hz, 3H).

Example 272

5-bromo-N-[(1R,2S)-1-[1-(4-fluorophenyl)indazol-5-yl]oxy-1-(3-methoxyphenyl) ropan-2-yl]thiophene-2-carboxamide

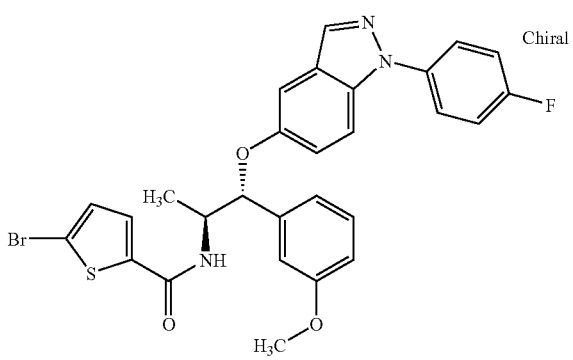

Prepared as described in Example 269 from (1R,2S)-1-(1-(4-fluorophenyl)-1H-indazol-5-yloxy)-1-(3-methoxyphenyl)propan-2-amine (6a, 70 mg, 0.18 mmol) and 5-bromothiophene-2-carboxylic acid (44.4 mg, 0.21 mmol)

Yield: 90 mg, (86%).
APCI-MS: m/z 580.1/582.1 [MH⁺]
¹H-NMR (400 MHz, DMSO-d₆) δ 8.63 (d, J=6.8 Hz, 1H), 8.15 (s, 1H), 7.75-7.67 (m, 3H), 7.63 (d, J=5.6 Hz, 1H), 7.39 (t, J=9.2 Hz, 2H), 7.27-7.20 (m, 3H), 7.11 (s, 1H), 7.00-6.96 (m, 2H), 6.82 (dd, J=8.3, 2.4 Hz, 1H), 5.38 (d, J=5.8 Hz, 1H), 4.30 (m, 1H), 3.70 (s, 3H), 1.30 (d, J=6.9 Hz, 3H).

Example 273

N-[(1R,2S)-1-[1-(4-fluorophenyl)indazol-5-yl]oxy-1-(3-methoxyphenyl)propan-2yl]-5-methylsulfonyl-thiophene-2-carboxamide

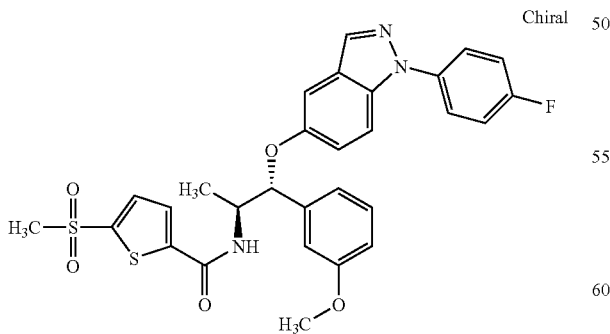

Prepared as described in Example 269 from (1R,2S)-1-(1-(4-fluorophenyl)-1H-indazol-5-yloxy)-1-(3-methoxyphenyl)propan-2-amine (6a, 70 mg, 0.18 mmol) and 5-(methylsulfonyl)thiophene-2-carboxylic acid (44.3 mg, 0.21 mmol)

Yield: 92 mg, (88%).
APCI-MS: m/z 580.1 [MH⁺]
¹H-NMR (400 MHz, DMSO-d₆) δ 8.92 (d, J=7.0 Hz, 1H), 8.16 (s, 1H), 7.86 (d, J=4.9 Hz, 1H), 7.78 (d, J=4.9 Hz, 1H), 7.75-7.68 (m, 3H), 7.39 (t, J=8.7 Hz, 2H), 7.28-7.21 (m, 2H), 7.12 (d, J=2.6 Hz, 1H), 7.02-6.97 (m, 2), 6.82 (dd, J=8.2, 2.4 Hz, 1H), 5.40 (d, J=5.8 Hz, 1H), 4.35 (m, 1H), 3.71 (s, 3H), 3.35 (s, 3H), 1.32 (d, J=6.8 Hz, 3H).

Example 274

N-[(1R,2S)-1-[1-(4-fluorophenyl)indazol-5-yl]oxy-1-(3-methoxyphenyl)propan-2yl]-5-methyl-1,3-thiazole-2-carboxamide

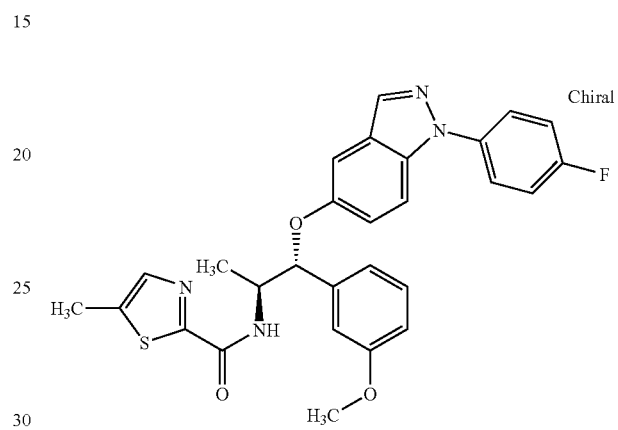

Prepared as described in Example 269 from (1R,2S)-1-(1-(4-fluorophenyl)-1H-indazol-5-yloxy)-1-(3-methoxyphenyl)propan-2-amine (6a, 70 mg, 0.18 mmol) and 5-methylthiazole-2-carboxylic acid (30 mg, 0.21 mmol).

Yield: 71 mg, (76%).
APCI-MS: m/z 517.2 [MH⁺]
¹H-NMR (400 MHz, DMSO-d₆) δ8.59 (d, J=11.0 Hz, 1H), 8.17 (s, 1H), 7.75-7.8 (m, 3H), 7.56 (s, 1H), 7.39 (t, J=8.7 Hz, 2H), 7.24-7.20 (m, 2H), 7.13 (d, J=2.6 Hz, 1H), 7.01 (m, 2H), 6.79 (dd, J=8.2, 2.5 Hz, 1H), 5.46 (d, J=6.2 Hz, 1H), 4.38 (m, 1H), 3 69 (s, 3H), 2.42 (s, 3H), 1.34 (d, J=7.0 Hz, 3H).

Example 275

4-cyano-N-[(1R,2S)-1-[1-(4-fluorophenyl)indazol-5-yl]oxy-1-(3-methoxyphenyl) ropan-2-yl]thiophene-2-carboxamide

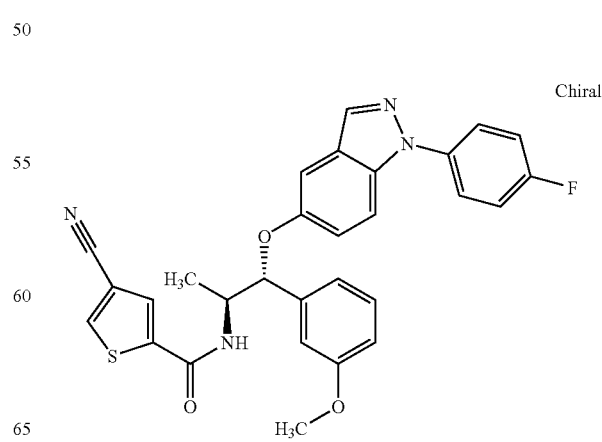

Prepared as described in Example 269 from (1R,2S)-1-(1-(4-fluorophenyl)-1H-indazol-5-yloxy)-1-(3-methoxyphenyl)propan-2-amine (6a, 70 mg, 0.18 mmol) and 4-cyanothiophene-2-carboxylic acid (32.9 mg, 0.21 mmol).

Yield: 78 mg, (82%).

APCI-MS: m/z 527.2 [MH$^+$]

$^1$H-NMR (400 MHz, DMSO-d$_6$) δ 8.72 (d, J=8.3 Hz, 1H), 8.17 (s, 1H), 7.90 (d, J=5.0 Hz, 1H), 7.75-7.68 (m, 3H), 7.52 (d, J=4.2 Hz, 1H), 7.39 (t, J=8.8 Hz, 2H), .28-7.22 (m, 2H), 7.14 (d, J=2.3 Hz, 1H), 7.04-6.99 (m, 2H), 6.82 (dd, J=8.2, 2.4 Hz, 1H) 5.39 (d, J=5.6 Hz, 1H), 4.36 (m, 1H), 3.72 (s, 3H), 1.33 (d, J=6.8 Hz, 3H).

Example 276

5-bromo-N-(1R,2S)-1-[1-(4-fluorophenyl)indazol-5-yl]oxy-1-(3-methoxyphenyl) ropan-2-yl]furan-2-carboxamide

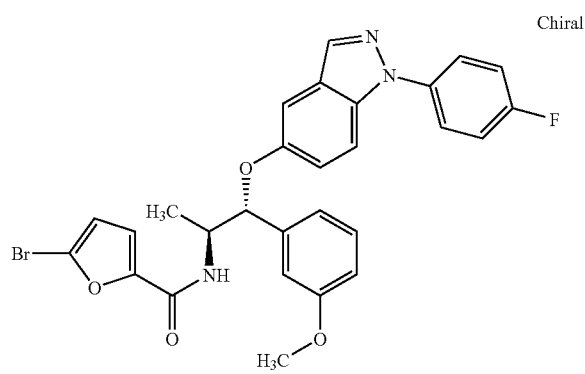

Prepared as described in Example 269 from (1R,2S)-1-(1-(4-fluorophenyl)-1H-indazol-5-yloxy)-1-(3-methoxyphenyl)propan-2-amine (6a, 70 mg, 0.18 mmol) and 5-bromofuran-2-carboxylic acid (41.0 mg, 0.21 mmol).

Yield: 92 mg, (90%).

APCI-MS: m/z 564.1/566.1 [MH$^+$]

$^1$H-NMR (400 MHz, DMSO-d$_6$) δ 8.44 (d, J=8.4 Hz, 1H), 8.17 (s, 1H), 7.75-.68 (m, 3H), 7.39 (t, J=9.0 Hz, 2H), 7.26-7.20 (m, 2H), 7.12-7.10 (m, 2H), 7.00-6.97 (m, 2H), 6.81 (dd, J=8.3, 2.4 Hz, 1H), 6.72 (d, J=3.5 Hz, 1H), 5.37 (d, J=5.9 Hz, 1H), 4.33 (m, 1H), 3.70 (s, 3H), 1.30 (d, J=7.1 Hz, 3H).

Example 277

N-[(1R,2S)-1-[1-(4-fluorophenyl)indazol-5-yl]oxy-1-(3-methoxyphenyl)propan-2yl]-5-methyl-1,3,4-oxadiazole-2-carboxamide

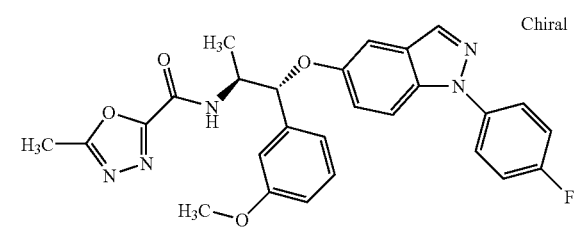

Potassium 5-methyl-[1,3,4]oxadiazole-2-carboxylate (31.8 mg, 0.19 mmol) was mixed with acetonitrile (195 μl). A slurry was formed. The mixture was cooled to 0-5° C. oxalyl chloride (14.99 μl, 0.17 mmol) was added and the reaction was stirred for 1 h at 0-5° C. (1R,2S)-1-(1-(4-fluorophenyl)-1H-indazol-5-yloxy)-1-(3-methoxyphenyl)propan-2-amine (6a, 25 mg, 0.06 mmol) was dissolved in dry THF (400 μl). N,N-diisopropylethylamine (65.6 μl, 0.38 mmol) was added. The THF solution was cooled to 0-5° C. The acid chloride slurry was drop wise added to the amine solution. The reaction was stirred at 0-5° C. After 1.5 h the reaction was poured into a mixture of EtOAc and diluted ammonia (ca 5%). The mixture was shaken, the organic layer collected. The water phase was washed twice with EtOAc. The combined organic layers were dried over sodium sulphate.

The crude product was purified using prep HPLC.

Yield: 16 mg, (52%).

APCI-MS: m/z 502.2 [MH$^+$]

$^1$H-NMR (400 MHz, DMSO-d$_6$) δ 9.27 (d, J=10.2 Hz, 1H), 8.17 (s, 1H), 7.75-7.68 (m, 3H), 7.39 (t, J=8.4 Hz, 2H), 7.26-7.20 (m, 2H), 7.12 (d, J=2.4 Hz, 1H), 7.02-6.99 (m, 2H), 6.81 (dd, J=8.2, 2.5 Hz, 1H), 5.37 (d, J=7.0 Hz, 1H), 4.39 (m, 1H), 3.70(s, 3H), 2.54 (s, 3H), 1.35 (d, J=7.7 Hz, 3H).

Example 278

N-[(1R,2S)-1-[1-(4-fluorophenyl)indazol-5-yl]oxy-1-(3-methoxyphenyl)propan-2yl]-1H-imidazole-4-carboxamide

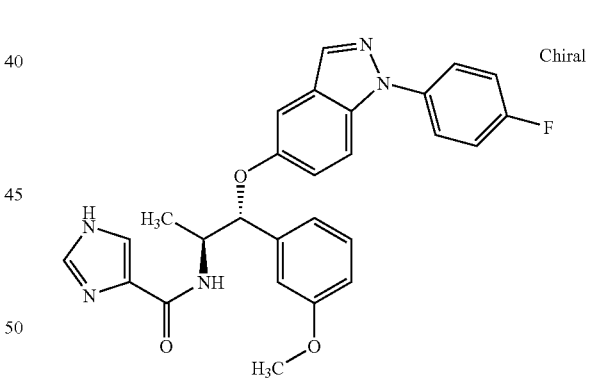

Prepared as described in Example 269 from (1R,2S)-1-(1-(4-fluorophenyl)-1H-indazol-5-yloxy)-1-(3-methoxyphenyl)propan-2-amine (6a, 50 mg, 0.13 mmol) and 1H-imidazole-4-carboxylic acid (17 mg, 0.15 mmol).

Yield: 18 mg, (29%).

APCI-MS: m/z 486.3 [MH$^+$]

$^1$H-NMR (400 MHz, DMSO-d$_6$) δ 8.16 (s, OH), 7.75-7.68 (m, 3H), 7.39 (t, J=8.9 Hz, 2H), 7.28-7.21 (m, 2H), 7.12 (d, J=2.3 Hz, 1H), 7.01-6.98 (m, 2H), 6.83 (dd, J=8.3, 2.4 Hz, 1H), 5.44 (d, J=5.2 Hz, 1H), 4.40 (m, 1H), 3.71 (s, 3H), 1.28 (d, J=7.8 Hz, 3H).

Example 279

N-[(1R,2S)-1-[1-(4-fluorophenyl)indazol-5-yl]oxy-1-(3-methoxyphenyl)propan-2yl]-1H-pyrazole-3-carboxamide

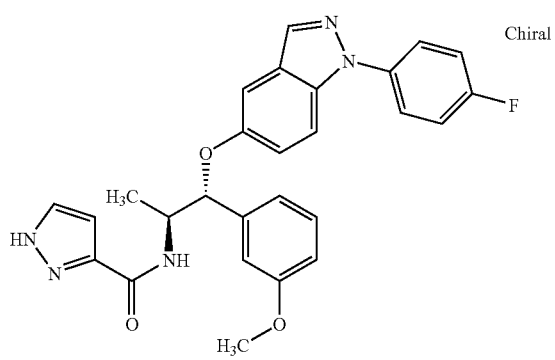

Prepared as described in Example 269 from (1R,2S)-1-(1-(4-fluorophenyl)-1H-indazol-5-yloxy)-1-(3-methoxyphenyl)propan-2-amine (6a, 50 mg, 0.13 mmol) and 1H-pyrazole-3-carboxylic acid (17 mg, 0.15 mmol).

Yield: 32 mg, (51.6%).

APCI-MS: m/z 486.2 [MH$^+$]

$^1$H-NMR (400 MHz, DMSO-d$_6$) δ 8.16 (s, 1H), 7.75-7.67 (m, 2H), 7.39 (t, J=8.7 Hz, 1H), 7.27-7.21 (m, 1H), 7.12 (d, J=2.8 Hz, 1H), 7.02-6.99 (m, 1H), 6.81 (dd, J=8.2, 2.4 Hz, 1H), 5.46 (d, J=6.3 Hz, 1H), 4.40 (m, 1H), 3.70 (s, 3H), 1.28 (d, J=6.9 Hz 3H).

Example 280

N-[(1R,2S)-1-[1-(4-fluorophenyl)indazol-5-yl]oxy-1-(3-methoxyphenyl)propan-2yl]1,2-oxazole-3-carboxamide

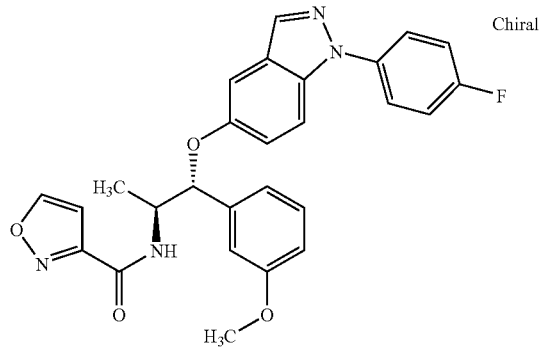

Prepared as described in Example 269 from (1R,2S)-1-(1-(4-fluorophenyl)-1H-indazol-5yloxy)-1-(3-methoxyphenyl)propan-2-amine (6a, 50 mg, 0.13 mmol) and isoxazole-3-carboxylic acid (17 mg, 0.15 mmol).

Yield: 37 mg, (59%).

APCI-MS: m/z 487.2 [MH$^+$]

$^1$H-NMR (400 MHz, DMSO-d$_6$) δ 9.04 (s, 1H), 8.78 (d, J=8.1 Hz, 1H), 8.17 (s, 1H), 7.75-7.68 (m, 3H), 7.39 (t, J=9.0 Hz, 2H), 7.26-7.20 (m, 2H), 7.11 (d, J=2.3 Hz, 1H), 7.02-6.99 (m, 2H), 6.82-6.79 (m, 2H), 5.38 (d, J=6.4 Hz, 1H), 4.39 (m, 1H), 3.70 s, 3H), 1.33 (d, J=6.6 Hz, 3H).

Example 281

N-[(1R,2S)-1-[1-(4-fluorophenyl)indazol-5-yl]oxy-1-(3-methoxyphenyl)propan-2yl]-1H-1,2,4-triazole-3-carboxamide

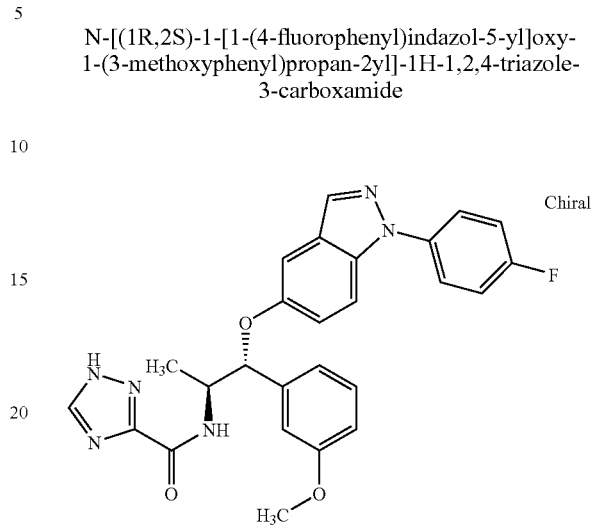

Prepared as described in Example 269 from (1R,2S)-1-(1-(4-fluorophenyl)-1H-indazol-5-yloxy)-1-(3-methoxyphenyl)propan-2-amine (6a, 50 mg, 0.13 mmol) and 1H-1,2,4-triazole-3-carboxylic acid (17 mg, 0.15 mmol).

Yield: 23 mg, (37%).

APCI-MS: m/z 487.2 [MH$^+$]

$^1$H-NMR (400 MHz, DMSO-d$_6$) δ 8.17 (s, OH), 7.75-7.68 (m, 3H), 7.39 (t, J=9.0 Hz, 2H), 7.25-7.21 (m, 2H), 7.12 (d, J=3.2 Hz, 1H), 7.03-6.99 (m, 2H), 6.79 (dd, J=8.4, 2.4 Hz, 1H), 5.45 (d, J=6.7 Hz, 1H), 4.42 (m, 1H), 3.69 (s, 3H), 1.32 (d, J=7.2 Hz, 3H).

Example 282

N-(1R,2S)-1-[1-(4-fluorophenyl)indazol-5-yl]oxy-1-(3-methoxyphenyl)propan-2-yl]-5-methyl-1H-pyrazole-3-carboxamide

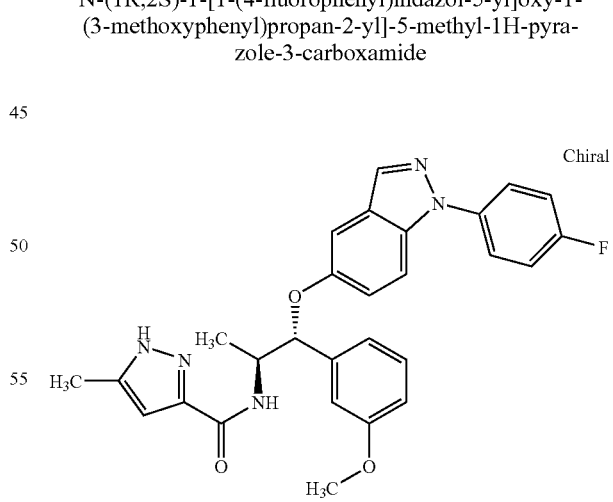

Prepared as described in Example 269 from (1R,2S)-1-(1-(4-fluorophenyl)-1H-indazol-5-yloxy)-1-(3-methoxyphenyl)propan-2-amine (6a, 50 mg, 0.13 mmol) and 5-methyl-1H-pyrazole-3-carboxylic acid (19 mg, 0.15 mmol).

Yield: 34 mg, (53%).

APCI-MS: m/z 500.2 [MH$^+$]

¹H-NMR (400 MHz, DMSO-d₆) δ 8.16 (s, 1H), 7.87 (d, J=8.6 Hz, 1H), 7.75-.67 (m, 3H), 7.39 (t, J=9.0 Hz, 2H), 7.26-7.20 (m, 2H), 7.11 (d, J=2.0 Hz, 1H), 7.01-.98 (m, 2H), 6.81 (dd, J=8.2, 2.3 Hz, 1H), 6.35 (s, 1H), 5.45 (d, J=6.0 Hz, 1H), 4.37 (m, H), 3.70 (s, 3H), 2.22 (s, 3H), 1.26 (d, J=7.2 Hz, 3H).

Example 283

N-[(1R,2S)-1-[1-(4-fluorophenyl)indazol-5-yl]oxy-1-(3-methoxyphenyl)propan-2yl]-1-methyl-imidazole-4-carboxamide

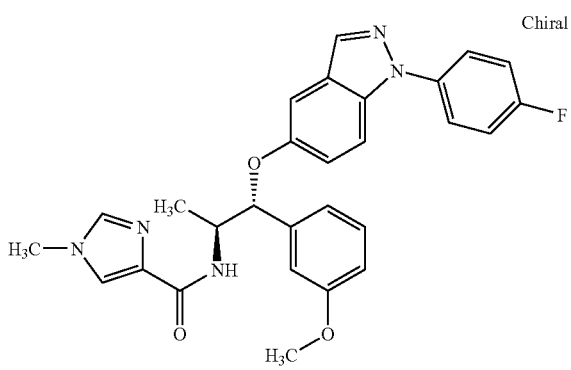

Prepared as described in Example 269 from (1R,2S)-1-(1-(4-fluorophenyl)-1H-indazol-5-yloxy)-1-(3-methoxyphenyl)propan-2-amine (6a, 50 mg, 0.13 mmol) and 1-methyl-1H-imidazole-4-carboxylic acid (19 mg, 0.15 mmol).

Yield: 20 mg, (31%).

APCI-MS: m/z 500.2 [MH⁺]

¹H-NMR (400 MHz, DMSO-d₆) δ8.16 (s, 1H), 7.81 (s, 1H), 7.75-7.68 (m, 3H), 7.39 (t, J=8.8 Hz, 2H), 7.28-7.21 (m, 2H), 7.12 (d, J=2.3 Hz, 1H), 7.01-6.98 (m, 2H), 6.82(dd, J=8.2, 2.1 Hz, 1H), 5.45 (d, J=4.9 Hz, 1H), 4.39 (m, 1H), 3.73 (s, 3H), 3.71 (s, 3H), .26 (d, J=7.2 Hz, 3H).

Example 284

N-[(1R_2S)-1-[1-(4-fluorophenyl)indazol-5-yl]oxy-1-(3-methoxyphenyl)propan-2-yl]-5-methyl-1,2-oxazole-4-carboxamide

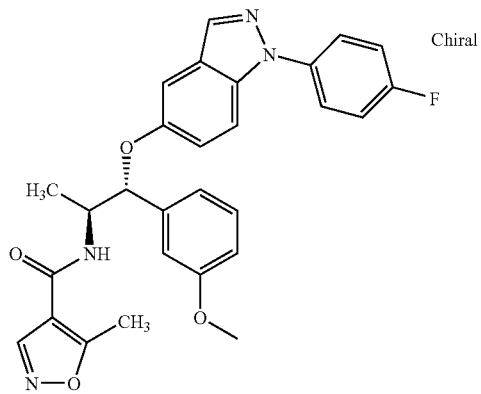

Prepared as described in Example 269 from (1R,2S)-1-(1-(4-fluorophenyl)-1H-indazol-5-yloxy)-1-(3-methoxyphenyl)propan-2-amine (6a, 50 mg, 0.13 mmol) and 5-methyl-isoxazole-4-carboxylic acid (19 mg, 0.15 mmol).

Yield: 36 mg, (56%).

APCI-MS: m/z 501.2 [MH⁺]

¹H-NMR (400 MHz, DMSO-d₆) δ 8.31 (s, 1H), 8.19 (s, 1H), 7.76-7.68 (m, 3H), 7.40 (t, J=8.7 Hz, 2H), 7.27-7.19 (m, 2H), 7.13 (d, J=2.3 Hz, 1H), 7.00-6.98 (m, 2), 6.82 (dd, J=8.2, 2.4 Hz, 1H), 5.37 (d, J=6.9 Hz, 1H), 4.32 (m, 1H), 3.73 (s, 3H), 2.17 (s, 3H), 1.32 (d, J=6.5 Hz, 3H).

Example 285

N-[(1R,2S)-1-[1-(4-fluorophenyl)indazol-5-yl]oxy-1-(3-methoxyphenyl)propan-2yl]-1-methyl-triazole-4-carboxamide

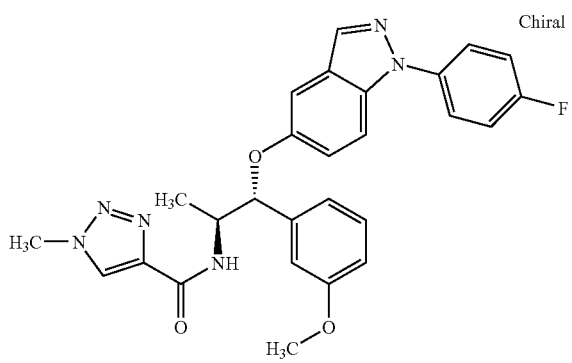

Prepared as described in Example 269 from (1R,2S)-1-(1-(4-fluorophenyl)-1H-indazol-5-yloxy)-1-(3-methoxyphenyl)propan-2-amine (6a, 50 mg, 0.13 mmol) and 1-methyl-1H-1,2,3-triazole-4-carboxylic acid (19 mg, 0.15 mmol).

Yield: 44 mg, (69%).

APCI-MS: m/z 501.2 [MH⁺]

¹H-NMR (400 MHz, DMSO-d₆) δ 8.43 (s, 1H), 8.35 (d, J=9.0 Hz, 1H), 8.17 (s, 1H), 7.75-7.68 (m, 3H), 7.39 (t, J=8.8 Hz, 2H), 7.24-7.20 (m, 2H), 7.11 (d, J=2.4 Hz, 1H), 7.02-7.00 (m, 2H), 6.79 (dd, J=8.3, 2.6 Hz, 1H), 5.44 (d, J=6.8 Hz, 1H), 4.41 (m, 1H), 4 05 (s, 3H), 3.69 (s, 3H), 1.32 (d, J=6.7 Hz, 3H).

Example 286

N-[(1R,2S)-1-[1-(4-fluorophenyl)indazol-5-yl]oxy-1-(3-methoxlphenyl)propan-2-yl]-4,5-dimethyl-furan-2-carboxamide

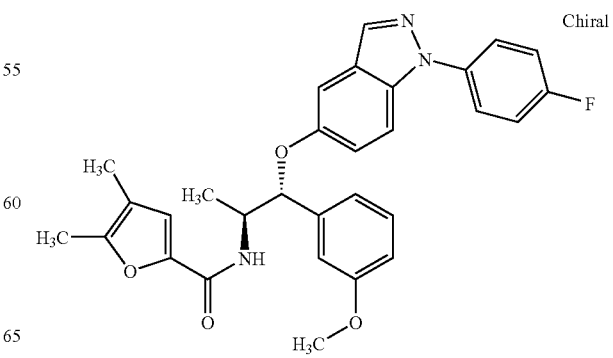

Prepared as described in Example 269 from (1R,2S)-1-(1-(4-fluorophenyl)-1H-indazol-5-yloxy)-1-(3-methoxyphenyl)propan-2-amine (6a, 50 mg, 0.13 mmol) and 4,5-dimethylfuran-2-carboxylic acid (21 mg, 0.15 mmol).

Yield: 49 mg, (75%).

APCI-MS: m/z 514.2 [MH$^+$]

$^1$H-NMR (400 MHz, DMSO-d$_6$) δ 8.16 (s, 1H), 8.05 (d, J=8.8 Hz, 1H), 7.75-7.68 (m, 3H), 7.39 (t, J=8.9 Hz, 2H), 7.26-7.19 (m, 2H), 7.10 (d, J=2.2 Hz, 1H), 7.00-.97 (m, 2H), 6.85 (s, 1H), 6.80 (dd, J=8.4, 2.4 Hz, 1H), 5.39 (d, J=6.7 Hz, 1H), 4.31 (m, 1H), 3.70 (s, 3H), 2.21 (s, 3H), 1.90 (s, 3H), 1.27 (d, J=7.6 Hz, 3H).

Example 287

N-(1R,2S)-1-[1-(4-fluorophenyl)indazol-5-yl]oxy-1-(3-methoxyphenyl)propan-2-yl]-1,5-dimethyl-pyrazole-3-carboxamide

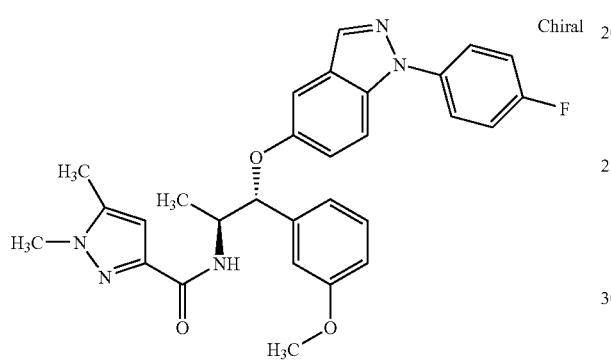

Prepared as described in Example 269 from (1R,2S)-1-(1-(4-fluorophenyl)-1H-indazol-5-yloxy) 1-(3-methoxyphenyl)propan-2-amine (6a, 50 mg, 0.13 mmol) and 1,5-dimethyl-1H-pyrazole-3-carboxylic acid (21 mg, 0.15 mmol).

Yield: 42 mg, (64%).

APCI-MS: m/z 514.2 [MH$^+$]

$^1$H-NMR (400 MHz, DMSO-d$_6$) δ 8.16 (s, 1H), 7.76-7.67 (m, 4H), 7.39 (t, J=9.4 Hz, 2H), 7.26-7.20 (m, 2H), 7.12 (d, J=2.3 Hz, 1H), 7.01-6.98 (m, 2H), 6.80 (dd, J=8.3, 2.1 Hz, 1H), 6.35 (s, 1H), 5.46 (d, J=5.7 Hz, 1H), 4.37 (m, 1H), 3.73 (s, 3H), 3.71 (s, H), 2.23 (s, 3H), 1.25 (d, J=6.3 Hz, 3H).

Example 288

N-[(1R,2S)-1-[1-(4-fluorophenyl)indazol-5-yl]oxy-1-(3-methoxyphenyl)propan-2yl]-5-methyl-1,3-thiazole-4-carboxamide

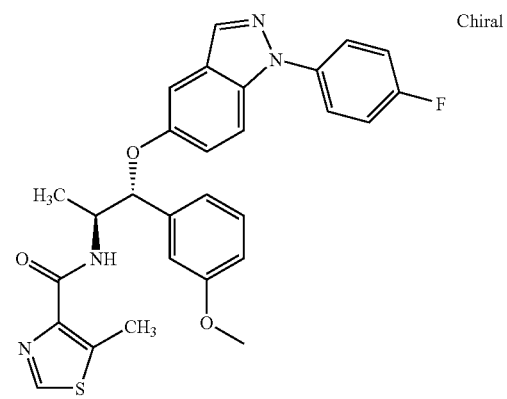

Prepared as described in Example 269 from (1R,2S)-1-(1-(4-fluorophenyl)-1H-indazol-5-yloxy)-1-(3-methoxyphenyl)propan-2-amine (6a, 50 mg, 0.13 mmol) and 5-methylthiazole-4-carboxylic acid (21 mg, 0.15 mmol).

Yield: 29 mg, (44%).

APCI-MS: m/z 517.2 [MH$^+$]

$^1$H-NMR (400 MHz, DMSO-d$_6$) δ 8.88 (s, 1H), 8.18-8.16 (m, 1H), 7.75-7.67 m, 3H), 7.39 (t, J=8.8 Hz, 2H), 7.27-7.22 (m, 2H), 7.13 (d, J=2.3 Hz, 1H), 7.02-6.99 (m, 2H), 6.82 (dd, J=8.1, 2.3 Hz, 1H), 5.50 (d, J=6.0 Hz, 1H), 4.41 (m, 1H), 3.70 (s, 3H), 2.69 (s, 3H), 1.27 (d, J=6.3 Hz, 3H).

Example 289

N-[(1R,2S)-1-[1-(4-fluorophenyl)indazol-5-yl]oxy-1-(3-methoxyphenyl)propan-2yl]-4-methyl-1,3-thiazole-5-carboxamide

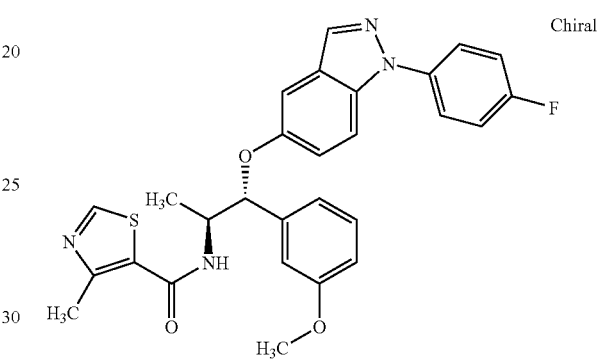

Prepared as described in Example 269 from (1R,2S)-1-(1-(4-fluorophenyl)-1H-indazol-5-yloxy)-1-(3-methoxyphenyl)propan-2-amine (6a, 50 mg, 0.13 mmol) and 4-methylthiazole-5-carboxylic acid (21 mg, 0.15 mmol).

Yield: 38 mg, (58%).

APCI-MS: m/z 517.2 [MH$^+$]

$^1$H-NMR (400 MHz, DMSO-d$_6$) δ 9.00 (s, 1H), 8.33 (d, J=8.0 Hz, 1H), 8.18 (s, 1H), 7.76-7.68 (m, 3H), 7.39 (t, J=9.0 Hz, 2H), 7.28-7.21 (m, 2H), 7.13 (d, J=2.2 Hz, 1H), 7.03-6.98 (m, 2H), 6.83 (dd, J=8.1, 2.3 Hz, 1H), 5.36 (d, J=6.7 Hz, 1H), 4.35 (m, 1H), 3.71(s, 3H), 2.40 (s, 3H), 1.31 (d, J=7.1 Hz, 3H).

Example 290

N-[(1R,2S)-1-[1-(4-fluorophenyl)indazol-5-yl]oxy-1-(3-methoxyphenyl)propan-2yl]-4-methyl-1,3-thiazole-2-carboxamide

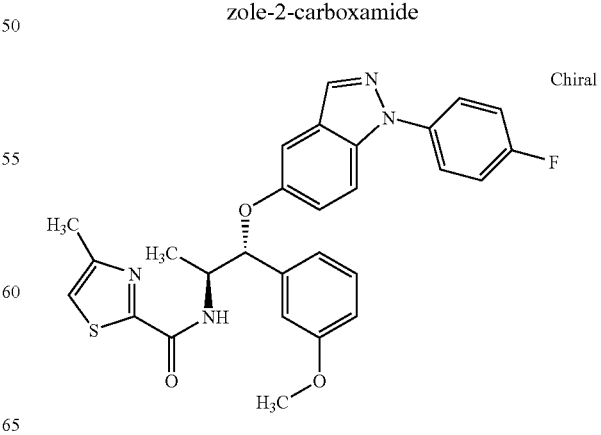

Prepared as described in Example 269 from (1R,2S)-1-(1-(4-fluorophenyl)-1H-indazol-5-yloxy)-1-(3-methoxyphenyl)propan-2-amine (6a, 50 mg, 0.13 mmol) and 4-methylthiazole-2-carboxylic acid (21 mg, 0.15 mmol).

Yield: 38 mg, (58%).

APCI-MS: m/z 517.2 [MH$^+$]

$^1$H-NMR (400 MHz, DMSO-d$_6$) δ 8.59 (d, J=9.7 Hz, 1H), 8.17 (s, 1H), 7.75-.68 (m, 3H), 7.57 (s, 1H), 7.39 (t, J=9.1 Hz, 2H), 7.24-7.21 (m, 2H), 7.13 (d, J=2.8 Hz, 1H), 7.02-7.00 (m, 2H), 6.79 (dd, J=7.9, 2.1 Hz, 1H), 5.46 (d, J=6.4 Hz, 1H), 4.38 (m, 1H), 3.9 (s, 3H), 2.42 (s, 3H), 1.34 (d, J=6.6 Hz, 3H).

Example 291

N-[(1R,2S)-1-[1-(4-fluorophenyl)indazol-5-yl]oxy-1-(3-methoxyphenyl)propan-2yl]-4,5-dimethyl-thiophene-2-carboxamide

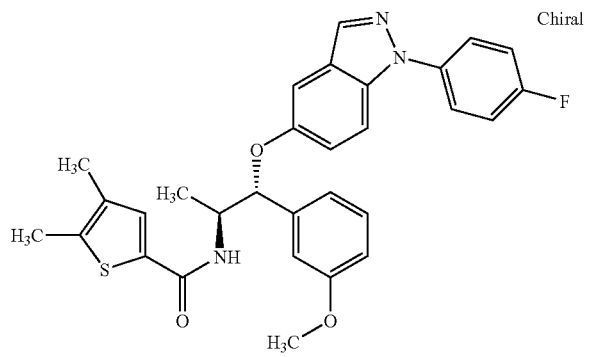

Prepared as described in Example 269 from (1R,2S)-1-(1-(4-fluorophenyl)-1H-indazol-5-yloxy)-1-(3-methoxyphenyl)propan-2-amine (6a, 50 mg, 0.13 mmol) and 4,5-dimethylthiophene-2-carboxylic acid (23 mg, 0.15 mmol).

Yield: 43 mg, (64%).

APCI-MS: m/z 530.2 [MH$^+$]

$^1$H-NMR (400 MHz, DMSO-d$_6$) δ 8.32 (d, J=9.3 Hz, 1H), 8.15 (s, 1H), 7.75-7.67 (m, 3H), 7.49 (s, 1H), 7.39 (t, J=8.8 Hz, 2H), 7.27-7.20 (m, 2H), 7.09 (d, J=2.8 Hz, 1H), 7.01-6.96 (m, 2H), 6.81 (dd, J=8.2, 2.6 Hz, 1H), 5.38 (d, J=5.8 Hz, 1H), 4.28 (m, 1H), 3 71 (s, 3H), 2.28 (s, 3H), 2.07 (s, 3H), 1.27 (d, J=6.7 Hz, 3H).

Example 292

N-[(1R,2S)-1-[1-(4-fluorophenyl)indazol-5-yl]oxy-1-(3-methoxyphenyl)propan-2-yl]-3-methoxy-thiophene-2-carboxamide

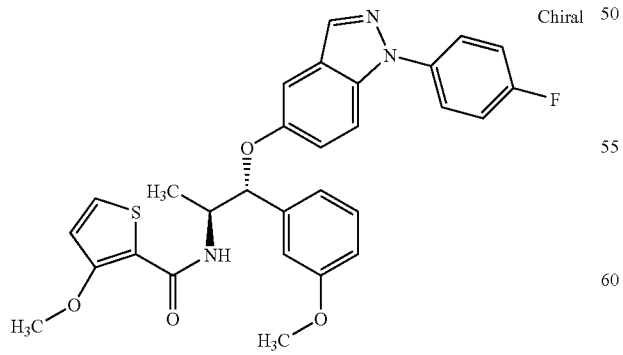

Prepared as described in Example 269 from (1R,2S)-1-(1-(4-fluorophenyl)-1H-indazol-5-yloxy)-1-(3-methoxyphenyl)propan-2-amine (6a, 50 mg, 0.13 mmol) and 3-methoxythiophene-2-carboxylic acid (24 mg, 0.15 mmol).

Yield: 44 mg, (65%).

APCI-MS: m/z 532.2 [MH$^+$]

$^1$H-NMR (400 MHz, DMSO-d$_6$) δ 8.18 (s, 1H), 7.76-7.70 (m, 4H), 7.53 (d, J=9.8 Hz, 1H), 7.40 (t, J=8.6 Hz, 2H), 7.32 (t, J=8.1 Hz, 1H), 7.26 (dd, J=9.3, 2.6 Hz, 1H), 7.16 (d, J=2.2 Hz, 1H), 7.09 (d, J=5.2 Hz, 1H), 7.04-7.01 (m, 2H), 6.88 (dd, J=8.2, 2.3 Hz, H), 5.53 (d, J=4.1 Hz, 1H), 4.46 (m, 1H), 3.88 (s, 3H), 3.74 (s, 3H), 1.18 (d, J=6.3 Hz, H).

Example 293

N-[(1R,2S)-1-[1-(4-fluorophenyl)indazol-5-yl]oxy-1-(3-methoxyphenyl)propan-2yl]-1,9-diazabicyclo[4.3.0]nona-2,4,6,8-tetraene-8-carboxamide

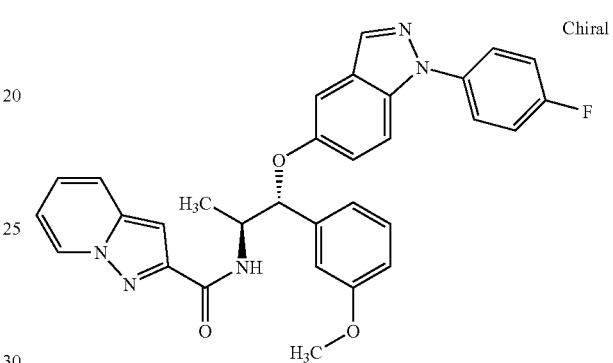

Prepared as described in Example 269 from (1R,2S)-1-(1-(4-fluorophenyl)-1H-indazol-5-yloxy)-1-(3-methoxyphenyl)propan-2-amine (6a, 50 mg, 0.13 mmol) and pyrazolo[1,5-a]pyridine-2-carboxylic acid (24 mg, 0.15 mmol).

Yield: 37 mg, (54%).

APCI-MS: m/z 536.2 [MH$^+$]

$^1$H-NMR (400 MHz, DMSO-d$_6$) δ 8.66 (d, J=7.0 Hz, 1H), 8.26 (d, J=9.2 Hz, 1H), 8.17 (s, 1H), 7.76-7.68 (m, 4H), 7.39 (t, J=8.8 Hz, 2H), 7.29-7.23 (m, 3H), 7.14 d, J=2.2 Hz, 1H), 7.04-7.00 (m, 3H), 6.94 (s, 1H), 6.80 (dd, J=8.5, 2.5 Hz, 1H), 5.51 (d, J=5.9 Hz, 1H), 4.46 (m, 1H), 3.69 (s, 3H), 1.33 (d, J=7.4 Hz, 3H).

Example 294

N-[(1R,2S)-1-[1-(4-fluorophenyl)indazol-5-yl]oxy-1-(3-methoxyphenyl)propan-2yl]-1H-benzoimidazole-2-carboxamide

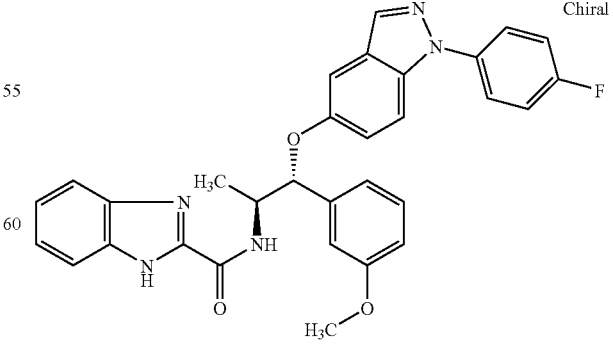

Prepared as described in Example 269 from (1R,2S)-1-(1-(4-fluorophenyl)-1H-indazol-5-yloxy)-1-(3-methoxyphenyl)propan-2-amine (6a, 50 mg, 0.13 mmol) and 1H-benzo[d]imidazole-2-carboxylic acid (24 mg, 0.15 mmol).

Yield: 25 mg, (36%).

APCI-MS: m/z 536.2 [MH+]

1H-NMR (400 MHz, DMSO-d$_6$) δ 8.80 (d, J=9.2 Hz, 1H), 8.18 (d, J=0.7 Hz, 1H), 7.75-7.68 (m, 3H), 7.61 (s, 1H), 7.39 (t, J=8.8 Hz, 2H), 7.30-7.19 (m, 4H), 7.14 (d, J=2.3 Hz, 1H), 7.05-7.03 (m, 2H), 6.77 (dd, J=7.3, 1.9 Hz, 1H), 5.48 (d, J=6.7 Hz, 1H), 4.48 (dt, J=9.2, 6.7 Hz, 1H), 3.67 (s, 3H), 1.39 (d, J=6.9 Hz, 2H)

Example 295

5-chloro-N-[(1R,2S)-1-[1-(4-fluorophenyl)indazol-5-yl]oxy-1-(3-methoxyphenyl) ropan-2-yl]thiophene-2-carboxamide

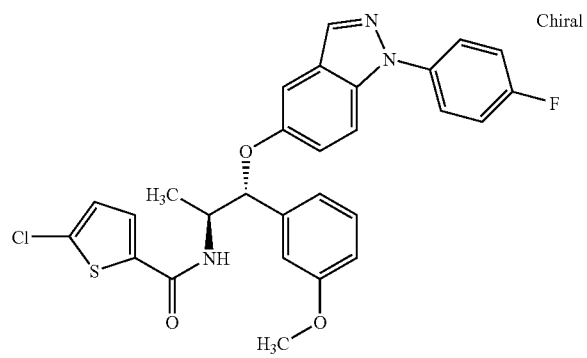

Prepared as described in Example 269 from (1R,2S)-1-(1-(4-fluorophenyl)-1H-indazol-5-yloxy)-1-(3-methoxyphenyl)propan-2-amine (6a, 50 mg, 0.13 mmol) and 5-chlorothiophene-2-carboxylic acid (24 mg, 0.15 mmol).

Yield: 39 mg, (57%).

APCI-MS: m/z 536.1 [MH+]

1H-NMR (400 MHz, DMSO-d$_6$) δ 8.65 (d, J=7.9 Hz, 1H), 8.16 (s, 1H), 7.75-.67 (m, 4H), 7.39 (t, J=8.8 Hz, 2H), 7.28-7.20 (m, 2H), 7.15 (d, J=4.3 Hz, 1H), 7.11 (d, J=3.0 Hz, 1H), 7.01-6.96 (m, 2H), 6.82 (dd, J=8.1, 2.4 Hz, 1H), 5.38 (d, J=5.8 Hz, 1H), 4.30 (m, 1H), 3.71 (s, 3H), 1.30 (d, J=7.1 Hz, 3H).

Example 296

N-[(1R,2S)-1-[1-(4-fluorophenyl)indazol-5-yl]oxy-1-(3-methoxyphenyl)propan-2-yl]benzothiophene-2-carboxamide

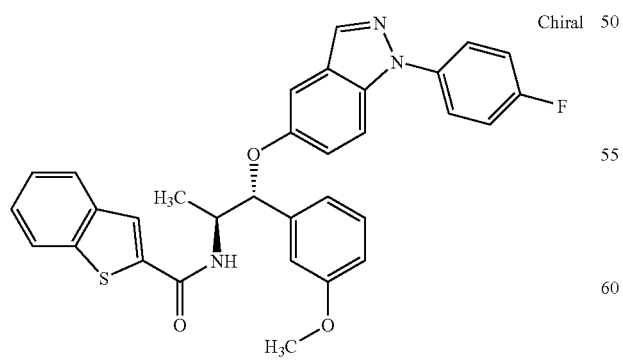

Prepared as described in Example 269 from (1R,2S)-1-(1-(4-fluorophenyl)-1H-indazol-5-yloxy)-1-(3-methoxyphenyl)propan-2-amine (6a, 50 mg, 0.13 mmol) and benzo[b]thiophene-2-carboxylic acid (27 mg, 0.15 mmol).

Yield: 45 mg, (64%).

APCI-MS: m/z 552.2 [MH+]

1H-NMR (400 MHz, DMSO-d$_6$) δ 8.84 (d, J=5.0 Hz, 1H), 8.16 (s, 1H), 8.12 (s, 1H), 8.00-7.91 (m, 2H), 7.74-7.68 (m, 3H), 7.46-7.36 (m, 4H), 7.29-7.23 (m, 2H), 7.13 (d, J=2.2 Hz, 1H), 7.05-7.00 (m, 2H), 6.82 (dd, J=8.4, 2.8 Hz, 1H), 5.44 (d, J=5.5 Hz, 1H) 4.37 (m, 1H), 3.71 (s, 3H), 1.34 (d, J=7.9 Hz, 3H).

Example 297

N-[(1R,2S)-1-[1-(4-fluorophenyl)indazol-5-yl]oxy-1-(3-methoxyphenyl)propan-2-yl]benzothiazole-2-carboxamide

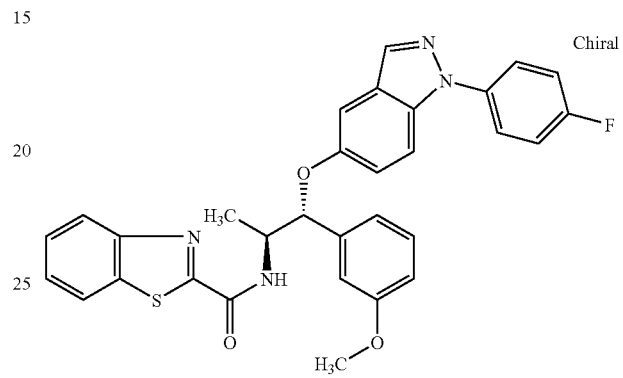

Prepared as described in Example 269 from (1R,2S)-1-(1-(4-fluorophenyl)-1H-indazol-5-yloxy)-1-(3-methoxyphenyl)propan-2-amine (6a, 50 mg, 0.13 mmol) and benzo[d]thiazole-2-carboxylic acid (27 mg, 0.15 mmol).

Yield: 22 mg, (31%).

APCI-MS: m/z 553.2 [MH+]

1H-NMR (400 MHz, DMSO-d$_6$) δ 9.08 (d, J=9.8 Hz, 1H), 8.21-8.12 (m, 3H), .75-7.68 (m, 3H), 7.65-7.55 (m, 2H), 7.39 (t, J=9.0 Hz, 2H), 7.26-7.20 (m, 2H), 7.14 (d, J=2.1 Hz, 1H), 7.04-7.02 (m, 2H), 6.78 (dd, J=8.2, 2.5 Hz, 1H), 5.48 (d, J=7.0 Hz, 1H), 4.44 (m, 1H), 3.67 (s, 3H), 1.41 (d, J=6.6 Hz, 3H).

Example 298

N-[(1R,2S)-1-[1-(4-fluorophenyl)indazol-5-yl]oxy-1-(3-methoxyphenyl)propan-2yl]-3-hydroxy-5-(trifluoromethyl)thiophene-2-carboxamide

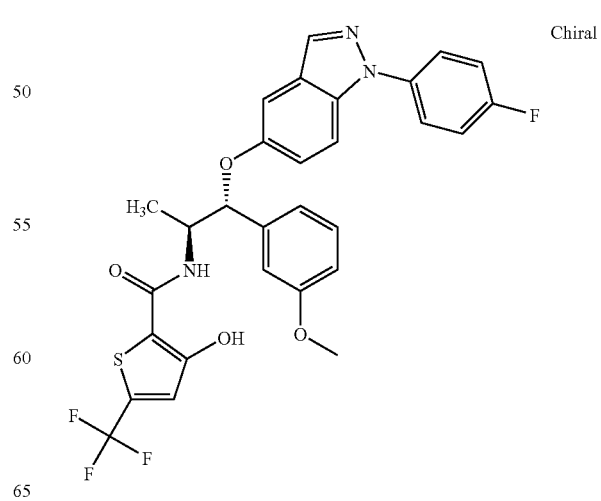

Prepared as described in Example 269 from (1R,2S)-1-(1-(4-fluorophenyl)-1H-indazol-5-yloxy)-1-(3-methoxyphenyl)propan-2-amine (6a, 50 mg, 0.13 mmol) and 3-hydroxy-5-(trifluoromethyl)thiophene-2-carboxylic acid (32 mg, 0.15 mmol).

Yield: 18 mg, (24%).

APCI-MS: m/z 586.2 [MH$^+$]

$^1$H-NMR (400 MHz, DMSO-d$_6$) δ 12.12 (s, 1H), 8.17 (s, 1H), 7.90 (d, J=9.2 Hz, 1H), 7.76-7.68 (m, 3H), 7.40 (t, J=8.8 Hz, 2H), 7.31-7.18 (m, 4H), 7.03-7.00 (m, 2H), 6.86 (dd, J=8.2, 2.3 Hz, 1H), 5.56 (d, J=4.8 Hz, 1H), 4.46 (m, 1H), 3.74 (s, 3H), 1.20 (d, =6.5 Hz, 3H).

Example 299

N-[(1R,2S)-1-[1-(4-fluorophenyl)indazol-5-yl]oxy-1-(3-methoxyphenyl)propan-2yl]-5-(methoxymethyl)thiophene-2-carboxamide

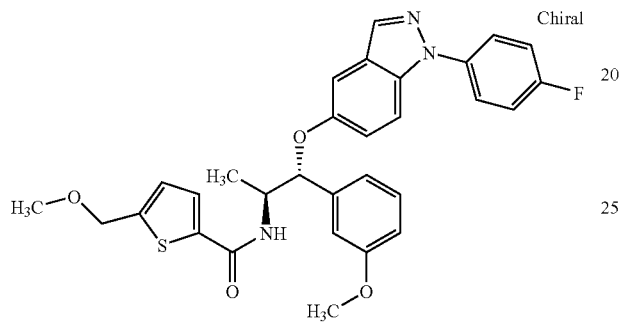

Prepared as described in Example 269 from (1R,2S)-1-(1-(4-fluorophenyl)-1H-indazol-5-yloxy)-1-(3-methoxyphenyl)propan-2-amine (6a, 50 mg, 0.13 mmol) and 5-(methoxymethyl)thiophene-2-carboxylic acid (26 mg, 0.15 mmol).

Yield: 48 mg, (69%).

APCI-MS: m/z 546.2 [MH$^+$]

$^1$H-NMR (400 MHz, DMSO-d$_6$) δ 8.51 (d, J=7.3 Hz, 1H), 8.15 (s, 1H), 7.75-7.65 (m, 4H), 7.39 (t, J=9.0 Hz, 2H), 7.28-7.21 (m, 2H), 7.11 (d, J=2.4 Hz, 1H), 7.02-.97 (m, 3H), 6.81 (dd, J=8.1, 2.3 Hz, 1H), 5.39 (d, J=6.4 Hz, 1H), 4.54 (s, 2H), 4.31 (m, 1H), 3. 1 (s, 3H), 3.26 (s, 3H), 1.30 (d, J=6.9 Hz, 3H).

Example 300

N-((1R,2S)-1-(2-chlorophenyl)-1-(1-(4-fluorophenyl)-1H-indazol-5-yloxy)propan-2-yl)pivalamide

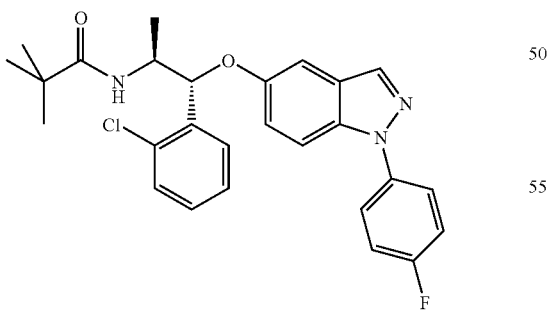

Prepared as described in Example 1 using (1R,2S)-1-(2-chlorophenyl)-1-(1-(4-fluorophenyl) 1H-indazol-5-yloxy) propan-2-amine (300a, 18 mg, 0.05 mmol) and Pivaloyl chloride (17 μl, 0.14 mmol). Yield 22 mg (100%).

APCI-MS: m/z 480.1 [MH$^+$]

$^1$H NMR (300 MHz, DMSO-d$_6$) δ 8.20 (d, J=0.8 Hz, 1H), 7.78-7.67 (m, 3H), .55-7.48 (m, 1H), 7.46-7.24 (m, 6H), 7.19 (dd, J=9.2, 2.4 Hz, 1H), 7.03 (d, J=2.3 Hz, H), 5.56 (d, J=6.5 Hz, 1H), 4.50-4.37 (m, 1H), 1.24 (d, J=6.9 Hz, 3H), 0.95 (s, 9H).

(1R,2S)-1-(2-chlorophenyl)-1-(1-(4-fluorophenyl)-1H-indazol-5-yloxy)propan-2amine (300a)

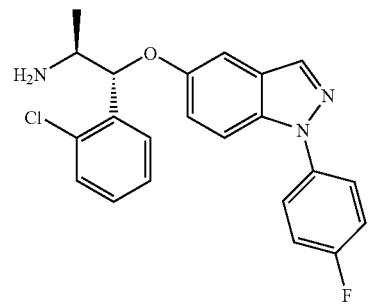

Prepared as described in Example 6 using (1R,2S)-2-amino-1-(2-chlorophenyl)propan-1-ol hydrochloride (300b, 49 mg, 0.22 mmol). Yield 21 mg (24%).

APCI-MS: m/z 396.0 [MH$^+$]

$^1$H NMR (300 MHz, CD$_3$OD) δ 8.01 (d, J=0.9 Hz, 1H), 7.70-7.57 (m, 3H), 7. 3-7.41 (m, 2H), 7.34-7.22 (m, 5H), 6.99 (d, J=2.3 Hz, 1H), 5.66 (d, J=4.0 Hz, 1H), .45-3.35 (m, 1H), 1.18 (d, J=6.6 Hz, 3H).

(1R,2S)-2-amino-1-(2-chlorophenyl)propan-1-ol hydrochloride (300b)

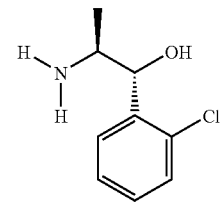

Prepared as described in Example 6 using tert-butyl (1R, 2S)-1-(2-chlorophenyl)-1-hydroxypropan-2-ylcarbamate (300c, 65 mg, 0.23 mmol). Yield 49 mg (97%)

APCI-MS: m/z 186.1 [MH$^+$]

tert-butyl (1R,2S)-1-(2-chlorophenyl)-1-hydroxypropan-2-ylcarbamate (300c)

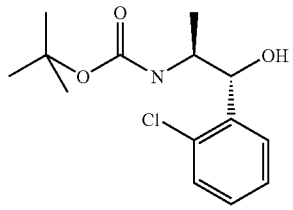

Prepared as described in Example 6 using (S)-tert-butyl 1-(2-chlorophenyl)-1-oxopropan-2-ylcarbamate (300d, 0.11 g, 0.39 mmol). Yield 67 mg (60%)

$^1$H NMR (300 MHz, CD$_3$OD) δ7.60 (dd, J=7.5, 1.8 Hz, 1H), 7.36-7.19 (m, 3H), .04 (d, J=4.9 Hz, 1H), 4.02-3.91 (m, 1H), 1.38 (s, 9H), 1.03 (d, J=6.8 Hz, 3H).

(S)-tert-butyl 1-(2-chlorophenyl)-1-oxopropan-2-ylcarbamate (300d)

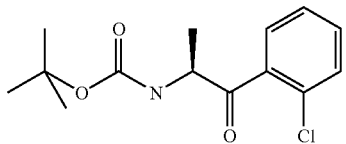

Prepared as described in Example 6 using (S)-tert-butyl 1-(methoxy(methyl)amino)-1-oxopropan-2-ylcarbamate (182 mg, 0.78 mmol) and (2-chlorophenyl)magnesium chloride (403 mg, 2.35 mmol). Yield 110 mg (50%).

$^{1}$H NMR (300 MHz, DMSO-$d_6$) δ 7.66-7.37 (m, 5H), 4.67 (quintet, J=7.3 Hz, 1H) 1.32 (s, 9H), 1.20 (d, J=7.3 Hz, 3H).

Example 301 tert-butyl 3-((1R,2S)-1-(1-(4-fluorophenyl)-1H-indazol-5-yloxy)-1-(3-methoxyphenyl)propan-2-ylcarbamoyl)pyrrolidine-1-carboxylate

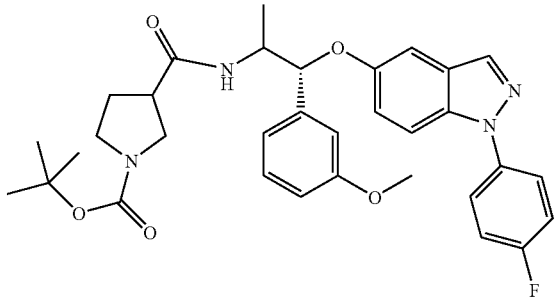

Prepared as described in Example 83 using (1R,2S)-1-(1-(4-fluorophenyl)-1H-indazol-5-yloxy)-1-(3-methoxyphenyl)propan-2-amine (6a, 50 mg, 0.13 mmol) and 1-(tert-butoxycarbonyl) yrrolidine-3-carboxylic acid (37 mg, 0.17 mmol). Yield 38 mg (50%).

APCI-MS: m/z 589.4 [MH$^+$]

$^{1}$H NMR (300 MHz, DMSO-$d_6$) δ 8.18-8.11 (m, 2H), 7.79-7.66 (m, 3H), 7.40 (t, J=8.8 Hz, 2H), 7.30-7.17 (m, 2H), 7.13-7.09 (m, 1H), 6.99-6.90 (m, 2H), 6.82 (dd, J=8.2, 2.4 Hz, 1H), 5.27 (d, J=4.9 Hz, 1H), 4.23-4.10 (m, 1H), 3.72 (s, 3H), 3.332.79 (m, 5H), 1.97-1.49 (m, 2H), 1.37 (s, 9H), 1.17 (d, J=6.8 Hz, 3H).

Example 302

2,2-difluoro-N-((1R,2S)-1-(1-(4-fluorophenyl)-1H-indazol-5-yloxy)-1-(3-methoxyphenyl)propan-2-yl)propanamide

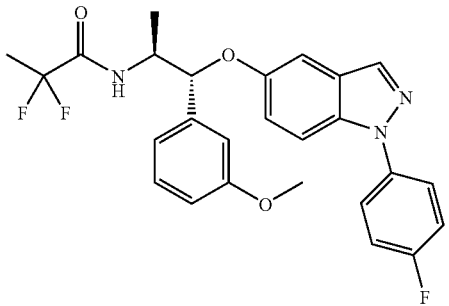

Ethyl 2,2-difluoropropanoate (400 µl) and (1R,2S)-1-(1-(4-fluorophenyl)-1H-indazol-5-yloxy)-1-(3-methoxyphenyl)propan-2-amine (6a, 135 mg, 0.34 mmol) was heated to 150° C. for 30 min. Then it was diluted with acetonitrile and purified by semiprep HPLC followed by flash chromatography on silica gel (n-heptane/ethyl acetate, 4:1) Yield 60 mg (36%).

APCI-MS: m/z 484.2 [MH$^+$]

$^{1}$H NMR (300 MHz, DMSO-$d_6$) δ 8.69 (d, J=8.7 Hz, 1H), 8.18 (d, J=0.8 Hz, 1H), 7.78-7.65 (m, 3H), 7.44-7.35 (m, 2H), 7.29-7.16 (m, 2H), 7.11 (d, J=2.1 Hz, 1H), 7.00-6.93 (m, 2H), 6.82 (dd, J=8.0, 2.3 Hz, 1H), 5.24 (d, J=7.0 Hz, 1H), 4.28-4.14 (m, 1 H), 3.72 (s, 3H), 1.52 (t, J=19.5 Hz, 3H), 1.31 (d, J=6.6 Hz, 3H).

Example 303

(R)-2-amino-N-((1R,2S)-1-(1-(4-fluorophenyl)-1H-indazol-5-yloxy)-1-(3-methoxyphenyl)propan-2-yl)propanamide trifluoroacetic acid salt

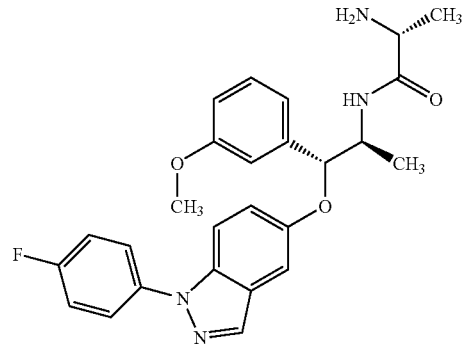

Tert-butyl (R)-1-((1R,2S)-1-(1-(4-fluorophenyl)-1H-indazol-5-yloxy)-1-(3-methoxyphenyl)propan-2-ylamino)-1-oxopropan-2-ylcarbamate (303a, 25 mg, 0.04 mmol) in DCM/TFA 1:1 (1 ml) was shaken for 1 h and then evaporated. Yield 25 mg (100%).

APCI-MS: m/z 463.1 [MH$^+$]

$^{1}$H NMR (400 MHz, DMSO-$d_6$) δ 8.63 (d, J=8.0 Hz, 1H), 8.17 (d, J=0.7 Hz, 1H), 8.02 (d, J=4.1 Hz, 3H), 7.78-7.68 (m, 3H), 7.44-7.37 (m, 2H), 7.30 (t, J=7.9 Hz, 1H) 7.23 (dd, J=9.1, 2.4 Hz, 1H), 7.07 (d, J=2.1 Hz, 1H), 6.98-6.84 (m, 3H), 5.37 (d, J=3.5 Hz, 1H), 4.20-4.11 (m, 1H), 3.81-3.71 (m, 4H), 1.33 (d, J=7.1 Hz, 3H), 1.18 (d, J=6.7 Hz, 3H).

tert-butyl (R)-1-((1R,2S)-1-(1-(4-fluorophenyl)-1H-indazol-5-yloxy)-1-(3-methoxyphenyl)propan-2-ylamino)-1-oxopropan-2-ylcarbamate (303a)

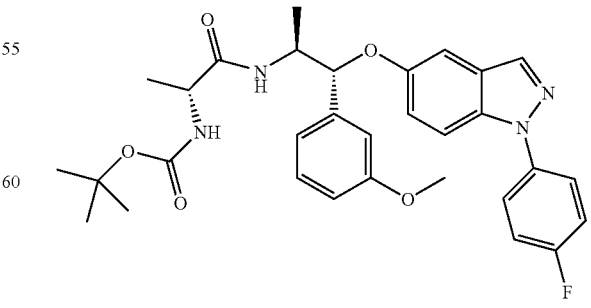

Prepared as described in Example 83 from (1R,2S)-1-(1-(4-fluorophenyl)-1H-indazol-5-yloxy)-1-(3-methoxyphenyl)propan-2-amine (6a, 50 mg, 0.13 mmol) and (R)-2(tert-butoxycarbonylamino)propanoic acid (32 mg, 0.17 mmol). Yield 25 mg (34%).

APCI-MS: m/z 563.4 [MH+]

Example 304

(R)—N-((1R,2S)-1-(1-(4-fluorophenyl)-1H-indazol-5-yloxy)-1-(3-methoxyphenyl) ropan-2-yl)pyrrolidine-2-carboxamide trifluoroacetic acid salt

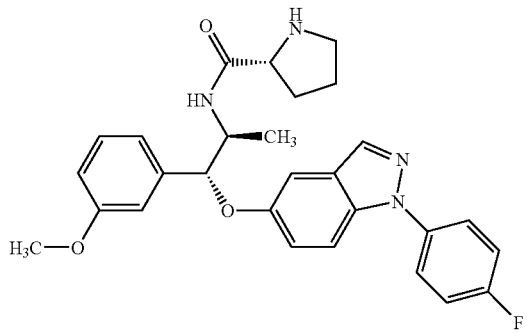

Prepared as described in Example 303 from (R)-tert-butyl 2-((1R,2S)-1-(1-(4-fluorophenyl)-1H-indazol-5-yloxy)-1-(3-methoxyphenyl)propan-2-ylcarbamoyl)pyrrolidine-1-carboxylate (304a, 31 mg, 0.05 mmol) Yield 32 mg (100%).

APCI-MS: m/z 489.1 [MH+]

$^1$H NMR (400 MHz, DMSO-d$_6$) δ 9.10 (s, 1H), 8.76 (d, J=8.1 Hz, 1H), 8.55 (s, 1H), 8.17 (d, J=0.7 Hz, 1H), 7.77-7.69 (m, 3H), 7.41 (t, J=8.8 Hz, 2H), 7.30 (t, J=8.0 Hz, 1H), 7.23 (dd, J=9.2, 2.3 Hz, 1H), 7.09 (d, J=2.3 Hz, 1H), 6.98-6.91 (m, 2H), 6.86 (dd, J=8.1, 2.1 Hz, 1H), 5.38 (d, J=4.1 Hz, 1H), 4.24-4.14 (m, 1H), 4.11-4.02 (m, 1H), 3.73 (s, 3H), 3.31-3.13 (m, 2H), 2.35-2.22 (m, 1H), 1.93-1.74 (m, 3H), 1.20 (d, J=6.7 Hz, 3H).

(R)-tert-butyl 2-((1R,2S)-1-(1-(4-fluorophenyl)-1H-indazol-5-yloxy)-1-(3-methoxyphenyl)propan-2-ylcarbamoyl)pyrrolidine-1-carboxylate (304a)

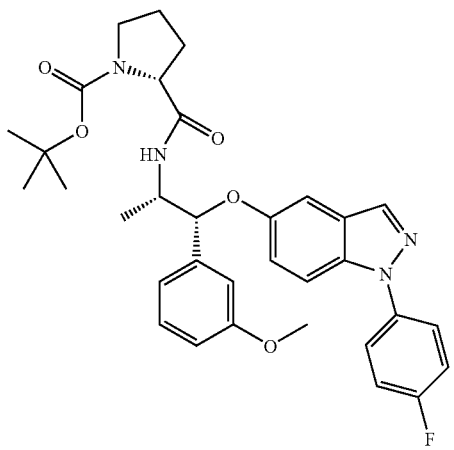

Prepared as described in Example 83 from (1R,2S)-1-(1-(4-fluorophenyl)-1H-indazol-5-yloxy)-1-(3-methoxyphe-nyl)propan-2-amine (6a, 50 mg, 0.13 mmol) and (R)-1-(tert-butoxycarbonyl) yrrolidine-2-carboxylic acid (37 mg, 0.17 mmol). Yield 31 mg (41%).

APCI-MS: m/z 589.5 [MH+]

Example 305

N-((2S,3S)-4-(2,4-difluorophenoxy)-3-(1-(4-fluorophenyl)-1H-indazol-5-yloxy)butan-2-yl)-2,2,2-trifluoroacetamide

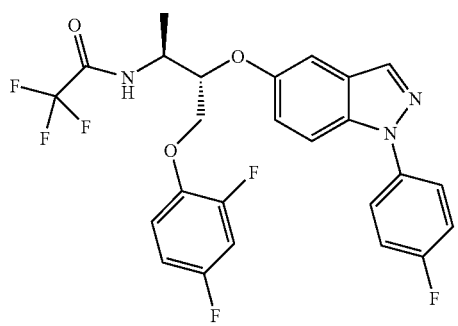

Prepared as described in Example 1 using (2S,3S)-4-(2,4-difluorophenoxy)-3-(1-(4-fluorophenyl)-1H-indazol-5-yloxy)butan-2-amine (90 mg, 0.21 mmol) and 2,2,2-trifluoroacetic anhydride (0.119 mL, 0.84 mmol). Yield 71 mg (64%)

APCI-MS: m/z 534.3 [MH+]

$^1$H-NMR (400 MHz, CD$_3$OD): δ 8.13 (d, J=0.7 Hz, 1H), 7.71 (m, 2H), 7.64 (d, J=9.0 Hz, 1H), 7.45 (d, J=2.3 Hz, 1H), 7.32 (m, 2H), 7.25 (dd, J$_1$=2.3 Hz, J$_2$=9.1 Hz, 1H), 7.09 (m, 1H), 6.97 (m, 1H), 6.85 (m, 1H), 4.79 (m, 1H), 4.51 (p, J=6.5 Hz, 1H), 4.34 (dd, J$_1$=0.6 Hz, J$_2$=3.9 Hz, 1H), 4.26 (dd, J$_1$=10.6 Hz, J$_2$=5.4 Hz, 1H), 1.42 (d, J=7.1 Hz, 3H).

(2S,3S)-4-(2,4-difluorophenoxy)-3-(1-(4-fluorophenyl)-1H-indazol-5-yloxy)butan-2 -amine (305a)

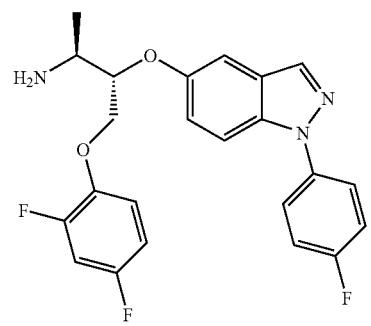

Prepared as described in Example 1a from (2S,3S)-4-(2,4-difluorophenoxy)-3-hydroxybutan-2-aminium chloride (290 mg, 1.14 mmol) and 1-(4-fluorophenyl)-5-iodo-1H-indazole (464 mg, 1.37 mmol). Yield: 90 mg (18%).

$^1$H-NMR (400 MHz, CD$_2$Cl$_2$): δ 8.07 (s, 1H), 7.68 (m, 2H), 7.60 (d, J=9.0 Hz, 1H), 7.37 (broad s, 1H), 7.28-7.18 (m, 3H), 6.97 (m, 1H), 6.87 (m, 1H), 6.79 (m, 1H), 4.45 (broad s, 1H), 4.33 (m, 2H), 3.48 (broad s, 1H), 1.27 (d, J=6.0 Hz, 3H).

(2S,3S)-4-(2,4-difluorophenoxy)-3-hydroxybutan-2-aminium chloride (305b)

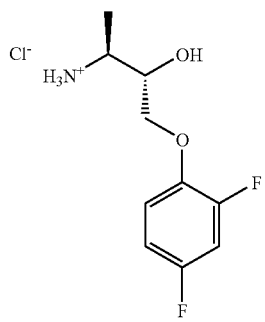

Benzyl (2S,3S)-4-(2,4-difluorophenoxy)-3-hydroxybutan-2-ylcarbamate (426 mg, 1.21 mmol) in ethanol (20 mL) was hydrogenated over Pd (10% on carbon) (40.0 mg) at r.t. and atmospheric pressure overnight. The mixture was filtered through celite, evaporated, dissolved in ethanol and filtered through a syringe filter. On evaporation a white solid was obtained. This was dissolved in ethanol (4 mL) and diethyl ether (6 mL) and 1M HCl in diethyl ether was added (1.5 mL) under stirring. Evaporation, coevaporation from dichloromethane/diethylether gave the title compound as a solid, (290 mg, 94%).

$^1$H-NMR (400 MHz, CD$_3$OD): δ 7.16 (m, 1H), 7.01 (m, 1H), 6.90 (m, 1H), 4.18 -4.01 (m, 3H), 3.58 (m, 1H), 1.32 (d, J=6.9 Hz, 3H).

Benzyl (2S,3S)-4-(2,4-difluorophenoxy)-3-hydroxybutan-2-ylcarbamate (305c)

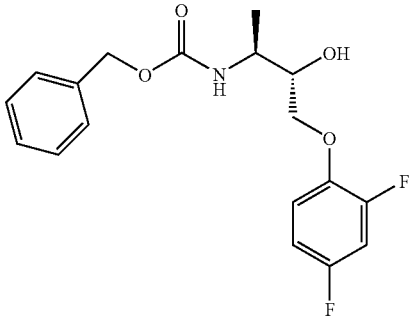

Prepared as described in Example 6c from (S)-benzyl 4-(2,4-difluorophenoxy)-3-oxobutan-2-ylcarbamate (657 mg, 1.88 mmol). Yield: 426 mg (64% yield)

$^1$H-NMR (400 MHz, CD$_2$Cl$_2$): δ 7.39-7.28 (m, 5H), 7.00-6.78 (m, 3H), 5.18 (broad s, 1H), 5.09 (s, 2H), 4.11-3.88 (m, 4H), 1.22 (d, J=6.9 Hz, 3H).

(S)-benzyl 4-(2,4-difluorophenoxy)-3-oxobutan-2-ylcarbamate (305d)

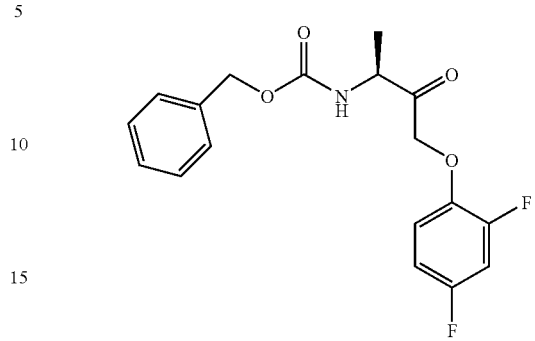

A mixture of (S)-benzyl 4-bromo-3-oxobutan-2-ylcarbamate (prepared according to R. V. Hoffman et al., J. Org. Chem. 2001, 66, 5790-5795) (600 mg, 2.00 mmol), 2,4-difluorophenol (312 mg, 2.40 mmol) and potassium fluoride (380 mg, 6.54 mmol) in DMF (4 mL) was stirred at r.t. for 17 h. Water (15 mL) and dichloromethane (3 mL) were added and the mixture was stirred for 30 min. The mixture was added to a phase separator. The water phase was once more stirred with dichloromethane (3 mL), and added to the phase separator. The organic phases were concentrated and the residue was purified by flash chromatography on silica gel (cyclohexane/ethyl acetate 3/1) to give the title compound as a white solid (658 mg, 94% yield).

$^1$H-NMR (400 MHz, CD$_2$Cl$_2$): δ 7.40-7.28 (m, 5H), 6.95-6.86 (m, 2H), 6.81 (m, 1H), 5.40 (broad s, 1H), 5.10 (s 2H), 4.81 (m, 2H), 4.60 (p, J=7.1 Hz, 1H), 1.41 (d, J=7.2 Hz, 3H).

Example 306

N-((1R,2S)-1-(2,3-dihydrobenzofuran-6-yl)-1-(1-(4-fluorophenyl)-1H-indazol-5-yloxy)propan-2-yl)-2,2-difluoropropanamide

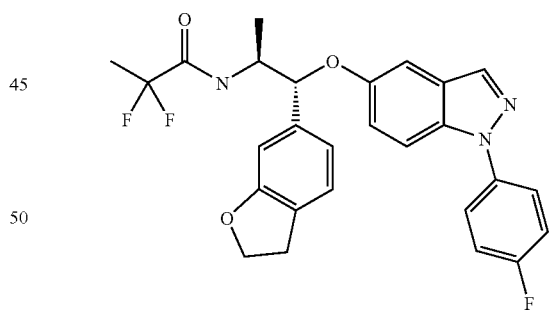

To a solution of (1R,2S)-1-(2,3-dihydrobenzofuran-6-yl)-1-(1-(4-fluorophenyl)-1H- ndazol-5-yloxy)propan-2-amine (306a, 85 mg, 0.21 mmol) in NMP (1 mL) was added a solution of 2,2-difluoropropanoic acid (37 mg, 0.34 mmol), 2-(3H-[1,2,3]triazolo[4,5-b]pyridin-3-yl)-1,1 3,3-tetramethylisouronium hexafluorophosphate(V) (0.128 g, 340 nmol), and N-ethyl-N-isopropylpropan-2-amine (140 µL, 840 µmol) in NMP (2 mL). The mixture was stirred at r.t. for 2 h. Then aq. HCl (1N, 30 mL) was added, and the mixture was extracted with ethyl acetate (3×45 ml). The organic phase was dried and purified by flash chromatography on silica gel with ethyl acetane/n-heptane (2:1) to give 65 mg (62%) of the title compound.

APCI-MS: m/z 496.3 [MH+]

$^1$H NMR (400 MHz, DMSO-d$_6$) ∂ 8.67 (d, J=8.1 Hz, 1H), 8.18 (d, J=0.7 Hz, 1), 7.74 (dd, J=9.0, 4.8 Hz, 2H), 7.69 (d, J=9.2 Hz, 1H), 7.40 (t, J=8.8 Hz, 2H), 7.18 m, 2H), 7.09 (d, J=2.3 Hz, 1H), 6.86 (d, J=7.6 Hz, 1H), 6.76 (s, 1H), 5.21 (d, J=6.7 Hz, H), 4.47 (dd, J=15.1, 8.9 Hz, 2H), 4.17 (m1H), 3.11 (t, J=8.7 Hz, 2H), 1.63-1.47 (m, 3H), 1.29 (d, J=6.7 Hz, 3H).

(1R,2S)-1-(2,3-Dihydrobenzofuran-6-yl)-1-(1-(4-fluorophenyl)-1H-indazol-5yloxy)propan-2-amine (306a)

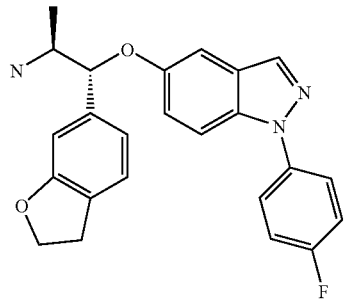

A stirred mixture of (1R,2R)-2-amino-1-(2,3-dihydrobenzofuran-6-yl)propan-1-ol (306b, 180 mg, 0.93 mmol), 1-(4-fluorophenyl)-5-iodo-1H-indazole (346 mg, 1.02 mmol), and cesium carbonate (0.910 g, 2.79 mmol) in butyronitrile (2 mL) was degassed for 5 min. Then copper(I) iodide (35 mg, 190 μmol) was added. The tube was sealed and heated at 105° C. for 12 h. The solvent was removed, the residue was taken in dichloromethane (20 mL), and filtered on a prepact silica column (10 g), washed with dichloromethane (50 ml) followed by ethyl acetate (50 ml). Than the product was eluted with a mixture of 0.35M ammmonia solution in ethylacetate/methanol (5:95) (100 ml) to give 80 mg (22%) of subtitle compound.

APCI-MS: m/z 404 [MH+]

(1R,2R)-2-Amino-1-(2,3-dihydrobenzofuran-6-yl)propan-1-ol (306b)

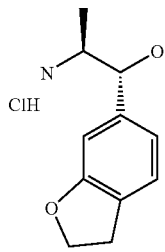

t-Butyl (1R,2R)-1-(2,3-dihydrobenzofuran-6-yl)-1-hydroxypropan-2-ylcarbamate (1.58 g, 5.39 mmol) was stirred in a solution of HCl in EtOAc (1M, 20 ml) at 60° C. for 2 h. After cooling the solid precipitate was filtered and dried to afford the subtitle compound as hydrochloride (1.22 g, 98%).

APCI-MS: m/z 194 [MH+]

$^1$H NMR (400 MHz, dmso) ∂ 7.98 (s, 3H), 7.20 (d, J=7.6 Hz, 1H), 6.80 (d, J=7. Hz, 1H), 6.75 (s, 1H), 5.97 (d, J=4.2 Hz, 1H), 4.83 (t, J=3.5 Hz, 2H), 4.52 (t, J=8.7 Hz, 1H), 3.36 (m, 1H), 3.15 (t, J=8.7 Hz, 2H), 0.93 (d, J=6.7 Hz, 3H).

t-Butyl (1R,2R)-1-(2,3-dihydrobenzofuran-6-yl)-1-hydroxypropan-2-ylcarbamate (306c)

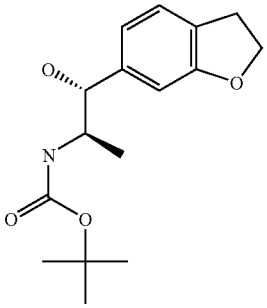

(R)-t-butyl 1-(2,3-dihydrobenzofuran-6-yl)-1-oxopropan-2-ylcarbamate (306d, 2.21 g, 7.59 mmol) was dissolved in propan-2-ol (6.35 mL, 83.4 mmol) and toluene (10 mL). Al(OiPr)$_3$ (0.310 g, 1.52 mmol) was added, and the reaction vessel was capped and flushed with argon. The mixture was stirred at 50° C. overnight. Then another portion of Al(OiPr)$_3$ (330 mg) was added, and stirring was continued for 5 h. The mixture was cooled to r.t., and partitioned between aq. HCl (1N, 25 ml) and ethyl acetate (80 ml). The organic layer was separated and dried. The solvent was removed in vacuo and purified by flash chromatography on silica gel with n-heptane/ethyl acetate (6:4) to give 1.58 g (71%) of subtitle compound.

APCI-MS: m/z 194.2 [MH+—BOC]

(R)-t-Butyl 1-(2,3-dihydrobenzofuran-6-yl)-1-oxo-propan-2-ylcarbamate (306d)

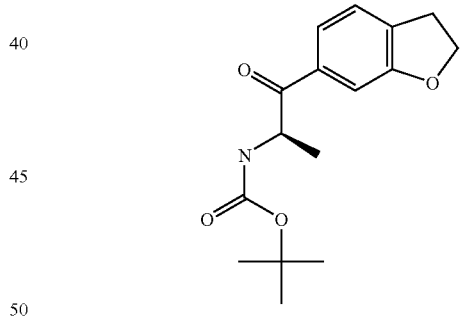

Magnesium (711 mg, 29.3 mmol) was placed in a screw-cap reaction tube, and a solution of 6-bromo-2,3-dihydrobenzofuran (4.16 g, 20.9 mmol) in tetrahydrofuran (30 mL) was added, followed by a small crystal of iodine. The tube was sealed and flushed with argon. The mixture was heated at 60° C. for 1 h, and then the reaction mixture was allowed to cool to r.t. A slurry of (S)-tert-butyl 1-(methoxy(methyl)amino)-1-oxopropan-2-ylcarbamate (4.85 g, 20.9 mmol) in THF (20 ml) was cooled on a acetone/ice bath to −10° C., and a solution isopropylmagnesium chloride (2 M in THF, 10.5 mL, 21 mmol) was slowly added. The mixture was stirred for 15 min, the cooling bath was removed. Stirring was continued for 10 min. Then the preformed Grignard reagent was added in small portions with stirring. After the addition the mixture was allowed to reach r.t. and stirred for 2 h. The solvent was evaporated, and the mixture was poured into an ice-cold ethyl acetate (150 ml) and aq. HCl (1M, 35 ml) mixture. The organic layer was separated, washed with water and brine, filtered, and evaporated. The product was purified by flash chromatography on silica with ethyl acetate/n-heptane (3:7) to give 2.21 g (36%) of the subtitle compound.

APCI-MS: m/z 192.2 [MH$^+$—BOC]

Example 307

N-((1R,2S)-1-(2,3-dihydrobenzofuran-6-yl)-1-(1-(4-fluorophenyl)-1H-indazol-5-yloxy)propan-2-yl)-2,2,2-trifluoroacetamide

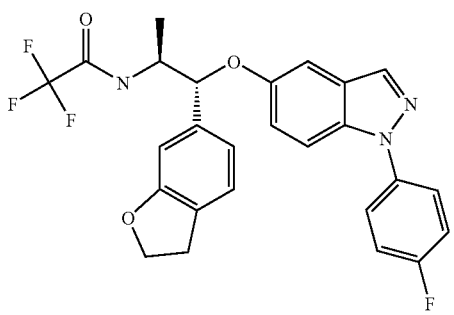

To a solution of (1R,2S)-1-(2,3-dihydrobenzofuran-6-yl)-1-(1-(4-fluorophenyl)-1H ndazol-5-yloxy)propan-2-amine (44 mg, 11 μmol) in THF (1.5 mL) was added DIPEA (36 μL, 220 μmol), and the mixture was stirred for 20 min. Then a solution of trifluoroacetic anhydride (31 μL, 220 μmol) in THF (0.6 ml) was added in 100 μl portions. The mixture was stirred for 2 h. The solvent was removed, and the row product was partitioned between aq. HCl (1N) and ethyl acetate. The organic layer was dried and submitted to flash chromatography on silica gel with ethyl acetate/n-heptane (2:3) to give 40 mg (73%) of the title compound.

APCI-MS: m/z 500 [MH$^+$]

$^1$H NMR (400 MHz, dmso) δ 9.50 (d, J=8.5 Hz, 1H), 8.18 (s, 1H), 7.74 (m, 2H) 7.69 (d, J=9.2 Hz, 1H), 7.40 (dd, J=15.4, 2.3 Hz, 2H), 7.22-7.15 (m, 2H), 7.10 (d, J=2.1 Hz, 1H), 6.86 (d, J=7.6 Hz, 1H), 6.76 (s, 1H), 5.24 (d, J=6.2 Hz, 2H), 4.48 (td, J=8.6, 5.6 Hz, 2H), 4.20 (dd, J=14.7, 6.7 Hz, 1H), 3.11 (t, J=8.7 Hz, 2H), 1.31 (d, J=6.7 Hz, 3H)

Example 308

2,2,2-trifluoro-N-((1R,2S)-1-(1-(4-fluorophenyl)-1H-indazol-5-yloxy)-1-(3methoxy-4-(methylthio)phenyl)propan-2-yl)acetamide

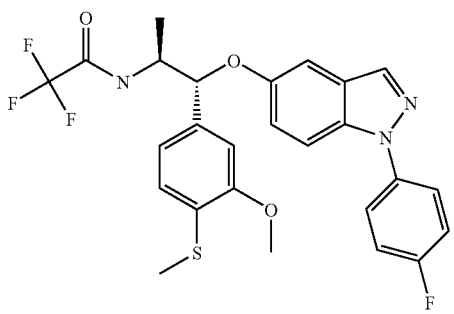

To a stirred solution of (1R,2S)-1-(1-(4-fluorophenyl)-1H-indazol-5-yloxy)-1-(3- ethoxy-4-(methylthio)phenyl)propan-2-amine (308a, 32 mg, 70 μmol) in THF (2 mL) was added N-ethyl-N-isopropylpropan 2-amine (12 μL, 70 μmol), and the mixture was stirred for 20 min. Then trifluoroacetic anhydride (21 μL, 150 μmol) was added, and the mixture was stirred for 2 h. The solvent was removed, and the crude product was partitioned between aq. HCl (1N) and ethyl acetate. The organic layer was dried and purified by HPLC go afford 6 mg (15%) of the title compound.

APCI-MS: m/z 534.1 [MH$^+$]

$^1$H NMR (400 MHz, DMSO-d$_6$) δ 9.49 (d, J=8.5 Hz, 1H), 8.18 (d, J=0.7 Hz, 1H), 7.74 (m 2H), 7.69 (d, J=9.0 Hz, 1H), 7.40 (dd, J=21.1, 3.6 Hz, 2H), 7.20 (dd, J=9.1, 2.4 Hz, 1H), 7.15 (d, J=2.1 Hz, 1H), 7.08 (d, J=8.5 Hz, 1H), 6.98 (m, 2H), 5.26 (d, J=6.4 Hz, 1H), 4.27 (dd, J=14.9, 6.7 Hz, 1H), 3.80 (s, 3H), 2.33 (s, 3H), 1.34 (d, J=6.7 Hz, 3H).

(1R,2S)-1-(1-(4-fluorophenyl)-1H-indazol-5-yloxy)-1-(3-methoxy-4-(methylthio)phenyl)propan-2-amine (308a)

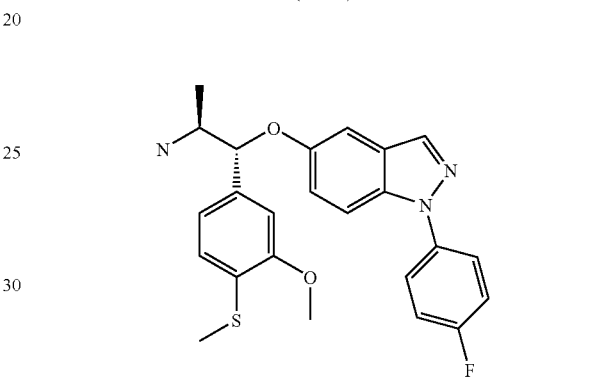

A mixture of (1R,2S)-2-amino-1-(3-methoxy-4-(methylthio)phenyl)propan-1-ol (308b, 17 g, 70 μmol), 1-(4-fluorophenyl)-5-iodo-1H-indazole (30 mg, 90 μmol), and cesium carbonate (73 mg, 220 μmol) in butyronitrile (1 mL) was stirred for 5 min. Then copper(I) iodide (19 μg, 10 μmmol) was added, and the mixture was stirred at 105° C. for 3 h. After cooling to r.t. the solvent was evaporated under reduced pressure, and the mixture was partitioned between aq. HCl (1N) and ethyl acetate. The layers were separated, the water layer was extracted with ethyl acetate. The combined organic extracts were dried, the solvent was removed in vacuo The residue was purified by HPLC to give 7 mg (21) of the title compound.

APCI-MS: m/z 438.1 [MH$^+$]

(1R,2R)-2-amino-1-(3-methoxy-4-(methylthio)phenyl)propan-1-ol (308b)

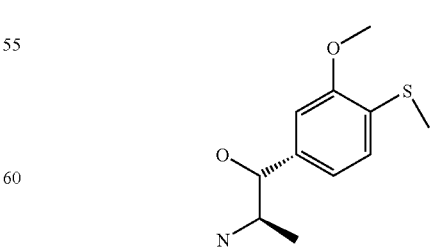

t-Butyl (R)-1-hydroxy-1-(3-methoxy-4-(methylthio)phenyl)propan-2-ylcarbamate (308c, 44 μg, 130 μmol) was dissolved in a solution of HC in ethyl acetate (1M, 5 mL) and stirred at 60° C. for 2 h. The solvent was evaporated, and the diastereomers were separated by HPLC (XBridge column). The subtitle compound is the first eluted product, 17 mg (55%).

APCI-MS: m/z 228.1 [MH⁺]

t-Butyl (2R)-1-hydroxy-1-(3-methoxy-4-(methylthio)phenyl)propan-2-ylcarbamate (308c)

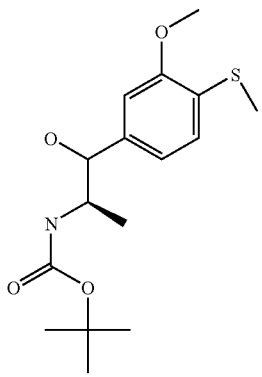

To a stirred solution of (R)-t-butyl 1-(3-methoxy-4-(methylthio)phenyl)-1-oxopropan-2-ylcarbamate (308d, 55 µg, 170 µmol) in THF (2 mL) at r.t. was added sodium tetrahydroborate (48 µg, 1.27 mmol) in small portions, and the mixture was stirred for 3 h.

The mixture was quenched with aq. 1N HCl, and extracted with ethyl acetate. The organic layers were dried, the solvent was removed and the residue was purified by HPLC to give 44 mg (80%) of the subtitle compound.

APCI-MS: m/z 227.4 [MH⁺—BOC]

(R)-t-Butyl 1-(3-methoxy-4-(methylthio)phenyl)-1-oxopropan-2-ylcarbamate (308d)

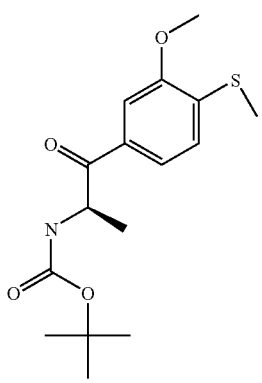

Magnesium (17 µg, 0.69 mmol) was placed in a screwcap reaction tube, and a solution of (4-bromo-2-methoxyphenyl)(methyl)sulfane (308e, 100 µg, 0.43 mmol) in tetrahydrofuran (1 mL) was added, followed by a small crystal of iodine. The tube was sealed and flushed with argon. The mixture was stirred at 60° C. overnight. After cooling (S)-tert-butyl 1-(methoxy(methyl)amino)-1-oxopropan-2-ylcarbamate (35 µg, 150 µmol) was added as a solid, and the mixture was stirred at r.t. for 1 h. Then the solvent was evaporated, the mixture was partitioned between aq. HCl (1N) and ethyl acetate. The organic layer was separated and dried. The product was isolated by HPLC to afford 10 mg (10%).

APCI-MS: m/z 226.2 [MH⁺—BOC]

(4-bromo-2-methoxyphenyl)(methyl)sulfane (308e)

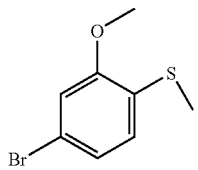

To a solution of 4-bromo-2-methoxybenzenethiol (1.21 g, 5.52 mmol) in DMF (5 mL) was added potassium carbonate (2.29 g, 16.5 mmol) under argon. The resulting mixture was stirred for 10 min, and then iodomethane (3.44 mL, 55.2 mmol) was slowly added over 2 min. The resulting mixture was stirred at r.t. overnight. Then the reacxtion mixture was pured into water (75 ml), and extracted with ethyl acetate. The organic layer was dried and the solvent was evaporated, the residue was purified by flash chromatography on silica gel with n-heptane/ethyl acetate (7:3) to give 920 mg (72%) of the subtitle compound.

GC/MS: 234.1

4-Bromo-2-methoxybenzenethiol (308f)

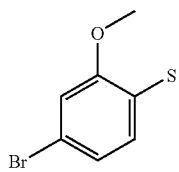

To a stirred solution of potassium carbonate (308 g, 2.44 g, 17.6 mmol) in MeOH (20 mL) was added S4-bromo-2-methoxyphenyl dimethylcarbamothioate (0.64 g, 2.21 mmol). The mixture was heated with reflux for 4 h, then cooled on ice bath. Water (20 ml) was added, and the pH was adjusted to neutral by addition of with aq. HCl (3N). The mixture was extracted with DCM, the organic layers were dried, filtered, and concentrated under reduced pressure to give a light brown liquid which was characterized with GC/MS and used without further purification, 440 mg (91%).

GC/MS: 219.1

S-4-bromo-2-methoxyphenyl dimethylcarbamothioate (308g)

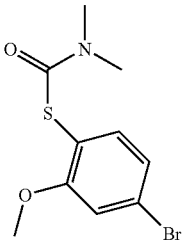

O-4-Bromo-2-methoxyphenyl dimethylcarbamothioate (503 mg, 1.73 mmol) was suspended in N,N-dimethylaniline (2.5 mL), and the reaction mixture was heated in a microwave (240° C., 300 W) for 75 min. The mixture was then diluted with aq. HCl (3N, 20 mL) and extracted 3 times with ether (30 ml). The organic layers were combined, dried, filtered, and purified by HPLC to afford 330 mg (66%) of the subtitle compound.

APCI-MS: m/z 291.8 [MH$^+$]

O-4-bromo-2-methoxyphenyl dimethylcarbamothioate (308h)

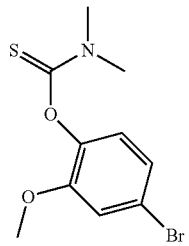

A mixture of 4-bromoguaiacol (2.05 g, 10.1 mmol) and 1,4-diazabicyclo(2.2.2)octane (1.42 g, 12.6 mmol) in NMP (24 mL) was heated at 50° C. to give a dark-yellow solution. A solution of dimethylthiocarbamoyl chloride (1.37 g, 11.1 mmol) in NMP (2 ml) was added dropwise to the previous solution over 1-2 min. Some precipitated has formed during the addition. The mixture was stirred at 50° C. for 3 h, and then water (25 ml) was added over 5 min at 50° C. The mixture was stirred overnight at r.t., and the precipitate was isolated by filtration, washed twice with water, and dried in vacuo at 50° C. to yield a pale creamed-coloured crystalline solid, 2.11 g (72%).

APCI-MS: m/z 291.8 [MH$^+$]

Example 309

Human Glucocorticoid Receptor (GR) Assay

The assay is based on a commercial kit from Panvera/Invitrogen (Part number P2893). The assay technology is fluorescence polarization. The kit utilises recombinant human GR (Panvera, Part number P2812), a Fluoromone™ labelled tracer (GS Red, Panvera, Part number P2894) and a Stabilizing Peptide 10× (Panvera, Part number P2815). The GR and Stabilizing Peptide reagents are stored at −70° C. while the GS Red is stored at −20° C. Also included in the kit are 1M DTT (Panvera, Part number P2325, stored at −20° C.) and GR Screening buffer 10× (Panvera, Part number P2814, stored at −70° C. initially but once thawed stored at r.t.). Avoid repeated freeze/thaws for all reagents. The GR Screening buffer 10× comprises 100 mM potassium phosphate, 200 mM sodium molybdate, 1 mM EDTA and 20% DMSO.

Test compounds (1 μL) and controls (1 μL) in 100% DMSO were added to black polystyrene 384-well plates (Greiner low volume black flat-bottom, part number 784076). 0% control was 100% DMSO and 100% control was 10M Dexamethasone. Background solution (8 μL; assay buffer 10×, Stabilizing Peptide, DTT and ice cold MQ water) was added to the background wells. GS Red solution (7 μL; assay buffer 10×, Stabilizing Peptide, DTT, GS Red and ice cold water) was added to all wells except background wells. GR solution (7 μL; assay buffer 10×, Stabilizing Peptide, DTT, GR and ice cold water) was added to all wells. The plate was sealed and incubated in a dark at r.t. for 2 h. The plate was read in an Analyst plate reader (LJL Biosystems/Molecular Devices Corporation) or other similar plate reader capable of recording fluorescence polarization (excitation wavelength 530 nm, emission wavelength 590 nM and a dichroic mirror at 561 nm). The IC$_{50}$ values were calculated using XLfit model 205.

| Example | GRhu FL__FP__v2 Mean IC50 (nM) |
|---|---|
| 1 | 2.3 |
| 2 | 2.7 |
| 3 | 3.2 |
| 4 | 5.9 |
| 5 | 2.1 |
| 6 | 1.8 |
| 7 | 2 |
| 8 | 2.3 |
| 9 | 2 |
| 10 | 2.4 |
| 11 | 2.1 |
| 12 | 2.8 |
| 13 | 5.1 |
| 14 | 3.4 |
| 15 | 6.8 |
| 16 | 2.4 |
| 17 | 12 |
| 18 | 2.8 |
| 19 | 5.2 |
| 20 | 9 |
| 21 | 3.2 |
| 22 | 4.7 |
| 23 | 3.2 |
| 24 | 3.2 |
| 25 | 11 |
| 26 | 5.9 |
| 27 | 3.2 |
| 28 | 25 |
| 29 | 6.4 |
| 30 | 6.6 |
| 31 | 2.8 |
| 32 | 7.7 |
| 33 | 18 |
| 34 | 2.4 |
| 35 | 2.1 |
| 36 | 10 |
| 37 | 2.4 |
| 38 | 2.4 |
| 39 | 6.4 |
| 40 | 3.4 |
| 41 | 2.6 |
| 42 | 3 |
| 43 | 2.2 |
| 44 | 2.7 |
| 45 | 2.6 |
| 46 | 3.4 |
| 47 | 2.5 |
| 48 | 2.9 |
| 49 | 2.8 |
| 50 | 2.9 |
| 51 | 4.3 |
| 52 | 3.1 |
| 53 | 3.5 |
| 54 | 2.9 |
| 55 | 3.3 |
| 56 | 4.4 |
| 57 | 4.1 |
| 58 | 2.7 |
| 59 | 3.3 |
| 60 | 3.3 |
| 61 | 3.3 |
| 62 | 3.5 |
| 63 | 4.4 |
| 64 | 3.9 |
| 65 | 3.8 |
| 66 | 4.2 |
| 67 | 4.1 |
| 68 | 1.7 |
| 69 | 76 |

-continued

| Example | GRhu FL_FP_v2 Mean IC50 (nM) |
|---|---|
| 70 | 89 |
| 71 | 4.6 |
| 72 | 3.7 |
| 73 | 5.1 |
| 74 | 3.7 |
| 75 | 5.3 |
| 76 | 2.2 |
| 77 | 2.6 |
| 78 | 3.2 |
| 79 | 2.6 |
| 80 | 3.7 |
| 81 | 3.5 |
| 82 | 5.3 |
| 83 | 5.8 |
| 84 | 2.3 |
| 85 | 2.1 |
| 86 | 3.8 |
| 87 | 3.4 |
| 88 | 3.2 |
| 89 | 4.4 |
| 90 | 4.2 |
| 91 | 5.2 |
| 92 | 3.8 |
| 93 | 3.7 |
| 94 | 3.1 |
| 95 | 3.4 |
| 96 | 3.5 |
| 97 | 3.3 |
| 98 | 3.4 |
| 99 | 3.8 |
| 100 | 9.2 |
| 101 | 15 |
| 102 | 2.5 |
| 103 | 2.6 |
| 104 | 3.6 |
| 105 | 3.2 |
| 106 | 3.7 |
| 107 | 4 |
| 108 | 4.9 |
| 109 | 23 |
| 110 | 29 |
| 111 | 15 |
| 112 | 21 |
| 113 | 24 |
| 114 | 3.2 |
| 115 | 3.8 |
| 116 | 7.7 |
| 117 | 5.2 |
| 118 | 2.9 |
| 119 | 3.1 |
| 120 | 210 |
| 121 | 2.8 |
| 122 | 2.1 |
| 123 | 4.2 |
| 124 | 2.7 |
| 125 | 6.4 |
| 126 | 2.9 |
| 127 | 4 |
| 128 | 3.9 |
| 129 | 11 |
| 130 | 2.5 |
| 131 | 4 |
| 132 | 4.1 |
| 133 | 3.3 |
| 134 | 3.6 |
| 135 | 3.1 |
| 136 | 3 |
| 137 | 360 |
| 138 | 3.5 |
| 139 | 4.1 |
| 140 | 3.6 |
| 141 | 3.3 |
| 142 | 5.6 |
| 143 | 23 |
| 144 | 3 |
| 145 | 5.5 |

-continued

| Example | GRhu FL_FP_v2 Mean IC50 (nM) |
|---|---|
| 146 | 78 |
| 147D1E1 | 97 |
| 147D1E2 | 24 |
| 147D2E1 | 7.4 |
| 147D2E2 | 12 |
| 148 | 280 |
| 149 | 5.5 |
| 150 | 4.6 |
| 151 | 3.2 |
| 152 | 3.6 |
| 153 | 3.6 |
| 154 | 4.7 |
| 155 | 5 |
| 156 | 4.2 |
| 157 | 5.3 |
| 158 | 3.4 |
| 159 | 4.2 |
| 160 | 4.1 |
| 161 | 8.5 |
| 162 | 14 |
| 163 | 16 |
| 164 | 4.2 |
| 165 | 6.4 |
| 166 | 6.9 |
| 167 | 8.6 |
| 168 | 6.2 |
| 169 | 8.1 |
| 170 | 7.1 |
| 171 | 5.6 |
| 172 | 4.3 |
| 173 | 4.6 |
| 174 | 4.1 |
| 175 | 4.3 |
| 176 | 4.9 |
| 177 | 3.9 |
| 178 | 3.9 |
| 179 | 3.7 |
| 180 | 6.8 |
| 181 | 3.2 |
| 182 | 5.5 |
| 183 | 4.6 |
| 184 | 5.1 |
| 185 | 5.5 |
| 186 | 6.6 |
| 187 | 4.5 |
| 188 | 7.3 |
| 189 | 7.8 |
| 190 | 4.5 |
| 191 | 5.9 |
| 192 | 4.3 |
| 193 | 6.5 |
| 194 | 3.9 |
| 195 | 3.3 |
| 196 | 6.2 |
| 197 | 4.9 |
| 198 | 3.8 |
| 199 | 7.4 |
| 200 | 4.6 |
| 201 | 5.9 |
| 202 | 5.3 |
| 203 | 5.4 |
| 204 | 6.7 |
| 205 | 6.6 |
| 206 | 7.5 |
| 207 | 8.8 |
| 208 | 8.2 |
| 209 | 4.1 |
| 210 | 5.2 |
| 211 | 3 |
| 212 | 5.2 |
| 213 | 4.4 |
| 214 | 4.5 |
| 215 | 4.4 |
| 216 | 4.7 |
| 217 | 3.9 |
| 218 | 3.3 |

-continued

| Example | GRhu FL__FP__v2 Mean IC50 (nM) |
|---|---|
| 219 | 2.8 |
| 220 | 4.2 |
| 221 | 4.4 |
| 222 | 3.5 |
| 223 | 3.9 |
| 224 | 5.7 |
| 225 | 4.8 |
| 226 | 7.2 |
| 227 | 3.1 |
| 228 | 8 |
| 229 | 5.5 |
| 230 | 4.8 |
| 231 | 5.1 |
| 232 | 5.4 |
| 233 | 6.1 |
| 234 | 6.4 |
| 235 | 5.4 |
| 236 | 7.2 |
| 237 | 8.4 |
| 238 | 6.8 |
| 239 | 9 |
| 240 | 5.9 |
| 241 | 4.9 |
| 242 | 5.5 |
| 243 | 5.5 |
| 244 | 8.3 |
| 245 | 5.5 |
| 246 | 6 |
| 247 | 4.4 |
| 248 | 4.8 |
| 249 | 5 |
| 250 | 6.9 |
| 251 | 5.3 |
| 252 | 4.7 |
| 253 | 7.5 |
| 254 | 8.5 |
| 255 | 5.1 |
| 256 | 5.3 |
| 257 | 13 |
| 258 | 4.4 |
| 259 | 5.3 |
| 260 | 14 |
| 261 | 5.7 |
| 262 | 4.5 |
| 263 | 4.2 |
| 264 | 6.5 |
| 265 | 25 |
| 266 | 2.9 |
| 267 | 3.7 |
| 268 | 3.1 |
| 269 | 12 |
| 270 | 8.1 |
| 271 | 21 |
| 272 | 4.3 |
| 273 | 7.9 |
| 274 | 3.9 |

-continued

| Example | GRhu FL__FP__v2 Mean IC50 (nM) |
|---|---|
| 275 | 4 |
| 276 | 12 |
| 277 | 4.7 |
| 278 | 3.4 |
| 279 | 3.8 |
| 280 | 3.6 |
| 281 | 3.8 |
| 282 | 2.4 |
| 283 | 4.7 |
| 284 | 22 |
| 285 | 3.5 |
| 286 | 4.7 |
| 287 | 4.3 |
| 288 | 5 |
| 289 | 3.9 |
| 290 | 3.1 |
| 291 | 6.4 |
| 292 | 5.7 |
| 293 | 4.4 |
| 294 | 4.1 |
| 295 | 5.7 |
| 296 | 4 |
| 297 | 8.6 |
| 298 | 15 |
| 299 | 3.1 |
| 300 | 2.4 |
| 301 | 5.2 |
| 302 | 3.2 |
| 303 | 5 |
| 304 | 7.5 |
| 305 | 8.3 |
| 306 | 2.5 |
| 307 | 4.8 |
| 308 | 6.9 |

The invention claimed is:

1. 2,2,2-Trifluoro-N-[(1R,2S)-1-[1-(4-fluorophenyl) indazol-5-yl]oxy-1-(3-methoxyphenyl)propan-2-yl]acetamide, or a pharmaceutically acceptable salt thereof.

2. A pharmaceutical composition comprising a compound or a pharmaceutically acceptable salt thereof as claimed in claim 1, and a pharmaceutically acceptable adjuvant, diluent or carrier.

3. A method of treating asthma, which comprises administering to a mammal in need of such treatment an effective amount of a compound or a pharmaceutically acceptable salt thereof as claimed in claim 1.

4. A method of treating COPD, which comprises administering to a mammal in need of such treatment an effective amount of a compound or a pharmaceutically acceptable salt thereof as claimed in claim 1.

* * * * *

UNITED STATES PATENT AND TRADEMARK OFFICE
CERTIFICATE OF CORRECTION

PATENT NO. : 7,728,030 B2
APPLICATION NO. : 12/005066
DATED : June 1, 2010
INVENTOR(S) : Markus Berger et al.

It is certified that error appears in the above-identified patent and that said Letters Patent is hereby corrected as shown below:

Title Page of Patent, right hand column, line 4 (Other Publications), "-N-puridazinyl-," should read -- -N-pyridazinyl-, --.

Column 266, lines 36-37, "(4-fluorophenyl) indazol" should read -- (4-fluorophenyl)indazol --.

Signed and Sealed this

Ninth Day of November, 2010

David J. Kappos
*Director of the United States Patent and Trademark Office*